(12) United States Patent
Borriello

(10) Patent No.: US 11,185,586 B2
(45) Date of Patent: *Nov. 30, 2021

(54) ALLOGENEIC TUMOR CELL VACCINE

(71) Applicant: ALLOPLEX BIOTHERAPEUTICS, INC., Woburn, MA (US)

(72) Inventor: Frank Borriello, Winchester, MA (US)

(73) Assignee: ALLOPLEX BIOTHERAPEUTICS, INC., Woburn, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/899,318

(22) Filed: Jun. 11, 2020

(65) Prior Publication Data

US 2020/0330596 A1 Oct. 22, 2020

Related U.S. Application Data

(63) Continuation-in-part of application No. 15/821,105, filed on Nov. 22, 2017, now Pat. No. 11,058,752.

(60) Provisional application No. 62/425,424, filed on Nov. 22, 2016.

(51) Int. Cl.
| | |
|---|---|
| *A61K 39/395* | (2006.01) |
| *A61K 39/00* | (2006.01) |
| *A61P 35/00* | (2006.01) |
| *A61K 45/06* | (2006.01) |

(52) U.S. Cl.
CPC ...... *A61K 39/39558* (2013.01); *A61K 39/001138* (2018.08); *A61P 35/00* (2018.01); *A61K 45/06* (2013.01); *A61K 2039/5152* (2013.01); *A61K 2039/5158* (2013.01)

(58) Field of Classification Search
CPC ...... A61K 39/39558; A61K 2039/5152; A61K 2039/5158
USPC ...................................................... 424/133.1
See application file for complete search history.

(56) References Cited

U.S. PATENT DOCUMENTS

| 10,731,128 B2 * | 8/2020 | Borriello .............. C12N 5/0638 |
|---|---|---|
| 2002/0006413 A1 | 1/2002 | Sobol et al. |
| 2003/0100074 A1 | 5/2003 | Yu et al. |
| 2009/0162404 A1 | 6/2009 | Podack |
| 2010/0150950 A1 | 6/2010 | Coccia et al. |
| 2010/0297189 A1 | 11/2010 | Dobric et al. |
| 2011/0014162 A1 | 1/2011 | Lowdell |
| 2013/0071403 A1 | 3/2013 | Rolland et al. |
| 2018/0185463 A1 | 7/2018 | Borriello |
| 2018/0267024 A1 | 9/2018 | Deml et al. |
| 2019/0038671 A1 | 2/2019 | Fan et al. |
| 2020/0330596 A1 | 10/2020 | Borriello |

FOREIGN PATENT DOCUMENTS

| WO | 9928349 A2 | 6/1999 |
|---|---|---|
| WO | 03045428 A2 | 6/2003 |

OTHER PUBLICATIONS

Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3)793-804 (2007)).*
Macey, Marion G., Flow cytometry: principles and applications, Humana Press, 2007.
Mackay C.R., Chemokines: immunology's high impact factors. Nat Immunol., vol. 2: 95-101, (2001).
Mackett, M., et al., General Method for Production and Selection of Infectious Vaccinia Virus Recombinants Expressing Foreign Genes. J Virol 1984, 49:857-864.
Mackett, M., et al., Vaccinia virus: A selectable eukaryotic cloning and expression vector. Proc Natl Acad Sci USA 1982, 79:7415-7419.
Magram, J. et al., Developmental regulation of a cloned adult beta-globin gene in transgenic mice, Nature 1985, 315:338-340.
Makaryan, V., et al., TCIRG1 associated Congenital Neutropenia. Hum Mutat. Jul. 2014; 35(7): 824-827.
Makrides, S.C., Strategies for achieving high-level expression of genes in *Escherichia coli*. Microbiol Rev 1996, 60:512-538.
Mason, AJ., et al., A deletion truncating the gonadotropin-releasing hormone gene is responsible for hypogonadism in the hpg mouse. Science 1986, 234:1366-1371.
Matsuzaki, H., et al., Chromosome engineering in *Saccharomyces cerevisiae* by using a site-specific recombination system of a yeast plasmid. J. Bacteriology, 172:610-618, 1990.
Mazzei GJ et al., Recombinant Soluble Trimeric CD40 Ligand Is Biologically Active. J Biol Chem. Mar. 31, 1995; 270(13):7025-8.
McLachlin, J.R., et al. Retroviral-Mediated Gene Transfer. Prog Nucleic Acid Res Mol Biol 1990, 38:91-135.
Metzger T.C. et al., "Control of central and peripheral tolerance by Aire", Immunol. Rev. 2011, vol. 241: 89-103, (2011).
Meyers and Miller; "Optimal alignments in linear space"; Computer Applic. Biol. Sci., 4:11-17 (1988).
Morgenstern, J.P., et al., Advanced mammalian gene transfer: high titre retroviral vectors with multiple drug selection markers and a complementary helper-free packaging cell line. Nucleic Acids Res 1990, 18:3587-3596.

(Continued)

*Primary Examiner* — Lynn A Bristol
(74) *Attorney, Agent, or Firm* — McCarter & English, LLP; Beverly W. Lubit

(57) ABSTRACT

The described invention provides allogeneic tumor cell vaccines comprising tumor cell lines or tumor cell line variants that are genetically engineered to express a core group of three immunomodulatory molecules, and optionally additional R immunomodulatory polypeptides for induction of one or more subpopulations of PBMCs to proliferate in response to the expressed immunomodulatory molecules and to then enter an effector phase for killing of tumor cells. According to some embodiments, the tumor cell vaccine candidate can induce an immune response in the recipient cancer patient that cross reacts with the patient's own (autologous) tumor cells, the effects of which are sufficient to result in enhanced anti-tumor immunity contributing to the increased survival of a vaccinated patient cohort compared to a matched unvaccinated patient cohort.

7 Claims, 69 Drawing Sheets
(59 of 69 Drawing Sheet(s) Filed in Color)
Specification includes a Sequence Listing.

(56) References Cited

OTHER PUBLICATIONS

Mulligan, R.C., et al, Selection for animal cells that express the *Escherichia coli* gene coding for xanthine-guanine phosphoribosyltransferase. Proc Natl Acad Sci USA 1981, 78:2072.
Murphy, Kenneth. Janeway's Immunobiology: 8th ed. Chapter 15: Garland Science. (2012), pp. 611-668.
Nash, H.A., Purification of Bacteriophage lambda, Int Protein. Nature, 247, 543-545, 1974).
Needleman, S., et al, "A General Method Applicable to the Search for Similarities in the Amino Acid Sequence of Two Proteins", (1970), J. Mol. Biol. 48:443.
Nocentini, G., et al. Pharmacological modulation of GITRL/GITR system: therapeutic perspectives. British Journal of Pharmacology (2012) 165 2089-2099.
Nunes-Duby, S.E., et al., Similarities and differences among 105 members of the Int family of site-specific recombinases. Nucleic Acids Res. 26:391-406, 1998.
O'Hare, K., et al., Transformation of mouse fibroblasts to methotrexate resistance by a recombinant plasmid expressing a prokaryotic dihydrofolate reductase. Proc Natl Acad Sci USA 1981, 78:1527.
Oliver, K.G., et al. Multiplexed Analysis of Human Cytokines by Use of the FlowMetrix System. Clin Chem 1998;44(9):2057-2060.
Ornitz, D.M., et al., Elastase I Promoter Directs Expression of Human Growth Hormone and SV40 T Antigen Genes to Pancreatic Acinar Cells in Transgenic Mice. Cold Spring Harbor Symp Quant Biol 1986, 50:399-409.
Palucka K. et al., Cancer immunotherapy via dendritic cells. Nature Reviews Cancer (Apr. 2012) 12: 265-276.
Panicali D., et al., Construction of poxviruses as cloning vectors: Insertion of the thymidine kinase gene from herpes simplex virus into the DNA of infectious vaccinia virus. Proc Natl Acad Sci USA 1982, 79:4927-4931.
PCT/US2017/063016 International Search Report and Written Opinion, dated Apr. 30, 2018, 13 pgs.
Pearson, W. R., et al, "Improved tools for biological sequence comparison", (1988), Proc. Natl. Acad. Sci. 85:2444-2448.
Pinkert, C.A., et al. An albumin enhancer located 10 kb upstream functions along with its promoter to direct efficient, liver-specific expression in transgenic mice. Genes Devel, 1987, 1:268-276.
Plasterk, R.H.A., et al., Resident Aliens. The Tc1/mariner superfamily of transposable elements. TIG 15:326-332, 1999.
Qian, F., et al. Pivotal Role of Mitogen-Activated Protein Kinase-Activated Protein Kinase 2 in Inflammatory Pulmonary Diseases. Curr Protein Pept Sci. 2016 ; 17(4): 332-342.
Rabinovitch A. et al. Roles of cytokines in the pathogenesis and therapy of type 1 diabetes. Cell Biochem Biophys, vol. 48(2-3):159-63, (2007).
Raker, V. K. et al. Tolerogenic Dendritic Cells for Regulatory T Cell Induction in Man. Front Immunol, vol. 6(569):1-11, (2015).
Readhead, C., et al., Expression of a myelin basic protein gene in transgenic shiverer mice: Correction of the dysmyelinating phenotype, Cell 1987, 48:703-712.
Rieger, R., et al. Chimeric form of tumor necrosis factor-alpha has enhanced surface expression and antitumor activity, Cancer Gene Therapy, 2009, 16, 53-64.
Rossi, D. et al. The biology of chemokines and their receptors. Annu Rev Immunol,, vol. 18: 217-242, (2000).
Rossowska, J., et al. Temporary elimination of IL-10 enhanced the effectiveness of cyclophosphamide and BMDC-based therapy by decrease of the suppressor activity of MDSCs and activation of antitumour immune response. Immunobiology 220 (2015) 389-398.
Sadowski, J., Site-Specific Recombinases: Changing Partners and Doing the Twist. Bacteriol., 165:341-357, 1986.
Saenger, Y.M., et al. Immunomodulatory Molecules of the Immune System, H.L. Kaufman and J.D. Wolchok (eds.) General Principles of Tumor Immunotherapy, Chapter 5, 67-121.
Salmons, B., et al. Targeting of Retroviral Vectors for Gene Therapy. Human Gene Ther 1993, 4:129-141.
Santerre, R.F., et al., Expression of prokaryotic genes for hygromycin B and G418 resistance as dominant-selection markers in mouse L cells. Gene 1984, 30:147.
Schrum S. et al. Synthesis of the CC-chemokines MIP-1alpha, MIP-1beta, and RANTES is associated with a type 1 immune response. J Immunol, vol. 157: 3598-3604, (1996).
Schwartz, R. H., "T cell anergy", Annu. Rev. Immunol., vol. 21: 305-334 (2003).
Shani, M., Tissue-specific expression of rat myosin light-chain 2 gene in transgenic mice, Nature 1985, 314:283-286.
Shi Y et al., Granulocyte-macrophage colony-stimulating factor (GM-CSF) and T-cell responses: what we do and don't know, Cell Research (2006) 16: 126-133.
Shirota, H., et al. CpG-conjugated apoptotic tumor cells elicit potent tumor-specific immunity, Cancer Immunol Immunother (2011) 60:659-669.
Shortman, K., et al., Steady-state and inflammatory dendritic-cell development, Nature Reviews Immunology, vol. 7. 19-30 (2007).
Smith and Waterman, Comparison of Biosequences. Adv. Appl. Math. 2:482 (1981).
Spickofsky, N., et al., Procedures for constructing cDNA expression libraries in Epstein-Barr virus shuttle vectors capable of stable episomal replication. DNA Prot Eng Tech 1990, 2:14-18.
Sprent J. et al. The thymus and central tolerance. Philos Trans R Soc Lond B Biol Sci, vol. 356(1409): 609-616, (2001).
Stahl, P.H., et al. Handbook of Pharmaceutical Salts: Properties, Selection, and Use (Wiley VCH, Zurich, Switzerland: 2002.
Studier, F.W. et al., Use of T7 RNA polymerase to direct expression of cloned genes. Methods Enzymol 1990, 185:60-89.
Swift, G. H., et al., Tissue-specific expression of the rat pancreatic elastase I gene in transgenic mice. Cell 1984, 38:639-646.
Szybalska, E.H., et al, Genetics of Human Cell Lines, IV. Dna-Mediated Heritable Transformation of a Biochemical Trait. Proc Natl Acad Sci USA 1962, 48:2026.
Takahashi, H., et al., Induction of CD8+ cytotoxic T cells by immunization with purified HIV-1 envelope protein in ISCOMs. Nature 1990, 344:873-875.
Taub D.D. et al. Recombinant human interferon-inducible protein 10 is a chemoattractant for human monocytes and T lymphocytes and promotes T cell adhesion to endothelial cells . . . J Exp Med., vol. 177:1809-1814, (1993).
Taylor, I. C.A., et al., Factor Substitution in a Human HSP70 Gene Promoter: TATA-Dependent and TATA-Independent Interactions. Mol Cell Biol 1990, 10:165-75.
Ueno H, et al., Harnessing Human Dendritic Cell Subsets for Medicine. Immunol. Rev. (2010) 234: 199-212.
Underwood, K.W., et al., Catalytically Active MAP KAP Kinase 2 Structures in Complex with Staurosporine and ADP Reveal Differences with the Autoinhibited Enzyme. Structure, vol. 11, 627-636, Jun. 2003.
Van Doren, K., et al., Efficient Transformation of Human Fibroblasts by Adenovirus Simian Virus 40 Recombinants. Mol Cell Biol 1984, 4:1653-1656.
Van Kooten C et al., CD40-CD40 ligand. J. Leukoc Biol. Jan. 2000; 67(1):2-17.
Vollmer, J., et al. Immunotherapeutic applications of CpG oligodeoxynucleotide TLR9 agonists. Advanced drug delivery reviews 61 (3): 195-204.
Wagner, E., et al., Transferrin-polycation conjugates as carriers for DNA uptake into cells. Proc. Natl. Acad. Sci. USA 87, 3410-3414 (1990).
Wakkach, A., et al. Characterization of IL-10-Secreting T Cells Derived from Regulatory CD4+CD25+ Cells by the TIRC7 Surface Marker. The Journal of Immunology, 2008, 180: 6054-6063.
Warren, HS., et al., Future prospects for vaccine adjuvants. Critical Reviews in Immunology 1988, 8:83.
Whiteside, T. L., The tumor microenvironment and its role in promoting tumor growth, Oncogene (2008) 27, 5904-5912.
Wigler, M., et al., Transfer of purified herpes virus thymidine kinase gene to cultured mouse cells. Cell 1977, 11:223-232.
Wigler, M., et al., Transformation of mammalian cells with an amplifiable dominant acting gene. Proc Natl Acad Sci USA 1980, 77:3567.

(56) References Cited

OTHER PUBLICATIONS

Williams, K.J. et al., Correlation between the Induction of Heat Shock Protein 70 and Enhanced Viral Reactivation in Mammalian Cells Treated with Ultraviolet Light and Heat Shock. Cancer Res 1989, 49:2735-42.
Woodlock, TJ., et al., Active specific immunotherapy for metastatic colorectal carcinoma: phase I study of an allogeneic cell vaccine plus low-dose interleukin-1 alpha. J Immunother 1999, 22:251-259.
Wooten, J. and Federhen, S., Statistics of Local Complexity in Amino Acid Sequences and Sequence Databases. Comput. Chem., 17:149-163 (1993).
Wu, G.Y., et al., Receptor-mediated in Vitro Gene Transformation by a Soluble DNA Carrier System*. J. Biol. Chem. 262, 4429-4432 (1987).
Xu, L., et al. MMI-0100 inhibits cardiac fibrosis in myocardial infarction by direct actions on cardiomyocytes and fibroblasts via MK2 inhibition. J Mol Cell Cardiol. Dec. 2014; 77: 86-101.
Youn B. et al. Chemokines, chemokine receptors and hematopoiesis. Immunol Rev, vol. 177: 150-174, (2000).
Yu, H., et al Crosstalk between cancer and immune cells: role of STAT3 in the tumour microenvironment. (2007) Nature Rev. Immunol. 7:41-51.
Zhao Y. et al., Identification of stem cells from human umbilical cord blood with embryonic and hematopoietic characteristics. Exp. Cell Res., 312, 2454 (2006).
Zinn, K., et al., Regulated expression of an extrachromosomal human p-interferon gene in mouse cells. Proc Natl Acad Sci USA 1982, 79:4897.
Pearson W.R. (1994) Using the FASTA Program to Search Protein and DNA Sequence Databases. In: Griffin A.M., Giffin H.G. (eds) Computer Analysis of Sequence Data. Methods in Molecular Biology 24:307-331 1994 Humana Press.
PCT/US2017/63016 International Preliminary Report on Patentability, dated Sep. 25, 2018, 5 pgs.
Ricklin, Daniel, et al. "Complement: a Key System for Immune Surveillance and Homeostasis." Nature Immunology, U.S. National Library of Medicine, Sep. 2010, www.ncbi.nlm.nih.gov/pmc/articles/PMC2924908/.
Spear, Paul, et al. "NKG2D Ligands as Therapeutic Targets." Cancer Immunity, Academy of Cancer Immunology, May 1, 2013 vol. 13, p. 8. www.ncbi.nlm.nih.gov/pmc/articles/PMC3700746/.
Murphy, Kenneth. Janeway's Immunobiology: 8th ed. Chapter 8: Garland Sciences. pp. 275-334.
Curotto De Lafaille, M.A., et al. Natural and Adaptive Foxp3+ Regulatory T Cells: More of the Same or a Division of Labor? Immunity, 30(6): 626-635, (2009).
Dunn, GP et al., The Three Es of Cancer Immunoediting. Ann. Rev. Immunol. (2004): 329-60.
Marcus, Assaf, et al. "Recognition of Tumors by the Innate Immune System and Natural Killer Cells." Advances in Immunology, U.S. National Library of Medicine, 2014, www.ncbi.nlm.nih.gov/pmc/articles/PMC4228931.
Hastings, K.T. Innate and Adaptive Immune Responses to Cancer in Fundamentals of Cancer Prevention. Alberts, D.S., and L.M. Hess, (eds.) Springer-Verlag Berlin Heidelberg. 2008. pp. 79-108.
Gabrilovich, DI., "Myeloid-derived suppressor cells," Cancer Immunol. Res. (2017) 5(1): 3-8.
Gabrilovich, DE et al, Coordinated regulation of myeloid cells by tumours. Nat Rev lmmunol.(2012)12:253-68.
Koehn BH, et al. GVHD-associated, inflammasome-mediated loss of function in adoptively transferred myeloid-derived suppressor cells. Blood (2015) 126:1621-8.
Nagaraj S, et al. Altered recognition of antigen is a mechanism of CD8+ T cell tolerance in cancer. Nat Med. (2007) 13: 828-35.
Lu, T. et al., Tumor-infiltrating myeloid cells induce tumor cell resistance to cytotoxic T cells in mice. J. Clinical Investigation. (2011) 121: 4015-29.
Molon, B. et al., Chemokine nitration prevents intratumoral infiltration of antigen-specific T cells. J Exp Med. (2011) 208: 1949-62.

Tartour, E. et al., Angiogenesis and immunity: a bidirectional link potentially relevant for the monitoring of antiangiogenic therapy and the development of novel therapeutic combination with immunotherapy. Cancer Metastasis Rev. (2011) 30: 83-95.
Casella, I., et al., Autocrine-paracrine VEGF loops potentiate the maturation of megakaryocytic precursors through Flt1 receptor. Blood. (2003) 101:1316-23.
Shojaei, F. et al., G-CSF-initiated myeloid cell mobilization and angiogenesis mediate tumor refractoriness to anti-VEGF therapy in mouse models. Proc Natl Acad Sci U S A. (2009) 106: 6742-7.
Gottschalk et al. (2015) "The Role of Invariant Natural Killer T Cells in Dendritic Cell Licensing, Cross-Priming, and Memory CD8+ T Cell Generation." Front Immunol 6:379.
Nair, S. and Dhodapkar, M.V. (2017). "Natural Killer T Cells in Cancer Immunotherapy." Frontiers in Immunology 8:1178.
McNamara, DA et al., Tamoxifen inhibits endothelial cell proliferation and attenuates VEGF-mediated angiogenesis and migration in vivo . . . Eur. J. Surg. Oncol. (2001) 27(8): 714-718.
Richards, David M, et al. "Monocytes and Macrophages in Cancer: Development and Functions." Cancer Microenvironment (2013) 6:179-191.
Bingle L, et al The role of tumor-associated macrophages in tumor progression: implications for new anticancer therapies. J Pathol. (2002) 196: 254-265.
O'Sullivan T, et al. Cancer immunoediting by the innate immune system in the absence of adaptive immunity. J Exp Med. (2012) 209: 1869-1882.
Croci, D. O., Dynamic cross-talk between tumor and immune cells in orchestrating the immunosuppressive network at the tumor microenvironment. Cancer Immunol Immunother (2007) 56:1687-1700.
Drake, C.G., et al. Current status of immunological approaches for the treatment of prostate cancer. Curr Opin Urol. May 2010 ; 20(3): 241-246.
Earley, M.C., et al. Report from a Workshop on Multianalyte Microsphere Arrays. Cytometry 2002;50:239-242.
Elshal, M.F.,et al., Multiplex Bead Array Assays: Performance Evaluation and Comparison of Sensitivity to ELISA. Methods 38(4): 317-323, Apr. 2006.
Faas, M.M., et al. Monocyte intracellular cytokine production during human endotoxaemia with or without a second in vitro LPS challenge: effect of RWJ-67657, a p38 MAP-kinase inhibitor, on LPS-hyporesponsiveness. Clin Exp Immunol 2002; 127:337-343.
Frey, N.V., et al., The Promise of Chimeric Antigen Receptor T-Cell Therapy, Oncology (2016).
Fujiyama, K., et al, IgG H chain [*Homo sapiens*]. NCBI PDB Accession No. BAN63131. Submitted Jan. 13, 2013; downloaded from the internet< https://www.ncbi.nlm.nih.gov/protein/BAN63131> on Feb. 21, 2018; Genbank Supplement pp. 1-2 (cited in PCT/US2017/63016 International Search Report).
Gorman, C.M., Mammalian cell expression. Curr Op Biotechnol 1990, 1:36-47.
Graf D et al., A soluble form of TRAP (CD40 ligand) is rapidly released after T cell activation. Eur J Immunol. Jun. 1995; 25(6):1749-54.
Grosschedl, R., et al. Introduction of a μ immunoglobulin gene into the mouse germ line: Specific expression in lymphoid cells and synthesis of functional antibody. Cell 1984, 38:647-658.
Grossman, M., et al. Retroviruses: delivery vehicle to the liver. Curr Opin Genet Devel 1993, 3:110-114.
Groth, A.C., et al., Phage Integrases: Biology and Applications. J. Mol. Biol. 335:667-678, 2004.
Gulley, J.L. et al. Immunotherapy for Prostate Cancer: Recent Advances, Lessons Learned, and Areas for Further Research. Clin Cancer Res; 17(12) Jun. 15, 2011.
Hamer, D.H., et al., SV40 recombinants carrying rabbit beta-globin gene coding sequences. Cell 1979, 17:725-735.
Hammer, R.E., et al. Diversity of alpha-fetoprotein gene expression in mice is generated by a combination of separate enhancer elements. Science 1987, 235:53-58.
Hanahan, D. Heritable formation of pancreatic ß-cell tumours in transgenic mice expressing recombinant insulin/simian virus 40 oncogenes. Nature 1985, 315:115-122.

(56) References Cited

OTHER PUBLICATIONS

Henikoff & Henikoff; "Amino acid substitution matrices from protein blocks"; Proc. Natl. Acad. Sci. USA vol. 89, pp. 10915-10919, Nov. 1992.
Higano C S, et al., Integrated Data From 2 Randomized, Double-Blind, Placebo Controlled, Phase 3 Trials of Active Cellular Immunotherapy With Sipuleucel-T in Advanced Prostate Cancer. Cancer (2009) 115: 3670-3679.
Higgins, D. G., et al, "Fast and sensitive multiple sequence alignments on a microcomputer", (1989) CABIOS 5:151-153.
Higgins, D.G., et al, "Clustal: a package for performing multiple sequence alignment on a microcomputer", (1988), Gene 73:237-244.
Hoover, HC., et al., Adjuvant active specific immunotherapy for human colorectal cancer: 6.5-year median follow-up of a phase III prospectively randomized trial. J Clin Oncol 1993, 11:390.
Huang, X., et al., "Parallelization of a local similarity algorithm", (1992) Computer Applications in the Biosciences 8:155-165.
Hunter TB, et al., An Agonist Antibody Specific for CD40 Induces Dendritic Cell Maturation and Promotes Autologous Anti-tumour T-cell Responses in an In vitro Mixed Autologous Tumour Cell/Lymph Node Cell Model (2007) Scandanavian J. Immunology 65, 479-486.
Jancey, J., et al., "Effective recruitment and retention of older adults in physical activity research: PALS study", Am J Health Behav, vol. 30(6): 626-635, (2009).
Janeway, CA, Jr., The priming of helper T cells . . . Semin. Immunol., vol. 1(1): 13-20 (1989).
Jensen, S.M. et al. Adoptive cellular immunotherapy of cancer: a three-signal paradigm for translating recent developments into improved treatment strategies. Springer Science & Business Media, 2007, Tumor Immunology and Cancer Vaccines, vol. 123, Chapter 13, 293-336.
Jiang T.T. Regulatory T Cells: New Keys for Further Unlocking the Enigma of Fetal Tolerance and Pregnancy Complications. J Immunol., vol. 192(11): 4949-4956, (2014).
Kantoff P W, et al., Sipuleucel-T Immunotherapy for Castration-Resistant Prostate Cancer. N. Engl. J. Med. (2010) 363: 411-422.
Karlin & Altschul; "Applications and statistics for multiple high-scoring segments in molecular sequences"; Proc. Natl. Acad. Sci. USA, vol. 90, pp. 5873-5877, Jun. 1993.
Karpusas M et al., 2 å crystal structure of an extracellular fragment of human CD40 ligand. Structure. Oct. 15, 1995; 3(10):1031-9.
Kaufman and Wolchok (eds.), General Principles of Tumor Immunotherapy, Chapter 5, 67-121 (2007).
Kelsey, G.D., et al. Species- and tissue-specific expression of human alpha 1-antitrypsin in transgenic mice. Genes Devel 1987, 1:161-171.
Klein, L. Aire Gets Company for Immune Tolerance. Cell, vol. 163(4):794-795, (2015).
Kleinnijenhuis, J., et al. Innate Immune Recognition of Mycobacterium tuberculosis. (2011) Clin. Dev. Immunol. 405310 (12 pgs.).
Knapinska, A.M., et al. Chaperone Hsp27 Modulates AUF1 Proteolysis and AU-Rich Element-Mediated mRNA Degradation. Molecular and Cellular Biology, Apr. 2011, vol. 31., No. 7, 1419-1431.
Kollias, G., et al., Regulated expression of human A gamma-, beta-, and hybrid gamma beta-globin genes in transgenic mice: manipulation of the developmental expression patterns, Cell 1986, 46:89-94.
Kootstra, N.A. et al., Gene Therapy with Viral Vectors. Ann. Rev. Pharm. Toxicol., 43:413-439, 2003.
Kozlowska, A., et al. Therapeutic gene modified cell based cancer vaccines. Gene 525 (2013) 200-207.
Krieg, AM., et al. (1995). CpG motifs in bacterial DNA trigger direct B-cell activation. Nature. 374 (6522): 546-9.
Krug, A., et al. Identification of CpG oligonucleotide sequences with high induction of IFN-alpha/beta in plasmacytoid dendritic cells . . . Eur. J. Immunol. 2001. 31: 2154-2163.
Krumlauf, R., et al. Developmental regulation of alpha-fetoprotein genes in transgenic mice . . . Mol Cell Biol 1985, 5:1639-1648.

Kumar N.P. et al. 2015. Coincident diabetes mellitus modulates Th1-, Th2-, and Th17-cell responses in latent tuberculosis in an IL-10- and TGF-beta-dependent manner. Eur J Immunol. 2016. 46:390-399. doi: 10.1002/eji.201545973.
Kumar, C, et al., AKT crystal structure and AKT-specific inhibitors. Oncogene (2005) 24, 7493-7501.
Leder, A., et al. Consequences of widespread deregulation of the c-myc gene in transgenic mice: Multiple neoplasms and normal development. Cell 1986, 45:485-495.
Lefebvre, E., et al. Antifibrotic Effects of the Dual CCR2/CCR5 Antagonist Cenicriviroc in Animal Models of Liver and Kidney Fibrosis. PLoS One 11(6): e0158156. doi:10.1371/ journal.pone. 0158156, Jun. 2016.
Liu, Q., et al. Developing irreversible inhibitors of the protein kinase cysteinome. Chem Biol. Feb. 21, 2013; 20(2):146-159.
Loetscher P. et al. The Ligands of CXC Chemokine Receptor 3, I-TAC, Mig, and IP10, Are Natural Antagonists for CCR3*. J. Biol. Chem., vol. 276: 2986-2991, (2001).
Logan, J., et al, Adenovirus tripartite leader sequence enhances translation of mRNAs late after infection. Proc Natl Acad Sci USA 1984, 81:3655-3659.
Lowy, I., et al., Isolation of transforming DNA: cloning the hamster aprt gene . . . Cell 1980, 22:817.
MacDonald, R.J. Expression of the pancreatic elastase I gene in transgenic mice. Hepatology 1987, 7:425-515.
McLaughlin, SK et al., Adeno-Associated Virus General Transduction Vectors: Analysis of Proviral Structures. J Virol 1988, 62:1963-9173.
Pelgner, PL., et al., Lipofection: A highly efficient, lipid-mediated DNA-transfection procedure. Proc. Natl. Acad. Sci. U.S.A. 84:7413, 1987.
Ono, T., et al., Plasmid DNAs directly injected into mouse brain with lipofectin can be incorporated and expressed by brain cells. Neuroscience Letters vol. 117, Issue 3, :259-263, 1990.
Brigham, KL., et al., In vivo transfection of expression in murine lungs with a functioning prokaryotic gene using a cationic liposome vehicle. Am. J. Med. Sci. 298:278, 1989.
Straubinger, RM., et al., Liposomes as carriers for intracellular delivery of nucleic acids. Methods in Enzymology 101:512-527, 1983.
Wu, GY., et al., Receptor-mediated Gene Delivery and Expression in Vivo. Journal of Biological Chemistry 263, No. 29, pp. 14621-14624, 1988.
Wu, CH., et al., Targeting Genes: Delivery and Persistent Expression of a Foreign Gene Driven by Mammalian Regulatory Elements in Vivo. Journal of Biological Chemistry, vol. 264, No. 29. pp. 16985-16987, 1989.
Wolff, JA., et al., Direct gene transfer into mouse muscle in vivo. Science 247:1465, 1990.
Alberts, B. et al, The Adaptive Immune System from Molecular Biology of the Cell, 4th Ed. Chapter 24, 1363-1420 (2002).
Pardoll, D. "Cancer Immunotherapy with Vaccines and Checkpoint Blockade" in. The Molecular Basis of Cancer. Chapter 52. pp. 709-738. Mendelsohn, J., et al (eds). Elsevier Health Sciences, 2015.
Galluzzi, L, et al. Classification of Current Anticancer Immunotherapies. Oncotarget, vol. 5, No. 24. 12472-12508 (2014).
Sharma, R, et al. Failure of Immunological Cells to Eradicate Tumor and Cancer Cells: an overview. Turkish Journal of Biology, 38:786-799 (2014).
O'Konek, J.J., et al. "Immune Regulation of Tumor Immunity by NKT Cells." in Natural Killer T Cells: Balancing the Regulation of Tumor Immunity. Springer New York, 2012, Ch. 4, 55-70. Terabe and Berzofsky, eds.
Abel, A.M., et al. Natural Killer Cells: Development, Maturation, and Clinical Utilization. Frontiers in Immunology. vol. 9, Article 1869, Aug. 2018.
Anderson, M.H., et al. Cytotoxic T Cells. J. Investigative Dermatology, (2006) vol. 126, 32-41.
Balato, A., et al. Natural Killer T Cells: An Unconventional T-Cell Subset with Diverse Effector and Regulatory Functions. J. Investigative Dermatology. (2009), vol. 129. 1628-1642.

(56) References Cited

OTHER PUBLICATIONS

Campbell, J. et al., CCR7 Expression and Memory T Cell Diversity in Humans. J Immunol 2001; 166:877-884.
Cappuzzello, E., et al. Cytokines for the induction of antitumor effectors: The paradigm of Cytokine-Induced Killer (CIK) cells. Cytokine & Growth Factor Reviews 36 (2017) 99-105.
Chow, K.V., et al. Innate Allorecognition Results in Rapid Accumulation of Monocyte-Derived Dendritic Cells. The Journal of Immunology, 2016, 197: 2000-2008.
Deroost, K. and Langhorne, J. Gamma/Delta T Cells and Their Role in Protection Against Malaria. Frontiers in Immunology. Dec. 2018, vol. 9, Article 2973.
Gati, A., et al. CD158 Receptor Controls Cytotoxic T-Lymphocyte Susceptibility to Tumor-Mediated Activation Induced Cell Death by Interfering with Fas Signaling. Cancer Research, 63, 7475-7482, Nov. 1, 2003.
Guo, Y and Han, W., Cytokine-induced killer (CIK) cells: from basic research to clinical translation. Chinese Journal of Cancer (2015) 34:6.
Meng, M., et al. A dynamic transcriptomic atlas of cytokine induced killer cells. J. Biol. Chem. published online Oct. 17, 2018 as Manuscript RA118.003280 (29 pgs).
Van Kaer, L., et al. Invariant natural killer T cells: bridging innate and adaptive immunity. Cell Tissue Res. Jan. 2011 ; 343(1): 43-55. doi:10.1007/s00441-010-1023-3.
Krovi, S.H. and Gapin, L. Invariant Natural Killer T Cell Subsets—More Than Just Developmental Intermediates. Frontiers in Immunology. Jun. 2018, vol. 9, Article 1393.
Kumar, A., et al. Natural Killer T Cells: An Ecological Evolutionary Developmental Biology Perspective. Frontiers in Immunology. Dec. 2017, vol. 8, Article 1858.
Moynihan, K.D. and Irvine, D.J., Roles for Innate Immunity in Combination Immunotherapies. Cancer Res; 77(19); 5215-21. (2017).
Paul, S. and Girdhari, L. The Molecular Mechanism of Natural Killer Cells Function and Its Importance in Cancer Immunotherapy. Frontiers in Immunology. Sep. 2017, vol. 8, Article 1124.
Pauza, C.D., et al. Gamma Delta T Cell Therapy for Cancer: It is Good to be Local. Frontiers in Immunology. Jun. 2018. vol. 9, Article 1305.
Santiago-Schwarz, F., et al. Distinct Characteristics of Lymphokine-Activated Killer (LAK) Cells Derived From Patients With B-Cell Chronic Lymphocytic Leukemia (B-CLL). A Factor in B-CLL Serum Promotes Natural Killer Cell-Like LAK Cell Growth. Blood, vol. 76, No. 7 (Oct. 1, 1990). pp. 1355-1360.
Souza-Fonseca-Guimaraes, F., et al. The Emergence of Natural Killer Cells as a Major Target in Cancer Immunotherapy. Trends in Immunology, Feb. 2019, vol. 40, No. 2, 142-158.
Torina, A., et al. The Janus Face of NKT Cell Function in Autoimmunity and Infectious Diseases. Int. J. Mol. Sci. 2018, 19, 440; doi:10.3390/ijms19020440.
Vivier, E., et al. Targeting natural killer cells and natural killer T cells in cancer. Nat Rev Immunol. (2012) 12(4):239-252. doi:10.1038/nri3174.
Voo, KS., et al. Targeting of TLRs Inhibits CD4+ Regulatory T Cell Function and Activates Lymphocytes in Human Peripheral Blood Mononuclear Cells. The Journal of Immunology, 2014, 193: 627-634.
Park Jang-June et al: "Expression of anti-HVEM single-chain antibody on tumor cells induces tumor-specific immunity with long-term memory", Cancer Immunology, Immunotherapy, NIH Author Manuscript, Springer, Berlin/Heidelberg, vol. 61, No. 2, Aug. 30, 2011 (Aug. 30, 2011), pp. 203-214.
Watkins SK, et al. IL-12 rapidly alters the functional profile of tumor-associated and tumor-infiltrating macrophages in vitro and in vivo. J Immunol. (2007) 178:1357-1362.
Chao MP, et al. The CD47-SIRPalpha pathway in cancer immune evasion and potential therapeutic implications. Curr Opin Immunol. (2012) 24: 225-232.
Brutkiewicz, R.R. "CD1d Ligands: The Good, the Bad, and the Ugly." The Journal of Immunology (2006) 177 (2)769-775.

Mak, T.W. et al. "NK, yo T and NKT Cells." in Primer to the Immune Response. 2nd Ed. 2014. Chapter 11, 247-268. Elsevier.
Girardi, E. and Zajonc, D.M. (2012). "Molecular basis of lipid antigen presentation by CD1d and recognition by natural killer T cells." Immunol Rev. 250(1): 167-179.
Kumar, V. and Delovitch, T.L. (2014) "Different subsets of natural killer T cells may vary in their roles in health and disease." Immunology 142: 321-336.
Claverie, J.M. and States, D.J. Information enhancement methods for large scale sequence analysis. Comput. Chem., 17:191-201 (1993).
Lopez, Jamie A., et al. "Perforin Forms Transient Pores on the Target Cell Plasma Membrane to Facilitate Rapid Access of Granzymes during Killer Cell Attack." Blood Journal, American Society of Hematology, vol. 121, No. 14, 2659-2668, 2013.
Murphy, Kenneth M., et al. "T-Cell Mediated Immunity." Janeways Immunobiology. 9th ed., GS, Garland Science, Taylor & Francis Group, 2017. pp. 387-395.
Falschlehner, C., et al. "Following TRAIL's Path in the Immune System." Immunology 127, 145-154 Jun. 2009.
Ito, H. and Seishima, M. (2010), "Regulation of the Induction and Function of Cytotoxic T Lymphocytes by Natural Killer T Cell." J Biomed Biotechnol, Art. ID. 641757, 8 pages.
Seaman, W.E. (2000) "Natural Killer Cells and Natural Killer T Cells." Arthritis & Rheumatism 43(6): 1204-1217.
Mandal, A and Viswanathan, C (2015). "Natural killer cells: In health and disease." Hematol. Oncol. Stem Cell The. 8(2): 47-55.
Lanier, LL, NKG2D Receptor and Its Ligands in Host Defense. Cancer Immunol. Res. (2015) 3(6): 575-82.
Murphy, Kenneth M., et al. Janeways Immunobiology. 9th ed., GS, Garland Science, Taylor & Francis Group, 2017. p. 129-130.
Godfrey, D.I., et al. (2004). "NKT cells: what's in a name?" Immunology, Nature Reviews 4:231-237.
Bennstein, S.B. (2017), "Unraveling Natural Killer T-Cells Development" Front Immunol. 8:1950.
Van Acker, HH, t al., "CD56 in the immune system: more than a marker for cytotoxicity?" Front. Immunol. (2017) 8:892.
Liu, J., et al. The Regulation of CD1d+ and CD1d− Tumors by NKT Cells: The Roles of NKT Cells in Regulating CD1d+ and CD1d− Tumor Immunity. "Natural Killer T Cells Balancing the Regulation of Tumor Immunity." Springer New York, 2012, Ch. 5, Terabe and Berzofsky, eds.
Liao, CM et al. (2014) "The Functions of Type I and Type II Natural Killer I (NKT) Cells in Inflammatory Bowel Diseases." Inflamm Bowel Dis. 19(6): 1330-1338.
Gutegemann, S., et al. (2007). "Cytokine-induced killer cells are type II natural killer T cells." GMS German Medical Science 5:1-4.
Gao, X., et al. "Cytokine-Induced Killer Cells As Pharmacological Tools for Cancer Immunotherapy." Frontiers Immunol. 8:774, 2017.
Wu YL, et al. Gamma delta T Cells and Their Potential for Immunotherapy. Int J Biol Sci 2014; 10(2):119-135. doi:10.7150/ijbs.7823.
Soghoian, D. Z. and Streeck, H. "Cytolytic CD4+T Cells in Viral Immunity." Expert Rev Vaccines. Dec. 2010 ; 9(12): 1453-1463. doi:10.1586/erv.10.132. www.ncbi.nlm.nih.gov/pmc/articles/PMC3033049/.
Peterfalvi, A., et al. "Invariant Valpha7.2-Jalpha33 TCR Is Expressed in Human Kidney and Brain Tumors Indicating Infiltration by Mucosal-Associated Invariant T (MAIT) Cells." International Immunology 20(12), 1517-1525, 2008.
Benichou, G, and A W Thomson. "Direct versus Indirect Allorecognition Pathways: on the Right Track." American Journal of Transplantation : Official Journal of the American Society of Transplantation and the American Society of Transplant Surgeons, U.S. National Library of Medicine, Apr. 2009, www.ncbi.nlm.nih.gov/pmc/articles/PMC3746751/.
Ebihara, T., et al. "Induction of NKG2D Ligands on Human Dendritic Cells by TLR Ligand Stimulation and RNA Virus Infection." International Immunology, vol. 19, No. 10, pp. 1145-1155, 2007. doi:10.1093/intimm/dxm073.
Hwu, P. et al. "Cancer and the Celuular Immune Response" in The Molecular Basis of Cancer. Chapter 51. Mendelsohn, J. et al (eds) Elsevier Health Sciences, 2015, pp. 695-708.

(56) References Cited

OTHER PUBLICATIONS

Wortham, B. W., et al. TLR and NKG2D Signaling Pathways Mediate CS-Induced Pulmonary Pathologies. PLoS One 8(10): e78735. doi:10.1371/journal.pone.0078735 (2013).
Qian, C. and Cao, X, (2013), "Regulation of Toll-like receptor signaling pathways in innate immune responses," Ann. NY Acad. Sci. 1283: 67-74.
Obata, T. et al., MAP kinase pathways activated by stress: The p38 MAPK pathway. Crit. Care Med. 28 (4 Suppl.: N67-N77) (2000).
Dong, C. et al., (2002) "MAP kinases in the immune response," Annu. Rev. Immunol. 20: 55-72.
Kleiveland, C.R., "Peripheral Blood Monouclear Cells" in: Verhoeckx, K. et al. (eds). The Impact of Food Bioactives on Health (2015), Springer, Cham. Doi.org/10.1007/978-3-319-1610404. Chapter 15, p. 161-167.
So T et al, Immune Regulation and Control of Regulatory T cells by OX40 and 4-1BB. Cytokine Growth Factor Rev. (2008) 19 (3-4): 253-62.
Huang, L. et al., OX40L induces helper T cell differentiation during cell immunity of asthma through PI3K/ AKT and P38 MAPK signaling pathway. J. Trans. Med. (2018) 16: 74; doi: 10.1186/s12967-018-1436-4.
Desmedt, T et al, Ox40 Costimulation Enhances the Development of T Cell Responses Induced by Dendritic Cells In Vivo. J. Immunol (2002) 168: 661-670. doi: 10.4049/jimmunol.168.2.661.
Ohshima, Y. et al., OX40 Costimulation Enhances Interleukin-4 (IL-4) Expression at Priming and Promotes the Differentiation of Naive Human CD4+ T Cells Into High IL-4-Producing Effectors. Blood (1998) 92: 3338-3345.
Paterson DJ, et al. Antigens of activated rat T lymphocytes includig a molecule of 50,000 Mr detectde only on CD4 positive T blasts. Mol Immunol. (1987) 24:1281-1290. doi: 10.1016/0161-5890(87)90122-2.
Kaur D. and Brightling C. OX40/OX40 Ligand Interactions in T-Cell Regulation and Asthma. Chest. (2012) 141:494-499. doi: 10.1378/chest.11-1730.
Vu MD, et al. OX40 costimulation turns off Foxp3+ Tregs. Blood. (2007) 110:2501-10.
So T, and Croft M. Cutting Edge: OX40 Inhibits TGF-beta- and Antigen-Driven Conversion of Naive CD4 T Cells into CD25+ Foxp3+ T cells. J Immunol. (2007) 179:1427-30.
Dolfi, DV, et al., Late Signals from CD27 Prevent Fas-Dependent Apoptosis of Primary CD8+ T Cells1. J. Immunol. (2008) 180(5): 2912-2921.
Murphy, Kenneth. Janeway's Immunobiology: 8th ed. Chapter 9: T Cell-Mediated Immunity. Garland Science. (2012).
Guinn, B, et al., 4-1BBL Cooperates with B7-1 and B7-2 in Converting a B Cell Lymphoma Cell Line into a Long-Lasting Antitumor Vaccine1. J. Immuno. (1999) 162: 5003-5010.
Grell M. et al., The Transmembrane Form of Tumor Necrosis Factor Is the Prime Activating Ligand of the 80 kDa Tumor Necrosis Factor Receptor, Cell, vol. 83, 793-802 (1995).
Shouval, DS., et al., Interleukin-10 Receptor Signaling in Innate Immune Cells Regulates Mucosal Immune Tolerance and Anti-Inflammatory Macrophage Function. Immunity (2014) 40: 706-719.
Moore, KW, et al., Interleukin-10 and the interleukin-10 receptor. Annu. Rev. Immunol. (2001) 19: 683-765.
Saraiva, M., and O'Garra, A. The regulation of IL-10 production by immune cells. Nat. Rev. Immunol. (2010) 10:180-181.
Bluestone, JA et al., CTLA4Ig: Bridging the Basic Immunology with Clinical Application. Immunity. (2006)24:233-238.
Bour-Jordan, H. et al., Intrinsic and extrinsic control of peripheral T-cell tolerance by costimulatory molecules of the CD28/B7 family. Immunol Rev. (2011) 241:180-205. doi:10.1111/j.1600-065X.2011.01011.x.
Battaglia, M. et al., "Rapamycin promotes expansion of functional CD4+CD25+Foxp3+ regulator T cells of both healthy subjects and type 1 diabetic patients", J. Immunol., vol. 177: 8338-8347, (2006).

Butterfield, L., Dendritic Cells in Cancer Immunotherapy Clinical Trials: Are We Making Progress?, Frontiers of Immunology, 2013 4: 454.
Chang, S., Overview of Prostate-Specific Membrane Antigen, Reviews in Urology, vol. 6 Suppl. 10, S13 (2004).
Clark, R.A. Resident memory T cells in human health and disease . . . Sci. Transl. Med., 7, 269rv1, (2015).
Desai-Mehta, A. et al. Hyperexpression of CD40 Ligand by B and T Cells in Human Lupus and Its Role in Pathogenic Autoantibody Production. J. Clin. Invest. vol. 97(9), 2063-2073, (1996).
Dyall R., et al., Heteroclitic Immunization Induces Tumor Immunity, J. Exp. Med., vol. 188, No. 9, Nov. 2, 1998.
Eager, R. & Nemunaitis, J., GM-CSF Gene-Transduced Tumor Vaccines, Molecular Therapy, vol. 12, No. 1, 18 (Jul. 2005).
Elgueta R et al., Molecular mechanism and function of CD40/CD40L engagement in the immune system. Immunological reviews. 2009; 229(1).
Esenstein, JH et al, Immunity, "CD28 costimulation: from mechanism therapy" (2016) 44(5): 973-988.
Uchida, Atsushi et al., Int J. Canc, "Autologous Mixed Lymphocyte-Tumor Reaction and Autologous Mixed Lymphocyte Reaction.II. Generation of Specific and Non-Specific Killer T Cells Capable of Lysing Autologous Tumor", (1988) 41:651-656.
Kimmel, A. R., Identification and Characterization of Specific Clones: Strategy for Confirming the Validity of Presumptive Clones, (1987) Methods Enzymol. 152:507.
Kronenberg, M. et al., "Regulation of immunity by self-reactive T cells", Nature, vol. 435: 598-604 (2005).
Lacy, P. and Stow, JL, "Cytokine release from innate immune cells: association with diverse membrane trafficking pathways," Blood (2011) 118: 9-18.
Mason et al., Science, "A Deletion Truncating the Gonadotropin-Releasing Hormone Gene Is Responsible for Hypogonadism in the hpg Mouse", 1986, 234:1366-1371.
Takanori So, et al., Cytokine Growth Factor Rev., "Immune Regulation and Control of Regulatory Tcells by OX40 and 4-1BB" (2008) 19:253-262.
Okkenhaug et al., J Biol Chem., "Grb2 Forms an Inducible Protein Complex with CD28 through a Src Homology 3 Domain-Proline Interaction", (1998) 273: 21194-21202.
Pardoll, D., The blockade of immune checkpoints in cancer immunotherapy, Nature Reviews: Cancer, vol. 12, Apr. 2012, 253.
Paul, W. E., "Chapter 1: The immune system: an introduction," Fundamental Immunology, 4th Edition, Ed. Paul, W.E., Lippicott-Raven Publishers, Philadelphia, (1999), at p. 102.
Sani, Nature, "Tissue-specific expression of rat myosin light-chain 2 gene in transgenic mice", (1985), 314:283-286.
Steinman, Ann. Rev. Immunol., "The Dendritic Cell System and It's Role in Immunogenicity", 9:271-296 (1991).
Stjernsward J, et al. in 1970, Clin Exp Immunol Tumour-distinctive Cellular Immunity to Renal Carcinoma:, 6: 963-668.
Taams, L. S. et al., "Human anergic/suppressive CD4+CD25+ T cells: a highly differentiated and apoptosis-prone population", Eur. J. Immunol. vol. 31: 1122-1131 (2001).
Wahl, G. M. and S. L. Berger, "Molecular Hybridization of Immobilized Nucleic Acids: Theoretical Concepts and Practical Considerations" (1987) Methods Enzymol. 152:399-407.
Wang et al., "Expressio of heat-stable antigen on tumor cells provides co-stimulation for tumor-specific T cell proliferation and cytotoxicity in mice", (Eur J Immunol. May 1995;25(5):1163-7.
Weinberg, AD, et al., "OX-40: life beyond the effector T cell stage," Semin. Immunol. (1998) 10(6): 471-80.
Wu et al., Journal of Biological Chemistry, "Receptor-mediated gene delivery and expression in vivo", 263:14621, 1988.
Wu et al., Journal of Biological Chemistry, "Targeting Genes: Delivery and Persistent Exression of a Foreign Gene Driven by Mammalian Regulatory Elements in Vivo", 264:16985, 1989.
Xiu et al. (J Mol Med (Berl). "Surface anchorage of superantigen SEA promotes induction of specific antitumor immune response by tumor-derived exosomes", May 2007;85(5):511-21. Epub Jan. 12, 2007.

(56) References Cited

OTHER PUBLICATIONS

Adams, J.M., et al. The c-myc oncogene driven by immunoglobulin enhancers induces lymphoid malignancy in transgenic mice. Nature 1985, 318:533-538.
Alexander, W., et al., Expression of the c-myc Oncogene under Control of an Immunoglobulin Enhancer in E[L-myc Transgenic Mice. Mol Cell Biol 1987, 7:1436-1444.
Alexandraki K. et al. Inflammatory Process in Type 2 Diabetes. The Role of Cytokines. Annals of the New York Academy of Sciences, 1084: 89-117, (2006).
Altschul, P., et al. Gapped BLAST and PSI-BLAST: a new generation of protein database search programs. Nucleic Acids Res. 25:3389-3402 (1997).
Ausubel, et al. Current Protocols in Molecular Biology, Chapter 19, Eds., Greene Publishing and Wiley-Interscience, New York (2005).
Bendall, S.C., et al. Single-Cell Mass Cytometry of Differential Immune and Drug Responses Across a Human Hematopoietic Continuum. Science, vol. 332:687-696; May 6, 2011.
Bendall, S.C., et al., From single cells to deep phenotypes in cancer. Nature Biotechnology, vol. 30 No. 7:639-647; Jul. 2012.
Bestor, T.H., Transposons Reanimated in Mice. Cell, 122(3):322-325, 2005.
Bitter, G.A., et al., Expression and Secretion Vectors for Yeast. Meth Enzymol 1987, 153:516-544.
Bode, C., CpG DNA as a vaccine adjuvant, Expert Rev Vaccines. Apr. 2011; 10(4): 499-511).
Boesen, J.J.B., et al., Circumvention of chemotherapy-induced myelosuppression by transfer of themdr1 gene. Biotherapy 1994, 6:291-302.
Bonifant CL, et al., Toxicity and management in CAR T-cell therapy, Molecular Therapy—Oncolytics (2016) 3, 16011; doi:10.1038/mto.2016.11.
Bradley L.M. et al. Islet-Specific Th1, But Not Th2, Cells Secrete Multiple Chemokines and Promote Rapid Induction of Autoimmune Diabetes. J Immunol, vol. 162:2511-2520, (1999).
Broach, J.R., et al., Recombination within the yeast plasmid 2μ circle is site-specific. Cell, 29:227-234, 1982.
Browning, M., Antigen presenting cell/tumor cell fusion vaccines for cancer, Human Vaccines & Immunotherapeutics 9:7, 1545-1548; Jul. 2013;DOI: 10.4161/hv.24235.
Cai, G., The CD160, BTLA, LIGHT/HVEM pathway: a bidirectional switch regulating T-cell activation, Immunol. Rev., May; 229(1):244-58 (2009).
Carbone, E et al. A New Mechanism of NK Cell Cytotoxicity Activation: The CD40-CD40 Ligand Interaction. J Exp Med. Jun. 16, 1997; 185(12):2053-60.
Carmi, Y, et al. Tumor-binding antibodies and tumor immunity. Oncotarget, vol. 6, No. 34, 35129-35130 (2015).
Carmi, Y., et al. Allogeneic IgG combined with dendritic cell stimuli induces anti-tumor T cell immunity. Nature. May 7, 2015; 521(7550): 99-104.
Choulika, A., et al., Transfer of Single Gene-Containing Long Terminal Repeats into the Genome of Mammalian Cells by a Retroviral Vector Carrying the cre Gene and the loxP Site. J Virol 1996, 70:1792-1798.
Colberre-Garapin, F., et al., A new dominant hybrid selective marker for higher eukaryotic cells. J Mol Biol 1981, 150:1-14.
Corpet, F., "Multiple sequence alignment with hierarchical clustering", (1988) Nucleic Acids Research 16:10881-90.
Martin, PJ et al., A 44 kilodalton cell surface homodimer regulates interleukin 2 production by activated human T lymphocytes . . . J Immunol. (1986) 136: 3282-3287.
Weiss, A. et al., Synergy between the T3/antigen receptor complex and Tp44 in the activation of human T cells. J Immunol. (1986) 137:819-825.
Chen, L. and Flies, D.B., Molecular mechanisms of T cell co-stimulation and co-inhibition. Nat Rev Immunol. 2013;13:227-242.
Gray Parkin, K., et al., Expression of CD28 by Bone Marrow Stromal Cells and Its Involvement in B Lymphopoiesis. J Immunol. (2002) 169:2292-2302.

Rozanski, CH et al., Sustained antibody responses depend on CD28 function in bone marrow-resident plasma cells. J Exp Med. (2011) 208:1435-1446.
Venuprasad, K., et al., Human Neutrophil-Expressed CD28 Interacts with Macrophage B7 to Induce Phosphatidylinositol 3-Kinase-Dependent IFN-gamma Secretion and Restriction of Leishmania Growth1. Eur J Immunol. (2001) 31:1536-1543.
Woerly, G. et al., CD28 and secretory immunoglobulin A-dependent activation of eosinophils: inhibition of mediator release by the anti-allergic drug, suplatast tosilate. Clin Exp Allergy. (2004) 34:1379-1387.
Bhatia, S. et al., Different cell surface oligomeric states of B7-1 and B7-2: Implications for signaling. Proc Natl Acad Sci U S A. (2005) 102:15569-15574.
Lenschow, DJ et al., Differential up-regulation of the B7-1 and B7-2 costimulatory molecules after Ig receptor engagement by antigen. J Immunol. (1994) 153:1990-1997.
Sharpe, A.H. and Freeman, G.J, The B7-CD28 superfamily. Nat Rev Immunol. (2002) 2:116-126.
Krummel, MF and Allison, JP., CD28 and CTLA-4 have opposing effects on the response of T cells to stimulation. J Exp Med. 1995;182:459-465.
Walunas, TL et al., CTLA-4 can function as a negative regulator of T cell activation. Immunity. (1994) 1:405-413.
Yao, S. et al., B7-H2 Is a Costimulatory Ligand for CD28 in Human. Immunity (2011) 34:729-740.
Grohmann, U., et al., CTLA-4-Ig regulates tryptophan catabolism in vivo. Nat Immunol. (2002) 3:1097-1101.
Njau, NM and Jacob, J., The CD28/B7 Pathway: A Novel Regulator of Plasma Cell Function. Adv Exp Med Biol. (2013) 785:67-75.
Carreno, BM and Collins, M., The B7 Family of Ligands and Its Receptors: New Pathways for Costimulation and Inhibition of Immune Responses. Annu Rev Immunol. (2002) 20: 29-53.
Evans, EJ et al., Crystal structure of a soluble CD28-Fab complex. Nat Immunol. (2005) 6:271-279.
Metzler, WJ et al., Solution structure of human CTLA-4 and delineation of a CD80/CD86 binding site conserved in CD28. Nat Struct Biol. (1997) 4: 527-531.
Boomer, JS and Green, JM, An enigmatic tail of CD28 signaling. Cold Spring Harb Perspect Biol. (2010) 2:a002436.
Fraser, JD et al., Regulation of interleukin-2 gene enhancer activity by the T cell accessory molecule CD28. Science. (1991) 251:313-316.
June, CH et al., T-Cell Proliferation Involving the CD28 Pathway Is Associated with Cyclosporine-Resistant Interleukin 2 Gene Expression. Mol Cell Biol. (1987) 7:4472-4481.
Thompson, CB et al., CD28 activation pathway regulates the production of multiple Tcell-derived lymphokines/cytokines. Proc Natl Acad Sci U S A. (1989) 86:1333-1337.
August, A. and Dupont, B. CD28 of T lymphocytes associates with phosphatidylinositol 3-kinase. Int Immunol. (1994) 6:769-774.
Pages, F., et al., Binding of phosphatidyl-inositol-3-OH kinase to CD28 is required for T-cell signalling. Nature. (1994) 369: 327-329.
Prasad, KV et al., T-cell antigen CD28 interacts with the lipid kinase phosphatidylinositol 3-kinase by a cytoplasmic Tyr(P)-Met-Xaa-Met motif. Proc Natl Acad Sci U S A. (1994) 91: 2834-2838.
Rudd, CE and Schneider, H., Unifying concepts in CD28, ICOS and CTLA4 co-receptor signalling. Nat Rev Immunol. (2003) 3: 544-556.
Cai, YC et al., Selective CD28pYMNM Mutations Implicate Phosphatidylinositol 3-Kinase in CD86-CD28-Mediated Costimulation. Immunity. (1995) 3: 417-426.
Kim, HH et al., Growth Factor Receptor-bound Protein 2 SH2/SH3 Domain Binding to CD28 and Its Role in Co-signaling. J Biol Chem. (1998) 273: 296-301.
Okkenhaug, K., et al., Grb2 Forms an Inducible Protein Complex with CD28 through a Src Homology 3 Domain-Proline Interaction. J Biol Chem. (1998) 273: 21194-21202.
Raab, M et al., p56Lck and p59Fyn regulate CD28 binding to phosphatidylinositol 3-kinase, growth factor receptor-bound protein GRB-2, and T cell-specific protein-tyrosine kinase ITK: Implications for T-cell costimulation. Proc Natl Acad Sci U S A. (1995) 92: 8891-8895.

(56) References Cited

OTHER PUBLICATIONS

Stein, PH et al., The Cytoplasmic Domain of CD28 Is both Necessary and Sufficient for Costimulation of Interleukin-2 Secretion and Association with Phosphatidylinositol 3'-Kinase. Mol Cell Biol. (1994) 14: 3392-3402).
Holdorf, AD et al., Proline Residues in CD28 and the Src Homology (SH)3 Domain of Lck Are Required for T Cell Costimulation. J Exp Med. (1999) 190: 375-384.
King, PD et al., Analysis of CD28 cytoplasmic tail tyrosine residues as regulators and substrates for the protein tyrosine kinases, EMT and LCK . . . J Immunol. (1997) 158: 580-590.
Watanabe, R. et al., Grb2 and Gads Exhibit Different Interactions with CD28 and Play Distinct Roles in CD28-Mediated Costimulation. J Immunol. (2006) 177:1085-1091.
Lyddane, C et al., Cutting Edge: CD28 Controls Dominant Regulatory T Cell Activity during Active Immunization. J Immunol. (2006) 176: 3306-3310.
Salomon B. et al., B7/CD28 Costimulation Is Essential for the Homeostasis of the CD4+CD25+ Immunoregulatory T Cells that Control Autoimmune Diabetes. Immunity. 2000;12:431-440.
De Kouchkovsky, D et al., microRNA-17-92 Regulates IL-10 Production by Regulatory T Cells and Control of Experimental Autoimmune Encephalomyelitis. J Immunol. (2013) 191: 1594-1605.
Alter, G., et al. CD107a as a functional marker for the identification of natural killer cell activity. Journal of Immunological Methods 294 (2004) 15-22.
Campbell, K.S. and Purdy, A.K., "Structure/function of human killer cell immunoglobulin-like receptors: lessons from polymorphisms, evolution, crystal structures and mutations," Immunol. (2011) 132(3): 315-325.
Chapman, TL, et al,"The inhibitory receptor LIR-1 uses a common binding interaction to recognize class I MHC molecues and the viral homolog UL18," Immunity (1999) 11 (5): 603-13.
Moretta, A. et al., "A Novel surface antigen expressed by a subset of human CD3-CD16+ natural killer cells. Role in cell activation and regulaton of cytolytic function." J. Exptl. Med. (1990) 3: 695-714.
Wolint, Petra, et al. "Immediate Cytotoxicity but Not Degranulation Distinguishes Effector and Memory Subsets of CD8+ T Cells" J. Experimental Medicine, vol. 199, No. 7, Apr. 5, 2004 925-936 (Apr. 5, 2004).
Levine, B., et al., Antiviral Effect and Ex Vivo CD4+ T Cell Proliferation in HIV-Positive Patients as a Result of CD28 Costimulation. 1996, Science 272:1939-1943.
Levine, B., et al., Effects of CD28 costimulation on long-term proliferation of CD4+ T cells in the absence of exogenous feeder cells . . . 1997, J. Immunol. 159:5921-5930.
Appay, V., et al. Memory CD8+ T cells vary in differentiation phenotype in different persistent virus infections. (2002) Nature Med. 8, 379-385.
Sallusto, F., et al. Two subsets of memory T lymphocytes with distinct homing potentials and effector functions. (1999), Nature 401:708-712.
Dematteis, S. et al., "Immunosuppressive Treg cells acquire the phenotype of effector T cells in chronic lymphocytic leukemia patients," J. Translational Medicine (2018) 16: article 172.
Zhao Y. et al., A unique human blood-derived cell population displays high potential for producing insulin. Biochemical and Biophysical Research Communications 360 (2007) 205-211.
Sternberg, N. and Hamilton, D., Bacteriophage P1 site-specific recombination: I. Recombination between loxP sites. J. Mol. Biol., 150:467-486, 1981.
Huynh, TV.,et al., in "DNA Cloning Techniques, vol. I: A Practical Approach," 1985, (D. Glover, ed.), pp. 49-78, IRL Press, Oxford.
Berenbaum, Synergy, additivism and antagonism in immunosuppression, Clin. Exp. Immunol., 28: 1-18, 1977.
Berenbaum, What is Synergy?, Pharmacol. Rev., 41: 93-141, 1989.
Borriello et al., First International Precision Vaccines Conference: Multidisciplinary Approaches to Next-Generation Vaccines, mSphere, Aug. 1, 2018;3(4): 1-12.
Crittenden et al., Current Clinical Trials Testing Combinations of Immunotherapy and Radiation, Semin Radiat Oncol Jan. 25, 2015(1): 54-64.
De Corte et al., (epi information I "Assessment of Assertions of Synergy as a Basis for Inventive Step in Compositions Comprising Mixtures", 1: 1-12, Feb. 2019).
Encke et al., Genetic vaccination with Flt3-L and GM-CSF as adjuvants: Enhancement of cellular and humoral immune responses that results in protective immunity in a murine model of hepatitis C virus infection, World J Gastroenterol Nov. 28, 2006; 12(44): 7118-7125.
Tallarida, Drug Synergism and Dose Effect Analysis, Ed. Chapman & Hall, pp. 1-71, 2002.
Xu et al., Comparative ability of various plasmid-based cycokines and chemokines to adjuvant the activity of HIV plasmid DNA vaccines, Vaccine 26, 2008, 4819-4829.
U.S. Appl. No. 15/821,105, filed Nov. 22, 2017, US-2018-0185463-A1, Allowed.
U.S. Appl. No. 16/660,442, filed Oct. 22, 2019, U.S. Pat. No. 10,731,128, Issued.
International Search Report and Written Opinion for International Application No. PCT/US2020/056698, dated Feb. 8, 2021, issued by the International Searching Authority dated Feb. 8, 2021.

* cited by examiner

ALLOGENEIC TUMOR CELL VACCINE

RELATED APPLICATIONS

The present application is a continuation in part of U.S. application Ser. No. 15/821,105 (filed Nov. 22, 2017), which claims the benefit of priority to U.S. provisional application No. 62/425,424 (filed Nov. 22, 2016).

SEQUENCE LISTING

The instant application contains a Sequence Listing which has been submitted electronically in ASCII format and is hereby incorporated by reference in its entirety. Said ASCII copy, created on Jul. 14, 2021, is named 128663-00103_SL.txt and is 269,110 bytes in size.

FIELD OF THE INVENTION

The described invention relates generally to immunological approaches to the treatment of cancer, and more particularly to cancer vaccines comprising modified tumor cells.

BACKGROUND OF THE INVENTION

The human immune system may generally be divided into two arms, referred to as "innate immunity" and "adaptive immunity." The innate arm of the immune system is predominantly responsible for an initial inflammatory response via a number of soluble factors, including the complement system and the chemokine/cytokine system; and a number of specialized cell types including mast cells, macrophages, dendritic cells (DCs), and natural killer cells. The adaptive immune arm involves a delayed and a longer lasting antibody response together with CD8+ and CD4+ T cell responses that play a critical role in immunological memory against an antigen. A third arm of the immune system may be identified as involving γδ T cells and T cells with limited T cell receptor repertoires such as natural killer T (NKT) cells and Mucosal-associated invariant T (MAIT) cells.

Cells of the Immune System

There are a large number of cellular interactions that comprise the immune system. These interactions occur through specific receptor-ligand pairs that signal in both directions so that each cell receives instructions based on the temporal and spatial distribution of those signals.

Murine models have been highly useful in discovering immunomodulatory pathways, but clinical utility of these pathways does not always translate from an inbred mouse strain to an outbred human population, since an outbred human population may have individuals that rely to varying extents on individual immunomodulatory pathways.

Cells of the immune system include lymphocytes, monocytes/macrophages, dendritic cells, the closely related Langerhans cells, natural killer (NK) cells, mast cells, basophils, and other members of the myeloid lineage of cells. In addition, a series of specialized epithelial and stromal cells provide the anatomic environment in which immunity occurs, often by secreting critical factors that regulate growth and/or gene activation in cells of the immune system, which also play direct roles in the induction and effector phases of the response. (Paul, W. E., "Chapter 1: The immune system: an introduction," Fundamental Immunology, 4th Edition, Ed. Paul, W. E., Lippicott-Raven Publishers, Philadelphia, (1999), at p. 102).

The cells of the immune system are found in peripheral organized tissues, such as the spleen, lymph nodes, Peyer's patches of the intestine and tonsils. Lymphocytes also are found in the central lymphoid organs, the thymus, and bone marrow where they undergo developmental steps that equip them to mediate the myriad responses of the mature immune system. A substantial portion of lymphocytes and macrophages comprise a recirculating pool of cells found in the blood and lymph, providing the means to deliver immunocompetent cells to sites where they are needed and to allow immunity that is generated locally to become generalized. (Paul, W. E., "Chapter 1: The immune system: an introduction," Fundamental Immunology, 4th Edition, Ed. Paul, W. E., Lippicott-Raven Publishers, Philadelphia, (1999), at p. 102).

The term "lymphocyte" refers to a small white blood cell formed in lymphatic tissue throughout the body and in normal adults making up about 22-28% of the total number of leukocytes in the circulating blood that plays a large role in defending the body against disease. Individual lymphocytes are specialized in that they are committed to respond to a limited set of structurally related antigens through recombination of their genetic material (e.g. to create a T cell receptor and a B cell receptor). This commitment, which exists before the first contact of the immune system with a given antigen, is expressed by the presence of receptors specific for determinants (epitopes) on the antigen on the lymphocyte's surface membrane. Each lymphocyte possesses a unique population of receptors, all of which have identical combining sites. One set, or clone, of lymphocytes differs from another clone in the structure of the combining region of its receptors and thus differs in the epitopes that it can recognize. Lymphocytes differ from each other not only in the specificity of their receptors, but also in their functions. (Paul, W. E., "Chapter 1: The immune system: an introduction," Fundamental Immunology, 4th Edition, Ed. Paul, W. E., Lippicott-Raven Publishers, Philadelphia, (1999), at p. 102).

Two broad classes of lymphocytes are recognized: the B-lymphocytes (B-cells), which are precursors of antibody-secreting cells, and T-lymphocytes (T-cells).

B-Lymphocytes

B-lymphocytes are derived from hematopoietic cells of the bone marrow. A mature B-cell can be activated with an antigen that expresses epitopes that are recognized by its cell surface. The activation process may be direct, dependent on cross-linkage of membrane Ig molecules by the antigen (cross-linkage-dependent B-cell activation), or indirect, via interaction with a helper T-cell, in a process referred to as cognate help. In many physiological situations, receptor cross-linkage stimuli and cognate help synergize to yield more vigorous B-cell responses (Paul, W. E., "Chapter 1: The immune system: an introduction," Fundamental Immunology, 4th Edition, Ed. Paul, W. E., Lippicott-Raven Publishers, Philadelphia, (1999)).

Cross-linkage dependent B-cell activation requires that the antigen express multiple copies of the epitope complementary to the binding site of the cell surface receptors, because each B-cell expresses Ig molecules with identical variable regions. Such a requirement is fulfilled by other antigens with repetitive epitopes, such as capsular polysaccharides of microorganisms or viral envelope proteins. Cross-linkage-dependent B-cell activation is a major protective immune response mounted against these microbes (Paul, W. E., "Chapter 1: The immune system: an introduction", Fundamental Immunology, 4th Edition, Ed. Paul, W. E., Lippicott-Raven Publishers, Philadelphia, (1999)).

Cognate help allows B-cells to mount responses against antigens that cannot cross-link receptors and, at the same time, provides costimulatory signals that rescue B cells from inactivation when they are stimulated by weak cross-linkage events. Cognate help is dependent on the binding of antigen by the B-cell's membrane immunoglobulin (Ig), the endocytosis of the antigen, and its fragmentation into peptides within the endosomal/lysosomal compartment of the cell. Some of the resultant peptides are loaded into a groove in a specialized set of cell surface proteins known as class II major histocompatibility complex (MHC) molecules. The resultant class II/peptide complexes are expressed on the cell surface and act as ligands for the antigen-specific receptors of a set of T-cells designated as $CD4^+$ T-cells. The $CD4^+$ T-cells bear receptors on their surface specific for the B-cell's class II/peptide complex. B-cell activation depends not only on the binding of the T cell through its T cell receptor (TCR), but this interaction also allows an activation ligand on the T-cell (CD40 ligand) to bind to its receptor on the B-cell (CD40) signaling B-cell activation. In addition, T helper cells secrete several cytokines that regulate the growth and differentiation of the stimulated B-cell by binding to cytokine receptors on the B cell (Paul, W. E., "Chapter 1: The immune system: an introduction, "Fundamental Immunology, 4th Edition, Ed. Paul, W. E., Lippicott-Raven Publishers, Philadelphia, (1999)).

During cognate help for antibody production, the CD40 ligand is transiently expressed on activated $CD4^+$ T helper cells, and it binds to CD40 on the antigen-specific B cells, thereby transducing a second costimulatory signal. The latter signal is essential for B cell growth and differentiation and for the generation of memory B cells by preventing apoptosis of germinal center B cells that have encountered antigen. Hyperexpression of the CD40 ligand in both B and T cells is implicated in pathogenic autoantibody production in human SLE patients (Desai-Mehta, A. et al., "Hyperexpression of CD40 ligand by B and T cells in human lupus and its role in pathogenic autoantibody production," J. Clin. Invest. Vol. 97(9), 2063-2073, (1996)).

T-Lymphocytes

T-lymphocytes derived from precursors in hematopoietic tissue undergo differentiation in the thymus, and are then seeded to peripheral lymphoid tissue and to the recirculating pool of lymphocytes. T-lymphocytes or T cells mediate a wide range of immunologic functions. These include the capacity to help B cells develop into antibody-producing cells, the capacity to increase the microbicidal action of monocytes/macrophages, the inhibition of certain types of immune responses, direct killing of target cells, and mobilization of the inflammatory response. These effects depend on T cell expression of specific cell surface molecules and the secretion of cytokines (Paul, W. E., "Chapter 1: The immune system: an introduction", Fundamental Immunology, 4th Edition, Ed. Paul, W. E., Lippicott-Raven Publishers, Philadelphia, (1999)).

T cells differ from B cells in their mechanism of antigen recognition. Immunoglobulin, the B cell's receptor, binds to individual epitopes on soluble molecules or on particulate surfaces. B-cell receptors see epitopes expressed on the surface of native molecules. While antibody and B-cell receptors evolved to bind to and to protect against microorganisms in extracellular fluids, T cells recognize antigens on the surface of other cells and mediate their functions by interacting with, and altering, the behavior of these antigen-presenting cells (APCs). There are three main types of APCs in peripheral lymphoid organs that can activate T cells: dendritic cells, macrophages and B cells. The most potent of these are the dendritic cells, whose only function is to present foreign antigens to T cells. Immature dendritic cells are located in tissues throughout the body, including the skin, gut, and respiratory tract. When they encounter invading microbes at these sites, they endocytose the pathogens and their products, and carry them via the lymph to local lymph nodes or gut associated lymphoid organs. The encounter with a pathogen induces the dendritic cell to mature from an antigen-capturing cell to an APC that can activate T cells. APCs display three types of protein molecules on their surface that have a role in activating a T cell to become an effector cell: (1) MHC proteins, which present foreign antigen to the T cell receptor; (2) costimulatory proteins which bind to complementary receptors on the T cell surface; and (3) cell-cell adhesion molecules, which enable a T cell to bind to the APC for long enough to become activated ("Chapter 24: The adaptive immune system," Molecular Biology of the Cell, Alberts, B. et al., Garland Science, NY, (2002)).

T-cells are subdivided into two distinct classes based on the cell surface receptors they express. The majority of T cells express T cell receptors (TCR) consisting of $\alpha$ and $\beta$-chains. A small group of T cells express receptors made of $\gamma$ and $\delta$ chains. Among the $\alpha/\beta$ T cells are two sub-lineages: those that express the coreceptor molecule CD4 ($CD4^+$ T cells); and those that express CD8 ($CD8^+$ T cells). These cells differ in how they recognize antigen and in their effector and regulatory functions.

$CD4^+$ T cells are the major regulatory cells of the immune system. Their regulatory function depends both on the expression of their cell-surface molecules, such as CD40 ligand whose expression is induced when the T cells are activated, and the wide array of cytokines they secrete when activated.

CD8+(cytotoxic) T cells, like CD4+ Helper T cells, are generated in the thymus and express the T-cell receptor. However, rather than the CD4 molecule, cytotoxic T cells express a dimeric co-receptor, CD8, usually composed of one $CD8\alpha$ and one $CD8\beta$ chain. CD8+ T cells recognize peptides presented by MHC Class I molecules, found on all nucleated cells. The CD8 heterodimer binds to a conserved portion (the $\alpha3$ region) of MHC Class I during T cell/antigen presenting cell interactions. CD8+ T cells (often called cytotoxic T lymphocytes, or CTLs) are important for immune defense against intracellular pathogens, including viruses and bacteria, and for tumour surveillance. When a CD8+ T cell recognizes its antigen and becomes activated, it has three major mechanisms to kill infected or malignant cells. The first is secretion of cytokines, primarily TNF-$\alpha$ and IFN$\gamma$, which have anti-tumour and anti-viral microbial effects. The second major function is the production and release of cytotoxic granules. These granules, also found in NK cells, contain two families of proteins, perforin, and granzymes. Perforin forms a pore in the membrane of the target cell, similar to the membrane attack complex of complement. This pore allows the granzymes also contained in the cytotoxic granules to enter the infected or malignant cell. Granzymes are serine proteases which cleave the proteins inside the cell, shutting down the production of viral proteins and ultimately resulting in apoptosis of the target cell. CD8+ T cells are able to release their granules, kill an infected cell, then move to a new target and kill again, often referred to as serial killing. The third major function of CD8+ T cell destruction of infected cells is via Fas/FasL interactions. Activated CD8+ T cells express FasL on the cell surface, which binds to its receptor, Fas, on the surface of the target cell. This binding causes the Fas molecules on the surface of the target cell to trimerize, which pulls together signaling molecules. These signaling molecules result in the activation of the caspase cascade, which also results in apoptosis of the target cell. Because CD8+ T cells can express both molecules, Fas/FasL interactions are a mechanism by which CD8+ T cells can kill each other, called fratricide, to eliminate immune effector cells during the contraction phase at the end of an immune response.

T cells also mediate important effector functions, some of which are determined by the patterns of cytokines they secrete. The cytokines can be directly toxic to target cells and can mobilize potent inflammatory mechanisms.

In addition, T cells, particularly $CD8^+$ T cells, can develop into cytotoxic T-lymphocytes (CTLs) capable of efficiently lysing target cells that express antigens recognized by the CTLs (Paul, W. E., "Chapter 1: The immune system: an introduction," Fundamental Immunology, 4th Edition, Ed. Paul, W. E., Lippicott-Raven Publishers, Philadelphia, (1999)).

T cell receptors (TCRs) recognize a complex consisting of a peptide derived by proteolysis of the antigen bound to a specialized groove of a class II or class I MHC protein. $CD4^+$ T cells recognize only peptide/class II complexes while $CD8^+$ T cells recognize peptide/class I complexes (Paul, W. E., "Chapter 1: The immune system: an introduction," Fundamental Immunology, 4th Edition, Ed. Paul, W. E., Lippicott-Raven Publishers, Philadelphia, (1999)).

The TCR's ligand (i.e., the peptide/MHC protein complex) is created within APCs. In general, class II MHC molecules bind peptides derived from proteins that have been taken up by the APC through an endocytic process. These peptide-loaded class II molecules are then expressed on the surface of the cell, where they are available to be bound by $CD4^+$ T cells with TCRs capable of recognizing the expressed cell surface complex. Thus, $CD4^+$ T cells are specialized to react with antigens derived from extracellular sources (Paul, W. E., "Chapter 1: The immune system: an introduction," Fundamental Immunology, 4th Edition, Ed. Paul, W. E., Lippicott-Raven Publishers, Philadelphia, (1999)).

In contrast, class I MHC molecules are mainly loaded with peptides derived from internally synthesized proteins, such as viral proteins. These peptides are produced from cytosolic proteins by proteolysis by the proteosome and are translocated into the rough endoplasmic reticulum. Such peptides, generally composed of nine amino acids in length, are bound into the class I MHC molecules and are brought to the cell surface, where they can be recognized by $CD8^+$ T cells expressing appropriate receptors. This gives the T cell system, particularly $CD8^+$ T cells, the ability to detect cells expressing proteins that are different from, or produced in much larger amounts than, those of cells of the remainder of the organism (e.g., viral antigens) or mutant antigens (such as active oncogene products), even if these proteins in their intact form are neither expressed on the cell surface nor secreted (Paul, W. E., "Chapter 1: The immune system: an introduction," Fundamental Immunology, 4th Edition, Ed. Paul, W. E., Lippicott-Raven Publishers, Philadelphia, (1999)).

T cells can also be classified based on their function as helper T cells; T cells involved in inducing cellular immunity; suppressor T cells; and cytotoxic T cells.

Helper T Cells

Helper T cells are T cells that stimulate B cells to make antibody responses to proteins and other T cell-dependent antigens. T cell-dependent antigens are immunogens in which individual epitopes appear only once or a limited number of times such that they are unable to cross-link the membrane immunoglobulin (Ig) of B cells or do so inefficiently. B cells bind the antigen through their membrane Ig, and the complex undergoes endocytosis. Within the endosomal and lysosomal compartments, the antigen is fragmented into peptides by proteolytic enzymes, and one or more of the generated peptides are loaded into class II MHC molecules, which traffic through this vesicular compartment. The resulting peptide/class II MHC complex is then exported to the B-cell surface membrane. T cells with receptors specific for the peptide/class II molecular complex recognize this complex on the B-cell surface. (Paul, W. E., "Chapter 1: The immune system: an introduction," Fundamental Immunology, 4th Edition, Ed. Paul, W. E., Lippicott-Raven Publishers, Philadelphia (1999)).

B-cell activation depends both on the binding of the T cell through its TCR and on the interaction of the T-cell CD40 ligand (CD40L) with CD40 on the B cell. T cells do not constitutively express CD40L. Rather, CD40L expression is induced as a result of an interaction with an APC that expresses both a cognate antigen recognized by the TCR of the T cell and CD80 or CD86. CD80/CD86 is generally expressed by activated, but not resting, B cells so that the helper interaction involving an activated B cell and a T cell can lead to efficient antibody production. In many cases, however, the initial induction of CD40L on T cells is dependent on their recognition of antigen on the surface of APCs that constitutively express CD80/86, such as dendritic cells. Such activated helper T cells can then efficiently interact with and help B cells. Cross-linkage of membrane Ig on the B cell, even if inefficient, may synergize with the CD40L/CD40 interaction to yield vigorous B-cell activation. The subsequent events in the B-cell response, including proliferation, Ig secretion, and class switching of the Ig class being expressed, either depend on or are enhanced by the actions of T cell-derived cytokines (Paul, W. E., "Chapter 1: The immune system: an introduction," Fundamental Immunology, 4th Edition, Ed. Paul, W. E., Lippicott-Raven Publishers, Philadelphia, (1999)).

$CD4^+$ T cells tend to differentiate into cells that principally secrete the cytokines IL-4, IL-5, IL-6, and IL-10 ($T_H2$ cells) or into cells that mainly produce IL-2, IFNγ, and lymphotoxin ($T_H1$ cells). The $T_H2$ cells are very effective in helping B-cells develop into antibody-producing cells, whereas the $T_H1$ cells are effective inducers of cellular immune responses, involving enhancement of microbicidal activity of monocytes and macrophages, and consequent increased efficiency in lysing microorganisms in intracellular vesicular compartments. Although $CD4^+$ T cells with the phenotype of $T_H2$ cells (i.e., IL-4, IL-5, IL-6 and IL-10) are efficient helper cells, $T_H1$ cells also have the capacity to be helpers (Paul, W. E., "Chapter 1: The immune system: an introduction," Fundamental Immunology, 4th Edition, Ed. Paul, W. E., Lippicott-Raven Publishers, Philadelphia, (1999)).

Natural Killer (NK) Cells

Natural Killer (NK) Cells are lymphocytes in the same family as T and B cells, coming from a common progenitor. However, as cells of the innate immune system, NK cells are classified as group I Innate Lymphocytes (ILCs) and respond quickly to a wide variety of pathological challenges. NK cells protect against disease, for example killing virally infected cells, and detecting and controlling early signs of cancer. NK cells were first noticed for their ability to kill tumour cells without any priming or prior activation (in contrast to cytotoxic T cells, which need priming by antigen presenting cells). They are named for this 'natural' killing. Additionally, NK cells secrete cytokines such as IFNγ and TNFα, which act on other immune cells like Macrophage and Dendritic cells to enhance the immune response.

While on patrol, NK cells constantly contact other cells. Whether or not the NK cell kills these cells depends on a balance of signals from activating receptors and inhibitory receptors on the NK cell surface. Activating receptors recognize molecules that are expressed on the surface of cancer cells and infected cells, and 'switch on' the NK cell. Inhibitory receptors act as a check on NK cell killing. Most normal healthy cells express MHC I receptors which mark these cells as 'self'. Inhibitory receptors on the surface of the NK cell recognize cognate MHC I, and this 'switches off' the NK cell, preventing it from killing. Cancer cells and infected cells often lose their MHC I, leaving them vulnerable to NK cell killing. Once the decision is made to kill, the NK cell releases cytotoxic granules containing perforin and granzymes, which leads to lysis of the target cell.

T cell Involvement in Cellular Immunity Induction

T cells also may act to enhance the capacity of monocytes and macrophages to destroy intracellular microorganisms. In particular, interferon-gamma (IFNγ) produced by helper T cells enhances several mechanisms through which mononuclear phagocytes destroy intracellular bacteria and parasitism including the generation of nitric oxide and induction of tumor necrosis factor (TNF) production. $T_H1$ cells are effective in enhancing the microbicidal action, because they produce IFNγ. In contrast, two of the major cytokines produced by $T_H2$ cells, IL-4 and IL-10, block these activities (Paul, W. E., "Chapter 1: The immune system: an introduction," Fundamental Immunology, 4th Edition, Ed. Paul, W. E., Lippicott-Raven Publishers, Philadelphia, (1999)).

Regulatory T (Treg) Cells

Immune homeostasis is maintained by a controlled balance between initiation and downregulation of the immune response. The mechanisms of both apoptosis and T cell anergy (a tolerance mechanism in which the T cells are intrinsically functionally inactivated following an antigen encounter (Scwartz, R. H., "T cell anergy", Annu. Rev. Immunol., Vol. 21: 305-334 (2003)) contribute to the downregulation of the immune response. A third mechanism is provided by active suppression of activated T cells by suppressor or regulatory $CD4^+$ T (Treg) cells (Reviewed in Kronenberg, M. et al., "Regulation of immunity by self-reactive T cells", Nature, Vol. 435: 598-604 (2005)). $CD4^+$ Tregs that constitutively express the IL-2 receptor alpha (IL-2Ra) chain ($CD4^+$ $CD25^+$) are a naturally occurring T cell subset that are anergic and suppressive (Taams, L. S. et al., "Human anergic/suppressive $CD4^+$ $CD25^+$ T cells: a highly differentiated and apoptosis-prone population", Eur. J. Immunol. Vol. 31: 1122-1131 (2001)). Depletion of $CD4^+$ $CD25^+$ Tregs results in systemic autoimmune disease in mice. Furthermore, transfer of these Tregs prevents development of autoimmune disease. Human $CD4^+$ $CD25^+$ Tregs, similar to their murine counterpart, are generated in the thymus and are characterized by the ability to suppress proliferation of responder T cells through a cell-cell contact-dependent mechanism, the inability to produce IL-2, and the anergic phenotype in vitro. Human $CD4^+$ $CD25^+$ T cells can be split into suppressive ($CD25^{high}$) and nonsuppressive ($CD25^{low}$) cells, according to the level of CD25 expression. A member of the forkhead family of transcription factors, FOXP3, has been shown to be expressed in murine and human $CD4^+$ $CD25^+$ Tregs and appears to be a master gene controlling $CD4^+$ $CD25^+$ Treg development (Battaglia, M. et al., "Rapamycin promotes expansion of functional $CD4^+$ $CD25^+$ $Foxp3^+$ regulator T cells of both healthy subjects and type 1 diabetic patients", J. Immunol., Vol. 177: 8338-8347, (2006)).

Cytotoxic T Lymphocytes $CD8^+$ T cells that recognize peptides from proteins produced within the target cell have cytotoxic properties in that they lead to lysis of the target cells. The mechanism of CTL-induced lysis involves the production by the CTL of perforin, a molecule that can insert into the membrane of target cells and promote the lysis of that cell. Perforin-mediated lysis is enhanced by granzymes, a series of enzymes produced by activated CTLs. Many active CTLs also express large amounts of fas ligand on their surface. The interaction of fas ligand on the surface of CTL with fas on the surface of the target cell initiates apoptosis in the target cell, leading to the death of these cells. CTL-mediated lysis appears to be a major mechanism for the destruction of virally infected cells.

T-memory Cells

Following the recognition and eradication of pathogens through adaptive immune responses, the vast majority (90-95%) of T cells undergo apoptosis with the remaining cells forming a pool of memory T cells, designated central memory T cells (TCM), effector memory T cells (TEM), and resident memory T cells (TRM) (Clark, R. A., "Resident memory T cells in human health and disease", Sci. Transl. Med., 7, 269rv1, (2015)).

Compared to standard T cells, these memory T cells are long-lived with distinct phenotypes such as expression of specific surface markers, rapid production of different cytokine profiles, capability of direct effector cell function, and unique homing distribution patterns. Memory T cells exhibit quick reactions upon re-exposure to their respective antigens in order to eliminate the reinfection of the offender and thereby restore balance of the immune system rapidly. Increasing evidence substantiates that autoimmune memory T cells hinder most attempts to treat or cure autoimmune diseases (Clark, R. A., "Resident memory T cells in human health and disease", Sci. Transl. Med., Vol. 7, 269rv1, (2015)).

For an effective immune response to an antigen, antigen presenting cells (APCs) must process and display the antigen in a proper major histocompatibility complex (MHC) context to a T cell, which then will result in T cell stimulation of cytotoxic and helper T cells. Following antigen presentation, successful interaction of co-stimulatory molecules on both APCs and T cells must occur or activation will be aborted. GM-CSF and IL-12 serve as effective pro-inflammatory molecules in many tumor models. For example, GM-CSF induces myeloid precursor cells to proliferate and differentiate into dendritic cells (DCs), although additional signals are necessary to activate their maturation to effective antigen—presenting cells necessary for activation of T cells. Barriers to effective immune therapies include tolerance to the targeted antigen that can limit induction of cytotoxic CD8 T cells of appropriate magnitude and function, poor trafficking of the generated T cells to sites of malignant cells, and poor persistence of the induced T cell response. DCs that phagocytose tumor-cell debris process the material for MHC presentation, upregulate expression of costimulatory molecules, and migrate to regional lymph nodes to stimulate tumor-specific lymphocytes. This pathway results in the proliferation and activation of CD4+ and CD8+ T cells that react to tumor-associated antigens. Indeed, such cells can be detected frequently in the blood, lymphoid tissues, and malignant lesions of patients.

Lymphocytes are a type of white blood cell involved in immune system regulation. Lymphocytes are much more common in the lymphatic system, and include B cells, T cells, killer T-cells, and natural killer (NK) cells. There are two broad categories of lymphocytes, namely T cells and B cells. T-cells are responsible for cell-mediated immunity whereas B-cells are responsible for humoral immunity (relating to antibodies). T-cells are so-named such because these lymphocytes mature in the thymus; B-cells mature in bone marrow. B cells make antibodies that bind to pathogens to enable their destruction. CD4+(helper) T cells co-ordinate the immune response. CD8+(cytotoxic) T cells and Natural Killer (NK) cells are able to kill cells of the body that are, e.g., infected by a virus or display an antigenic sequence.

Immune Response

Generally speaking, immune responses are initiated by an encounter between an individual and a foreign substance, e.g., an infectious microorganism. The infected individual rapidly responds with both a humoral immune response with the production of antibody molecules specific for the antigenic determinants/epitopes of the immunogen, and a cell mediated immune response with the expansion and differentiation of antigen-specific regulatory and effector T-lymphocytes, including both cells that produce cytokines and killer T cells, capable of lysing infected cells. Primary immunization with a given microorganism evokes antibodies and T cells that are specific for the antigenic determinants/epitopes found on that microorganism, but that usually fail to recognize or recognize only poorly antigenic determinants expressed by unrelated microbes (Paul, W. E., "Chapter 1: The immune system: an introduction," Fundamental Immunology, 4th Edition, Ed. Paul, W. E., Lippicott-Raven Publishers, Philadelphia, (1999), at p. 102).

As a consequence of this initial response, the immunized individual develops a state of immunologic memory. If the same or a closely related microorganism is encountered again, a secondary response ensues. This secondary response generally consists of an antibody response that is more rapid, greater in magnitude and composed of antibodies that bind to the antigen with greater affinity and are more effective in clearing the microbe from the body, and a similarly enhanced and often more effective T-cell response. However, immune responses against infectious agents do not always lead to elimination of the pathogen. (Paul, W. E., "Chapter 1: The immune system: an introduction," Fundamental Immunology, 4th Edition, Ed. Paul, W. E., Lippicott-Raven Publishers, Philadelphia, (1999), at p. 102).

Immune Tolerance of Cancer

Cancer is characterized by genetic instability of particular cells but has also been described as a disorder of the immune system, based on the fact that the immune system fails, at least in certain segments of the afflicted human population, to respond optimally to cancerous cells that have taken on a distinctly non-self phenotype that should be recognized as foreign. Several reasons have been advanced to explain the basis of this observation. For example, first, cancer cells consist mainly of self-antigens, in striking contrast to the situation with infectious organisms. Some antigens that are classified as cancer antigens are actually normal antigens that are overexpressed, or normal antigens that have a mutation in only one or two amino acids in the polypeptide chain. Second, cancer cells down-regulate MHC, and thus do not much present tumor cell-derived peptides by way of MHC. Third, cancer cells, and associated tumor-associated macrophages, express cytokines that dampen the immune response (see, e.g., Yu et al (2007) Nature Rev. Immunol. 7:41-51). This dampening is caused, for example, by the secretion of interleukin-10 (IL-10) by the cancer cells or by the associated macrophages. Fourth, unlike the situation with infections, cancer cells do not provide any immune adjuvant. Pathogens express a variety of naturally-occurring immune adjuvants, which take the form of toll-like receptor (TLR) agonists and NOD agonists (see, e.g., Kleinnijenhuis et al (2011) Clin. Dev. Immunol. 405310 (12 pages)). Generally, optimal activation of dendritic cells requires contact of an immune adjuvant with one or more toll-like receptors (TLRs) expressed by the dendritic cell. Without activation of the dendritic cell, contact between the dendritic cell and T cells (immune synapse) fails to result in optimal activation of the T cell.

Insights into the mechanisms underlying immune-evasion, together with combination treatment regimens that potentiate the potency of therapeutic vaccination—either directly or indirectly—through combination with immune checkpoint inhibitors or other therapies, have served as a basis for the development of vaccines that induce effective antitumor immunity.

Immune Surveillance and Immune Editing

Tumor immune editing is divided into three phases: an elimination phase, an equilibrium phase, and an escape phase. The elimination phase, also known as immune surveillance, is the process by which the immune system identifies cancerous or pre-cancerous cells and eliminates them before they grow out of control. This phase can be complete when all cancerous or precancerous cells are eliminated. If some tumor cells are not eliminated, a temporary state of equilibrium may be achieved between the immune system and tumor cell growth. In this equilibrium phase, tumors cells can either remain dormant or continue to evolve by accumulating further changes to genomic DNA that can modulate the antigens they present. During this process, the immune system exerts a selective pressure on evolving cells, whereby the tumor cells that are less able to be recognized have a survival advantage. Eventually the immune response is unable to recognize cells of the tumor, resulting in the transition to the escape phase wherein tumor cells progressively grow out of control.

Tumor Microenvironment

The tumor microenvironment provides a consistently effective barrier to immune cell function because tumors actively downregulate all phases of anti-tumor immune responses using a spectrum of different strategies and mechanisms. Many molecular mechanisms that cause dysfunction of immune cells in the tumor microenvironment have been identified, including those directly mediated by factors produced by tumors, and others resulting from alterations of normal tissue homeostasis in the presence of cancer. Most human tumors appear to be able to interfere with one or more stages of immune cell development, differentiation, migration, cytotoxicity and other effector functions (T L Whiteside, The tumor microenvironment and its role in promoting tumor growth, Oncogene (2008) 27, 5904-5912).

One such mechanism involves accumulation in tumors of $T_{reg}$ (CD4+CD25$^{bright}$ Foxp3$^+$ T cells) and myeloid-derived cells (CD34$^+$ CD33$^+$ CD13$^+$ CD11b$^+$ CD15$^-$), which are common features of human tumors, and have been linked to poor prognosis in patients with cancer (T L Whiteside, The tumor microenvironment and its role in promoting tumor growth, Oncogene (2008) 27, 5904-5912). Under normal conditions, $T_{reg}$ cells are involved in the important role of preventing autoimmunity, but in cancer, they expand, migrate to tumors, downregulate autologous effector T-cell proliferation and suppress anti-tumor responses of both CD4$^+$ CD25$^-$ and CD8$^+$ CD25$^-$ T cells using distinct molecular pathways. The $T_{reg}$ cells in the tumor are a heterogeneous population of regulatory CD3+ CD4+ T cells, comprising natural $T_{reg}$, antigen-specific Tr1 cells, and other less well defined subsets of suppressor cells. Tr1 cells are induced in the tumor microenvironment, which is rich in IL-10, TGF-β, and prostaglandin E2 (PGE2), all of which have been shown to promote Tr1 generation (T L Whiteside, The tumor microenvironment and its role in promoting tumor growth, Oncogene (2008) 27, 5904-5912).

Myeloid suppressor cells (MSCs) also suppress T-cell responses in the tumor microenvironment, where they secrete TGF-β or induce TGF-β secretion. Immunosuppressive CD34+ cell-derived myeloid cells have been identified in the peripheral blood of cancer patients. In tumor-bearing mice, MSCs accumulate in the spleen and peripheral circulation in very high amounts, exerting potent immunosuppression and favoring tumor growth. MSCs also control the availability of essential amino acids such as L-arginine and produce high levels of reactive oxygen species. The MSCs found in tumors also constitutively express iNOS and arginase 1, an enzyme involved in metabolism of L-arginine, which also synergizes with iNOS to increase superoxide and NO production, which have been found to interfere with lymphocyte responses. GM-CSF, which is also often secreted by tumor cells, recruits MSCs and induces dose-dependent in vivo immune suppression and tumor promotion, while at the same time, GM-CSF has been used as immune adjuvant in antitumor vaccines. GM-CSF was observed to increase a subset of TGF-β-producing MSCs in the circulation of patients with metastatic melanoma. The concurrent stimulatory and suppressive roles suggest that GM-CSF and MSCs are involved in maintaining immune homeostasis in normal tissue, but in the tumor microenvironment promote tumor cell escape (T L Whiteside, The tumor microenvironment and its role in promoting tumor growth, Oncogene (2008) 27, 5904-5912).

Tumor Immunotherapy

Cancer therapy is evolving rapidly as new molecular targets are being discovered. Despite the advent of biologics targeting specific pathways (e.g., HERCEPTIN®, ERBITUX®) and small molecules designed against specific targets (tamoxifen, GLEEVEC™) nonspecific modalities such as chemotherapy and radiation remain a standard of care.

Anti-cancer immunotherapy has been a goal for many years with a variety of approaches being tested. One difficulty of developing this immunotherapy is that target antigens are often tissue specific molecules found on both cancer cells and normal cells, and either do not elicit immunity or show non-specificity regarding cell killing (Kaufman and Wolchok eds., General Principles of Tumor Immunotherapy, Chpt 5, 67-121 (2007)). Furthermore, tumor cells have features that make immune recognition difficult, such as loss of expression of antigens that elicit immune response, lack of MHC class II, and downregulation of MHC class I expression. These features can lead to non-recognition of tumor cells by both CD4+ and CD8+ T cells (Kaufman and Wolchok eds., General Principles of Tumor Immunotherapy, Chpt 5, 67-121 (2007)). Tumors may also evade detection through active mechanisms, such as the production of immunosuppressive cytokines (Kaufman and Wolchok eds., General Principles of Tumor Immunotherapy, Chpt 5, 67-121 (2007)).

DCs generated ex vivo by culturing hematopoietic progenitor cells or monocytes with cytokine combinations have been tested as therapeutic vaccines in cancer patients for more than a decade (Ueno H, et al., Immunol. Rev. (2010) 234: 199-212). For example, treatment of metastatic prostate cancer with sipuleucel-T (also known as APC 8015), which is a cellular product based on enriched blood APCs that are briefly cultured with a fusion protein of prostatic acid phosphatase (PAP) and granulocyte macrophage colony-stimulating factor (GM-CSF), resulted in an approximately 4-month-prolonged median survival in Phase III trials (Higano C S, et al., Cancer (2009) 115: 3670-3679; Kantoff P W, et al., N. Engl. J. Med. (2010) 363: 411-422). This study concluded that DC-based vaccines are safe and can induce the expansion of circulating CD4+ T-cells and CD8+ T-cells specific for tumor antigens. As a result of this and similar studies, sipuleucel-T has been approved by the US Food and Drug Administration (FDA) for the treatment of metastatic prostate cancer, thereby paving the clinical development and regulatory path for the next generation of cellular immunotherapy products (Palucka K and Banchereau J, Nature Reviews Cancer (April 2012) 12: 265-276).

Vaccination strategies involving DCs to induce tumor-specific effector T cells that can reduce the tumor mass specifically and that can induce immunological memory to control tumor relapse have been developed. For example, DCs can be provided with tumor-specific antigens by culturing DCs ex vivo with an adjuvant and a tumor-specific antigen, and then injecting these cells back into the patient. Tumor cells obtained from an excised tumor, needle biopsy, core biopsy, vacuum-assisted biopsy or peritoneal lavage have been used to generate immunogenic compositions comprising tumor-specific-antigen presenting dendritic cells.

Cancer Treatment Strategies

Antibody therapies such as HERCEPTIN™ and ERBITUX™ are passive immunotherapies, but have yielded considerable improvement in clinical outcome, as measured by, e.g. the recurrence rate, progression free survival and overall survival. More recently, PD-1 and CTLA4 inhibitors have been reported to block discrete checkpoints in an active host immune response allowing an endogenous anti-cancer immune response to be sustained. The term "immune checkpoints" refers to the array of inhibitory pathways that are necessary for maintaining self-tolerance and modulating the duration and extent of immune responses to minimize damage to normal tissue. Immune checkpoint molecules such as PD-1, PD-L1, and CTLA-4 are cell surface signaling receptors that play an important role in modulating the T-cell response in the tumor microenvironment. Tumor cells have been shown to utilize these checkpoints to their benefit by up regulating their expression and activity. With the tumor cell's ability to commandeer some immune checkpoint pathways as a mechanism of immune resistance, it has been hypothesized that checkpoint inhibitors that bind to molecules of immune cells to activate or inactivate them may relieve the inhibition of an immune response. Recent discoveries have identified immune checkpoints or targets, like PD-1, PD-L1, PD-L2, CTLA4, TIM3, LAG3, CCR4, OX40, OX40L, IDO, and A2AR, as proteins responsible for immune evasion. Specific immune checkpoint inhibitors, including antibodies against CTLA-4, PD-1 receptor or its ligand PD-L1 have produced impressive results in the clinic in a range of cancers, leading to FDA approvals for YERVOY™ (Ipilimumab; CTLA-4 antagonist), OPDIVO™ (Nivolumab; PD-1 antagonist) and KEYTRUDA™ (Pembrolizumab; PD-1 antagonist) in multiple tumor indications and with ongoing registration trials in many more. This method of therapy, however, can only be successful if a pre-existing antitumor immune response is present within a patient (Pardoll, D., The blockade of immune checkpoints in cancer immunotherapy, Nature Reviews: Cancer, Vol. 12, April 2012, 253). Recent cellular therapies, such as chimeric antigen receptor T-cell therapy (CAR-T), attempt to use synthetic biology to redirect T-cells to specific cell surface tumor antigens. Genetic modification of T-cells is used to confer tumor antigen recognition by transgenic expression of chimeric antigen receptor (CAR). CARs are engineered molecules that can be introduced into T cells to enable them to target tumor antigens (Frey, N. V., Porter, D. L., The Promise of Chimeric Antigen Receptor T-Cell Therapy, Oncology (2016); 30(1)) pii 219281). CAR T cells have been shown to have some efficacy against hematologic malignancies and to a lesser extent solid tumors. CAR T therapy, however, has been shown to cause several types of toxicities, including cytokine release syndrome, neurological toxicity, non-tumor recognition, and anaphylaxis (Bonifant C L, et al., Toxicity and management in CAR T-cell therapy, Molecular Therapy—Oncolytics (2016) 3, 16011).

Therapeutic vaccination against cancer is an important modality complementing current standard therapies, and may lead to long-term control of cancer. GVAX™, a prototypical example, is a GM-CSF gene transduced tumor vaccine within either an autologous or allogeneic population of tumor cells. It is believed that GM-CSF secretion of genetically modified tumor cells stimulates cytokine release at the vaccine site to activate antigen presenting cells to induce a tumor specific cellular immune response (Eager, R. & Nemunaitis, J., GM-CSF Gene-Transduced Tumor Vaccines, Molecular Therapy, Vol. 12, No. 1, 18 (July 2005)). Lethally irradiated tumor cell vaccines engineered to secrete GM-C SF (GVAX) showed promising efficacy in various models of melanoma, renal cell, prostate, and non-small cell lung, pancreatic, as well as head and neck squamous cell carcinoma, but due to the multiple immunological checkpoint blockades, GVAX as a monotherapy is unlikely to be clinically effective in advanced disease. There remains a need for improved compositions and methods for immunologic strategies to treating diseases such as cancer that can be refractory to traditional therapeutic approaches.

Dendritic cell (DC)-tumor cell fusions have been developed to generate hybrid cells that express the relevant tumor associated antigens derived from the parent tumor cells, and also have the ability to process and present such antigens to appropriate cells of the immune system. The DC-tumor cell fusions provide a greater variety of tumor antigens, but have been met with limited success in human trials, likely due to the autologous components required, the heterogeneity of the product caused by maturation of DC cells, and variations in antigen loading (Browning, M., Antigen presenting cell/tumor cell fusion vaccines for cancer, Human Vaccines & Immunotherapeutics 9:7, 1545-1548; July 2013; Butterfield, L., Dendritic Cells in Cancer Immunotherapy Clinical Trials: Are We Making Progress?, Frontiers of Immunology, 2013 4: 454).

Immunogenic Potential of Vaccines

Vaccines against infectious agents are prime examples of specific receptor-ligand interactions being used to shape an immune response for the therapeutic goal of preventing or reducing infection (e.g. flu vaccine). Generally, an antigen is presented to the immune system in the context of an adjuvant (e.g., a synthetic small molecule immunomodulator).

The allogeneic tumor vaccines of the described invention are distinct from such vaccines in several key features. First, they are designed to be capable of treating existing tumors, although prevention of tumor formation is theoretically also possible. Second, their efficacy tends to be limited by the fact that while tumors express neoantigens (i.e. new, non-self elements) that are foreign and new to the individual, they are also undoubtedly human tumor cells and thus not always recognized as foreign (i.e. non-self) by the individual.

The aforementioned difficulties notwithstanding, evidence has now emerged 1) that endogenous antitumor responses exist, 2) that these immune responses can be modulated, and 3) that this modulation can be measured in terms of overall survival in standard clinical trials.

According to some aspects of the described invention, a series of immunomodulators that can be co-expressed either on a tumor cell line or tumor cell line variant derived from a cancer patient, or on a multiply genetically modified allogeneic tumor cell line or tumor cell line variant has been identified that, when used as a tumor vaccine, may serve 1) to efficiently load the broad array of tumor antigens into the endogenous antigen presenting cells, 2) to efficiently stimulate several cell types by enhancing the normal signals received during an immune response, 3) to impede the mechanisms by which T regulatory cells suppress the immune response, 4) to impede the signals by which immune responses are generally resolved, and 5) to result in enhanced overall survival of cancer patients vaccinated with such a formulation. Although in certain embodiments, the modified tumor cell line or tumor cell line variant can be derived from the patient who receives the vaccine, the allogeneic tumor cell line or tumor cell line variant vaccine approach is distinct from a personalized therapy approach, because the modified tumor cells are not necessarily derived from the individual who ultimately receives the vaccine. Instead, an allogeneic tumor cell vaccine aims to focus an immune response on the many elements that individual tumors of the same tumor type have in common.

One strategy for exploiting the large number of potential tumor antigens for each individual type of cancer is to vaccinate with whole tumor cells to avoid accidentally excluding potentially relevant antigens. The invention described herein provides, among other things, a vaccine with whole tumor cells possessing an array of tumor antigens and modified to express three or more immune modulators.

BRIEF SUMMARY OF THE INVENTION

According to some aspects, the described invention provides an allogeneic tumor cell vaccine comprising: (1) a population of live, proliferation-incompetent genetically engineered tumor cells expressing one or more tumor specific antigens, the population comprising: at least three stably expressed immunomodulatory molecules, wherein the at least three immunomodulatory molecules are OX40 Ligand (OX40L), CD27 Ligand (CD70) and CD28 Ligand (CD28L) comprising CD80, CD86, or both, for induction of one or more subpopulations of PBMCs to proliferate in response to the expressed immunomodulatory molecules and to then enter an effector phase for killing of tumor cells; wherein the subpopulations of PBMC cells comprise one or more of T-lymphocytes, natural killer (NK) cells, dendritic cells (DCs) or B lymphocytes; and (2) a pharmaceutically acceptable carrier.

According to some embodiments, the population of live, proliferation-incompetent genetically engineered tumor cells expressing one or more tumor specific antigens further comprises one or more additional stably expressed immunomodulatory molecules selected from R1-R44. According to some embodiments, the tumor cells are rendered proliferation-incompetent by irradiation. According to some embodiments, induction of the T-lymphocytes comprises activation of the subpopulation of T lymphocytes, expansion of the T lymphocytes, or both. According to some embodiments, induction of the NK cells comprises activation of the subpopulation of NK cells, expansion of the subpopulation of NK cells or both. According to some embodiments, induction of the subpopulation of DCs comprises activation of the subpopulation of DCs, expansion of the subpopulation of DCs or both. According to some embodiments, induction of the subpopulation of B lymphocytes comprises activation of the subpopulation of B lymphocytes, expansion of the subpopulation of B lymphocytes or both. According to some embodiments, the subpopulation of NK cells comprises a subpopulation of memory-like NK cells. According to some embodiments, the subpopulation of T lymphocytes comprises a subpopulation of CD8+ cytotoxic T-lymphocytes (CTL). According to some embodiments, the subpopulation of T lymphocytes comprises a subpopulation of memory T cells. According to some embodiments, the subpopulation of T lymphocytes comprises a subpopulation of regulatory T cells. According to some embodiments, the subpopulation of T lymphocytes comprises a subpopulation of helper T cells. According to some embodiments, the subpopulation of B lymphocytes comprises a subpopulation of memory B cells.

According to some embodiments, the vaccine (1) enhances immune activation of cells effective to recognize and act against those tumor cells that comprise the target tumor antigen in vivo without systemic inflammation; (2) reduces immunosuppression in a tumor microenvironment for tumor cells comprising the target tumor antigen; or (3) increases cell death of tumor cells expressing the target tumor antigen.

According to some embodiments, the tumor cell is derived from a cancer selected from the group consisting of: melanoma, colorectal carcinoma, leukemia, chronic myeloid leukemia, prostate cancer, head and neck cancer, Squamous Cell Carcinoma, tongue cancer, larynx cancer, tonsil cancer, hypopharynx cancer, nasalpharynx cancer, breast cancer, colon cancer, lung cancer, pancreatic cancer, glioblastoma and brain cancer. According to some embodiments, the melanoma tumor cell is characterized by expression of one or more of gp100, tyrosinase, Melan-A, tyrosinase-related protein (TRP-2-INT2), melanoma antigen-1 (MAGE-A1), NY-ESO-1, preferentially expressed antigen of melanoma (PRAIVIE) CDK4 and multiple myeloma oncogene 1 (MUM-1). According to some embodiments, the colorectal cancer tumor cell is characterized by expression of one or more of carcinoembryonic antigen (CEA), MAGE, HPV, human telomerase reverse transcriptase (hTERT), EPCAM, PD-1, PD-L1, p53, and cell surface-associated mucin 1 (MUC1).

According to some embodiments, the population of live, proliferation-resistant tumor cells is derived from a biological sample derived from a subject. According to some embodiments, the population of live proliferation resistant tumor cells is derived from a tumor cell line. According to some embodiments, the population of live, proliferation-resistant tumor cells is effective to elicit immune activation without systemic inflammation. According to some embodiments, the vaccine elicits an immune response that improves progression free survival, overall survival, or both relative to placebo controls. According to some embodiments, the one or more additional stably expressed immunomodulatory molecules selected from R1-R44 is a cytokine, a TNF-family member, a secreted receptor, a chaperone, an IgG superfamily member and/or a chemokine receptor. According to some embodiments, wherein the immunostimulatory molecules are presented at the exterior surface of the genetically engineered tumor cells.

According to another aspect, the described invention provides a method of inducing an immune response to a cancer in a subject comprising administering the allogeneic tumor cell vaccine of claim 1 to the subject parenterally or locally into a tumor, wherein the allogeneic tumor cell vaccine is type-matched to the subject's cancer. According to some embodiments, the cancer is selected from melanoma or colorectal cancer. According to some embodiments, the subject has an infectious viral disease with progression to a cancer. According to some embodiments, the method further comprises administering a checkpoint inhibitor to the subject.

According to another aspect, the described invention provides a method of treating cancer in a subject, comprising administering to the subject an allogeneic tumor cell vaccine comprising: (1) a population of live, proliferation-incompetent genetically engineered tumor cells expressing one or more tumor specific antigens, the population comprising: at least three stably expressed immunomodulatory molecules, wherein the at least three immunomodulatory molecules are OX40 Ligand (OX40L), CD27 Ligand (CD70) and CD28 Ligand (CD28L) comprising CD80, CD86, or both, for induction of one or more subpopulations of PBMCs to proliferate in response to the expressed immunomodulatory molecules and to then enter an effector phase for killing of tumor cells; wherein the subpopulations of PBMC cells comprise one or more of T-lymphocytes, natural killer (NK) cells, dendritic cells (DCs) or B lymphocytes; and (2) a pharmaceutically acceptable carrier in an amount that reduces tumor burden in the subject. According to some embodiments, the effective amount improves clinical outcome. According to some embodiments, the effective amount improves progression free survival, overall survival, or both, of the subject relative to a placebo control. According to some embodiments, the cancer is melanoma or colorectal cancer.

According to another aspect, the allogeneic tumor cell vaccine comprising: (1) a population of live, proliferation-incompetent genetically engineered tumor cells expressing one or more tumor specific antigens, the population comprising: at least three stably expressed immunomodulatory molecules, wherein the at least three immunomodulatory molecules are OX40 Ligand (OX40L), CD27 Ligand (CD70) and CD28 Ligand (CD28L) comprising CD80, CD86, or both, for induction of one or more subpopulations of PBMCs to proliferate in response to the expressed immunomodulatory molecules and to then enter an effector phase for killing of tumor cells; wherein the subpopulations of PBMC cells comprise one or more of T-lymphocytes, natural killer (NK) cells, dendritic cells (DCs) or B lymphocytes; and (2) a pharmaceutically acceptable carrier, is produced by a process comprising: providing an allogeneic parental tumor cell line comprising a population of live tumor cells; introducing into the population of live tumor cells an exogenous nucleic acid encoding a stably expressed immunomodulatory molecule, wherein the immunomodulatory molecule is OX40 Ligand (OX40L); introducing into the population of live tumor cells an exogenous nucleic acid encoding a stably expressed immunomodulatory molecule, wherein the immunomodulatory molecule is CD27 Ligand (CD70); introducing into the population of live tumor cells an exogenous nucleic acid encoding a stably expressed immunomodulatory molecule, wherein the immunomodulatory molecule is CD28 Ligand (CD28L) comprising CD80, CD86, or both; wherein stable expression of OX40 Ligand (OX40L), CD27 Ligand (CD70) and CD28 Ligand (CD28L) comprising CD80, CD86, or both induces one or more subpopulations of PBMCs to proliferate in response to the expressed immunomodulatory molecules and to then enter an effector phase for killing of tumor cells; generating tumor cell line variants by selecting for tumor cell clones that stably express an immunogenic amount of the exogenous subset of the immunomodulatory molecules; and selecting in a mixed lymphocyte tumor cell reaction clonally derived cell line variants by one or more of the following parameters selected from: cellular proliferation, cellular subset differentiation, cytokine release profile, and tumor cell lysis; wherein the selected clonally derived cell line variant is effective to stimulate activation of one or more of T-lymphocytes, natural killer (NK) cells, dendritic cells (DCs) or B lymphocytes.

According to some embodiments, the process for producing the allogeneic tumor cell vaccine further comprises introducing into the population of live tumor cells an exogenous nucleic acid encoding one or more stably expressed immunomodulatory molecules selected from R1-R44. According to some embodiments, the tumor cells are rendered proliferation incompetent by irradiation. According to some embodiments, the parental tumor cell line is from a tumor selected from the group consisting of: melanoma, and colorectal carcinoma. According to some embodiments, the exogenous nucleic acid comprises DNA or RNA. According to some embodiments, the introducing step comprises viral transduction. According to some embodiments, the introducing step comprises electroporation. According to some embodiments, the introducing step comprises utilizing one or more of: liposome mediated transfer, adenovirus, adeno-associated virus, herpes virus, a retroviral based vector, lipofection, and a lentiviral vector. According to some embodiments, the introducing step comprises introducing the exogenous nucleic acid by transfection of a lentiviral vector.

These and other advantages of the invention will be apparent to those of ordinary skill in the art by reference to the following detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 57A shows viSNE density contour plots of CyTOF staining data showing relative changes in immune cell subset abundance and phenotype. FIG. 57B shows single-cell phenotype analysis. SK lines are represented by a number code; SK, unmodified parent line; 3, secreted GM-CSF and membrane expressed FLT-3L; 4, secreted FLT3L and membrane expressed GM-CSF; 5, a non-cleavable form of CD40L; 6, a non-cleavable form of TNF-a; 3-4 is a combination of 3 and 4; 3-4-5 is a combination of 3,4 and 5; and 3-4-6 is a combination of 3,4 and 6.

FIG. 60(*iii*) and FIG. 60(*iv*) show the CD8 population after incubation of the PBMCs in the mixed lymphocyte tumor response assay with the parent cell line (FIG. 60(*iii*)) and the genetically engineered 14-18-30 expressing SKMEL2 tumor cells (FIG. 60(*iv*)). The dotted circle in the bottom panel of graphs shows the CD8 gate. 61A and FIG. 61B show that in vitro CD8+ T cell expansion from hPBMC comparing a day 9 culture of the parent SKMEL2 cell line (FIG. 61A) and genetically modified 14-18-30 cell line (FIG. 61B) expressing a combination of the immunomodulators shown in Table 2, results in tumor cell killing.

DETAILED DESCRIPTION

Definitions

Figure 1:
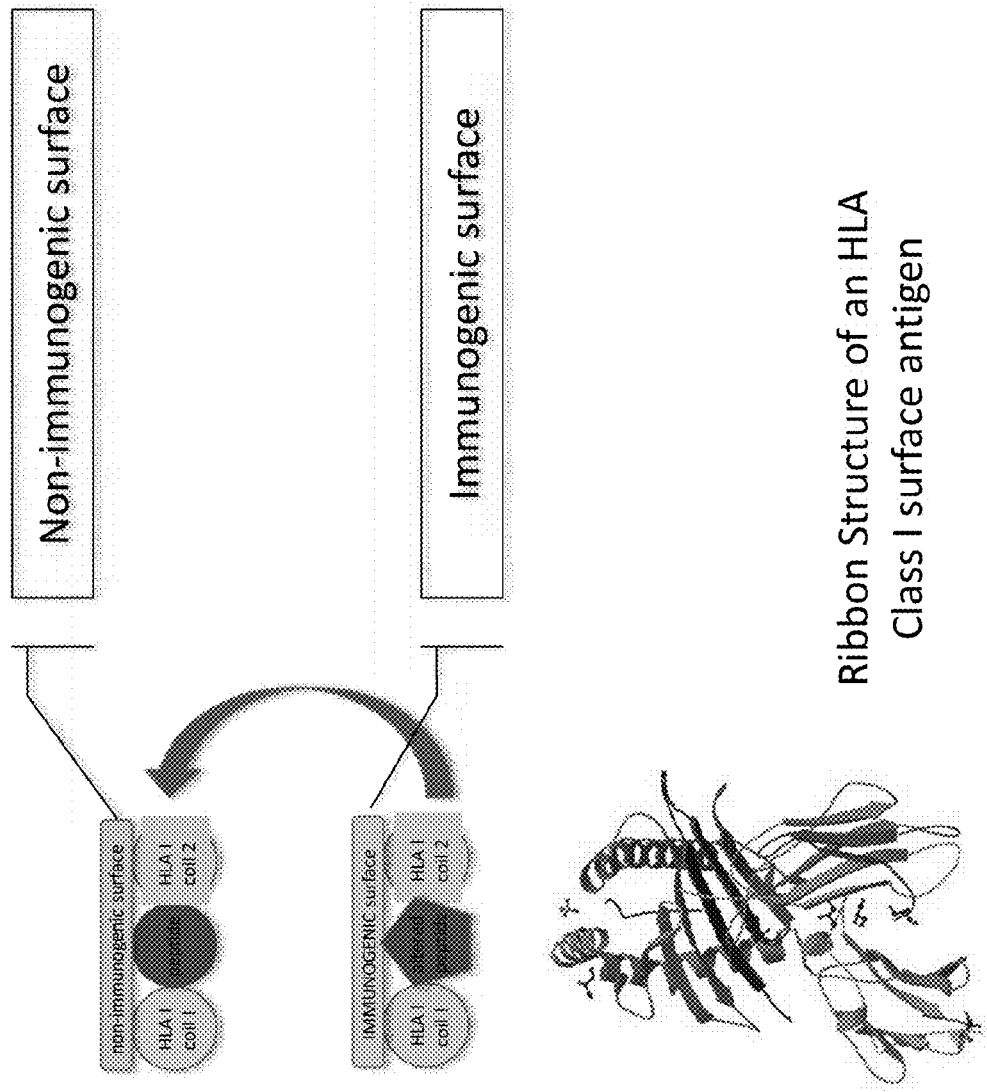
FIG. 1 shows one embodiment of a heteroclitic cross reaction between a peptide native to a tumor cell line and a peptide native to a tumor cell of a patient receiving immunotherapy.

The term "activation" or "lymphocyte activation" refers to stimulation of lymphocytes by specific antigens, nonspecific mitogens, or allogeneic cells resulting in synthesis of RNA, protein and DNA and production of lymphokines; it is followed by proliferation and differentiation of various effector and memory cells. For example, a mature B cell can be activated by an encounter with an antigen that expresses epitopes that are recognized by its cell surface immunoglobulin Ig). The activation process may be a direct one, dependent on cross-linkage of membrane Ig molecules by the antigen (cross-linkage-dependent B cell activation) or an indirect one, occurring most efficiently in the context of an intimate interaction with a helper T cell ("cognate help process"). T-cell activation is dependent on the interaction of the TCR/CD3 complex with its cognate ligand, a peptide bound in the groove of a class I or class II MHC molecule. The molecular events set in motion by receptor engagement are complex. Among the earliest steps appears to be the activation of tyrosine kinases leading to the tyrosine phosphorylation of a set of substrates that control several signaling pathways. These include a set of adapter proteins that link the TCR to the ras pathway, phospholipase Cγ1, the tyrosine phosphorylation of which increases its catalytic activity and engages the inositol phospholipid metabolic pathway, leading to elevation of intracellular free calcium concentration and activation of protein kinase C, and a series of other enzymes that control cellular growth and differentiation. Full responsiveness of a T cell requires, in addition to receptor engagement, an accessory cell-delivered costimulatory activity, e.g., engagement of CD28 on the T cell by CD80 and/or CD86 on the antigen presenting cell (APC). The soluble product of an activated B lymphocyte is immmunoglobulins (antibodies). The soluble product of an activated T lymphocyte is lymphokines.

B cell activation. A mature B cell can be activated by an encounter with an antigen that expresses epitopes that are recognized by its cell surface immunoglobulin Ig). The activation process may be a direct one, dependent on cross-linkage of membrane Ig molecules by the antigen (cross-linkage-dependent B cell activation) or an indirect one, occurring most efficiently in the context of an intimate interaction with a helper T cell ("cognate help process"). The soluble product of an activated B lymphocyte is immunoglobulins (antibodies).

T-cell activation is dependent on the interaction of the TCR/CD3 complex with its cognate ligand, a peptide bound in the groove of a class I or class II MHC molecule. The molecular events set in motion by receptor engagement are complex. Among the earliest steps appears to be the activation of tyrosine kinases leading to the tyrosine phosphorylation of a set of substrates that control several signaling pathways. These include a set of adapter proteins that link the TCR to the ras pathway, phospholipase Cγ1, the tyrosine phosphorylation of which increases its catalytic activity and engages the inositol phospholipid metabolic pathway, leading to elevation of intracellular free calcium concentration and activation of protein kinase C, and a series of other enzymes that control cellular growth and differentiation. Full responsiveness of a T cell requires, in addition to receptor engagement, an accessory cell-delivered costimulatory activity, e.g., engagement of CD28 on the T cell by CD80 and/or CD86 on the antigen presenting cell (APC). The soluble product of an activated T lymphocyte is lymphokines.

Dendritic cell activation. Pathogen invasion induces a rapid inflammatory response initiated through the recognition of pathogen-derived molecules by pattern recognition receptors (PRRs) expressed on both immune and non-immune cells. Joffre, O., et al., Immunol. Rev. (2009) 277(1): 234-47. GET The initial wave of pro-inflammatory cytokines and chemokines limits pathogen spread and recruits and activates immune cells to eradicate the invaders. Dendritic cells (DCs) are responsible for initiating a subsequent phase of immunity, dominated by the action of pathogen-specific T and B cells. As for the early pro-inflammatory response, DC activation is triggered by PRR signals, which convert resting DCs into potent antigen-presenting cells capable of promoting the expansion and effector differentiation of naive pathogen-specific T cells. While DCs can be activated indirectly by inflammatory cytokines, these cells are unable to induce a functional T-cell response, and may function in tolerance induction.

As used herein, the terms "activating CD8+ T cells" or "CD8+ T cell activation" refer to a process (e.g., a signaling event) causing or resulting in one or more cellular responses of a CD8+ T cell (CTL), selected from: proliferation, differentiation, cytokine secretion, cytotoxic effector molecule release, cytotoxic activity, and expression of activation markers. As used herein, an "activated CD8+ T cell" refers to a CD8+ T cell that has received an activating signal, and thus demonstrates one or more cellular responses, selected from proliferation, differentiation, cytokine secretion, cytotoxic effector molecule release, cytotoxic activity, and expression of activation markers. Suitable assays to measure CD8+ T cell activation are known in the art and are described herein.

As used herein, the terms "expanding a CD8+ T cell" or "CD8+ T cell expansion" refer to a process wherein a population of CD8+ T cells undergoes a series of cell divisions and thereby increases in cell number. The term "expanded CD8+ T cells" relates to CD8+ T cells obtained through CD8+ T cell expansion. Suitable assays to measure T cell expansion are known in the art and are described herein.

As used herein, the term "activating an NK cell" or "NK cell activation" refers to a process (e.g., a signaling event) causing or resulting in an NK cell being capable of killing cells with deficiencies in WIC class I expression. As used herein, an "activated NK cell" refers to an NK cell that has received an activating signal, and is thus capable of killing cells with deficiencies in WIC class I expression. Suitable assays to measure NK cell activation are known in the art and are described herein.

As used herein, the terms "expanding an NK cell" or "NK cell expansion" refer to a process wherein a population of NK cells undergoes a series of cell divisions and thereby increases in cell number. The term "expanded NK cells" relates to NK cells obtained through NK cell expansion. Suitable assays to measure NK cell expansion are known in the art and are described herein.

As used herein, the term "administration" and its various grammatical forms as it applies to a mammal, cell, tissue, organ, or biological fluid, refers without limitation to contact of an exogenous ligand, reagent, placebo, small molecule, pharmaceutical agent, therapeutic agent, diagnostic agent, or composition to the subject, cell, tissue, organ, or biological fluid, and the like. "Administration" can refer, e.g., to therapeutic, pharmacokinetic, diagnostic, research, placebo, and experimental methods. "Administration" also encompasses in vitro and ex vivo treatments, e.g., of a cell, by a reagent, diagnostic, binding composition, or by another cell.

The term "allogeneic" as used herein means that the donor and the recipient (host) are of different genetic makeup, but of the same species. As used herein, an "allogeneic cell" refers to a cell that is not derived from the recipient, meaning the individual to which the cell is to be administered, that is, it has a different genetic constitution than the recipient individual. An allogeneic cell is generally obtained from the same species as the individual to which the cell is to be administered. For example, the allogeneic cell can be a human cell, as disclosed herein, for administering to a human patient such as a cancer patient. As used herein, an "allogeneic tumor cell" refers to a tumor cell that is not derived from the recipient, meaning the individual to which the allogeneic cell is to be administered. Generally, the allogeneic tumor cell expresses one or more tumor antigens that can stimulate an immune response against a tumor in an individual to which the cell is to be administered. As used herein, an "allogeneic cancer cell," for example, a lung cancer cell, refers to a cancer cell that is not derived from the recipient individual to which the allogeneic cell is to be administered.

The terms "amino acid residue" or "amino acid" or "residue" are used interchangeably to refer to an amino acid that is incorporated into a protein, a polypeptide, or a peptide, including, but not limited to, a naturally occurring amino acid and known analogs of natural amino acids that can function in a similar manner as naturally occurring amino acids. The amino acids may be L- or D-amino acids. An amino acid may be replaced by a synthetic amino acid, which is altered so as to increase the half-life of the peptide, increase the potency of the peptide, or increase the bioavailability of the peptide. The single letter designation for amino acids is used predominately herein. Such single letter designations are as follows: A is alanine; C is cysteine; D is aspartic acid; E is glutamic acid; F is phenylalanine; G is glycine; H is histidine; I is isoleucine; K is lysine; L is leucine; M is methionine; N is asparagine; P is proline; Q is glutamine; R is arginine; S is serine; T is threonine; V is valine; W is tryptophan; and Y is tyrosine. The following represents groups of amino acids that are conservative substitutions for one another: 1) Alanine (A), Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

The terms "apoptosis" or "programmed cell death" refer to a highly regulated and active process that contributes to biologic homeostasis comprised of a series of biochemical events that lead to a variety of morphological changes, including blebbing, changes to the cell membrane, such as loss of membrane asymmetry and attachment, cell shrinkage, nuclear fragmentation, chromatin condensation, and chromosomal DNA fragmentation, without damaging the organism.

Apoptotic cell death is induced by many different factors and involves numerous signaling pathways, some dependent on caspase proteases (a class of cysteine proteases) and others that are caspase independent. It can be triggered by many different cellular stimuli, including cell surface receptors, mitochondrial response to stress, and cytotoxic T cells, resulting in activation of apoptotic signaling pathways.

The caspases involved in apoptosis convey the apoptotic signal in a proteolytic cascade, with caspases cleaving and activating other caspases that then degrade other cellular targets that lead to cell death. The caspases at the upper end of the cascade include caspase-8 and caspase-9. Caspase-8 is the initial caspase involved in response to receptors with a death domain (DD) like Fas.

Receptors in the TNF receptor family are associated with the induction of apoptosis, as well as inflammatory signaling. The Fas receptor (CD95) mediates apoptotic signaling by Fas-ligand expressed on the surface of other cells. The Fas-FasL interaction plays an important role in the immune system and lack of this system leads to autoimmunity, indicating that Fas-mediated apoptosis removes self-reactive lymphocytes. Fas signaling also is involved in immune surveillance to remove transformed cells and virus infected cells. Binding of Fas to oligimerized FasL on another cell activates apoptotic signaling through a cytoplasmic domain termed the death domain (DD) that interacts with signaling adaptors including FAF, FADD and DAX to activate the caspase proteolytic cascade. Caspase-8 and caspase-10 first are activated to then cleave and activate downstream caspases and a variety of cellular substrates that lead to cell death.

Mitochondria participate in apoptotic signaling pathways through the release of mitochondrial proteins into the cytoplasm. Cytochrome c, a key protein in electron transport, is released from mitochondria in response to apoptotic signals, and activates Apaf-1, a protease released from mitochondria. Activated Apaf-1 activates caspase-9 and the rest of the caspase pathway. Smac/DIABLO is released from mitochondria and inhibits IAP proteins that normally interact with caspase-9 to inhibit apoptosis. Apoptosis regulation by Bcl-2 family proteins occurs as family members form complexes that enter the mitochondrial membrane, regulating the release of cytochrome c and other proteins. TNF family receptors that cause apoptosis directly activate the caspase cascade, but can also activate Bid, a Bcl-2 family member, which activates mitochondria-mediated apoptosis. Bax, another Bcl-2 family member, is activated by this pathway to localize to the mitochondrial membrane and increase its permeability, releasing cytochrome c and other mitochondrial proteins. Bcl-2 and Bcl-xL prevent pore formation, blocking apoptosis. Like cytochrome c, AIF (apoptosis-inducing factor) is a protein found in mitochondria that is released from mitochondria by apoptotic stimuli. While cytochrome C is linked to caspase-dependent apoptotic signaling, AIF release stimulates caspase-independent apoptosis, moving into the nucleus where it binds DNA. DNA binding by AIF stimulates chromatin condensation, and DNA fragmentation, perhaps through recruitment of nucleases.

The mitochondrial stress pathway begins with the release of cytochrome c from mitochondria, which then interacts with Apaf-1, causing self-cleavage and activation of caspase-9. Caspase-3, -6 and -7 are downstream caspases that are activated by the upstream proteases and act themselves to cleave cellular targets.

Granzyme B and perforin proteins released by cytotoxic T cells induce apoptosis in target cells, forming transmembrane pores, and triggering apoptosis, perhaps through cleavage of caspases, although caspase-independent mechanisms of Granzyme B mediated apoptosis have been suggested.

Fragmentation of the nuclear genome by multiple nucleases activated by apoptotic signaling pathways to create a nucleosomal ladder is a cellular response characteristic of apoptosis. One nuclease involved in apoptosis is DNA fragmentation factor (DFF), a caspase-activated DNAse (CAD). DFF/CAD is activated through cleavage of its associated inhibitor ICAD by caspases proteases during apoptosis. DFF/CAD interacts with chromatin components such as topoisomerase II and histone H1 to condense chromatin structure and perhaps recruit CAD to chromatin. Another apoptosis activated protease is endonuclease G (EndoG). EndoG is encoded in the nuclear genome but is localized to mitochondria in normal cells. EndoG may play a role in the replication of the mitochondrial genome, as well as in apoptosis. Apoptotic signaling causes the release of EndoG from mitochondria. The EndoG and DFF/CAD pathways are independent since the EndoG pathway still occurs in cells lacking DFF.

Hypoxia, as well as hypoxia followed by reoxygenation can trigger cytochrome c release and apoptosis. Glycogen synthase kinase (GSK-3) a serine-threonine kinase ubiquitously expressed in most cell types, appears to mediate or potentiate apoptosis due to many stimuli that activate the mitochondrial cell death pathway. Loberg, R D, et al., J. Biol. Chem. 277 (44): 41667-673 (2002). It has been demonstrated to induce caspase 3 activation and to activate the proapoptotic tumor suppressor gene p53. It also has been suggested that GSK-3 promotes activation and translocation of the proapoptotic Bcl-2 family member, Bax, which, upon aggregation and mitochondrial localization, induces cytochrome c release. Akt is a critical regulator of GSK-3, and phosphorylation and inactivation of GSK-3 may mediate some of the antiapoptotic effects of Akt.

The term "autologous" as used herein means derived from the same individual.

The term "cancer" as used herein refers to diseases in which abnormal cells divide without control and are able to invade other tissues. There are more than 100 different types of cancer. Most cancers are named for the organ or type of cell in which they start—for example, cancer that begins in the colon is called colon cancer; cancer that begins in melanocytes of the skin is called melanoma. Cancer types can be grouped into broader categories. The main categories of cancer include: carcinoma (meaning a cancer that begins in the skin or in tissues that line or cover internal organs, and its subtypes, including adenocarcinoma, basal cell carcinoma, squamous cell carcinoma, and transitional cell carcinoma); sarcoma (meaning a cancer that begins in bone, cartilage, fat, muscle, blood vessels, or other connective or supportive tissue); leukemia (meaning a cancer that starts in blood-forming tissue (e.g., bone marrow) and causes large numbers of abnormal blood cells to be produced and enter the blood; lymphoma and myeloma (meaning cancers that begin in the cells of the immune system); and Central nervous system cancers (meaning cancers that begin in the tissues of the brain and spinal cord). The term "myelodysplastic syndrome" refers to a type of cancer in which the bone marrow does not make enough healthy blood cells (white blood cells, red blood cells, and platelets) and there are abnormal cells in the blood and/or bone marrow. Myelodysplastic syndrome may become acute myeloid leukemia (AML).

The term "cell line" as used herein, means a permanently established cell culture developed from a single cell and therefore consisting of cells with a uniform genetic makeup that will proliferate indefinitely.

The term "chemotherapy" as used herein refers to a treatment that uses drugs to stop the growth of cancer cells.

The term "contact" and its various grammatical forms as used herein refers to a state or condition of touching or of immediate or local proximity. Contacting a composition to a target destination may occur by any means of administration known to the skilled artisan.

The term "costimulatory molecule" as used herein refers to one of two or more molecules that are displayed on the cell surface that have a role in activating a T cell to become an effector cell. For example MHC proteins, which present foreign antigen to the T cell receptor, also require costimulatory proteins which bind to complementary receptors on the T cell's surface to result in activation of the T cell.

As used herein, the term "cytokine" refers to small soluble protein substances secreted by cells which have a variety of effects on other cells. Cytokines mediate many important physiological functions including growth, development, wound healing, and the immune response. They act by binding to their cell-specific receptors located in the cell membrane, which allows a distinct signal transduction cascade to start in the cell, which eventually will lead to biochemical and phenotypic changes in target cells. Cytokines can act both locally and distantly from a site of release. They include type I cytokines, which encompass many of the interleukins, as well as several hematopoietic growth factors; type II cytokines, including the interferons and interleukin-10; tumor necrosis factor ("TNF")-related molecules, including TNFα and lymphotoxin; immunoglobulin super-family members, including interleukin 1 ("IL-1"); and the chemokines, a family of molecules that play a critical role in a wide variety of immune and inflammatory functions. The same cytokine can have different effects on a cell depending on the state of the cell. Cytokines often regulate the expression of, and trigger cascades of other cytokines. Non limiting examples of cytokines include e.g., Granulocyte-macrophage colony-stimulating factor (GM-CSF), Granulocyte colony-stimulating factor (G-CSF), Fms-related tyrosine kinase 3 ligand (FLT3LG), interleukin-1 (IL-1), IL-1, IL-2, IL-3, IL-4, IL-5, IL-6, IL-7, IL-8, IL-9, IL-10, IL-11, IL-12/IL-23 P40, IL13, IL-15, IL-15/IL15-RA, IL-17, IL-18, IL-21, IL-23, TGF-β, MCP-1, TNF-α and interferon alpha (IFNα), IFNγ

The term "cytotoxic T lymphocytes" (CTLs) refers to effector CD8+ T cells. Cytotoxic T cells kill by inducing their targets to undergo apoptosis. They induce target cells to undergo programmed cell death via extrinsic and intrinsic pathways.

As used herein, the term "dendritic cell" or "DC" describes a diverse population of morphologically similar cell types found in a variety of lymphoid and non-lymphoid tissues that present foreign antigens to T cells, see Steinman, Ann. Rev. Immunol. 9:271-296 (1991).

The term "derived from" as used herein encompasses any method for receiving, obtaining, or modifying something from a source of origin.

The term "derivative" or "variant" with respect to a peptide or DNA sequence (e.g. immune modulator peptide sequence) as used herein refers to a non-identical peptide or DNA sequence that is modified from its original sequence. The differences in the sequences may by the result of changes, by design, in sequence or structure. Designed changes may be specifically designed and introduced into the sequence for specific purposes. Such specific changes may be made in vitro using a variety of mutagenesis techniques. Such sequence variants generated specifically may be referred to as "mutants" or "derivatives" of the original sequence. The terms "derivative" or "variant" with respect to cells as used herein refers to a cell line that has been modified from its cell line of origin (e.g. modified to express recombinant DNA sequences).

The term "detectable marker" encompasses both selectable markers and assay markers. The term "selectable markers" refers to a variety of gene products to which cells transformed with an expression construct can be selected or screened, including drug-resistance markers, antigenic markers useful in fluorescence-activated cell sorting, adherence markers such as receptors for adherence ligands allowing selective adherence, and the like.

The term "detectable response" refers to any signal or response that may be detected in an assay, which may be performed with or without a detection reagent. Detectable responses include, but are not limited to, radioactive decay and energy (e.g., fluorescent, ultraviolet, infrared, visible) emission, absorption, polarization, fluorescence, phosphorescence, transmission, reflection or resonance transfer.

Detectable responses also include chromatographic mobility, turbidity, electrophoretic mobility, mass spectrum, ultraviolet spectrum, infrared spectrum, nuclear magnetic resonance spectrum and x-ray diffraction. Alternatively, a detectable response may be the result of an assay to measure one or more properties of a biologic material, such as melting point, density, conductivity, surface acoustic waves, catalytic activity or elemental composition. A "detection reagent" is any molecule that generates a detectable response indicative of the presence or absence of a substance of interest. Detection reagents include any of a variety of molecules, such as antibodies, nucleic acid sequences and enzymes. To facilitate detection, a detection reagent may comprise a marker.

The term "differentiate" and its various grammatical forms as used herein refers to the process of development with an increase in the level of organization or complexity of a cell or tissue, accompanied with a more specialized function.

The term "dose" as used herein refers to the quantity of a therapeutic substance prescribed to be taken at one time.

The term "effector cell" as used herein refers to a cell that carries out a final response or function. The main effector cells of the immune system, for example, are activated lymphocytes and phagocytes.

Engineered Leukocyte Stimulator cells ("ENLIST™ cells) signify a population of proliferation incompetent tumor cells genetically engineered to express a core group of three immunomodulatory molecules used to stimulate mononuclear cells for the treatment of cancer.

The term "enrich" as used herein refers to increasing the proportion of a desired substance, for example, to increase the relative frequency of a subtype of cell compared to its natural frequency in a cell population. Positive selection, negative selection, or both are generally considered necessary to any enrichment scheme. Selection methods include, without limitation, magnetic separation and FACS. Regardless of the specific technology used for enrichment, the specific markers used in the selection process are critical, since developmental stages and activation-specific responses can change a cell's antigenic profile.

As used herein, the term "exogenous polypeptide" refers to a polypeptide that is not produced by a wild-type cell of that type or is present at a lower level in a wild-type cell than in a cell containing the exogenous polypeptide. According to some embodiments, an exogenous polypeptide is a polypeptide encoded by a nucleic acid that was introduced into the cell, which nucleic acid is optionally not retained by the cell.

As used herein, the term "exogenous immunomodulatory molecule" includes a polypeptide comprising (e.g., intracellularly or at the cell surface) an allogeneic cell (e.g. an allogeneic cell line) that specifically binds a cognate polypeptide (e.g., receptor) on an immune cell, such as an immune killer cell (e.g. an NK cell or a CD8+ T cell), thereby providing a signal which mediates stimulation of the immune cell, such as the proliferation, activation, expansion and the like of the immune cell. According to one embodiment, one or more exogenous immunomodulatory polypeptides are sufficient to stimulate an immune killer cell ex vivo or in vivo. Exemplary exogenous immunomodulatory polypeptides are described in more detail below.

As used herein, the term "express" or "expression" encompasses the biosynthesis of mRNA, polypeptide biosynthesis, polypeptide activation, e.g., by post-translational modification, or an activation of expression by changing the subcellular location or by recruitment to chromatin. Expression may be, e.g., increased by a number of approaches, including: increasing the number of genes encoding the polypeptide, increasing the transcription of the gene (such as by placing the gene under the control of a constitutive promoter), increasing the translation of the gene, knock out of a competitive gene, or a combination of these and/or other approaches.

The term "expression vector" refers to a DNA molecule comprising a gene that is expressed in a host cell. Typically, gene expression is placed under the control of certain regulatory elements including, but not limited to, promoters, tissue specific regulatory elements, and enhancers. Such a gene is said to be "operably linked to" the regulatory elements.

As used herein, the terms "first" and "second" with respect to exogenous immunomodulatory molecules are used for convenience of distinguishing when there is more than one type of exogenous stimulatory polypeptide. Use of these terms is not intended to confer a specific order or orientation of the exogenous stimulatory polypeptides unless explicitly so stated.

The term "flow cytometry" as used herein refers to a tool for interrogating the phenotype and characteristics of cells. It senses cells or particles as they move in a liquid stream through a laser (light amplification by stimulated emission of radiation)/light beam past a sensing area. The relative light-scattering and color-discriminated fluorescence of the microscopic particles is measured. Flow Analysis and differentiation of the cells is based on size, granularity, and whether the cell is carrying fluorescent molecules in the form of either antibodies or dyes. As the cell passes through the laser beam, light is scattered in all directions, and the light scattered in the forward direction at low angles (0.5-10°) from the axis is proportional to the square of the radius of a sphere and so to the size of the cell or particle. Light may enter the cell; thus, the 90° light (right-angled, side) scatter may be labeled with fluorochrome-linked antibodies or stained with fluorescent membrane, cytoplasmic, or nuclear dyes. Thus, the differentiation of cell types, the presence of membrane receptors and antigens, membrane potential, pH, enzyme activity, and DNA content may be facilitated. Flow cytometers are multiparameter, recording several measurements on each cell; therefore, it is possible to identify a homogeneous subpopulation within a heterogeneous population (Marion G. Macey, Flow cytometry: principles and applications, Humana Press, 2007). Fluorescence-activated cell sorting (FACS), which allows isolation of distinct cell populations too similar in physical characteristics to be separated by size or density, uses fluorescent tags to detect surface proteins that are differentially expressed, allowing fine distinctions to be made among physically homogeneous populations of cells.

The term "functional equivalent" or "functionally equivalent" are used interchangeably herein to refer to substances, molecules, polynucleotides, proteins, peptides, or polypeptides having similar or identical effects or use.

As used herein, the term "gene" is used broadly to refer to any segment of nucleic acid associated with expression of a given RNA or protein. Thus, genes include regions encoding expressed RNAs (which typically include polypeptide coding sequences) and, often, the regulatory sequences required for their expression. Genes can be obtained from a variety of sources, including cloning from a source of interest or synthesizing from known or predicted sequence information, and may include sequences designed to have specifically desired parameters.

The term "heteroclitic" is used herein to refer to peptides of higher biological potency than the original peptide. A "heteroclitic immunogen" is an immunogen that elicits an immune response that cross-reacts to an original poorly immunogenic antigen.

The terms "immune response" and "immune-mediated" are used interchangeably herein to refer to any functional expression of a subject's immune system, against either foreign or self-antigens, whether the consequences of these reactions are beneficial or harmful to the subject.

The term "immunosuppression" as used herein and its other grammatical forms refer to a decrease of the body's immune response and ability of the immune system to fight infections and other diseases. For example, some immunosuppression may be induced with drugs, or may result from disease.

The terms "immunomodulatory", "immune modulator" and "immune modulatory" are used interchangeably herein to refer to a substance, agent, or cell that is capable of augmenting or diminishing immune responses directly or indirectly by expressing chemokines, cytokines and other mediators of immune responses.

As used herein the term "immunostimulatory amount" of the disclosed compositions refers to an amount of an immunogenic composition that is effective to stimulate an immune response, for example, as measured by ELISPOT assay (cellular immune response), ICS (intracellular cytokine staining assay) and major histocompatibility complex (WIC) tetramer assay to detect and quantify antigen-specific T cells, quantifying the blood population of antigen-specific CD4+ T cells, or quantifying the blood population of antigen specific CD8+ T cells by a measurable amount, or where the increase is by at least 10%, at least 20%, at least 30%, at least 40%, at least 50%, at least 60%, at least 70%, at least 80%, at least 90%, at least 95%, at least 96%, at least 97%, at least 98%, at least 99%, at least 100%, when compared to a suitable control (e.g., a control composition where dendritic cells are not loaded with tumor-specific cells, or not loaded with peptide derived from tumor-specific cells).

The term "integrate into the genome" as used herein refers to a recombinant DNA sequence being concomitantly joined to the genomic DNA comprising a host cell's genome.

The term "Kaplan Meier plot" or "Kaplan Meier survival curve" as used herein refers to the plot of probability of clinical study subjects surviving in a given length of time while considering time in many small intervals. The Kaplan Meier plot assumes that: (i) at any time subjects who are censored (i.e., lost) have the same survival prospects as subjects who continue to be followed; (ii) the survival probabilities are the same for subjects recruited early and late in the study; and (iii) the event (e.g., death) happens at the time specified. Probabilities of occurrence of events are computed at a certain point of time with successive probabilities multiplied by any earlier computed probabilities to get a final estimate. The survival probability at any particular time is calculated as the number of subjects surviving divided by the number of subjects at risk. Subjects who have died, dropped out, or have been censored from the study are not counted as at risk.

The term "labeling" as used herein refers to a process of distinguishing a compound, structure, protein, peptide, antibody, cell or cell component by introducing a traceable constituent. Common traceable constituents include, but are not limited to, a fluorescent antibody, a fluorophore, a dye or a fluorescent dye, a stain or a fluorescent stain, a marker, a fluorescent marker, a chemical stain, a differential stain, a differential label, and a radioisotope.

The terms "marker" or "cell surface marker" are used interchangeably herein to refer to an antigenic determinant or epitope found on the surface of a specific type of cell. Cell surface markers can facilitate the characterization of a cell type, its identification, and eventually its isolation. Cell sorting techniques are based on cellular biomarkers where a cell surface marker(s) may be used for either positive selection or negative selection, i.e., for inclusion or exclusion, from a cell population.

The term "mediate" and its various grammatical forms as used herein means to bring about a result.

The term "minimal residual disease" as used herein refers to a very small number of cancer cells that remain in the body during or after treatment. Minimal residual disease can be found only by highly sensitive laboratory methods that are able to find one cancer cell among one million normal cells.

The terms "mixed lymphocyte tumor reaction" or "MLTR" are used interchangeably herein to refer to a reaction similar to a mixed lymphocyte reaction but rather than using allogeneic lymphocytes to stimulate a response, allogeneic tumor cells are used instead. The MLTR method comprises contacting tumor cells being tested for immunogenic potential with mixed lymphocytes from peripheral blood mononuclear cells, followed by measuring one or more of cellular proliferation of the lymphocytes, cellular subset differentiation of the lymphocytes, cytokine release profile of the lymphocytes, and tumor cell death.

The term "modify" and its various grammatical forms as used herein refers to a change of the form or qualities of The term "modulate" and its various grammatical forms as used herein means to regulate, alter, adapt, or adjust to a certain measure or proportion. Such modulation may be any change, including an undetectable change.

The term "modified" or "modulated" as used herein with respect to an immune response to tumor cells refers to changing the form or character of the immune response to the tumor cells via one or more recombinant DNA techniques such that the immune cells are able to recognize and kill tumor cells.

The term "myeloid suppressor cells" or "myeloid-derived suppressor cells" as used herein refers to a heterogeneous population of cells characterized by myeloid origin, immature state, and ability to potently suppress T cell responses. These cells regulate immune responses and tissue repair in healthy individuals and the population rapidly expands during inflammation.

As used herein the term "natural killer (NK) cells" refers to lymphocytes in the same family as T and B cells, classified as group I innate lymphocytes. They have an ability to kill tumor cells without any priming or prior activation, in contrast to cytotoxic T cells, which need priming by antigen presenting cells. NK cells secrete cytokines such as IFNγ and TNFα, which act on other immune cells, like macrophages and dendritic cells, to enhance the immune response. Activating receptors on the NK cell surface recognize molecules expressed on the surface of cancer cells and infected cells and switch on the NK cell. Inhibitory receptors act as a check on NK cell killing. Most normal healthy cells express MHCI receptors, which mark them as "self" Inhibitory receptors on the surface of the NK cell recognize cognate MHCI, which switches off the NK cell, preventing it from killing. Once the decision is made to kill, the NK cell releases cytotoxic granules containing perforin and granzymes, which leads to lysis of the target cell. Natural killer reactivity, including cytokine secretion and cytotoxicity, is controlled by a balance of several germ-line encoded inhibitory and activating receptors such as killer immunoglobulin-like receptors (KIRs) and natural cytotoxicity receptors (NCRs). The presence of the MHC Class I molecule on target cells serves as one such inhibitory ligand for MHC Class I-specific receptors, the Killer cell Immunoglobulin-like Receptor (KIR), on NK cells. Engagement of KIR receptors blocks NK activation and, paradoxically, preserves their ability to respond to successive encounters by triggering inactivating signals. Therefore, if a KIR is able to sufficiently bind to MHC Class I, this engagement may override the signal for killing and allows the target cell to live. In contrast, if the NK cell is unable to sufficiently bind to MHC Class I on the target cell, killing of the target cell may proceed. Consequently, those tumors which express low MHC Class I and which are thought to be capable of evading a T-cell-mediated attack may be susceptible to an NK cell-mediated immune response instead.

The term "nucleic acid" is used herein to refer to a deoxyribonucleotide or ribonucleotide polymer in either single- or double-stranded form, and, unless otherwise limited, encompasses known analogues having the essential nature of natural nucleotides in that they hybridize to single-stranded nucleic acids in a manner similar to naturally occurring nucleotides (e.g., peptide nucleic acids). Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507). Measuring the effects of base incompatibility by quantifying the rate at which two strands anneal can provide information as to the similarity in base sequence between the two strands being annealed. A nucleic acid that selectively hybridizes undergoes hybridization, under stringent hybridization conditions, of the nucleic acid sequence to a specified nucleic acid target sequence to a detectably greater degree (e.g., at least 2-fold over background) than its hybridization to non-target nucleic acid sequences and to the substantial exclusion of non-target nucleic acids.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). For example, such a sequence is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e-3 and e-100 indicating a closely related sequence.

The term "open reading frame" as used herein refers to a sequence of nucleotides in a DNA molecule that has the potential to encode a peptide or protein: it starts with a start triplet (ATG), is followed by a string of triplets each of which encodes an amino acid, and ends with a stop triplet (TAA, TAG or TGA).

The phrase "operably linked" refers (1) to a first sequence(s) or domain being positioned sufficiently proximal to a second sequence(s) or domain so that the first sequence(s) or domain can exert influence over the second sequence(s) or domain or a region under control of that second sequence or domain; and (2) to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, are in the same reading frame. According to some embodiments, the phrase "operatively linked" refers to a linkage in which two or more protein domains or polypeptides are ligated or combined via recombinant DNA technology or chemical reaction such that each protein domain or polypeptide of the resulting fusion protein retains its original function.

The term "overall survival" (OS) as used herein refers to the length of time from either the date of diagnosis or the start of treatment for a disease, such as cancer, that patients diagnosed with the disease are still alive.

The term "parenteral" and its other grammatical forms as used herein refers to administration of a substance occurring in the body other than by the mouth or alimentary canal. For example, the term "parenteral" as used herein refers to introduction into the body by way of an injection (i.e., administration by injection), including, for example, subcutaneously (i.e., an injection beneath the skin), intramuscularly (i.e., an injection into a muscle); intravenously (i.e., an injection into a vein), intrathecally (i.e., an injection into the space around the spinal cord or under the arachnoid membrane of the brain), intrasternal injection, or infusion techniques.

The terms "peripheral blood mononuclear cells" or "PBMCs" are used interchangeably herein to refer to blood cells having a single round nucleus such as, for example, a lymphocyte or a monocyte.

The term "pharmaceutical composition" as used herein refers to a composition that is employed to prevent, reduce in intensity, cure or otherwise treat a target condition, syndrome, disorder or disease.

The term "pharmaceutically acceptable carrier" as used herein refers to any substantially non-toxic carrier conventionally useable for administration of pharmaceuticals in which the isolated polypeptide of the present invention will remain stable and bioavailable. The pharmaceutically acceptable carrier must be of sufficiently high purity and of sufficiently low toxicity to render it suitable for administration to the mammal being treated. It further should maintain the stability and bioavailability of an active agent. The pharmaceutically acceptable carrier can be liquid or solid and is selected, with the planned manner of administration in mind, to provide for the desired bulk, consistency, etc., when combined with an active agent and other components of a given composition.

The term "pharmaceutically acceptable salt" as used herein refers to those salts which are, within the scope of sound medical judgment, suitable for use in contact with the tissues of humans and lower animals without undue toxicity, irritation, allergic response and the like and are commensurate with a reasonable benefit/risk ratio. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts may be prepared as alkaline metal or alkaline earth salts, such as sodium, potassium or calcium salts of the carboxylic acid group. By "pharmaceutically acceptable salt" is meant those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, P. H. Stahl, et al. describe pharmaceutically acceptable salts in detail in "Handbook of Pharmaceutical Salts: Properties, Selection, and Use" (Wiley VCH, Zurich, Switzerland: 2002). The salts may be prepared in situ during the final isolation and purification of the compounds described within the present invention or separately by reacting a free base function with a suitable organic acid. Representative acid addition salts include, but are not limited to, acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate(isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid. Basic addition salts may be prepared in situ during the final isolation and purification of compounds described within the invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Pharmaceutically acceptable salts also may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium or magnesium) salts of carboxylic acids may also be made.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids.

The terms "polypeptide", "peptide" and "protein" also are inclusive of modifications including, but not limited to, glycosylation, lipid attachment, sulfation, gamma-carboxylation of glutamic acid residues, hydroxylation, and ADP-ribosylation. It will be appreciated, as is well known and as noted above, that polypeptides may not be entirely linear. For instance, polypeptides may be branched as a result of ubiquitination, and they may be circular, with or without branching, generally as a result of posttranslational events, including natural processing event and events brought about by human manipulation which do not occur naturally. Circular, branched and branched circular polypeptides may be synthesized by non-translation natural process and by entirely synthetic methods, as well. According to some embodiments, the peptide is of any length or size.

The term "proliferate" and its various grammatical forms as used herein refers to the process that results in an increase of the number of cells, and is defined by the balance between cell division and cell loss through cell death or differentiation.

The terms "protein domain" and "domain" are used interchangeably to refer to a portion of a protein that has its own tertiary structure. Large proteins are generally composed of several domains connected to one another via flexible regions of polypeptide chain.

The following terms are used herein to describe the sequence relationships between two or more nucleic acids or polynucleotides: (a) "reference sequence", (b) "comparison window", (c) "sequence identity", (d) "percentage of sequence identity", and (e) "substantial identity." (a) The term "reference sequence" refers to a sequence used as a basis for sequence comparison. A reference sequence may be a subset or the entirety of a specified sequence; for example, as a segment of a full-length cDNA or gene sequence, or the complete cDNA or gene sequence. (b) The term "comparison window" refers to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be at least 30 contiguous nucleotides in length, at least 40 contiguous nucleotides in length, at least 50 contiguous nucleotides in length, at least 100 contiguous nucleotides in length, or longer. Those of skill in the art understand that to avoid a high similarity to a reference sequence due to inclusion of gaps in the polynucleotide sequence, a gap penalty typically is introduced and is subtracted from the number of matches. Methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73:237-244 (1988); Higgins and Sharp, *CABIOS* 5:151-153 (1989); Corpet, et al., Nucleic Acids Research 16:10881-90 (1988); Huang, et al., Computer Applications in the *Biosciences,* 8:155-65 (1992), and Pearson, et al., *Methods in Molecular Biology,* 24:307-331 (1994). The BLAST family of programs, which can be used for database similarity searches, includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995). Unless otherwise stated, sequence identity/similarity values provided herein refer to the value obtained using the BLAST 2.0 suite of programs using default parameters. Altschul et al., *Nucleic Acids Res.* 25:3389-3402 (1997). Software for performing BLAST analyses is publicly available, e.g., through the National Center for Biotechnology-Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits then are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff (1989) *Proc. Natl. Acad. Sci. USA* 89:10915). In addition to calculating percent sequence identity, the BLAST algorithm also performs a statistical analysis of the similarity between two sequences (see, e.g., Karlin & Altschul, *Proc. Natl. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. BLAST searches assume that proteins may be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs may be employed to reduce such low-complexity alignments. For example, the SEG (Wooten and Federhen, *Comput. Chem.,* 17:149-163 (1993)) and XNU (Claverie and States, *Comput. Chem.,* 17:191-201 (1993)) low-complexity filters may be employed alone or in combination. (c) The term "sequence identity" or "identity" in the context of two nucleic acid or polypeptide sequences is used herein to refer to the residues in the two sequences that are the same when aligned for maximum correspondence over a specified comparison window. When percentage of sequence identity is used in reference to proteins it is recognized that residue positions that are not identical often differ by conservative amino acid substitutions, i.e., where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer*

*Applic. Biol. Sci.,* 4:11-17 (1988) e.g., as implemented in the program PC/GENE (Intelligenetics, Mountain View, Calif., USA). (d) The term "percentage of sequence identity" is used herein mean the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. (e) The term "substantial identity" of polynucleotide sequences means that a polynucleotide comprises a sequence that has at least 70% sequence identity, at least 80% sequence identity, at least 90% sequence identity and at least 95% sequence identity, compared to a reference sequence using one of the alignment programs described using standard parameters. One of skill will recognize that these values may be adjusted appropriately to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or at least 70%, at least 80%, at least 90%, or at least 95%. Another indication that nucleotide sequences are substantially identical is if two molecules hybridize to each other under stringent conditions. However, nucleic acids that do not hybridize to each other under stringent conditions are still substantially identical if the polypeptides that they encode are substantially identical. This may occur, e.g., when a copy of a nucleic acid is created using the maximum codon degeneracy permitted by the genetic code. One indication that two nucleic acid sequences are substantially identical is that the polypeptide that the first nucleic acid encodes is immunologically cross reactive with the polypeptide encoded by the second nucleic acid. Mutations may also be made to the nucleotide sequences of the present proteins by reference to the genetic code, including taking into account codon degeneracy.

The term "prime" (or "priming") as used herein refers to the process of increasing sensitivity to. When used in an immunological sense it refers to a process whereby a specific antigen is presented to naïve lymphocytes causing them to differentiate. Priming involves several steps: antigen uptake, processing, and cell surface expression bound to MHC molecules by an antigen presenting cell, recirculation and antigen-specific trapping of helper T cell precursors in lymphoid tissue, and T cell proliferation and differentiation. Janeway, C A, Jr., "The priming of helper T cells, Semin. Immunol. 1(1): 13-20 (1989).

The term "progression free survival" or "PFS" as used herein refers to length of time during and after the treatment of a disease, such as cancer, that a patient lives with the disease but it does not get worse. In a clinical trial, measuring the progression free survival is one way to determine how well a new treatment works.

The term "recurrence" as used herein with respect to cancer refers to a cancer that has recurred (come back), usually after a period of time during which the cancer could not be detected. The cancer may come back to the same place as the original (primary) tumor or to another place in the body.

The term "relapse-free survival (RFS)" as used herein refers to the length of time after primary treatment for a cancer during which the patient survives without any signs or symptoms of that cancer. Also called disease-free survival (DFS) and progression free survival (PFS).

The term "release" or "release of cytokine effector molecules" is meant to refer to the complex and tightly controlled process by which soluble mediators of the immune response are delivered from a given immune cell type to the external milieu after activation of a signaling cascade in response to receptor stimulation. In classical secretory pathways, cytokines with signal peptides are cotranslationally inserted into the endoplasmic reticulum (ER) for synthesis as either soluble or transmembrane precursors. They then are trafficked in vesicles to the Golgi complex for further processing, and at the trans-Golgi network (TGN) they are loaded into vesicles or carriers for constitutive delivery to the cell surface or other organelles. In specialized cell types, additional modes of secretion are proffered by loading cytokines and other cargo into granules for storage and later release. See Lacy, P. and Stow, J L, "Cytokine release from innate immune cells: association with diverse membrane trafficking pathways," Blood (2011) 118: 9-18. Cytokine release can be directly evoked by immunoglobulin- or complement receptor-mediated signaling or by pathogens through a diverse array of cellular receptors, including pattern recognition receptors such as TLRs.

The term "response rate" as used herein refers to the percentage of patients whose cancer shrinks or disappears after treatment.

The term "resistant cancer" as used herein refers to a cancer that does not respond to a treatment at the beginning of such treatment or sometime during such treatment.

The term "reporter gene" ("reporter") or "assay marker" refers to a gene and/or peptide that can be detected, or easily identified and measured. The expression of the reporter may be measured at either the RNA level, or at the protein level. The gene product, which may be detected in an experimental assay protocol, includes, but is not limited to, marker enzymes, antigens, amino acid sequence markers, cellular phenotypic markers, nucleic acid sequence markers, and the like. Researchers may attach a reporter gene to another gene of interest in cell culture, bacteria, animals, or plants. For example, some reporters are selectable markers, or confer characteristics upon on organisms expressing them allowing the organism to be easily identified and assayed. To introduce a reporter gene into an organism, researchers may place the reporter gene and the gene of interest in the same DNA construct to be inserted into the cell or organism. For bacteria or eukaryotic cells in culture, this may be in the form of a plasmid. Commonly used reporter genes may include, but are not limited to, fluorescent proteins, luciferase, beta-galactosidase, and selectable markers, such as chloramphenicol and kanomycin.

The term "secrete" as used herein when referring to a cell means a process whereby molecules manufactured within the cell are moved to a space outside of the cell.

The term"serial killer cell" as used herein refers to a population of cells that exhibit an ability to kill multiple tumor or pathogen-infected cells, while showing resistance to such killing action. There are multiple kinds of cells that display this effector function, e.g., NK cells, NKT cells, LAK cells, CIK cells, MAIT cells, CD8+ CTLs, CD4+ CTLs. The serial killer effector function may be direct, through cytolytic or cytotoxic activities, or indirect, through the immunoregulation of other cells and proteins that target pathogenic and cancerous cells.

The term "stably expressed exogenous immunomodulatory molecules" as used herein refers to exogenous immunomodulatory molecules that are expressed for a period of time that is sufficient to stimulate one or more of T-lymphocytes, natural killer (NK) cells, dendritic cells (DCs) or B lymphocytes sufficient to stimulate the T-lymphocytes, natural killer (NK) cells, dendritic cells (DCs) or B lymphocytes. According to some embodiments, the period of time is between 1 hour and 72 hours, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45 50, 55, 60, 65, 70, 71 or 72 hours. According to some embodiments, the period of time is more than 72 hours.

The term "stimulate" in any of its grammatical forms as used herein refers to inducing activation or increasing activity.

As used herein, the term "stimulate an immune cell" or "stimulating an immune cell" refers to a process (e.g., involving a signaling event or stimulus) causing or resulting in a cellular response, such as activation and/or expansion, of an immune cell, e.g. an NK cell and/or a CD8+ T cell. According to some embodiments, stimulating an immune cell (e.g., an NK cell and/or a CD8+ T cell) refers to providing a stimulus or signal (e.g., a stimulating polypeptide) that results in the activation and/or expansion of the immune cell.

As used herein, the term "sufficient to stimulate an immune cell" refers to an amount or level of a signaling event or stimulus, e.g. of exogenous immunomodulatory polypeptide, that promotes a cellular response of an immune cell.

As used herein, the terms "subject" or "individual" or "patient" are used interchangeably to refer to a member of an animal species of mammalian origin, including humans.

The phrase "subject in need thereof" as used herein refers to a patient that (i) will be administered an immunogenic composition according to the described invention, (ii) is receiving an immunogenic composition according to the described invention; or (iii) has received an immunogenic composition according to the described invention, unless the context and usage of the phrase indicates otherwise.

The term "SUPLEXA™ cells means autologous blood cells that have been stimulated in vitro by Engineered Leukocyte Stimulator (ENLIST™) cells.

The term "therapeutic agent" as used herein refers to a drug, molecule, nucleic acid, protein, metabolite, composition or other substance that provides a therapeutic effect. The term "active" as used herein refers to the ingredient, component or constituent of the compositions of the described invention responsible for the intended therapeutic effect. The terms "therapeutic agent" and "active agent" are used interchangeably herein. The term "therapeutic component" as used herein refers to a therapeutically effective dosage (i.e., dose and frequency of administration) that eliminates, reduces, or prevents the progression of a particular disease manifestation in a percentage of a population. An example of a commonly used therapeutic component is the ED50 which describes the dose in a particular dosage that is therapeutically effective for a particular disease manifestation in 50% of a population.

The terms "therapeutic amount", "therapeutically effective amount", an "amount effective", or "pharmaceutically effective amount" of an active agent is used interchangeably to refer to an amount that is sufficient to provide the intended benefit of treatment. However, dosage levels are based on a variety of factors, including the type of injury, the age, weight, sex, medical condition of the patient, the severity of the condition, the route of administration, and the particular active agent employed. Thus the dosage regimen may vary widely, but can be determined routinely by a physician using standard methods. Additionally, the terms "therapeutic amount", "therapeutically effective amounts" and "pharmaceutically effective amounts" include prophylactic or preventative amounts of the compositions of the described invention. In prophylactic or preventative applications of the described invention, pharmaceutical compositions or medicaments are administered to a patient susceptible to, or otherwise at risk of, a disease, disorder or condition in an amount sufficient to eliminate or reduce the risk, lessen the severity, or delay the onset of the disease, disorder or condition, including biochemical, histologic and/or behavioral symptoms of the disease, disorder or condition, its complications, and intermediate pathological phenotypes presenting during development of the disease, disorder or condition. It is generally preferred that a maximum dose be used, that is, the highest safe dose according to some medical judgment. The terms "dose" and "dosage" are used interchangeably herein.

The term "therapeutic effect" as used herein refers to a consequence of treatment, the results of which are judged to be desirable and beneficial. A therapeutic effect can include, directly or indirectly, the arrest, reduction, or elimination of a disease manifestation. A therapeutic effect can also include, directly or indirectly, the arrest reduction or elimination of the progression of a disease manifestation.

For any therapeutic agent described herein the therapeutically effective amount may be initially determined from preliminary in vitro studies and/or animal models. A therapeutically effective dose may also be determined from human data. The applied dose may be adjusted based on the relative bioavailability and potency of the administered compound. Adjusting the dose to achieve maximal efficacy based on the methods described above and other well-known methods is within the capabilities of the ordinarily skilled artisan.

General principles for determining therapeutic effectiveness, which may be found in Chapter 1 of Goodman and Gilman's The Pharmacological Basis of Therapeutics, 10th Edition, McGraw-Hill (New York) (2001), incorporated herein by reference, are summarized below.

Pharmacokinetic principles provide a basis for modifying a dosage regimen to obtain a desired degree of therapeutic efficacy with a minimum of unacceptable adverse effects. In situations where the drug's plasma concentration can be measured and related to the therapeutic window, additional guidance for dosage modification can be obtained.

Drug products are considered to be pharmaceutical equivalents if they contain the same active ingredients and are identical in strength or concentration, dosage form, and route of administration. Two pharmaceutically equivalent drug products are considered to be bioequivalent when the rates and extents of bioavailability of the active ingredient in the two products are not significantly different under suitable test conditions.

The term "therapeutic window" refers to a concentration range that provides therapeutic efficacy without unacceptable toxicity. Following administration of a dose of a drug, its effects usually show a characteristic temporal pattern. A lag period is present before the drug concentration exceeds the minimum effective concentration ("MEC") for the desired effect. Following onset of the response, the intensity of the effect increases as the drug continues to be absorbed and distributed. This reaches a peak, after which drug elimination results in a decline in the effect's intensity that disappears when the drug concentration falls back below the MEC. Accordingly, the duration of a drug's action is determined by the time period over which concentrations exceed the MEC. The therapeutic goal is to obtain and maintain concentrations within the therapeutic window for the desired response with a minimum of toxicity. Drug response below the MEC for the desired effect will be subtherapeutic, whereas for an adverse effect, the probability of toxicity will increase above the MEC. Increasing or decreasing drug dosage shifts the response curve up or down the intensity scale and is used to modulate the drug's effect. Increasing the dose also prolongs a drug's duration of action but at the risk of increasing the likelihood of adverse effects. Accordingly, unless the drug is nontoxic, increasing the dose is not a useful strategy for extending a drug's duration of action.

Instead, another dose of drug should be given to maintain concentrations within the therapeutic window. In general, the lower limit of the therapeutic range of a drug appears to be approximately equal to the drug concentration that produces about half of the greatest possible therapeutic effect, and the upper limit of the therapeutic range is such that no more than about 5% to about 10% of patients will experience a toxic effect. These figures can be highly variable, and some patients may benefit greatly from drug concentrations that exceed the therapeutic range, while others may suffer significant toxicity at much lower values. The therapeutic goal is to maintain steady-state drug levels within the therapeutic window. For most drugs, the actual concentrations associated with this desired range are not and need not be known, and it is sufficient to understand that efficacy and toxicity are generally concentration-dependent, and how drug dosage and frequency of administration affect the drug level. For a small number of drugs where there is a small (two- to three-fold) difference between concentrations resulting in efficacy and toxicity, a plasma-concentration range associated with effective therapy has been defined.

In this case, a target level strategy is reasonable, wherein a desired target steady-state concentration of the drug (usually in plasma) associated with efficacy and minimal toxicity is chosen, and a dosage is computed that is expected to achieve this value. Drug concentrations subsequently are measured and dosage is adjusted if necessary to approximate the target more closely.

In most clinical situations, drugs are administered in a series of repetitive doses or as a continuous infusion to maintain a steady-state concentration of drug associated with the therapeutic window. To maintain the chosen steady-state or target concentration ("maintenance dose"), the rate of drug administration is adjusted such that the rate of input equals the rate of loss. If the clinician chooses the desired concentration of drug in plasma and knows the clearance and bioavailability for that drug in a particular patient, the appropriate dose and dosing interval can be calculated.

As used herein the term "treating" includes abrogating, substantially inhibiting, slowing or reversing the progression of a condition, substantially ameliorating clinical symptoms of a condition, or substantially preventing the appearance of clinical symptoms of a condition. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously asymptomatic for the disorder(s).

A "tumor," as used herein, refers to all neoplastic cell growth and proliferation, whether malignant or benign, and all precancerous and cancerous cells and tissues.

The terms "tumor burden" or "tumor load" as used herein refer to the number of cancer cells, the size of a tumor, or the amount of cancer in the body.

The term "vaccinated" as used herein refers to being treated with a vaccine.

The term "vaccination" as used herein refers to treatment with a vaccine.

The term "vaccine" as used herein refers a substance or group of substances meant to cause the immune system to respond to a tumor or to microorganisms, or help the body recognize and destroy cancer cells or microorganisms. The term vaccine also refers to an artificial stimulus used to stimulate a robust immune response against that exposure (e.g. infectious agent, cancer cell).

The term "vaccine therapy" as used herein refers to a type of treatment that uses a substance or group of substances to stimulate the immune system to destroy a tumor or infectious microorganisms.

As used herein, the term "variant" refers to a polypeptide which differs from the original protein by one or more amino acid substitutions, deletions, insertions, or other modifications. These modifications do not significantly change the biological activity of the original protein. In many cases, a variant retains at least 10%, 20%, 30%, 40%, 50%, 60%, 70%, 80%, 90%, 95%, or 100% of the biological activity of original protein. The biological activity of a variant can also be higher than that of the original protein. A variant can be naturally-occurring, such as by allelic variation or polymorphism, or be deliberately engineered.

The amino acid sequence of a variant is substantially identical to that of the original protein. In many embodiments, a variant shares at least 50%, 60%, 70%, 80%, 85%, 90%, 95%, 99%, or more global sequence identity or similarity with the original protein. Sequence identity or similarity can be determined using various methods known in the art, such as Basic Local Alignment Tool (BLAST), dot matrix analysis, or the dynamic programming method. In one example, the sequence identity or similarity is determined by using the Genetics Computer Group (GCG) programs GAP (Needleman-Wunsch algorithm) The amino acid sequences of a variant and the original protein can be substantially identical in one or more regions, but divergent in other regions The term "wild-type" as used herein refers to the typical form of an organism, strain, gene, protein, nucleic acid, or characteristic as it occurs in nature. Wild-type refers to the most common phenotype in the natural population. The terms "wild-type" and "naturally occurring" are used interchangeably.

II. Allogeneic Vaccine

The present disclosure features allogeneic tumor cell vaccines comprising tumor cells expressing an exogenous immunomodulatory molecule, and methods of using the allogeneic tumor cell vaccine to stimulate an immune response. Vaccine proteins can induce immune responses that find use in the described invention e.g. in the treatment of cancer or infectious diseases. According to some embodiments, the allogeneic tumor cell vaccines described herein are effective to enhance immune activation of cells effective to recognize and act against tumor cells comprising the target tumor antigen in vivo without systemic inflammation; reduce immunosuppression in a tumor microenvironment for tumor cells comprising the target tumor antigen; or increase cell death of tumor cells expressing the target tumor antigen. According to some embodiments, the allogeneic tumor cell vaccines described herein are capable of immune activation without systemic inflammation.

According to some aspects, the disclosure features an allogeneic tumor cell vaccine comprising (1) a population of proliferation-incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising (a) a plurality of stably expressed exogenous immunomodulatory molecules sufficient to stimulate the T-lymphocytes, natural killer (NK) cells, dendritic cells (DCs) or B lymphocytes; and (2) a pharmaceutically acceptable carrier.

Tumor Specific Antigens

According to some embodiments, the disclosure provides a population of proliferation-incompetent tumor cells expressing one or more tumor specific antigens. According to some embodiments, the tumor specific antigens may be encoded by a primary open reading frame of gene products that are differentially expressed by tumors, and not by normal tissues. According to some embodiments, the tumor specific antigens may be encoded by mutated genes, intronic sequences, or translated alternative open reading frames, pseudogenes, antisense strands, or may represent the products of gene translocation events. According to some embodiments, the tumor cell provides a broad array of tumor specific antigens, many of which are of unknown nature. According to some embodiments, the tumor antigen is a neoantigen.

According to some embodiments, the tumor specific antigen is selected from one of the following groups: (a) nonmutated shared antigens (e.g., melanoma-associated antigen (MAGE), B-melanoma antigen (BAGE), renal tumor antigen (RAGE), and a cancer testis antigen (e.g. NY-ESO); (b) differentiation antigens (e.g., prostate-specific membrane antigen [PSMA] and prostate-specific antigen (PSA) in prostate carcinoma, Mart1/MelanA and tyrosinase present in many melanomas, and carcino embryonic antigen (CEA) present in a large percentage of colon cancers), which are tissue restricted and present in lineage-specific tumor cell; (c) mutated oncogenes and tumor suppressor genes (e.g., mutated ras, rearranged bcr/abl, mutated p53), which provide novel epitopes for immune recognition; (d) unique idiotypes (e.g., immunoglobulin antigensin myeloma and B-cell myeloma, T-cell receptor (TCR) expressed in CTCL), (e) oncovirus-derived epitopes (e.g., the human papillomavirus-encoded E6 and E7 proteins, Epstein-Barr virus-associated antigens present in primary brain lymphoma); and (f) nonmutated oncofetal proteins such as CEA, α-fetoprotein, and survivin. According to some embodiments, the tumor specific antigen is selected from an antigen listed in the publically available Cancer Antigenic Peptide Database (on the world wide web at caped.icp.ucl.ac.be/Peptide/list, incorporated by reference in its entirety herein). According to some embodiments, the tumor specific antigen is selected from an antigen set forth in Table 1, shown below.

TABLE 1

| Gene/Protein | Tumor |
| --- | --- |
| PPP1R3B | melanoma |
| alpha-actinin-4 | lung carcinoma |
| ARTC1 | melanoma |

TABLE 1-continued

| Gene/Protein | Tumor |
| --- | --- |
| CASP-8 | head and neck squamous cell carcinoma |
| beta-catenin | melanoma |
| Cdc27 | melanoma |
| CDK4 | melanoma |
| CDK12 | melanoma |
| CDKN2A | melanoma |
| CLPP | melanoma |
| CSNK1A1 | melanoma |
| EFTUD2 | melanoma |
| Elongation factor 2 | lung squamous CC |
| FN1 | melanoma |
| GAS7 | melanoma |
| GPNMB | melanoma |
| HAUS3 | melanoma |
| HSDL1 | ovarian cancer |
| LDLR-fucosyltransferaseAS fusion protein | melanoma |
| HLA-A2d | renal cell carcinoma |
| HLA-A11d | melanoma |
| hsp70-2 | renal cell carcinoma bladder tumor |
| MART2 | melanoma |
| MATN | melanoma |
| k-ras | non-small cell lung carcinoma |
| MUM-1f | melanoma |
| MUM-2 | melanoma |
| MUM-3 | melanoma |
| neo-PAP | melanoma |
| NFYC | lung squamous cell carcinoma |
| OS-9 | melanoma |
| PTPRK | melanoma |
| N-ras | melanoma |
| BRAF600 | melanoma |
| SIRT2 | melanoma |
| SNRPD1 | melanoma |
| Triosephosphate isomerase | melanoma |
| Myosin class I | melanoma |
| BCR-ABL fusion protein (b3a2) | chronic myeloid leukemia |
| B-RAF | melanoma |
| CASP-5 | colorectal, gastric, and endometrial carcinoma |
| dek-can fusion protein | myeloid leukemia |
| ETV6-AML1 fusion protein | acute lymphoblastic leukemia |
| FLT3-ITD | acute myelogenous leukemia |
| FNDC3B | chronic lymphocytic leukemia |
| OGT | colorectal carcinoma |
| p53 | head and neck squamous cell carcinoma |
| pml-RARalpha fusion protein | promyelocytic leukemia |
| PRDX5 | melanoma |
| K-ras | pancreatic adenocarcinoma |
| SYT-SSX1 or -SSX2 fusion protein | sarcoma |
| KIAAO205 | mutation |
| ME1 | mutation |
| EGFRvIII | Mutation |
| TGF-betaRII | colorectal carcinoma |
| gp100/Pmel17 | melanoma |
| mammaglobin-A | breast cancer |
| Melan-A/MART-1 | melanoma |
| NY-BR-1 | breast cancer |
| OA1 | melanoma |
| PAP | prostate cancer |
| PSA | prostate carcinoma |
| RAB38/NY-MEL-1 | melanoma |
| TRP-1/gp75 | melanoma |
| TRP-2 | melanoma |

TABLE 1-continued

| Gene/Protein | Tumor |
|---|---|
| tyrosinase | melanoma |
| DKK1 | testis, prostate, |
| ENAH (hMena) | breast, prostate stroma and epithelium of colon-rectum, pancreas, endometrium |
| G250/MN/CAIX | stomach, liver, pancreas |
| Kallikrein 4 | prostate and ovarian cancer |
| D393-CD20n | B cell lymphomas and leukemias |
| Cyclin-A1 | AML, testicular, endometrial and epithelial ovarian cancer |
| GAGE-1,2,8 | |
| GAGE-3,4,5,6,7 | |
| GnTVf | |
| GPC3 | Hepatocellular carcinoma, melanoma, lung squamous cell carcinoma, hepatoblastoma, ovarian clear cell carcinoma, neuroblastoma, stomach kidney |
| HERV-E | |
| HERV-K-MEL | melanoma |
| KK-LC-1 | |
| KM-HN-1 | |
| LAGE-1 | Melanoma, non-small cell lung carcinoma, bladder, prostate and head and neck cancer |
| LY6K | Breast cancer |
| MAGE-A1 | melanoma |
| MAGE-A2 | melanoma |
| MAGE-A3 | melanoma |
| MAGE-A4 | melanoma |
| MAGE-A5 | melanoma |
| MAGE-A6 | melanoma |
| MAGE-A7 | melanoma |
| MAGE-A8 | melanoma |
| MAGE-A9 | melanoma |
| MAGE-A10 | melanoma |
| MAGE-A11 | melanoma |
| MAGE-A12m | melanoma |
| MAGE-C1 | melanoma |
| MAGE-C2 | melanoma |
| MAGE-n | melanoma |
| mucink | |
| NA88-A | |
| NY-ESO-1/LAGE-2 | melanoma |
| Neutrophil granule proteases | |
| OFA-iLR | |
| PTH-rP | |
| S2 | |
| SAGE | |
| Sp17 | |
| SSX-2 | |
| SSX-4 | |
| TAG | |
| TAG-1 | |
| TAG-2 | |
| hTERT | colorectal carcinoma |
| TPBG | |
| TRAG-3 | |
| TRP2-6b | |
| TRP2-INT2g | |
| TTK | |
| XAGE-1b/GAGED2a | |
| ART-4 | |
| CDCA1/NUF2 | |
| Cep55/c10orf3 | |
| CML28 (EXOSC5) | |
| DAM-6, -10 (MAGE-B1) | |
| IMP-3 | |
| OVA66 | |
| OY-TES-1 | |
| PASD1 | |
| RHAMM/CD168 | |

TABLE 1-continued

| Gene/Protein | Tumor |
|---|---|
| SART-3 | |
| SART-1 | |

According to some embodiments, the tumor cell is from a cancer selected from the group consisting of melanoma, colorectal carcinoma, leukemia, chronic myeloid leukemia, prostate cancer, head and neck cancer, squamous cell carcinoma, tongue cancer, larynx cancer, tonsil cancer, hypopharynx cancer, nasalpharynx cancer, breast cancer, colon cancer, lung cancer, pancreatic cancer, glioblastoma and brain cancer.

According to some embodiments, the melanoma tumor cell is characterized by the expression of one or more of gp100, tyrosinase, Melan-A, tyrosinase-related protein (TRP-2-INT2), melanoma antigen-1 (MAGE-A1), NY-ESO-1, preferentially expressed antigen of melanoma (PRAIVIE) CDK4 and multiple myeloma oncogene 1 (MUM-1).

According to some embodiments, the colorectal cancer tumor cell is characterized by the expression of one or more of carcinoembryonic antigen (CEA), MAGE, HPV, human telomerase reverse transcriptase (hTERT), EPCAM, PD-1, PD-L1, p53, cell surface-associated mucin 1 (MUC1).

Immunologic antigenic specificity may arise from one or more of the amino acid sequence of the antigen, from the degree of expression of that antigen by the tumor cell, from post-translational modification of the antigen, and the like.

Immunologic antigen specificity to a certain type of cancer cell may also arise from one or more of a particular fingerprint of a plurality of tumor antigens, from the fact that a particular antigen, while expressed by a wide variety of tumor cells, has particular use in immunotherapy against a smaller number of tumor types, from the fact that a particular collection of MHC class I presentable and MHC class II presentable epitopes exist on a particular polypeptide or polypeptide fragment, and by omitting one or more peptides that may provoke immunotolerance. The skilled artisan can locate the relevant nucleic acid and polypeptide sequences, e.g., on the U.S. government's web site, at ncbi.nlm.nih.

According to some embodiments, the tumor cells are derived from a sample from a subject. According to some embodiments, the tumor cells are derived from a tumor cell line or tumor cell line variant.

According to some embodiments, tumor antigen specificity of the present invention may be determined by the parental tumor cell line or tumor cell line variant that is selected for modification with immunomodulators.

Parent Cell Lines

According to some embodiments, tumor cell line or tumor cell line variants may be derived from established cell lines from either public sources (e.g. NIH, DCTD Tumor Repository operated by Charles River Laboratories Inc.) or commercial sources (e.g. ATCC, Sigma Alrich, Thermo Fischer Scientific, Genescript, DSM2). According to some embodiments, new cell lines can be established de novo from tumor cells derived from the tumor of a cancer patient.

According to some embodiments, cancer tissues, cancer cells, cells infected with a cancer-causing agent, other preneoplastic cells, and cell lines of human origin can be used as a source. According to some embodiments, a cancer cell can be from an established tumor cell line or tumor cell line variant such as, without limitation, an established non-small cell lung carcinoma (NSCLC), a bladder cancer, a melanoma, an ovarian cancer, a renal cell carcinoma, a prostate carcinoma, a sarcoma, a breast carcinoma, a squamous cell carcinoma, a head and neck carcinoma, a hepatocellular carcinoma, a pancreatic carcinoma, or a colon carcinoma cell line.

According to some embodiments, the established cell lines comprise the LNCaP clone FGC (ATCC CRL-1740), which itself is derived from a metastatic prostate cancer that had migrated to a lymph node. According to some embodiments, the established cell lines comprise the PC-3 (ATCC CRL-1435) cell line, which itself is derived from metastatic prostate cancer that migrated to bone. According to some embodiments, the tumor cell line or tumor cell line variants are derived from one or more of the following ATCC cell lines: VCaP (ATCC CRL-2876); MDA PCa 2b (ATCC CRL-2422); or DU 145 (ATCC HTB-81).

According to some embodiments, the established cell lines comprise the SK-MEL-2 clone (ATCC HTB-68), which itself is derived from metastasis on skin of thigh.

According to some embodiments, the established cell lines comprise one or more of mammary carcinoma cell lines designated COO-G, DU4475, ELL-G, HIG-G, MCF/7, MDA-MB-436, MX-1, SW-613, and VAN-G. According to some embodiments, the established cell lines comprise one or more of alveolar soft part sarcoma cell lines designated ASPS, and ASPS-1. According to some embodiments, the established cell lines comprise one or more lung cell lines designated LX-1, COS-G, H-MESO-1, H-MESO-1A, NCI-H23, and NCI-H460. According to some embodiments, the established cell lines comprise one or more colon cancer cell lines designated CX-5, GOB-G, HCC-2998, HCT-15, KLO-G, KM20L2, MRI-H-194, LOVO I, LOVO II, and MRI-H-250. According to some embodiments, the established cell lines comprise one or more melanoma cell lines designated NIS-G, TRI-G, WIL-G, MRI-H-121B, MRI-H-187, MRI-H-221, and MRI-H-255. According to some embodiments, the established cell lines comprise one or more cervical cancer cell lines designated MRI-H-177, MRI-H-186, MRI-H-196, and MRI-H-215. According to some embodiments, the established cell lines comprise one or more kidney cancer cell lines designated MRI-H-121 and MRI-H-166. According to some embodiments, the established cell lines comprise one or more endometrium cancer cell lines designated MRI-H-147 and MRI-H-220. According to some embodiments, the established cell lines comprise one or more ovarian cancer cell lines designated MRI-H-258, MRI-H-273, MRI-H-1834, and SWA-G. According to some embodiments, the established cell lines comprise one or more sarcoma cell lines designated HS-1, OGL-G, and DEL-G. According to some embodiments, the established cell lines comprise the epidermoid cell line designated DEAC-1. According to some embodiments, the established cell line comprises the glioblastoma cell line designated SF 295. According to some embodiments, the established cell line comprises the prostate cancer cell line designated CWR-22. According to some embodiments, the established cell line comprises the Burkitt's lymphoma cell line designated DAU. According to some embodiments, the foregoing established cell lines described herein are commercially available, e.g. from American Type Culture Collection (ATCC), European Collection of Cell Cultures (ECACC), or any depository listed as an International Depositary Authority (IDA) under Article 7 of the Budapest Treaty.

According to some embodiments, exemplary established cell lines comprise one or more of the following cell lines shown below:

| Designation | Tissue of Origin | Histologic Type |
|---|---|---|
| 786-0 | Kidney | Renal Cell Carcinoma |
| A2780 | Ovary | Adenocarcinoma |
| A498 | Kidney | Renal Cell Carcinoma |
| A549 | Lung | Non-small Cell |
| A704 | Kidney | Renal Cell Carcinoma |
| ACHN | Kidney | Renal Cell Carcinoma |
| ASPS-1 | Lymph | Node Alveolar Soft Part Sarcoma |
| BT-549 | Breast | Adenocarcinoma |
| CAKI-1 | Kidney | Renal Cell Carcinoma |
| CCRF-CEM | Lymph | Leukemia |
| CCRF-SB | Lymph | Leukemia |
| CHA-59 | Bone | Osteosarcoma |
| COLO 205 | Colon | Adenocarcinoma |
| DMS-114 | Lung | Small Cell |
| DU-145 | Prostate | Carcinoma |
| EKVX | Lung | Adenocarcinoma |
| HCC-2998 | Colon | Adenocarcinoma |
| HCT-15 | Colon | Carcinoma |
| HCT-116 | Colon | Adenocarcinoma |
| HOP-18 | Lung | Large Cell Carcinoma |
| HOP-62 | Lung | Adenocarcinoma |
| HL-60 | Ascites | Pro-myelocytic Leukemia |
| H-MESO-1 | | Mesothelioma |
| HS 578T | Breast | Adenocarcinoma |
| HS 913T | Lung | Mixed Cell |
| HT-29 | Colon | Adenocarcinoma |
| IGR-OV1 | Ovary | Adenocarcinoma |
| KM-12 | Colon | Adenocarcinoma |
| KM 20L2 | Colon | Adenocarcinoma |
| K-562 | Lymph | Leukemia |
| LOVO | Colon | Adenocarcinoma |
| LOX IMVI | Lymph Node Metastisis | Amelanotic Melanoma |
| LXFL 529 | Lung | Large Cell Carcinoma |
| NCI-H1299 | Lung | Adenocarcinoma |
| NCI-H2887 | Lung | Adenocarcinoma |
| NCI-H3122 | Lung | Adenocarcinoma |
| NCI-H322M | Lung | Adenocarcinoma |
| NCI-H3255 | Lung | Adenocarcinoma |
| NCI-H358M | Lung | Bronchioalveolar Carcinoma |
| NCI-H460 | Lung | Large Cell |
| NCI-H522 | Lung | Adenocarcinoma |
| NCI-H69 | Lung | Small Cell Carcinoma |
| NCI-H82 | Lung | Small Cell Carcinoma |
| NCI-H838 | Lung | Adenocarcinoma |
| NCI/ADR-RES | Ovary | Adenocarcinoma |
| OVCAR-3 | Ovary | Adenocarcinoma |
| OVCAR-4 | Ovary | Adenocarcinoma |
| OVCAR-5 | Ovary | Adenocarcinoma |
| OVCAR-8 | Ovary | Adenocarcinoma |
| PC-3 | Prostate | Carcinoma |
| PC-3/M | Prostate | Carcinoma |
| RPMI-7951 | Skin | Melanoma |
| RPMI-8226 | Lymph | Leukemia |
| RXF 393 | Kidney | Renal Cell Carcinoma |
| RXF 631 | Kidney | Renal Cell Carcinoma |
| TK-10 | Kidney | Renal Cell Carcinoma |
| UACC-62 | Skin | Melanoma |
| UACC-257 | Skin | Melanoma |
| UCSD 242L | Skin | Melanoma |
| UCSD 354K | Skin | Melanoma |
| UO-31 | Kidney | Renal Cell Carcinoma |
| U-251 | CNS | Glioblastoma |
| WIDR | Colon | Adenocarcinoma |
| XF 498 | CNS | Glioblastoma |

According to some embodiments, the choice of the parental cell line from which the tumor cell line or tumor cell line variant may be derived affects the specificity of the allogeneic vaccine. For example, the use of a tumor cell line or tumor cell line variant derived from metastatic prostate cancer that migrated to the bone of a patient may result in an allogeneic vaccine that elicits an immune response specific for metastatic prostate cancer in the bone of a patient.

According to some embodiments, the tumor cell line or tumor cell line variants may be derived from a parental cell that comprises a universal cancer specific antigen. For example, the use of a parental tumor cell line or tumor cell line variant derived from metastatic prostate cancer that migrated to the bone of a patient may result in an allogeneic vaccine that elicits an immune response against all prostate cancer cells.

According to some embodiments, the tumor cell line or tumor cell line variants are derived from patient derived cells derived from various cancers. According to some embodiments, fresh tissue surgically removed from a tumor is enzymatically digested by type IV collagenase, followed by collection of disaggregated cells. According to some embodiments, disaggregated cells may then be grown in vitro in growth media with 10% fetal bovine serum on an extracellular matrix substrate, such as collagen or fibronectin, to promote attachment. According to some embodiments, adherent cells may then be passaged until the immortal cancer cells outgrow the non-cancerous fibroblast cells.

For example, according to some embodiments, the tumor cell line or tumor cell line variants may be derived from a solid tumor comprising tumor cells, including cancer stem cells, a metastatic cancer comprising metastatic tumor cells, comprising cancer stem cells, or a non-metastatic cancer. According to some embodiments, the cancer may originate in the bladder, blood, bone, bone marrow, brain, breast, colon, esophagus, duodenum, small intestine, large intestine, colon, rectum, anus, gum, head, kidney, liver, lung, nasopharynx, neck, ovary, prostate, skin, stomach, testis, tongue, or uterus. According to some embodiments, the cancer may be of a histological type, e.g., a cancer that begins in the skin or tissues that line or cover internal organs (carcinoma); a cancer that begins in bone or in the soft tissue of the body including cartilage, fat, muscle, blood vessels, and fibrous tissue (sarcoma); a cancer that starts in blood-forming tissue (leukemia); a cancer that begins in cells of the immune system (lymphoma); a cancer that arises in plasma cells (myeloma), or a brain/spinal cord cancer.

Examples of carcinomas include, without limitation, giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; an adenocarcinoma; a gastrinoma, a cholangiocarcinoma; a hepatocellular carcinoma; a combined hepatocellular carcinoma and cholangiocarcinoma; a trabecular adenocarcinoma; an adenoid cystic carcinoma; an adenocarcinoma in adenomatous polyp; an adenocarcinoma, familial polyposis *coli*; a solid carcinoma; a carcinoid tumor; a branchiolo-alveolar adenocarcinoma; a papillary adenocarcinoma; a chromophobe carcinoma; an acidophil carcinoma; an oxyphilic adenocarcinoma; a basophil carcinoma; a clear cell adenocarcinoma; a granular cell carcinoma; a follicular adenocarcinoma; a non-encapsulating sclerosing carcinoma; adrenal cortical carcinoma; an endometroid carcinoma; a skin appendage carcinoma; an apocrine adenocarcinoma; a sebaceous adenocarcinoma; a ceruminous adenocarcinoma; a mucoepidermoid carcinoma; a cystadenocarcinoma; a papillary cystadenocarcinoma; a papillary serous cystadenocarcinoma; a mucinous cystadenocarcinoma; a mucinous adenocarcinoma; a signet ring cell carcinoma; an infiltrating duct carcinoma; a medullary carcinoma; a lobular carcinoma; an inflammatory carcinoma; paget's disease, a mammary acinar cell carcinoma; an adenosquamous carcinoma; an adenocarcinoma w/squamous metaplasia; a sertoli cell carcinoma; embryonal carcinoma; choriocarcinoma.

Examples of sarcomas include, without limitation, glomangiosarcoma; sarcoma; fibrosarcoma; myxosarcoma; liposarcoma; leiomyosarcoma; rhabdomyosarcoma; embryonal rhabdomyosarcoma; alveolar rhabdomyosarcoma; stromal sarcoma; carcinosarcoma; synovial sarcoma; hemangiosarcoma; kaposi's sarcoma; lymphangiosarcoma; osteosarcoma; juxtacortical osteosarcoma; chondrosarcoma; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; myeloid sarcoma; mast cell sarcoma.

Examples of leukemias include, without limitation, leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; and hairy cell leukemia.

Examples of lymphomas and myelomas include, without limitation, malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant melanoma; amelanotic melanoma; superficial spreading melanoma; malignant melanoma in giant pigmented nevus; epithelioid cell melanoma; multiple myeloma.

Examples of brain/spinal cord cancers include, without limitation, pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant.

Examples of other cancers include, without limitation, a thymoma; an ovarian stromal tumor; a thecoma; a granulosa cell tumor; an androblastoma; a leydig cell tumor; a lipid cell tumor; a paraganglioma; an extra-mammary paraganglioma; a pheochromocytoma; blue nevus, malignant; fibrous histiocytoma, malignant; mixed tumor, malignant; mullerian mixed tumor; nephroblastoma; hepatoblastoma; mesenchymoma, malignant; brenner tumor, malignant; phyllodes tumor, malignant; mesothelioma, malignant; dysgerminoma; teratoma, malignant; struma ovarii, malignant; mesonephroma, malignant; hemangioendothelioma, malignant; hemangiopericytoma, malignant; chondroblastoma, malignant; granular cell tumor, malignant; malignant histiocytosis; immunoproliferative small intestinal disease.

For any given tumor type, several tumor cell line or tumor cell line variants may be commercially available. According to some embodiments, pooling of several of these cells lines, either as a mixture of whole cells or by making a membrane preparation out of the mixture of whole cells, may provide an array of cell surface tumor antigens for that tumor type.

According to some embodiments, the tumor cells or tumor cell line or tumor cell line variants are rendered proliferation incompetent by irradiation.

Exogenous Immunomodulatory Molecules

According to some embodiments, an exogenous immunomodulatory molecule of the disclosed invention is a polypeptide that, alone or in combination with other exogenous immunomodulatory molecules, mediates stimulation of an immune cell. According to some embodiments, an exogenous immunomodulatory molecule of the disclosed invention is a polypeptide that, alone or in combination with other exogenous immunomodulatory molecules, mediates stimulation of T-lymphocytes, natural killer (NK) cells, dendritic cells (DCs) or B lymphocytes. According to some embodiments, the NK cell is a memory-like NK cell. According to some embodiments, the T lymphocyte is a cytotoxic T-lymphocyte (CTL) (CD8+ T cell). According to some embodiments, the T lymphocyte is a memory T cell. According to some embodiments, the T lymphocyte is a regulatory T cell. According to some embodiments, the T lymphocyte is a helper T cell. According to some embodiments, the B lymphocyte is a memory B cell. It is a feature of the present invention that, according to some embodiments, the exogenous immunomodulatory molecules comprising the population of tumor cells are effective to stimulate more than one type of immune cell, e.g. the allogeneic tumor cell vaccine comprising a population of proliferation incompetent tumor cells of the present disclosure are effective to stimulate one or more of T-lymphocytes (e.g. CD8+ T cells), natural killer (NK) cells, dendritic cells (DCs) or B lymphocytes.

According to some embodiments, stimulating an immune cell refers to expansion of the immune cell. According to some embodiments, stimulating an immune cell refers to activation of the immune cell. According to some embodiments, stimulating an immune cell refers to an increase in cytoxicity of the immune cell. According to some embodiments, stimulating the immune cell refers to a combination of one or more of expansion, activation and/or increased cytoxicity of the immune cell. According to some embodiments, the one or more exogenous immunomodulatory molecules expressed by the population of tumor cells are effective to activate and/or expand immune cells (e.g. T-lymphocytes (e.g. CD8+ T cells), natural killer (NK) cells, dendritic cells (DCs) or B lymphocytes) ex vivo. According to some embodiments, the one or more exogenous immunomodulatory molecules expressed by the population of tumor cells are effective to activate and/or expand immune killer cells (e.g. T-lymphocytes (e.g. CD8+ T cells), natural killer (NK) cells, dendritic cells (DCs) or B lymphocytes) in vivo. Assays to detect if the exogenous immunostimulatory molecules are effective to stimulate an immune killer cell are described herein. According to one aspect, the disclosure thus provides an allogeneic tumor cell vaccine comprising a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising a plurality of stably expressed exogenous immunomodulatory molecules sufficient to stimulate the T-lymphocytes (e.g. CD8+ T cells), natural killer (NK) cells, dendritic cells (DCs) or B lymphocytes.

According to some embodiments, the allogeneic vaccine comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least three stably expressed exogenous immunomodulatory molecules effective to stimulate the T-lymphocytes, natural killer (NK) cells, dendritic cells (DCs) or B lymphocytes. According to some embodiments, the allogeneic vaccine comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least four stably expressed exogenous immunomodulatory molecules effective to stimulate the T-lymphocytes, natural killer (NK) cells, dendritic cells (DCs) or B lymphocytes. According to some embodiments, the allogeneic vaccine comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least five stably expressed exogenous immunomodulatory molecules effective to stimulate the T-lymphocytes, natural killer (NK) cells, dendritic cells (DCs) or B lymphocytes. According to some embodiments, the allogeneic vaccine comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least five stably expressed exogenous immunomodulatory molecules effective to stimulate the T-lymphocytes, natural killer (NK) cells, dendritic cells (DCs) or B lymphocytes. According to some embodiments, the allogeneic vaccine comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least six stably expressed exogenous immunomodulatory molecules effective to stimulate the T-lymphocytes, natural killer (NK) cells, dendritic cells (DCs) or B lymphocytes. According to some embodiments, the allogeneic vaccine comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least seven stably expressed exogenous immunomodulatory molecules effective to stimulate the T-lymphocytes, natural killer (NK) cells, dendritic cells (DCs) or B lymphocytes. According to some embodiments, the allogeneic vaccine comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least eight stably expressed exogenous immunomodulatory molecules effective to stimulate the T-lymphocytes, natural killer (NK) cells, dendritic cells (DCs) or B lymphocytes. According to some embodiments, the allogeneic vaccine comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least nine stably expressed exogenous immunomodulatory molecules effective to stimulate the T-lymphocytes, natural killer (NK) cells, dendritic cells (DCs) or B lymphocytes. According to some embodiments, the allogeneic vaccine comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least ten stably expressed exogenous immunomodulatory molecules effective to stimulate the T-lymphocytes, natural killer (NK) cells, dendritic cells (DCs) or B lymphocytes. According to some embodiments, the allogeneic vaccine comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least eleven stably expressed exogenous immunomodulatory molecules effective to stimulate the T-lymphocytes, natural killer (NK) cells, dendritic cells (DCs) or B lymphocytes. According to some embodiments, the allogeneic vaccine comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least twelve stably expressed exogenous immunomodulatory molecules effective to stimulate the T-lymphocytes, natural killer (NK) cells, dendritic cells (DCs) or B lymphocytes. According to some embodiments, the allogeneic vaccine comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least thirteen stably expressed exogenous immunomodulatory molecules effective to stimulate the T-lymphocytes, natural killer (NK) cells, dendritic cells (DCs) or B lymphocytes. According to some embodiments, the allogeneic vaccine comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least fourteen stably expressed exogenous immunomodulatory molecules effective to stimulate the T-lymphocytes, natural killer (NK) cells, dendritic cells (DCs) or B lymphocytes. According to some embodiments, the allogeneic vaccine comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least fifteen stably expressed exogenous immunomodulatory molecules effective to stimulate the T-lymphocytes, natural killer (NK) cells, dendritic cells (DCs) or B lymphocytes. According to some embodiments, the allogeneic vaccine comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least sixteen stably expressed exogenous immunomodulatory molecules effective to stimulate the T-lymphocytes, natural killer (NK) cells, dendritic cells (DCs) or B lymphocytes. According to some embodiments, the allogeneic vaccine comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least seventeen stably expressed exogenous immunomodulatory molecules effective to stimulate the T-lymphocytes, natural killer (NK) cells, dendritic cells (DCs) or B lymphocytes. According to some embodiments, the allogeneic vaccine comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least eighteen stably expressed exogenous immunomodulatory molecules effective to stimulate the T-lymphocytes, natural killer (NK) cells, dendritic cells (DCs) or B lymphocytes. According to some embodiments, the allogeneic vaccine comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least nineteen stably expressed exogenous immunomodulatory molecules effective to stimulate the T-lymphocytes, natural killer (NK) cells, dendritic cells (DCs) or B lymphocytes. According to some embodiments, the allogeneic vaccine comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least twenty stably expressed exogenous immunomodulatory molecules effective to stimulate the T-lymphocytes, natural killer (NK) cells, dendritic cells (DCs) or B lymphocytes. According to some embodiments, the allogeneic vaccine comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least twenty-one stably expressed exogenous immunomodulatory molecules effective to stimulate the T-lymphocytes, natural killer (NK) cells, dendritic cells (DCs) or B lymphocytes. According to some embodiments, the allogeneic vaccine comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least twenty-two stably expressed exogenous immunomodulatory molecules effective to stimulate the T-lymphocytes, natural killer (NK) cells, dendritic cells (DCs) or B lymphocytes. According to some embodiments, the allogeneic vaccine comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least twenty-three stably expressed exogenous immunomodulatory molecules effective to stimulate the T-lymphocytes, natural killer (NK) cells, dendritic cells (DCs) or B lymphocytes. According to some embodiments, the allogeneic vaccine comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least twenty-four stably expressed exogenous immunomodulatory molecules effective to stimulate the T-lymphocytes, natural killer (NK) cells, dendritic cells (DCs) or B lymphocytes. According to some embodiments, the allogeneic vaccine comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least twenty-five stably expressed exogenous immunomodulatory molecules effective to stimulate the T-lymphocytes, natural killer (NK) cells, dendritic cells (DCs) or B lymphocytes. According to some embodiments, the allogeneic vaccine comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least twenty-six stably expressed exogenous immunomodulatory molecules effective to stimulate the T-lymphocytes, natural killer (NK) cells, dendritic cells (DCs) or B lymphocytes. According to some embodiments, the allogeneic vaccine comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least twenty-seven stably expressed exogenous immunomodulatory molecules effective to stimulate the T-lymphocytes, natural killer (NK) cells, dendritic cells (DCs) or B lymphocytes. According to some embodiments, the allogeneic vaccine comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least twenty-eight stably expressed exogenous immunomodulatory molecules effective to stimulate the T-lymphocytes, natural killer (NK) cells, dendritic cells (DCs) or B lymphocytes. According to some embodiments, the allogeneic vaccine comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least twenty-nine stably expressed exogenous immunomodulatory molecules effective to stimulate the T-lymphocytes, natural killer (NK) cells, dendritic cells (DCs) or B lymphocytes. According to some embodiments, the allogeneic vaccine comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising at least thirty stably expressed exogenous immunomodulatory molecules effective to stimulate the T-lymphocytes, natural killer (NK) cells, dendritic cells (DCs) or B lymphocytes.

According to some embodiments, the allogeneic vaccine comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population characterized by the expression of three stably expressed exogenous immunomodulatory molecules effective to stimulate the T-lymphocytes, natural killer (NK) cells, dendritic cells (DCs) or B lymphocytes.

According to some embodiments, the population of tumor cells comprises a first exogenous immunomodulatory molecule and a second exogenous immunomodulatory molecule. According to some embodiments, the population of tumor cells comprises a first exogenous immunomodulatory molecule, a second exogenous immunomodulatory molecule and a third exogenous stimulatory molecule. According to some embodiments, the first exogenous immunomodulatory molecule and the second exogenous immunomodulatory molecule comprise a chimeric or fusion molecule, for example a molecule created through the joining of two or more separate genes, each of which encodes at least one domain of a protein so that the genes are transcribed and translated as a single unit, producing a single polypeptide. According to some embodiments, the allogeneic vaccine described herein comprises tumor cells comprising one or more exogenous immunomodulatory molecules, wherein a first tumor cell, or population of tumor cells, comprises a first immunomodulatory molecule, and a second tumor cell, or population of tumor cells, comprises a second immunomodulatory molecule. According to some embodiments, the allogeneic vaccine described herein comprises tumor cells comprising one or more exogenous immunomodulatory molecules, wherein a first tumor cell, or population of tumor cells, comprises a first and a second immunomodulatory molecule, and a second tumor cell, or population of tumor cells, comprises a third immunomodulatory molecule. Thus, it is understood that the exogenous immunomodulatory molecules described herein can be present in a tumor cell population in cis (all on the same cell) or in trans (each, or a combination of each, on different cells). According to some embodiments, the exogenous immunostimulatory molecules are presented at the surface of the genetically engineered tumor cells.

According to some embodiments, the exogenous immunomodulatory molecules are particularly selected from a group for their ability to either initiate an anti-tumor immune response, and/or to sustain an anti-tumor immune response, and/or for their ability to abrogate pre-existing immunosuppression characteristically present in cancer patients, or a combination of all three. According to some embodiments, combinations of immunomodulatory molecules are evaluated and selected by a human mixed lymphocyte tumor cell reaction. According to some embodiments, the exogenous immunomodulatory molecule is selected from a cytokine, a TNF-family member, a secreted receptor, a chaperone, an IgG superfamily member and a chemokine receptor.

According to some embodiments, the allogeneic tumor cell vaccine of the present disclosure comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising a plurality of stably expressed exogenous immunomodulatory molecules effective to stimulate the T-lymphocytes, natural killer (NK) cells, dendritic cells (DCs) or B lymphocytes, wherein the exogenous immunomodulatory molecules comprise one or more cytokine proteins; wherein the exogenous immunomodulatory molecules comprise one or more TNF family member proteins; wherein the exogenous immunomodulatory molecules comprise one or more secreted receptor proteins; wherein the exogenous immunomodulatory molecules comprise one or more chaperone proteins; wherein the exogenous immunomodulatory molecules comprise one or more IgG superfamily member proteins; and/or wherein the exogenous immunomodulatory molecules comprise one or more chemokine receptor proteins.

According to some embodiments, the allogeneic tumor cell vaccine of the present disclosure comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising a plurality of stably expressed exogenous immunomodulatory molecules effective to stimulate the T-lymphocytes, natural killer (NK) cells, dendritic cells (DCs) or B lymphocytes, wherein the exogenous immunomodulatory molecules comprise one or more cytokine family member proteins and one or more TNF family member proteins; wherein the exogenous immunomodulatory molecules comprise one or more cytokine family member proteins and one or more secreted receptor proteins; wherein the exogenous immunomodulatory molecules comprise one or more cytokine family member proteins and one or more chaperone proteins; wherein the exogenous immunomodulatory molecules comprise one or more cytokine family member proteins and one or more IgG superfamily member proteins; wherein the exogenous immunomodulatory molecules comprise one or more cytokine family member proteins and one or more chemokine receptor proteins.

According to some embodiments, the allogeneic tumor cell vaccine of the present disclosure comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising a plurality of stably expressed exogenous immunomodulatory molecules effective to stimulate the T-lymphocytes, natural killer (NK) cells, dendritic cells (DCs) or B lymphocytes, wherein the exogenous immunomodulatory molecules comprise one or more TNF family member proteins and one or more secreted receptor proteins; wherein the exogenous immunomodulatory molecules comprise one or more TNF family member proteins and one or more chaperone proteins; wherein the exogenous immunomodulatory molecules comprise one or more TNF family member proteins and one or more IgG superfamily member proteins; wherein the exogenous immunomodulatory molecules comprise one or more TNF family member proteins and one or more chemokine receptor proteins.

According to some embodiments, the allogeneic tumor cell vaccine of the present disclosure comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising a plurality of stably expressed exogenous immunomodulatory molecules effective to stimulate the T-lymphocytes, natural killer (NK) cells, dendritic cells (DCs) or B lymphocytes, wherein the exogenous immunomodulatory molecules comprise one or more secreted receptor proteins and one or more chaperone proteins; wherein the exogenous immunomodulatory molecules comprise one or more secreted receptor proteins and one or more IgG superfamily member proteins; wherein the exogenous immunomodulatory molecules comprise one or more secreted receptor proteins and one or more chemokine receptor proteins.

According to some embodiments, the allogeneic tumor cell vaccine of the present disclosure comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising a plurality of stably expressed exogenous immunomodulatory molecules effective to stimulate the T-lymphocytes, natural killer (NK) cells, dendritic cells (DCs) or B lymphocytes, wherein the exogenous immunomodulatory molecules comprise one or more chaperone proteins and one or more IgG superfamily member proteins; wherein the exogenous immunomodulatory molecules comprise one or more chaperone proteins and one or more chemokine receptor proteins.

According to some embodiments, the allogeneic tumor cell vaccine of the present disclosure comprises a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising a plurality of stably expressed exogenous immunomodulatory molecules effective to stimulate the T-lymphocytes, natural killer (NK) cells, dendritic cells (DCs) or B lymphocytes, wherein the exogenous immunomodulatory molecules comprise one or more IgG superfamily member proteins and one or more chemokine receptor proteins.

According to some embodiments, the exogenous immunomodulatory molecule is an immune stimulatory molecule.

According to some embodiments, the exogenous immunomodulatory molecule is selected from the group shown in Table 2. According to some embodiments, the exogenous immunomodulatory molecule is from a mouse. According to some embodiments, the exogenous immunomodulatory molecule is from a human.

TABLE 2

| Category | Examples |
| --- | --- |
| Cytokines | Granulocyte-macrophage colony-stimulating factor (GM-CSF), Granulocyte colony-stimulating factor (G-CSF), Fms-related tyrosine kinase 3 ligand (Flt3L), Flt3, interleukin-1 (IL-1), IL-1a, IL-1b, Il-1rα, IL-2, IL-3, IL-4, IL-5, IL-6, IL-7, IL-8, IL-9, IL-10, IL-10rα, IL-11, IL-12, IL-12p40, IL-12p70, IL-12/IL-23 P40, IL13, IL-15, IL-15/IL15-RA, IL-17, IL-17A, IL-18, IL-21, IL-23, TGF-β, MCP-1, TNF-α and interferon alpha (IFNα), IFNγ, MIP1b, Rantes, Tweak, TREM-1, mIFNα, mINγ |
| TNF-family members | Tumor necrosis factor alpha (TNFα), TNF, 4-1BBL, APRIL, BAFF, LIGHT, RANK ligand (RANKL), CD40 ligand (CD40L), OX40 Ligand (OX40L), FAS ligand (FASL), CD27 ligand (CD27L), CD30 ligand (CD30L), CD137 ligand (CD137L), TNFSF8, TNFSF9, TNFSF10, TNFSF11, TNFS12, TNFSF13, TNFSF13B, TNFSF14, TNFSF15, TNFSF18, TNFβ, TNFSF1B, TNFγ, Ectodysplasin A (EDA) |
| Receptors | TGFbeta Receptor III |
| Chaperone Proteins | GRP78/BiP, GRP94, GRP170, Calnexin, calreticulin, Hsp47, ERp29, Protein disulfide isomerase (PDI), Peptidyl prolyl cis-trans-isomerase (PPI), Erp57, Hsp60, Hsp70, Hsp90, Hsp100 |
| IgG Superfamily Members | CD80, CD86, ICOS ligand, PVR/CD155, CD48, Nectin2, NK-T-B antigen, PD-L2 |
| Chemokine Receptors | CXCR1, CXCR2, CXCR3, CXCR5, CXCR6, CXCR8, CCR8, CCR1, CCR2, CCR3, CCR5, CCR4, CCR6, CCR7, CCR9, CCR10, XCR1, CXCR3 |
| Others | Transforming Growth Factor Beta (TGFb) receptor, PSGL1, HSP70, HSP-90B1 (GRP94/96), TL1A |

According to some embodiments, the exogenous immunomodulatory molecule is selected from one of more of a TNF-family member, a secreted receptor, a chaperone protein, an IgG superfamily member, a chemokine receptor. According to some embodiments, the TNF-family member is selected from a TNF-family member listed in Table 2. According to some embodiments, the secreted receptor is selected from a secreted receptor listed in Table 2. According to some embodiments, the chaperone protein is selected from a chaperone protein listed in Table 2. According to some embodiments, the IgG superfamily member is selected from an IgG superfamily member listed in Table 2. According to some embodiments, the chemokine receptor is selected from a chemokine receptor listed in Table 2.

According to some embodiments, the exogenous immunomodulatory molecule in Table 2 is in a membrane bound form (i.e. comprises a membrane anchor). According to other embodiments, the exogenous immunomodulatory molecule is in a secreted form. According to some embodiments, the membrane bound form of the immunomodulator is one or more selected from the group consisting of 4-1BB ligand, BAFF, April, CD40 ligand, CD80, CD86, Flt3 Ligand, GM-CSF, HSP90, ICOS ligand, IL-12, IL-15, IL-18, IL-2, IL-21, IL-23, IL7, LIGHT, OX40 ligand, RANK ligand and TNF. According to some embodiments, the secreted form of the immunomodulator is one or more selected from the group consisting of Flt3 ligand, GM-CSF, IL10R, IL7 and TGFbeta Receptor.

According to some embodiments, the exogenous immunomodulatory molecule in Table 2 is a molecule with a wild-type amino acid sequence. According to some embodiments, the exogenous immunomodulatory molecule in Table 2 is a molecule with a variant amino acid sequence.

According to some embodiments, the exogenous immunomodulatory molecule is one or more selected from the group consisting of 4-1BB Ligand, APRIL, BAFF, CD27 Ligand, CD30L, CD40 Ligand, CD80, CD86, FLT-3 Ligand, FLT-3 ligand engineered to remove transmembrane region, GM-CSF, GMCSF engineered with CD8 membrane anchor and IRES compatible Signal Sequence, HSP-70, HSP-90, ICOS Ligand, IL-10R, IL-12, IL-15, IL-18, IL-2, IL-21, IL-23, IL-7, IL-7 engineered with CD8 membrane anchor, LIGHT, OX-40 Ligand, RANK Ligand, TGF-b Receptor, and TNF.

According to some embodiments, the one or more exogenous immunomodulatory molecules comprise at least three essential immunomodulatory molecules, wherein the at least three essential immunomodulatory molecules are OX40 Ligand (OX40L), CD27 Ligand (CD70), and CD28 Ligand (CD28L) comprising CD80, CD86 or both. According to some embodiments, additional immunomodulatory components identified as R may also be present.

According to some embodiments, the allogeneic vaccine comprises a population of proliferation incompetent tumor cells expressing one or more tumor specific antigens and three stably expressed essential exogenous immunomodulatory molecules, OX40L, CD70, and CD28L, effective to stimulate the MNC population. According to some embodiments, the ENLIST™ cells population comprising a population of tumor cells expressing one or more tumor specific antigens and the three stably expressed essential exogenous immunomodulatory molecules OX40L, CD70, and CD28L comprising CD80, CD86 or both is effective to stimulate synergistic expansion of CTLs. According to some embodiments, the allogeneic vaccine further comprises one or more subsets of R immunomodulators comprising 3, 4, 5, 6, 7, 8, 9, 10, 11, 12, 13, 14, 15, 16, 17, 18, 19, 20, 21, 22, 23, 24, or 25 immunomodulators. According to some embodiments, the allogeneic vaccine comprises a population of tumor cells expressing one or more tumor specific antigens, wherein the tumor cells are genetically engineered to stably express at least the three stably expressed exogenous immunomodulatory molecules OX40L, CD70, and CD28L comprising CD80, CD86 or both, plus one R subset comprising 3-25, inclusive immunomodulators. According to some embodiments, the allogeneic vaccine comprises a population of tumor cells expressing one or more tumor specific antigens, wherein the tumor cells are genetically engineered to stably express at least the three stably expressed exogenous immunomoculatory molecules OX40L, CD70, and CD28L comprising CD80, CD86 or both, plus two R subsets comprising 3-25, inclusive immunomodulators. According to some embodiments, the allogeneic vaccine comprises a population of tumor cells expressing one or more tumor specific antigens, wherein the tumor cells are genetically engineered to stably express at least the three stably expressed exogenous immunomoculatory molecules OX40L, CD70, and CD28L comprising CD80, CD86 or both, plus three R subsets comprising 3-25, inclusive immunomodulators. According to some embodiments, the allogeneic vaccine comprises a population of tumor cells expressing one or more tumor specific antigens, wherein the tumor cells are genetically engineered to stably express at least the three essential stably expressed exogenous immunomodulatory molecules OX40L, CD70, and CD28L comprising CD80, CD86 or both, plus four R subsets comprising 3-25, inclusive immunomodulators. According to some embodiments, the allogeneic vaccine comprises a population of tumor cells expressing one or more tumor specific antigens, wherein the tumor cells are genetically engineered to stably express at least the three essential stably expressed exogenous immunomoculatory molecules OX40L, CD70, and CD28L comprising CD80, CD86 or both, plus five R subsets comprising 3-25, inclusive immunomodulators. According to some embodiments, the allogeneic vaccine comprises a population of tumor cells expressing one or more tumor specific antigens, wherein the tumor cells are genetically engineered to stably express at least the three essential stably expressed exogenous immunomoculatory molecules OX40L, CD70, and CD28L comprising CD80, CD86 or both, plus six R subsets comprising 3-25, inclusive immunomodulators. According to some embodiments, the allogeneic vaccine comprises a population of tumor cells expressing one or more tumor specific antigens, wherein the tumor cells are genetically engineered to stably express at least the three essential stably expressed exogenous immunomoculatory molecules OX40L, CD70, and CD28L comprising CD80, CD86 or both, plus seven R subsets comprising 3-25, inclusive immunomodulators. According to some embodiments, the allogeneic vaccine comprises a population of tumor cells expressing one or more tumor specific antigens, wherein the tumor cells are genetically engineered to stably express at least the three essential stably expressed exogenous immunomoculatory molecules OX40L, CD70, and CD28L comprising CD80, CD86 or both, plus eight R subsets comprising 3-25, inclusive immunomodulators. According to some embodiments, the allogeneic vaccine comprises a population of tumor cells expressing one or more tumor specific antigens, wherein the tumor cells are genetically engineered to stably express at least the three essential stably expressed exogenous immunomoculatory molecules OX40L, CD70, and CD28L comprising CD80, CD86 or both, plus nine R subsets comprising 3-25, inclusive immunomodulators. According to some embodiments, the allogeneic vaccine comprises a population of tumor cells expressing one or more tumor specific antigens, wherein the tumor cells are genetically engineered to stably express at least the three essential stably expressed exogenous immunomoculatory molecules OX40L, CD70, and CD28L comprising CD80, CD86 or both, plus ten R subsets comprising 3-25, inclusive immunomodulators.

According to some embodiments, the exogenous immunomodulatory molecule $R^1$ is APRIL. According to some embodiments, the exogenous immunomodulatory molecule $R^2$ is BAFF. According to some embodiments, the exogenous immunomodulatory molecule $R^3$ is 4-IBB Ligand. According to some embodiments, the exogenous immunomodulatory molecule $R^4$ is CD30L. According to some embodiments, the exogenous immunomodulatory molecule $R^5$ is CD40 Ligand. According to some embodiments, the exogenous immunomodulatory molecule $R^6$ is CD80. According to some embodiments, the exogenous immunomodulatory molecule $R^7$ is CD86. According to some embodiments, the exogenous immunomodulatory molecule $R^8$ is FLT-3 Ligand. According to some embodiments, the exogenous immunomodulatory molecule $R^9$ is HSP-70. According to some embodiments, the exogenous immunomodulatory molecule $R^{10}$ is HSP-90. According to some embodiments, the exogenous immunomodulatory molecule $R^{11}$ is ICOS Ligand. According to some embodiments, the exogenous immunomodulatory molecule $R^{12}$ is IL-10R. According to some embodiments, the exogenous immunomodulatory molecule $R^{13}$ is IL-12. According to some embodiments, the exogenous immunomodulatory molecule $R^{14}$ is IL-15. According to some embodiments, the exogenous immunomodulatory molecule $R^{15}$ is IL-18. According to some embodiments, the exogenous immunomodulatory molecule $R^{16}$ is IL-2. According to some embodiments, the exogenous immunomodulatory molecule $R^{17}$ is IL-21. According to some embodiments, the exogenous immunomodulatory molecule $R^{18}$ is IL-23. According to some embodiments, the exogenous immunomodulatory molecule $R^{19}$ is IL-7. According to some embodiments, the exogenous immunomodulatory molecule $R^{20}$ is LIGHT. According to some embodiments, the exogenous immunomodulatory molecule $R^{21}$ is RANK Ligand. According to some embodiments, the exogenous immunomodulatory molecule $R^{22}$ is TGF-b Receptor. According to some embodiments, the exogenous immunomodulatory molecule $R^{23}$ is TNF. According to some embodiments, the exogenous immunomodulatory molecule $R^{24}$ is GM-CSF.

According to some embodiments, the exogenous immunomodulatory molecule R comprises between 1 and 30 immunomodulators, inclusive, i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, exogenous immunomodulatory molecules selected from the group consisting of APRIL, BAFF, 4-IBB Ligand, CD30 Ligand, CD40 Ligand, CD80, CD86, FLT-3 Ligand, FLT-3 ligand engineered to remove transmembrane region, GM-CSF, GMCSF engineered with CD8 membrane anchor and IRES compatible Signal Sequence, HSP-70, HSP-90, ICOS Ligand, IL-10R, IL-12, IL-15, IL-18, IL-2, IL-21, IL-23, IL-7, IL-7 engineered with CD8 membrane anchor, LIGHT, OX-40 Ligand, RANK Ligand, TGF-b Receptor, and TNF. According to some embodiments, the exogenous immunomodulatory molecule comprises between 1 and 30, inclusive, i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, exogenous immunomodulatory molecules, wherein at least three immunomodulatory molecules are, OX40 Ligand (OX40L), CD27 Ligand, and CD28 Ligand comprising CD80, CD86 or both, and wherein additional immunomodulatory components identified as $R^1$-$R^{24}$ are selected from the group consisting of APRIL, BAFF, 4-IBBL Ligand (4-IBBL), CD30L, CD40 Ligand, CD80, CD86, FLT-3 Ligand, FLT-3 ligand engineered to remove transmembrane region, GMCSF engineered with CD8 membrane anchor and IRES compatible Signal Sequence, HSP-70, HSP-90, ICOS Ligand, IL-10R, IL-12, IL-15, IL-18, IL-2, IL-21, IL-23, IL-7, IL-7 engineered with CD8 membrane anchor, LIGHT, RANK Ligand, TGF-b Receptor, and TNF.

According to some embodiments, the exogenous immunomodulatory molecule R comprises between 1 and 20, inclusive, i.e., 1, 2, 3, 4, 5, 6, 7, 8, 9, 10, 11, 12, 13, 14, 15, 16, 17, 18, 19 or 20, exogenous immunomodulatory molecules selected from the group consisting of APRIL, BAFF, 4-IBB Ligand, CD30L, CD40 Ligand, CD80, CD86, FLT-3 Ligand, FLT-3 ligand engineered to remove transmembrane region, GM-CSF, GMCSF engineered with CD8 membrane anchor and IRES compatible Signal Sequence, HSP-70, HSP-90, ICOS Ligand, IL-10R, IL-12, IL-15, IL-18, IL-2, IL-21, IL-23, IL-7, IL-7 engineered with CD8 membrane anchor, LIGHT, OX-40 Ligand, RANK Ligand, TGF-b Receptor, and TNF. According to some embodiments, the exogenous immunomodulatory molecule comprises between 1 and 20, inclusive, i.e., 1, 2, 3, 4, 5, 6, 7, 8, 9, 10, 11, 12, 13, 14, 15, 16, 17, 18, 19 or 20, exogenous immunomodulatory molecules, wherein at least three immunomodulatory molecules are OX40 Ligand (OX40L), CD27 Ligand, and CD28 Ligand, and wherein additional immunomodulatory components identified as $R^1$-$R^{24}$ are selected from the group consisting of APRIL, BAFF, 4-IBB Ligand, CD30L, CD40 Ligand, CD80, CD86, FLT-3 Ligand, FLT-3 ligand engineered to remove transmembrane region, GMCSF engineered with CD8 membrane anchor and IRES compatible Signal Sequence, HSP-70, HSP-90, ICOS Ligand, IL-10R, IL-12, IL-15, IL-18, IL-2, IL-21, IL-23, IL-7, IL-7 engineered with CD8 membrane anchor, LIGHT, RANK Ligand, TGF-b Receptor, and TNF.

According to some embodiments, the exogenous immunomodulatory molecule R comprises between 1 and 10, inclusive, i.e., 1, 2, 3, 4, 5, 6, 7, 8, 9 or 10, exogenous immunomodulatory molecules selected from the group consisting of APRIL, BAFF, 4-IBB Ligand, CD30L, CD40 Ligand, CD80, CD86, FLT-3 Ligand, FLT-3 ligand engineered to remove transmembrane region, GM-CSF, GMCSF engineered with CD8 membrane anchor and IRES compatible Signal Sequence, HSP-70, HSP-90, ICOS Ligand, IL-10R, IL-12, IL-15, IL-18, IL-2, IL-21, IL-23, IL-7, IL-7 engineered with CD8 membrane anchor, LIGHT, OX-40 Ligand, RANK Ligand, TGF-b Receptor, and TNF. According to some embodiments, the exogenous immunomodulatory molecule comprises between 1 and 10, inclusive, i.e., 1, 2, 3, 4, 5, 6, 7, 8, 9 or 10, exogenous immunomodulatory molecules, wherein at least three immunomodulatory molecules are OX40 Ligand (OX40L), CD27 Ligand, and CD28 Ligand, and wherein additional immunomodulatory components identified as $R^1$-$R^{24}$ are selected from the group consisting of APRIL, BAFF, 4-IBB Ligand, CD30L, CD40 Ligand, CD80, CD86, FLT-3 Ligand, FLT-3 ligand engineered to remove transmembrane region, GMCSF engineered with CD8 membrane anchor and IRES compatible Signal Sequence, HSP-70, HSP-90, ICOS Ligand, IL-10R, IL-12, IL-15, IL-18, IL-2, IL-21, IL-23, IL-7, IL-7 engineered with CD8 membrane anchor, LIGHT, RANK Ligand, TGF-b Receptor, and TNF.

According to some embodiments, the exogenous immunomodulatory molecule R comprises between 5 and 20, inclusive, i.e., 5, 6, 7, 8, 9, 10, 11, 12, 13, 14, 15, 16, 17, 18, 19, or 20, exogenous immunomodulatory molecules selected from the group consisting of APRIL, BAFF, 4-IBB Ligand, CD30L, CD40 Ligand, CD80, CD86, FLT-3 Ligand, FLT-3 ligand engineered to remove transmembrane region, GM-CSF, GMCSF engineered with CD8 membrane anchor and IRES compatible Signal Sequence, HSP-70, HSP-90, ICOS Ligand, IL-10R, IL-12, IL-15, IL-18, IL-2, IL-21, IL-23, IL-7, IL-7 engineered with CD8 membrane anchor, LIGHT, OX-40 Ligand, RANK Ligand, TGF-b Receptor, and TNF. According to some embodiments, the exogenous immunomodulatory molecule comprises between 5 and 20, inclusive, i.e., 5, 6, 7, 8, 9, 10, 11, 12, 13, 14, 15, 16, 17, 18, 19, or 20 exogenous immunomodulatory molecules, wherein at least three immunomodulatory molecules are OX40 Ligand (OX40L), CD27 Ligand, and CD28 Ligand, and wherein additional immunomodulatory components identified as $R^1$-$R^{24}$ are selected from the group consisting of APRIL, BAFF, CD27 Ligand, CD30L, CD40 Ligand, CD80, CD86, FLT-3 Ligand, FLT-3 ligand engineered to remove transmembrane region, GMCSF engineered with CD8 membrane anchor and IRES compatible Signal Sequence, HSP-70, HSP-90, ICOS Ligand, IL-10R, IL-12, IL-15, IL-18, IL-2, IL-21, IL-23, IL-7, IL-7 engineered with CD8 membrane anchor, LIGHT, RANK Ligand, TGF-b Receptor, and TNF.

According to some embodiments, the exogenous immunomodulatory molecule R comprises between 10 and 15, inclusive, i.e., 10, 11, 12, 13, 14 or 15, exogenous immunomodulatory molecules selected from the group consisting of APRIL, BAFF, 4IBB Ligand, CD30L, CD40 Ligand, CD80, CD86, FLT-3 Ligand, FLT-3 ligand engineered to remove transmembrane region, GM-CSF, GMCSF engineered with CD8 membrane anchor and IRES compatible Signal Sequence, HSP-70, HSP-90, ICOS Ligand, IL-10R, IL-12, IL-15, IL-18, IL-2, IL-21, IL-23, IL-7, IL-7 engineered with CD8 membrane anchor, LIGHT, OX-40 Ligand, RANK Ligand, TGF-b Receptor, and TNF. According to some embodiments, the exogenous immunomodulatory molecule comprises between 10 and 15, inclusive, i.e., 10, 11, 12, 13, 14 or 15 exogenous immunomodulatory molecules, wherein at least three immunomodulatory molecules are OX40 Ligand (OX40L), CD27 Ligand, and CD28 Ligand, and wherein additional immunomodulatory components identified as $R^1$-$R^{24}$ are selected from the group consisting of APRIL, BAFF, 4-IBB Ligand, CD30L, CD40 Ligand, CD80, CD86, FLT-3 Ligand, FLT-3 ligand engineered to remove transmembrane region, GMCSF engineered with CD8 membrane anchor and IRES compatible Signal Sequence, HSP-70, HSP-90, ICOS Ligand, IL-10R, IL-12, IL-15, IL-18, IL-2, IL-21, IL-23, IL-7, IL-7 engineered with CD8 membrane anchor, LIGHT, RANK Ligand, TGF-b Receptor, and TNF.

According to some embodiments, the exogenous immunomodulatory molecule R comprises 14 exogenous immunomodulatory molecules selected from the group consisting of APRIL, BAFF, 4-IBB Ligand, CD30L, CD40 Ligand, CD80, CD86, FLT-3 Ligand, FLT-3 ligand engineered to remove transmembrane region, GM-CSF, GMCSF engineered with CD8 membrane anchor and IRES compatible Signal Sequence, HSP-70, HSP-90, ICOS Ligand, IL-10R, IL-12, IL-15, IL-18, IL-2, IL-21, IL-23, IL-7, IL-7 engineered with CD8 membrane anchor, LIGHT, OX-40 Ligand, RANK Ligand, TGF-b Receptor, and TNF. According to some embodiments, the exogenous immunomodulatory molecule comprises 14 exogenous immunomodulatory molecules, wherein at least three immunomodulatory molecules are OX40 Ligand (OX40L), CD27 Ligand, and CD28 Ligand, and wherein additional immunomodulatory components identified as $R^1$-$R^{24}$ are selected from the group consisting of APRIL, BAFF, 4-IBB Ligand, CD30L, CD40 Ligand, CD80, CD86, FLT-3 Ligand, FLT-3 ligand engineered to remove transmembrane region, GM-CSF, GMCSF engineered with CD8 membrane anchor and IRES compatible Signal Sequence, HSP-70, HSP-90, ICOS Ligand, IL-10R, IL-12, IL-15, IL-18, IL-2, IL-21, IL-23, IL-7, IL-7 engineered with CD8 membrane anchor, LIGHT, OX-40 Ligand, RANK Ligand, TGF-b Receptor, and TNF.

According to some embodiments, each of the exogenous immunomodulatory molecules 4-1BB Ligand, APRIL, BAFF, CD27 Ligand, CD30L, CD40 Ligand, CD80, CD86, FLT-3 Ligand, GM-CSF, HSP-70, HSP-90, ICOS Ligand, IL-10R, IL-12, IL-15, IL-18, IL-2, IL-21, IL-23, IL-7, LIGHT, OX-40 Ligand, RANK Ligand, TGF-b Receptor, and TNF is a wild type molecule. According to some embodiments, each of the exogenous immunomodulatory molecules 4-1BB Ligand, APRIL, BAFF, CD27 Ligand, CD30L, CD40 Ligand, CD80, CD86, FLT-3 Ligand, GM-CSF, HSP-70, HSP-90, ICOS Ligand, IL-10R, IL-12, IL-15, IL-18, IL-2, IL-21, IL-23, IL-7, LIGHT, OX-40 Ligand, RANK Ligand, TGF-b Receptor, and TNF is a mutant or variant sequence.

According to some embodiments, the exogenous immunomodulatory molecule $R^{24}$ is a CD86 variant that has been engineered with an IRES compatible signal sequence. According to some embodiments, the exogenous immunomodulatory molecule $R^{25}$ is a FLT3L variant that has been engineered to remove the transmembrane region. According to some embodiments, the exogenous immunomodulatory molecule $R^{26}$ is a GM-CSF variant that has been engineered with a CD8 membrane anchor and IRES compatible Signal Sequence. According to some embodiments, the exogenous immunomodulatory molecule $R^{27}$ is an HSP70 variant that has been engineered with a CD8 membrane anchor. According to some embodiments, the exogenous immunomodulatory molecule $R^{28}$ is an HSP-90B1 (GRP94/96) variant that has been engineered with a CD8 membrane anchor. According to some embodiments, the exogenous immunomodulatory molecule $R^{29}$ is an HSP90 variant that has been engineered with a CD8 membrane anchor. According to some embodiments, the exogenous immunomodulatory molecule $R^{30}$ is an ICOSL variant that has been engineered with an IRES compatible signal sequence. According to some embodiments, the exogenous immunomodulatory molecule $R^{31}$ is an IL10R variant that has been engineered to remove the transmembrane region. According to some embodiments, the exogenous immunomodulatory molecule $R^{32}$ is an IL-Rα variant that has been engineered to remove transmembrane region (VSV-GM-CSF tag). According to some embodiments, the exogenous immunomodulatory molecule $R^{33}$ is an IL12 variant that has been engineered to be a single chain with a CD8 membrane anchor. According to some embodiments, the exogenous immunomodulatory molecule $R^{34}$ is an IL15 variant that has been engineered with CD8 membrane anchor. According to some embodiments, the exogenous immunomodulatory molecule $R^{35}$ is an IL18 variant that has been engineered with a CD8 membrane anchor. According to some embodiments, the exogenous immunomodulatory molecule $R^{36}$ is an IL2 variant that has been engineered with a CD8 membrane anchor and IRES compatible sequence. According to some embodiments, the exogenous immunomodulatory molecule $R^{37}$ is an IL21 variant that has been engineered with a CD8 membrane anchor. According to some embodiments, the exogenous immunomodulatory molecule $R^{38}$ is an IL23 variant that has been engineered to be a single chain with a CD8 membrane anchor. According to some embodiments, the exogenous immunomodulatory molecule $R^{39}$ is an IL7 variant that has been engineered with a CD8 membrane anchor. According to some embodiments, the exogenous immunomodulatory molecule $R^{40}$ is an TGFb-R variant that has been engineered to remove transmembrane region. According to some embodiments, the exogenous immunomodulatory $R^{41}$ molecule is an TGFb Receptor III variant engineered to remove transmembrane region. According to some embodiments, the exogenous immunomodulatory molecule $R^{42}$ is an mIFNα variant modified to be membrane bound. According to some embodiments, the exogenous immunomodulatory molecule $R^{43}$ is an mIFNαγ variant which is modified to be membrane bound. According to some embodiments, the exogenous immunomodulatory molecule $R^{44}$ is an CD40L variant which is cleavage resistant.

Table 3 below sets forth R groups $R^1$-$R^{44}$

TABLE 3

| Rx | Description |
|---|---|
| $R^1$ | APRIL |
| $R^2$ | BAFF |
| $R^3$ | 4-IBB Ligand |
| $R^4$ | CD30 Ligand |
| $R^5$ | CD40 Ligand |
| $R^6$ | CD80 |
| $R^7$ | CD86 |
| $R^8$ | FLT-3 Ligand |
| $R^9$ | HSP-70 |
| $R^{10}$ | HSP-90 |
| $R^{11}$ | ICOS Ligand |
| $R^{12}$ | IL-10R |
| $R^{13}$ | IL-12 |
| $R^{14}$ | IL-15 |
| $R^{15}$ | IL-18 |
| $R^{16}$ | IL-2 |
| $R^{17}$ | IL-21 |
| $R^{18}$ | IL-23 |
| $R^{19}$ | IL-7 |
| $R^{20}$ | LIGHT |
| $R^{21}$ | RANK ligand |
| $R^{22}$ | TGF-b Receptor |
| $R^{23}$ | TNF |
| $R^{24}$ | CD86 variant engineered with an IRES compatible signal sequence |
| $R^{25}$ | FLT3L variant engineered to remove the transmembrane region |
| $R^{26}$ | GMCSF variant with a CD8 membrane anchor and IRES compatible Signal Sequence |
| $R^{27}$ | HSP70 variant with a CD8 membrane anchor |
| $R^{28}$ | HSP-90B1 (GRP94/96) variant engineered with a CD8 membrane anchor |
| $R^{29}$ | HSP90 variant engineered with a CD8 membrane anchor |
| $R^{30}$ | ICOSL variant engineered with an IRES compatible signal sequence |
| $R^{31}$ | IL10R variant engineered to remove the transmembrane region |
| $R^{32}$ | IL-Rα variant engineered to remove transmembrane region (VSV-GM-CSF tag) |
| $R^{33}$ | IL12 variant engineered to be a single chain with a CD8 membrane anchor |
| $R^{34}$ | IL15 variant engineered with CD8 membrane anchor |
| $R^{35}$ | IL18 variant engineered with a CD8 membrane anchor |
| $R^{36}$ | IL2 variant engineered with a CD8 membrane anchor and IRES compatible sequence |
| $R^{37}$ | IL21 variant engineered with a CD8 membrane anchor |

TABLE 3-continued

| Rx | Description |
|---|---|
| $R^{38}$ | IL23 variant engineered to be a single chain with a CD8 membrane anchor |
| $R^{39}$ | IL7 variant engineered with a CD8 membrane anchor |
| $R^{40}$ | TGFb-R variant engineered to remove transmembrane region |
| $R^{41}$ | TGFb Receptor III variant engineered to remove transmembrane region |
| $R^{42}$ | mIFNα variant modified to be membrane bound |
| $R^{43}$ | mIFNαγ variant which is modified to be membrane bound |
| $R^{44}$ | CD40L variant which is cleavage resistant |

According to some embodiments, at least 12 vectors comprise 14 immunomodulators, wherein at least three immunomodulatory molecules are OX40 Ligand (OX40L), CD27 Ligand (CD70), and CD28 Ligand (CD28L) comprising CD80, CD86 or both, and wherein the remaining 11 immunomodulators are selected from $R^1$-$R^{44}$ in Table 3. According to some embodiments, at least 11 vectors comprise 14 immunomodulators, wherein at least three immunomodulatory molecules are OX40 Ligand (OX40L), CD27 Ligand (CD70), and CD28 Ligand (CD28L) comprising CD80, CD86 or both, and wherein the remaining 11 immunomodulators are selected from $R^1$-$R^{44}$ in Table 3. According to some embodiments, at least 10 vectors comprise 14 immunomodulators, wherein at least three immunomodulatory molecules are OX40 Ligand (OX40L), CD27 Ligand (CD70), and CD28 Ligand (CD28L) comprising CD80, CD86 or both, and wherein the remaining 11 immunomodulators are selected from $R^1$-$R^{44}$ in Table 3. According to some embodiments, 14 immunomodulators are selected from Table 2, wherein at least three immunomodulatory molecules are OX40 Ligand (OX40L), CD27 Ligand (CD70), and CD28 Ligand (CD28L) comprising CD80, CD86 or both, and wherein the remaining 11 immunomodulators are selected from $R^1$-$R^{44}$ in Table 3 and wherein the 14 immunomodulators are in 12 vectors. According to some embodiments, 14 immunomodulators are selected from Table 2, wherein at least three immunomodulatory molecules are OX40 Ligand (OX40L), CD27 Ligand (CD70), and CD28 Ligand (CD28L) comprising CD80, CD86 or both, and wherein the remaining 11 immunomodulators are selected from $R^1$-$R^{44}$ in Table 3 and wherein the 14 immunomodulators are in 11 vectors. According to some embodiments, 14 immunomodulators are selected from Table 2, wherein at least three immunomodulatory molecules are OX40 Ligand (OX40L), CD27 Ligand (CD70), and CD28 Ligand (CD28L) comprising CD80, CD86 or both, and wherein the remaining 11 immunomodulators are selected from $R^1$-$R^{44}$ in Table 3 and wherein the 14 immunomodulators are in 10 vectors. The vectors may further comprise tags.

According to some embodiments, the immunomodulators are codon optimized. "Codon optimization" means a modification of a codon of a polynucleotide encoding a protein with a codon that is used first before others in a specific organism such that the coded protein can be more efficiently expressed therein. Because most amino acids are described by several codons that are referred to as "synonym" or "synonymous codon", genetic codes have degeneracy. However, codon usage by a specific organism is not random, and it is rather biased to specific codon triplets. Such codon usage bias may be even higher in relation with a certain gene, a gene with common function or ancestor origin, protein expressed at high level vs. proteins with low copy number, or a group protein coding region of a genome of an organism.

Cytokines

According to one embodiment, the disclosure encompasses an allogeneic tumor cell vaccine comprising a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising one or more cytokines. Thus, the disclosure encompasses a cytokine, including a full-length, fragment, homologue, variant or mutant of the cytokine. A cytokine includes a protein that is capable of affecting the biological function of another cell. A biological function affected by a cytokine can include, but is not limited to, cell growth, cell differentiation or cell death. According to some embodiments, a cytokine of the present disclosure is capable of binding to a specific receptor on the surface of a cell, thereby stimulating an immune cell (e.g. T lymphocytes (e.g., CD8+ T cell), natural killer (NK) cells, dendritic cells (DCs) or B lymphocytes).

According to some embodiments, the cytokine is selected from Granulocyte-macrophage colony-stimulating factor (GM-CSF), Granulocyte colony-stimulating factor (G-CSF), Fms-related tyrosine kinase 3 ligand (FLT3LG), interleukin-1 (IL-1), IL-1a, IL-1b, Il-1ra, IL-2, IL-3, IL-4, IL-5, IL-6, IL-7, IL-8, IL-9, IL-10, IL-11, IL-12p40, IL-12p70, IL-12/IL-23 P40, IL13, IL-15, IL-15/IL15-RA, IL-17, IL-17A, IL-18, IL-21, IL-23, TGF-β, MCP-1, TNF-α and interferon alpha (IFNα), IFNγ, MIP1b, Rantes, Tweak, and TREM-1. According to some embodiments, the cytokine is granulocyte-macrophage colony-stimulating factor (GM-CSF). According to some embodiments, the cytokine is Fms-related tyrosine kinase 3 ligand (FLT3LG).

According to some embodiments, the cytokine is secreted. According to some embodiments, the cytokine is membrane bound.

Granulocyte-Macrophage Colony Stimulating Factor (GM-CSF)

Granulocyte-macrophage colony-stimulating factor (GM-CSF; colony stimulating factor 2; CSF2) is found in monocytes/macrophages and activated T cells, and can act as a growth factor to stimulate and recruit dendritic cells. GM-CSF is a monomeric glycoprotein secreted by cells of the immune system, as well as endothelial cells and fibroblasts. Human GM-CSF is a 144 amino acid protein comprising a 17 amino acid signal peptide that can be cleaved to produce a mature 127 amino acid protein. Biological activity of GM-CSF occurs via binding to heteromeric cell surface receptors that are expressed on monocytes, macrophages, granulocytes, lymphocytes, endothelial cells and alveolar epithelial cells. The GM-CSF receptor (GM-CSFR) typically has a low expression (e.g. 20-200/cell), but has a high affinity (Shi Y et al., Granulocyte-macrophage colony-stimulating factor (GM-CSF) and T-cell responses: what we do and don't know, Cell Research (2006) 16: 126-133).

In some mouse models, vaccination with syngeneic mouse melanoma cells that secrete GM-CSF stimulates a more potent and long-lasting antitumor immunity than vaccines produced by other cytokines. Melanoma patients treated with soluble GM-CSF as an adjuvant therapy displayed an increase in disease free survival compared to controls. GM-CSF has been used as an immune adjuvant in various ways, including, without limitation, systemic and topical application of soluble GM-CSF, GM-CSF fusion proteins, transfection of tumor cells with GM-CSF and injection of GM-CSF DNA. Recombinant GM-CSF has been used an adjuvant for various peptide, protein, and viral vaccines, and has been shown to be an effective adjuvant in patients with melanoma, breast, and ovarian cancer. A fusion protein comprising GM-CSF has also been shown to enhance immunogenicity of an antigen. GM-CSF has been tested for use in a gene therapy approach where allogeneic or autologous GM-CSF expressing cells are used as a vaccine (Kaufman and Wolchok eds., General Principles of Tumor Immunotherapy, Chpt 5, 67-121 (2007)). Such vaccines have had varying degrees of effectiveness among several different cancer types.

According to some embodiments, a tumor cell line or tumor cell line variant may express the GM-CSF peptide of SEQ ID NO: 13. According to some embodiments, a tumor cell line or tumor cell line variant may comprise one or more proteins with a sequence identity of at least 60% to the protein of SEQ ID NO: 13. According to some embodiments, a tumor cell line or tumor cell line variant may comprise one or more proteins with a sequence identity of at least 70% to the protein of SEQ ID NO: 13. According to some embodiments, a tumor cell line or tumor cell line variant may comprise one or more proteins with a sequence identity of at least 80% to the protein of SEQ ID NO: 13. According to some embodiments, a tumor cell line or tumor cell line variant may comprise one or more proteins with a sequence identity of at least 90% to the protein of SEQ ID NO: 13. According to some embodiments, a tumor cell line or tumor cell line variant may comprise one or more proteins with a sequence identity of at least 95% to the protein of SEQ ID NO: 13. According to some embodiments, a tumor cell line or tumor cell line variant may comprise one or more proteins with a sequence identity of at least 96% to the protein of SEQ ID NO: 13. According to some embodiments, a tumor cell line or tumor cell line variant may comprise one or more proteins with a sequence identity of at least 97% to the protein of SEQ ID NO: 13. According to some embodiments, a tumor cell line or tumor cell line variant may comprise one or more proteins with a sequence identity of at least 98% to the protein of SEQ ID NO: 13. According to some embodiments, a tumor cell line or tumor cell line variant may comprise one or more proteins with a sequence identity of at least 99% to the protein of SEQ ID NO: 13.

According to some embodiments, a tumor cell line or tumor cell line variant may comprise one or more proteins comprising a fusion between GM-CSF and HLA-I to enable membrane expression. According to some embodiments, a tumor cell line or tumor cell line variant may comprise one or more proteins with a sequence identity of at least 60% to the protein of SEQ ID NO: 42 or SEQ ID NO: 5. According to some embodiments, a tumor cell line or tumor cell line variant may comprise one or more proteins with a sequence identity of at least 70% to the protein of SEQ ID NO: 42 or SEQ ID NO: 5. According to some embodiments, a tumor cell line or tumor cell line variant may comprise one or more proteins with a sequence identity of at least 80% to the protein of SEQ ID NO: 42 or SEQ ID NO: 5. According to some embodiments, a tumor cell line or tumor cell line variant may comprise one or more proteins with a sequence identity of at least 90% to the protein of SEQ ID NO: 42 or SEQ ID NO: 5. According to some embodiments, a tumor cell line or tumor cell line variant may comprise one or more proteins with a sequence identity of at least 95% to the protein of SEQ ID NO: 42 or SEQ ID NO: 5. According to some embodiments, a tumor cell line or tumor cell line variant may comprise one or more proteins with a sequence identity of at least 96% to the protein of SEQ ID NO: 42 or SEQ ID NO: 5. According to some embodiments, a tumor cell line or tumor cell line variant may comprise one or more proteins with a sequence identity of at least 97% to the protein of SEQ ID NO: 42 or SEQ ID NO: 5. According to some embodiments, a tumor cell line or tumor cell line variant may comprise one or more proteins with a sequence identity of at least 98% to the protein of SEQ ID NO: 42 or SEQ ID NO: 5. According to some embodiments, a tumor cell line or tumor cell line variant may comprise one or more proteins with a sequence identity of at least 99% to the protein of SEQ ID NO: 42 or SEQ ID NO: 5.

Fms-Like Tyrosine Kinase-3 Ligand (Flt-3L)

The human Flt3L protein is a membrane bound hematopoietic four helical bundle cytokine encoded by the FLT3LG gene. Flt3L acts as a growth factor that stimulates proliferation and differentiation of various blood cell progenitors, and is crucial for production and development of dendritic cells. Mice that lack Flt3L have low levels of dendritic cells, while Flt3L administered to mice or humans results in very high levels of dendritic cells (Shortman et al., Steady-state and inflammatory dendritic-cell development, Nature Reviews Immunology, Vol. 7. 19-30 (2007)).

According to some embodiments, a tumor cell line or tumor cell line variant expresses the Flt3L peptide of SEQ ID NO: 14. According to some embodiments, a tumor cell line or tumor cell line variant may comprise one or more proteins with a sequence identity of at least 60% to the protein of SEQ ID NO: 14. According to some embodiments, a tumor cell line or tumor cell line variant may comprise one or more proteins with a sequence identity of at least 70% to the protein of SEQ ID NO: 14. According to some embodiments, a tumor cell line or tumor cell line variant may comprise one or more proteins with a sequence identity of at least 80% to the protein of SEQ ID NO: 14. According to some embodiments, a tumor cell line or tumor cell line variant may comprise one or more proteins with a sequence identity of at least 90% to the protein of SEQ ID NO: 14. According to some embodiments, a tumor cell line or tumor cell line variant may comprise one or more proteins with a sequence identity of at least 95% to the protein of SEQ ID NO: 14. According to some embodiments, a tumor cell line or tumor cell line variant may comprise one or more proteins with a sequence identity of at least 96% to the protein of SEQ ID NO: 14. According to some embodiments, a tumor cell line or tumor cell line variant may comprise one or more proteins with a sequence identity of at least 97% to the protein of SEQ ID NO: 14. According to some embodiments, a tumor cell line or tumor cell line variant may comprise one or more proteins with a sequence identity of at least 98% to the protein of SEQ ID NO: 14. According to some embodiments, a tumor cell line or tumor cell line variant may comprise one or more proteins with a sequence identity of at least 99% to the protein of SEQ ID NO: 14.

According to some embodiments, a tumor cell line or tumor cell line variant comprises a soluble form of Flt3L. According to some embodiments, a tumor cell line or tumor cell line variant may comprise one or more proteins with a sequence identity of at least 60% to the protein of SEQ ID NO: 44. According to some embodiments, a tumor cell line or tumor cell line variant may comprise one or more proteins with a sequence identity of at least 70% to the protein of SEQ ID NO: 44. According to some embodiments, a tumor cell line or tumor cell line variant may comprise one or more proteins with a sequence identity of at least 80% to the protein of SEQ ID NO: 44. According to some embodiments, a tumor cell line or tumor cell line variant may comprise one or more proteins with a sequence identity of at least 90% to the protein of SEQ ID NO: 44. According to some embodiments, a tumor cell line or tumor cell line variant may comprise one or more proteins with a sequence identity of at least 95% to the protein of SEQ ID NO: 44. According to some embodiments, a tumor cell line or tumor cell line variant may comprise one or more proteins with a sequence identity of at least 96% to the protein of SEQ ID NO: 44. According to some embodiments, a tumor cell line or tumor cell line variant may comprise one or more proteins with a sequence identity of at least 97% to the protein of SEQ ID NO: 44. According to some embodiments, a tumor cell line or tumor cell line variant may comprise one or more proteins with a sequence identity of at least 98% to the protein of SEQ ID NO: 44. According to some embodiments, a tumor cell line or tumor cell line variant may comprise one or more proteins with a sequence identity of at least 99% to the protein of SEQ ID NO: 44.

One skilled in the art, once armed with the teachings provided herein, would appreciate that the invention encompasses any cytokine, whether well-known in the art now, or discovered in the future.

According to some embodiments, an allogeneic tumor cell vaccine comprising a population of proliferation incompetent tumor cells expressing one or more tumor specific antigens, comprises one or more (e.g., 2, 3, 4, 5, or more) cytokines, or variants or fragments thereof.

TNF-Family Members

According to one embodiment, the disclosure encompasses an allogeneic tumor cell vaccine, comprising a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising one or more TNF-family members. Thus, the disclosure encompasses a TNF-family member protein, including a full-length, fragment, homologue, variant or mutant of the TNF-family protein. According to some embodiments, the TNF superfamily member is selected from one or more of tumor necrosis factor alpha (TNFα), CD40 ligand (CD40L), OX40 Ligand (OX40L), FAS ligand (FASL), CD27 ligand (CD27L), CD30 ligand (CD30L), CD137 ligand (CD137L), TNFSF8, TNFSF9, TNF SF10, TNF SF11, TNF S12, TNFSF13, TNFSF13B, TNFSF14, TNFSF15, TNFSF18, TNFβ, TNFSF1B, TNFγ, Ectodysplasin A (EDA). According to some embodiments, the TNF superfamily member is TNFα. According to some embodiments, the TNF superfamily member is CD40L.

According to some embodiments, the TNF family member is membrane bound.

The tumor necrosis factor (TNF) superfamily is a protein superfamily of type II transmembrane proteins containing TNF homology domain and forming trimers. Members of this superfamily can be released from the cell membrane by extracellular proteolytic cleavage and function as a cytokine. These proteins are expressed predominantly by immune cells and regulate diverse cell functions, including regulation of immune response and inflammation, but also proliferation, differentiation, apoptosis and embryogenesis. The superfamily contains 19 members that bind to 29 members of the TNF receptor superfamily.

OX40L (TNFSF4, bTNF Superfamily Member 4)

The OX40 Ligand (OX40L)(CD252, TNFSF4) which was originally termed glycoprotein 34 kDa (GP34) belongs to the TNF superfamily; it is mainly expressed on the surface of antigen-presenting cells (APC), including activated dendritic cells (DCs), B cells, macrophages, T cells as well as endothelial cells [Huang, L. et al., J. Trans. Med. (2018) 16: 74; doi: 10.1186/s12967-018-1436-4, citing DeSmedt, T et al, J. Immunol (2002) 168: 661-670. doi: 10.4049/jimmunol.168.2.661; Ohshima, Y. et al., Blood (1998) 92: 3338-3345].

OX40 (ACT35, CD134, TNFRSF4) is constitutively expressed on the cell surface of activated CD4+ T cells [Id., citing Ogawa R, et al., Cytokine Growth Factor Rev. (2008) 19:253-262. doi: 10.1016/j.cytogfr.2008.04.003, Paterson D J, et al. Mol Immunol. (1987) 24:1281-1290. doi: 10.1016/0161-5890(87)90122-2]. It can specially bind to OX40L and initiate a series of reactions which contribute to facilitate the proliferation and survival of CD4+ T cells and cytokine secretion [Id., citing Kaur D, Brightling C. Chest. (2012) 141:494-499. doi: 10.1378/chest.11-1730]. The OX-40 receptor (OX-40R) is a transmembrane protein found on the surface of activated CD4(+) T cells. Weinberg, A D, et al., "OX-40: life beyond the effector T cell stage," Semin. Immunol. (1998) 10(6): 471-80). When engaged by an agonist such as anti-OX-40 antibody or the OX-40 ligand (OX-40L) during antigen presentation to T cell lines, the OX-40R generates a costimulatory signal that is as potent as CD28 costimulation. Id. Engagement of OX-40R enhances effector and memory-effector T cell function by up-regulating IL-2 production and increasing the life-span of effector T cells. Id.

CD25-Foxp3-naïve CD4 T cells can acquire Foxp3 driven by TGF-βR and IL-2R signals leading to differentiation into an inducible Treg (iTreg). So, T et al, Cytokine Growth Factor Rev. (2008) 19 (3-4): 253-62. Costimulatory signals from OX40 have been found to be antagonistic for Foxp3 induction in antigen-responding naïve CD4 T cells and suppress the development of high numbers of CD25+ Foxp3+iTregs (Id, citing Vu M D, et al. Blood. (2007) 110:2501-10; So T, Croft M. J Immunol. (2007) 179:1427-30).

According to some embodiments of the disclosed invention, a tumor cell line or tumor cell line variant may be engineered to express a membrane bound form of OX40L on the membrane of the tumor cell of SEQ ID NO: 108. According to some embodiments, a tumor cell line or tumor cell line variant may comprise one or more proteins with a sequence identity of at least 60% to the protein of SEQ ID NO: 108. According to some embodiments, a tumor cell line or tumor cell line variant may comprise one or more proteins with a sequence identity of at least 70% to the protein of SEQ ID NO: 108. According to some embodiments, a tumor cell line or tumor cell line variant may comprise one or more proteins with a sequence identity of at least 80% to the protein of SEQ ID NO: 108. According to some embodiments, a tumor cell line or tumor cell line variant may comprise one or more proteins with a sequence identity of at least 90% to the protein of SEQ ID NO: 108. According to some embodiments, a tumor cell line or tumor cell line variant may comprise one or more proteins with a sequence identity of at least 95% to the protein of SEQ ID NO: 108. According to some embodiments, a tumor cell line or tumor cell line variant may comprise one or more proteins with a sequence identity of at least 96% to the protein of SEQ ID NO: 108. According to some embodiments, a tumor cell line or tumor cell line variant may comprise one or more proteins with a sequence identity of at least 97% to the protein of SEQ ID NO: 108. According to some embodiments, a tumor cell line or tumor cell line variant may comprise one or more proteins with a sequence identity of at least 98% to the protein of SEQ ID NO: 108. According to some embodiments, a tumor cell line or tumor cell line variant may comprise one or more proteins with a sequence identity of at least 99% to the protein of SEQ ID NO: 108.

CD27 Ligand (CD70)

CD27 ligand (CD70), a type II transmembrane protein, is a member of the TNF superfamily. It is expressed on activated T and B lymphocytes, as well as NK cells. CD27 Ligand and its receptor CD27 regulate the immune response by promoting T cell expansion and differentiation, as well as NK enhancement. CD27 signals, during the later phase of the primary CD8+ T cell response, prevent apoptosis of antigen-specific CD8+ T cells. Lack of CD27 signals decreases the quality of memory CD8+ T cell responses. Memory CD8+ T cells, which express surface CD27 similar to naïve cells, however, do not require CD27 costimulation during a secondary response. Thus, in vivo, CD27 acts indirectly to regulate primary antigen-specific CD8+ T cell responses by preventing apoptosis of CD8+ T cells during the later phase of the primary response, and is required for optimal quality of memory cells, but is not required during normally primed secondary CD8+ T cell responses. Dolfi, D V, et a., J. Immunol. (2008) 180(5): 2912-2921). Full length CD27 Ligand (CD70) is a 193 amino acid protein, consisting of a 17 amino acid cytoplasmic domain, a 21 amino acid transmembrane domain, and a 155 amino acid extracellular domain. Human soluble CD70 corresponds to the 155 amino acid extracellular domain of the full length CD70 protein.

According to some embodiments of the disclosed invention, a tumor cell line or tumor cell line variant may be engineered to express a membrane bound form of CD70 on the membrane of the tumor cell.

According to some embodiments of the disclosed invention, a tumor cell line or tumor cell line variant may be engineered to express a soluble form of CD70.

According to some embodiments of the disclosed invention, the tumor cell line or tumor cell line variant may be engineered to express a membrane bound form of CD70 on the membrane of the tumor cells of SEQ ID NO: 109. According to some embodiments, the tumor cell line or tumor cell line variant may comprise one or more proteins with a sequence identity of at least 60% to the protein of SEQ ID NO: 109. According to some embodiments, the tumor cell line or tumor cell line variant may comprise one or more proteins with a sequence identity of at least 70% to the protein of SEQ ID NO: 109. According to some embodiments, the tumor cell line or tumor cell line variant may comprise one or more proteins with a sequence identity of at least 80% to the protein of SEQ ID NO: 109. According to some embodiments, the tumor cell line or tumor cell line variant may comprise one or more proteins with a sequence identity of at least 90% to the protein of SEQ ID NO: 109. According to some embodiments, the tumor cell line or tumor cell line variant may comprise one or more proteins with a sequence identity of at least 95% to the protein of SEQ ID NO: 109. According to some embodiments, the tumor cell line or tumor cell line variant may comprise one or more proteins with a sequence identity of at least 96% to the protein of SEQ ID NO: 109. According to some embodiments, the tumor cell line or tumor cell line variant may comprise one or more proteins with a sequence identity of at least 97% to the protein of SEQ ID NO: 109. According to some embodiments, the tumor cell line or tumor cell line variant may comprise one or more proteins with a sequence identity of at least 98% to the protein of SEQ ID NO: 109. According to some embodiments, the tumor cell line or tumor cell line variant may comprise one or more proteins with a sequence identity of at least 99% to the protein of SEQ ID NO: 109.

4-IBBL

Naïve CD8 T cells require more co-stimulatory activity to drive them to become activated effector cells than do naïve CD4 T cells. This requirement can be met in two ways. The simplest is priming by activated DCs, which have high intrinsic co-stimulatory activity. In some viral infections, dendritic cells become sufficiently activated to directly induce CD8 T cells to produce the IL-2 required for their differentiation into cytotoxic effector cells, without help from CD4 T cells. This property of DCs have been exploited to generate cytotoxic T cell responses against tumors. In the majority of viral infections, however, CD8 T-cell activation requires additional help, which is provided by CD4 effector T cells. CD4 T cells that recognize related antigens presented by the APC can amplify the activation of naïve CD T cells by further activating the APC. B7 expressed by the DC first activates the CD4 T cells to express IL-2 and CD40L. CD40L binds CD40 on the DC, delivering an additional signal that increases the expression of B7 and 4-IBBL by the dendritic cell, which in turn provides additional costimulation to the naïve CD8 T cell. The IL-2 produced by activated CD4 T cells also acts to promote effector CD8 T-cell differentiation. Murphy, Kenneth. *Janeway's Immunobiology:* 8th ed. Chapter 15: Garland Science. (2012), at 372.

4-IBB has a pattern of expression that follows the primary activation of T cells and is restricted to activated CD4+ and CD8+ T cells. Guinn, B, et al., J. Immuno. (1999) 162: 5003-5010. Engagement of the 4-IBB receptor has been shown to relay strong costimulatory signals within activated T cells, which lead to their enhanced proliferation and cytokine secretion. Id. Such signaling prevents activation-induced cell death following TCR cross-linking in the absence of other accessory signals. Id. 4-IBBL, a high affinity ligand for 4-IBB, expressed on the surface of activated APCs, is a type II membrane protein that shows homology to members of the TNF receptor family. T cells purified from CD28−/− mice have been shown to secrete cytokines and proliferate in response to lymphomas expressing 4-IBBL; this response can be inhibited by the soluble 4-IBB receptor fusion protein. Id. In the absence of a CD28 signal, the 4-IBBL:4-IBB interaction has been shown to play a role in the production of a Th2 response in mixed lymphocyte reactions. Id.

According to some embodiments of the disclosed invention, an R subset of immunomodulators may comprise a membrane bound form of 4-IBBL. According to some embodiments of the disclosed invention, an R subset of immunomodulators may comprise a soluble form of 4-IBBL.

CD40L

The ligand of CD40, known as CD154 or CD40L, is a type II transmembrane protein, with a variable molecular weight between 32 and 39 kDa because of post-translation modifications (Elgueta R et al., Molecular mechanism and function of CD40/CD40L engagement in the immune system. Immunological reviews. 2009; 229(1):10.1111/j.1600-065X.2009.00782.x. doi:10.1111/j.1600-065X.2009.00782.x, citing van Kooten C et al., J. Leukoc Biol. 2000 January; 67(1):2-17.). A soluble form of CD40L has been reported that has activities similar to the transmembrane form (Id. citing Graf D et al., Eur J Immunol. 1995 June; 25(6):1749-54; Mazzei G J et al., J Biol Chem. 1995 Mar. 31; 270(13):7025-8.).

In nature, CD40L is a member of the TNF superfamily and is characterized by a sandwich extracellular structure that is composed of a β-sheet, α-helix loop, and a β-sheet, which allows for the trimerization of CD40L (Id. citing Karpusas M et al., Structure. 1995 Oct. 15; 3(10):1031-9). CD40L is expressed primarily by activated T cells, as well as activated B cells and platelets; under inflammatory conditions it is also induced on monocytic cells, natural killer cells, mast cells, and basophils (Id. citing Carbone E et al., J Exp Med. 1997 Jun. 16; 185(12):2053-60). The widespread expression of the costimulatory pair of CD40L and CD40 indicates the pivotal roles they play in different cellular immune processes.

CD40L has three binding partners: CD40, α5β1 integrin and αIIbβ3 integrin. CD40L acts as a costimulatory molecule and is particularly important on a subset of T cells called T follicular helper cells (TFH cells), where it promotes B cell maturation and function by engaging CD40 on the B cell surface facilitating cell-cell communication. A defect in the CD40L gene results in an inability to undergo immunoglobulin class switching and is associated with hyper-IgM syndrome. Absence of CD40L also stops the formation of germinal centers thereby prohibiting antibody affinity maturation, an important process in the adaptive immune system.

CD40 has been found to be expressed on APCs, while its ligand, CD40L, has been found on activated T cells. CD40 has been found to play a critical role in the humoral immune response, and has been identified as enabling APCs to activate T cells. Several pathologies have been associated with the CD40/CD40L pathway including lupus and atherosclerosis, but anti-CD40L antibodies have been limited to clinical applications of thrombic complications from CD40 expression on activated platelets (Kaufman and Wolchok eds., General Principles of Tumor Immunotherapy, Chpt 5, 67-121 (2007)).

CD40 has also been found on several types of cancer, including solid tumors and hematologic malignancies. Signaling through CD40 in hematological cancer may mediate growth or regression, while CD40 signaling in solid tumors is only tumoricidal. These characteristics are found even in SCID mouse models, and therefore are likely due to TNF death domain signaling. There is also evidence of immune modulation, for example blockade of the CD40/CD40L pathway mitigates the protective effect of GM-CSF secreting melanoma vaccines (Kaufman and Wolchok eds., General Principles of Tumor Immunotherapy, Chpt 5, 67-121 (2007)).

Tumor cell vaccines expressing CD40L have proved useful in cancer models. For example, ligation of CD40 with CD40L or anti-CD40 antibodies has shown synergy with GM-CSF, IFN-gamma, IL-2, and CTLA-4 blockade. Furthermore, anti-CD40 antibodies have been reported to have anti-tumor activity in a pre-clinical mouse model (Kaufman and Wolchok eds., General Principles of Tumor Immunotherapy, Chpt 5, 67-121 (2007)).

According to some embodiments, an R subset of immunomodulators may comprise CD40 Ligand (CD40L). According to some embodiments of the disclosed invention, the tumor cell line or tumor cell line variant may be engineered to express a noncleavable CD40L peptide of SEQ ID NO: 6. According to some embodiments, a tumor cell line or tumor cell line variant may comprise one or more proteins with a sequence identity of at least 60% to the protein of SEQ ID NO: 6. According to some embodiments, a tumor cell line or tumor cell line variant may comprise one or more proteins with a sequence identity of at least 70% to the protein of SEQ ID NO: 6. According to some embodiments, a tumor cell line or tumor cell line variant may comprise one or more proteins with a sequence identity of at least 80% to the protein of SEQ ID NO: 6. According to some embodiments, a tumor cell line or tumor cell line variant may comprise one or more proteins with a sequence identity of at least 90% to the protein of SEQ ID NO: 6. According to some embodiments, a tumor cell line or tumor cell line variant may comprise one or more proteins with a sequence identity of at least 95% to the protein of SEQ ID NO: 6. According to some embodiments, a tumor cell line or tumor cell line variant may comprise one or more proteins with a sequence identity of at least 96% to the protein of SEQ ID NO: 6. According to some embodiments, a tumor cell line or tumor cell line variant may comprise one or more proteins with a sequence identity of at least 97% to the protein of SEQ ID NO: 6. According to some embodiments, a tumor cell line or tumor cell line variant may comprise one or more proteins with a sequence identity of at least 98% to the protein of SEQ ID NO: 6. According to some embodiments, a tumor cell line or tumor cell line variant may comprise one or more proteins with a sequence identity of at least 99% to the protein of SEQ ID NO: 6.

According to some embodiments, the tumor cell line or tumor cell line variant may be engineered to express the non-cleavable membrane bound CD40L peptide of SEQ ID NO: 7 on the membrane surface of the tumor cell. According to some embodiments, a tumor cell line or tumor cell line variant may comprise one or more proteins with a sequence identity of at least 60% to the protein of SEQ ID NO: 7. According to some embodiments, a tumor cell line or tumor cell line variant may comprise one or more proteins with a sequence identity of at least 70% to the protein of SEQ ID NO: 7. According to some embodiments, a tumor cell line or tumor cell line variant may comprise one or more proteins with a sequence identity of at least 80% to the protein of SEQ ID NO: 7. According to some embodiments, a tumor cell line or tumor cell line variant may comprise one or more proteins with a sequence identity of at least 90% to the protein of SEQ ID NO: 7. According to some embodiments, a tumor cell line or tumor cell line variant may comprise one or more proteins with a sequence identity of at least 95% to the protein of SEQ ID NO: 7. According to some embodiments, a tumor cell line or tumor cell line variant may comprise one or more proteins with a sequence identity of at least 96% to the protein of SEQ ID NO: 7. According to some embodiments, a tumor cell line or tumor cell line variant may comprise one or more proteins with a sequence identity of at least 97% to the protein of SEQ ID NO: 7. According to some embodiments, a tumor cell line or tumor cell line variant may comprise one or more proteins with a sequence identity of at least 98% to the protein of SEQ ID NO: 7. According to some embodiments, a tumor cell line or tumor cell line variant may comprise one or more proteins with a sequence identity of at least 99% to the protein of SEQ ID NO: 7.

Tumor Necrosis Factor Alpha (TNFα)

Tumor necrosis factor (TNF; tumor necrosis factor alpha (TNFα); cachexin, cachectin) is a cytokine, primarily produced by activated macrophages and lymphocytes, which is involved in systemic inflammation. It is also one of the cytokines involved in the acute phase of an immunogenic response. TNF may be produced by other cell types such as, for example, CD4+ lymphocytes, NK cells, neutrophils, mast cells, eosinophils, and neurons.

In its primary role as a regulator of immune cells, TNF is capable of inducing fever, apoptotic cell death, cachexia, inflammation, and inhibition of tumorigenesis; of inhibiting viral replication; and of initiating a response to sepsis vial IL-1 and IL-6 producing cells. Dysregulated TNF production has been associated with a wide array of human diseases, including Alzheimer's disease, major depression, psoriasis, and inflammatory bowel disease (IBD). TNF can be produced ectopically in the setting of malignancy and parallels parathyroid hormone both in causing secondary hypercalcemia and in the cancers with which excessive production is associated.

TNF comprises a 26 kDa membrane bound form and 17 kDa soluble cytokine form. The soluble form of TNF is derived from proteolytic cleavage of the membrane bound form by TNF-alpha converting enzyme (TACE) (Grell M. et al., The Transmembrane Form of Tumor Necrosis Factor Is the Prime Activating Ligand of the 80 kDa Tumor Necrosis Factor Receptor, Cell, Vol. 83, 793-802). TACE is a matrix metalloprotease that recognizes a cleavage site in the extracellular domain of full-length TNF (Rieger, R., Chimeric form of tumor necrosis factor-alpha has enhanced surface expression and antitumor activity, Cancer Gene Therapy, 2009, 16, 53-64). Deletion of the cleavage site on TNF results in enhanced membrane stability of TNF (Id.).

TNF has antiproliferative and cytotoxic effects on cells, is known to reduce tumor blood flow and tumor vascular damage, and is able to modulate immune response by stimulating macrophage and NK cell activity. However, the use of TNF as a therapeutic itself has been limited by dose-dependent hypotension and capillary leak that can cause a sepsis-like syndrome. For that reason, it must be delivered in a manner that limits systemic effects. TNF has been added to standard chemotherapy agents to improve response rates. Other approaches to administering TNF include injection of adenovirus altered to express TNF in gastrointestinal malignancies. A tumor vascular-targeted TNF compound has also been developed (Kaufman and Wolchok eds., General Principles of Tumor Immunotherapy, Chpt 5, 67-121 (2007)). Recombinant TNF has been used as an immunostimulant under the name tasonermin, while HUMIRA® is an antibody to TNF, useful for the treatment of inflammatory diseases (e.g. psoriasis and rheumatoid arthritis). In recognition of this role, molecules such as antibodies have been designed to interfere with TNF activity. However, such therapies pose the risk of initiating a cytokine storm caused by the inappropriate systemic release of cytokines, resulting in a positive feedback loop of white blood cell activation/cytokine release that potentially can be fatal.

According to some embodiments, a subset of R immunomodulators may comprise TNF. According to some embodiments, a tumor cell line or tumor cell line variant may be genetically engineered to express the membrane bound form of TNF on the membrane of the tumor cell. For example, according to some embodiments, the cell line variants comprise the peptide of SEQ ID NO: 8. According to some embodiments, a tumor cell line or tumor cell line variant may comprise one or more proteins with a sequence identity of at least 60% to the protein of SEQ ID NO: 8. According to some embodiments, a tumor cell line or tumor cell line variant may comprise one or more proteins with a sequence identity of at least 70% to the protein of SEQ ID NO: 8. According to some embodiments, a tumor cell line or tumor cell line variant may comprise one or more proteins with a sequence identity of at least 80% to the protein of SEQ ID NO: 8. According to some embodiments, a tumor cell line or tumor cell line variant may comprise one or more proteins with a sequence identity of at least 90% to the protein of SEQ ID NO: 8. According to some embodiments, a tumor cell line or tumor cell line variant may comprise one or more proteins with a sequence identity of at least 95% to the protein of SEQ ID NO: 8. According to some embodiments, a tumor cell line or tumor cell line variant may comprise one or more proteins with a sequence identity of at least 96% to the protein of SEQ ID NO: 8. According to some embodiments, a tumor cell line or tumor cell line variant may comprise one or more proteins with a sequence identity of at least 97% to the protein of SEQ ID NO: 8. According to some embodiments, a tumor cell line or tumor cell line variant may comprise one or more proteins with a sequence identity of at least 98% to the protein of SEQ ID NO: 8. According to some embodiments, a tumor cell line or tumor cell line variant may comprise one or more proteins with a sequence identity of at least 99% to the protein of SEQ ID NO: 8.

According to some embodiments, a tumor cell line or tumor cell line variant may be genetically engineered to express a non-cleavable membrane bound form of TNF. For example, according to some embodiments, the tumor cell line or tumor cell line variant may comprise the TNF protein of SEQ ID NO: 8 with one or more of amino acids VRSSSRTPSDKP (SEQ ID NO: 104) deleted (see e.g. SEQ ID NO: 26).

According to some embodiments, a tumor cell line or tumor cell line variant may be genetically engineered to express a soluble form of TNF. For example, according to some embodiments, the tumor cell line or tumor cell line variant may express the TNF protein of SEQ ID NO: 8 with part or the entire transmembrane region removed. For example, according to some embodiments, the tumor cell line or tumor cell line variant may comprise a derivative TNF protein of SEQ ID NO: 8 with one or more of amino acids F, S, F, L, I, V, A, G, A, T, T, L, F, C, L, L, H, F, G, V, I deleted (see e.g. SEQ ID NO: 27).

According to some embodiments, a tumor cell line or tumor cell line variant may be genetically engineered to express a non-cleavable membrane bound chimeric form of CD40L and TNF. For example, according to some embodiments, the ligand binding portion of a TNF molecule may be fused with the transmembrane and proximal extracellular domains of CD40L, such that the TNF lacks a defined TNF alpha cleaving enzyme (TACE) site. According to some embodiments, the intracellular, transmembrane, and partial extracellular portions CD40L may be fused with the extracellular region of TNF distal to the TACE cleavage site. According to some embodiments, the chimeric form of CD40L/TNF may comprise the CD40L sequence of SEQ ID NO: 9 and the TNF sequence of SEQ ID NO: 10. According to some embodiments, the CD40L/TNF sequences are operably linked via a linking peptide between 1 and 30 amino acids in length. According to some embodiments, a tumor cell line or tumor cell line variant may be genetically engineered to comprise a fusion protein with a sequence identity of at least 60% to the proteins of SEQ ID NO: 9 and SEQ ID NO: 10. According to some embodiments, a tumor cell line or tumor cell line variant may be genetically engineered to comprise a fusion protein with a sequence identity of at least 70% to the proteins of SEQ ID NO: 9 and SEQ ID NO: 10. According to some embodiments, a tumor cell line or tumor cell line variant may be genetically engineered to comprise a fusion protein with a sequence identity of at least 80% to the proteins of SEQ ID NO: 9 and SEQ ID NO: 10. According to some embodiments, a tumor cell line or tumor cell line variant may be genetically engineered to comprise a fusion protein with a sequence identity of at least 90% to the proteins of SEQ ID NO: 9 and SEQ ID NO: 10. According to some embodiments, a tumor cell line or tumor cell line variant may be genetically engineered to comprise a fusion protein with a sequence identity of at least 95% to the proteins of SEQ ID NO: 9 and SEQ ID NO: 10. According to some embodiments, a tumor cell line or tumor cell line variant may be genetically engineered to comprise a fusion protein with a sequence identity of at least 96% to the proteins of SEQ ID NO: 9 and SEQ ID NO: 10. According to some embodiments, a tumor cell line or tumor cell line variant may be genetically engineered to comprise a fusion protein with a sequence identity of at least 97% to the proteins of SEQ ID NO: 9 and SEQ ID NO: 10. According to some embodiments, a tumor cell line or tumor cell line variant may be genetically engineered to comprise a fusion protein with a sequence identity of at least 98% to the proteins of SEQ ID NO: 9 and SEQ ID NO: 10. According to some embodiments, a tumor cell line or tumor cell line variant may be genetically engineered to comprise a fusion protein with a sequence identity of at least 99% to the proteins of SEQ ID NO: 9 and SEQ ID NO: 10.

According to some embodiments, a tumor cell line or tumor cell line variant may be genetically engineered to express a non-cleavable membrane bound form of TNF with a sequence identity of at least 60% to the protein of SEQ ID NO: 11. According to some embodiments, a tumor cell line or tumor cell line variant may be genetically engineered to express a non-cleavable membrane bound form of TNF with a sequence identity of at least 70% to the protein of SEQ ID NO: 11. According to some embodiments, a tumor cell line or tumor cell line variant may be genetically engineered to express a non-cleavable membrane bound form of TNF with a sequence identity of at least 80% to the protein of SEQ ID NO: 11. According to some embodiments, a tumor cell line or tumor cell line variant may be genetically engineered to express a non-cleavable membrane bound form of TNF with a sequence identity of at least 90% to the protein of SEQ ID NO: 11. According to some embodiments, a tumor cell line or tumor cell line variant may be genetically engineered to express a non-cleavable membrane bound form of TNF with a sequence identity of at least 95% to the protein of SEQ ID NO: 11. According to some embodiments, a tumor cell line or tumor cell line variant may be genetically engineered to express a non-cleavable membrane bound form of TNF with a sequence identity of at least 96% to the protein of SEQ ID NO: 11. According to some embodiments, a tumor cell line or tumor cell line variant may be genetically engineered to express a non-cleavable membrane bound form of TNF with a sequence identity of at least 97% to the protein of SEQ ID NO: 11. According to some embodiments, a tumor cell line or tumor cell line variant may be genetically engineered to express a non-cleavable membrane bound form of TNF with a sequence identity of at least 98% to the protein of SEQ ID NO: 11. According to some embodiments, a tumor cell line or tumor cell line variant may be genetically engineered to express a non-cleavable membrane bound form of TNF with a sequence identity of at least 99% to the protein of SEQ ID NO: 11.

According to some embodiments, a tumor cell line or tumor cell line variant may be genetically engineered to express a non-cleavable membrane bound chimeric form of CD40L and TNF. For example, according to some embodiments, the ligand portion of a TNF molecule may be fused with extracellular portions of CD40L, wherein CD40L comprises an extracellular portion that is non-cleavable and the TNF lacks a defined TACE site (e.g. cleavage site between amino acids 76 and 77). According to some embodiments, some or all of a CD40L peptide sequence is fused with the extracellular region of a TNF peptide sequence distal to the TACE cleavage site. According to some embodiments, the chimeric form of CD40L/TNF may comprise the sequence of SEQ ID NO: 31. According to some embodiments, a tumor cell line or tumor cell line variant may be genetically engineered to comprise a fusion protein with a sequence identity of at least 60% to the protein of SEQ ID NO: 31. According to some embodiments, a tumor cell line or tumor cell line variant may be genetically engineered to comprise a fusion protein with a sequence identity of at least 70% to the protein of SEQ ID NO: 31. According to some embodiments, a tumor cell line or tumor cell line variant may be genetically engineered to comprise a fusion protein with a sequence identity of at least 80% to the protein of SEQ ID NO: 31. According to some embodiments, a tumor cell line or tumor cell line variant may be genetically engineered to comprise a fusion protein with a sequence identity of at least 90% to the protein of SEQ ID NO: 31. According to some embodiments, a tumor cell line or tumor cell line variant may be genetically engineered to comprise a fusion protein with a sequence identity of at least 95% to the protein of SEQ ID NO: 31. According to some embodiments, a tumor cell line or tumor cell line variant may be genetically engineered to comprise a fusion protein with a sequence identity of at least 96% to the protein of SEQ ID NO: 31. According to some embodiments, a tumor cell line or tumor cell line variant may be genetically engineered to comprise a fusion protein with a sequence identity of at least 97% to the protein of SEQ ID NO: 31. According to some embodiments, a tumor cell line or tumor cell line variant may be genetically engineered to comprise a fusion protein with a sequence identity of at least 98% to the protein of SEQ ID NO: 31. According to some embodiments, a tumor cell line or tumor cell line variant may be genetically engineered to comprise a fusion protein with a sequence identity of at least 99% to the protein of SEQ ID NO: 31.

According to some embodiments, an allogeneic tumor cell vaccine, comprising a population of proliferation incompetent tumor cells expressing one or more tumor specific antigens, comprises one or more (e.g., 2, 3, 4, 5, or more) TNF-family member proteins, or variants or fragments thereof.

Secreted Receptors

According to one embodiment, the disclosure encompasses an allogeneic tumor cell vaccine, comprising a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising one or more secreted receptors.

According to some embodiments, R immunomodulators may comprise one or more (e.g., 2, 3, 4, 5, or more) secreted receptor proteins, or variants or fragments thereof. According to some embodiments, the secreted receptor is IL10R, TGFβR3, or both.

Interleukin-10 (IL-10) is a key immunosuppressive cytokine that is produced by a wide range of leukocytes, as well as nonhematopoietic cells. Shouval, D S., et al., Immunity (2014) 40: 706-719. IL-10 mediates its anti-inflammatory effects through IL-10 receptor (IL-10R)-dependent signals emanating from the cell surface. The IL-10R is a heterotetramer that consists of two subunits of IL-10Rα and two subunits of IL-10Rβ. Id., citing Moore, K W, et al., Annu. Rev. Immunol. (2001) 19: 683-765). Whereas the IL-10Rα subunit is unique to IL-10 signaling, the IL-10Rβ subunit is shared by other cytokine receptors, including IL-22, IL-26, and interferon λ, Id. IL-10 downstream signaling through the IL-10R inhibits the induction of proinflammatory cytokines by blocking NF-κB-dependent signals. (Id., citing Saraiva, M., and O'Garra, A. Nat. Rev. Immunol. (2010) 10: 180-181).

Transforming growth factor-beta receptor 3 (TbetaRIII or TbetaR3) is an 853 amino acid transmembrane proteoglycan, which contains a short 41 amino acid cytoplasmic domain. It is ubiquitously expressed on nearly all cell types. The level of TbetaRIII expression is cell type specific. It is a member of the TGF-beta superfamily signaling pathways, which have essential roles in mediating cell proliferation, apoptosis, differentiation, and migration in most human tissues. TbetaRIII is the most abundantly expressed TGF-beta superfamily receptor and functions as a TGF-beta superfamily co-receptor, by binding the TGF-beta superfamily members, TGF-beta1, TGF-beta2, or TGF-beta3, inhibin, BMP-2, BMP-4, BMP-7, and GDF-5 and presents these ligand to their respective signaling receptors to activate or repress (in the case of inhibin) TGF-beta1, BMP, or activin signaling to the Smad transcription factors. For example, in the case of TGF-beta1, 2, or 3, TbetaRIII presents ligand to the TGF-beta type II receptor (TbetaRII). Once bound to ligand, TbetaRII then recruits and transphosphorylates the TGF-beta type I receptor (TbetaR1), activating its kinase function and leading to the phosphorylation of Smad2/3. Phosphorylation of Smad2 and Smad3 leads to formation of a complex with Smad4, and accumulation of this complex in the nucleus, where along with co-activators and co-repressors they regulate the transcription of genes involved in proliferation, angiogenesis, apoptosis, and differentiation. In addition to regulating receptor mediated Smad signaling, TbetaRIII also mediates ligand dependent and independent p38 pathway signaling. TbetaRIII can also undergo ectodomain shedding to generate soluble TbetaRIII (sTbetaRIII), which binds and sequesters TGF-beta superfamily members to inhibit their signaling. Although sTbetaRIII expression has been demonstrated to correlate with the cell surface expression of TbetaRIII, little is known about the regulation of sTbetaRIII production. TbetaRIII shedding may be mediated in part by the membrane type matrix metalloproteases (MT-MMP) MT1-MMP and/or MT3-MMP, and plasmin, a serine proteinase which has been shown to cleave the extracellular domain of TbetaRIII In addition, TbetaRIII shedding is modulated by pervanadate, a tyrosine phosphatase inhibitor. Supporting this, TAPI-2, a MT-MMP and ADAM protease inhibitor, has been shown to inhibit TbetaRIII shedding. The regulation of TbetaRIII expression is sufficient to alter TGF-beta signaling. The cytoplasmic domain of TbetaRIII interacts with GAIP interacting protein, C terminus (GIPC), a PDZ-domain containing protein, which stabilizes TbetaRIII cell surface expression and increases TGF-beta signaling. The interaction between TbetaRIII and GIPC also plays an important role in TbetaRIII mediated inhibition of TGF-beta signaling, cell migration, and invasion during breast cancer progression. The cytoplasmic domain of TbetaRIII is phosphorylated by TbetaRII, which results in TbetaRIII binding to the scaffolding protein beta-arrestin2. The TbetaRIII/beta-arrestin2 interaction results in the co-internalization of beta-arrestin2/TbetaRIII/TbetaRII and the down-regulation of TGF-beta signaling. The interaction between TbetaRIII and beta-arrestin2 regulates BMP signaling as well as TGF-beta signaling. TbetaRIII complexes with ALK6, a BMP type I receptor, in a beta-arrestin2 dependent manner to mediate the internalization of ALK6 and stimulation of ALK6 specific BMP signaling events. Through its interaction with beta-arrestin2, TbetaRIII negatively regulates NFκ-B signaling in the context of breast cancer, regulates epithelial cellular adhesion to fibronectin, fibrillogenesis, and focal adhesion formation via regulation of alpha5beta1 internalization and trafficking to nascent focal adhesions, activates Cdc42, to alter the actin cytoskeleton and suppresses migration in normal and cancerous ovarian epithelial cells. During development, TbetaRIII has an important role in the formation of the atrioventricular cushion in the heart. Consistent with an important role for TbetaRIII during development, TGFbetaR3 null mice are embryonic lethal due to heart and liver defects. TGFbetaR3 has been recently identified as a tumor suppressor in multiple types of human cancers, including breast, lung, ovarian, pancreatic and prostate cancer. The loss of TGFbetaR3 in these cancer types correlates with disease progression, and results in increased motility and invasion in vitro and increased invasion and metastasis in vivo. (http://atlasgeneticsoncology.org/Genes/TGFBR3ID-42541ch1p33.html, visited Aug. 26, 2019).

Chaperones

According to some embodiments, a subset of R immunomodulators may comprise one or more chaperone proteins. According to one embodiment, the disclosure encompasses an allogeneic tumor cell vaccine, comprising a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising one or more chaperone proteins. Thus, the disclosure encompasses a chaperone protein, including a full-length, fragment, homologue, variant or mutant of the chaperone protein. Chaperones are a functionally related group of proteins assisting protein folding in the cell under physiological and stress conditions. According to some embodiments, the chaperone protein is selected from one or more of GRP78/BiP, GRP94, GRP170, Calnexin, calreticulin, HSP47, ERp29, Protein disulfide isomerase (PDI), Peptidyl prolyl cis-trans-isomerase (PPI), Erp57, Hsp60, Hsp70, Hsp90, Hsp100.

According to some embodiments, the chaperone protein is membrane bound.

According to some embodiments, an allogeneic tumor cell vaccine, comprising a population of proliferation incompetent tumor cells expressing one or more tumor specific antigens, comprises one or more (e.g., 2, 3, 4, 5, or more) chaperone proteins, or variants or fragments thereof.

Immunoglobulin Superfamily (IgSF)

According to some embodiments, a subset of R immunomodulators may comprise one or more IgSF proteins. According to one embodiment, the disclosure encompasses an allogeneic tumor cell vaccine, comprising a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising one or more IgS family proteins. Thus, the disclosure encompasses a member of the IgSF superfamily, including a full-length, fragment, homologue, variant or mutant of the IgSF superfamily member. The immunoglobulin superfamily (IgSF) is a class of proteins that are associated with the adhesion, binding and recognition processes of cells. Molecules are categorized as members of this superfamily based on shared structural features with immunoglobulins; they all possess a domain known as an immunoglobulin domain or fold. Members of the IgSF include cell surface antigen receptors, co-receptors and co-stimulatory molecules of the immune system, molecules involved in antigen presentation to lymphocytes, cell adhesion molecules, certain cytokine receptors and intracellular muscle proteins. Members of the IgSF can be classified as follows: antigen receptors (e.g. antibodies or immunoglobulins: IgA, IgD, IgE, IgG, IgM); antigen presenting molecules (e.g. MHC class I, MHC class II); co-receptors (e.g. CD4, CD8); co-stimulatory or inhibitory molecules (e.g. CD28, Cd80, CD86); receptors on Natural killer cells (e.g. killer-cell immunoglobulin-like receptors (KIR)); receptors on leukocytes (e.g., leukocyte immunoglobulin-like receptors (LILR)); IgSF CAMs (e.g., NCAMs, ICAM-1); cytokine receptors; growth factor receptors; receptor tyrosine kinases/phosphatases; IgG binding receptors.

According to some embodiments, the IgSF member is membrane bound.

Poliovirus Receptor (PVR/CD155) is a transmembrane glycoprotein belonging to the immunoglobulin superfamily. PVR/CD155 mediates NK cell adhesion and triggers NK cell effector functions. PVR/CD155 binds two different NK cell receptors: CD96 and CD226. These interactions accumulate at the cell-cell contact site, leading to the formation of a mature immunological synapse between NK cell and target cell. This may trigger adhesion and secretion of lytic granules and IFN-gamma (IFNγ) and activate cytoxicity of activated NK cells, and may also promote NK cell-target cell modular exchange, and PVR transfer to the NK cell.

Poliovirus receptor-related 2 (PVRL2), also known as Nectin-2, is a single-pass type I membrane glycoprotein with two Ig-like C2-type domains and an Ig-like V-type domain. This protein is one of the plasma membrane components of adherens junctions.

CD48 antigen (Cluster of Differentiation 48), also known as B-lymphocyte activation marker (BLAST-1) or signaling lymphocytic activation molecule 2 (SLAMF2), is a protein that in humans is encoded by the CD48 gene. CD48 is a member of the CD2 subfamily of the IgSF, which includes SLAM (signaling lymphocyte activation molecules) proteins, such as CD84, CD150, CD229 and CD244. CD48 is found on the surface of lymphocytes and other immune cells, dendritic cells and endothelial cells, and participates in activation and differentiation pathways in these cells.

NK-T-B antigen (NTBA) is a surface molecule expressed on NK, T, and B cells. In human NK cells, NTBA has been shown to act primarily as a coreceptor since it could trigger cytolytic activity only in cells expressing high surface densities of natural cytotoxicity receptors (NCR). Molecular cloning revealed that NTBA is a member of the Ig superfamily characterized by structural features that allowed its assignment to the CD2 family.

According to one embodiment, the IgSF protein is IgG. According to one embodiment, the IgSF protein is PVR/CD155. According to one embodiment, the IgSF protein is CD48. According to one embodiment, the IgSF protein is Nectin2. According to one embodiment, the IgSF protein is NK-T-B antigen.

Immunoglobulins (Ig) are glycoproteins produced by immune cells. Antibodies are serum proteins, the molecules of which possess small areas of their surface that are complementary to small chemical groupings on their targets. These complementary regions (referred to as complementary determining regions (CDRs), or antibody combining sites, or antigen binding sites) of which there are at least two per antibody molecule, and in some types of antibody molecules ten, eight, or in some species as many as 12, may react with their corresponding complementary region on the antigen (the antigenic determinant or epitope) to link several molecules of multivalent antigen together to form a lattice. Immunoglobulins play a critical role in an immune response by binding to particular antigens, such as those exhibited by bacteria or viruses. According to some embodiments, the binding of immunoglobulins to antigens may target them for destruction by the subject's immune cells.

The basic structural unit of a whole antibody molecule consists of four polypeptide chains, two identical light (L) chains (each containing about 220 amino acids) and two identical heavy (H) chains (each usually containing about 440 amino acids). The two heavy chains and two light chains are held together by a combination of noncovalent and covalent (disulfide) bonds. The molecule is composed of two identical halves, each with an identical antigen-binding site composed of the N-terminal region of a light chain and the N-terminal region of a heavy chain. Both light and heavy chains usually cooperate to form the antigen binding surface.

In mammals, there are five classes of antibodies, IgA, IgD, IgE, IgG, and IgM, each with its own class of heavy chain-α (for IgA), δ (for IgD), ε (for IgE), γ (for IgG) and μ (for IgM). In addition, there are four subclasses of IgG immunoglobulins (IgG1, IgG2, IgG3, IgG4) having γ1, γ2, γ3, and γ4 heavy chains respectively. In its secreted form, IgM is a pentamer composed of five four-chain units, giving it a total of 10 antigen binding sites. Each pentamer contains one copy of a J chain, which is covalently inserted between two adjacent tail regions.

Diverse libraries of immunoglobulin heavy (VH) and light (Vκ and Vλ) chain variable genes from peripheral blood lymphocytes also can be amplified by polymerase chain reaction (PCR) amplification. Genes encoding single polypeptide chains in which the heavy and light chain variable domains are linked by a polypeptide spacer can be made by randomly combining heavy and light chain V-genes using PCR.

According to some embodiments, the tumor cell line or tumor cell line variants may be engineered to express an IgG1 heavy chain constant region. In nature, the Ig gamma-1 (IgG-1) chain C region is a protein encoded by the IGHG1 gene in humans. According to some embodiments, a tumor cell line or tumor cell line variant may express a membrane bound form IgG-1 chain C protein of SEQ ID NO: 1. According to some embodiments, a tumor cell line or tumor cell line variant may be genetically engineered to express a secreted form of IgG-1 chain C of SEQ ID NO: 2. According to some embodiments, a tumor cell line or tumor cell line variant may be genetically engineered to express a secreted form of IgG-1 chain C of SEQ ID NO: 3. According to some embodiments, a tumor cell line or tumor cell line variant may be genetically engineered to comprise one or more proteins with a sequence identity of at least 60% to one or more of proteins with an amino acid sequence SEQ ID NO: 1, SEQ ID NO: 2, and SEQ ID NO: 3. According to some embodiments, a tumor cell line or tumor cell line variant may be genetically engineered to comprise one or more proteins with a sequence identity of at least 70% to one or more of proteins with an amino acid sequence SEQ ID NO: 1, SEQ ID NO: 2, and SEQ ID NO: 3. According to some embodiments, a tumor cell line or tumor cell line variant may be genetically engineered to comprise one or more proteins with a sequence identity of at least 80% to one or more of proteins with an amino acid sequence SEQ ID NO: 1, SEQ ID NO: 2, and SEQ ID NO: 3. According to some embodiments, a tumor cell line or tumor cell line variant may be genetically engineered to comprise one or more proteins with a sequence identity of at least 90% to one or more of proteins with an amino acid sequence SEQ ID NO: 1, SEQ ID NO: 2, and SEQ ID NO: 3. According to some embodiments, a tumor cell line or tumor cell line variant may be genetically engineered to comprise one or more proteins with a sequence identity of at least 95% to one or more of proteins with an amino acid sequence SEQ ID NO: 1, SEQ ID NO: 2, and SEQ ID NO: 3. According to some embodiments, a tumor cell line or tumor cell line variant may be genetically engineered to comprise one or more proteins with a sequence identity of at least 96% to one or more of proteins with an amino acid sequence SEQ ID NO: 1, SEQ ID NO: 2, and SEQ ID NO: 3. According to some embodiments, a tumor cell line or tumor cell line variant may be genetically engineered to comprise one or more proteins with a sequence identity of at least 97% to one or more of proteins with an amino acid sequence SEQ ID NO: 1, SEQ ID NO: 2, and SEQ ID NO: 3. According to some embodiments, a tumor cell line or tumor cell line variant may be genetically engineered to comprise one or more proteins with a sequence identity of at least 98% to one or more of proteins with an amino acid sequence SEQ ID NO: 1, SEQ ID NO: 2, and SEQ ID NO: 3. According to some embodiments, a tumor cell line or tumor cell line variant may be genetically engineered to comprise one or more proteins with a sequence identity of at least 99% to one or more of proteins with an amino acid sequence SEQ ID NO: 1, SEQ ID NO: 2, and SEQ ID NO: 3.

According to some embodiments, a tumor cell line or tumor cell line variant may be genetically engineered to comprise one or more proteins with a sequence identity of at least 60% to one or more proteins with amino acid sequence SEQ ID NO: 12, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 45, and SEQ ID NO: 46. According to some embodiments, a tumor cell line or tumor cell line variant may be genetically engineered to comprise one or more proteins with a sequence identity of at least 70% to one or more proteins with amino acid sequence SEQ ID NO: 12, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 45, and SEQ ID NO: 46. According to some embodiments, a tumor cell line or tumor cell line variant may be genetically engineered to comprise one or more proteins with a sequence identity of at least 80% to one or more proteins with amino acid sequence SEQ ID NO: 12, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 45, and SEQ ID NO: 46. According to some embodiments, a tumor cell line or tumor cell line variant may be genetically engineered to comprise one or more proteins with a sequence identity of at least 90% to one or more proteins with amino acid sequence SEQ ID NO: 12, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 45, and SEQ ID NO: 46. According to some embodiments, a tumor cell line or tumor cell line variant may be genetically engineered to comprise one or more proteins with a sequence identity of at least 95% to one or more proteins with amino acid sequence SEQ ID NO: 12, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 45, and SEQ ID NO: 46. According to some embodiments, a tumor cell line or tumor cell line variant may be genetically engineered to comprise one or more proteins with a sequence identity of at least 96% to one or more proteins with amino acid sequence SEQ ID NO: 12, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 45, and SEQ ID NO: 46. According to some embodiments, a tumor cell line or tumor cell line variant may be genetically engineered to comprise one or more proteins with a sequence identity of at least 97% to one or more proteins with amino acid sequence SEQ ID NO: 12, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 45, and SEQ ID NO: 46. According to some embodiments, a tumor cell line or tumor cell line variant may be genetically engineered to comprise one or more proteins with a sequence identity of at least 98% to one or more proteins with amino acid sequence SEQ ID NO: 12, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 45, and SEQ ID NO: 46. According to some embodiments, a tumor cell line or tumor cell line variant may be genetically engineered to comprise one or more proteins with a sequence identity of at least 99% to one or more proteins with amino acid sequence SEQ ID NO: 12, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 45, and SEQ ID NO: 46.

According to some embodiments, the tumor cell line or tumor cell line variant may be engineered to express an IgG protein that is capable of binding to tumor cell specific antigens. For example, the tumor cell line or tumor cell line variant may be engineered to express an IgG protein capable of binding to a prostate cancer specific antigen; e.g., the extracellular region of prostate-specific membrane antigen (PSMA) (See Chang, S., Overview of Prostate-Specific Membrane Antigen, Reviews in Urology, Vol. 6 Suppl. 10, S13 (2004)). According to some embodiments, the tumor cell line or tumor cell line variant may be engineered to express an IgG protein that is capable of binding to immune cell specific antigens. For example, the tumor cell line or tumor cell line variant may be engineered to express an IgG protein capable of binding to T cell markers, e.g., CD3, CD4, or CD8. According to another example, the tumor cell line or tumor cell line variant may be engineered to express an IgG protein capable of binding to dendritic cell markers, e.g. CD11c or CD123.

According to some embodiments, the tumor cell line or tumor cell line variants may be engineered to express an IgG3 heavy chain constant region. In nature, the IgG3 heavy chain constant region comprises CH1-hinge-CH2-CH3 domains, and is encoded by the IGHG3 gene in humans; the IGHG3 gene comprises structural polymorphisms comprising different hinge lengths. According to some embodiments, a tumor cell line or tumor cell line variant may be genetically engineered to express an IgG-3 heavy chain constant region of SEQ ID NO: 4. According to some embodiments, a tumor cell line or tumor cell line variant may be genetically engineered to express a derivative of SEQ ID NO: 4 with amino acids 1-76 missing. According to some embodiments, a tumor cell line or tumor cell line variant may be genetically engineered to express the derivative of SEQ ID NO: 4 with amino acids 1-76 missing. According to some embodiments, a tumor cell line or tumor cell line variant may be genetically engineered to express the derivative of SEQ ID NO: 4 with amino acids 77-98 replaced with amino acids QMQGVNCTVSS (SEQ ID NO: 101). According to some embodiments, a tumor cell line or tumor cell line variant may be genetically engineered to express the derivative of SEQ ID NO: 4 comprising an E213Q variant (SEQ ID NO: 16). According to some embodiments, a tumor cell line or tumor cell line variant may be genetically engineered to express the derivative of SEQ ID NO: 4 comprising a P221L variant (SEQ ID NO: 17). According to some embodiments, a tumor cell line or tumor cell line variant may be genetically engineered to express the derivative of SEQ ID NO: 4 comprising an E224Q variant (SEQ ID NO: 18). According to some embodiments, a tumor cell line or tumor cell line variant may be genetically engineered to express the derivative of SEQ ID NO: 4 comprising a Y226F variant (SEQ ID NO: 19). According to some embodiments, a tumor cell line or tumor cell line variant may be genetically engineered to express the derivative of SEQ ID NO: 4 comprising a D242N variant (SEQ ID NO: 20). According to some embodiments, a tumor cell line or tumor cell line variant may be genetically engineered to express the derivative of SEQ ID NO: 4 comprising a N245D variant (SEQ ID NO: 21). According to some embodiments, a tumor cell line or tumor cell line variant may be genetically engineered to express the derivative of SEQ ID NO: 4 comprising a T269A variant (SEQ ID NO: 22). According to some embodiments, a tumor cell line or tumor cell line variant may be genetically engineered to express the derivative of SEQ ID NO: 4 comprising a S314N variant (SEQ ID NO: 23). According to some embodiments, a tumor cell line or tumor cell line variant may be genetically engineered to express the derivative of SEQ ID NO: 4 comprising a deleted 5314 (SEQ ID NO: 24). According to some embodiments, a tumor cell line or tumor cell line variant may be genetically engineered to express the derivative of SEQ ID NO: 4 comprising F366Y variant (SEQ ID NO: 25).

According to some embodiments, a tumor cell line or tumor cell line variant may be genetically engineered to comprise one or more proteins with a sequence identity of at least 60% to the protein of SEQ ID NO: 4. According to some embodiments, a tumor cell line or tumor cell line variant may be genetically engineered to comprise one or more proteins with a sequence identity of at least 70% to the protein of SEQ ID NO: 4. According to some embodiments, a tumor cell line or tumor cell line variant may be genetically engineered to comprise one or more proteins with a sequence identity of at least 80% to the protein of SEQ ID NO: 4. According to some embodiments, a tumor cell line or tumor cell line variant may be genetically engineered to comprise one or more proteins with a sequence identity of at least 90% to the protein of SEQ ID NO: 4. According to some embodiments, a tumor cell line or tumor cell line variant may be genetically engineered to comprise one or more proteins with a sequence identity of at least 95% to the protein of SEQ ID NO: 4. According to some embodiments, a tumor cell line or tumor cell line variant may be genetically engineered to comprise one or more proteins with a sequence identity of at least 96% to the protein of SEQ ID NO: 4. According to some embodiments, a tumor cell line or tumor cell line variant may be genetically engineered to comprise one or more proteins with a sequence identity of at least 97% to the protein of SEQ ID NO: 4. According to some embodiments, a tumor cell line or tumor cell line variant may be genetically engineered to comprise one or more proteins with a sequence identity of at least 98% to the protein of SEQ ID NO: 4. According to some embodiments, a tumor cell line or tumor cell line variant may be genetically engineered to comprise one or more proteins with a sequence identity of at least 99% to the protein of SEQ ID NO: 4.

According to some embodiments, a tumor cell line or tumor cell line variant may be engineered to express one or more IgG heavy chain variable regions. According to some embodiments, a tumor cell line or tumor cell line variant may be engineered to express a lambda/kappa light chain constant and/or light chain variable region. According to some embodiments, the hinge region of IgG binds to the FcγR receptors on immune cells. According to some embodiments, the IgG is effective to activate the FcγR and enhance presentation of antigens (e.g. PSA associated with prostate cancer cells).

According to some embodiments, a tumor cell line or tumor cell line variant may be engineered to express an intact monoclonal or polyclonal antibody on the cell surface of the tumor cell. According to some embodiments, the intact monoclonal or polyclonal antibody may be designed to deliver a molecule that elicits an immunogenic response. For example, according to some embodiments, the intact monoclonal antibody may be designed to bind to DNA to deliver CpG motifs to immune cells.

According to some embodiments, the immunostimulatory activity of bacterial DNA may be mimicked by engineering an immunomodulator to deliver unmethylated CpG motifs to immune cells. For example, according to some embodiments, the IgG may be engineered to bind to biotin, which is then capable of delivering biotinylated CpG to cells of the immune system. According to some embodiments, CpG motifs may be bound directly or indirectly to the surface of the tumor cells of the tumor cell vaccine to prevent systemic effects. According to some embodiments, CpG motifs may be conjugated to one or more antigens presented on the surface of tumor cells from the tumor cell line or tumor cell line variant. According to some embodiments, the CpG is a class A CpG. According to some embodiments, the CpG is a class B CpG. According to some embodiments, the CpG is a class C CpG. According to some embodiments, the CpG is a CpG 30-mer of the sequence

```
                                      (SEQ ID NO: 102)
5' EEAACCGTATCGGCGATATCGGTTEEEEEG 3'.
```

As used herein with respect to CpG motifs, "E" is a G-phosphorothioate and this linkage refers to the 3' end of the nucleotide (i.e. the phosphorothioate bond substitutes a sulfur atom for a non-bridging oxygen in the nucleotide backbone). According to some embodiments, the CpG is a biotinylated 30-mer of the sequence

```
                                      (SEQ ID NO: 102)
5'-biotin-EEAACCGTATCGGCGATATCGGTTEEEEEG-3'.
```

According to some embodiments, the CpG is a CpG 30-mer of the sequence

```
                                      (SEQ ID NO: 103)
5' EEAACCGTATGCGGCATATCGGTTEEEEEG 3'.
```

According to some embodiments, the CpG is a biotinylated CpG 30-mer of the sequence

```
                                      (SEQ ID NO: 103)
5'-biotin-EEAACCGTATGCGGCATATCGGTTEEEEEG-3'.
```

According to some embodiments, the IgG may be engineered as a hybrid of one or more IgG subclasses. For example, according to some embodiments, the IgG comprises sequences from IgG1 and IgG3. According to some embodiments, the IgG may be engineered to have an affinity for biotin. According to some embodiments, a tumor cell line or tumor cell line variant may be genetically engineered to comprise one or more proteins with a sequence identity of at least 60% to the protein of SEQ ID NO: 45. According to some embodiments, a tumor cell line or tumor cell line variant may be genetically engineered to comprise one or more proteins with a sequence identity of at least 70% to the protein of SEQ ID NO: 45. According to some embodiments, a tumor cell line or tumor cell line variant may be genetically engineered to comprise one or more proteins with a sequence identity of at least 80% to the protein of SEQ ID NO: 45. According to some embodiments, a tumor cell line or tumor cell line variant may be genetically engineered to comprise one or more proteins with a sequence identity of at least 90% to the protein of SEQ ID NO: 45. According to some embodiments, a tumor cell line or tumor cell line variant may be genetically engineered to comprise one or more proteins with a sequence identity of at least 95% to the protein of SEQ ID NO: 45. According to some embodiments, a tumor cell line or tumor cell line variant may be genetically engineered to comprise one or more proteins with a sequence identity of at least 96% to the protein of SEQ ID NO: 45. According to some embodiments, a tumor cell line or tumor cell line variant may be genetically engineered to comprise one or more proteins with a sequence identity of at least 97% to the protein of SEQ ID NO: 45. According to some embodiments, a tumor cell line or tumor cell line variant may be genetically engineered to comprise one or more proteins with a sequence identity of at least 98% to the protein of SEQ ID NO: 45. According to some embodiments, a tumor cell line or tumor cell line variant may be genetically engineered to comprise one or more proteins with a sequence identity of at least 99% to the protein of SEQ ID NO: 45.

According to some embodiments, the IgG comprises one or more mutations relative to wild type IgG that enhance affinity for Fc receptors for IgG (FcγR). According to some embodiments, a tumor cell line or tumor cell line variant may be genetically engineered to comprise one or more proteins of SEQ ID NO: 45 with one or more of mutations T323A and E325A. According to some embodiments, a tumor cell line or tumor cell line variant may be genetically engineered to comprise one or more proteins with a sequence identity of at least 60% to the proteins of one or more of SEQ ID NO: 41, SEQ ID NO: 30, and SEQ ID NO: 43. According to some embodiments, a tumor cell line or tumor cell line variant may be genetically engineered to comprise one or more proteins with a sequence identity of at least 70% to the proteins of one or more of SEQ ID NO: 41, SEQ ID NO: 30, and SEQ ID NO: 43. According to some embodiments, a tumor cell line or tumor cell line variant may be genetically engineered to comprise one or more proteins with a sequence identity of at least 80% to the proteins of one or more of SEQ ID NO: 41, SEQ ID NO: 30, and SEQ ID NO: 43. According to some embodiments, a tumor cell line or tumor cell line variant may be genetically engineered to comprise one or more proteins with a sequence identity of at least 90% to the proteins of one or more of SEQ ID NO: 41, SEQ ID NO: 30, and SEQ ID NO:

43. According to some embodiments, a tumor cell line or tumor cell line variant may be genetically engineered to comprise one or more proteins with a sequence identity of at least 95% to the proteins of one or more of SEQ ID NO: 41, SEQ ID NO: 30, and SEQ ID NO: 43. According to some embodiments, a tumor cell line or tumor cell line variant may be genetically engineered to comprise one or more proteins with a sequence identity of at least 96% to the proteins of one or more of SEQ ID NO: 41, SEQ ID NO: 30, and SEQ ID NO: 43. According to some embodiments, a tumor cell line or tumor cell line variant may be genetically engineered to comprise one or more proteins with a sequence identity of at least 97% to the proteins of one or more of SEQ ID NO: 41, SEQ ID NO: 30, and SEQ ID NO: 43. According to some embodiments, a tumor cell line or tumor cell line variant may be genetically engineered to comprise one or more proteins with a sequence identity of at least 98% to the proteins of one or more of SEQ ID NO: 41, SEQ ID NO: 30, and SEQ ID NO: 43. According to some embodiments, a tumor cell line or tumor cell line variant may be genetically engineered to comprise one or more proteins with a sequence identity of at least 99% to the proteins of one or more of SEQ ID NO: 41, SEQ ID NO: 30, and SEQ ID NO: 43.

According to some embodiments, an allogeneic tumor cell vaccine comprises a population of proliferation incompetent tumor cells expressing one or more tumor specific antigens, the tumor cells comprising one or more (e.g., 2, 3, 4, 5, or more) IgSF proteins, or variants or fragments thereof.

Chemokine Receptors

According to some embodiments, a subset of R immunomodulators may comprise one or more chemokine receptors. Chemokine receptors are defined as mediators that activate cellular responses upon binding of chemokines. Twenty-three subtypes of human chemokine receptors have been identified, all of which are members of the seven-transmembrane (7TM) domain superfamily of receptors. They can be divided into two main groups: the G protein—coupled chemotactic chemokine receptors (n=19) and the atypical chemokine receptors (n=4). Chemokine binding, membrane anchoring, and signaling domains for receptors from both groups come from a single polypeptide chain. Structural and biochemical evidence exists that these receptors form homo- and heterodimers.

According to some embodiments, the chemokine receptor is membrane bound.

According to one embodiment, the disclosure encompasses an allogeneic tumor cell vaccine, comprising a population of proliferation incompetent tumor cells expressing one or more tumor specific antigens, wherein the tumor cells are genetically engineered to stimulate one or more of T lymphocytes, natural killer (NK) cells, dendritic cells (DCs) or B lymphocytes, the population comprising one or more chemokine receptors. Thus, the disclosure encompasses a chemokine receptor, including a full-length, fragment, homologue, variant or mutant of the chemokine receptor. A cytokine includes a protein that is effective to affect the biological function of another cell. A biological function affected by a cytokine can include, but is not limited to, cell growth, cell differentiation or cell death. For example, a chemokine receptor of the present disclosure is capable of stimulating an immune cell (e.g. T lymphocytes (e.g., CD8+ T cell), natural killer (NK) cells, dendritic cells (DCs) or B lymphocytes).

According to some embodiments, the chemokine receptor is selected from one or more of CXCR1, CXCR2, CXCR3, CXCR5, CXCR6, CXCR8, CCR8, CCR1, CCR2, CCR3, CCR5, CCR4, CCR6, CCR7, CCR9, CCR10, CXCR1, and CXCR3.

CD28 Ligand (CD28L)

Ligation of the CD28 receptor on T cells provides a critical second signal alongside T cell receptor (TCR) ligation for naive T cell activation. Esenstein, J H et al, Immunity (2016) 44(5): 973-988). CD28 drives critical intracellular biochemical events including unique phosphorylation and transcriptional signaling, metabolism, and the production of key cytokines, chemokines, and survival signals that are essential for long-term expansion and differentiation of T cells (Id., citing Bluestone, J A et al., Immunity. (2006)24: 233-238; Bour-Jordan, H. et al., Immunol Rev. (2011) 241:180-205; Martin, P J et al., J Immunol. (1986) 136: 3282-3287; Weiss, A. et al., J Immunol. (1986) 137:819-825).

CD28 is the founding member of a subfamily of costimulatory molecules characterized by an extracellular variable immunoglobulin-like domain. Other members of the subfamily include ICOS, CTLA4, PD1, PD1H, and BTLA (Id., citing Chen, L. and Flies, D. B., Nat Rev Immunol. 2013; 13:227-242). CD28 is expressed constitutively on mouse T cells, whereas the expression of other family members ICOS and CTLA4 is induced by T cell receptor stimulation and in response to cytokines such as interleukin 2 (IL-2). CD28 is expressed on roughly 80% of human CD4+ T cells and 50% CD8+ T cells. The proportion of CD28 positive T cells in humans declines with age. Although CD28 expression has been identified on other cell lineages, including bone marrow stromal cells, plasma cells, neutrophils, and eosinophils, the functional importance of CD28 on these cells is not completely understood (Id., citing Gray Parkin, K., et al., J Immunol. (2002) 169:2292-2302; Rozanski, C H et al., J Exp Med. (2011) 208:1435-1446; Venuprasad, K., et al., Eur J Immunol. (2001) 31:1536-1543; Woerly, G. et al., Clin Exp Allergy. (2004) 34:1379-1387).

The CD28 ligands CD80 and CD86 diverge in their expression patterns, multimeric states, and functionality, adding another layer of complexity to the regulation of CD28 signaling. CD80 is present in predominantly dimeric form on the cell surface whereas CD86 is monomeric (Id., citing Bhatia, S. et al., Proc Natl Acad Sci USA. (2005) 102:15569-155742005). CD86 is expressed constitutively on antigen presenting cells (APCs) and is rapidly upregulated by innate stimuli of APCs (Id., citing Lenschow, D J et al., J Immunol. (1994) 153:1990-1997), whereas the other CD28 ligand, CD80, is upregulated at later time points (Id., citing Sharpe, A J and Freeman, G J, Nat Rev Immunol. (2002) 2:116-126). CD86 may therefore be more important in the initiation of immune responses. CD80 and CD86 are induced by different stimuli in different cell types and they are not interchangeable in function.

CD28 and CTLA4 have opposing effects on T cell stimulation. CD28 provides an activating signal and CTLA4 provides an inhibitory signal, which is now considered a prototypical immune checkpoint (Id., citing Krummel, M F and Allison, J P, J Exp Med. 1995; 182:459-465; Walunas, T L et al., Immunity. (1994) 1:405-413). ICOS, which also contributes to activation, binds to its ligand B7H2 (ICOSL), which also serves as a ligand for human CD28 and CTLA4 (Id., citing Chen, L. and Flies, D B, Nat Rev Immunol. (2013) 13:227-242; Yao, S. et al., Immunity (2011) 34:729-740). Thus, this family of receptors and ligands has considerable complexity in both binding pattern and biological effect. Overall, the opposing roles of CD28 and ICOS compared with CTLA4 allow this family of receptors and ligands to serve as a rheostat for the immune response through competing pro- and anti-inflammatory effects. Id.

It has been suggested that CD80 and CD86 may also act as signal transducing receptors themselves, since ligation with CTLA4Ig has been shown to regulate tryptophan metabolism in APCs (Id., citing Grohmann, U et al., Nat Immunol. (2002) 3:1097-1101). In addition to T cells, plasma cells also express CD28. CD28 signals may regulate antibody production by plasma cells or plasma cell survival although the precise role that CD28 plays in plasma cell biology is still unclear (Id., citing Njau, N M and Jacob, J., Adv Exp Med Biol. (2013) 785:67-75).

The CD28 gene is composed of four exons encoding a protein of 220 amino acids that is expressed on the cell surface as a glycosylated, disulfide-linked homodimer of 44 kDa. Members of the CD28 family share a number of common features. These receptors consist of paired V-set immunoglobulin superfamily (IgSF) domains attached to single transmembrane domains and cytoplasmic domains that contain critical signaling motifs (Id., citing Carreno, B M and Collins, M, Annu Rev Immunol. (2002) 20: 29-53). The CD28 and CTLA4 ligands, CD80 and CD86, consist of single V-set and C1-set IgSF domains. The interaction of these costimulatory receptors with ligand is mediated through the MYPPPY motif (SEQ ID NO: 105) within the receptor V-set domains (Id., citing Evans, E J et al., Nat Immunol. (2005) 6:271-279; Metzler, W J et al., Nat Struct Biol. (1997) 4: 527-531).

CD28 engagement by its ligand initiates signal transduction events that are dependent on specific associations of proteins with the cytoplasmic tail of CD28. Despite having no intrinsic enzymatic activity, the 41 amino acid cytoplasmic tail of human CD28 contains highly conserved tyrosine-based signaling motifs that are phosphorylated in response to TCR or CD28 stimulation, and bind targets with SH2 domains in a phosphotyrosine-dependent manner. Proline rich sequences within the cytoplasmic tail also bind SH3-domain containing proteins. In particular, the membrane proximal YMNM motif (SEQ ID NO: 106), and the distal PYAP motif (SEQ ID NO: 107) have been shown to complex with several kinases and adaptor proteins, with some proteins being able to bind to either or both motifs via SH2 and/or SH3 domain interactions (Id., citing Boomer, J S and Green, J M, Cold Spring Harb Perspect Biol. (2010) 2: a002436). These motifs are important for IL-2 gene expression, which is mediated by the CD28-dependent activation of NFAT, AP-1, and NF-κB family transcription factors (Id., citing Fraser, J D et al., Science. (1991) 251:313-316; June, C H et al., Mol Cell Biol. (1987) 7: 4472-4481; Thompson, C B et al., Proc Natl Acad Sci USA. (1989) 86:1333-1337).

The membrane-proximal YXXM motif is shared between CD28, CTLA4, and ICOS, and is a consensus site for the p85 subunit of the lipid kinase phosphatidylinositol 3-kinase (PI3K) (Id., citing August, A. and Dupont, B. Int Immunol. (1994) 6:769-774; Pages, F., et al., Nature. (1994) 369: 327-329; Prasad, K V et al., Proc Natl Acad Sci USA. (1994) 91: 2834-2838; Rudd, C E and Schneider, H., Nat Rev Immunol. (2003) 3: 544-556). In addition to the +3 methionine of the CD28 sequence, YMNM (SEQ ID NO: 106), which confers PI3K specificity, the +2 asparagine confers specificity for the adaptor proteins GRB2 and GADS on CD28 (Id., citing Cai, Y C et al., Immunity. (1995) 3: 417-426; Kim, H H et al., J Biol Chem. (1998) 273: 296-301; Okkenhaug, K. and Rottapel, R., 1998; Okkenhaug et al., J Biol Chem. (1998) 273: 21194-21202; Raab, M et al., Proc Natl Acad Sci USA. (1995) 92: 8891-8895; Stein, P H et al., Mol Cell Biol. (1994) 14: 3392-3402). Both ICOS and CTLA4 can bind to PI3K but lack the ability to bind GRB2, which may account for some of the functional and signaling differences between these costimulatory receptors (Id., citing Rudd, C E and Schneider, H Nat Rev Immunol. (2003) 3: 544-556). The importance of the YMNM motif (SEQ ID NO: 106) in mediating proliferation and IL-2 secretion has been controversial, Signaling events downstream of the C-terminal PYAP motif (SEQ ID NO: 107) are thought to include the phosphorylation and activation of the kinases PDK1 and PKCθ, and the subsequent inactivation of GSK3β, ultimately leading to enhanced transcription of NFAT-dependent genes, including IL-2. SH3-mediated binding and activation of the Src kinase Lck (Id., citing Holdorf, A D et al., J Exp Med. (1999) 190: 375-384; King, P D et al., J Immunol. (1997) 158: 580-590) is proposed as a potential regulator of this pathway. The adaptor proteins, GRB2 and GADS can bind to CD28 either through their SH3 domains at the distal PYAP motif (SEQ ID NO: 107) or via their SH2 domains to the membrane proximal YMNM motif (SEQ ID NO: 106). However, it is the C-terminal PYAP motif (SEQ ID NO: 107) that is thought to play the greater role in NF-κB activation, suggesting that other signaling molecules important for NF-κB activation bind to the C-terminal PYAP motif (SEQ ID NO: 107), such as Lck, as discussed above ((Id., citing Holdorf, A D et al., J Exp Med. (1999) 190: 375-384; Watanabe, R. et al., J Immunol. (2006) 177:1085-1091).

Although CD28 ligation is critical in promoting proliferation and effector function of conventional T cells, it also promotes the anti-inflammatory function of regulatory T (Treg) cells. Thus, CD28 serves both pro- and anti-inflammatory roles depending on the cell type and context in which it is expressed. CD28 signals are critical for allowing effector T cells to overcome Treg cell-mediated suppression to immunization (Id., citing Lyddane, C et al., J Immunol. (2006) 176: 3306-3310), but CD28 in another context prevents spontaneous autoimmunity by promoting Treg function (Id., citing Salomon B. et al., Immunity. 2000; 12:431-440).

CD28 supports T cell homeostasis and function in a variety of ways. CD28 signals support the expression of miR17-92 family members, which are critical for maximal IL-10 production by Treg cells (de Kouchkovsky, D et al., J Immunol. (2013) 191: 1594-1605). Thymocytes require simultaneous TCR and CD28 signals to upregulate Foxp3 and differentiate into Treg cells. CD28 is also necessary for the production of peripheral induced Treg cells. CD4+ CD25− T cells required CD28 ligation to differentiate into functional Foxp3+ Treg cells when activated with TGF-β.

According to some embodiments of the disclosed invention, the population of proliferation incompetent tumor cells may be engineered to express a membrane bound form of CD80 on the membrane of the ENLIST™ of SEQ ID NO: 110 corresponding to accession number NM_005191.4. According to some embodiments, the population of proliferation incompetent tumor cells may be engineered to comprise one or more proteins with a sequence identity of at least 60% to the protein of SEQ ID NO: 110. According to some embodiments, the population of proliferation incompetent tumor cells may be engineered to comprise one or more proteins with a sequence identity of at least 70% to the protein of SEQ ID NO: 110. According to some embodiments, the population of proliferation incompetent tumor cells may be engineered to comprise one or more proteins with a sequence identity of at least 80% to the protein of SEQ ID NO: 110. According to some embodiments, the population of proliferation incompetent tumor cells may be engineered to comprise one or more proteins with a sequence identity of at least 90% to the protein of SEQ ID NO: 110. According to some embodiments, the population of proliferation incompetent tumor cells may be engineered to comprise one or more proteins with a sequence identity of at least 95% to the protein of SEQ ID NO: 110. According to some embodiments, the population of proliferation incompetent tumor cells may be engineered to comprise one or more proteins with a sequence identity of at least 96% to the protein of SEQ ID NO: 110. According to some embodiments, the population of proliferation incompetent tumor cells may be engineered to comprise one or more proteins with a sequence identity of at least 97% to the protein of SEQ ID NO: 110. According to some embodiments, the population of proliferation incompetent tumor cells may be engineered to comprise one or more proteins with a sequence identity of at least 98% to the protein of SEQ ID NO:110. According to some embodiments, the population of proliferation incompetent tumor cells may be engineered to comprise one or more proteins with a sequence identity of at least 99% to the protein of SEQ ID NO: 110.

According to some embodiments of the disclosed invention, the population of proliferation incompetent tumor cells may be engineered to express a membrane bound form of CD86 on the membrane of the population of proliferation incompetent tumor cells of SEQ ID NO: 111 corresponding to accession number NP 787058.5. According to some embodiments, the population of proliferation incompetent tumor cells may be engineered to comprise one or more proteins with a sequence identity of at least 60% to the protein of SEQ ID NO: 111. According to some embodiments, the population of proliferation incompetent tumor cells may be engineered to comprise one or more proteins with a sequence identity of at least 70% to the protein of SEQ ID NO: 111. According to some embodiments, the population of proliferation incompetent tumor cells may be engineered to comprise one or more proteins with a sequence identity of at least 80% to the protein of SEQ ID NO: 111. According to some embodiments, the population of proliferation incompetent tumor cells may be engineered to comprise one or more proteins with a sequence identity of at least 90% to the protein of SEQ ID NO: 111. According to some embodiments, the population of proliferation incompetent tumor cells may be engineered to comprise one or more proteins with a sequence identity of at least 95% to the protein of SEQ ID NO: 111. According to some embodiments, the population of proliferation incompetent tumor cells may be engineered to comprise one or more proteins with a sequence identity of at least 96% to the protein of SEQ ID NO: 111. According to some embodiments, the population of proliferation incompetent tumor cells may be engineered to comprise one or more proteins with a sequence identity of at least 97% to the protein of SEQ ID NO: 111. According to some embodiments, the population of proliferation incompetent tumor cells may be engineered to comprise one or more proteins with a sequence identity of at least 98% to the protein of SEQ ID NO:111. According to some embodiments, the population of proliferation incompetent tumor cells may be engineered to comprise one or more proteins with a sequence identity of at least 99% to the protein of SEQ ID NO: 111.

According to some embodiments, the allogeneic vaccine is adapted for rapid in vitro evaluation using human peripheral blood mononuclear cells from healthy subjects and cancer patients to examine inter-individual variability as well as normal to patient differences, thus avoiding animal experimentation.

According to some embodiments, the allogeneic vaccine is adapted to provide clinical benefit in the short term by the induction of strong anti-allogeneic vaccine responses, and, in the long term, to provide a long lived and cross reactive response to the endogenous unmodified host tumor. According to some embodiments, the immune response against the allogeneic tumor cell vaccine comprises a heteroclitic cross reaction between a peptide native to the tumor cell line or tumor cell line variant and a peptide native to the tumor cells of a patient receiving the vaccine (See, e.g., FIG. 1). According to some embodiments, the heteroclitic cross-reaction enhances immunogenicity via enhanced binding of a T cell receptor with a tumor cell peptide-MHC complex that normally provides a non-immunogenic surface. According to some embodiments, the allogeneic tumor cell vaccine comprises peptides altered relative to tumor cells of a subject with cancer, where the altered peptides provide an immunogenic surface that results in a heteroclitic cross-reaction to the non-immunogenic peptide of tumor cells from the subject with cancer. According to some embodiments, the heteroclitic recognition and alloreactive antigen recognition of the tumor cell vaccine provides a broad array of antigens useful to elicit an immune response against the tumor cells of a patient receiving the vaccine. According to some embodiments, the allogeneic vaccine is adapted to provide a clinical benefit, e.g., in the form of progression free survival, relapse-free survival, or overall survival. According to some embodiments, the allogeneic vaccine is effective to provide heteroclitic immunization induced tumor immunity (Dyall R., et al., Heteroclitic Immunization Induces Tumor Immunity, J. Exp. Med., Vol. 188, No. 9, Nov. 2, 1998, incorporated by reference herein in its entirety).

According to some embodiments, the allogeneic vaccine is derived from tumor cell line or tumor cell line variants genetically modified to comprise recombinant immunomodulatory signals that are expressed in therapeutic amounts. According to some embodiments, the allogeneic vaccine is derived from a uniform starting material, such as a tumor cell line or tumor cell line variant, wherein multiple discrete biologics are expressed in the starting material in either soluble or membrane bound form. According to some embodiments, expression and activity of the soluble and membrane bound forms are confirmed, in vitro, by flow cytometry and mixed lymphocyte tumor assays using peripheral blood mononuclear cells, respectively. According to some embodiments, expression and activity of the soluble and membrane bound forms are confirmed, in vitro, by flow cytometry and mixed lymphocyte tumor assays using peripheral blood mononuclear cells of the vaccinated cancer patient against the allogeneic tumor cells used to immunize.

According to some embodiments, the allogeneic vaccine comprises exogenous immunomodulatory molecules, each encoding a membrane bound or secreted signaling molecule. According to some embodiments, each membrane bound immunomodulatory molecule is adapted to deliver a therapeutic amount in sub-pharmacologic doses that is active in a spatially and temporally restricted manner to provide signaling predominantly at the time and place of antigen presentation. According to some embodiments, the membrane bound immunomodulatory molecules are adapted to decrease the probability of systemic side effects. According to some embodiments, the secreted immunomodulatory molecules are adapted to deliver local, not systemic, signals.

According to some aspects, the allogeneic vaccine comprises genetic material that is effective to genetically introduce one or more immunomodulatory molecules into a tumor cell line or tumor cell line variant. According to some embodiments, the genetic material can be introduced by viral transduction techniques and isolated by positive selection for the genetically introduced immune modulator. For example, according to some embodiments, the positive selection of the genetically introduced immune modulator molecule comprises selection using antibodies. According to some embodiments, the immunomodulatory molecules are diverse and complementary with respect to impact on key immune cell subsets such as dendritic cells, and lymphocyte sub-populations (e.g. T cells, Natural Killer cells, and T-regulatory cells). According to some embodiments, the allogeneic vaccine comprises a variety of immunomodulatory molecules directed to a variety of immunomodulatory pathways on various immune cell subsets, wherein not all pathways will equally contribute to an immunogenic response in individual cancer patients. According to some embodiments, the immunomodulatory molecules genetically introduced into a tumor cell line or tumor cell line variant are stably expressed.

According to some embodiments, the allogeneic tumor cell vaccine of the present disclosure comprises a population of proliferation incompetent tumor cells expressing one or more tumor specific antigens, the allogeneic tumor cell comprising a core of three stably expressed essential exogenous immunomodulatory molecules, OX40 Ligand (OX40L), CD27 Ligand (CD70), and CD28 Ligand (CD28L) comprising CD80, CD86 or both. According to some embodiments, the allogeneic tumor cell vaccine further comprises one or more additional subsets of stably expressed exogenous immunomodulator molecules, designated as R groups (by analogy to those in a core chemical structure), with each subset comprising 3-25 immunomodulators. According to some embodiments, a subset R can comprise 3, 4, 5, 6, 7, 8, 9, 10, 11, 12, 13, 14, 15, 16, 17, 18, 19, 20, 21, 22, 23, 24, or 25 immunomodulators. According to some embodiments, the allogeneic tumor cell vaccine of the present disclosure comprises a population of proliferation incompetent tumor cells expressing one or more tumor specific antigens, wherein the tumor cells are genetically engineered to stably express at least the three stably expressed exogenous immunomoculatory molecules OX40 Ligand (OX40L), CD27 Ligand (CD70), and CD28 Ligand (CD28L) comprising CD80, CD86 or both, plus one R subset comprising 3-25 immunomodulators. According to some embodiments, the allogeneic tumor cell vaccine of the present disclosure comprises a population of proliferation incompetent tumor cells expressing one or more tumor specific antigens, wherein the tumor cells are genetically engineered to stably express at least the three stably expressed exogenous immunomoculatory molecules 4-1BBL, GM-CSF, OX40L, plus two R subsets comprising 3-25 immunomodulators. According to some embodiments, the allogeneic tumor cell vaccine of the present disclosure comprises a population of proliferation incompetent tumor cells expressing one or more tumor specific antigens wherein the tumor cells are genetically engineered to stably express at least the three stably expressed exogenous immunomoculatory molecules OX40 Ligand (OX40L), CD27 Ligand (CD70), and CD28 Ligand (CD28L) comprising CD80, CD86 or both, plus three R subsets comprising 3-25 immunomodulators. According to some embodiments, the allogeneic tumor cell vaccine of the present disclosure comprises a population of proliferation incompetent tumor cells expressing one or more tumor specific antigens, wherein the tumor cells are genetically engineered to stably express at least the three essential stably expressed exogenous immunomodulatory molecules OX40 Ligand (OX40L), CD27 Ligand (CD70), and CD28 Ligand (CD28L) comprising CD80, CD86 or both, plus four R subsets comprising 3-25 immunomodulators. According to some embodiments, the allogeneic tumor cell vaccine of the present disclosure comprises a population of proliferation incompetent tumor cells expressing one or more tumor specific antigens, wherein the tumor cells are genetically engineered to stably express at least the three essential stably expressed exogenous immunomoculatory molecules OX40 Ligand (OX40L), CD27 Ligand (CD70), and CD28 Ligand (CD28L) comprising CD80, CD86 or both, plus five R subsets comprising 3-25 immunomodulators. According to some embodiments, the allogeneic tumor cell vaccine of the present disclosure comprises a population of proliferation incompetent tumor cells expressing one or more tumor specific antigens, wherein the tumor cells are genetically engineered to stably express at least the three essential stably expressed exogenous immunomoculatory molecules OX40 Ligand (OX40L), CD27 Ligand (CD70), and CD28 Ligand (CD28L) comprising CD80, CD86 or both, plus six R subsets comprising 3-25 immunomodulators. According to some embodiments, the allogeneic tumor cell vaccine of the present disclosure comprises a population of proliferation incompetent tumor cells expressing one or more tumor specific antigens, wherein the tumor cells are genetically engineered to stably express at least the three essential stably expressed exogenous immunomoculatory molecules OX40 Ligand (OX40L), CD27 Ligand (CD70), and CD28 Ligand (CD28L) comprising CD80, CD86 or both, plus seven R subsets comprising 3-25 immunomodulators. According to some embodiments, the allogeneic tumor cell vaccine of the present disclosure comprises a population of proliferation incompetent tumor cells expressing one or more tumor specific antigens, wherein the tumor cells are genetically engineered to stably express at least the three essential stably expressed exogenous immunomoculatory molecules OX40 Ligand (OX40L), CD27 Ligand (CD70), and CD28 Ligand (CD28L) comprising CD80, CD86 or both, plus eight R subsets comprising 3-25 immunomodulators. According to some embodiments, the allogeneic tumor cell vaccine of the present disclosure comprises a population of proliferation incompetent tumor cells expressing one or more tumor specific antigens, wherein the tumor cells are genetically engineered to stably express at least the three essential stably expressed exogenous immunomoculatory molecules OX40 Ligand (OX40L), CD27 Ligand (CD70), and CD28 Ligand (CD28L) comprising CD80, CD86 or both, plus nine R subsets comprising 3-25 immunomodulators. According to some embodiments, the allogeneic tumor cell vaccine of the present disclosure comprises a population of proliferation incompetent tumor cells expressing one or more tumor specific antigens, wherein the tumor cells are genetically engineered to stably express at least the three essential stably expressed exogenous immunomoculatory molecules OX40 Ligand (OX40L), CD27 Ligand (CD70), and CD28 Ligand (CD28L) comprising CD80, CD86 or both, plus ten R subsets comprising 3-25 immunomodulators.

Assessing Immunogenic Potential

Mixed Lymphocyte Tumor Cell Reactivity

According to some embodiments, the genetically introduced immunomodulators may be assessed for their immunogenic potential by a mixed lymphocyte tumor cell reaction (MLTR). The MLTR assay comprises incubating mixed lymphocytes with tumor cell line or tumor cell line variants (or controls) for several days to allow the tumor cells of the tumor cell line or tumor cell line variant to elicit an immune response from the mixed lymphocytes in vitro. This method can provide a rapid in vitro method to assess mixed lymphocyte responses (such as cellular proliferation of lymphocytes, cellular subset differentiation of lymphocytes, cytokine release profile of lymphocytes, and tumor cell death) to tumor cells or lysates. This approach can enable comprehensive monitoring of cellular, humoral, or both, immunity responses to phenotypically modified transfected tumor cells using human peripheral blood mononuclear cells. The MLTR also can provide an alternative to murine tumor survival studies, and can result in selection of optimal tumor cell line or tumor cell line variants for anti-tumor response. A similar assay has been described by Hunter T B et al., (2007) Scandanavian J. Immunology 65, 479-486, which is incorporated herein by reference in its entirety.

The MLTR was first described by Stjernsward J, et al. in 1970 (Clin Exp Immunol 6: 963-668, incorporated by reference in its entirety herein) and was based on the mixed lymphocyte response (MLR) method. Uchida A, et al. describe generation of specific and non-specific killer T cells using a MLTR (Int J. Canc (1988) 41: 651-656, incorporated by reference in its entirety herein). The MLTR is an accepted model of an immune response, as shown for example by Eini et al. (Biochemical Pharmacology Volume 98, Issue 1, 1 Nov. 2015, Pages 110-118, incorporated by reference in its entirety herein), which uses the MLTR assay to evaluate immune response modulation (e.g., elevation in proinflammatory cytokine release); Wang et al., (Eur J Immunol. 1995 May; 25(5):1163-7, incorporated by reference in its entirety herein) which assess the effect of heat stable antigen on T-cell proliferation using a MLTR assay; and Xiu et al. (J Mol Med (Berl). 2007 May; 85(5):511-21. Epub 2007 Jan. 12, incorporated by reference in its entirety herein), which use an MLTR assay to determine the effect of superantigen staphylococcal enterotoxin A (SEA)-coated tumor cells on tumor-specific T cell response.

According to some embodiments, tumor cell line or tumor cell line variants may be tested for immunogenic potential by contacting transfected tumor cells with mixed lymphocytes from peripheral blood mononuclear cells, followed by measuring at least one of cellular proliferation, cellular subset differentiation, cytokine release profile, and tumor cell lysate.

According to some embodiments, mixed lymphocytes may be obtained from peripheral blood mononuclear cells isolated by a Ficoll-Paque gradient. Briefly, anticoagulant-treated blood may be diluted in the range of 1:2 to 1:4 with PBS/EDTA to reduce aggregation of erythrocytes. The diluted blood may then be layered above a Ficoll-Paque solution in a centrifuge tube, without mixing. The layered blood/Ficoll-Paque may be centrifuged for 40 minutes at 400×g between 18° and 20° C., without the use of the centrifuge brake, resulting in the formation of blood fractions comprising, from top to bottom, a first fraction comprising blood plasma; a second fraction comprising mononuclear cells; a third fraction comprising Ficoll-Paque media; and a fourth fraction comprising granulocytes and erythrocytes.

The fractions may be further processed to isolate specific fraction components. For example, to further process mononuclear cells, the second fraction comprising mononuclear cells may be carefully removed from the Ficoll-Paque gradient using a Pasteur pipet. Alternatively, the second fraction may be removed directly by puncturing the tube with a needle and directly withdrawing the second fraction. The second fraction may then be washed and centrifuged at 300×g, 18° and 20° C., three times with PBS/EDTA, discarding the supernatant after each round.

According to some embodiments, tumor cell line or tumor cell line variants may be co-cultured with the PBMCs comprising lymphocytes for seven days to allow for direct evaluation of activation of anti-tumor response in the presence of immunomodulators from the tumor cell line or tumor cell line variants.

According to some embodiments, one parameter used for measuring activation of lymphocytes may be cellular proliferation. According to some embodiments, proliferation may be detected by $^3$H-thymidine incorporation. Briefly, approximately $5 \times 10^3$ tumor cell line or tumor cell line variant cells may be co-cultured with approximately $1 \times 10^6$ mixed lymphocytes in round bottomed 96-well plates. After three days of culture, cells may be pulsed with 1 µCi of $^3$H-thymidine for 18 hours. The cells may then be harvested onto filter mats, and $^3$H-thymidine incorporation may be measured using a scintillation counter. Proliferation of tumor cell line or tumor cell line variants compared to non-transfected tumor cell controls may be measured. An increase, a decrease, or no change in proliferation relative to controls, are possible outcomes.

According to some embodiments, another parameter for measuring activation of lymphocytes may be the cytokine release profile. For example, the number of responsive T cells in the mixed lymphocyte population may be quantified by enzyme linked immunospot (ELISpot) analysis of IFN-gamma and/or IL-2 production by PBMCs. Briefly, PBMCs comprising mixed lymphocytes and a tumor cell line or tumor cell line variant may be co-cultured between 3 and 7 days. Co-cultured cells may then be harvested and incubated on ELISpot plates pre-coated with anti-IFN-gamma and/or anti-IL-2 antibodies. After 20 hours, cells may be removed by washing 2 times in distilled water and two times in washing buffer. ELISpot plates may then be contacted with biotinylated anti-IFN-gamma and/or anti-IL-2 antibodies and streptavidin alkaline phosphatase in blocking buffer for 1-2 hours. After washing, plates may be contacted with alkaline phosphatase substrate until dark spot emerge. Plates may then be washed in tap water and air dried. Spots are then quantified manually or by plate reader and compared to non-transfected tumor cell line or tumor cell line variant control group.

According to some embodiments, another parameter for measuring activation of lymphocytes may be by quantifying cellular subset differentiation. For example, the differentiation of CD45+/CD3+ T-lymphocytes to CD45+/CD3+/CD4+ helper T-lymphocytes, CD45+/CD3+/CD8+ cytotoxic T-lymphocytes, and CD45+/CD3+/CD25+ activated T-lymphocytes may be quantified by flow cytometry analysis.

According to some embodiments, another parameter for measuring activation of lymphocytes may be by quantifying tumor cell cytotoxicity. Cytotoxicity of tumor cells may be measured by any number of established methods. For example, according to some embodiments, an LDH-Cytotoxicity colorimetric assay kit (BioVision Cat. #K311-400) may be used to measure cytotoxicity of tumor cells by testing for lactate dehydrogenase (LDH) released from damaged cells into the growth media. Briefly, 100 µl of media from each of the control group (comprising untransfected tumor cells), the experimental group (comprising immune modulator transfected tumor cells), and media alone may be pipetted into the wells of a 96 well plate. 100 µl of the LDH reaction mixture, comprising dye solution and catalyst solution, may then be added to the wells of the 96 well plate and incubated for 30 minutes at room temperature. Then the samples may be measured for light absorbance at 490-500 nm using a microliter plate reader.

Stimulation of Immune Cells

As described herein, the present disclosure provides an allogeneic tumor cell vaccine comprising a population of proliferation incompetent tumor cells expressing one or more tumor specific antigens, wherein the tumor cells are genetically engineered to stimulate one or more immune cells (e.g., one or more of T lymphocytes, natural killer (NK) cells, dendritic cells (DCs) or B lymphocytes). The stimulation of the immune cells can enhance normal cellular functions, or initiate normal cell functions in an abnormal cell.

According to some embodiments, stimulating the T-lymphocytes comprises activating and/or expanding the T lymphocytes. According to some embodiments, stimulating the NK cells comprises activating and/or expanding the NK cells. According to some embodiments, stimulating the DCs comprises activating and/or expanding the DCs. According to some embodiments, stimulating the B lymphocytes comprises activating and/or expanding the B lymphocytes.

According to some embodiments, the disclosure provides an allogeneic tumor cell vaccine comprising a population of proliferation incompetent tumor cells expressing one or more tumor specific antigens that are effective to stimulate immune killer cells. Immune killer cells that may be stimulated include, for example, cytolytic T cells (CD8+ cells), memory CD8+ T cells, and NK cells. According to one embodiment, the killer immune cells are Natural Killer (NK) cells. According to one embodiment, the NK cells are memory-like NK cells. According to one embodiment, the killer immune cells are CD8+ T-cells. According to one embodiment, the CD8+ T-cells are memory T cells. Accordingly, the present invention also provides populations of cells resulting from stimulation with the allogeneic tumor cell vaccines described herein.

It is a feature of the present invention that, according to some embodiments, the allogeneic tumor cell vaccines are effective to stimulate more than one type of immune killer cell at the same time, for example, more than one of cytolytic T cells (CD8+ cells), memory CD8+ T cells and NK cells. According to some embodiments, the allogeneic tumor cell vaccines are effective to stimulate both CD8+ T cells and NK cells.

According to some embodiments, the allogeneic tumor cell vaccine stimulates CD8+ T cells, where the expression of certain exogenous immunomodulatory molecules, compared to other exogenous stimulatory molecules, stimulate CD8+ T cells that kill more effectively than others.

According to some embodiments, the allogeneic tumor cell vaccine stimulates NK cells, where the expression of certain exogenous immunomodulatory molecules, compared to other exogenous stimulatory molecules, stimulate NK cells that kill more effectively than others.

According to some embodiments, "stimulating the immune killer cells" refers to expansion of the immune killer cell. According to some embodiments, "stimulating the immune killer cells" refers to activation of the immune killer cell. According to some embodiments, "stimulating the immune killer cells" refers to an increase in cytoxicity of the immune killer cell.

According to some embodiments, the allogeneic tumor cell vaccines as described herein are sufficient to stimulate a population of immune killer cells ex vivo. In other embodiments, the allogeneic tumor cell vaccines as described herein are sufficient to stimulate a population of immune killer cells in vivo.

NK Cell Activation and Expansion

According to one embodiment, the allogeneic tumor cell vaccines described herein are effective to activate NK cells.

According to one embodiment, the allogeneic tumor cell vaccines described herein are effective to expand NK cells.

Degranulation/Cytotoxicity

The defining functional feature of NK cells remains their intrinsic ability to conduct "natural killing" of cellular targets without prior sensitization.

According to one embodiment, the allogeneic tumor cell vaccines described herein are effective to activate and expand NK cells, such that the NK cells that are activated and expanded by the allogeneic tumor cell vaccines described herein exhibit higher degranulation activity compared to control NK cells. For example, degranulation activity can be estimated through the determination of CD107a expression, for example by flow cytometry. CD107a surface expression correlates closely with degranulation and release of cytotoxic granules. Degranulation as measured by CD107a expression correlates to cytotoxic activity of an effector cell, such as an NK cell. The method of determining degranulation activity through the determination of CD107a expression is well known to a person skilled in the art. See, for example, Alter G, Malenfant J M, Altfeld M. CD107a as a functional marker for the identification of natural killer cell activity. J Immunol Methods. 2004; 294: 15-22, the entire contents of which are incorporated herein by reference.

According to one embodiment, the expanded and activated NK cells, obtained following ex vivo or in vivo stimulation with the allogeneic tumor cell vaccines of the invention, comprise at least about 50%, about 60%, about 70%, about 80% or about 90% increased cytotoxicity, e.g. as measured by degranulation activity, compared to non expanded NK cells. According to one embodiment, the expanded and activated NK cells comprise at least about 100% increased cytotoxicity compared to non expanded NK cells. According to one embodiment, the expanded and activated NK cells comprise at least about 200% increased cytotoxicity compared to non expanded NK cells. According to one embodiment, the expanded and activated NK cells comprise at least about 300% increased cytotoxicity compared to non-ex vivo expanded NK cells. According to one embodiment the expanded and activated NK cells comprise at least about 400% increased cytotoxicity compared to non-ex vivo expanded NK cells.

According to one embodiment the expanded and activated NK cells, obtained following ex vivo or in vivo stimulation with the allogeneic tumor cell vaccines of the invention, comprise at least about 50%, about 60%, about 70%, about 80% or about 90% increased degranulation activity compared to non expanded NK cells. According to one embodiment, the expanded and activated NK cells comprise at least about 100% increased degranulation activity compared to non expanded NK cells. According to one embodiment, the expanded and activated NK cells comprise at least about 200% increased degranulation activity compared to non expanded NK cells. According to one embodiment, the expanded and activated NK cells comprise at least about 300% increased degranulation activity compared to non-ex vivo expanded NK cells. According to one embodiment, the expanded and activated NK cells comprise at least about 400% increased degranulation activity compared to non-ex vivo expanded NK cells.

Markers of NK Cell Maturation and Activation

Human NK cells are phenotypically characterized by the expression of CD56 and the absence of CD3 and can be further subdivided into a $CD56^{bright}$ population and a $CD56^{dim}$ population. The $CD56^{bright}$ population produces immunoregulatory cytokines, including interferon-γ (IFNγ), tumor necrosis factor-beta (TNF-β), tumor necrosis factor-α (TNF-α), granulocyte macrophage-colony stimulating factor (GMCSF), IL-10, and IL-13 (4). The $CD56^{dim}$ subset is the terminally differentiated successor of the $CD56^{bright}$ population and is primarily responsible for exerting cytolytic functions. However, $CD56^{dim}$ NK cells can produce cytokines, specifically IFNγ, after cell triggering via NKp46 of NKp30 activating receptors or after stimulation with combinations of IL-2, IL-12, and IL-15.

According to one embodiment, various markers of NK cell maturation and/or activation can be detected using, e.g. flow cytometric methods. For example, a classical marker of NK cells is the activating receptor FcγRIII, also called CD16.

The activation of NK cells leads to the release of cytotoxic granules containing perforin and various granzymes and to cytokine production, most prominently interferon-γ (IFNγ). In addition, the expression at the cell surface of death-inducing ligands belonging to the tumor necrosis factor (TNF) family, such as Fas ligand (FasL) and TNF-related apoptosis-inducing ligand (TRAIL), also drives the activation of the caspase enzymatic cascade through the binding to the death receptors (DRs), namely, Fas, DR4 (TRAIL-RI), and DR5 (TRAIL-RII), on target cells.

According to one embodiment, the allogeneic tumor cell vaccines described herein upregulate at least one NK cell activating receptor (e.g., an activating receptor listed in Table 3) by at least about 20%, about 30%, about 40%, about 50%, about 60%, about 70%, about 80%, about 90%, about 100%, about 150%, about 200%, about 300% or more. According to one embodiment, the allogeneic tumor cell vaccines described herein upregulate at least one NK cell activating receptor by at least about 75%, i.e., at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 100%, at least about 110%, at least about 120%, at least about 130%, at least about 140%, at least about 150%, at least about 160%, at least about 170%, at least about 180%, at least about 190%, at least about 200%. According to one embodiment, the allogeneic tumor cell vaccines described herein upregulate at least one NK cell activating receptor by at least about 100%. According to one embodiment, the allogeneic tumor cell vaccines described herein upregulate at least one NK cell activating receptor by at least about 200%.

According to another embodiment, the allogeneic tumor cell vaccines described herein downregulate expression of at least one NK cell receptor, such as an inhibitory receptor or a chemokine receptor (e.g. CCR7). For example, certain NK cell inhibitory receptors are called KIRs (Killing Inhibitory Receptors or CD158). Non-limiting examples of inhibitory receptors are inhibitory killer immunoglobulin-like receptors (KIRs), GL183, KIR2DL 1, Lir-1, NKB1, and NKG2A.

According to one embodiment, the allogeneic tumor cell vaccines described herein downregulate at least one NK cell inhibitory receptor (e.g., an inhibitory receptor listed in Table 4 below) by at least about 20%, at least about 30%, at least about 40%, at least about 50%, at least about 60%, at least about 70%, at least about 80%, at least about 90%, at least about 100%, at least about 110%, 120%, at least about 130%, about 140%, at least about 150%, at least about 160%, at least about 170%, at least about 180%, at least about 190%, at least about 200%, at least about 220%, at least about 230%, at least about 240%, at least about 250%, at least about 260%, at least about 270%, at least about 280%, at least about 290%, at least about 300% or more. According to one embodiment, the allogeneic tumor cell vaccines described herein downregulate at least one NK cell inhibitory receptor by at least about 75%. According to one embodiment, the allogeneic tumor cell vaccines described herein downregulate at least one NK cell inhibitory receptor by at least about 100%. According to one embodiment, the allogeneic tumor cell vaccines described herein downregulate at least one NK cell inhibitory receptor by at least about 200%.

The change in receptor expression can be calculated by mean fluorescence intensity (MFI) ratios:

$$MFI_{day\ X}/MFI_{day\ 0}$$

where x is the number of days of expansion of the NK cell.

When the MFI for day X samples is higher than for day 0, the MFI ratio will be higher than 1, which indicates the relative extent of upregulation in that receptor. Thus, a MFI ratio of e.g. 1.5 would mean a 50% upregulation of a specific receptor. The calculation of MFI ratios is well known to persons skilled in the art.

Various NK cell activating or inhibitory receptors are shown below in Table 4. Bold type indicates family.

TABLE 4

| Receptor Family | Species | Activating/Inhibitory |
|---|---|---|
| CD16 | H | Act |
| KIR | H | Act/Inhib |
| KIR2DL1 | | Inhib |
| KIR2DL2/3 | | Inhib |
| KIR2DL4 | | Act |
| KIR2DL5 | | Inhib |
| KIR3DL1 | | Inhib |
| KIR3DL2 | | Inhib |
| KIR2DS1 | | Act |
| KIR2DS2 | | Act |
| KIR2DS3 | | Act |
| KIR2DS4 | | Act |
| KIR2DS5 | | Act |
| KIR3DS1 | | Act |
| CD94-NKG2 | H/M | Act/Inhib |
| NKG2A | | Inhib |
| NKG2C | | Act |
| NKG2E | | Act |
| NKG2D | H/M | Act |
| NCRs | H/M | Act |
| NKp30 | | Act |
| NKp44 | | Act |
| NKp46 | | Act |
| NKp80 | | Act |
| LILR | H/M | Inhib |
| 2B4 | H/M | Act/Inhib |
| KLRG1 | H/M | Inhib |
| DNAM-1 | H/M | Act |

Abbreviations in Table 4: ACT, activation; BAT-3, HLA-B-associated transcript 3; H, human; HA, hemagglutinin; HLA, human leukocyte antigen; INHIB, inhibitory; KIR, killer immunoglobulin-like receptor; KLRG1, killer cell lectin-like receptor G1; LILR, leukocyte immunoglobulin-like receptor; M, mouse; MHC, major histocompatibility complex; MULT-1, mouse UL16-binding-like transcript-1; NCR, natural cytotoxicity receptor; NK, natural killer; PVR, polio virus receptor; RAE-1, retinoic acid early transcript-1.

CD8+ T Cell Activation and Expansion

According to one embodiment, the allogeneic tumor cell vaccines described herein are effective to activate CD8+ T-cells. According to one embodiment, the allogeneic tumor cell vaccines described herein are effective to expand CD8+ T-cells. According to one embodiment, the allogeneic tumor cell vaccines described herein are effective to activate and expand CD8+ T-cells.

T cell activation and expansion can be measured by various assays as described herein. For example, T cell activities that may be measured include the induction of proliferation of T cells, the induction of signaling in T cells, the induction of expression of activation markers in T cells, the induction of cytokine secretion by T cells, and the cytotoxic activity of T cells. For example, in certain embodiments, CD8+ T cell activation is measured by a proliferation assay.

Cytokine Secretion

The activation of CD8+ T-cells by an allogeneic tumor cell vaccines of the invention may be assessed or measured by determining secretion of cytokines, such as gamma interferon (IFNγ), tumor necrosis factor alpha (TNFa), interleukin-12 (IL-12) or interleukin 2 (IL-2). according to some embodiments, ELISA is used to determine cytokine secretion, for example secretion of gamma interferon (IFNγ), tumor necrosis factor alpha (TNFa), interleukin-12 (IL-12) or interleukin 2 (IL-2). The ELISPOT (enzyme-linked immunospot) technique may be used to detect T cells that secrete a given cytokine (e.g., gamma interferon (IFNγ)) in response to stimulation with the engineered tumor cells described herein. T cells are cultured with engineered tumor cells in wells which have been coated with anti-IFNγ antibodies. The secreted IFNγ is captured by the coated antibody and then revealed with a second antibody coupled to a chromogenic substrate. Thus, locally secreted cytokine molecules form spots, with each spot corresponding to one IFNγ-secreting cell. The number of spots allows one to determine the frequency of IFNγ-secreting cells in the analyzed sample. The ELISPOT assay has also been described for the detection of tumor necrosis factor alpha, interleukin-4 (IL-4), IL-5, IL-6, IL-10, IL-12, granulocyte-macrophage colony-stimulating factor, and granzyme B-secreting lymphocytes (Klinman D, Nutman T. Current protocols in immunology. New York, N.Y.: John Wiley & Sons, Inc.; 1994. pp. 6.19.1-6.19.8, incorporated by reference in its entirety herein).

Flow cytometric analyses of intracellular cytokines may be used to measure the cytokine content in culture supernatants, but provides no information on the number of T cells that actually secrete the cytokine. When T cells are treated with inhibitors of secretion such as monensin or brefeldin A, they accumulate cytokines within their cytoplasm upon activation (e.g. with an engineered erythroid cell of the present invention). After fixation and permeabilization of the lymphocytes, intracellular cytokines can be quantified by cytometry. This technique allows the determination of the cytokines produced, the type of cells that produce these cytokines, and the quantity of cytokine produced per cell.

Cytotoxicity

The activation of CD8+ T-cells by an allogeneic tumor cell vaccines of the invention may be assessed by assaying the cytotoxic activity of the CD8+ T-cells.

The cytotoxic activity of T cells may be assessed by any suitable technique known to those of skill in the art. For example, a sample comprising T cells that have been exposed to the engineered erythroid cells according to the invention can be assayed for cytotoxic activity after an appropriate period of time, in a standard cytotoxic assay. Such assays may include, but are not limited to, the chromium release CTL assay and the Alamar Blue™ fluorescence assay known in the art.

Proliferation/Expansion

The ability of the allogeneic tumor cell vaccines of the invention to expand T cells can be evaluated using CFSE staining. To compare the initial rate of cell expansion, the cells are subject to CFSE staining to determine how well allogeneic tumor cell vaccines induced the proliferation of T cells. CFSE staining provides a much more quantitative endpoint and allows simultaneous phenotyping of the expanded cells. Every day after stimulation, an aliquot of cells is removed from each culture and analyzed by flow cytometry. CFSE staining makes cells highly fluorescent. Upon cell division, the fluorescence is halved and thus the more times a cell divides the less fluorescent it becomes. The ability of allogeneic tumor cell vaccines to induce T cell proliferation is quantitated by measuring the number of cells that divided once, twice, three times and so on. The allogeneic tumor cell vaccines that induce the greatest number of cell divisions at a particular time point is deemed as the most potent expander.

To determine how well these allogeneic tumor cell vaccines promote long-term growth of T cells, cell growth curves can be generated. These experiments are set up as the foregoing CFSE experiments, but no CFSE is used. Every 2-3 days of culture, T cells are removed from the respective cultures and counted using a Coulter counter which measures how many cells are present and the mean volume of the cells. The mean cell volume is the best predicator of when to restimulate the cells. In general, when T cells are properly stimulated they triple their cell volume. When this volume is reduced to more than about half of the initial blast, it may be necessary to restimulate the T cells to maintain a log linear expansion (Levine et al., 1996, Science 272:1939-1943; Levine et al., 1997, J. Immunol. 159:5921-5930). The time it takes each engineered erythroid cell to induce 20 population doublings is calculated. The relative differences of each allogeneic tumor cell vaccine to induce this level of T cell expansion is one criteria on which a particular allogeneic tumor cell vaccine is assessed.

In addition, the phenotypes of the cells expanded by each allogeneic tumor cell vaccine can be characterized to determine whether a particular subset is preferentially expanded. Prior to each restimulation, a phenotype analysis of the expanding T cell populations is performed to define the differentiation state of the expanded T cells using the CD27 and CD28 definitions proposed by Appay et al. (2002, Nature Med. 8, 379-385, incorporated by reference in its entirety herein) and CCR7 definitions proposed by Sallusto et al. (1999, Nature 401:708-712, incorporated by reference in its entirety herein). Perforin and Granzyme B intracellular staining can be used to perform a gross measure to estimate cytolytic potential.

Apoptosis Markers

According to certain embodiments of the present invention, stimulation, activation, and expansion of T cells using the allogeneic tumor cell vaccines as described herein enhances expression of certain key molecules in T cells that protect against apoptosis or otherwise prolong survival in vivo or in vitro. Apoptosis usually results from induction of a specific signal in the T cell. Thus, the engineered tumor cells of the invention may provide for protecting a T cell from cell death resulting from stimulation of the T cell. Therefore, also included in the present invention is enhanced T cell growth by protection from premature death or from absence or depletion of recognized T cell growth markers, such as Bcl-xL, growth factors, cytokines, or lymphokines normally necessary for T cell survival, as well as from Fas or Tumor Necrosis Factor Receptor (TNFR) cross-linking or by exposure to certain hormones or stress.

III. Methods of Making

Various methods of making allogeneic tumor cell vaccines are contemplated by the present disclosure.

According to some embodiments, the disclosure features an allogeneic tumor cell vaccine comprising a population of proliferation incompetent tumor cells, comprising at least three stably expressed exogenous immunomodulatory molecule, produced by a process comprising providing an allogeneic parental tumor cell line; introducing an exogenous nucleic acid encoding the at least one exogenous immunomodulatory molecule into a tumor cell; generating tumor cell line variants by selecting for tumor cell clones that stably express an immunogenic amount of the exogenous immunomodulatory molecule; and selecting in a mixed lymphocyte tumor cell reaction clonally derived cell line variants by one or more of the following parameters selected from cellular proliferation, cellular subset differentiation, cytokine release profile, and tumor cell lysis; wherein the selected clonally derived cell line variant is effective to stimulate activation of one or more of T-lymphocytes, natural killer (NK) cells, dendritic cells (DCs) or B lymphocytes. According to one embodiment, the tumor cells are rendered proliferation incompetent by irradiation. According to one embodiment, the exogenous nucleic acid comprises DNA or RNA. According to one embodiment, the introducing step comprises viral transduction. According to one embodiment, the introducing step comprises electroporation. According to one embodiment, the introducing step comprises utilizing one or more of liposome mediated transfer, adenovirus, adeno-associated virus, herpes virus, a retroviral based vector, lipofection, and a lentiviral vector. According to one embodiment, the introducing step comprises introducing the exogenous nucleic acid by transfection of a lentiviral vector.

Lentiviral Vectors

The described invention provides nucleic acid constructs that encode two or more immunomodulators that can be expressed in prokaryotic and eukaryotic cells. For example, the described invention provides expression vectors (e.g., DNA- or RNA-based vectors) containing nucleotide sequences that encode two or more immunomodulators. In addition, the described invention provides methods for making the vectors described herein, as well as methods for introducing the vectors into appropriate host cells for expression of the encoded polypeptides. In general, the methods provided herein include constructing nucleic acid sequences encoding two or more immunomodulators, and cloning the sequences into an expression vector. The expression vector can be introduced into host cells or incorporated into virus particles, either of which can be administered to a subject to, for example, treat cancer.

cDNA or DNA sequences encoding two or more immunomodulators can be obtained (and, if desired, modified) using conventional DNA cloning and mutagenesis methods, DNA amplification methods, and/or synthetic methods. In general, a sequence encoding two or more immunomodulators can be inserted into a cloning vector for genetic modification and replication purposes prior to expression. Each coding sequence can be operably linked to a regulatory element, such as a promoter, for purposes of expressing the encoded protein in suitable host cells in vitro and in vivo.

Expression vectors can be introduced into host cells for producing secreted immunomodulators. There are a variety of techniques available for introducing nucleic acids into viable cells. Techniques suitable for the transfer of nucleic acid into mammalian cells in vitro include the use of liposomes, electroporation, microinjection, cell fusion, polymer-based systems, DEAE-dextran, viral transduction, the calcium phosphate precipitation method, etc. For in vivo gene transfer, a number of techniques and reagents may also be used, including liposomes; and natural polymer-based delivery vehicles, such as chitosan and gelatin; viral vectors are also suitable for in vivo transduction. In some situations it is desirable to provide a targeting agent, such as an antibody or ligand specific for a cell surface membrane protein. Where liposomes are employed, proteins which bind to a cell surface membrane protein associated with endocytosis may be used for targeting and/or to facilitate uptake, e.g., capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262, 4429-4432 (1987); and Wagner et al., Proc. Natl. Acad. Sci. USA 87, 3410-3414 (1990).

Where appropriate, gene delivery agents such as, e.g., integration sequences can also be employed. Numerous integration sequences are known in the art (see, e.g., Nunes-Duby et al., Nucleic Acids Res. 26:391-406, 1998; Sadwoski, J. Bacteriol., 165:341-357, 1986; Bestor, Cell, 122 (3):322-325, 2005; Plasterk et al., TIG 15:326-332, 1999; Kootstra et al., Ann. Rev. Pharm. Toxicol., 43:413-439, 2003). These include recombinases and transposases. Examples include Cre (Sternberg and Hamilton, J. Mol. Biol., 150:467-486, 1981), lambda (Nash, Nature, 247, 543-545, 1974), FIp (Broach, et al., Cell, 29:227-234, 1982), R (Matsuzaki, et al., J. Bacteriology, 172:610-618, 1990), cpC31 (see, e.g., Groth et al., J. Mol. Biol. 335:667-678, 2004), sleeping beauty, transposases of the mariner family (Plasterk et al., supra), and components for integrating viruses such as AAV, retroviruses, and antiviruses having components that provide for virus integration such as the LTR sequences of retroviruses or lentivirus and the ITR sequences of AAV (Kootstra et al., Ann. Rev. Pharm. Toxicol., 43:413-439, 2003).

Cells may be cultured in vitro or genetically engineered, for example. Host cells can be obtained from normal or affected subjects, including healthy humans, cancer patients, private laboratory deposits, public culture collections such as the American Type Culture Collection, or from commercial suppliers.

Cells that can be used for production and secretion of two or more immunomodulators in vivo include, without limitation, epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, or granulocytes, various stem or progenitor cells, such as hematopoietic stem or progenitor cells (e.g., as obtained from bone marrow), umbilical cord blood, peripheral blood, fetal liver, etc., and tumor cells (e.g., human tumor cells). The choice of cell type depends on the type of tumor or infectious disease being treated or prevented, and can be determined by one of skill in the art.

Different host cells have characteristic and specific mechanisms for post-translational processing and modification of proteins. A host cell may be chosen which modifies and processes the expressed gene products in a specific fashion similar to the way the recipient processes its heat shock proteins (hsps).

According to some embodiments, an expression construct as provided herein can be introduced into an antigenic cell. As used herein, antigenic cells can include preneoplastic cells that are infected with a cancer-causing infectious agent, such as a virus, but that are not yet neoplastic, or antigenic cells that have been exposed to a mutagen or cancer-causing agent, such as a DNA-damaging agent or radiation, for example. Other cells that can be used are preneoplastic cells that are in transition from a normal to a neoplastic form as characterized by morphology or physiological or biochemical function.

Typically, the cancer cells and preneoplastic cells used in the methods provided herein are of mammalian origin. According to some embodiments, cancer cells (e.g., human tumor cells) can be used in the methods described herein. Cell lines derived from a preneoplastic lesion, cancer tissue, or cancer cells also can be used. Cancer tissues, cancer cells, cells infected with a cancer-causing agent, other preneoplastic cells, and cell lines of human origin can be used. According to some embodiments, a cancer cell can be from an established tumor cell line or tumor cell line variant such as, without limitation, an established non-small cell lung carcinoma (NSCLC), bladder cancer, melanoma, ovarian cancer, renal cell carcinoma, prostate carcinoma, sarcoma, breast carcinoma, squamous cell carcinoma, head and neck carcinoma, hepatocellular carcinoma, pancreatic carcinoma, or colon carcinoma cell line.

Parent cell lines are described supra.

Further, according to some embodiments, the allogeneic tumor cell vaccines provide for an adjuvant effect that further allows the immune system of a patient, when used in the various methods described herein, to be activated against a disease of interest.

Both prokaryotic and eukaryotic vectors can be used for expression of the two or more immunomodulators in the methods provided herein. Prokaryotic vectors include constructs based on *E. coli* sequences (see, e.g., Makrides, Microbiol Rev 1996, 60:512-538). Non-limiting examples of regulatory regions that can be used for expression in *E. coli* include lac, trp, 1pp, phoA, recA, tac, T3, T7 and lamda $P_L$. Non-limiting examples of prokaryotic expression vectors may include the Agt vector series such as Jamda.gt11 (Huynh et al., in "DNA Cloning Techniques, Vol. I: A Practical Approach," 1984, (D. Glover, ed.), pp. 49-78, IRL Press, Oxford), and the pET vector series (Studier et al., Methods Enzymol 1990, 185:60-89).

A variety of regulatory regions can be used for expression of the allogeneic tumor vaccines in mammalian host cells. For example, the SV40 early and late promoters, the cytomegalovirus (CMV) immediate early promoter, and the Rous sarcoma virus long terminal repeat (RSV-LTR) promoter can be used. Inducible promoters that may be useful in mammalian cells include, without limitation, promoters associated with the metallothionein II gene, mouse mammary tumor virus glucocorticoid responsive long terminal repeats (MMTV-LTR), the n-interferon gene, and the hsp70 gene (see, Williams et al., Cancer Res 1989, 49:2735-42; and Taylor et al., Mol Cell Biol 1990, 10:165-75). Heat shock promoters or stress promoters also may be advantageous for driving expression of the fusion proteins in recombinant host cells.

Animal regulatory regions that exhibit tissue specificity and have been utilized in transgenic animals also can be used in tumor cells of a particular tissue type: the elastase I gene control region that is active in pancreatic acinar cells (Swift et al., Cell 1984, 38:639-646; Ornitz et al., Cold Spring Harbor Symp Quant Biol 1986, 50:399-409; and MacDonald, Hepatology 1987, 7:425-515); the insulin gene control region that is active in pancreatic beta cells (Hanahan, Nature 1985, 315:115-122), the immunoglobulin gene control region that is active in lymphoid cells (Grosschedl et al., Cell 1984, 38:647-658; Adames et al., Nature 1985, 318: 533-538; and Alexander et al., Mol Cell Biol 1987, 7:1436-1444), the mouse mammary tumor virus control region that is active in testicular, breast, lymphoid and mast cells (Leder et al., Cell 1986, 45:485-495), the albumin gene control region that is active in liver (Pinkert et al., Genes Devel, 1987, 1:268-276), the alpha-fetoprotein gene control region that is active in liver (Krumlauf et al., Mol Cell Biol 1985, 5:1639-1648; and Hammer et al., Science 1987, 235:53-58); the alpha 1-antitrypsin gene control region that is active in liver (Kelsey et al., Genes Devel 1987, 1:161-171), the beta-globin gene control region that is active in myeloid cells (Mogram et al., Nature 1985, 315:338-340; and Kollias et al., Cell 1986, 46:89-94); the myelin basic protein gene control region that is active in oligodendrocyte cells in the brain (Readhead et al., Cell 1987, 48:703-712); the myosin light chain-2 gene control region that is active in skeletal muscle (Sani, Nature 1985, 314:283-286), and the gonadotropic releasing hormone gene control region that is active in the hypothalamus (Mason et al., Science 1986, 234:1372-1378).

An expression vector also can include transcription enhancer elements, such as those found in SV40 virus, Hepatitis B virus, cytomegalovirus, immunoglobulin genes, metallothionein, and .beta.-actin (see, Bittner et al., Meth Enzymol 1987, 153:516-544; and Gorman, Curr Op Biotechnol 1990, 1:36-47). In addition, an expression vector can contain sequences that permit maintenance and replication of the vector in more than one type of host cell, or integration of the vector into the host chromosome. Such sequences include, without limitation, to replication origins, autonomously replicating sequences (ARS), centromere DNA, and telomere DNA.

In addition, an expression vector can contain one or more selectable or screenable marker genes for initially isolating, identifying, or tracking host cells that contain DNA encoding the immunogenic proteins as described herein. For long term, high yield production of gp96-Ig and T cell costimulatory fusion proteins, stable expression in mammalian cells can be useful. A number of selection systems can be used for mammalian cells. For example, the Herpes simplex virus thymidine kinase (Wigler et al., Cell 1977, 11:223), hypoxanthine-guanine phosphoribosyltransferase (Szybalski and Szybalski, Proc Natl Acad Sci USA 1962, 48:2026), and adenine phosphoribosyltransferase (Lowy et al., Cell 1980, 22:817) genes can be employed in tk⁻, hgprf⁻, or aprf⁻ cells, respectively. In addition, antimetabolite resistance can be used as the basis of selection for dihydrofolate reductase (dhfr), which confers resistance to methotrexate (Wigler et al., Proc Natl Acad Sci USA 1980, 77:3567; O'Hare et al., Proc Natl Acad Sci USA 1981, 78:1527); gpt, which confers resistance to mycophenolic acid (Mulligan and Berg, Proc Natl Acad Sci USA 1981, 78:2072); neomycin phosphotransferase (neo), which confers resistance to the aminoglycoside G-418 (Colberre-Garapin et al., J Mol Biol 1981, 150:1); and hygromycin phosphotransferase (hyg), which confers resistance to hygromycin (Santerre et al., Gene 1984, 30:147). Other selectable markers such as histidinol and Zeocin™ also can be used.

A number of viral-based expression systems also can be used with mammalian cells to produce the allogeneic tumor cell vaccines. Vectors using DNA virus backbones have been derived from simian virus 40 (SV40) (Hamer et al., Cell 1979, 17:725), adenovirus (Van Doren et al., Mol Cell Biol 1984, 4:1653), adeno-associated virus (McLaughlin et al., J Virol 1988, 62:1963), and bovine papillomas virus (Zinn et al., Proc Natl Acad Sci USA 1982, 79:4897). When an adenovirus is used as an expression vector, the donor DNA sequence may be ligated to an adenovirus transcription/translation control complex, e.g., the late promoter and tripartite leader sequence. This fusion gene may then be inserted in the adenovirus genome by in vitro or in vivo recombination. Insertion in a non-essential region of the viral genome (e.g., region E1 or E3) can result in a recombinant virus that is viable and capable of expressing heterologous products in infected hosts. (See, e.g., Logan and Shenk, Proc Natl Acad Sci USA 1984, 81:3655-3659).

Bovine papillomavirus (BPV) can infect many higher vertebrates, including man, and its DNA replicates as an episome. A number of shuttle vectors have been developed for recombinant gene expression, which exist as stable, multicopy (20-300 copies/cell) extrachromosomal elements in mammalian cells. Typically, these vectors contain a segment of BPV DNA (the entire genome or a 69% transforming fragment), a promoter with a broad host range, a polyadenylation signal, splice signals, a selectable marker, and "poisonless" plasmid sequences that allow the vector to be propagated in *E. coli*. Following construction and amplification in bacteria, the expression gene constructs are transfected into cultured mammalian cells by, for example, calcium phosphate coprecipitation. For those host cells that do not manifest a transformed phenotype, selection of transformants is achieved by use of a dominant selectable marker, such as histidinol and G418 resistance.

Alternatively, the vaccinia 7.5K promoter can be used. (See, e.g., Mackett et al., Proc Natl Acad Sci USA 1982, 79:7415-7419; Mackett et al., J Virol 1984, 49:857-864; and Panicali et al., Proc Natl Acad Sci USA 1982, 79:4927-4931.) In cases where a human host cell is used, vectors based on the Epstein-Barr virus (EBV) origin (OriP) and EBV nuclear antigen 1 (EBNA-1; a trans-acting replication factor) can be used. Such vectors can be used with a broad range of human host cells, e.g., EBO-pCD (Spickofsky et al., DNA Prot Eng Tech 1990, 2:14-18); pDR2 and .lamda.DR2 (available from Clontech Laboratories).

Allogeneic tumor cell vaccines also can be made with retrovirus-based expression systems. Retroviruses, such as Moloney murine leukemia virus, can be used since most of the viral gene sequence can be removed and replaced with exogenous coding sequence while the missing viral functions can be supplied in trans. In contrast to transfection, retroviruses can efficiently infect and transfer genes to a wide range of cell types including, for example, primary hematopoietic cells. Moreover, the host range for infection by a retroviral vector can be manipulated by the choice of envelope used for vector packaging.

For example, a retroviral vector can comprise a 5' long terminal repeat (LTR), a 3' LTR, a packaging signal, a bacterial origin of replication, and a selectable marker. The gp96-Ig fusion protein coding sequence, for example, can be inserted into a position between the 5' LTR and 3' LTR, such that transcription from the 5' LTR promoter transcribes the cloned DNA. The 5' LTR contains a promoter (e.g., an LTR promoter), an R region, a U5 region, and a primer binding site, in that order. Nucleotide sequences of these LTR elements are well known in the art. A heterologous promoter as well as multiple drug selection markers also can be included in the expression vector to facilitate selection of infected cells. See, McLauchlin et al., Prog Nucleic Acid Res Mol Biol 1990, 38:91-135; Morgenstern et al., Nucleic Acid Res 1990, 18:3587-3596; Choulika et al., J Virol 1996, 70:1792-1798; Boesen et al., Biotherapy 1994, 6:291-302; Salmons and Gunzberg, Human Gene Ther 1993, 4:129-141; and Grossman and Wilson, Curr Opin Genet Devel 1993, 3:110-114.

Any of the cloning and expression vectors described herein may be synthesized and assembled from known DNA sequences using techniques that are known in the art. The regulatory regions and enhancer elements can be of a variety of origins, both natural and synthetic. Some vectors and host cells may be obtained commercially. Non-limiting examples of useful vectors are described in Appendix 5 of Current Protocols in Molecular Biology, 1988, ed. Ausubel et al., Greene Publish. Assoc. & Wiley Interscience, which is incorporated herein by reference; and the catalogs of commercial suppliers such as Clontech Laboratories, Stratagene Inc., and Invitrogen, Inc.

Recombinant Immunomodulators

According to some embodiments, two or more immunomodulators may be cloned into two or more plasmid constructs for transfection (via, e.g., lipids, calcium phosphate, cationic polymers, DEAE-dextran, activated dendrimers, magnetic beads, electroporation, biolistic technology, microinjection, laserfection/optoinjection) or transduction (via, e.g., retrovirus, lentivirus, adenovirus, adeno-associated virus) into cells of tumor cell line or tumor cell line variants. According to some embodiments, recombinant DNA encoding each immune modulator protein may be cloned into a lentiviral vector plasmid for integration into the genome of cells of tumor cell line or tumor cell line variants. According to some embodiments, recombinant DNA encoding the immune modulator protein may be cloned into a plasmid DNA construct encoding a selectable trait, such as an antibiotic resistance gene. According to some embodiments, recombinant DNA encoding the immune modulator protein may be cloned into a plasmid construct that is adapted to stably express each recombinant protein in the cells of the tumor cell line or tumor cell line variant. According to some embodiments, the transfected or transduced tumor cells may be clonally expanded to achieve a cell line variant with a homogenous site of integration of the recombinant DNA encoding each immune modulator protein into the genome of the cells of the tumor cell line or tumor cell line variant.

Lentiviral Constructs

According to some embodiments, the DNA sequences coding for exogenous immunomodulatory molecules may be cloned into a lentiviral vector for transduction into mammalian cells. According to some embodiments, the lentiviral system may comprise a lentiviral transfer plasmid encoding the two or more immune modulator sequences, packaging plasmids encoding the GAG, POL, TAT, and REV sequences, and an envelope plasmid encoding the ENV sequences. According to some embodiments, the lentiviral transfer plasmid uses a viral LTR promoter for gene expression. According to some embodiments, the lentiviral transfer plasmid uses a hybrid promoter, or other specialized promoter. According to some embodiments, the promoter of the lentiviral transfer plasmid is selected to express the two or more immune modulator sequences at a desired level relative to other immunomodulatory sequences. According to some embodiments, the relative level is measured on the level of transcription as mRNA transcripts. According to some embodiments, the relative level is measured on the level of translation as protein expression.

Multicistronic Plasmid Constructs

According to some embodiments, one or more immune modulator sequence may be cloned in a multicistronic vector for co-expression of one immune modulator with a second immune modulator or other recombinant sequence. According to some embodiments, an immune modulator sequence may be cloned into a plasmid comprising an IRES element to promote translation of two or more proteins from a single transcript. According to some embodiments, one or more immune modulator sequences is cloned into a multicistronic vector comprising sequences for a self cleaving 2A peptide to produce two or more exogenous immunomodulatory molecules from a single transcript.

Genetic Introduction of Exogenous Immunomodulatory Molecules

According to some embodiments, plasmid constructs comprising the recombinant immune modulator sequences may be transfected or transduced into tumor cell line or tumor cell line variants.

According to some embodiments, up to 25 immunomodulators (i.e., 1, 2, 3, 4, 5, 6, 7, 8, 9, 10, 11, 12, 13, 14, 15, 16, 17, 18, 19, 20, 2, 22, 23, 24 or 25) may be cloned into 10 separate vectors for transduction into mammalian cells. According to some embodiments, up to 25 immunomodulators (i.e., 1, 2, 3, 4, 5, 6, 7, 8, 9, 10, 11, 12, 13, 14, 15, 16, 17, 18, 19, 20, 21, 22, 23, 24, or 25) may be cloned into 11 separate vectors for transduction into mammalian cells. According to some embodiments, up to 25 immunomodulators (i.e., 1, 2, 3, 4, 5, 6, 7, 8, 9, 10, 11, 12, 13, 14, 15, 16, 17, 18, 19, 20, 21, 22, 23, 24, or 25) may be cloned into 12 separate vectors for transduction into mammalian cells. According to some embodiments, 14 or more immunomodulators (i.e., 1, 2, 3, 4, 5, 6, 7, 8, 9, 10, 11, 12, 13, 14 or more) may be cloned into 10 separate vectors for transduction into mammalian cells. According to some embodiments, 14 or more immunomodulators (i.e., 1, 2, 3, 4, 5, 6, 7, 8, 9, 10, 11, 12, 13, 14 or more) may be cloned into 11 separate vectors for transduction into mammalian cells. According to some embodiments, 14 or more immunomodulators (i.e., 1, 2, 3, 4, 5, 6, 7, 8, 9, 10, 11, 12, 13, 14 or more) may be cloned into 12 separate vectors for transduction into mammalian cells. According to some embodiments, 14 or more immunomodulators (i.e., 1, 2, 3, 4, 5, 6, 7, 8, 9, 10, 11, 12, 13, 14 or more) may be cloned into 13 separate vectors for transduction into mammalian cells. According to some embodiments, 14 or more immunomodulators (i.e., 1, 2, 3, 4, 5, 6, 7, 8, 9, 10, 11, 12, 13, 14 or more) may be cloned into 14 separate vectors for transduction into mammalian cells. According to some embodiments, 14 or more immunomodulators (i.e., 1, 2, 3, 4, 5, 6, 7, 8, 9, 10, 11, 12, 13, 14 or more) may be cloned into 14 or more separate vectors for transduction into mammalian cells.

According to some embodiments, the vector constructs further comprise one or more tags, as described herein.

Lentiviral System

According to some embodiments, the lentiviral system may be employed where the transfer vector with immune modulator sequences, an envelope vector, and a packaging vector are each transfected into host cells for virus production. According to some embodiments, the lentiviral vectors may be transfected into 293T cells by any of calcium phosphate precipitation transfection, lipid based transfection, or electroporation, and incubated overnight. For embodiments where the immune modulator sequence may be accompanied by a fluorescence reporter, inspection of the 293T cells for florescence may be checked after overnight incubation. The culture medium of the 293T cells comprising virus particles may be harvested 2 or 3 times every 8-12 hours and centrifuged to sediment detached cells and debris. The culture medium may then be used directly, frozen or concentrated as needed.

Tumor cell line or tumor cell line variants may be grown to a confluency of about 70% under standard tissue culture conditions. The cells may then be treated with hexadimethrine bromide (to enhance transduction of cells) and lentiviral particles comprising recombinant constructs in fresh media, and incubated for 18-20 hours followed by a media change.

Lipid Based Transfection

According to some embodiments, cells of tumor cell line or tumor cell line variants may be transfected with immune modulator sequences using a lipid based transfection method. According to some embodiments, established lipid based transfection reagents, such as LIPOFECTAMINE, may be used. Tumor cell line or tumor cell line variants may be grown to about 70-90% confluence in a tissue culture vessel. Appropriate amounts of Lipofectamine® and plasmid construct comprising the immune modulator sequences may be separately diluted in tissue culture media and briefly incubated at room temperature. The diluted Lipofectamine® and plasmid constructs in media may be mixed together and incubated briefly at room temperature. The plasmid LIPOFECTAMINE mixture may then be added to the cells of the tumor cell line or tumor cell line variants in the tissue culture vessel and incubated for 1-3 days under standard tissue culture conditions.

Selection of Expressing Clones

According to some embodiments, tumor cells of the tumor cell line or tumor cell line variant that have been transfected with immunmodulator sequences may be selected for various levels of expression.

According to some embodiments, the immunomodulator sequences may be accompanied by antibiotic resistance genes, which may be used to select for clones with stable integration of the recombinant DNA encoding the immunomodulator sequences. According to some embodiments, the immunomodulator sequences may be cloned into a plasmid construct comprising antibiotic resistance, such as the Neomycin/Kanamycin resistance gene. Transfected cells are treated with antibiotics according to the manufacturer's protocol for 1-2 weeks or more with daily media changes. At some point during antibiotic treatment, there is massive tumor cell death of all cells that have not stably integrated the antibiotic resistance gene, leaving behind small colonies of stably expressing clones. Each of the stably expressing clones may be picked, cultured in a separate tissue culture container, and tested for levels of immuno modulator expression by any established method, such as western blot, flow cytometry, and fluorescence microscopy.

According to some embodiments, transfected tumor cells may be selected for high expression of the immunomodulators by fluorescence activated cell sorting (FACS). According to some embodiments, immunomodulator sequences may be accompanied by one or more fluorescent proteins (e.g. GFP), which can be used to quantify expression of immunomodulator. For example, a bicistronic plasmid comprising an immunomodulator sequence connected to a GFP sequence via IRES sequence would result in both an immunomodulator and GFP protein translated from the same transcript. Thus, the GFP expression level would act as a proxy for the expression level of immunomodulator. Single cell suspensions of immunomodulator/GFP transfected tumor cells could be selected for the desired level of expression by FACS based on the fluorescence intensity. Any fluorescent protein may be used in this regard. For example, any of the following recombinant fluorescent proteins may be used: EBFP, ECFP, EGFP, YFP, mHoneydew, mBanana, mOrange, tdTomato, mTangerine, mStrawberry, mCherry, mGrape, mRasberry, mGrape2, mPlum.

Alternatively, the expression of the recombinant immunomodulator may be directly observed by fluorescent antibodies specific to each immunomodulator or specific to a tag engineered onto each immunomodulator. For example, according to some embodiments the extracellular region of an immunomodulator sequence may be fused with a FLAG tag or HA tag. Anti-FLAG or anti-HA antibodies may be used, along with a fluorophore attached to the primary antibody or a secondary antibody) to detect the expression of the immunomodulator on the surface of the transfected tumor cells. Tumor cells expressing the desired level of immunomodulator may be selected by FACS sorting and cultured separately.

Sequentially Add New Plasmid Constructs to the Clones

According to some embodiments, tumor cell line or tumor cell line variants that express one or more immune modulator sequence(s) are transfected with additional immunomodulators for stable expression in a sequential manner. By sequentially adding recombinant immunomodulators in successive fashion, cells of a tumor cell line or tumor cell line variant may be created that express several immunomodulators simultaneously. According to some embodiments, a tumor cell line or tumor cell line variant may be created that expresses two immunomodulators simultaneously. According to some embodiments, a tumor cell line or tumor cell line variant may be created that expresses three immunomodulators simultaneously. According to some embodiments, a tumor cell line or tumor cell line variant may be created that expresses four immunomodulators simultaneously. According to some embodiments, a tumor cell line or tumor cell line variant may be created that expresses five immunomodulators simultaneously. According to some embodiments, a tumor cell line or tumor cell line variant may be created that expresses six immunomodulators simultaneously. According to some embodiments, a tumor cell line or tumor cell line variant may be created that expresses seven immunomodulators simultaneously. According to some embodiments, a tumor cell line or tumor cell line variant may be created that expresses eight immunomodulators simultaneously. According to some embodiments, a tumor cell line or tumor cell line variant may be created that expresses nine immunomodulators simultaneously. According to some embodiments, a tumor cell line or tumor cell line variant may be created that expresses ten immunomodulators simultaneously. According to some embodiments, a tumor cell line or tumor cell line variant may be created that expresses eleven immunomodulators simultaneously. According to some embodiments, a tumor cell line or tumor cell line variant may be created that expresses twelve immunomodulators simultaneously. According to some embodiments, a tumor cell line or tumor cell line variant may be created that expresses thirteen immunomodulators simultaneously. According to some embodiments, a tumor cell line or tumor cell line variant may be created that expresses fourteen immunomodulators simultaneously. According to some embodiments, a tumor cell line or tumor cell line variant may be created that expresses fifteen immunomodulators simultaneously. According to some embodiments, a tumor cell line or tumor cell line variant may be created that expresses sixteen immunomodulators simultaneously. According to some embodiments, a tumor cell line or tumor cell line variant may be created that expresses seventeen immunomodulators simultaneously. According to some embodiments, a tumor cell line or tumor cell line variant may be created that expresses eighteen immunomodulators simultaneously. According to some embodiments, a tumor cell line or tumor cell line variant may be created that expresses nineteen immunomodulators simultaneously. According to some embodiments, a tumor cell line or tumor cell line variant may be created that expresses twenty immunomodulators simultaneously. According to some embodiments, a tumor cell line or tumor cell line variant may be created that expresses twenty-one immunomodulators simultaneously. According to some embodiments, a tumor cell line or tumor cell line variant may be created that expresses twenty-two immunomodulators simultaneously. According to some embodiments, a tumor cell line or tumor cell line variant may be created that expresses twenty-three immunomodulators simultaneously. According to some embodiments, a tumor cell line or tumor cell line variant may be created that expresses twenty-four immunomodulators simultaneously. According to some embodiments, a tumor cell line or tumor cell line variant may be created that expresses twenty-five immunomodulators simultaneously. According to some embodiments, a tumor cell line or tumor cell line variant may be created that expresses twenty-six immunomodulators simultaneously. According to some embodiments, a tumor cell line or tumor cell line variant may be created that expresses twenty-seven immunomodulators simultaneously. According to some embodiments, a tumor cell line or tumor cell line variant may be created that expresses twenty-eight immunomodulators simultaneously. According to some embodiments, a tumor cell line or tumor cell line variant may be created that expresses twenty-nine immunomodulators simultaneously. According to some embodiments, a tumor cell line or tumor cell line variant may be created that expresses thirty immunomodulators simultaneously.

Variably Expressing Clones

According to one aspect of the disclosed invention, multiple recombinant immune modulator peptides may be expressed in a single clonally derived tumor cell line or tumor cell line variant. According to some embodiments, the amount (or level) of each individual immune modulator expressed in each cell is the same as the level of expression of all other immune modulator peptides. According to some embodiments, however, the level of each individual immune modulator expressed in each cell is different from the level of expression of the other immunomodulators expressed in the cell. According to some embodiments, clonally derived tumor cell line or tumor cell line variants that express the same complement of immunomodulators stably express those immunomodulators in varying amounts relative to each other.

The relative amount of recombinant immune modulator expressed within each clonally derived tumor cell line or tumor cell line variant, and between tumor cell line or tumor cell line variants, can be measured on the level of transcription or translation. For example, the relative amount of recombinant immune modulator can be quantified by western blot, RT-PCR, flow cytometry, immunofluorescence, and northern blot, among others.

According to some embodiments, the differences in the amount of expressed immunomodulators relative to one another may be a result of random integration into more or less transcriptionally active regions of the genome of the tumor cell line or tumor cell line variant. According to some embodiments, the relative differences in the amount of expressed immune modulator may be achieved by elements engineered into the transfected or transduced DNA used to create the tumor cell line or tumor cell line variant.

For example, according to some embodiments, the level of expression of the exogenous immunomodulatory molecules may be achieved on the transcriptional level by engineering stronger or weaker gene promoter sequences to control expression of the immune modulator gene. According to some embodiments, one or more of the following promoters may be used to control expression of immunomodulators: simian virus 40 early promoter (SV40), cytomegalovirus immediate-early promoter (CMV), human Ubiquitin C promoter (UBC), human elongation factor 1α promoter (EF1A), mouse phosphoglycerate kinase 1 promoter (PGK), and chicken β-Actin promoter coupled with CMV early enhancer (CAGG).

According to some embodiments, the level of expression of the exogenous immunomodulatory molecules may be achieved on the translational level by engineering stronger or weaker Kozak consensus sequences around the start codon of the immune modulator transcript. According to some embodiments, the following nucleotide sequences may be provided to control immune modulator translation: GCCGCC(A/G)CCAUGG (SEQ ID NO: 15). According to some embodiments, a sequence that is at least 60% identical to SEQ ID NO: 15 may be provided to control immune modulator translation. According to some embodiments, a sequence that is at least 70% identical to SEQ ID NO: 15 may be provided to control immune modulator translation. According to some embodiments, a sequence that is at least 80% identical to SEQ ID NO: 15 may be provided to control immune modulator translation. According to some embodiments, a sequence that is at least 90% identical to SEQ ID NO: 15 may be provided to control immune modulator translation. According to some embodiments, a sequence that is at least 95% identical to SEQ ID NO: 15 may be provided to control immune modulator translation. According to some embodiments, a sequence that is at least 96% identical to SEQ ID NO: 15 may be provided to control immune modulator translation. According to some embodiments, a sequence that is at least 97% identical to SEQ ID NO: 15 may be provided to control immune modulator translation. According to some embodiments, a sequence that is at least 98% identical to SEQ ID NO: 15 may be provided to control immune modulator translation. According to some embodiments, a sequence that is at least 99% identical to SEQ ID NO: 15 may be provided to control immune modulator translation.

Non-viral approaches can also be employed for the introduction of a vector encoding one or more immunomodulatory molecules to a cell derived from a patient having a tumor or a tumor cell line or variant. For example, a nucleic acid molecule encoding an immunomodulatory molecule can be introduced into a cell by administering the nucleic acid molecule in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Preferably the nucleic acids are administered in combination with a liposome and protamine.

Methods for accomplishing transfection in vitro include the use of calcium phosphate, DEAE dextran, electroporation, and protoplast fusion. Liposomes can also be potentially beneficial for delivery of DNA into a cell.

IV. Therapeutic Compositions

Immunogenic compositions of the invention, including allogeneic tumor cell vaccines, are useful as therapeutics and prophylactics for the treatment of specific types of cancers. Advantageously, these vaccines may be tailored to treat the cancers of particular individuals, by generating vaccines that target specific tumor antigens expressed on a tumor in a subject. Allogeneic vaccines of the invention typically contain inactivated tumor cells or cells expressing tumor antigens that have been genetically modified to express exogenous immunomodulatory molecules, as described herein. According to some embodiments, an allogeneic tumor cell vaccine may comprise an amount of a tumor cell line or tumor cell line variant comprising two or more genes encoding immunomodulatory molecules. According to some embodiments, clones of tumor cell line or tumor cell line variants that maximally express the immunomodulatory molecules are identified and selected. According to some embodiments, expression of the immunomodulatory molecules by populations of the tumor cell line or tumor cell line variants is determined by flow cytometry. According to some embodiments, flow cytometry is used to gate on the maximally expressing population(s) of tumor cell line or tumor cell line variants.

According to some embodiments, the immunogenic amount is effective to stimulate an anti-tumor immune response to one or more tumor specific antigens. According to some embodiments, the immunogenic amount may be titrated to provide both safety and efficacy.

According to some embodiments, the immunogenic composition comprises a pharmaceutically acceptable carrier.

According to some embodiments, the immunogenic composition further comprises an adjuvant.

According to some embodiments, the tumor cell line or tumor cell line variant may comprise tumor cells derived from an established cell line. According to some embodiments, the tumor cell line or tumor cell line variant comprises tumor cells derived from a patient with cancer, wherein the tumor cells are derived from a solid tumor.

According to some embodiments, the tumor cell line or tumor cell line variant comprises an immunogenic amount of a disrupted tumor cell line or tumor cell line variant. Examples of methods for physical disruption include, without limitation, sonication, cavitation, dehydration, ion depletion, or by toxicity from exposure to one or more salts.

According to some embodiments, the immunogenic amount of the immunogenic composition can comprise at least $1\times10^3$ whole or disrupted tumor cell line or tumor cell line variant cells. According to some embodiments, the amount of the immunogenic composition can comprises at least $1\times10^4$ whole or disrupted tumor cell line or tumor cell line variant cells. According to some embodiments, the amount of the immunogenic composition can comprise at least $1\times10^5$ whole or disrupted tumor cell line or tumor cell line variant cells. According to some embodiments, the amount of the immunogenic composition can comprise at least $1\times10^6$ whole or disrupted tumor cell line or tumor cell line variant cells. According to some embodiments, the amount of the immunogenic composition can comprise at least $1 \times 10^7$ whole or disrupted tumor cell line or tumor cell line variant cells. According to some embodiments, the amount of the immunogenic composition can comprise at least $1 \times 10^8$ whole or disrupted tumor cell line or tumor cell line variant cells. According to some embodiments, the amount of the immunogenic composition can comprise at least $1 \times 10^9$ whole or disrupted tumor cell line or tumor cell line variant cells. According to some embodiments, the immunogenic amount can be a therapeutic amount.

According to some embodiments, the immunogenic amount is effective (1) to stimulate an immune response that reduces tumor burden, comprising one or more of a cytotoxic T cell population, a natural killer cell population, antibodies, APCs, a T cell population, a B cell population, and a dendritic cell population; and (2) to improve a clinical outcome parameter selected from one or more of progression-free survival, disease-free survival, time to progression, time to distant metastasis, and overall survival of the subject, when compared to a suitable control.

According to some embodiments, the immunogenic composition may be administered once per week, twice per week, once every two weeks, once every three weeks, once every four weeks, once per month, once every two months, once every three months, once every four months, once every five months, once every six months, once every seven months, once every eight months, once every nine months, once every ten months, once every eleven months, or once a year. According to some embodiments, administration occurs in one day or over 2 days, 3 days, 4, days, 5 days, 6 days, 7 days, 8, days, 9 days, 10 days, 11 days, 12 days, 13 days, 14 days, 15 days, 16 days, 17 days, 18 days, 19 days, 20 days, or more. According to some embodiments, administration may involve two or more administrations on the same day.

Combination Therapies

According to some embodiments, the disclosure provides methods that further comprise administering an additional agent to a subject. According to some embodiments, the invention pertains to co-administration and/or co-formulation.

According to some embodiments, administration of the immunogenic composition acts synergistically when co-administered with another agent and is administered at doses that are lower than the doses commonly employed when such agents are used as monotherapy.

According to some embodiments, inclusive of, without limitation, cancer applications, the present invention pertains to chemotherapeutic agents as additional agents. Examples of chemotherapeutic agents include, but are not limited to, alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; callystatin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII; dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex; razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel, and TAXOTERE doxetaxel; chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (TYKERB); inhibitors of PKC-.alpha., Raf, H-Ras, EGFR (e.g., erlotinib (Tarceva)) and VEGF-A that reduce cell proliferation and pharmaceutically acceptable salts, acids or derivatives of any of the above. In addition, the methods of treatment can further include the use of radiation.

Checkpoint Blockade/Blockage of Tumor Immunosuppression

Some human tumors can be eliminated by a patient's immune system. For example, administration of a monoclonal antibody targeted to an immune "checkpoint" molecule can lead to complete response and tumor remission. A mode of action of such antibodies is through inhibition of an immune regulatory molecule that the tumors have co-opted as protection from an anti-tumor immune response. By inhibiting these "checkpoint" molecules (e.g., with an antagonistic antibody), a patient's CD8+ T cells may be allowed to proliferate and destroy tumor cells.

According to some embodiments, the allogeneic vaccine composition further comprises one or more checkpoint inhibitors that may be effective to prevent premature termination of an effective immune response once such an immune response is initiated.

For example, administration of a monoclonal antibody targeted to by way of example, without limitation, CTLA-4 or PD-1 can lead to a complete response and tumor remission. The mode of action of such antibodies is through inhibition of CTLA-4 or PD-1 that the tumors have co-opted as protection from an anti-tumor immune response. By inhibiting these "checkpoint" molecules (e.g., with an antagonistic antibody), a patient's CD8+ T cells may be allowed to proliferate and destroy tumor cells.

Thus, the allogeneic vaccine compositions provided herein can be used in combination with one or more blocking antibodies targeted to an immune "checkpoint" molecule. For instance, according to some embodiments, the allogeneic vaccine compositions provided herein can be used in combination with one or more blocking antibodies targeted to a molecule such as CTLA-4 or PD-1. For example, the allogeneic vaccine compositions provided herein may be used in combination with an agent that blocks, reduces and/or inhibits PD-1 and PD-L1 or PD-L2 and/or the binding of PD-1 with PD-L1 or PD-L2 (by way of non-limiting example, one or more of nivolumab (ONO-4538/BMS-936558, MDX1106, OPDIVO, BRISTOL MYERS SQUIBB), pembrolizumab (KEYTRUDA, Merck), pidilizumab (CT-011, CURE TECH), MK-3475 (MERCK), BMS 936559 (BRISTOL MYERS SQUIBB), MPDL328OA (ROCHE)). According to some embodiments, the allogeneic vaccine compositions provided herein may be used in combination with an agent that blocks, reduces and/or inhibits the activity of CTLA-4 and/or the binding of CTLA-4 with one or more receptors (e.g. CD80, CD86, AP2M1, SHP-2, and PPP2R5A). For instance, according to some embodiments, the immune-modulating agent is an antibody such as, by way of non-limitation, ipilimumab (MDX-010, MDX-101, Yervoy, BMS) and/or tremelimumab (Pfizer). Blocking antibodies against these molecules can be obtained from, for example, Bristol Myers Squibb (New York, N.Y.), Merck (Kenilworth, N.J.), MedImmune (Gaithersburg, Md.), and Pfizer (New York, N.Y.).

Further, the allogeneic immune compositions provided herein can be used in combination with one or more blocking antibodies targeted to an immune "checkpoint" molecule such as for example, BTLA, HVEM, TIM3, GALS, LAG3, VISTA, KIR, 2B4, CD160 (also referred to as BY55), CGEN-15049, CHK 1 and CHK2 kinases, A2aR, CEACAM (e.g., CEACAM-1, CEACAM-3 and/or CEACAM-5), GITR, GITRL, galectin-9, CD244, CD160, TIGIT, SIRPα, ICOS, CD172a, and TMIGD2 and various B-7 family ligands (including, but are not limited to, B7-1, B7-2, B7-DC, B7-H1, B7-H2, B7-H3, B7-H4, B7-H5, B7-H6 and B7-H7).

Adjuvants

According to some embodiments, the compositions of the present invention may further comprise one or more additional substances which, because of their adjuvant nature, can act to stimulate the immune system to respond to the cancer antigens present on the inactivated tumor cell(s). Such adjuvants include, but are not limited to, lipids, liposomes, inactivated bacteria which induce innate immunity (e.g., inactivated or attenuated *Listeria monocytogenes*), compositions which mediate innate immune activation via Toll-like Receptors (TLRs), (NOD)-like receptors (NLRs), Retinoic acid inducible gene-based (RIG)-I-like receptors (RLRs), and/or C-type lectin receptors (CLRs). Examples of PAMPs include lipoproteins, lipopolypeptides, peptidoglycans, zymosan, lipopolysaccharide, neisserial porins, flagellin, profillin, galactoceramide, muramyl dipeptide. Peptidoglycans, lipoproteins, and lipoteichoic acids are cell wall components of Gram-positive. Lipopoly saccharides are expressed by most bacteria, with MPL being one example. Flagellin refers to the structural component of bacterial flagella that is secreted by pathogenic and commensal bacterial. a-Galactosylceramide (a-GalCer) is an activator of natural killer T (NKT) cells. Muramyl dipeptide is a bioactive peptidoglycan motif common to all bacteria. This list is not meant to be limiting.

According to some embodiments, the treatment regimen may comprise a standard anti-tumor therapy (such as surgery, radiation therapy, a targeted therapy that precisely identifies and attacks cancer cells, a hormone therapy, or a combination thereof). According to some embodiments, the standard anti-tumor therapy is effective to treat the tumor while preserving any existing anti-tumor immune response. According to some embodiments, the immunogenic composition is not applied after chemotherapy. According to some embodiments, the immunogenic composition is applied after low-dose chemotherapy.

According to some embodiments, the immunogenic composition comprises two or more clonally derived tumor cell line or tumor cell line variants. According to some embodiments, the two or more tumor cell line or tumor cell line variants comprise the same complement of recombinant immunomodulators. According to some embodiments, the two or more tumor cell line or tumor cell line variants comprise different panels of recombinant immunomodulators.

According to some embodiments, the tumor cell line or tumor cell line variants are treated with an agent that prevents cell division prior to administration to a subject. According to some embodiments, the tumor cell line or tumor cell line variants are irradiated. According to some embodiments, the tumor cell line or tumor cell line variants are treated with a chemical agent that prevents proliferation.

According to some embodiments, the tumor cell line or tumor cell line variants may be administered parenterally. According to some embodiments, the tumor cell line or tumor cell line variants may be administered locally into a surgical excision cavity. According to some embodiments, the tumor cell variants may be administered by intradermal injection. According to some embodiments, the tumor cell line or tumor cell line variants may be administered by subcutaneous injection. According to some embodiments, the tumor cell line or tumor cell line variants may be administered by intramuscular injection.

V. Methods of Treatment

According to some embodiments, the allogeneic tumor cell vaccines described herein are effective to enhance immune activation of cells, to recognize and act against tumor cells comprising the target tumor antigen in vivo without systemic inflammation; to reduce immunosuppression in a tumor microenvironment for tumor cells comprising the target tumor antigen; to reduce tumor burden, or to increase cell death of tumor cells expressing the target tumor antigen. According to some embodiments, the allogeneic tumor cell vaccines described herein are effective to induce immune activation without systemic inflammation. According to some embodiments, the allogeneic tumor cell vaccine is effective to elicit an immune response that improves progression free survival, overall survival, or both relative to placebo controls.

According to some embodiments, the allogeneic vaccine composition is administered to a subject diagnosed with cancer in combination with an agent that inhibits immunosuppressive molecules produced by tumor cells.

According to some embodiments, the described invention comprises an allogeneic tumor cell vaccine for an active immunotherapy that can be universally administered to all patients with a particular type of cancer. According to some embodiments, the allogeneic vaccine comprises a genetically modified allogeneic tumor-type specific cell, or a membrane lysate derived from modified allogeneic tumor-type specific cells, formulated in a pharmaceutically acceptable carrier. According to some embodiments, the modified allogeneic tumor-type specific cells are derived from previously established cell lines.

According to some embodiments, the allogeneic vaccine is adapted to treat patients with minimal residual disease and a functional immune system, which includes ecognition of self and response to non-self by innate immunity (resistance) and adaptive (specific) immunity comprising humoral immunity and cellular immunity). For example, according to some embodiments, the allogeneic vaccine is adapted to treat a patient with minimal residual disease obtained shortly after a primary lesion is surgically removed. According to some embodiments, the allogeneic vaccine is adapted for subcutaneous administration of the vaccine. According to some embodiments, the dose and schedule for administering the allogeneic vaccine are determined by using immunologic responses to the vaccine as a guide for eventual enhancement of overall survival.

According to some embodiments, the disclosure features a method of inducing an immune response to a cancer in a subject comprising administering the allogeneic tumor cell vaccine described herein, wherein the allogeneic tumor cell vaccine is type-matched to the subject's cancer.

Tumor cell line or tumor cell line variants as provided herein can be incorporated into a composition for administration to a subject (e.g., a research animal or a mammal, such as a human, having a clinical condition such as cancer or an infection). For example, an allogeneic tumor cell vaccine comprising a tumor cell line or tumor cell line variant genetically engineered to stably express a core group of three immunomodulatory molecules wherein the core group of immunomodulator molecules is OX40 Ligand (OX40L), CD27 Ligand (CD70) and CD28 Ligand (CD28L); and a pharmaceutically acceptable carrier; can be administered to a subject for the treatment of cancer. In another example, an allogeneic tumor cell vaccine comprising a tumor-type specific cell line variant is used to deliver a broad array of tumor antigens in the context of immunomodulatory signals sufficient to elicit an effective anti-tumor response as reflected in improved progression free survival, overall survival, or both relative to placebo controls, wherein the immunomodulatory signals comprised at least a core group of three immunomodulatory molecules wherein the core group of immunomodulator molecules is OX40 Ligand (OX40L), CD27 Ligand (CD70) and CD28 Ligand (CD28L); and optionally an additional number of immunomodulatory molecules comprising 3-25 immunomodulators ("R groups") selected from those set forth in Table 2.

Thus, the described invention provides methods for treating clinical conditions such as cancer with the allogeneic tumor vaccines provided herein.

According to various embodiments, the described invention pertains to cancers and/or tumors; for example, the treatment or prevention of cancers and/or tumors. The phrase "cancers or tumors" refers to an uncontrolled growth of cells and/or abnormal increased cell survival and/or inhibition of apoptosis which interferes with the normal functioning of the bodily organs and systems. Included are benign and malignant cancers, polyps, hyperplasia, as well as dormant tumors or micrometastases. Also included are cells having abnormal proliferation that is not impeded by the immune system (e.g. virus infected cells). The cancer may be a primary cancer or a metastatic cancer. The primary cancer may be an area of cancer cells at an originating site that becomes clinically detectable, and may be a primary tumor. In contrast, the metastatic cancer may be the spread of a disease from one organ or part to another non-adjacent organ or part. The metastatic cancer may be caused by a cancer cell that acquires the ability to penetrate and infiltrate surrounding normal tissues in a local area, forming a new tumor, which may be a local metastasis. The cancer may also be caused by a cancer cell that acquires the ability to penetrate the walls of lymphatic and/or blood vessels, after which the cancer cell is able to circulate through the bloodstream (thereby being a circulating tumor cell) to other sites and tissues in the body. The cancer may be due to a process such as lymphatic or hematogeneous spread. The cancer may also be caused by a tumor cell that comes to rest at another site, re-penetrates through the vessel or walls, continues to multiply, and eventually forms another clinically detectable tumor. The cancer may be this new tumor, which may be a metastatic (or secondary) tumor.

The cancer may be caused by tumor cells that have metastasized, which may be a secondary or metastatic tumor. The cells of the tumor may be like those in the original tumor. As an example, if a breast cancer or colon cancer metastasizes to the liver, the secondary tumor, while present in the liver, is made up of abnormal breast or colon cells, not of abnormal liver cells. The tumor in the liver may thus be a metastatic breast cancer or a metastatic colon cancer, not liver cancer.

Illustrative cancers that may be treated include, but are not limited to, carcinomas, e.g. various subtypes, including, for example, adenocarcinoma, basal cell carcinoma, squamous cell carcinoma, and transitional cell carcinoma), sarcomas (including, for example, bone and soft tissue), leukemias (including, for example, acute myeloid, acute lymphoblastic, chronic myeloid, chronic lymphocytic, and hairy cell), lymphomas and myelomas (including, for example, Hodgkin and non-Hodgkin lymphomas, light chain, non-secretory, MGUS, and plasmacytomas), and central nervous system cancers (including, for example, brain (e.g. gliomas (e.g. astrocytoma, oligodendroglioma, and ependymoma), meningioma, pituitary adenoma, and neuromas, and spinal cord tumors (e.g. meningiomas and neurofibroma).

According to certain embodiments, cancers/tumors that may be treated are those where the standard of care is no longer chemotherapy, since chemotherapy is known to interfere with immune responses, which are expected to occur during a successful vaccination protocol. Exemplary tumor types include tumor types treated with hormonal therapies such as prostate and breast cancers (e.g. Abiraterone® for prostate cancer and Tamoxifen® for breast cancer), tumor types treated with targeted therapies like antibodies (e.g. Rituxan® for B cell malignancies, Herceptin® for breast cancer), tumor types treated with kinase inhibitors such as GLEEVEC™ for chronic myelogenous leukemia and tumor types treated with other immune system sparing or enhancing modalities, such as checkpoint inhibitors, oncolytic viruses and CAR-T cells Representative cancers and/or tumors of the present invention are described herein.

The present disclosure also provides compositions containing an allogeneic tumor cell vaccine comprising a tumor cell line or tumor cell line variant comprising two or more stably expressed recombinant exogenous immunomodulatory molecules selected from a cytokine, a TNF-family member, a secreted receptor, a chaperone, an IgG superfamily member and a chemokine receptor. The present disclosure also provides compositions containing an allogeneic tumor cell vaccine comprising two, three, four or more tumor cell lines or tumor cell line variants each comprising two or more stably expressed recombinant exogenous immunomodulatory molecules selected from a cytokine, a TNF-family member, a secreted receptor, a chaperone, an IgG superfamily member and a chemokine receptor.

The present disclosure also provides compositions containing an allogeneic tumor cell vaccine comprising a tumor cell line or tumor cell line variant comprising two or more stably expressed recombinant membrane bound immunomodulatory molecules selected from those set forth in table 2, and a pharmaceutically acceptable carrier, as described herein, in combination with a physiologically and pharmaceutically acceptable carrier. The physiologically and pharmaceutically acceptable carrier can include any of the well-known components useful for immunization. The carrier can facilitate or enhance an immune response to an antigen administered in a vaccine. The cell formulations can contain buffers to maintain a preferred pH range, salts or other components that present an antigen to an individual in a composition that stimulates an immune response to the antigen. The physiologically acceptable carrier also can contain one or more adjuvants that enhance the immune response to an antigen. Pharmaceutically acceptable carriers include, for example, pharmaceutically acceptable solvents, suspending agents, or any other pharmacologically inert vehicles for delivering compounds to a subject. Pharmaceutically acceptable carriers can be liquid or solid, and can be selected with the planned manner of administration in mind so as to provide for the desired bulk, consistency, and other pertinent transport and chemical properties, when combined with one or more therapeutic compounds and any other components of a given pharmaceutical composition. Exemplary pharmaceutically acceptable carriers include, without limitation: water, saline solution, binding agents (e.g., polyvinylpyrrolidone or hydroxypropyl methylcellulose); fillers (e.g., lactose or dextrose and other sugars, gelatin, or calcium sulfate), lubricants (e.g., starch, polyethylene glycol, or sodium acetate), disintegrates (e.g., starch or sodium starch glycolate), and wetting agents (e.g., sodium lauryl sulfate). Compositions can be formulated for subcutaneous, intramuscular, or intradermal administration, or in any manner acceptable for immunization.

An "adjuvant" refers to a substance which, when added to an immunogenic agent such as a tumor cell expressing secreted vaccine protein, nonspecifically enhances or potentiates an immune response to the agent in the recipient host upon exposure to the mixture. Adjuvants can include, for example, oil-in-water emulsions, water-in oil emulsions, alum (aluminum salts), liposomes and microparticles, such as, polysytrene, starch, polyphosphazene and polylactide/polyglycosides.

Adjuvants can also include, for example, squalene mixtures (SAF-I), muramyl peptide, saponin derivatives, *mycobacterium* cell wall preparations, monophosphoryl lipid A, mycolic acid derivatives, nonionic block copolymer surfactants, Quil A, cholera toxin B subunit, polyphosphazene and derivatives, and immunostimulating complexes (ISCOMs) such as those described by Takahashi et al., Nature 1990, 344:873-875. For veterinary use and for production of antibodies in animals, mitogenic components of Freund's adjuvant (both complete and incomplete) can be used. In humans, Incomplete Freund's Adjuvant (IFA) is a useful adjuvant. Various appropriate adjuvants are well known in the art (see, for example, Warren and Chedid, CRC Critical Reviews in Immunology 1988, 8:83; and Allison and Byars, in Vaccines: New Approaches to Immunological Problems, 1992, Ellis, ed., Butterworth-Heinemann, Boston). Additional adjuvants include, for example, bacille Calmett-Guerin (BCG), DETOX (containing cell wall skeleton of *Mycobacterium phlei* (CWS) and monophosphoryl lipid A from *Salmonella minnesota* (MPL)), and the like (see, for example, Hoover et al., J Clin Oncol 1993, 11:390; and Woodlock et al., J Immunother 1999, 22:251-259).

According to some embodiments, an allogeneic tumor cell vaccine can be administered to a subject one or more times (e.g., once, twice, two to four times, three to five times, five to eight times, six to ten times, eight to 12 times, or more than 12 times). An allogeneic tumor cell vaccine as provided herein can be administered one or more times per day, one or more times per week, every other week, one or more times per month, once every two to three months, once every three to six months, or once every six to 12 months. An allogeneic tumor cell vaccine can be administered over any suitable period of time, such as a period from about 1 day to about 12 months. According to some embodiments, for example, the period of administration can be from about 1 day to 90 days; from about 1 day to 60 days; from about 1 day to 30 days; from about 1 day to 20 days; from about 1 day to 10 days; from about 1 day to 7 days. According to some embodiments, the period of administration can be from about 1 week to 50 weeks; from about 1 week to 50 weeks; from about 1 week to 40 weeks; from about 1 week to 30 weeks; from about 1 week to 24 weeks; from about 1 week to 20 weeks; from about 1 week to 16 weeks; from about 1 week to 12 weeks; from about 1 week to 8 weeks; from about 1 week to 4 weeks; from about 1 week to 3 weeks; from about 1 week to 2 weeks; from about 2 weeks to 3 weeks; from about 2 weeks to 4 weeks; from about 2 weeks to 6 weeks; from about 2 weeks to 8 weeks; from about 3 weeks to 8 weeks; from about 3 weeks to 12 weeks; or from about 4 weeks to 20 weeks.

According to some embodiments, after an initial dose (sometimes referred to as a "priming" dose) of an allogeneic tumor cell vaccine has been administered and a maximal antigen-specific immune response has been achieved, one or more boosting doses can be administered. For example, a boosting dose can be administered about 10 to 30 days, about 15 to 35 days, about 20 to 40 days, about 25 to 45 days, or about 30 to 50 days after a priming dose.

According to some embodiments, the methods provided herein can be used for controlling solid tumor growth and/or metastasis. The methods can include administering an effective amount of an allogeneic tumor cell vaccine as described herein to a subject in need thereof.

The vectors and methods provided herein can be useful for stimulating an immune response against a tumor. Such immune response is useful in treating or alleviating a sign or symptom associated with the tumor. A practitioner will appreciate that the methods described herein are to be used in concomitance with continuous clinical evaluations by a skilled practitioner (physician or veterinarian) to determine subsequent therapy. Such evaluations will aid and inform in evaluating whether to increase, reduce, or continue a particular treatment dose, mode of administration, etc.

The methods provided herein can thus be used to treat a tumor, including, for example, a cancer. The methods can be used, for example, to inhibit the growth of a tumor by preventing further tumor growth, by slowing tumor growth, or by causing tumor regression. Thus, the methods can be used, for example, to treat a cancer. It will be understood that the subject to which a compound is administered need not suffer from a specific traumatic state. Indeed, the allogeneic tumor cell vaccine described herein may be administered prophylactically, prior to development of symptoms (e.g., a patient in remission from cancer).

Anti-tumor and anti-cancer effects include, without limitation, modulation of tumor growth (e.g., tumor growth delay), tumor size, or metastasis, the reduction of toxicity and side effects associated with a particular anti-cancer agent, the amelioration or minimization of the clinical impairment or symptoms of cancer, extending the survival of the subject beyond that which would otherwise be expected in the absence of such treatment, and the prevention of tumor growth in an animal lacking tumor formation prior to administration, i.e., prophylactic administration.

Therapeutically effective amounts can be determined by, for example, starting at relatively low amounts and using step-wise increments with concurrent evaluation of beneficial effects. The methods provided herein thus can be used alone or in combination with other well-known tumor therapies, to treat a patient having a tumor. One skilled in the art will readily understand advantageous uses of the allogeneic tumor cell vaccines and methods provided herein, for example, in prolonging the life expectancy of a cancer patient and/or improving the quality of life of a cancer patient (e.g., a lung cancer patient).

According to some embodiments, a subject (i.e. a subject diagnosed with cancer) is treated by checkpoint inhibitor therapy prior to or concurrently with administration of the allogeneic vaccine composition. In certain embodiments, the cancer is a melanoma.

Subjects

The methods described herein are intended for use with any subject that may experience the benefits of these methods. Thus, "subjects," "patients," and "individuals" (used interchangeably) include humans as well as non-human subjects, particularly domesticated animals.

According to some embodiments, the subject and/or animal is a mammal, e g., a human, mouse, rat, guinea pig, dog, cat, horse, cow, pig, rabbit, sheep, or non-human primate, such as a monkey, chimpanzee, or baboon. In other embodiments, the subject and/or animal is a non-mammal, such, for example, a zebrafish. According to some embodiments, the subject and/or animal may comprise fluorescently-tagged cells (with e.g. GFP). According to some embodiments, the subject and/or animal is a transgenic animal comprising a fluorescent cell.

According to some embodiments, the subject and/or animal is a human According to some embodiments, the human is a pediatric human In other embodiments, the human is an adult human. In other embodiments, the human is a geriatric human In other embodiments, the human may be referred to as a patient.

According to certain embodiments, the human has an age in a range of from about 0 months to about 6 months old, from about 6 to about 12 months old, from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

According to other embodiments, the subject is a non-human animal, and therefore the invention pertains to veterinary use. According to a specific embodiment, the non-human animal is a household pet. According to another specific embodiment, the non-human animal is a livestock animal According to certain embodiments, the subject is a human cancer patient that cannot receive chemotherapy, e.g. the patient is unresponsive to chemotherapy or too ill to have a suitable therapeutic window for chemotherapy (e.g. experiencing too many dose- or regimen-limiting side effects). In certain embodiments, the subject is a human cancer patient having advanced and/or metastatic disease.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

It must be noted that as used herein and in the appended claims, the singular forms "a", "an", and "the" include plural references unless the context clearly dictates otherwise. All technical and scientific terms used herein have the same meaning.

The publications discussed herein are provided solely for their disclosure prior to the filing date of the present application and each is incorporated by reference in its entirety. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

The Examples make use of, but are not limited to, the methods described hereinbelow.
Western Blotting Briefly, cells are lysed with cold lysis buffer and centrifuged to pellet cellular debris. Protein concentration of the supernatant is determined by a protein quantification assay (e.g., Bradford Protein Assay, Bio-Rad Laboratories). The lysate supernatant is then combined with an equal volume of 2×SDS sample buffer and boiled at 100° C. for 5 minutes. Equal amounts of protein in sample buffer are loaded into the wells of an SDS-PAGE gel along with molecular weight marker and electrophoresed for 1-2 hours at 100 V. Proteins are then transferred to a nitrocellulose or PVDF membrane. The membrane is then blocked for 1 hour at room temperature using 5% non-fat dry milk in TBST blocking buffer. The membrane is then incubated with a 1:500 dilution of primary antibody in 5% non-fat dry milk in TBST blocking buffer, followed by three washes in 20 Mn Tris, Ph 7.5; 150 mM NaCl, 0.1% Tween 20 (TBST) for 5 minutes. The membrane is then incubated with conjugated secondary antibody at a 1:2000 dilution in 5% non-fat dry milk in TBST blocking buffer for 1 hour at room temperature, followed by three washes in TBST for 5 minutes each. Images of the blot are obtained using dark room development techniques for chemiluminesence detection, or using image scanning techniques for colorimetric or fluorescent detection.
Real Time PCR Real-time PCR techniques may be performed as described to analyze expression level of mRNAs (Zhao Y. et al., Biochemical and Biophysical Research Communications 360 (2007) 205-211). Briefly, total RNA is extracted from cells using the Quiagen kit (Valencia Calif.), followed by first strand cDNA synthesis using random hexamer primers (Fermentas, Hanover Md.). Real-time PCR is performed on each sample using the Mx3000p Quantitative PCR system (Stratagene, La Jolla, Calif.), for 40 cycles using validated gene specific RT-PCR primer sets for each gene of interest. Relative expression level of each transcript is corrected for that of the house keeping gene beta-actin as an internal control.
Immunofluorescence Briefly, adherent tumor cell line variant cells are fixed with 4% formaldehyde diluted in warm PBS for 15 minutes at room temperature. The fixative is aspirated and the cells washed three times with PBS for 5 minutes each. Cells are blocked in a 5% BSA blocking buffer for 60 minutes at room temperature. Blocking buffer is then aspirated and a solution of primary antibody (e.g. 1:100 dilution) is incubated with the cells overnight at 4° C. Cells are then rinsed three times with PBS for 5 minutes each, and subsequently incubated with a solution of fluorochrome conjugated secondary antibody (e.g. 1:1000 dilution) for 1-2 hours at room temperature. Cells are then washed three times with PBS for 5 minutes each and visualized by fluorescence microscopy.
Flow Cytometry Flow Cytomtery analysis may be performed as described (Zhao Y. et al., Exp. Cell Res., 312, 2454 (2006)). Briefly, tumor cell line variant cells that are either treated with trypsin/EDTA or left untreated are collected by centrifugation and re-suspended in PBS. The cells are fixed in 4% formaldehyde for 10 minutes at 37° C. For extracellular staining with antibodies, cells are not permeabilized. For intracellular staining, cells are permeabilized by adding ice-cold 100% methanol to pre-chilled cells to a final concentration of 90% methanol and incubated on ice for 30 minutes. Cells are immunostained by first resuspending cells in incubation buffer and adding dilutions of primary antibody. Cells are incubated with primary antibody for 1 hour at room temperature, followed by three washes with incubation buffer. Cells are then resuspended in incubation buffer with dilutions of conjugated secondary antibody for 30 minutes at room temperature, followed by three washes in incubation buffer. Stained cells are then analyzed by flow cytometry.
Enzyme-Linked Immunosorbent Assay (ELISA)

Briefly, a capture antibody, specific for a protein of interest, is coated onto the wells of a microplate. Samples, including a standard containing protein of interest, control specimens, and unknowns, are pipetted into wells of the microplate, where the protein antigen binds to the capture antibody. After washing 4 times, a detection antibody is added to the wells for one hour, binding to the immobilized protein captured during the first incubation. After removal of excess detection antibody and washing 4 times, a horse radish peroxidase (HRP) conjugate (secondary antibody or streptavidin) is added for 30 minutes to bind to the detection antibody. After washing 4 more times to remove the excess HRP conjugate, a substrate solution is added for 30 minutes in the dark to be converted by the enzyme to a detectable form (color signal). A stop solution is added to each well of the microplate and evaluated within 30 minutes of stopping the reaction. Intensity of the colored product may be directly proportional to the concentration of antigen present in the original specimen.
Human Mixed Lymphocyte Tumor Reaction (MLTR) Testing The mixed lymphocyte tumor reaction (MLTR) is an all human, in vitro assay, designed to optimize lead candidates. In the MLTR, optimization is achieved through the qualitative and quantitative assessment of human peripheral blood mononuclear cell (PBMC) responses to engineered allogeneic tumor cells. The MLTR measures proliferation and differentiation by flow cytometry and mass cytometry (CyTOF), by cytotoxicity, measured by lactate dehydrogenase (LDH) release assay, and by cytokine profile. According to some embodiments, allogeneic cell pools expressing a single immunomodulatory protein are used in the MLTR. According to some embodiments, allogenic cell pools expressing one or more, two or more, three or more, four or more or five or more immunomodulatory proteins are used in the MLTR.

The basic MLTR one day procedure is carried out as follows:

A vial of PBMC (20 MN cells) is thawed. Cells are then washed in dPBS. PMBC cells are resuspended at $2.5 \times 10^6$ cell per ml in X-VIVO (~8 ml). The cells are characterized by flow cytometry to document the nature of the cell population.

Use in the MLTR is carried out as follows:
$2.5 \times 10^5$ cell PBMC (100 µl of stock)
$0.5 \times 10^5$ allogeneic cells (100 µl of stock), when used
$0.5 \times 10^5$ allogeneic cell (100 µl of stock). These cells will be inactivated with Mitomycin C.
Positive control 50 µl of a 6× stock (anti-CD28/CD3)
Total volume 300 µl in a 96-well flat bottom–total volume of a 96-well is 360 µl.
Incubate for 4 days
100 µl is removed for cytokine analysis with Luminex
CyTOF is conducted on the remaining 200 µl.
Supernatants for Cytokine Profiling are removed after 1 day.

CyTOF has been previously described, for example in Bendall et al. (Science, Vol. 332, 6 May 2011) and Bendall and Nolan (Nature Biotechnology, Vol. 30 No. 7, July 2012), both of which are incorporated by reference in their entireties herein. Human markers employed in CyTOF staining are shown below in Table 6.

TABLE 6

Human Markers for CyTOF Staining

| | Marker | Clone | Metal |
|---|---|---|---|
| | HLA-DR | L243 | 89Y |
| | CD3 | UCHT1 | 115In |
| | CD27 | O323 | 141Pr |
| | CD19 | HIB19 | 142Nd |
| | CD134/OX40 | Ber-ACT35 | 143Nd |
| * | Granzyme B | GB11 | 144Nd |
| | CD258/LIGHT | 115520 | 145Nd |
| | CD8A | RPA t8 | 146Nd |
| | CD45RO | UCHL1 | 147Sm |
| | CD226/DNAM-1 | 11A8 | 149Sm |
| | CD194/CCR4 | L291H4 | 150Nd |
| | PD1 (CD279) | EH12.2H7 | 151Eu |
| | CD170 | 1A5 | 152Sm |
| | CD69 | FN50 | 153Eu |
| | CD70 | 113-16 | 154Sm |
| | CD4 | RPA T4 | 155Gd |
| | CD8b | SIDI8BEE | 156Gd |
| | IL-17R | W15177A | 158Gd |
| * | CTLA-4 CD152 | L3D10 | 159Tb |
| | CD278/ICOS | C398.4A | 160Gd |
| * | AHR | FF3399 | 161Dy |
| | CD56 | NCAM16.2 | 162Dy |
| | CD195/CCR5 | J418F1 | 163Dy |
| * | Ki67 | 8D5 | 164Dy |
| * | FoxP3 | Use Ebio | 165Ho |
| | CD40 | 5C3 | 166Er |
| * | Helios | 22F6 | 168Er |
| * | PU.1 | puph13 | 169Tm |
| * | RORgt | 1181A | 170Er |
| | CD127/IL-7R | 40131 | 171Yb |
| | CD38 | HIT2 | 172Yb |
| | CD25 | M-A251 | 173Yb |
| | CD86 | IT2.2 | 174Yb |
| * | T-bet | 4B10 | 175Lu |
| * | Perforin | dG9 | 176Yb |

* denotes intracellular target while all other are cell surface targets

Luminex Multiplex Assay

The Luminex xMAP technology (formerly LabMAP, FlowMetrix) uses digital signal processing capable of classifying polystyrene beads (microspheres) dyed with distinct proportions of red and near-infrared fluorophores. These proportions define 'spectral addresses' for each bead population. As a result, up to one hundred different detection reactions can be carried out simultaneously on the various bead populations in very small sample volumes (Earley et al. Report from a Workshop on Multianalyte Microsphere Arrays. Cytometry 2002; 50:239-242; Oliver et al. Clin Chem 1998; 44(9):2057-2060; Eishal and McCoy, Methods 38(4): 317-323, April 2006, all of which are incorporated by reference in their entireties herein).

The Luminex Multiplex Assay is commercially available and is described on the world wide web at thermofisher.com/us/en/home/life-science/protein-biology/protein-assays-analysis/luminex-multiplex-assays.html, incorporated by reference in its entirety herein.

Mitomycin C Preparation of Cells

Mitomycin C is prepared from dry powder (2 mg per vial) using 400 µl of DMSO (500× stock=5 mg/ml), dissolved completely and aliquoted into 25 ul volumes, and stored at −80 C. 20 µl of 1 aliquot is used in 10 ml warmed C5 to yield 10 µg/ml final working solution. The solution is filter sterilized.

The solution can be used on resuspended cells or adherent cells in flasks.

Cells are incubated at 37 C for 30 minutes in the dark, then washed in warm C5 3 times. Cells are resuspended in 1 ml X-VIVO. 40 ul are counted into 200 ul on plate. The cells are resuspended at a final concentration of $1 \times 10^6$/ml in X-VIVO (serum free media, Lonza).

Example 2

The described invention provides an approach for restoring immunologic balance in, for example, treating cancer, by targeting multiple immunomodulators with a single cellular platform. This approach enables the simultaneous modulation of multiple signals, and affords a spatially restricted site of action, important features that have limited traditional approaches for restoring immunologic balance.

According to one aspect of the disclosed invention, a tumor cell line variant expressing five or more recombinant peptides may be generated for use as a tumor cell vaccine to treat a cancer. For example, a tumor cell line may be selected for modification, and lentiviral transfection of recombinant immune modulator sequences may be used to stably integrate immunomodulators into the cell genome. Example 3 below describes 7 lentiviral vectors (vector 1, vector 2, vector 3, vector 4, vector 5, vector 6 and vector 7) that may be used to stably integrate immunomodulators into the cell genome.

According to some embodiments, two recombinant immunomodulator proteins may be transfected simultaneously, followed by transfections of two more recombinant immunomodulator proteins simultaneously, followed by transfection of a single recombinant immunomodulator protein to achieve the total of five recombinant peptides for use as a tumor cell vaccine. According to some embodiments, two recombinant peptides may be transfected simultaneously, followed by transfection of a single recombinant peptide, followed by transfection of a single recombinant peptide, followed by transfection of a single recombinant peptide to achieve the total of five recombinant peptides for use as a tumor cell vaccine. According to some embodiments, a single recombinant peptide is transfected, followed by transfection of two recombinant peptides simultaneously, followed by transfection of two recombinant peptides simultaneously to achieve a total of five recombinant peptide for use as a tumor cell vaccine.

Example 3 below describes lentiviral vectors (vector 44, vector 97, vector 84, vector 29, vector 107, vector 116, vector 86, vector 18, vector 17, vector 98, vector 5, vector 30, vector 109, vector 3, vector 4, vector 106, vector 16, vector 83, vector 31, vector 12, vector 99, vector 121, vector 105, vector 32, vector 37, vector 22, vector 19, vector 20, vector 89, vector 21, vector 23, vector 108, vector 15, vector 124, vector 65, vector 64, vector 88, vector 96, vector 14, vector 119, vector 120, vector 45, vector 60, vector 59, vector 8, vector 128, vector 35, and vector 6) that may be used to stably integrate immunomodulators into the cell genome.

According to one embodiment, vector 44 comprises one or more TNF family member immunomodulators. According to one embodiment, vector 29 comprises one or more TNF family member immunomodulators. According to one embodiment, vector 18 comprises one or more TNF family member immunomodulators. According to one embodiment, vector 17 comprises one or more TNF family member immunomodulators. According to one embodiment, vector 5 comprises one or more TNF family member immunomodulators. According to one embodiment, vector 16 comprises one or more TNF family member immunomodulators. According to one embodiment, vector 99 comprises one or more TNF family member immunomodulators. According to one embodiment, vector 15 comprises one or more TNF family member immunomodulators. According to one embodiment, vector 14 comprises one or more TNF family member immunomodulators. According to one embodiment, vector 45 comprises one or more TNF family member immunomodulators. According to one embodiment, vector 6 comprises one or more TNF family member immunomodulators. According to one embodiment, the one or more TNF family immunomodulators are selected from those listed in Table 2 or Table 3.

According to one embodiment, vector 44 comprises between 3-14 TNF family member immunomodulators. According to one embodiment, vector 29 comprises between 3-14 TNF family member immunomodulators. According to one embodiment, vector 18 comprises between 3-14 TNF family member immunomodulators. According to one embodiment, vector 17 comprises between 3-14 TNF family member immunomodulators. According to one embodiment, vector 5 comprises between 3-14 TNF family member immunomodulators. According to one embodiment, vector 16 comprises between 3-14 TNF family member immunomodulators. According to one embodiment, vector 99 comprises between 3-14 TNF family member immunomodulators. According to one embodiment, vector 15 comprises between 3-14 TNF family member immunomodulators. According to one embodiment, vector 14 comprises between 3-14 TNF family member immunomodulators. According to one embodiment, vector 45 comprises between 3-14 TNF family member immunomodulators. According to one embodiment, vector 6 comprises between 3-14 TNF family member immunomodulators. According to one embodiment, the between 3-14 TNF family immunomodulators are selected from those listed in Table 2 or Table 3.

According to one embodiment, vector 97 comprises one or more Ig family member immunomodulators. According to one embodiment, vector 84 comprises one or more Ig family member immunomodulators. According to one embodiment, vector 107 comprises one or more Ig family member immunomodulators. According to one embodiment, vector 98 comprises one or more Ig family member immunomodulators. According to one embodiment, vector 30 comprises one or more Ig family member immunomodulators. According to one embodiment, vector 83 comprises one or more Ig family member immunomodulators. According to one embodiment, vector 121 comprises one or more Ig family member immunomodulators. According to one embodiment, vector 119 comprises one or more Ig family member immunomodulators. According to one embodiment, the one or more Ig family member immunomodulators are selected from those listed in Table 2 or Table 3.

According to one embodiment, vector 97 comprises between 3-14 Ig family member immunomodulators. According to one embodiment, vector 84 comprises between 3-14 Ig family member immunomodulators. According to one embodiment, vector 107 comprises between 3-14 Ig family member immunomodulators. According to one embodiment, vector 98 comprises between 3-14 Ig family member immunomodulators. According to one embodiment, vector 30 comprises between 3-14 Ig family member immunomodulators. According to one embodiment, vector 83 comprises between 3-14 Ig family member immunomodulators. According to one embodiment, vector 121 comprises between 3-14 Ig family member immunomodulators. According to one embodiment, vector 119 comprises between 3-14 Ig family member immunomodulators. According to one embodiment, the between 3-14 Ig family member immunomodulators are selected from those listed in Table 2 or Table 3.

According to one embodiment, vector 116 comprises one or more chemokine immunomodulators. According to one embodiment, the one or more chemokine immunomodulators are selected from those listed in Table 2 or Table 3.

According to one embodiment, vector 116 comprises between 3-14 chemokine immunomodulators. According to one embodiment, the between 3-14 chemokine immunomodulators are selected from those listed in Table 2 or Table 3.

According to one embodiment, vector 109 comprises one or more growth factor immunomodulators.

According to one embodiment, vector 109 comprises between 3-14 growth factor immunomodulators.

According to one embodiment, vector 3 comprises one or more cytokine immunomodulators. According to one embodiment, vector 4 comprises one or more cytokine immunomodulators. According to one embodiment, vector 32 comprises one or more cytokine immunomodulators. According to one embodiment, vector 22 comprises one or more cytokine immunomodulators. According to one embodiment, vector 19 comprises one or more cytokine immunomodulators. According to one embodiment, vector 20 comprises one or more cytokine immunomodulators. According to one embodiment, vector 89 comprises one or more cytokine immunomodulators. According to one embodiment, vector 21 comprises one or more cytokine immunomodulators. According to one embodiment, vector 23 comprises one or more cytokine immunomodulators. According to one embodiment, vector 121 comprises one or more cytokine immunomodulators. According to one embodiment, vector 65 comprises one or more cytokine immunomodulators. According to one embodiment, vector 64 comprises one or more cytokine immunomodulators. According to one embodiment, vector 88 comprises one or more cytokine immunomodulators. According to one embodiment, vector 96 comprises one or more cytokine immunomodulators. According to one embodiment, vector 60 comprises one or more cytokine immunomodulators. According to one embodiment, vector 59 comprises one or more cytokine immunomodulators. According to one embodiment, vector 128 comprises one or more cytokine immunomodulators. According to one embodiment, the one or more cytokine immunomodulators are selected from those listed in Table 2 or Table 3.

According to one embodiment, vector 3 comprises between 3-14 cytokine immunomodulators. According to one embodiment, vector 4 comprises between 3-14 cytokine immunomodulators. According to one embodiment, vector 32 comprises between 3-14 cytokine immunomodulators. According to one embodiment, vector 22 comprises between 3-14 cytokine immunomodulators. According to one embodiment, vector 19 comprises between 3-14 cytokine immunomodulators. According to one embodiment, vector 20 comprises between 3-14 cytokine immunomodulators. According to one embodiment, vector 89 comprises between 3-14 cytokine immunomodulators. According to one embodiment, vector 21 comprises between 3-14 cytokine immunomodulators. According to one embodiment, vector 23 comprises between 3-14 cytokine immunomodulators. According to one embodiment, vector 121 comprises between 3-14 cytokine immunomodulators. According to one embodiment, vector 65 comprises between 3-14 cytokine immunomodulators. According to one embodiment, vector 64 comprises between 3-14 cytokine immunomodulators. According to one embodiment, vector 88 comprises between 3-14 cytokine immunomodulators. According to one embodiment, vector 96 comprises between 3-14 cytokine immunomodulators. According to one embodiment, vector 60 comprises between 3-14 cytokine immunomodulators. According to one embodiment, vector 59 comprises between 3-14 cytokine immunomodulators. According to one embodiment, vector 128 comprises between 3-14 cytokine immunomodulators. According to one embodiment, the between 3-14 cytokine immunomodulators are selected from those listed in Table 2 or Table 3.

According to one embodiment, vector 37 comprises one or more receptor immunomodulators. According to one embodiment, vector 124 comprises one or more receptor immunomodulators. According to one embodiment, vector 88 comprises one or more receptor immunomodulators. According to one embodiment, vector 8 comprises one or more receptor immunomodulators. According to one embodiment, the one or more receptor immunomodulators are selected from those listed in Table 2 or Table 3.

According to one embodiment, vector 37 comprises between 3-14 receptor immunomodulators. According to one embodiment, vector 124 comprises between 3-14 receptor immunomodulators. According to one embodiment, vector 88 comprises between 3-14 receptor immunomodulators. According to one embodiment, vector 8 comprises between 3-14 receptor immunomodulators. According to one embodiment, the between 3-14 receptor immunomodulators are selected from those listed in Table 2 or Table 3.

According to one embodiment, vector 86 comprises one or more other immunomodulators. According to one embodiment, vector 106 comprises one or more other immunomodulators. According to one embodiment, vector 107 comprises one or more other immunomodulators. According to one embodiment, vector 31 comprises one or more other immunomodulators. According to one embodiment, vector 12 comprises one or more other immunomodulators. According to one embodiment, vector 105 comprises one or more other immunomodulators. According to one embodiment, vector 108 comprises one or more other immunomodulators. According to one embodiment, vector 120 comprises one or more other immunomodulators. According to one embodiment, vector 35 comprises one or more other immunomodulators. According to one embodiment, the one or more other immunomodulators are selected from those listed in Table 2 or Table 3.

According to one embodiment, vector 86 comprises between 3-25 other immunomodulators. According to one embodiment, vector 106 comprises between 3-25 other immunomodulators. According to one embodiment, vector 107 comprises between 3-25 other immunomodulators. According to one embodiment, vector 31 comprises between 3-25 other immunomodulators. According to one embodiment, vector 12 comprises between 3-25 other immunomodulators. According to one embodiment, vector 105 comprises between 3-25 other immunomodulators. According to one embodiment, vector 108 comprises between 3-25 other immunomodulators. According to one embodiment, vector 120 comprises between 3-25 other immunomodulators. According to one embodiment, vector 35 comprises between 3-25 other immunomodulators. According to one embodiment, the between 3-25 other immunomodulators are selected from those listed in Table 2 or Table 3.

According to one embodiment of the disclosed invention, combinations of allogeneic cell pools, each expressing a single immunomodulatory protein, are used to model what a single cell expressing multiple immunomodulatory proteins might do (e.g. additivity, synergy, interference).

According to one aspect of the disclosed invention, a tumor cell line variant expressing one, two three, four or five or more recombinant peptides may be generated for use as a tumor cell vaccine to treat skin cancer. For example, the SK-MEL2 human melanoma cell line (ATCC HTB-68) may be selected for modification, and lentiviral transfection of recombinant immune modulator sequences may be used to stably integrate immunomodulators into the cell genome.

According to one aspect of the disclosed invention, a tumor cell line variant expressing one, two three, four or five or more recombinant peptides may be generated for use as a tumor cell vaccine to treat a prostate cancer. For example, the DU-145 human prostate carcinoma cell line may be selected for modification, and lentiviral transfection of recombinant immune modulator sequences may be used to stably integrate immunomodulators into the cell genome. According to some embodiments, two recombinant immunomodulator proteins may be transfected simultaneously, followed by transfections of two more recombinant immunomodulator proteins simultaneously, followed by transfection of a single recombinant immunomodulator protein to achieve the total of five recombinant peptides for use as a tumor cell vaccine. According to some embodiments, two recombinant peptides may be transfected simultaneously, followed by transfection of a single recombinant peptide, followed by transfection of a single recombinant peptide, followed by transfection of a single recombinant peptide to achieve the total of five recombinant peptides for use as a tumor cell vaccine. According to some embodiments, a single recombinant peptide is transfected, followed by transfection of two recombinant peptides simultaneously, followed by transfection of two recombinant peptides simultaneously to achieve a total of five recombinant peptide for use as a tumor cell vaccine.

According to another aspect of the present invention, two or more tumor cell line variants expressing one or more recombinant peptides may be generated for use as a tumor cell vaccine to treat a prostate cancer. For example, the DU-145 and PC-3 human prostate carcinoma cell line may be selected for modification, and lentiviral transfection of recombinant immune modulator sequences may be used to stably integrate immunomodulators into the cell genome.

CD40L Immunomodulator

The CD40L immune modulator cDNA sequence may be cloned into the lentiviral transfer plasmid construct pLenti-puro (Addgene Cat. No. 39481) driven by a CMV promoter with puromycin selectable marker. The CD40L immune modulator cDNA sequence may be engineered to be non-cleavable, which ultimately keeps the translated CD40L protein in a membrane bound state (e.g. SEQ ID NO: 7). A human influenza hemagglutinin tag (HA tag) may be also cloned onto the extracellular portion of the CD40L sequences. The translated HA tag has the peptide sequence YPYDVPDYA (SEQ ID NO: 28). Packaging plasmid psPAX2 (AddGene Cat. No. 12260) and envelope plasmid pLTR-RD114A (AddGene Cat. No. 17576) may also be selected for the lentiviral system.

Each of the lentiviral transfer plasmid, packaging plasmid, and envelope plasmid may be transfected into log phase growth 293T cells using Lipofectamine 2000 (ThermoFisher Cat. No. 11668027). Briefly, cells are seeded at 70% to 90% confluence. On the day of transfection, 12 µl of Lipofectamine reagent is diluted in 150 µl of serum free cell media. 5 µg of DNA for transfection is also diluted in 150 µl of serum free media. The diluted DNA is then added to the diluted Lipofectamine and incubated for 5 minutes at room temperature. The total volume of the mixture is then added dropwise to the media of the seeded 293T cells while swirling. Cells are then incubated for one to three days at 37 degrees.

The 293T cell culture medium comprising virus particle is harvested 3 times every 8-12 hours and centrifuged to pellet detached cells and debris. The culture medium containing virus particles is used directly to infect the DU-145 cell line.

The DU-145 cell line is cultured in Eagle's Minimum Essential Medium (EMEM) with 10% fetal bovine serum to a confluency of about 70%. Hexadimethrine bromide (Sigma-Aldrich Cat No. H9268) is then combined with media containing virus particles to make a final concentration of 8 µg/mL Hexadimethrine bromide. Culture media of the DU-145 cells is aspirated and replaced with media containing virus particles and 8 µg/mL Hexadimethrine bromide. DU-145 cells are cultured for 18-20 hours followed by media change.

Infected DU-145 cells are then grown in media containing 1 µg/mL Puromycin (ThermoFisher Cat. No. A1113802) until cell die off begins after about a week. Multiple surviving colonies of transfected cells are picked for expansion and tested for CD40L expression by Western blot. The Western blot is probed with mouse monoclonal anti-HA primary antibodies (Abcam Cat. No. ab18181) and goat anti-mouse HRP (Abcam Cat. No. ab205719) secondary antibodies to quantify the relative amounts of recombinant CD40L expressed in each clonal line. The highest stably expressing DU-145 line is labeled DU145-Gen1 and selected for further manipulation.

TNF-Alpha/GM-CSF

The DU145-Gen1 cells transfected to express CD40L are further transfected with a bi-cistronic lentiviral vector comprising TNF-alpha and GM-CSF sequences. Each of TNF-alpha cDNA and GM-CSF cDNA is first cloned into the pEF1α-IRES bicistronic mammalian expression vector (Clontech Cat. No. 631970) under the control of the human elongation factor 1 alpha (EF1α) promoter. A variant of TNF-alpha that cannot be cleaved by TACE is used so that the translated protein remains in membrane bound form. The TNF-alpha sequence is provided with a FLAG tag sequence on the extracellular region of TNF-alpha for easy detection of translated protein. The FLAG tag peptide sequence is DYKDDDDK (SEQ ID NO: 29). GM-CSF sequences capable of forming soluble GM-CSF are used. The entirety of the pEF1 promoter, TNF-alpha sequences, IRES sequences, and GM-CSF sequences is then cloned into the pLenti-puro (Addgene Cat. No. 39481) lentiviral vector (the original CMV promoter from the vector is removed during this process). Packaging plasmid psPAX2 (AddGene Cat. No. 12260) and envelope plasmid pLTR-RD114A (AddGene Cat. No. 17576) are also selected.

Each of the lentiviral transfer plasmid, packaging plasmid, and envelope plasmid is transfected into log phase growth 293T cells using Lipofectamine 2000 (ThermoFisher Cat. No. 11668027). Briefly, cells are seeded at 70% to 90% confluence. On the day of transfection, 12 µl of Lipofectamine reagent is diluted in 150 µl of serum free cell media. 5 µg of DNA for transfection is also diluted in 150 µl of serum free media. The diluted DNA is then added to the diluted Lipofectamine and incubated for 5 minutes at room temperature. The total volume of the mixture is then added dropwise to the media of the seeded 293T cells while swirling. Cells are then incubated for one to three days at 37 degrees.

The 293T cell culture medium comprising virus particle is harvested 3 times every 8-12 hours and centrifuged to pellet detached cells and debris. The culture medium containing virus particles is used directly to infect the DU145-Gen1 cell line.

The DU145-Gen1 cell line is cultured to a confluency of about 70%. Hexadimethrine bromide (Sigma-Aldrich Cat No. H9268) is then combined with media containing virus particles to make a final concentration of 8 µg/mL Hexadimethrine bromide. Culture media of the DU145-Gen1 cells is aspirated and replaced with media containing virus particles and 8 µg/mL Hexadimethrine bromide. DU145-Gen1 cells are cultured for 18-20 hours followed by media change.

The transduced DU145-Gen1 cells are then selected for clones that stably express the recombinant immunomodulators. The selection process is performed by fluorescence activated cell sorting using the FLAG tag on the TNF-alpha to identify cells that have integrated the immunomodulators. Live cells are probed with mouse monoclonal anti-FLAG antibody (Sigma Aldrich F3040) and rabbit anti-mouse FITC conjugated secondary antibody (Sigma Aldrich ASB3701170) in PBS with blocking buffer. The highest expressing cells are sorted, isolated, and cultured for further processing. After sorting based on the presence of the FLAG tag, expression of soluble GM-CSF is confirmed by Western blot. Concentrated media of sorted cultured cells is resolved by SDS-PAGE and probed by Western blot with mouse anti-GM-CSF antibody (ThermoFisher Cat. No. 3092) and goat anti-mouse HRP conjugated secondary antibody. Cell lysate may also be resolved by SDS-PAGE and probed for FLAG tag to verify the presence of TNF. Cell cultures that express high levels of recombinant GM-CSF and TNF-alpha are designated DU145-Gen2 and selected for further processing.

Flt-3L

The DU145-Gen2 cells transfected to express CD40L, GM-CSF, and TNF are further transfected with a lentiviral vector comprising Flt-3L immune modulator sequences. The Flt-3L cDNA is cloned into a pEF1α-IRES bicistronic mammalian expression vector (Clontech Cat. No. 631970), along with GFP protein sequences to be used as a marker for integration and expression. The sequence of Flt-3L is translated into a membrane bound peptide, while the GFP remains cytoplasmic. The entirety of the pEF1 promoter, Flt-3L sequences, IRES sequences, and GFP sequences is then cloned into the pLenti-puro (Addgene Cat. No. 39481) lentiviral vector (the original CMV promoter from the vector is removed during this process). Packaging plasmid psPAX2 (AddGene Cat. No. 12260) and envelope plasmid pLTR-RD114A (AddGene Cat. No. 17576) are also selected.

Each of the lentiviral transfer plasmid, packaging plasmid, and envelope plasmid is transfected into log phase growth 293T cells using Lipofectamine 2000 (ThermoFisher Cat. No. 11668027). Briefly, cells are seeded at 70% to 90% confluence. On the day of transfection, 12 µl of Lipofectamine reagent is diluted in 150 µl of serum free cell media. 5 µg of DNA for transfection is also diluted in 150 µl of serum free media. The diluted DNA is then added to the diluted Lipofectamine and incubated for 5 minutes at room temperature. The total volume of the mixture is then added dropwise to the media of the seeded 293T cells while swirling. Cells are then incubated for one to three days at 37 degrees.

The 293T cell culture medium comprising virus particle is harvested 3 times every 8-12 hours and centrifuged to pellet detached cells and debris. The culture medium containing virus particles is used directly to infect the DU145-Gen2 cell line.

The DU145-Gen2 cell line is cultured to a confluency of about 70%. Hexadimethrine bromide (Sigma-Aldrich Cat No. H9268) is then combined with media containing virus particles to make a final concentration of 8 µg/mL Hexadimethrine bromide. Culture media of the DU145-Gen2 cells is aspirated and replaced with media containing virus particles and 8 µg/mL Hexadimethrine bromide. DU145-Gen2 cells are cultured for 18-20 hours followed by media change.

The DU145-Gen2 cells are then selected for cells stably expressing the Flt-3L sequences using the GFP marker. The selection process is performed by fluorescence activated cell sorting (FACS) using the GFP marker to identify cells that have integrated the immune modulator. The highest expressing cells are sorted, isolated, and cultured for further processing. After sorting based on the presence of the GFP marker, the expression of Flt-3L is confirmed by Western blot. Cultured cell lysates are resolved by SDS-PAGE and probed by Western blot with rabbit polyclonal anti-Flt-3L antibody (AbCam Cat. No. ab9688) and goat anti-rabbit HRP conjugated secondary antibody (AbCam Cat. No. ab205718). Cell cultures that express high levels of recombinant Flt-3L are designated DU145-Gen3 and are selected for further processing.

IgG Heavy Chain

The DU145-Gen3 cells transfected to express CD40L, GM-CSF, TNF-alpha, and Flt-3L are further transfected with a lentiviral vector comprising IgG 1 (SEQ ID NO: 1), a membrane bound IgG1 heavy chain fragment. The IgG1 heavy chain cDNA is cloned into pEF1α-IRES bicistronic mammalian expression vector (Clontech Cat. No. 631970), along with RFP protein sequences to be used as a marker for integration and expression. The sequence of IgG1 heavy chain is translated into a membrane bound peptide, while the RFP remains cytoplasmic. The entirety of the pEF1 promoter, IgG1 heavy chain sequence, IRES sequence, and RFP sequence is then cloned into the pLenti-puro (Addgene Cat. No. 39481) lentiviral vector (the original CMV promoter from the vector is removed during this process). Packaging plasmid psPAX2 (AddGene Cat. No. 12260) and envelope plasmid pLTR-RD114A (AddGene Cat. No. 17576) are also selected.

Each of the lentiviral transfer plasmid, packaging plasmid, and envelope plasmid is transfected into log phase growth 293T cells using Lipofectamine 2000 (ThermoFisher Cat. No. 11668027). Briefly, cells are seeded at 70% to 90% confluence. On the day of transfection, 12 µl of Lipofectamine reagent is diluted in 150 µl of serum free cell media. 5 µg of DNA for transfection is also diluted in 150 µl of serum free media. The diluted DNA is then added to the diluted Lipofectamine and incubated for 5 minutes at room temperature. The total volume of the mixture is then added dropwise to the media of the seeded 293T cells while swirling. Cells are then incubated for one to three days at 37 degrees.

The 293T cell culture medium comprising virus particle is harvested 3 times every 8-12 hours and centrifuged to pellet detached cells and debris. The culture medium containing virus particles is used directly to infect the DU145-Gen3 cell line.

The DU145-Gen3 cell line is cultured to a confluency of about 70%. Hexadimethrine bromide (Sigma-Aldrich Cat No. H9268) is then combined with media containing virus particles to make a final concentration of 8 µg/mL Hexadimethrine bromide. Culture media of the DU145-Gen2 cells is aspirated and replaced with media containing virus particles and 8 µg/mL Hexadimethrine bromide. DU145-Gen3 cells are cultured for 18-20 hours followed by media change.

The DU145-Gen3 cells are then selected for cells stably expressing the IgG1 heavy chain sequences using the RFP marker. The selection process is performed by fluorescence activated cell sorting (FACS) using the RFP marker to identify cells that have integrated the immune modulator. The highest expressing cells are sorted, isolated, and cultured for further processing. After sorting based on the presence of the RFP marker, the expression of IgG1 heavy chain is confirmed by Western blot. Cell cultures that express high levels of recombinant IgG1 heavy chain are designated DU145-Gen4 and are selected for further processing.

The DU145-Gen4 tumor cell line transfected to express CD40L, GM-CSF, TNF, Flt-3L, and IgG1 heavy chain is characterized by RT-PCR, immunofluorescence, and Western blotting to confirm all recombinant immunomodulators are expressed by the cells and are in the right location (e.g. on the membrane of the cell).

Human Mixed Lymphocyte Tumor Reaction (MLTR) Testing

The DU145-Gen4 cells are tested for their immunomodulatory potential by primary and secondary MLTR assay against each of the other generations (i.e. DU145-Gen2 and DU145-Gen3) of modified cells and unmodified DU145 cells.

Peripheral blood mononuclear cells (PBMCs) are obtained from the peripheral blood of healthy individuals and from prostate cancer patients, and the blood cells separated using a Ficoll-Paque gradient. Anticoagulant-treated blood is diluted in the range of 1:2 to 1:4 with PBS/EDTA to reduce aggregation of erythrocytes. The diluted blood is then layered above a Ficoll-Paque solution in a centrifuge tube, without mixing. The layered blood/Ficoll-Paque is centrifuged for 40 minutes at 400×g between 18° and 20° C., without the use of the centrifuge brake, resulting in the formation of blood fractions. The fraction comprising mononuclear cells is selected for further processing.

Each of the cells from the transfected tumor cell line variants and from parental tumor cell line DU-145 (control) is co-cultured with PBMCs for seven days under standard tissue culture conditions, followed by evaluation for immune cell proliferation, immune cell differentiation, measured by flow cytometry and CyTOF, cytokine release profile, and cytoxicity, measured by LDH release assay.

Example 3

Vectors as employed herein are described in detail as follows:

Vector 1. Immunomodulator: scFv-Anti-Biotin-G3hinge-mIgG1 (to Generate Surface IgG)

Figure 2:
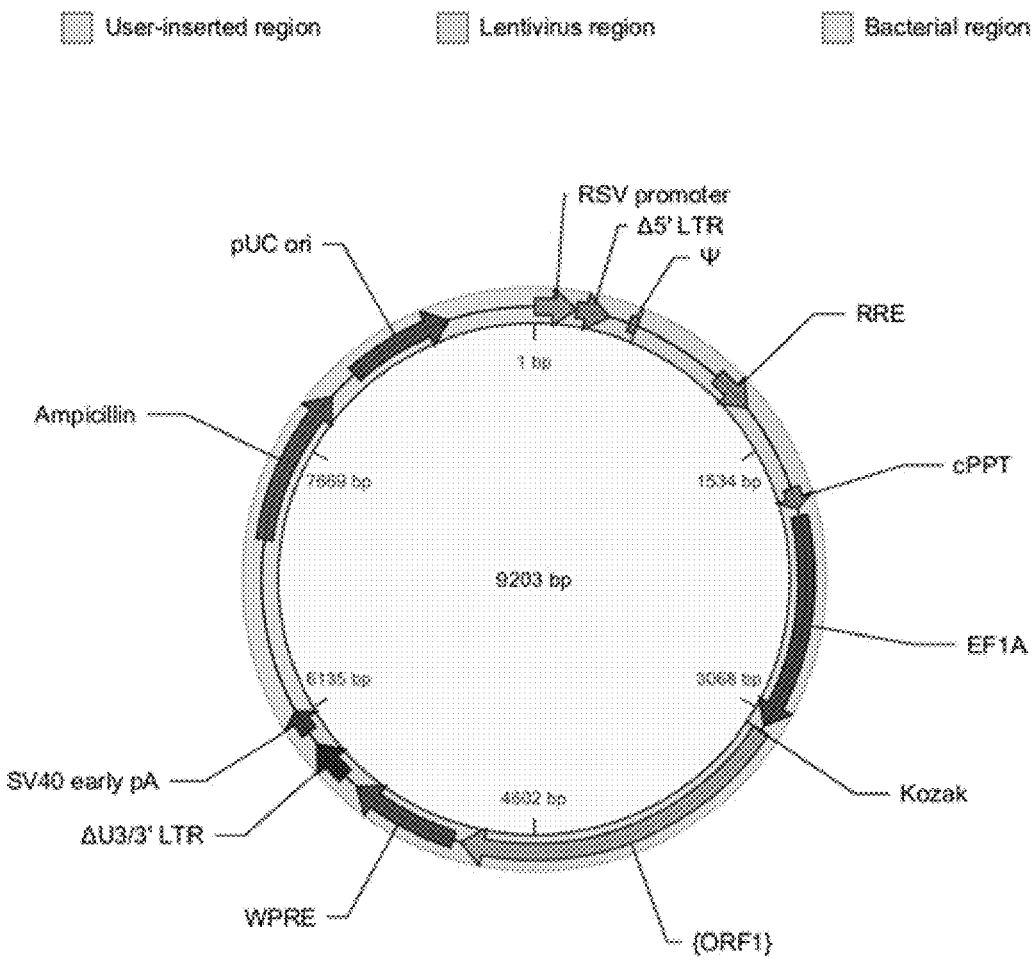
FIG. 2 shows a schematic of the organization of the scFv-anti-biotin-G3hinge-mIgG1 vector 1.

A schematic of the organization of vector 1, used for the immunomodulator scFv-anti-biotin-G3hinge-mIgG1 is shown in FIG. 2. Table 7, below, shows the vector component name, the corresponding nucleotide position in SEQ ID NO. 47, the full name of the component and a description.

TABLE 7

| Component Name | Nucleotide Position | Full Name | Description |
| --- | --- | --- | --- |
| RSV promoter | 1-229 | Rous sarcoma virus (RSV) enhancer/promoter | Allows Tat-independent production of viral mRNA. |
| Δ5' LTR | 230-410 | HIV-1 truncated 5' LTRT | Permits viral packaging and reverse transcription of the viral mRNA. |
| Ψ | 521-565 | HIV-1 psi packaging signal | Allows viral packaging. |
| RRET | 1075-1308 | HIV-1 Rev response element | Permits Rev-dependent nuclear export of unspliced viral mRNA. |
| cPPT | 1803-1920 | Central polypurine tract | Facilitates the nuclear import of HIV-1 cDNA through a central DNA flap. |
| EF1A | 1959-3137 | EF1A | Component entered by user |
| Kozak | 3162-3167 | Kozak | Component entered by user |
| {ORF1} | 3168-5005 | {ORF1} | Component entered by user |
| WPRE | 5044-5641 | Woodchuck hepatitis virus posttranscriptional regulatory element | Facilitates effective transcription termination at the 3'TLTR.T |
| ΔU3/3' LTR | 5723-5957 | HIV-1 truncated 3' LTR | Allows viral packaging but self-inactivates the 5'LTR for biosafety purposes. The element also contains apolyadenylation signal for transcription termination and polyadenylation of mRNA in transduced cells. |
| SV40 early pA | 6030-6164 | SV40 early polyadenation signal | Allows transcription termination and polyadenylation of mRNA. |
| Ampicillin | 7118-7978 | Ampicillin resistance gene | Allows selection of the plasmid in *E. coli*. |
| pUC ori | 8149-8737 | pUC origin of replication | Permits high-copy replication and maintenance in *E. coli*. |

When vector 1 is employed, anti-IgG is used for flow detection. A biotin+fluorescent labelled oligodeoxynucleotides (ODN) is used as a secondary detection method.

The following is a description of the immunomodulator scFv-anti-biotin-G3hinge-IgG1-Tm.

Type:
Immunoglobulin
Annotation:
H7 heavy chain leader
Anti-biotin Variable Heavy chain (VH) allows for loading biotin labeled CpG
Inter-domain disulfide linkage VH44 (G→C) and VL100 (G→C)
IgG3 hinge to enhance FcγR interaction
Linkage is standard
IgG1 (CH2-CH3-Tm-Cyt) used for interaction with FcγR/FcRn and membrane anchoring
T233A mutation to enhance FcRn and FcγR interaction The sequences are shown as follows:

```
H7 heavy chain leader
                                       (SEQ ID NO. 54)
MEFGLSWVFLVALFRGVQC anti-biotin murine vH with
inserted Cys for inter-domain linkage
                                       (SEQ ID NO. 55)
QVKLQESGPG LVAPSQSLSI TCTVSGFSLT AYGVDWVRQP

PGKCLEWLGV IWGGGRTNYN SGLMSRLSIR KDNSKSQVFL

TMNSLQTDDT AKYYCVKHTN WDGGFAYWGQ GTTVTVSS
```

```
                     -continued
linker
                                       (SEQ ID NO. 56)
GGGGSGGGGS GGGGS Light Chain Variable (human lambda variable)
                                       (SEQ ID NO. 57)
GSPGQSVSIS CSGSSSNIGN NYVYWYQHLP GTAPKLLIYS

DTKRPSGVPD RISGSKSGTS ASLAISGLQS EDEADYYCAS

WDDSLDGPVF GCGTKLTVL

IgG3 hinge for greater accessibility to FcγR
                                       (SEQ ID NO. 58)
LKTPLGDTTHTCPR CPEPKSCDTP PPCPRCPEPK SCDTPPPCPR

CPEPKSCDTP PPCPRCP
```

```
IgG1 CH2, CH3 Tm and cytoplasmic tail (T256A)
                                  (SEQ ID NO. 59)
LLGGPSVFLF PPKPKDTLMI SRAPEVTCVV VDVSHEDPEV

KFNWYVDGVE VHNAKTKPRE EQYNSTYRVV SVLTVLHQDW

LNGKEYKCKV SNKALPAPIE KTISKAKGQP REPQVYTLPP

SRDELTKNQV SLTCLVKGFY PSDIAVEWES NGQPENNYKT

TPPVLDSDGS FFLYSKLTVD KSRWQQGNVF SCSVMHEALH
```

```
                             -continued
NHYTQKSLSL SPELQLEESC AEAQDGELDG LWTTITIFIT

LFLLSVCYSA TVTFFKVKWI FSSVVDLKQT IIPDYRNMIG

QGA* scFv-anti-biotin-G3hinge-IgG1-Tm (598 ORF1)
                                  (SEQ ID NO. 60)
MEFGLSWVFLVALFRGVQCQVKLQESGPGLVAPSQSLSITCTVSGFSLTA

YGVDWVRQPPGKCLEWLGVIWGGGRTNYNSGLMSRLSIRKDNSKSQVFLT

MNSLQTDDTAKYYCVKHTNWDGGFAYWGQGTTVTVSSGGGGSGGGGSGGG

GSGSPGQSVSISCSGSSSNIGNNYVYWYQHLPGTAPKLLIYSDTKRPSGV

PDRISGSKSGTSASLAISGLQSEDEADYYCASWDDSLDGPVFGCGTKLTV

LLKTPLGDTTHTCPRCPEPKSCDTPPPCPRCPEPKSCDTPPPCPRCPEPK

SCDTPPPCPRCPAPELLGGPSVFLFPPKPKDTLMISRAPEVTCVVVDVSH

EDPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQ
```

```
QGNVFSCSVMHEALHNHYTQKSLSLSPELQLEESCAEAQDGELDGLWTTI

TIFITLFLLSVCYSATVTFFKVKWIFSSVVDLKQTIIPDYRNMIGQGA*
```

Vector 2. Immunomodulator: Full Anti-Biotin-G3hinge-mIgG1 (Using Heavy Chain/Ires/Light Chain)

Figure 3:
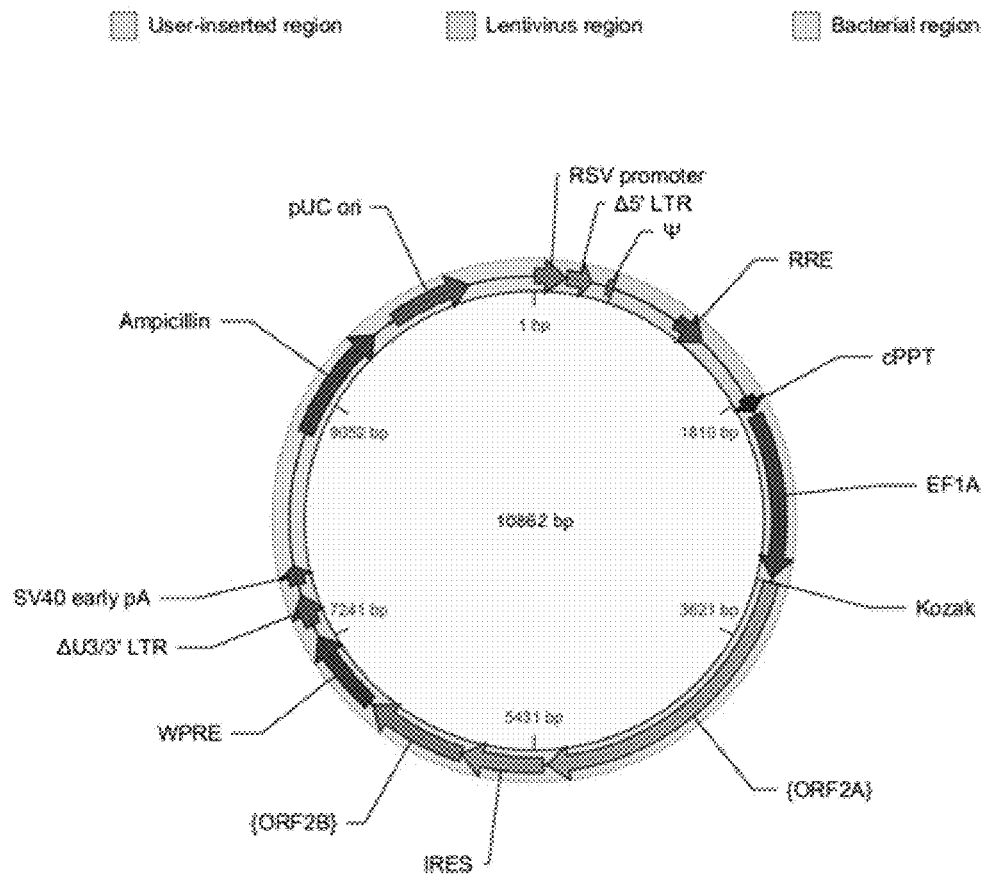
FIG. 3 shows a schematic of the organization of the full anti-biotin-G3hinge-mIgG1 vector 2.

A schematic of the organization of vector 2, used for the immunomodulator full anti-biotin-G3hinge-mIgG1 is shown in FIG. 3. Vector 2 is bicistronic. Table 8, below, shows the vector component name, the corresponding nucleotide position in SEQ ID NO. 48, the full name of the component and a description.

TABLE 8

| Component Name | Nucleotide Position | Full Name | Description |
|---|---|---|---|
| RSV promoter | 1-229 | Rous sarcoma virus (RSV) enhancer/promoter | Allows Tat-independent production of viral mRNA. |
| Δ5' LTR | 230-410 | HIV-1 truncated 5' LTRT | Permits viral packaging and reverse transcription of the viral mRNA. |
| Ψ | 521-56g | HIV-1 psi packaging signal | Allows viral packaging. |
| RRET | 1075-1308 | HIV-1 Rev response element | Permits Rev-dependent nuclear export of unspliced viral mRNA. |
| cPPT | 1803-1920 | Central polypurine tract | Facilitates the nuclear import of HIV-1 cDNA through a central DNA flap. |
| EF1A | 1950-3128 | EF1A | Component entered by user |
| Kozak | 3153-3158 | Kozak | Component entered by user |
| {ORF1} | 3159-5342 | {ORF2A} | Component entered by user |
| WPRE | 6703-7300 | Woodchuck hepatitis virus posttranscriptional regulatory element | Facilitates effective transcription termination at the 3'TLTR.T |
| ΔU3/3' LTR | 7382-7616 | HIV-1 truncated 3' LTR | Allows viral packaging but self-inactivates the 5'LTR for biosafety purposes. The element also contains apolyadenylation signal for transcription termination and polyadenylation of mRNA in transduced cells. |
| SV40 early pA | 7689-7823 | SV40 early polyadenation signal | Allows transcription termination and polyadenylation of mRNA. |
| Ampicillin | 8777-9637 | Ampicillin resistance gene | Allows selection of the plasmid in E. coli. |
| pUC ori | 9808-10396 | pUC origin of replication | Permits high-copy replication and maintenance in E. coli. |

When vector 2 is employed, anti-IgG is used for flow detection. Biotin+fluorescent labelled ODN is used as a secondary detection method.

The following is a description of the immunomodulator full anti-biotin-G3hinge-mIgG1 (using heavy chain/ires/light chain).

Type:
Membrane anchored Immunoglobulin
Annotation:
H7 heavy chain leader
IgG3 hinge to enhance FcγR interaction
T233A mutation to enhance FcRn and FcγR interaction
Anti-biotin Variable H allows for loading biotin labeled CpG
CH1 (generic)
LC Variable (human lambda variable)
LC Constant Region 1 from Lambda (http://www.uniprot.org/uniprot/P0CG04)
Interdomain disulfide linkage VH44 (G→C) and VL100 (G→C) (ref)
Linkage is standard
IgG1 (CH2-CH3-Tm-Cyt) for interaction with FcγR/FcRn and membrane anchoring L1 light chain leader (modified for IRES) MATDMRVPAQLLGLLLLWLSGARC (SEQ ID NO. 61)

The sequences are shown as follows:

H7 heavy chain leader
(SEQ ID NO. 54)
MEFGLSWVFLVALFRGVQC anti-biotin vH (murine)
(SEQ ID NO. 62)
QVKLQESGPG LVAPSQSLSI TCTVSGFSLT AYGVDWVRQP

PGKGLEWLGV IWGGGRTNYN SGLMSRLSIR KDNSKSQVFL

TMNSLQTDDT AKYYCVKHTN WDGGFAYWGQ GTTVTVSS

CH1 (generic)
(SEQ ID NO. 63)
PSVFP LAPSSKSTSG GTAALGCLVK DYFPEPVTVS

WNSGALTSGV HTFPAVLQSS GLYSLSSVVT VPSSSLGTQT

YICNVNHKPS NTKVDKKVE

IgG3 hinge for greater accessibility to FcyR
(SEQ ID NO. 64)
LKTP LGDTTHTCPR CPEPKSCDTP PPCPRCPEPK SCDTPPPCPR

CPEPKSCDTP PPCPRCP

IgG1 CH2, CH3 Tm and cytoplasmic tail (T256A)
(SEQ ID NO. 65)
APELLGGPSVFLF PPKPKDTLMI SRAPEVTCVV VDVSHEDPEV

KFNWYVDGVE VHNAKTKPRE EQYNSTYRVV SVLTVLHQDW

LNGKEYKCKV SNKALPAPIE KTISKAKGQP REPQVYTLPP

SRDELTKNQV SLTCLVKGFY PSDIAVEWES NGQPENNYKT

TPPVLDSDGS FFLYSKLTVD KSRWQQGNVF SCSVMHEALH

NHYTQKSLSL SPELQLEESC AEAQDGELDG LWTTITIFIT

LFLLSVCYSA TVTFFKVKWI FSSVVDLKQT IIPDYRNMIG

QGA*

Summary (578 ORF2a)
(SEQ ID NO. 66)
MEFGLSWVFLVALFRGVQCQVKLQESGPGLVAPSQSLSITCTVSGFSLTA

YGVDWVRQPPGKGLEWLGVIWGGGRTNYNSGLMSRLSIRKDNSKSQVFLT

MNSLQTDDTAKYYCVKHTNWDGGFAYWGQGTTVTVSSPSVFPLAPSSKST

SGGTAALGCLVKDYFPEPVTVSWNSGALTSGVHTFPAVLQSSGLYSLSSV

-continued

VTVPSSSLGTQTYICNVNHKPSNTKVDKKVELKTPLGDTTHTCPRCPEPK

SCDTPPPCPRCPEPKSCDTPPPCPRCPEPKSCDTPPPCPRCPAPELLGGP

SVFLFPPKPKDTLMISRAPEVTCVVVDVSHEDPEVKFNWYVDGVEVHNAK

TKPREEQYNSTYRVVSVLTVLHQDWLNGKEYKCKVSNKALPAPIEKTISK

AKGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYTQ

KSLSLSPELQLEESCAEAQDGELDGLWTTITIFITLFLLSVCYSATVTFF

KVKWIFSSVVDLKQTIIPDYRNMIGQGA*

IRES
(SEQ ID NO. 67)

L1 Signal (modified to be IRES compatible)
(SEQ ID NO. 61)
MATDMRVPAQLLGLLLLWLSGARC LC Variable (human lambda variable)
(SEQ ID NO. 69)
GSPGQSVSIS CSGSSSNIGN NYVYWYQHLP GTAPKLLIYS

DTKRPSGVPD RISGSKSGTS ASLAISGLQS EDEADYYCAS

WDDSLDGPVF GGGTKLTVL

LC Constant Region 1 from Lambda
(http://www.uniprot.org/uniprot/P0CG04)
(irrelevant)
(SEQ ID NO. 70)
GQPKANPTVT LFPPSSEELQ ANKATLVCLI SDFYPGAVTV

AWKADGSPVK AGVETTKPSK QSNNKYAASS YLSLTPEQWK

SHRSYSCQVT HEGSTVEKTV APTECS*

Summary (229 ORF2b)
(SEQ ID NO. 71)
MATDMRVPAQLLGLLLLWLSGARCGSPGQSVSISCSGSSSNIGNNYVYWY

QHLPGTAPKLLIYSDTKRPSGVPDRISGSKSGTSASLAISGLQSEDEADY

YCASWDDSLDGPVFGGGTKLTVLGQPKANPTVTLFPPSSEELQANKATLV

CLISDFYPGAVTVAWKADGSPVKAGVETTKPSKQSNNKYAASSYLSLTPE

QWKSHRSYSCQVTHEGSTVEKTVAPTECS*

Vector 3. Immunomodulator: sGM-CSF/Ires/mFLT3L

Figure 4:
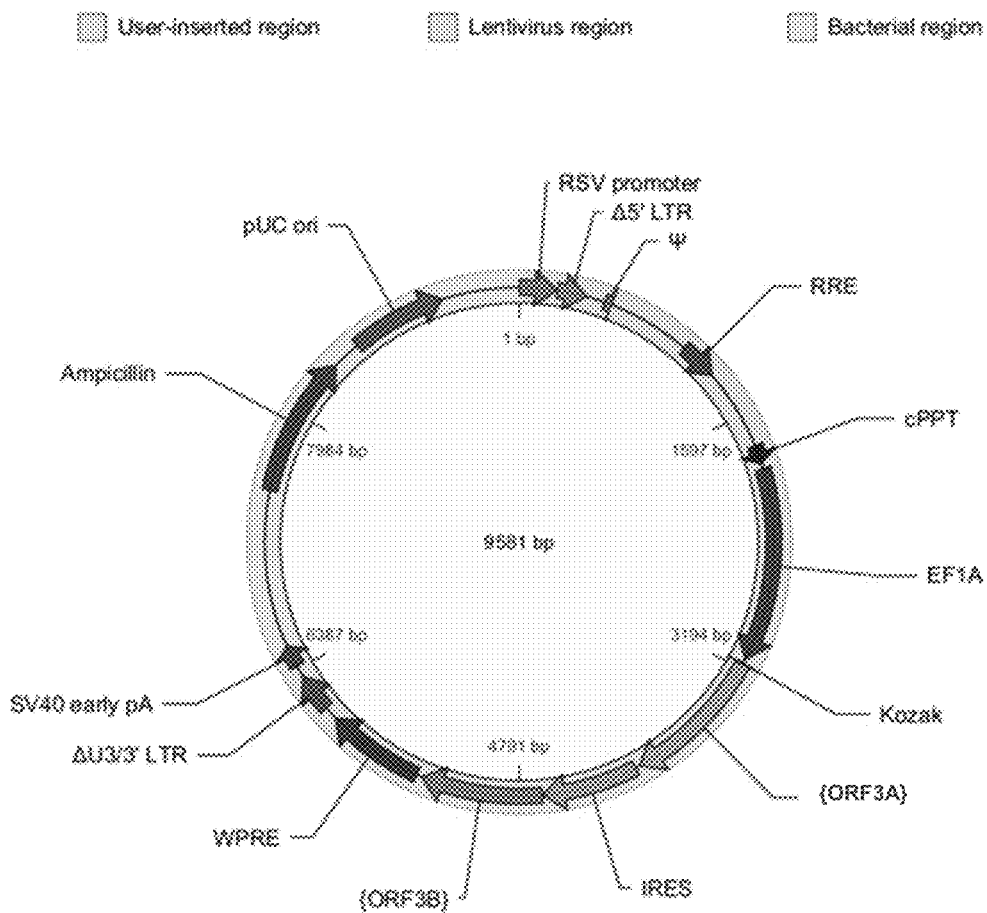
FIG. 4 shows a schematic of the organization of the sGM-CSF/ires/mFLT3L vector 3.

A schematic of the organization of vector 3, used for the immunomodulator sGM-CSF/ires/mFLT3L is shown in FIG. 4. Vector 3 is bicistronic. Table 9, below, shows the vector component name, the corresponding nucleotide position in SEQ ID NO. 49, the full name of the component and a description.

TABLE 9

| Component Name | Nucleotide Position | Full Name | Description |
|---|---|---|---|
| RSV promoter | 1-229 | Rous sarcoma virus (RSV) enhancer/promoter | Allows Tat-independent production of viral mRNA. |
| Δ5' LTR | 230-410 | HIV-1 truncated 5' LTRT | Permits viral packaging and reverse transcription of the viral mRNA. |
| Ψ | 521-565 | HIV-1 psi packaging signal | Allows viral packaging. |
| RRE | 1075-1308 | HIV-1 Rev response element | Permits Rev-dependent nuclear export of unspliced viral mRNA. |
| cPPT | 1803-1920 | Central polypurine tract | Facilitates the nuclear import of HIV-1 cDNA through a central DNA flap. |

TABLE 9-continued

| Component Name | Nucleotide Position | Full Name | Description |
| --- | --- | --- | --- |
| EF1A | 1950-3128 | EF1A | Component entered by user |
| Kozak | 3153-3158 | Kozak | Component entered by user |
| {ORF3A_wSPACER} | 3159-4040 | {ORF3A_wSPACER} | Component entered by user |
| IRES | 4065-4652 | IRES | Component entered by user |
| {ORF3B} | 4653-5392 | {ORF3B} | Component entered by user |
| WPRE | 5422-6019 | Woodchuck hepatitis virus posttranscriptional regulatory element | Facilitates effective transcription termination at the 3' LTR. |
| AU3/3' LTR | 6101-6335 | HIV-1 truncated 3' LTR | Allows viral packaging but self-inactivates the 5'LTR for biosafety purposes. The element also contains apolyadenylation signal for transcription termination and polyadenylation of mRNA in transduced cells. |
| SV40 early pA | 6408-6542 | SV40 early polyadenation signal | Allows transcription termination and polyadenylation of mRNA. |
| Ampicillin | 7496-8356 | Ampicillin resistance gene | Allows selection of the plasmid in *E. coli*. |
| pUC ori | 8527-9115 | pUC origin of replication | Permits high-copy replication and maintenance in *E. coli*. |

When vector 3 is employed, anti-FLT3L is used for flow detection. The highest surface FLT3L expressor will have the highest secreted GM-CSF expression.

The following is a description of the immunomodulator sGM-CSF/ires/mFLT3L.

Type:
cytokine, growth and differentiation factor
Annotation:
wild-type sequence
The sequences are shown as follows:

GM-CSF signal sequence
(SEQ ID NO. 72)
MWLQSLLLLG TVACSIS wild type GM-CSF sequence
(SEQ ID NO. 73)
APA RSPSPSTQPW EHVNAIQEAR RLLNLSRDTA AEMNETVEVI

SEMFDLQEPT CLQTRLELYK QGLRGSLTKL KGPLTMMASH

YKQHCPPTPE TSCATQIITF ESFKENLKDF LLVIPFDCWE PVQE*

IRES
(SEQ ID NO. 74)

FLT3L signal (modified to be IRES friendly)
(SEQ ID NO. 75)
MATVLAPAWSP TTYLLLLLLL SSGLS

FLT3L
(SEQ ID NO. 76)
GTQDC SFQHSPISSD FAVKIRELSD YLLQDYPVTV ASNLQDEELC

GGLWRLVLAQ RWMERLKTVA GSKMQGLLER VNTEIHFVTK

CAFQPPPSCL RFVQTNISRL LQETSEQLVA LKPWITRQNF

SRCLELQCQP DSSTLPPPWS PRPLEATAPT APQPPLLLLL

LLPVGLLLLA AAWCLHWQRT RRRTPRPGEQ VPPVPSPQDL

LLVEH*

Summary (144 ORF3a)
(SEQ ID NO. 77)
MWLQSLLLLGTVACSISAPARSPSPSTQPWEHVNAIQEARRLLNLSRDTA

AEMNETVEVISEMFDLQEPTCLQTRLELYKQGLRGSLTKLKGPLTMMASH

YKQHCPPTPETSCATQIITFESFKENLKDFLLVIPFDCWEPVQE*

Summary (236 ORF3b)
(SEQ ID NO. 78)
MATVLAPAWSPTTYLLLLLLLSSGLSGTQDCSFQHSPISSDFAVKIRELS

DYLLQDYPVTVASNLQDEELCGGLWRLVLAQRWMERLKTVAGSKMQGLLE

RVNTEIHFVTKCAFQPPPSCLRFVQTNISRLLQETSEQLVALKPWITRQN

FSRCLELQCQPDSSTLPPPWSPRPLEATAPTAPQPPLLLLLLLPVGLLLL

AAAWCLHWQRTRRRTPRPGEQVPPVPSPQDLLLVEH*

Vector 4. Immunomodulator: sFLT3L/Ires/(FLT3 Signal-GM-CSF-Tm)

Figure 5:
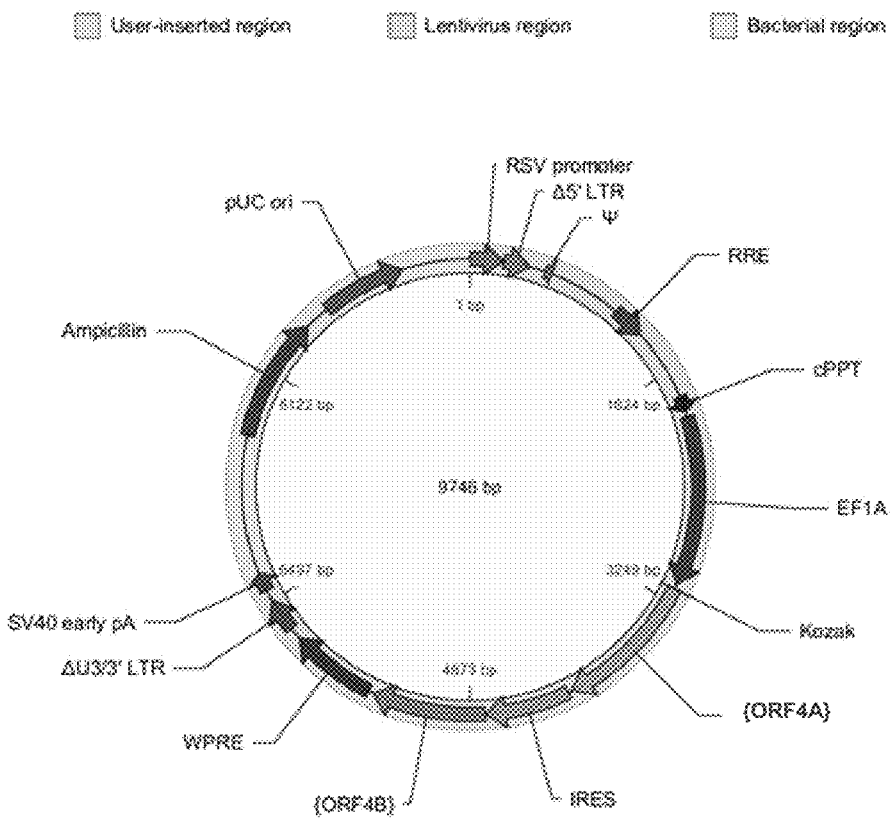
FIG. 5 shows a schematic of the organization of the sFLT3L/ires/(FLT3 signal-GM-C SF-Tm) vector 4.

A schematic of the organization of vector 4, used for the immunomodulator sFLT3L/ires/(FLT3 signal-GM-CSF-Tm) is shown in FIG. 5. Vector 4 is bicistronic. Table 10, below, shows the vector component name, the corresponding nucleotide position in SEQ ID NO. 50, the full name of the component and a description.

TABLE 10

| Component Name | Nucleotide Position | Full Name | Description |
|---|---|---|---|
| RSV promoter | 1-229 | Rous sarcoma virus (RSV) enhancer/promoter | Allows Tat-independent production of viral mRNA. |
| Δ5' LTR | 230-410 | HIV-1 truncated 5' LTRT | Permits viral packaging and reverse transcription of the viral mRNA. |
| Ψ | 521-565 | HIV-1 psi packaging signal | Allows viral packaging. |
| RRE | 1075-1308 | HIV-1 Rev response element | Permits Rev-dependent nuclear export of unspliced viral mRNA. |
| cPPT | 1803-1920 | Central polypurine tract | Facilitates the nuclear import of HIV-1 cDNA through a central DNA flap. |
| EF1A | 1950-3128 | EF1A | Component entered by user |
| Kozak | 3153-3158 | Kozak | Component entered by user |
| {ORF4A_wSPACER} | 3159-4157 | {ORF4A_wSPACER} | Component entered by user |
| IRES | 4182-4769 | IRES | Component entered by user |
| {ORF4B} | 4770-5557 | {ORF4B} | Component entered by user |
| WPRE | 5587-6184 | Woodchuck hepatitis virus posttranscriptional regulatory element | Facilitates effective transcription termination at the 3' LTR. |
| AU3/3' LTR | 6266-6500 | HIV-1 truncated 3' LTR | Allows viral packaging but self-inactivates the 5'LTR for biosafety purposes. The element also contains apolyadenylation signal for transcription termination and polyadenylation of mRNA in transduced cells. |
| SV40 early pA | 6573-6707 | SV40 early polyadenation signal | Allows transcription termination and polyadenylation of mRNA. |
| Ampicillin | 7661-8521 | Ampicillin resistance gene | Allows selection of the plasmid in E. coli. |
| pUC ori | 8692-9280 | pUC origin of replication | Permits high-copy replication and maintenance in E. coli. |

When vector 4 is employed, anti-GM-CSF is used for flow detection. The highest surface GMCSF expressor will have highest secreted FLT3L expression.

The following is a description of the immunomodulator sFLT3L/ires/(FLT3 signal-GM-CSF-Tm)

Type:
cytokine, growth and differentiation factor
Annotation:
wild-type sequence
The sequences are shown as follows:

```
wild type FLT3L sequence with transmembrane deleted
                                        (SEQ ID NO. 79)
MTVLAPAWSP TTYLLLLLLL SSGLSGTQDC SFQHSPISSD

FAVKIRELSD YLLQDYPVTV ASNLQDEELC GGLWRLVLAQ

RWMERLKTVA GSKMQGLLER VNTEIHFVTK CAFQPPPSCL

RFVQTNISRL LQETSEQLVA LKPWITRQNF SRCLELQCQP

DSSTLPPPWS PRPLEATAPT APQ*

IRES
                                        (SEQ ID NO. 80)

FLT3L signal (modified to be IRES friendly)
                                        (SEQ ID NO. 81)
MATVLAPAWSP TTYLLLLLLL SSGLS wild type GM-CSF sequence (minus native signal)
                                        (SEQ ID NO. 82)
APA RSPSPSTQPW EHVNAIQEAR RLLNLSRDTA AEMNETVEVI

SEMFDLQEPT CLQTRLELYK QGLRGSLTKL

KGPLTMMASHYKQHCPPTPE TSCATQIITF ESFKENLKDF

LLVIPFDCWE PVQE

CD8alpha transmembrane and cytoplasmic domain
                                        (SEQ ID NO. 83)
PTTTP APRPPTPAPTIASQPLSLRP EACRPAAGGA VHTRGLDFAC

DIYIWAPLAG TCGVLLLSLVITLYCNHRNR RRVCKCPRPV

VKSGDKPSLS ARYV*

Summary (183 ORF4a)
                                        (SEQ ID NO. 84)
MTVLAPAWSPTTYLLLLLLLSSGLSGTQDCSFQHSPISSDFAVKIRELSD

YLLQDYPVTVASNLQDEELCGGLWRLVLAQRWMERLKTVAGSKMQGLLER

VNTEIHFVTKCAFQPPPSCLRFVQTNISRLLQETSEQLVALKPWITRQNF

SRCLELQCQPDSSTLPPPWSPRPLEATAPTAPQ*

Summary for CYAGEN (253 ORF4b)
                                        (SEQ ID NO. 85)
MATVLAPAWSPTTYLLLLLLLSSGLSAPARSPSPSTQPWEHVNAIQEARR

LLNLSRDTAAEMNETVEVISEMFDLQEPTCLQTRLELYKQGLRGSLTKLK

GPLTMMASHYKQHCPPTPETSCATQIITFESFKENLKDFLLVIPFDCWEP

VQEPTTTPAPRPPTPAPTIASQPLSLRPEACRPAAGGAVHTRGLDFACDI

YIWAPLAGTCGVLLLSLVITLYCNHRNRRRVCKCPRPVVKSGDKPSLSAR

YV*
```

Vector 5. Immunomodulator: mCD40L

Figure 6:
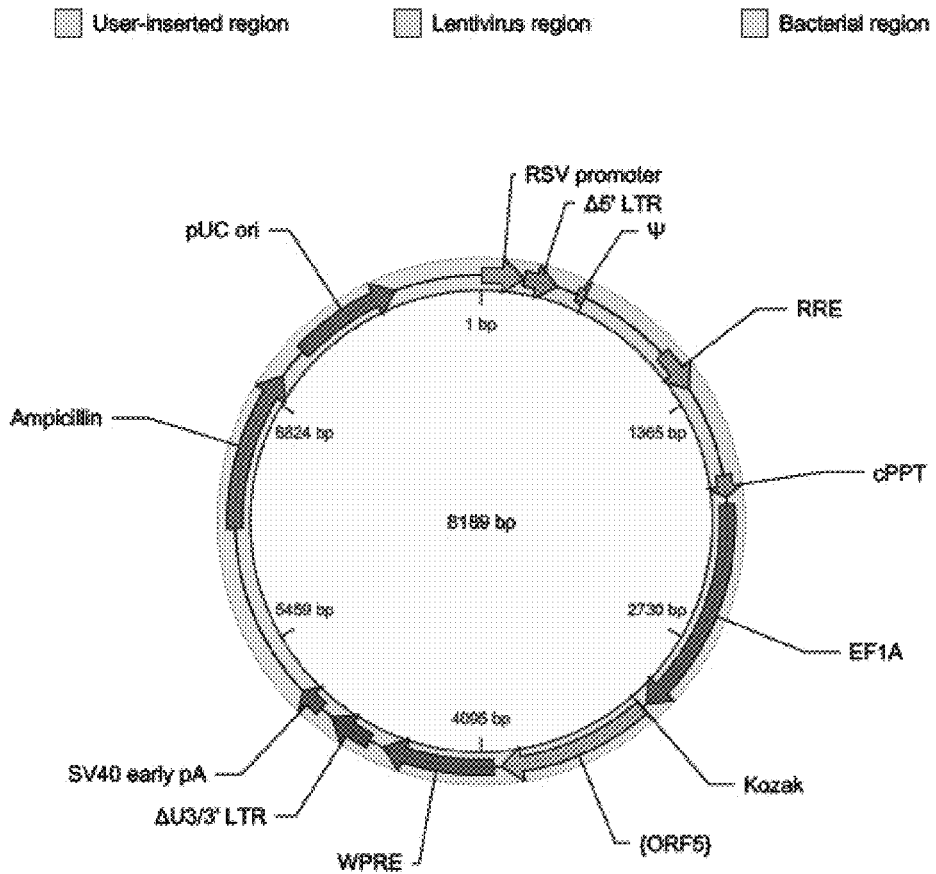
FIG. 6 shows a schematic of the organization of the mCD40L vector 5.

A schematic of the organization of vector 5, used for the immunomodulator mCD40L is shown in FIG. 6. Vector 5 is monocistronic. Table 11, below, shows the vector component name, the corresponding nucleotide position in SEQ ID NO. 51, the full name of the component and a description.

TABLE 11

| Component Name | Nucleotide Position | Full Name | Description |
|---|---|---|---|
| RSV promoter | 1-229 | Rous sarcoma virus (RSV) enhancer/promoter | Allows Tat-independent production of viral mRNA. |
| Δ5' LTR | 230-410 | HIV-1 truncated 5' LTRT | Permits viral packaging and reverse transcription of the viral mRNA. |
| Ψ | 521-565 | HIV-1 psi packaging signal | Allows viral packaging. |
| RRE | 1075-1308 | HIV-1 Rev response element | Permits Rev-dependent nuclear export of unspliced viral mRNA. |
| cPPT | 1803-1920 | Central polypurine tract | Facilitates the nuclear import of HIV-1 cDNA through a central DNA flap. |
| EF1A | 1959-3137 | EF1A | Component entered by user |
| Kozak | 3162-3167 | Kozak | Component entered by user |
| {ORF5} | 3168-3991 | {ORF5} | Component entered by user |
| WPRE | 4030-4627 | Woodchuck hepatitis virus posttranscriptional regulatory element | Facilitates effective transcription termination at the 3' LTR. |
| ΔU3/3' LTR | 4709-4943 | HIV-1 truncated 3' LTR | Allows viral packaging but self-inactivates the 5'LTR for biosafety purposes. The element also contains apolyadenylation signal for transcription termination and polyadenylation of mRNA in transduced cells. |
| SV40 early pA | 5016-5150 | SV40 early polyadenation signal | Allows transcription termination and polyadenylation of mRNA. |
| Ampicillin | 6104-6964 | Ampicillin resistance gene | Allows selection of the plasmid in E. coli. |
| pUC ori | 7135-7723 | pUC origin of replication | Permits high-copy replication and maintenance in E. coli. |

When Vector 5 is employed, anti-CD40L is used for flow detection.

The following is a description of the immunomodulator mCD40L.

Type:
TNF type II transmembrane protein
Annotation:
Mutations (UNDERLINED) introduced to make a non-cleavable version
The sequences are shown as follows:

```
Modified sequence to stop cleavage
                            (SEQ ID NO. 86)
MIETYNQTSP RSAATGLPIS MKIFMYLLTV FLITQMIGSA

LFAVYLHRRL DKIEDERNLH EDFVFMKTIQ RCNTGERSLS

LLNCEEIKSQ FEGFVKDIMLNKEETKKENS FEMPRGEEDS

QIAAHVISEA SSKTTSVLQW AEKGYYTMSN NLVTLENGKQ

LTVKRQGLYY IYAQVTFCSN REASSQAPFI ASLCLKSPGR

FERILLRAAN THSSAKPCGQ QSIHLGGVFE LQPGASVFVN

VTDPSQVSHG TGFTSFGLLK L*

Summary (261 ORF5)
                            (SEQ ID NO. 87)
MIETYNQTSPRSAATGLPISMKIEMYLLTVFLITQMIGSALFAVYLHRRL

DKIEDERNLHEDFVFMKTIQRCNTGERSLSLLNCEEIKSQFEGFVKDIML

NKEETKKENSFEMPRGEEDSQIAAHVISEASSKTTSVLQWAEKGYYTMSN

NLVTLENGKQLTVKRQGLYYIYAQVTFCSNREASSQAPFIASLCLKSPGR

FERILLRAANTHSSAKPCGQQSIHLGGVFELQPGASVEVNVTDPSQVSHG

TGFTSFGLLKL*
```

Vector 6. Immunomodulator: mTNFalpha (TNFa)

Figure 7:
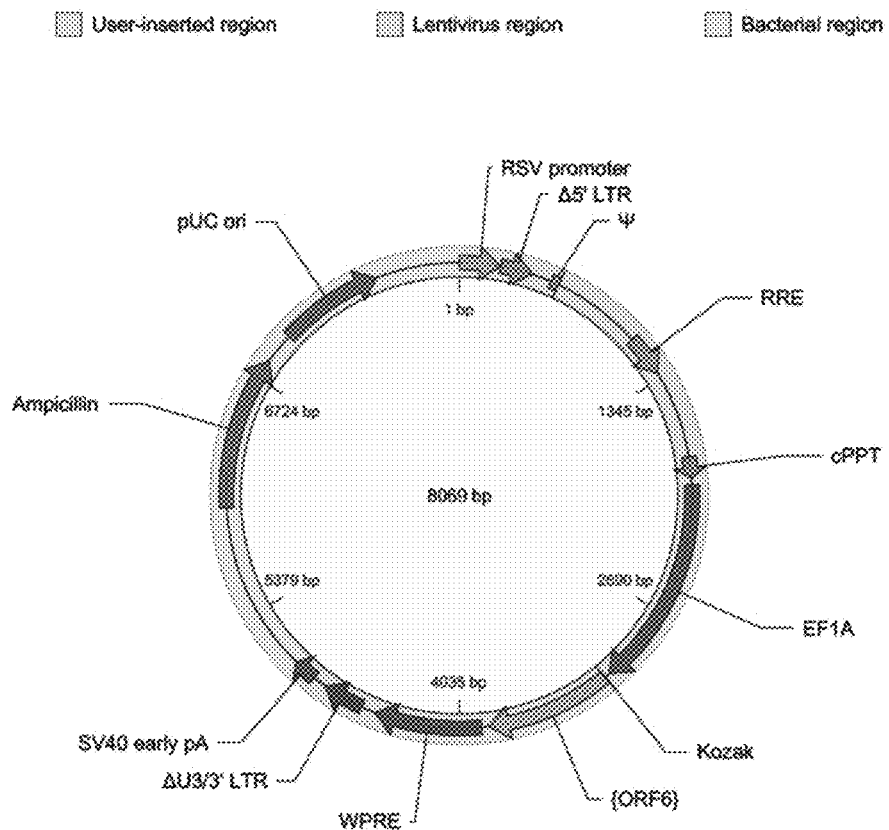
FIG. 7 shows a schematic of the organization of the mTNFa vector 6.

A schematic of the organization of vector 6, used for the immunomodulator mTNFα is shown in FIG. 7. Vector 6 is monocistronic. Table 12, below, shows the vector component name, the corresponding nucleotide position in SEQ ID NO. 52, the full name of the component and a description.

TABLE 12

| Component Name | Nucleotide Position | Full Name | Description |
|---|---|---|---|
| RSV promoter | 1-229 | Rous sarcoma virus (RSV) enhancer/promoter | Allows Tat-independent production of viral mRNA. |
| Δ5' LTR | 230-410 | HIV-1 truncated 5' LTRT | Permits viral packaging and reverse transcription of the viral mRNA. |
| Ψ | 521-565 | HIV-1 psi packaging signal | Allows viral packaging. |
| RRE | 1075-1308 | HIV-1 Rev response element | Permits Rev-dependent nuclear export of unspliced viral mRNA. |

TABLE 12-continued

| Component Name | Nucleotide Position | Full Name | Description |
| --- | --- | --- | --- |
| cPPT | 1803-1920 | Central polypurine tract | Facilitates the nuclear import of HIV-1 cDNA through a central DNA flap. |
| EF1A | 1959-3137 | EF1A | Component entered by user |
| Kozak | 3162-3167 | Kozak | Component entered by user |
| {ORF6} | 3168-3871 | {ORF6} | Component entered by user |
| WPRE | 3910-4507 | Woodchuck hepatitis virus posttranscriptional regulatory element | Facilitates effective transcription termination at the 3' LTR. |
| ΔU3/3' LTR | 4859-4823 | HIV-1 truncated 3' LTR | Allows viral packaging but self-inactivates the 5'LTR for biosafety purposes. The element also contains apolyadenylation signal for transcription termination and polyadenylation of mRNA in transduced cells. |
| SV40 early pA | 4896-5030 | SV40 early polyadenation signal | Allows transcription termination and polyadenylation of mRNA. |
| Ampicillin | 5984-6844 | Ampicillin resistance gene | Allows selection of the plasmid in *E. coli*. |
| pUC ori | 7015-7603 | pUC origin of replication | Permits high-copy replication and maintenance in *E. coli*. |

When vector 6 is employed, anti-TNFα is used for flow detection.

The following is a description of the immunomodulator mTNFα.

Type: TNF type II transmembrane protein

Annotation: Mutations were introduced to make a non-cleavable version.

Vector 7. Immunomodulator: mRANKL/Ires/FLT3 Signal-V5-scFV Anti-Biotin-Tm

Figure 8:
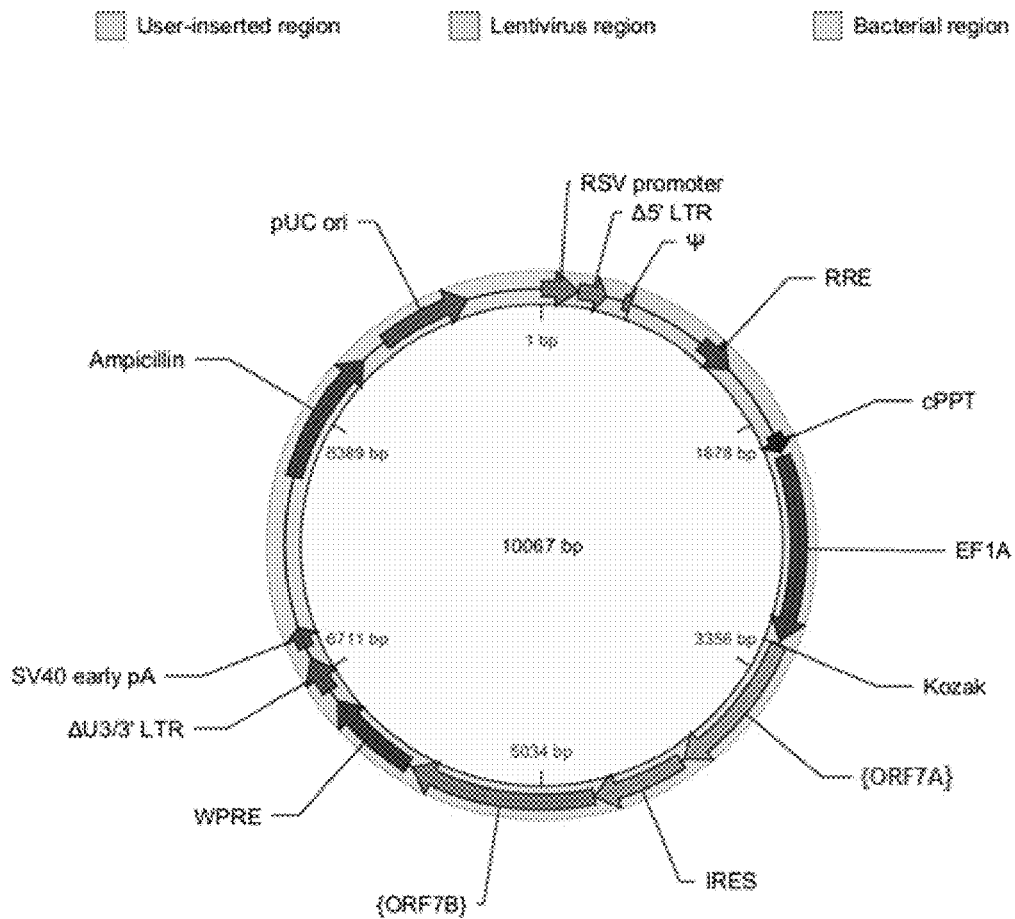
FIG. 8 shows a schematic of the organization of the mRANKL/ires/FLT3 signal-V5-scFV anti-biotin-Tm vector 7.

A schematic of the organization of vector 7, used for the immunomodulator mRANKL/ires/FLT3 signal-V5-scFV anti-biotin-Tm is shown in FIG. 8. Table 13, below, shows the vector component name, the corresponding nucleotide position, the full name of the component and a description.

TABLE 13

| Component Name | Nucleotide Position | Full Name | Description |
| --- | --- | --- | --- |
| RSV promoter | 1-229 | Rous sarcoma virus (RSV) enhancer/promoter | Allows Tat-independent production of viral mRNA. |
| Δ5' LTR | 230-410 | HIV-1 truncated 5' LTR | Permits viral packaging and reverse transcription of the viral mRNA. |
| Ψ | 521-565 | HIV-1 psi packaging signal | Allows viral packaging. |
| RRE | 1075-1308 | HIV-1 Rev response element | Permits Rev-dependent nuclear export of unspliced viral mRNA. |
| cPPT | 1803-1920 | Central polypurine tract | Facilitates the nuclear import of HIV-1 cDNA through a central DNA flap. |
| EF1A | 1950-3128 | EF1A | Component entered by user |
| Kozak | 3153-3158 | Kozak | Component entered by user |
| {ORF7_wSPACER} | 3159-4091 | {ORF7_wSPACER} | Component entered by user |
| IRES | 4116-4703 | IRES | Component entered by user |
| {ORF7B} | 4704-5878 | {ORF7B} | Component entered by user |
| WPRE | 5908-6505 | Woodchuck hepatitis virus posttranscriptional regulatory element | Facilitates effective transcription termination at the 3' LTR. |
| ΔU3/3' LTR | 6587-3821 | HIV-1 truncated 3' LTR | Allows viral packaging but self-inactivates the 5'LTR for biosafety purposes. The element also contains apolyadenylation signal for transcription termination and polyadenylation of mRNA in transduced cells. |
| SV40 early pA | 6894-7028 | SV40 early polyadenation signal | Allows transcription termination and polyadenylation of mRNA. |
| Ampicillin | 7982-8842 | Ampicillin resistance gene | Allows selection of the plasmid in *E. coli*. |
| pUC ori | 9013-9601 | pUC origin of replication | Permits high-copy replication and maintenance in *E. coli*. |

When vector 7 is employed, anti-RANKL is used for flow detection. Anti-V5 mAb is used as a secondary detection method.

The following is a description of the immunomodulator mRANKL/ires/FLT3 signal-V5-scFV anti-biotin-Tm.

Figure 9:
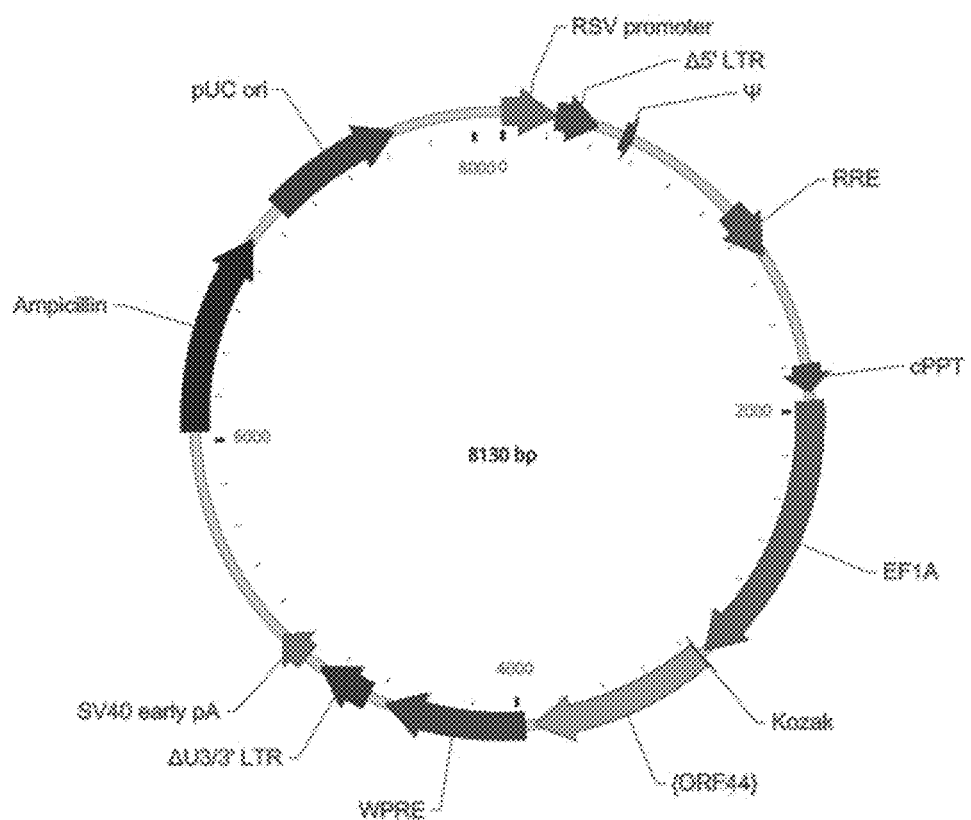
FIG. 9 shows a schematic of vector 44.

Type: TNF type II transmembrane protein
Annotation: wild-type sequence
Vector 44
FIG. 9 shows a schematic of vector 44.
Table 14 below, shows the vector component name, the corresponding nucleotide position, the full name of the component and a description.

TABLE 14

| Component Name | Nucleotide Position | Size (bp) | Description |
| --- | --- | --- | --- |
| RSV promoter | 1-229 | 229 | Rous sarcoma virus enhancer/promoter |
| Δ5' LTR | 230-410 | 181 | Truncated HW-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF44A} | 3168-3932 | 765 | None |
| WPRE | 3971-4568 | 598 | Woodchuck hepatitis virus posttranscriptional regulatory element |
| ΔU3/3' LTR | 4650-4884 | 235 | Truncated HIV-1 3' long terminal repeat |
| SV40 early pA | 4957-5091 | 135 | Simian virus 40 early polyadenylation signal |
| Ampicillin | 6045-6905 | 861 | Ampicillin resistance gene |
| pUC ori | 7076-7664 | 589 | pUC origin of replication |

Figure 10:
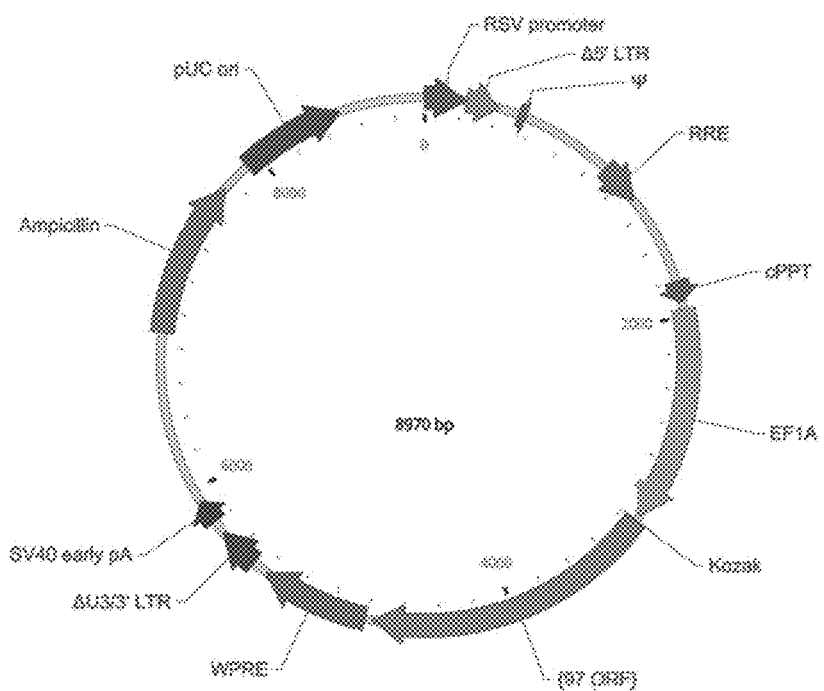
FIG. 10 shows a schematic of vector 97.

Vector 97
FIG. 10 shows a schematic of vector 97.
Table 15 below, shows the vector component name, the corresponding nucleotide position, the full name of the component and a description.

TABLE 15

| Component Name | Nucleotide Position | Size (bp) | Description |
| --- | --- | --- | --- |
| RSV promoter | 1-229 | 229 | Rous sarcoma virus enhancer/promoter |
| Δ5' LTR | 230-410 | 181 | Truncated HW-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF97} | 3168-4772 | 1605 | None |
| WPRE | 4811-5408 | 598 | Woodchuck hepatitis virus posttranscriptional regulatory element |
| ΔU3/3' LTR | 5490-5724 | 235 | Truncated HIV-1 3' long terminal repeat |
| SV40 early pA | 5797-5931 | 135 | Simian virus 40 early polyadenylation signal |
| Ampicillin | 6885-7745 | 861 | Ampicillin resistance gene |
| pUC ori | 7916-8504 | 589 | pUC origin of replication |

Figure 11:
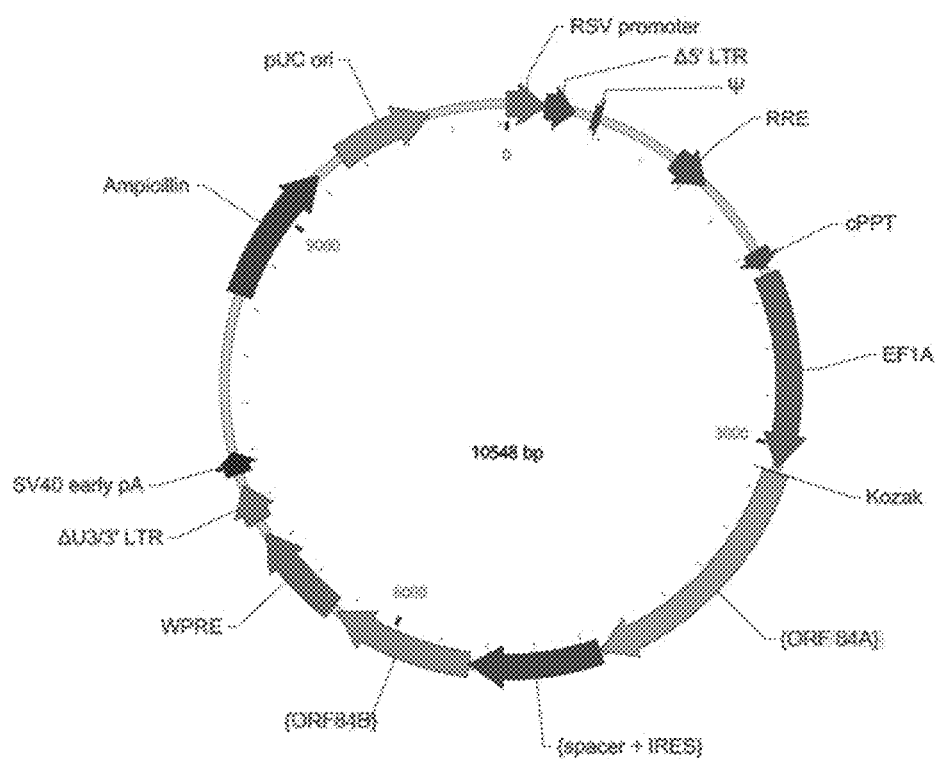
FIG. 11 shows a schematic of vector 84.

Vector 84.
FIG. 11 shows a schematic of vector 84.
Table 16 below, shows the vector component name, the corresponding nucleotide position, the full name of the component and a description.

TABLE 16

| Component Name | Nucleotide Position | Size (bp) | Description |
| --- | --- | --- | --- |
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |

TABLE 16-continued

| Component Name | Nucleotide Position | Size (bp) | Description |
|---|---|---|---|
| Kozak | 3162-3167 | 6 | Kozak translation initiation sequence |
| {ORF84A} | 3168-4709 | 1542 | None |
| IRES + SPACER | 4710-5501 | 792 | Linker |
| {ORF84B} | 5502-6350 | 849 | None |
| WPRE | 6389-6986 | 598 | Woodchuck hepatitis virus posttranscriptional regulatory element |
| ΔU3/3' LTR | 7068-7302 | 235 | Truncated HIV-1 3' long terminal repeat |
| SV40 early pA | 7375-7509 | 135 | Simian virus 40 early polyadenylation signal |
| Ampicillin | 8463-9323 | 861 | Ampicillin resistance gene |
| pUC ori | 9494-10082 | 589 | pUC origin of replication |

Vector 29.

Figure 12:
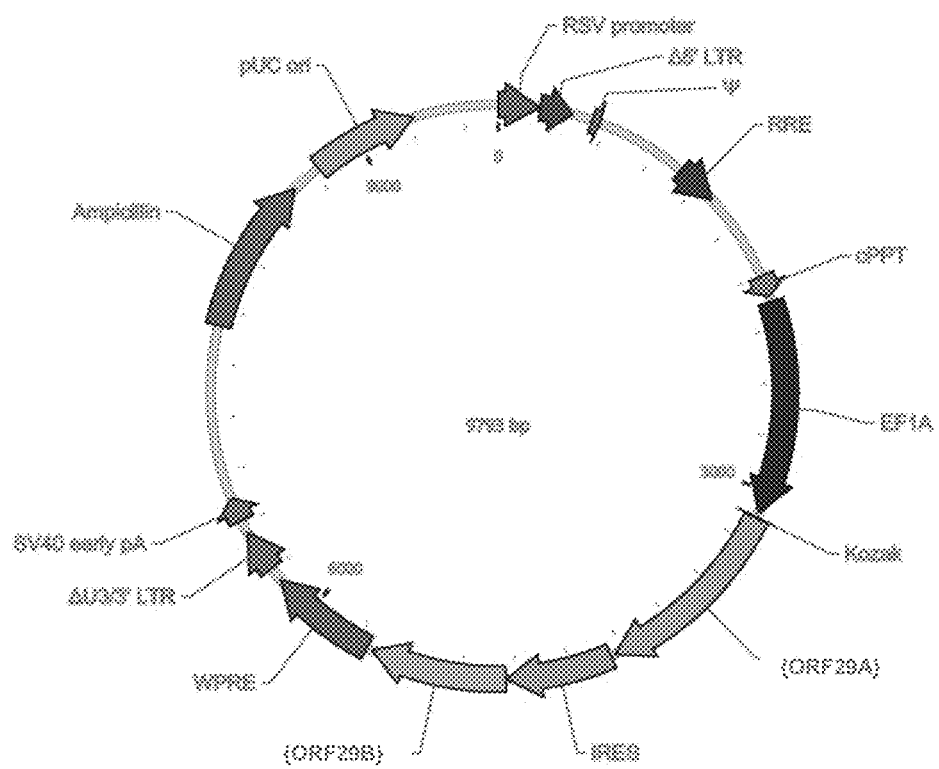
FIG. 12 shows a schematic of vector 29.

FIG. 12 shows a schematic of vector 29.

Table 17 below, shows the vector component name, the corresponding nucleotide position, the full name of the component and a description.

TABLE 17

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF29a(285aa) + SPACER} | 3159-4242 | 1084 | None |
| IRES | 4267-4854 | 588 | Encephalomyocarditis virus internal ribosome entry site |
| {ORF29b(250aa) visible} | 4855-5604 | 750 | None |
| WPRE | 5634-6231 | 598 | Woodchuck hepatitis virus posttranscriptional regulatory element |
| ΔU3/3' LTR | 6313-6547 | 235 | Truncated HIV-1 3' long terminal repeat |
| SV40 early pA | 6620-6754 | 135 | Simian virus 40 early polyadenylation signal |
| Ampicillin | 7708-8568 | 861 | Ampicillin resistance gene |
| pUC ori | 8739-9327 | 589 | pUC origin of replication |

Vector 107

Figure 13:
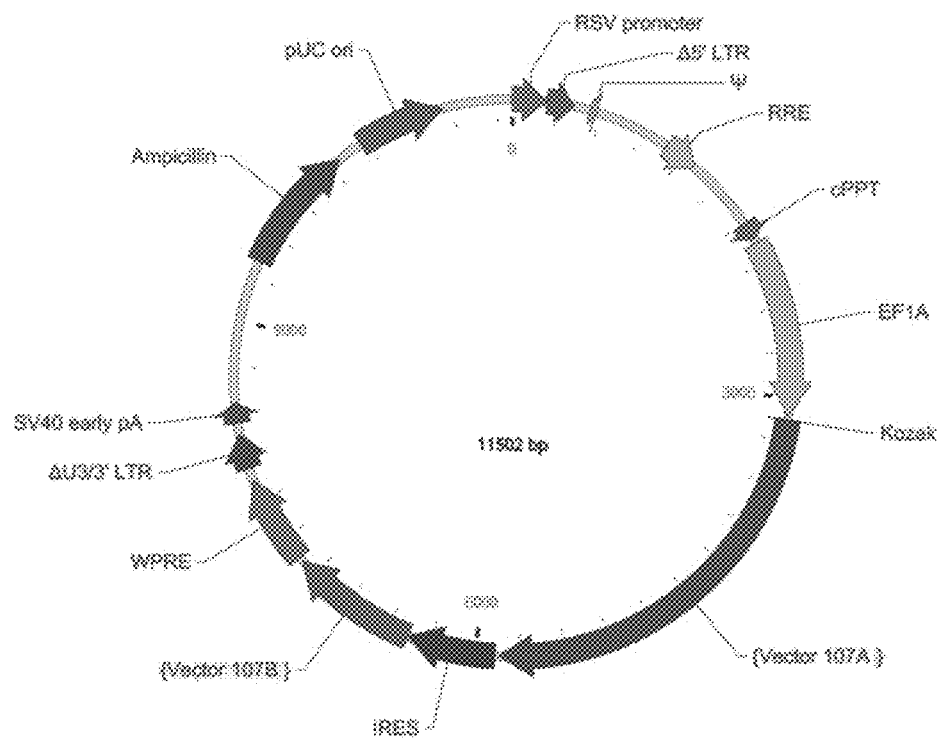
FIG. 13 shows a schematic of vector 107.

FIG. 13 shows a schematic of vector 107.

Table 18 below, shows the vector component name, the corresponding nucleotide position, the full name of the component and a description.

TABLE 18

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF3107A} | 3159-5843 | 2685 | None |
| IRES | 5868-6455 | 588 | Linker |
| {ORF107B} | 6456-7313 | 858 | None |
| WPRE | 7343-7940 | 598 | Woodchuck hepatitis virus posttranscriptional regulatory element |
| ΔU3/3' LTR | 8022-8256 | 235 | Truncated HIV-1 3' long terminal repeat |
| SV40 early pA | 8329-8463 | 135 | Simian virus 40 early polyadenylation signal |
| Ampicillin | 9417-10277 | 861 | Ampicillin resistance gene |
| pUC ori | 10448-11036 | 589 | pUC origin of replication |

Vector 116

Figure 14:
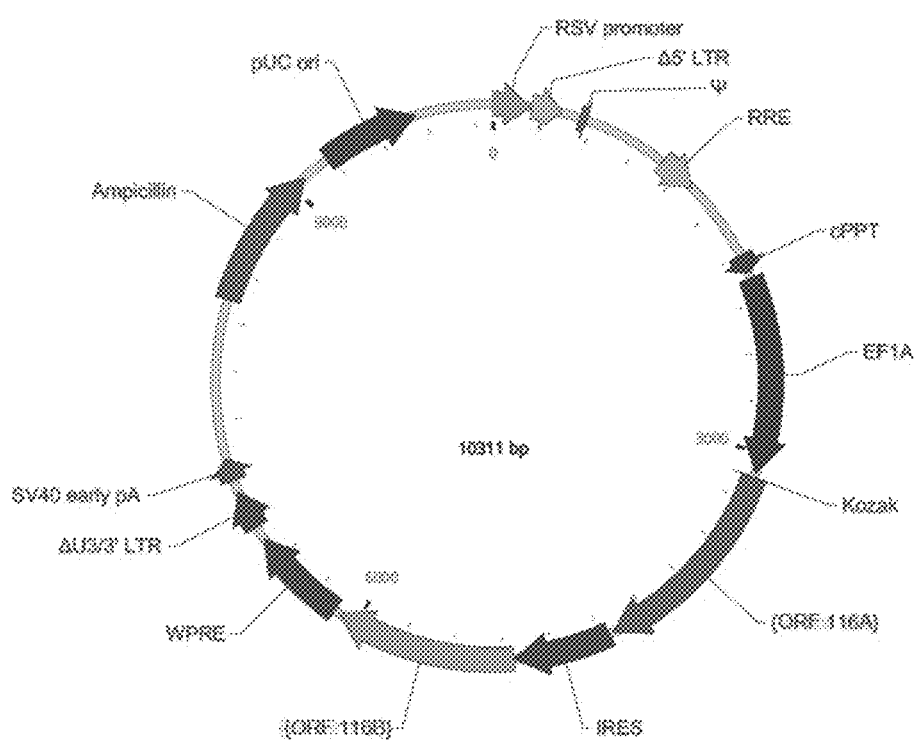
FIG. 14 shows a schematic of vector 116.

FIG. 14 shows a schematic of vector 116.

Table 19 below, shows the vector component name, the corresponding nucleotide position, the full name of the component and a description.

TABLE 19

| Component Name | Nucleotide Position | Size (bp) | Description |
| --- | --- | --- | --- |
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF116A} | 3159-4421 | 1263 | None |
| IRES | 446-5033 | 588 | Linker |
| {ORF116B} | 5034-6122 | 1089 | None |
| WPRE | 6152-6749 | 598 | Woodchuck hepatitis virus posttranscriptional regulatory element |
| ΔU3/3' LTR | 6831-7065 | 235 | Truncated HIV-1 3' long terminal repeat |
| SV40 early pA | 7138-7272 | 135 | Simian virus 40 early polyadenylation signal |
| Ampicillin | 8226-9086 | 861 | Ampicillin resistance gene |
| pUC ori | 9257-9845 | 589 | pUC origin of replication |

Vector 86

Figure 15:
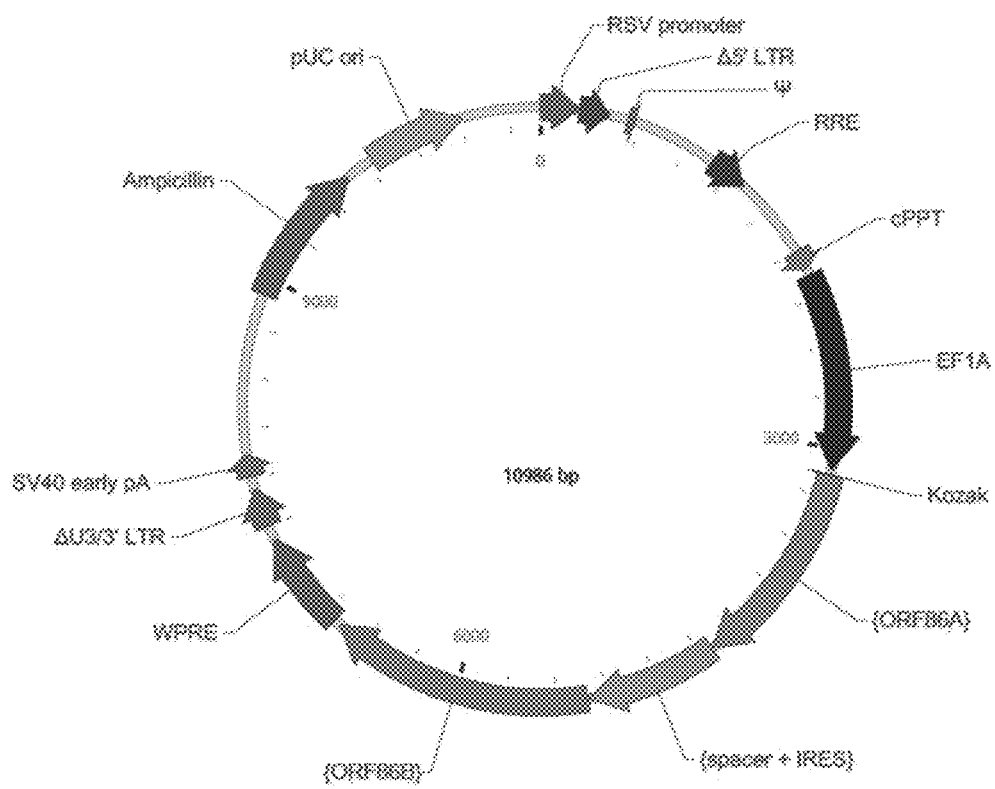
FIG. 15 shows a schematic of vector 86.

FIG. 15 shows a schematic of vector 86.

Table 20 below, shows the vector component name, the corresponding nucleotide position, the full name of the component and a description.

TABLE 20

| Component Name | Nucleotide Position | Size (bp) | Description |
| --- | --- | --- | --- |
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF86A} | 3168-4421 | 1254 | None |
| IRES + spacer | 4422-5213 | 792 | Linker |
| {ORF86B} | 5214-6788 | 1575 | None |
| WPRE | 6827-7424 | 598 | Woodchuck hepatitis virus posttranscriptional regulatory element |
| ΔU3/3' LTR | 7506-7740 | 235 | Truncated HIV-1 3' long terminal repeat |
| SV40 early pA | 7813-7947 | 135 | Simian virus 40 early polyadenylation signal |
| Ampicillin | 8901-9761 | 861 | Ampicillin resistance gene |
| pUC ori | 9932-10520 | 589 | pUC origin of replication |

Vector 18

Figure 16:
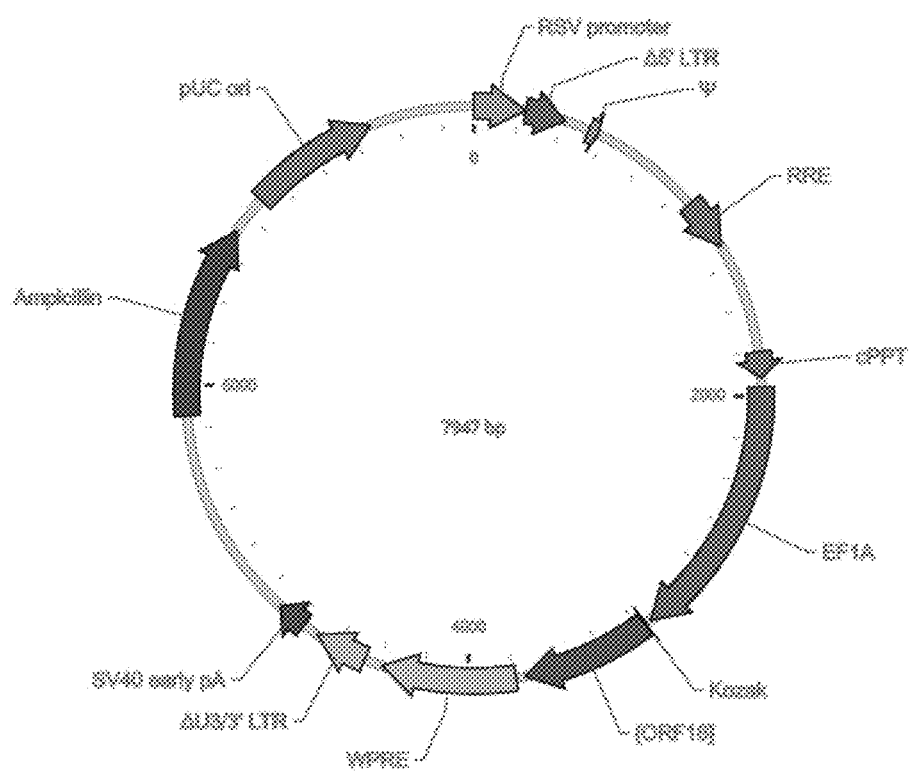
FIG. 16 shows a schematic of vector 18.

FIG. 16 shows a schematic of vector 18.

Table 21, below, shows the vector component name, the corresponding nucleotide position, the full name of the component and a description.

TABLE 21

| Component Name | Nucleotide Position | Size (bp) | Description |
| --- | --- | --- | --- |
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF18(193)} | 3168-3749 | 582 | None |
| WPRE | 3788-4385 | 598 | Woodchuck hepatitis virus posttranscriptional regulatory element |
| ΔU3/3' LTR | 4467-4701 | 235 | Truncated HIV-1 3' long terminal repeat |
| SV40 early pA | 4774-4908 | 135 | Simian virus 40 early polyadenylation signal |
| Ampicillin | 5862-6722 | 861 | Ampicillin resistance gene |
| pUC ori | 6893-7481 | 589 | pUC origin of replication |

Vector 17

Figure 17:
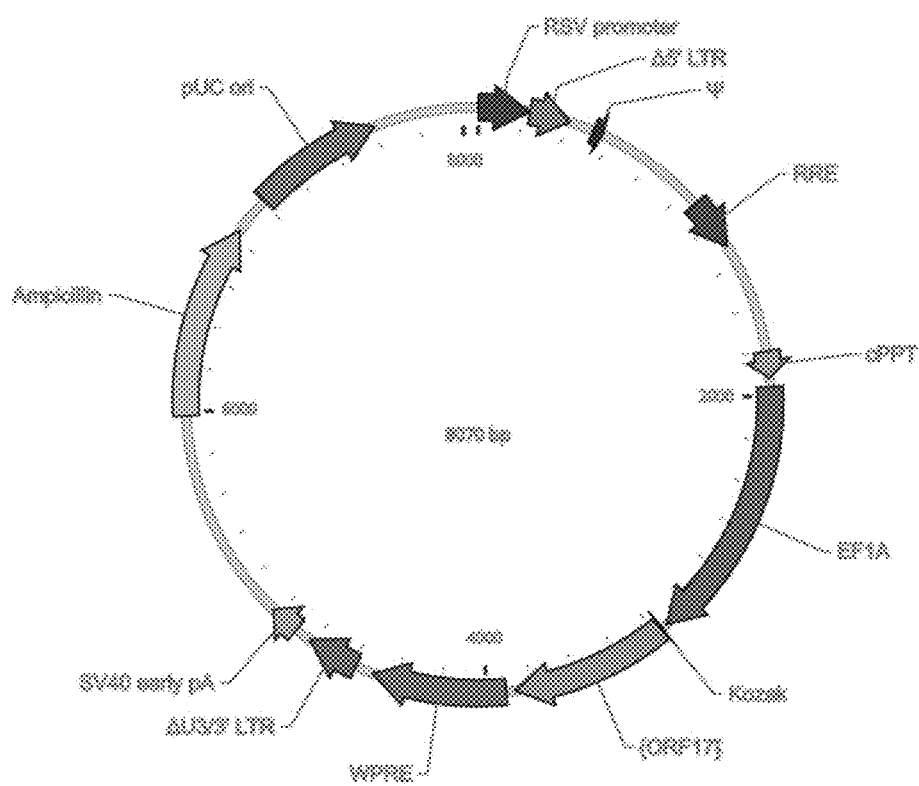
FIG. 17 shows a schematic of vector 17.

FIG. 17 shows a schematic of vector 17.

Table 22 below, shows the vector component name, the corresponding nucleotide position, the full name of the component and a description.

TABLE 22

| Component Name | Nucleotide Position | Size (bp) | Description |
| --- | --- | --- | --- |
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF17} | 3168-3872 | 705 | None |
| WPRE | 3911-4508 | 598 | Woodchuck hepatitis virus posttranscriptional regulatory element |
| ΔU3/3' LTR | 4590-4824 | 235 | Truncated HIV-1 3' long terminal repeat |
| SV40 early pA | 4897-5031 | 135 | Simian virus 40 early polyadenylation signal |
| Ampicillin | 5985-6845 | 861 | Ampicillin resistance gene |
| pUC ori | 7016-7604 | 589 | pUC origin of replication |

Vector 98

Figure 18:
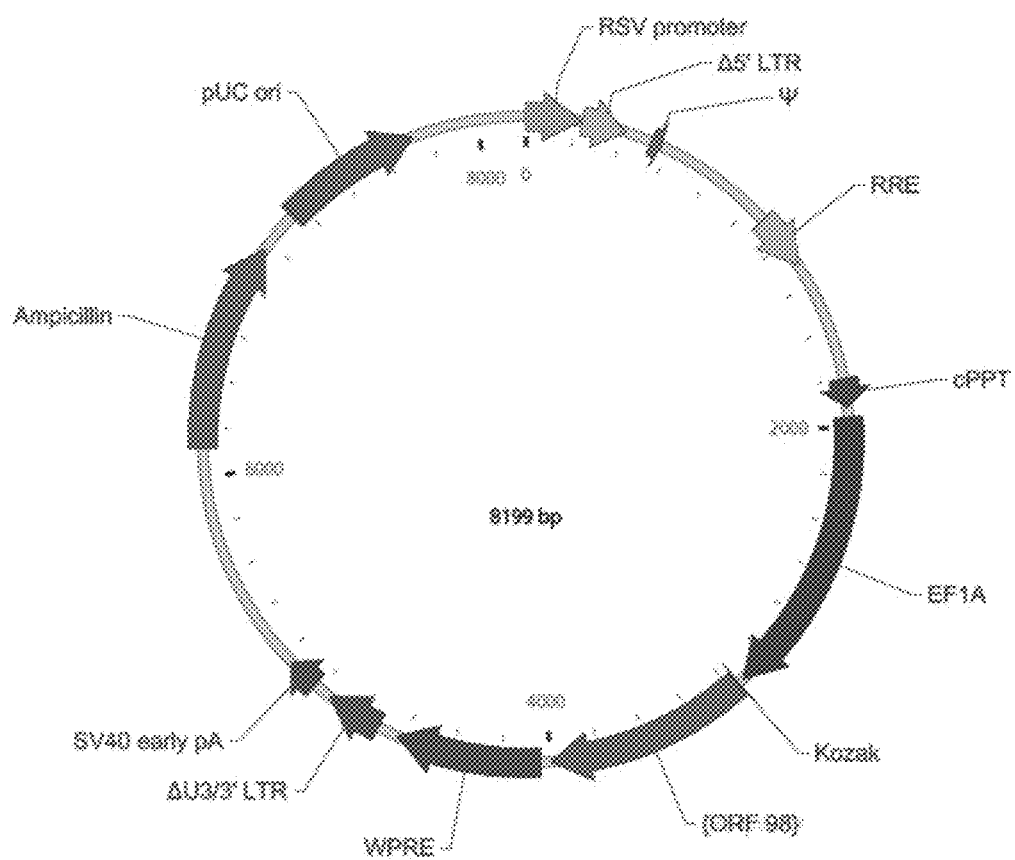
FIG. 18 shows a schematic of vector 98.

FIG. 18 shows a schematic of vector 98.

Table 23 below, shows the vector component name, the corresponding nucleotide position, the full name of the component and a description.

TABLE 23

| Component Name | Nucleotide Position | Size (bp) | Description |
| --- | --- | --- | --- |
| RSV promoter | 1-229 | 229 | Rous sarcoma virus enhancer/promoter |

TABLE 23-continued

| Component Name | Nucleotide Position | Size (bp) | Description |
|---|---|---|---|
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF98} | 3168-4001 | 834 | None |
| WPRE | 4040-4637 | 598 | Woodchuck hepatitis virus posttranscriptional regulatory element |
| ΔU3/3' LTR | 4719-4953 | 235 | Truncated HIV-1 3' long terminal repeat |
| SV40 early pA | 5026-5160 | 135 | Simian virus 40 early polyadenylation signal |
| Ampicillin | 6114-6974 | 861 | Ampicillin resistance gene |
| pUC ori | 7145-7733 | 589 | pUC origin of replication |

Vector 30

Figure 19:
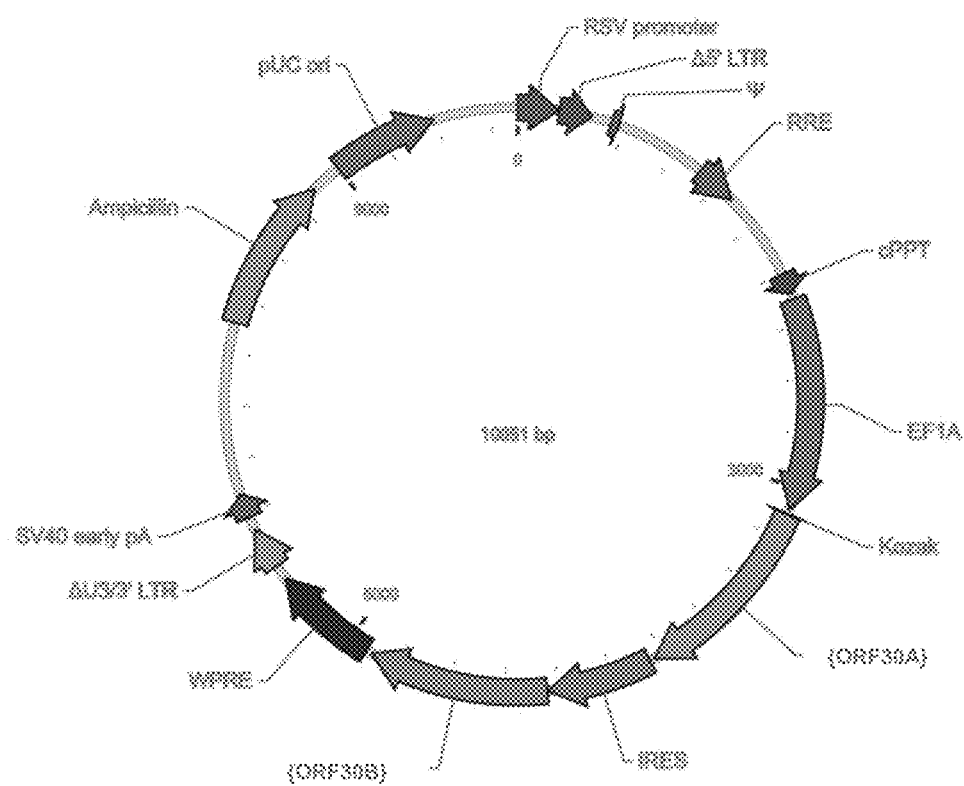
FIG. 19 shows a schematic of vector 30.

FIG. 19 shows a schematic of vector 30.

Table 24 below, shows the vector component name, the corresponding nucleotide position, the full name of the component and a description.

TABLE 24

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF30a(288aa) + SPACER} | 3159-4251 | 1093 | None |
| IRES | 4276-4863 | 588 | Linker |
| {ORF30B(332aa)} | 4864-5862 | 999 | None |
| WPRE | 5892-6489 | 598 | Woodchuck hepatitis virus posttranscriptional regulatory element |
| ΔU3/3' LTR | 6571-6805 | 235 | Truncated HIV-1 3' long terminal repeat |
| SV40 early pA | 6878-7012 | 135 | Simian virus 40 early polyadenylation signal |
| Ampicillin | 7966-8826 | 861 | Ampicillin resistance gene |
| pUC ori | 8997-9585 | 589 | pUC origin of replication |

Vector 109

Figure 20:
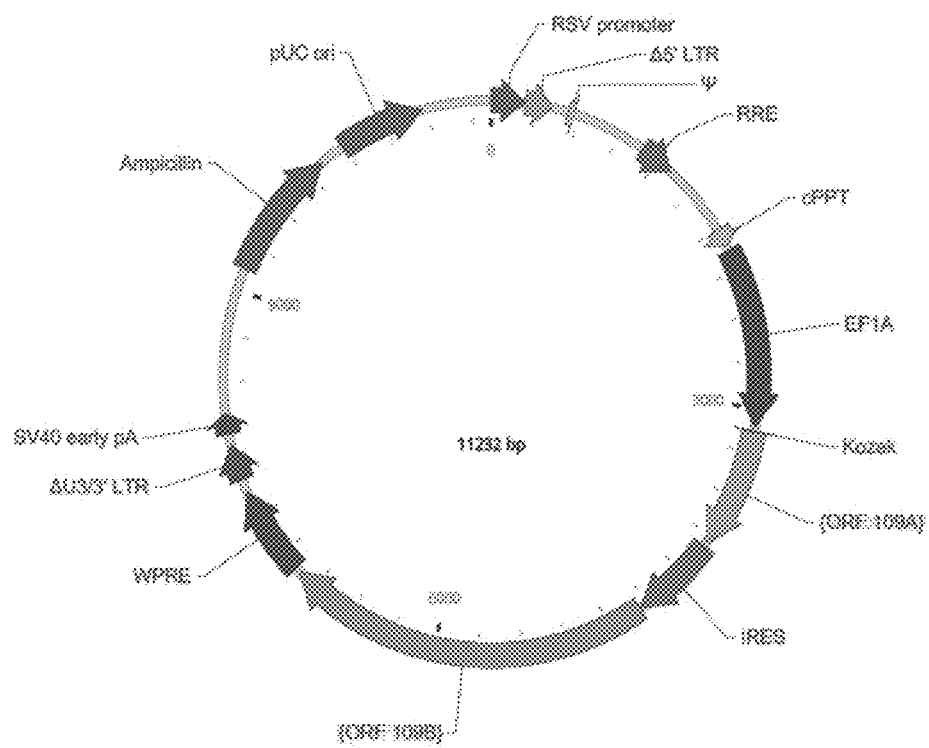
FIG. 20 shows a schematic of vector 109.

FIG. 20 shows a schematic of vector 109.

Table 25 below, shows the vector component name, the corresponding nucleotide position, the full name of the component and a description.

TABLE 25

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF109A} | 3159-3947 | 789 | None |
| IRES | 3972-4559 | 588 | Linker |
| {ORF109B} | 4560-7043 | 2484 | None |
| WPRE | 7073-7670 | 598 | Woodchuck hepatitis virus posttranscriptional regulatory element |
| ΔU3/3' LTR | 7752-7986 | 235 | Truncated HIV-1 3' long terminal repeat |
| SV40 early pA | 8059-8193 | 135 | Simian virus 40 early polyadenylation signal |
| Ampicillin | 9147-10007 | 861 | Ampicillin resistance gene |
| pUC ori | 10178-10766 | 589 | pUC origin of replication |

Vector 106

Figure 21:
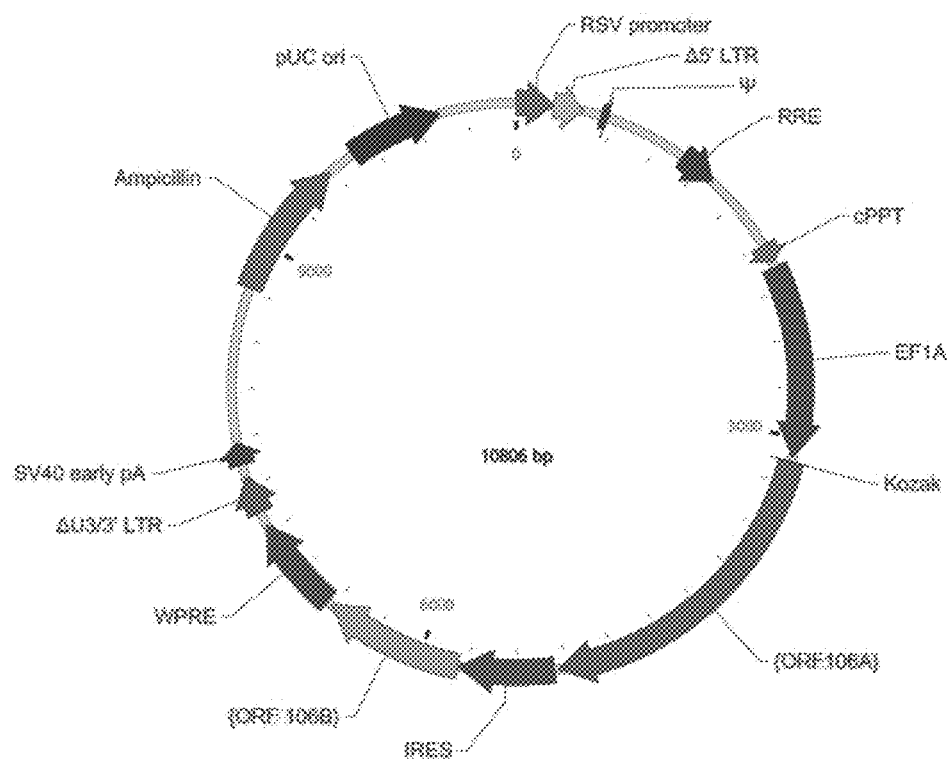
FIG. 21 shows a schematic of vector 106.

FIG. 21 shows a schematic of vector 106.

Table 26 below, shows the vector component name, the corresponding nucleotide position, the full name of the component and a description.

TABLE 26

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF106A} | 3159-5147 | 1989 | None |
| IRES | 5172-5759 | 588 | Linker |
| {ORF106B} | 5760-6617 | 858 | None |
| WPRE | 6477-7244 | 598 | Woodchuck hepatitis virus posttranscriptional regulatory element |
| ΔU3/3' LTR | 7326-7560 | 235 | Truncated HIV-1 3' long terminal repeat |
| SV40 early pA | 7633-7767 | 135 | Simian virus 40 early polyadenylation signal |
| Ampicillin | 8721-9581 | 861 | Ampicillin resistance gene |
| pUC ori | 9752-10340 | 589 | pUC origin of replication |

Vector 16

Figure 22:
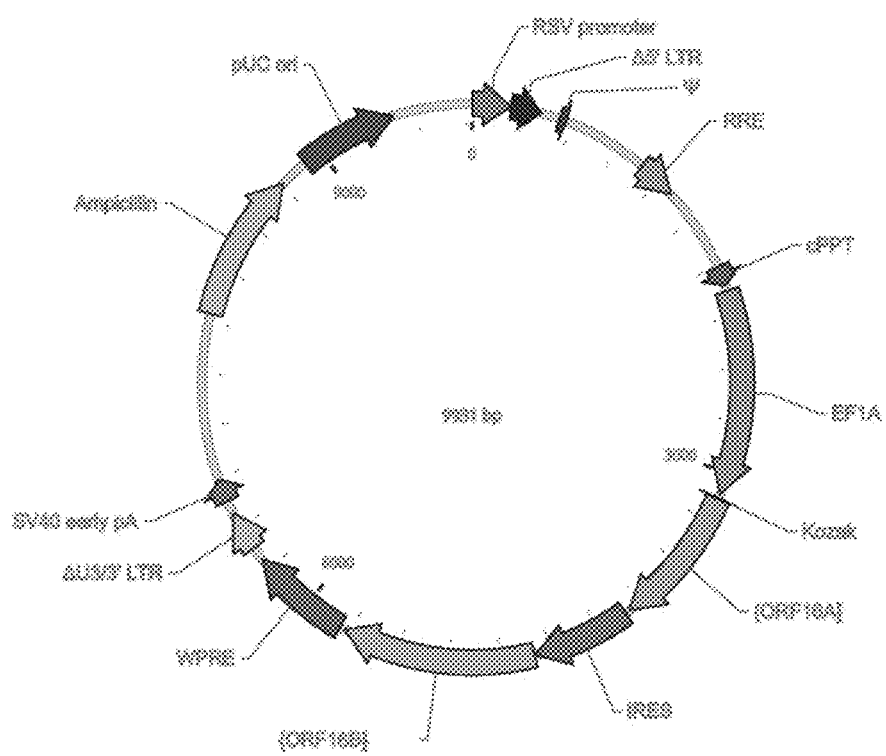
FIG. 22 shows a schematic of vector 16.

FIG. 22 shows a schematic of vector 16.

Table 27 below, shows the vector component name, the corresponding nucleotide position, the full name of the component and a description.

TABLE 27

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF16A}_w/SPACER | 3159-3984 | 826 | None |
| IRES | 4009-4596 | 588 | Linker |
| {ORF16B} | 4597-5742 | 1146 | None |
| WPRE | 5772-6369 | 598 | Woodchuck hepatitis virus posttranscriptional regulatory element |
| ΔU3/3' LTR | 6451-6685 | 235 | Truncated HIV-1 3' long terminal repeat |
| SV40 early pA | 6758-6892 | 135 | Simian virus 40 early polyadenylation signal |
| Ampicillin | 7846-8706 | 861 | Ampicillin resistance gene |
| pUC ori | 8877-945 | 589 | pUC origin of replication |

Vector 83

Figure 23:
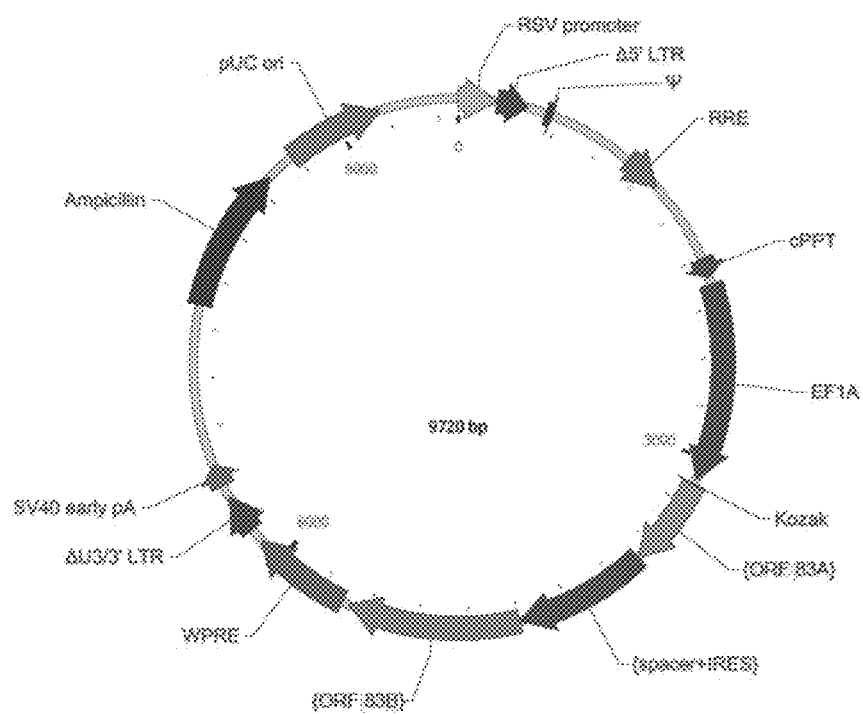
FIG. 23 shows a schematic of vector 83.

FIG. 23 shows a schematic of vector 83.

Table 28 below, shows the vector component name, the corresponding nucleotide position, the full name of the component and a description.

TABLE 28

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF83A} | 3168-3704 | 537 | None |
| IRES + spacer | 3705-4496 | 792 | Linker |
| {ORF83B} | 4497-5522 | 1026 | None |
| WPRE | 5561-6158 | 598 | Woodchuck hepatitis virus posttranscriptional regulatory element |
| ΔU3/3' LTR | 6240-6474 | 235 | Truncated HIV-1 3' long terminal repeat |
| SV40 early pA | 6547-6681 | 135 | Simian virus 40 early polyadenylation signal |
| Ampicillin | 7635-8495 | 861 | Ampicillin resistance gene |
| pUC ori | 8666-9254 | 589 | pUC origin of replication |

Vector 31

Figure 24:
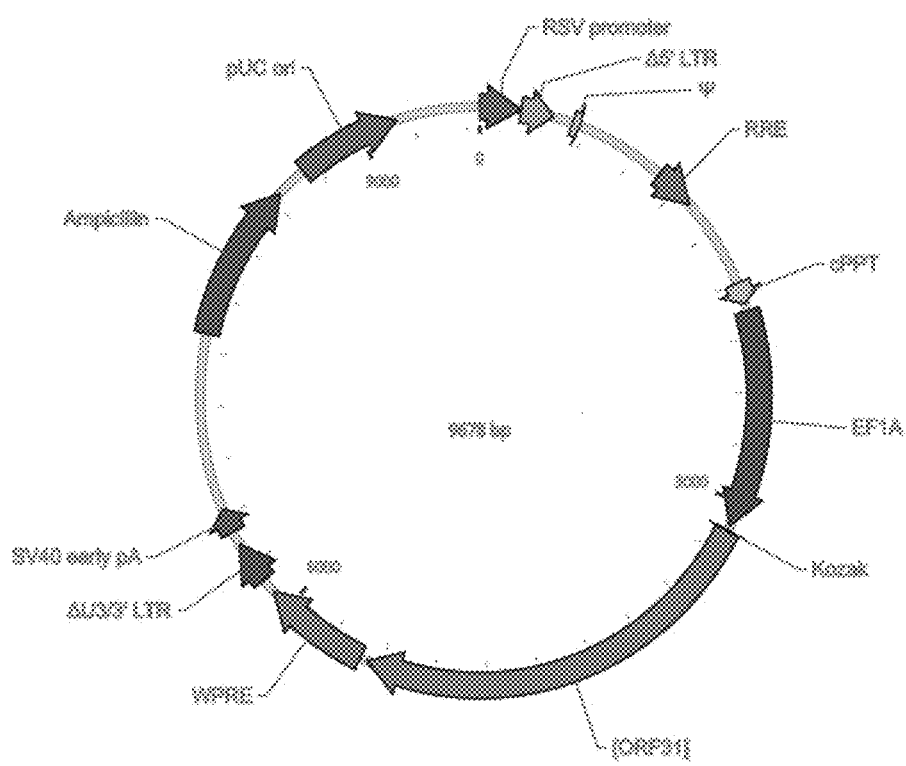
FIG. 24 shows a schematic of vector 31.

FIG. 24 shows a schematic of vector 31.

Table 29 below, shows the vector component name, the corresponding nucleotide position, the full name of the component and a description.

TABLE 29

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF31} | 3168-5480 | 2313 | None |
| WPRE | 5519-6116 | 598 | Woodchuck hepatitis virus posttranscriptional regulatory element |
| ΔU3/3' LTR | 6198-6432 | 235 | Truncated HIV-1 3' long terminal repeat |
| SV40 early pA | 6505-6639 | 135 | Simian virus 40 early polyadenylation signal |
| Ampicillin | 7593-8453 | 861 | Ampicillin resistance gene |
| pUC ori | 8624-9212 | 589 | pUC origin of replication |

Vector 12

Figure 25:
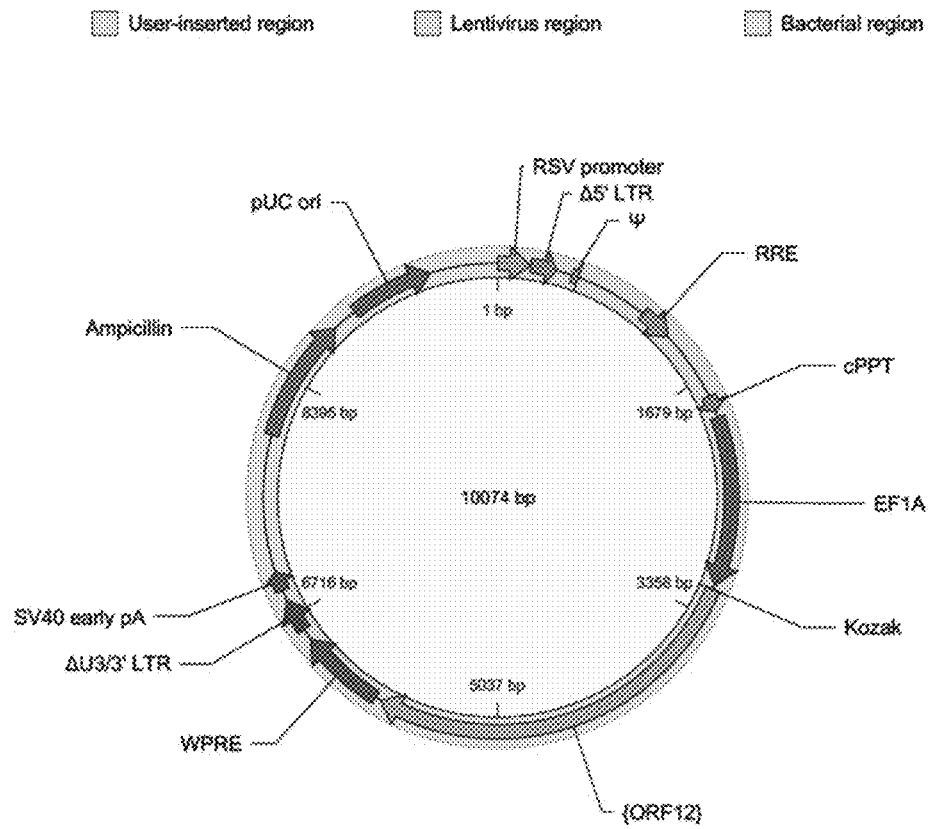
FIG. 25 shows a schematic of vector 12.

FIG. 25 shows a schematic of vector 12.

Table 30 below, shows the vector component name, the corresponding nucleotide position, the full name of the component and a description.

TABLE 30

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF12} | 3168-5876 | | None |
| WPRE | 5915-6512 | 598 | Woodchuck hepatitis virus posttranscriptional regulatory element |
| ΔU3/3' LTR | 6594-6828 | 235 | Truncated HIV-1 3' long terminal repeat |
| SV40 early pA | 6901-7035 | 135 | Simian virus 40 early polyadenylation signal |
| Ampicillin | 7989-8849 | 861 | Ampicillin resistance gene |
| pUC ori | 9020-9608 | 589 | pUC origin of replication |

Vector 99

Figure 26:
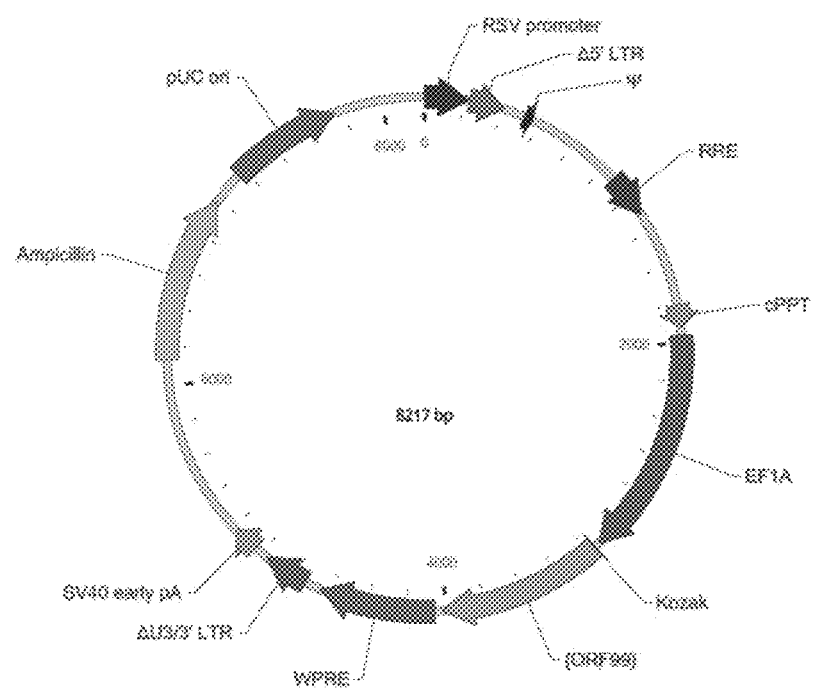
FIG. 26 shows a schematic of vector 99.

FIG. 26 shows a schematic of vector 99.

Table 31 below, shows the vector component name, the corresponding nucleotide position, the full name of the component and a description.

TABLE 31

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF99} | 3168-4019 | 852 | None |
| WPRE | 4058-4655 | 598 | Woodchuck hepatitis virus posttranscriptional regulatory element |
| ΔU3/3' LTR | 4737-4971 | 235 | Truncated HIV-1 3' long terminal repeat |
| SV40 early pA | 5044-5178 | 135 | Simian virus 40 early polyadenylation signal |
| Ampicillin | 6132-6992 | 861 | Ampicillin resistance gene |
| pUC ori | 7163-7751 | 589 | pUC origin of replication |

Figure 27:
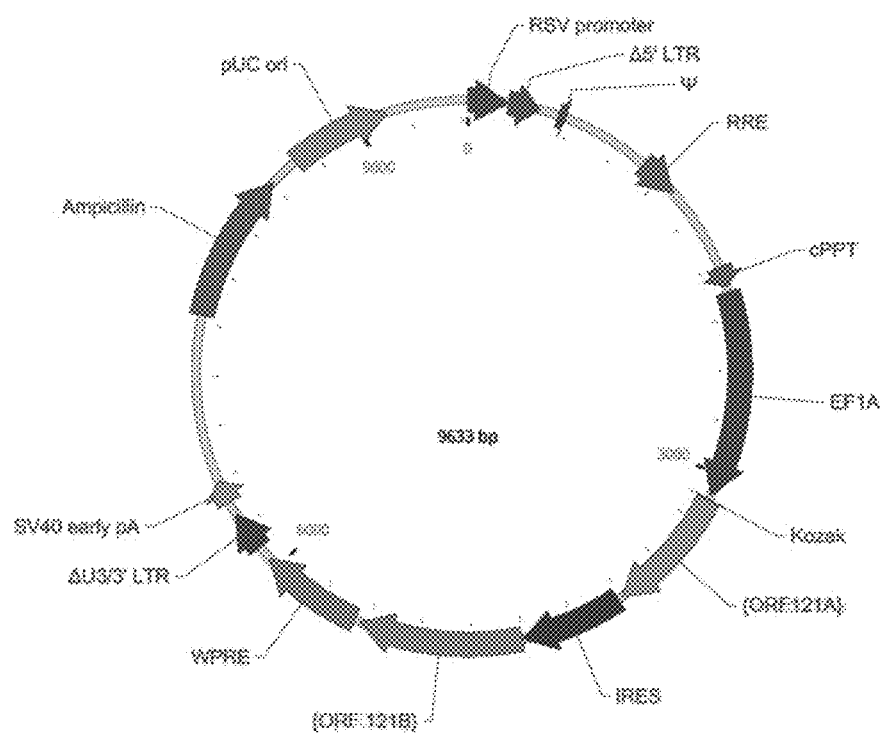
FIG. 27 shows a schematic of vector 121.

Vector 121
FIG. 27 shows a schematic of vector 121.
Table 32 below, shows the vector component name, the corresponding nucleotide position, the full name of the component and a description.

TABLE 32

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF121A} | 3159-3896 | 738 | None |
| IRES | 3921-4508 | 588 | Linker |
| {ORF121B} | 4509-5444 | 936 | None |
| WPRE | 5474-6071 | 598 | Woodchuck hepatitis virus posttranscriptional regulatory element |
| ΔU3/3' LTR | 6153-6387 | 235 | Truncated HIV-1 3' long terminal repeat |
| SV40 early pA | 6460-6594 | 135 | Simian virus 40 early polyadenylation signal |
| Ampicillin | 7548-8408 | 861 | Ampicillin resistance gene |
| pUC ori | 8579-9167 | 589 | pUC origin of replication |

Figure 28:
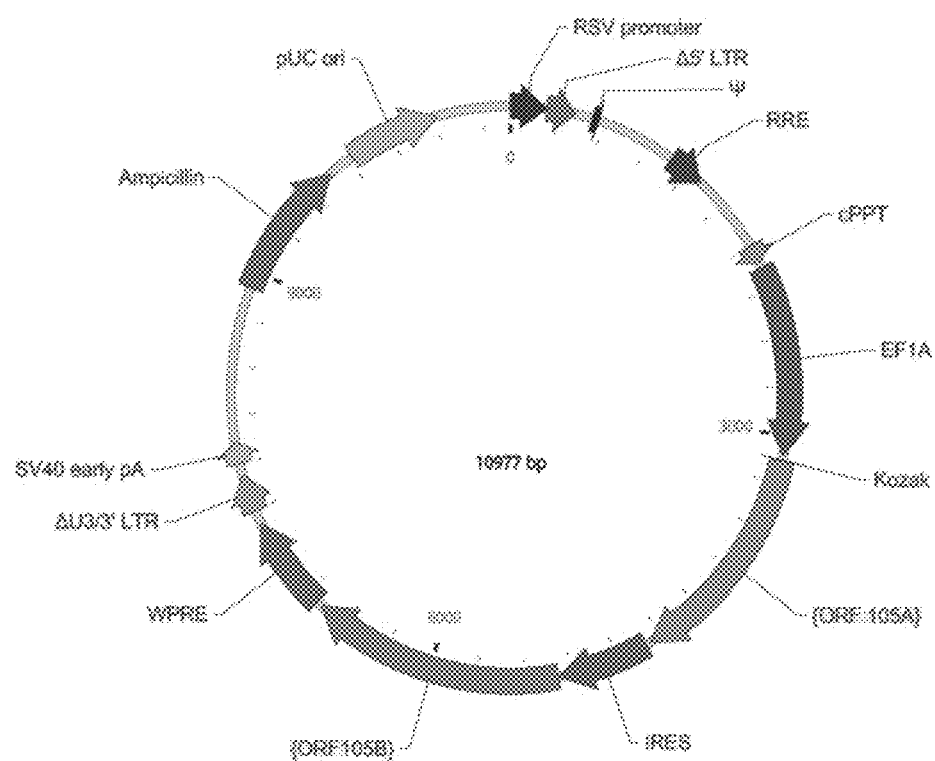
FIG. 28 shows a schematic of vector 105.

Vector 105
FIG. 28 shows a schematic of vector 105.
Table 33 below, shows the vector component name, the corresponding nucleotide position, the full name of the component and a description.

TABLE 33

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF105A} | 3159-4574 | 1416 | None |
| IRES | 4599-5186 | 588 | Linker |
| {ORF105B} | 5187-6788 | 1602 | None |
| WPRE | 6818-7415 | 598 | Woodchuck hepatitis virus posttranscriptional regulatory element |

TABLE 33-continued

| Component Name | Nucleotide Position | Size (bp) | Description |
|---|---|---|---|
| ΔU3/3' LTR | 7497-7731 | 235 | Truncated HIV-1 3' long terminal repeat |
| SV40 early pA | 7804-7938 | 135 | Simian virus 40 early polyadenylation signal |
| Ampicillin | 8892-9752 | 861 | Ampicillin resistance gene |
| pUC ori | 9923-14511 | 589 | pUC origin of replication |

Vector 32

Figure 29:
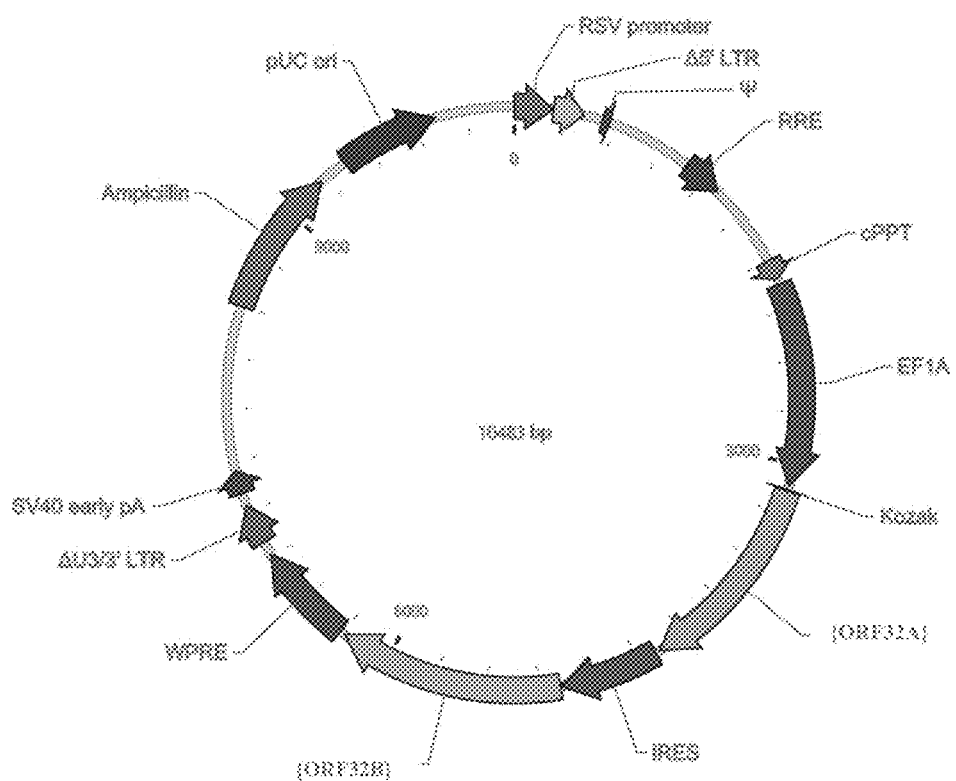
FIG. 29 shows a schematic of vector 32.

FIG. 29 shows a schematic of vector 32.

Table 34 below, shows the vector component name, the corresponding nucleotide position, the full name of the component and a description.

TABLE 34

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF32A} + SPACER | 3159-4359 | 1201 | None |
| IRES | 4384-4971 | 588 | Linker |
| {ORF32B} | 4972-6294 | 1323 | None |
| WPRE | 6324-6921 | 598 | Woodchuck hepatitis virus posttranscriptional regulatory element |
| ΔU3/3' LTR | 7003-7237 | 235 | Truncated HIV-1 3' long terminal repeat |
| SV40 early pA | 7310-7444 | 135 | Simian virus 40 early polyadenylation signal |
| Ampicillin | 8398-9258 | 861 | Ampicillin resistance gene |
| pUC ori | 9429-10017 | 589 | pUC origin of replication |

Vector 37

Figure 30:
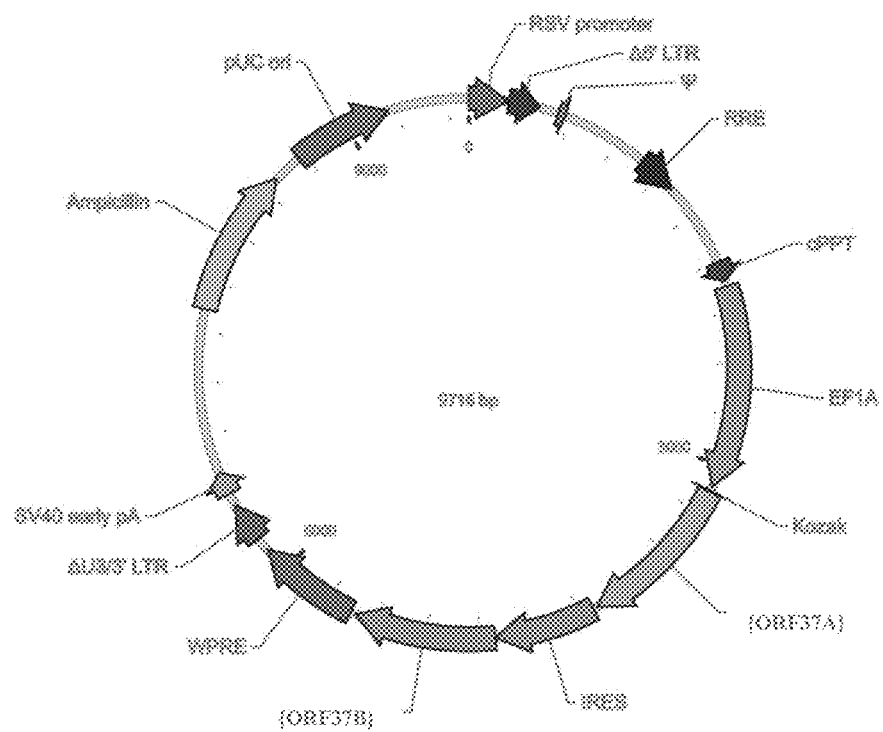
FIG. 30 shows a schematic of vector 37.

FIG. 30 shows a schematic of vector 37.

Table 35 below, shows the vector component name, the corresponding nucleotide position, the full name of the component and a description.

TABLE 35

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF37A} + SPACER | 3159-4093 | 935 | None |
| IRES | 4118-4705 | 588 | Linker |
| {ORF37B} | 4706-5527 | 822 | None |
| WPRE | 5557-6154 | 598 | Woodchuck hepatitis virus posttranscriptional regulatory element |
| ΔU3/3' LTR | 6236-6470 | 235 | Truncated HIV-1 3' long terminal repeat |
| SV40 early pA | 6543-6677 | 135 | Simian virus 40 early polyadenylation signal |
| Ampicillin | 7631-8491 | 861 | Ampicillin resistance gene |
| pUC ori | 8662-9250 | 589 | pUC origin of replication |

Figure 31:
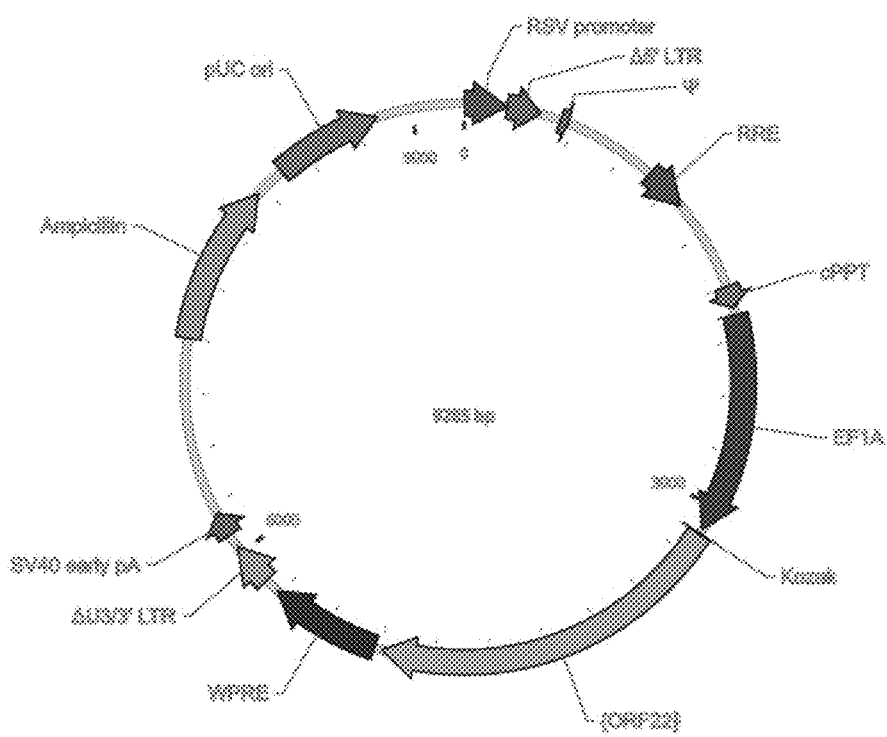
FIG. 31 shows a schematic of vector 22.

Vector 22
FIG. 31 shows a schematic of vector 22.
Table 36 below, shows the vector component name, the corresponding nucleotide position, the full name of the component and a description.

TABLE 36

| Component Name | Nucleotide Position | Size (bp) | Description |
| --- | --- | --- | --- |
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF22} | 3168-5087 | 1920 | None |
| WPRE | 5126-5723 | 598 | Woodchuck hepatitis virus posttranscriptional regulatory element |
| ΔU3/3' LTR | 5805-6039 | 235 | Truncated HIV-1 3' long terminal repeat |
| SV40 early pA | 6112-6246 | 135 | Simian virus 40 early polyadenylation signal |
| Ampicillin | 7200-8060 | 861 | Ampicillin resistance gene |
| pUC ori | 8231-8819 | 589 | pUC origin of replication |

Figure 32:
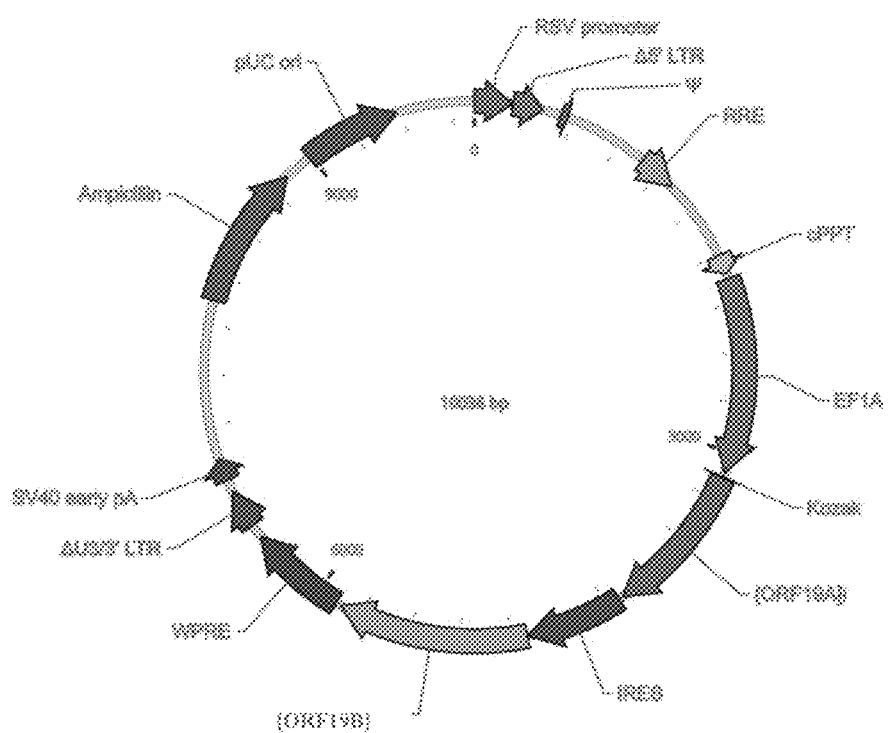
FIG. 32 shows a schematic of vector 19.

Vector 19
FIG. 32 shows a schematic of vector 19.
Table 37 below, shows the vector component name, the corresponding nucleotide position, the full name of the component and a description.

TABLE 37

| Component Name | Nucleotide Position | Size (bp) | Description |
| --- | --- | --- | --- |
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF19A} w_SPACER | 3159-40892 | 931 | None |
| IRES | 4114-4701 | 588 | Linker |
| {ORF19B) | 4702-5847 | 1146 | None |
| WPRE | 5877-6474 | 598 | Woodchuck hepatitis virus posttranscriptional regulatory element |
| ΔU3/3' LTR | 6556-6790 | 235 | Truncated HIV-1 3' long terminal repeat |
| SV40 early pA | 6863-6997 | 135 | Simian virus 40 early polyadenylation signal |
| Ampicillin | 7951-8811 | 861 | Ampicillin resistance gene |
| pUC ori | 8982-9570 | 589 | pUC origin of replication |

Figure 33:
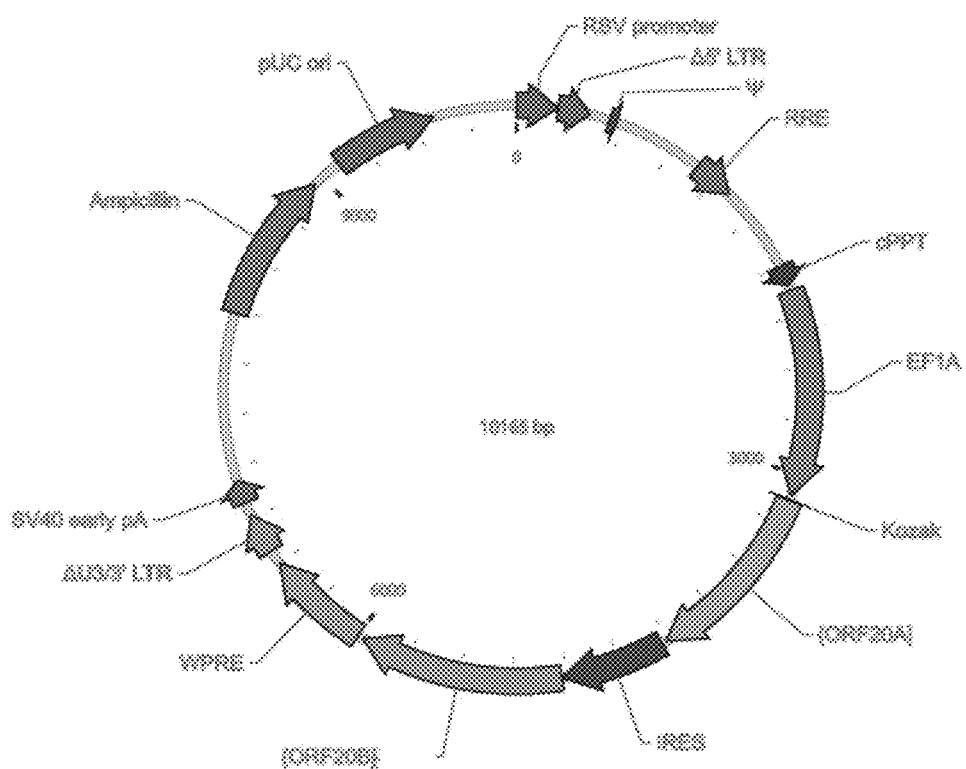
FIG. 33 shows a schematic of vector 20.

Vector 20
FIG. 33 shows a schematic of vector 20.
Table 38 below, shows the vector component name, the corresponding nucleotide position, the full name of the component and a description.

TABLE 38

| Component Name | Nucleotide Position | Size (bp) | Description |
| --- | --- | --- | --- |
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |

TABLE 38-continued

| Component Name | Nucleotide Position | Size (bp) | Description |
| --- | --- | --- | --- |
| EF1A- | 1950-3128 | 1179 | Human eukaryotic translation elongation factor 1 α1 promoter |
| Kozak | 3153-3158 | 6 | Kozak translation initiation sequence |
| {ORF20}w_spacer | 3159-4218 | 1060 | None |
| IRES | 4243-4830 | 588 | Linker |
| {ORF20B} | 4831-5976 | 1146 | None |
| WPRE | 6066-6603 | 598 | Woodchuck hepatitis virus posttranscriptional regulatory element |
| ΔU3/3' LTR | 6685-6919 | 235 | Truncated HIV-1 3' long terminal repeat |
| SV40 early pA | 6992-7126 | 135 | Simian virus 40 early polyadenylation signal |
| Ampicillin | 8080-8940 | 861 | Ampicillin resistance gene |
| pUC ori | 9111-9699 | 589 | pUC origin of replication |

Vector 89

Figure 34:
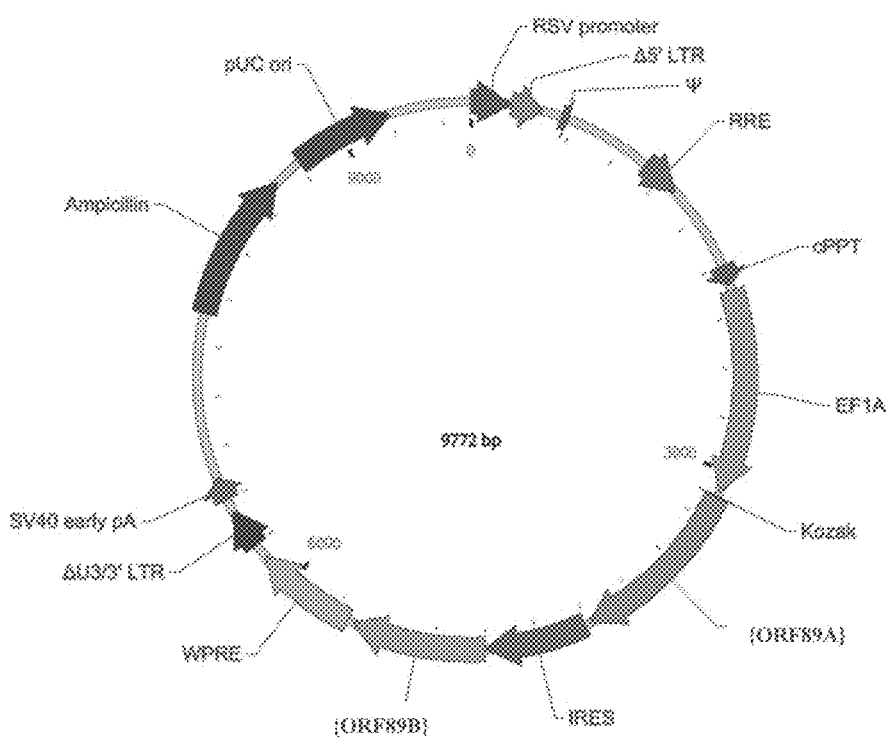
FIG. 34 shows a schematic of vector 89.

FIG. 34 shows a schematic of vector 89.

Table 39 below, shows the vector component name, the corresponding nucleotide position, the full name of the component and a description.

TABLE 39

| Component Name | Nucleotide Position | Size (bp) | Description |
| --- | --- | --- | --- |
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF89A} + Spacer | 3159-4194 | 1036 | None |
| IRES | 4219-4806 | 588 | Linker |
| {ORF89B} | 4807-5583 | 777 | None |
| WPRE | 5613-6210 | 598 | Woodchuck hepatitis virus posttranscriptional regulatory element |
| ΔU3/3' LTR | 6292-6526 | 235 | Truncated HIV-1 3' long terminal repeat |
| SV40 early pA | 6599-6733 | 135 | Simian virus 40 early polyadenylation signal |
| Ampicillin | 7687-8547 | 861 | Ampicillin resistance gene |
| pUC ori | 8718-9306 | 589 | pUC origin of replication |

Vector 21

Figure 35:
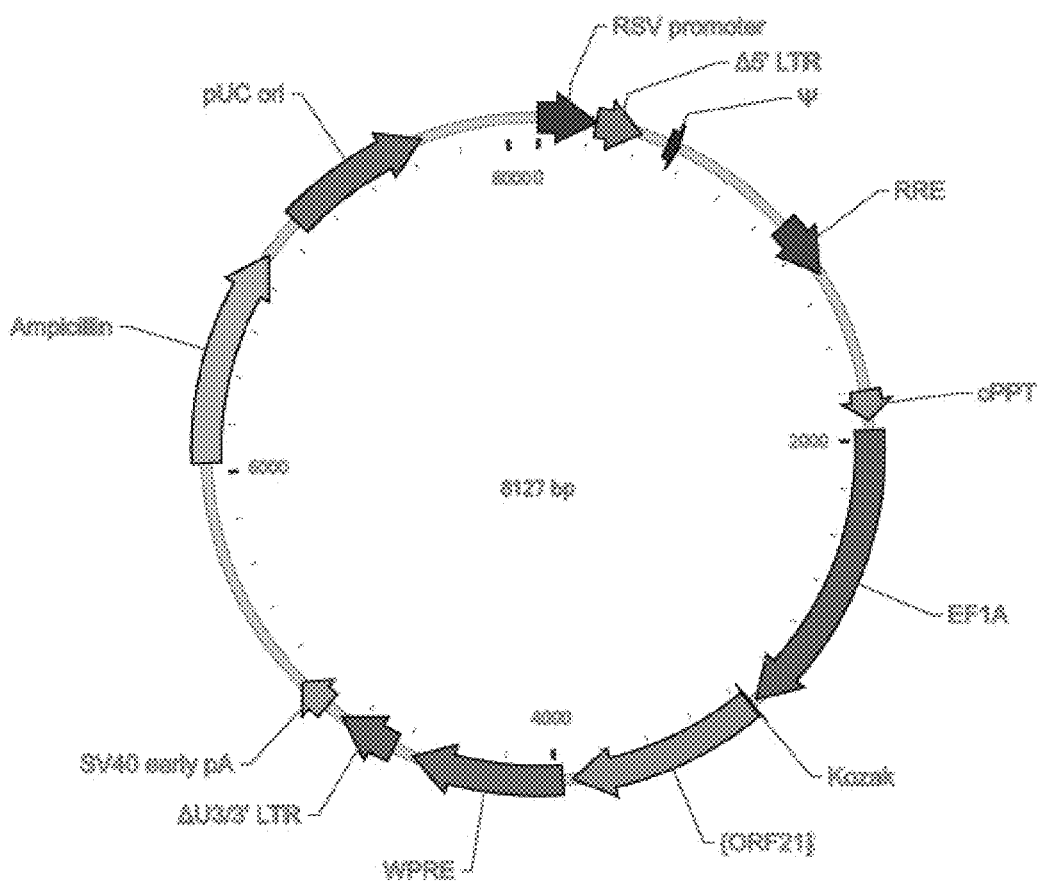
FIG. 35 shows a schematic of vector 21.

FIG. 35 shows a schematic of vector 21.

Table 40 below, shows the vector component name, the corresponding nucleotide position, the full name of the component and a description.

TABLE 40

| Component Name | Nucleotide Position | Size (bp) | Description |
| --- | --- | --- | --- |
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF21} | 3168-3929 | 762 | None |
| WPRE | 3968-4565 | 598 | Woodchuck hepatitis virus posttranscriptional regulatory element |
| ΔU3/3' LTR | 4647-4881 | 235 | Truncated HIV-1 3' long terminal repeat |
| SV40 early pA | 4954-5088 | 135 | Simian virus 40 early polyadenylation signal |
| Ampicillin | 6042-6902 | 861 | Ampicillin resistance gene |
| pUC ori | 7073-7661 | 589 | pUC origin of replication |

Figure 36:
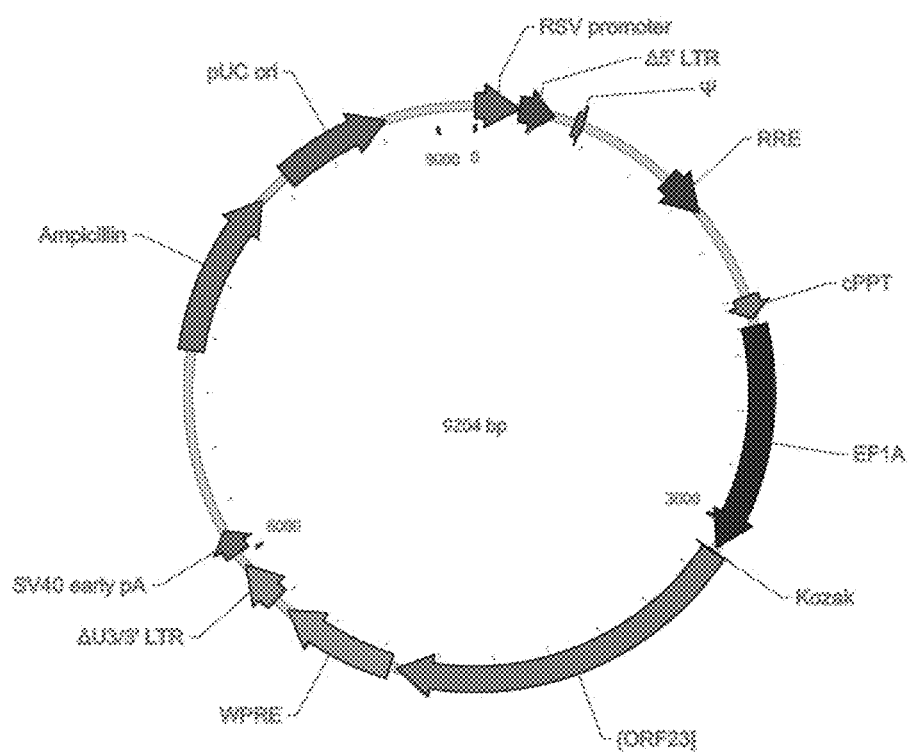
FIG. 36 shows a schematic of vector 23.

Vector 23
FIG. 36 shows a schematic of vector 23.
Table 41 below, shows the vector component name, the corresponding nucleotide position, the full name of the component and a description.

TABLE 41

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 11959-3137 | 1179 | Human eukaryotic translation elongation factor 1 α1 promoter |
| Kozak | 3162-3167 | 6 | Kozak translation initiation sequence |
| {ORF23} | 3168-5006 | 1839 | None |
| WPRE | 5045-5642 | 598 | Woodchuck hepatitis virus posttranscriptional regulatory element |
| ΔU3/3' LTR | 5724-958 | 235 | Truncated HIV-1 3' long terminal repeat |
| SV40 early pA | 6031-6165 | 135 | Simian virus 40 early polyadenylation signal |
| Ampicillin | 7119-7979 | 861 | Ampicillin resistance gene |
| pUC ori | 8150-8738 | 589 | pUC origin of replication |

Figure 37:
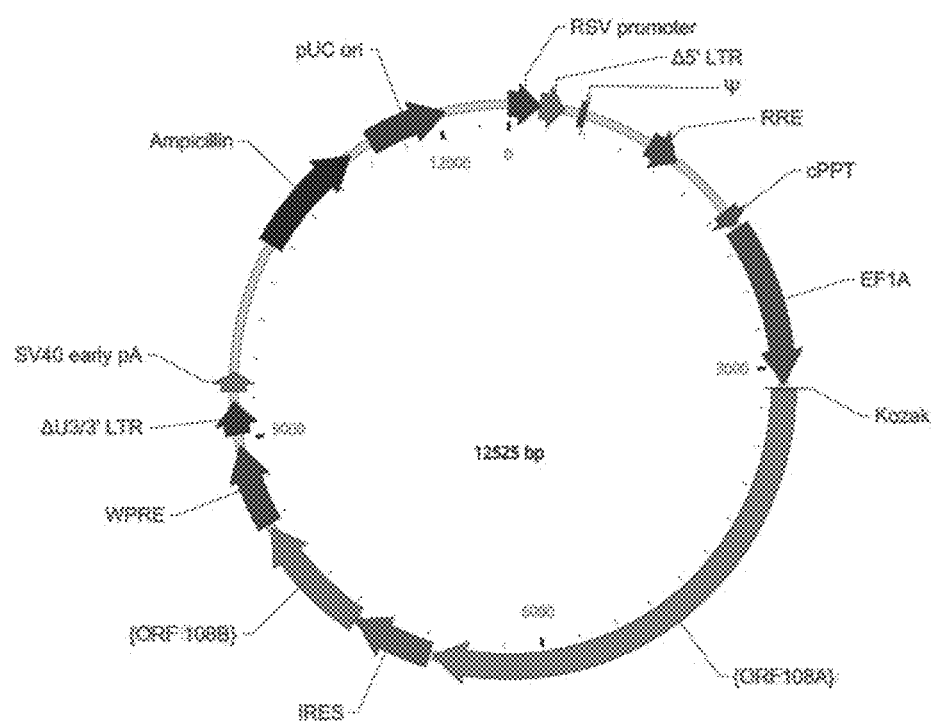
FIG. 37 shows a schematic of vector 108.

Vector 108
FIG. 37 shows a schematic of vector 108.
Table 42 below, shows the vector component name, the corresponding nucleotide position, the full name of the component and a description.

TABLE 42

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF108A} | 3159-6824 | 3666 | None |
| IRES | 6849-7436 | 588 | Linker |
| {ORF108B} | 7437-8336 | 900 | None |
| WPRE | 8366-8963 | 598 | Woodchuck hepatitis virus posttranscriptional regulatory element |
| ΔU3/3' LTR | 9045-9279 | 235 | Truncated HIV-1 3' long terminal repeat |
| SV40 early pA | 9352-9486 | 135 | Simian virus 40 early polyadenylation signal |
| Ampicillin | 10440-11300 | 861 | Ampicillin resistance gene |
| pUC ori | 11471-12059 | 589 | pUC origin of replication |

Figure 38:
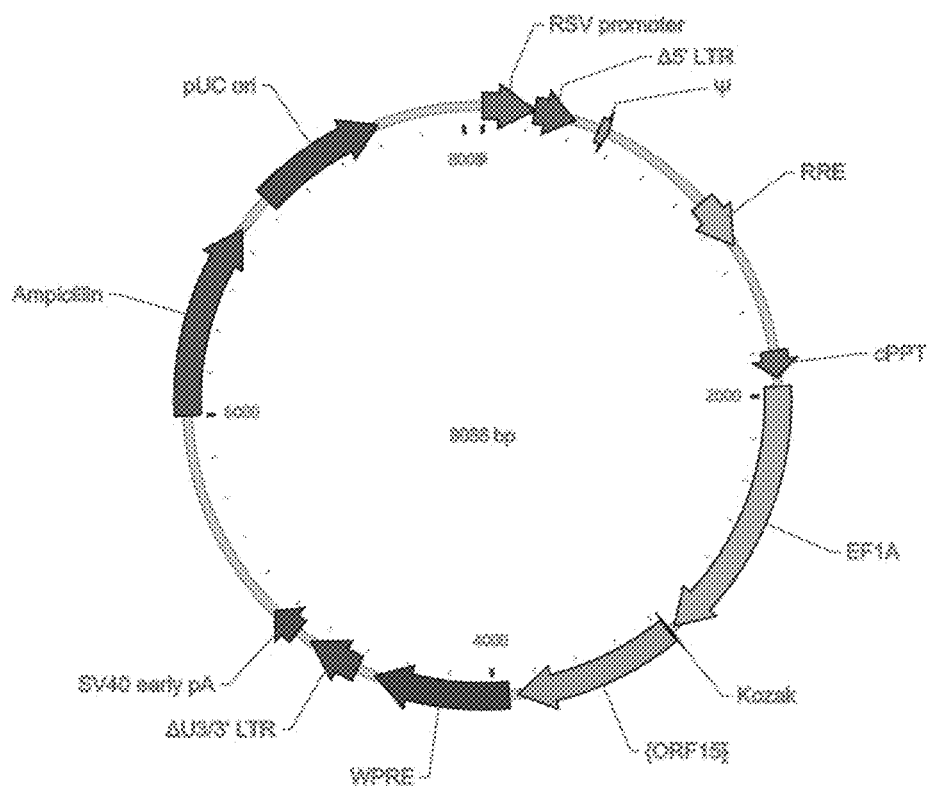
FIG. 38 shows a schematic of vector 15.

Vector 15
FIG. 38 shows a schematic of vector 15.
Table 43 below, shows the vector component name, the corresponding nucleotide position, the full name of the component and a description.

TABLE 43

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |

TABLE 43-continued

| Component Name | Nucleotide Position | Size (bp) | Description |
|---|---|---|---|
| EF1A | 1959-3137 | 1179 | Human eukaryotic translation elongation factor 1 α1 promoter |
| Kozak | 3153-3158 | 6 | Kozak translation initiation sequence |
| {ORF15} | 3168-3890 | 723 | None |
| WPRE | 3929-4526 | 598 | Woodchuck hepatitis virus posttranscriptional regulatory element |
| ΔU3/3' LTR | 4608-4842 | 235 | Truncated HIV-1 3' long terminal repeat |
| SV40 early pA | 4915-5049 | 135 | Simian virus 40 early polyadenylation signal |
| Ampicillin | 6003-6863 | 861 | Ampicillin resistance gene |
| pUC ori | 7034-7622 | 589 | pUC origin of replication |

Figure 39:
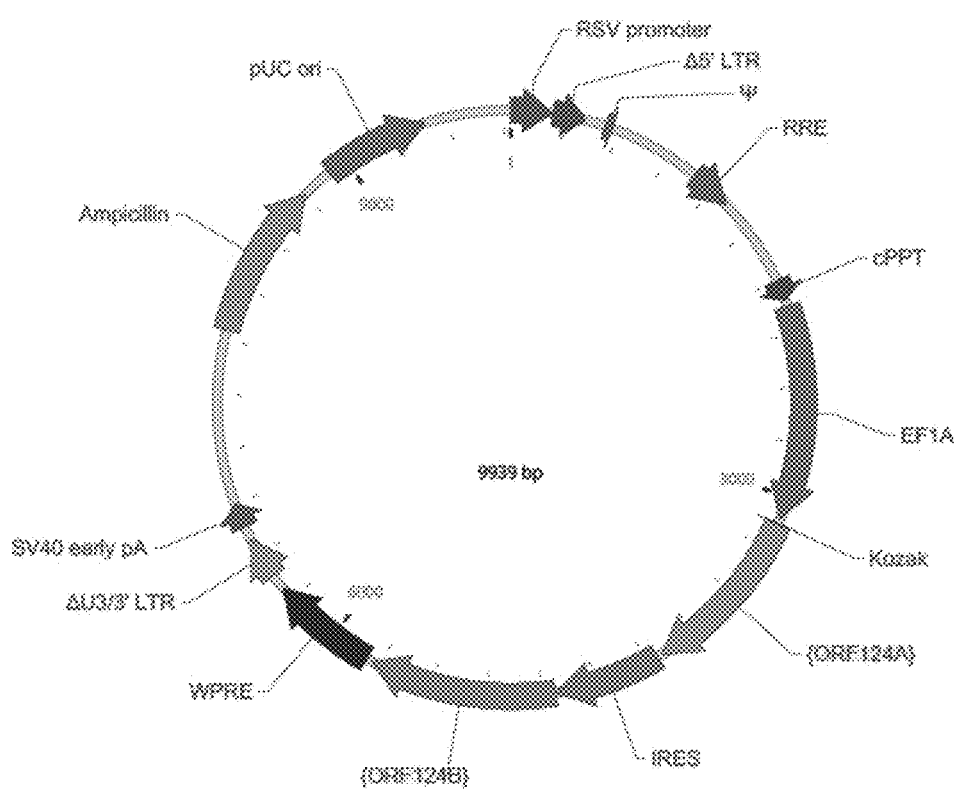
FIG. 39 shows a schematic of vector 124.

Vector 124
FIG. 39 shows a schematic of vector 124.
Table 44 below, shows the vector component name, the corresponding nucleotide position, the full name of the component and a description.

TABLE 44

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF124A} | 3159-4112 | 954 | None |
| IRES | 4137-4724 | 588 | Linker |
| {ORF124B} | 4725-5750 | 1026 | None |
| WPRE | 5780-6377 | 598 | Woodchuck hepatitis virus posttranscriptional regulatory element |
| ΔU3/3' LTR | 6459-6693 | 235 | Truncated HIV-1 3' long terminal repeat |
| SV40 early pA | 6766-6900 | 135 | Simian virus 40 early polyadenylation signal |
| Ampicillin | 7854-8714 | 861 | Ampicillin resistance gene |
| pUC ori | 8885-9473 | 589 | pUC origin of replication |

Figure 40:
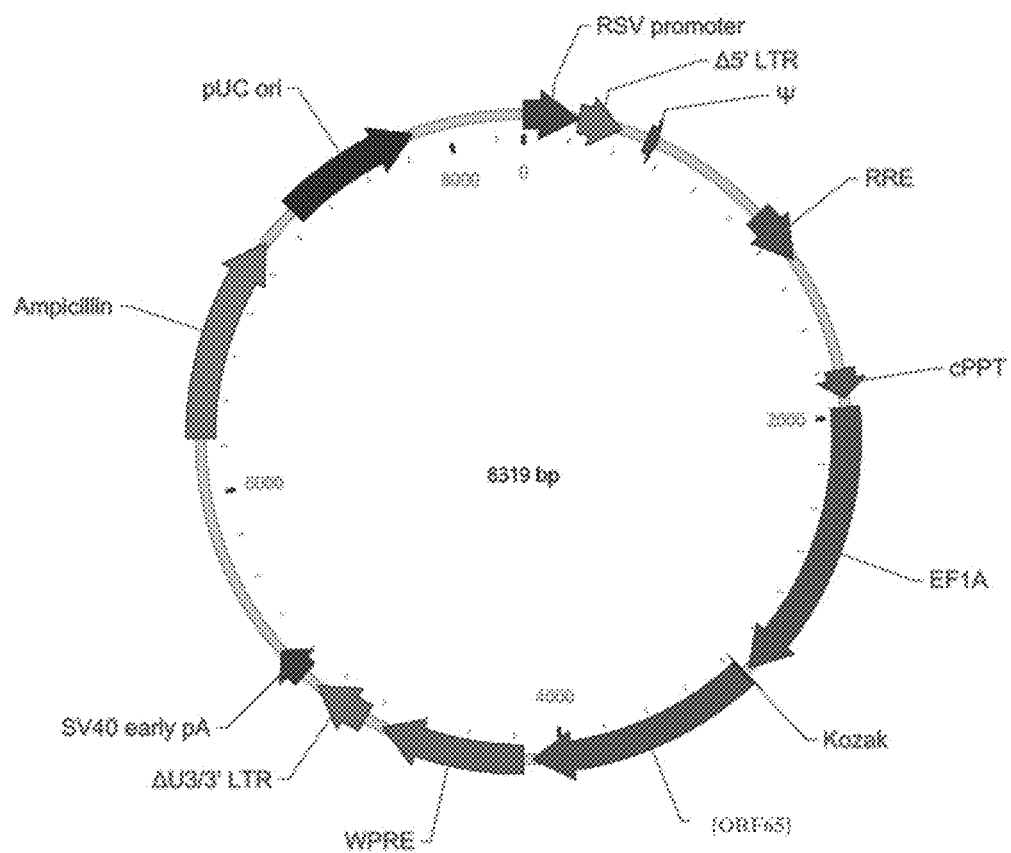
FIG. 40 shows a schematic of vector 65.

Vector 65
FIG. 40 shows a schematic of vector 65.
Table 45 below, shows the vector component name, the corresponding nucleotide position, the full name of the component and a description.

TABLE 45

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF65} | 3168-4121 | 954 | None |
| WPRE | 4160-4757 | 598 | Woodchuck hepatitis virus posttranscriptional regulatory element |
| ΔU3/3' LTR | 4839-5073 | 235 | Truncated HIV-1 3' long terminal repeat |
| SV40 early pA | 5146-5280 | 135 | Simian virus 40 early polyadenylation signal |
| Ampicillin | 6234-7094 | 861 | Ampicillin resistance gene |
| pUC ori | 7265-7853 | 589 | pUC origin of replication |

Figure 41:
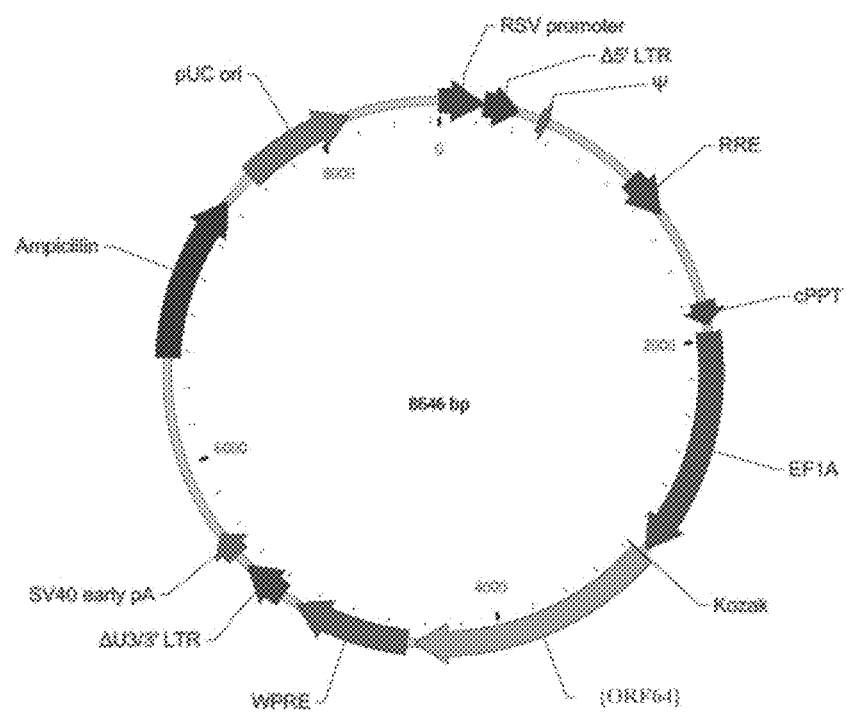
FIG. 41 shows a schematic of vector 64.

Vector 64
FIG. 41 shows a schematic of vector 64.
Table 46 below, shows the vector component name, the corresponding nucleotide position, the full name of the component and a description.

TABLE 46

| Component Name | Nucleotide Position | Size (bp) | Description |
| --- | --- | --- | --- |
| RSV promoter | 1-229 | 229 | Rous sarcoma virus enhancer/promoter |
| Δ5' LTR | 230-410 | 181 | Truncated HW-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF64} | 3168-4448 | 1281 | None |
| WPRE | 4487-5084 | 598 | Woodchuck hepatitis virus posttranscriptional regulatory element |
| ΔU3/3' LTR | 5166-5400 | 235 | Truncated HIV-1 3' long terminal repeat |
| SV40 early pA | 5473-5607 | 135 | Simian virus 40 early polyadenylation signal |
| Ampicillin | 6561-7421 | 861 | Ampicillin resistance gene |
| pUC ori | 7592-8180 | 589 | pUC origin of replication |

Figure 42:
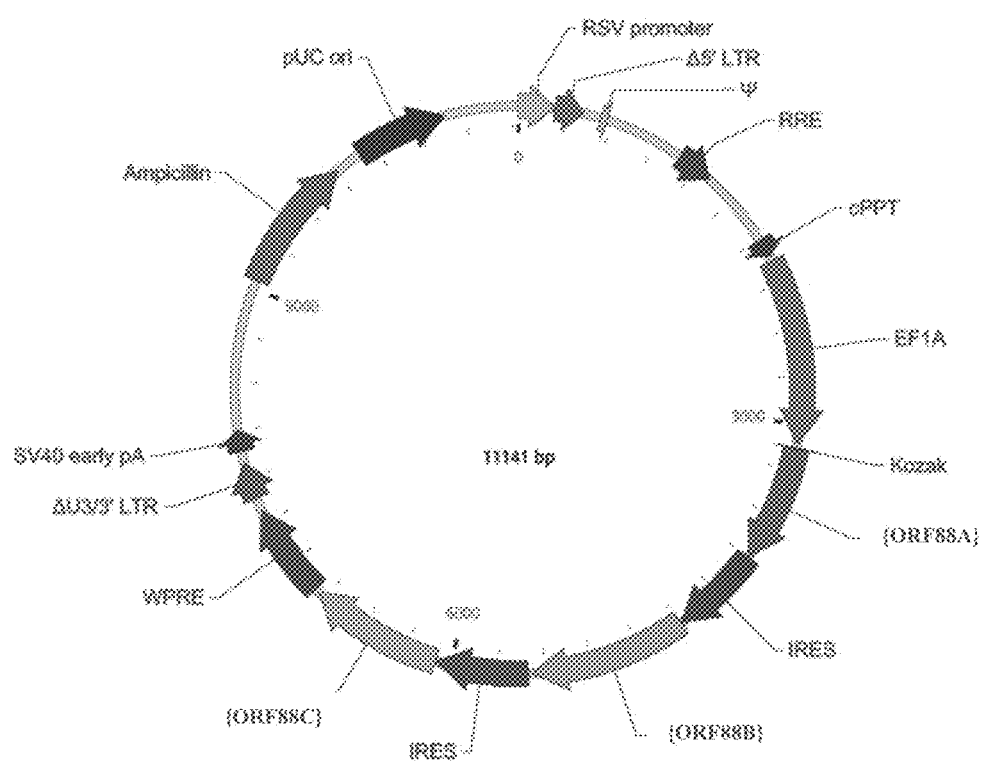
FIG. 42 shows a schematic of vector 88.

Vector 88
FIG. 42 shows a schematic of vector 88.
Table 47 below, shows the vector component name, the corresponding nucleotide position, the full name of the component and a description.

TABLE 47

| Component Name | Nucleotide Position | Size (bp) | Description |
| --- | --- | --- | --- |
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF88A} + spacer | 3159-3900 | 742 | None |
| IRES | 3901-4488 | 588 | Linker |
| {ORF88} + spacer | 4489-5485 | 997 | None |
| IRES | 5510-6097 | 588 | Linker |
| {ORF99C} | 6098-6952 | 855 | None |
| WPRE | 6982-7579 | 598 | Woodchuck hepatitis virus posttranscriptional regulatory element |
| ΔU3/3' LTR | 7661-7895 | 235 | Truncated HIV-1 3' long terminal repeat |
| SV40 early pA | 7968-8102 | 135 | Simian virus 40 early polyadenylation signal |
| Ampicillin | 9056-9916 | 861 | Ampicillin resistance gene |
| pUC ori | 10087-10675 | 589 | pUC origin of replication |

Figure 43:
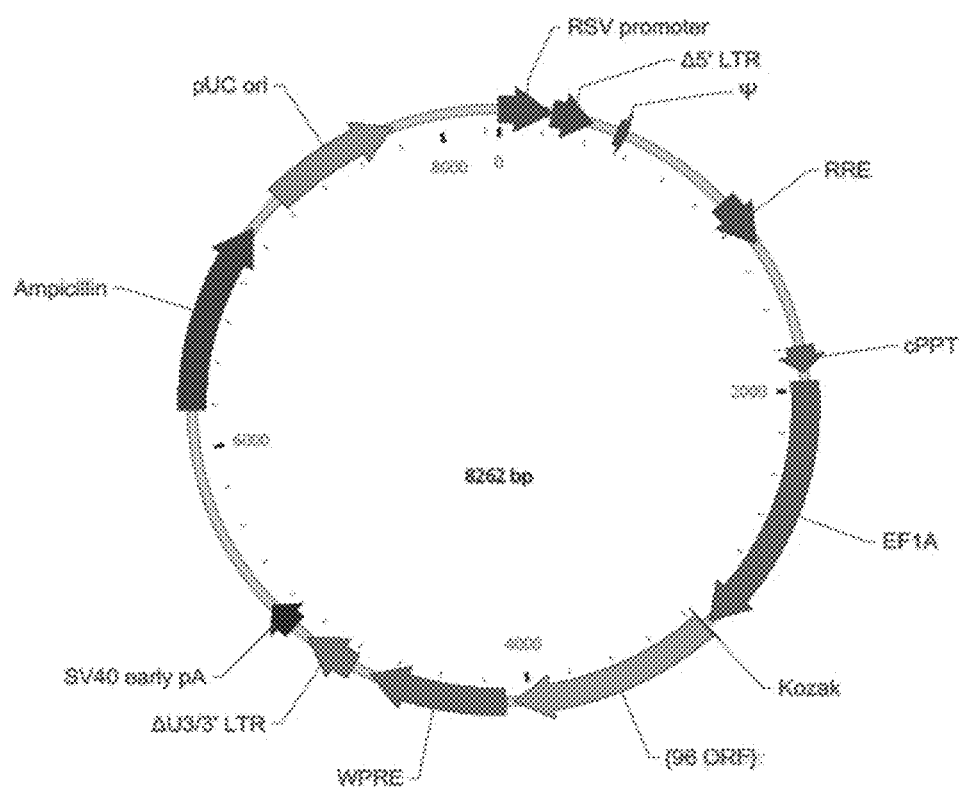
FIG. 43 shows a schematic of vector 96.

Vector 96
FIG. 43 shows a schematic of vector 96.
Table 48 below, shows the vector component name, the corresponding nucleotide position, the full name of the component and a description.

TABLE 48

| Component Name | Nucleotide Position | Size (bp) | Description |
| --- | --- | --- | --- |
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |

TABLE 48-continued

| Component Name | Nucleotide Position | Size (bp) | Description |
| --- | --- | --- | --- |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF96} | 3168-4064 | 897 | None |
| WPRE | 4103-4700 | 598 | Woodchuck hepatitis virus posttranscriptional regulatory element |
| ΔU3/3' LTR | 4782-5016 | 235 | Truncated HIV-1 3' long terminal repeat |
| SV40 early pA | 5089-5223 | 135 | Simian virus 40 early polyadenylation signal |
| Ampicillin | 6177-7037 | 861 | Ampicillin resistance gene |
| pUC ori | 7208-7796 | 589 | pUC origin of replication |

Figure 44:
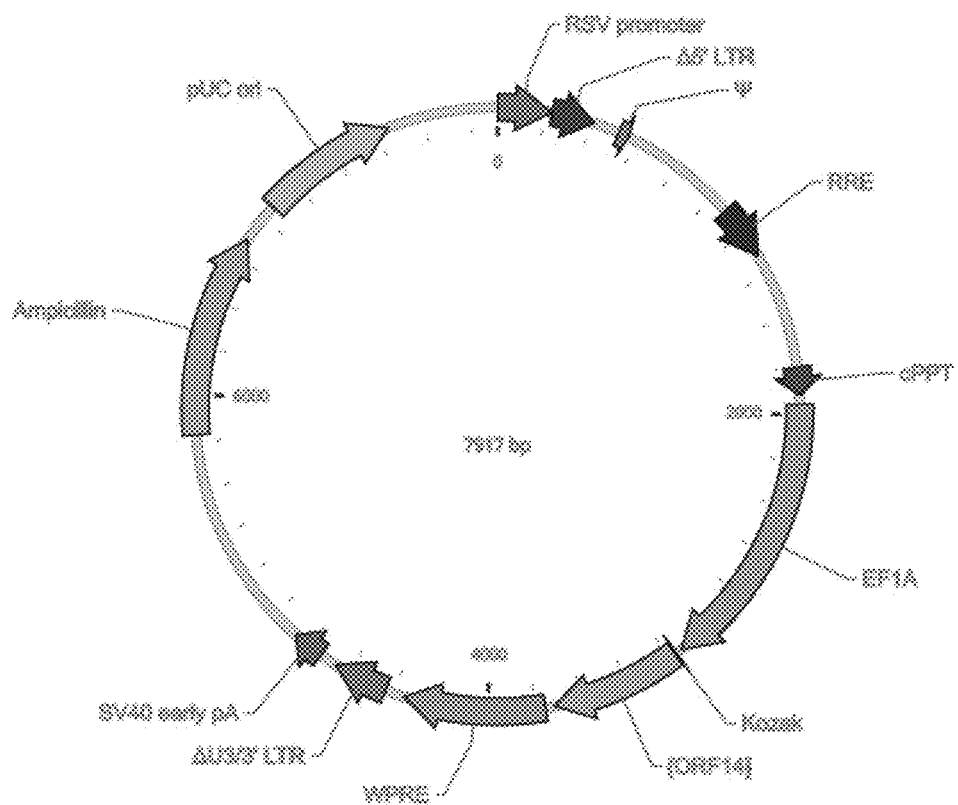
FIG. 44 shows a schematic of vector 14.

Vector 14
FIG. 44 shows a schematic of vector 14.
Table 49 below, shows the vector component name, the corresponding nucleotide position, the full name of the component and a description.

TABLE 49

| Component Name | Nucleotide Position | Size (bp) | Description |
| --- | --- | --- | --- |
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF14(183)} | 3168-3719 | 552 | None |
| WPRE | 3758-4355 | 598 | Woodchuck hepatitis virus posttranscriptional regulatory element |
| ΔU3/3' LTR | 4647-4671 | 235 | Truncated HIV-1 3' long terminal repeat |
| SV40 early pA | 4744-4878 | 135 | Simian virus 40 early polyadenylation signal |
| Ampicillin | 5832-6692 | 861 | Ampicillin resistance gene |
| pUC ori | 6863-7451 | 589 | pUC origin of replication |

Figure 45:
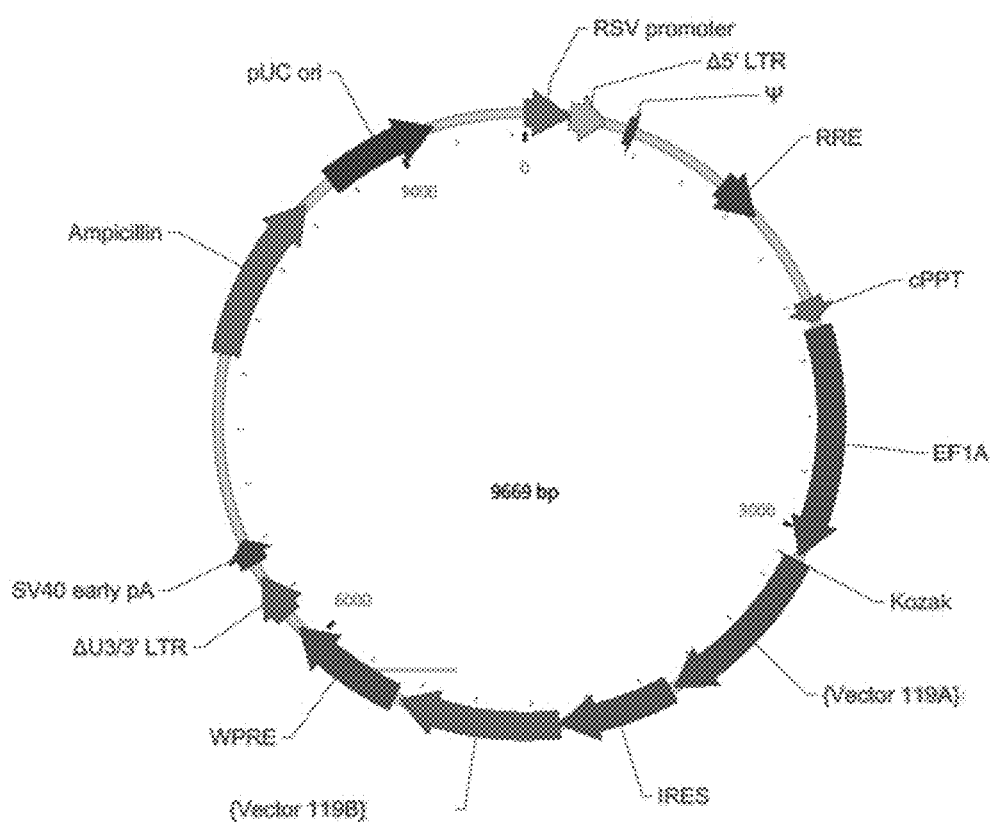
FIG. 45 shows a schematic of vector 119.

Vector 119
FIG. 45 shows a schematic of vector 119.
Table 50 below, shows the vector component name, the corresponding nucleotide position, the full name of the component and a description.

TABLE 50

| Component Name | Nucleotide Position | Size (bp) | Description |
| --- | --- | --- | --- |
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF119A} | 3159-4049 | 891 | None |
| IRES | 4074-4661 | 588 | Linker |
| {ORF119B} | 4662-5480 | 819 | None |
| WPRE | 5510-6107 | 598 | Woodchuck hepatitis virus posttranscriptional regulatory element |
| ΔU3/3' LTR | 6189-6423 | 235 | Truncated HIV-1 3' long terminal repeat |
| SV40 early pA | 6496-6630 | 135 | Simian virus 40 early polyadenylation signal |

TABLE 50-continued

| Component Name | Nucleotide Position | Size (bp) | Description |
|---|---|---|---|
| Ampicillin | 7584-8444 | 861 | Ampicillin resistance gene |
| pUC ori | 8615-9203 | 589 | pUC origin of replication |

Vector 120

Figure 46:
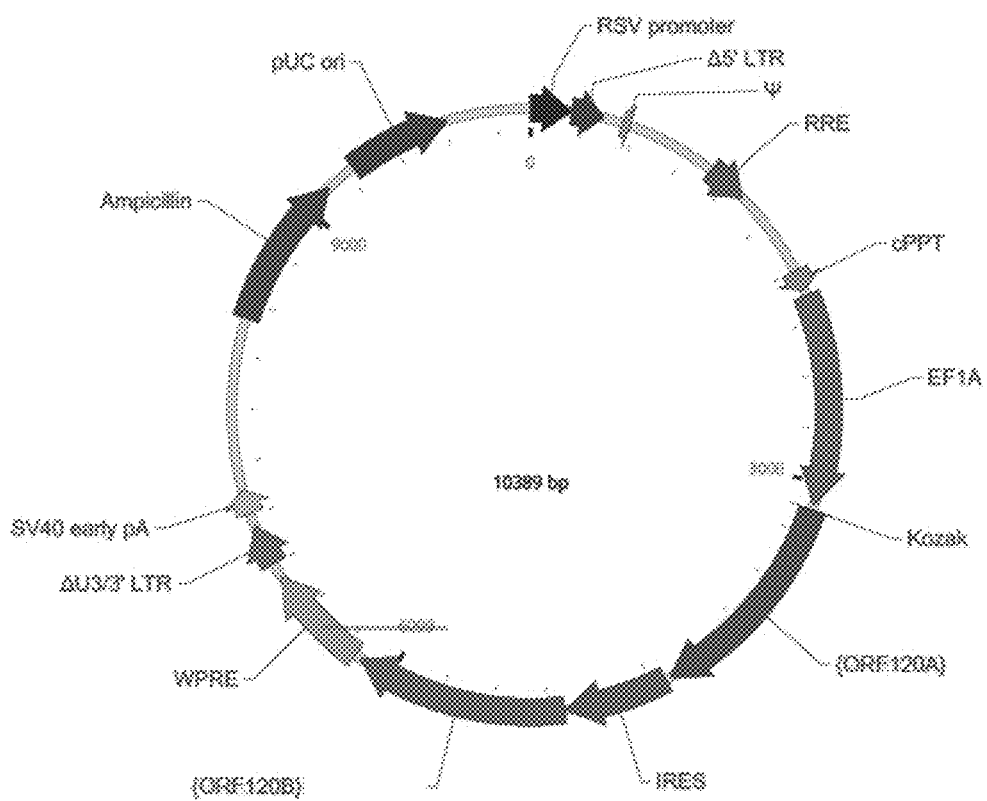
FIG. 46 shows a schematic of vector 120.

FIG. 46 shows a schematic of vector 120.

Table 51 below, shows the vector component name, the corresponding nucleotide position, the full name of the component and a description.

TABLE 51

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF120A} | 3159-4391 | 1233 | None |
| IRES | 4416-5003 | 588 | Linker |
| {ORF120B} | 5004-6200 | 1197 | None |
| WPRE | 6230-6827 | 598 | Woodchuck hepatitis virus posttranscriptional regulatory element |
| ΔU3/3' LTR | 6909-7143 | 235 | Truncated HIV-1 3' long terminal repeat |
| SV40 early pA | 7216-7350 | 135 | Simian virus 40 early polyadenylation signal |
| Ampicillin | 8304-9164 | 861 | Ampicillin resistance gene |
| pUC ori | 9335-9923 | 589 | pUC origin of replication |

Vector 45

Figure 47:
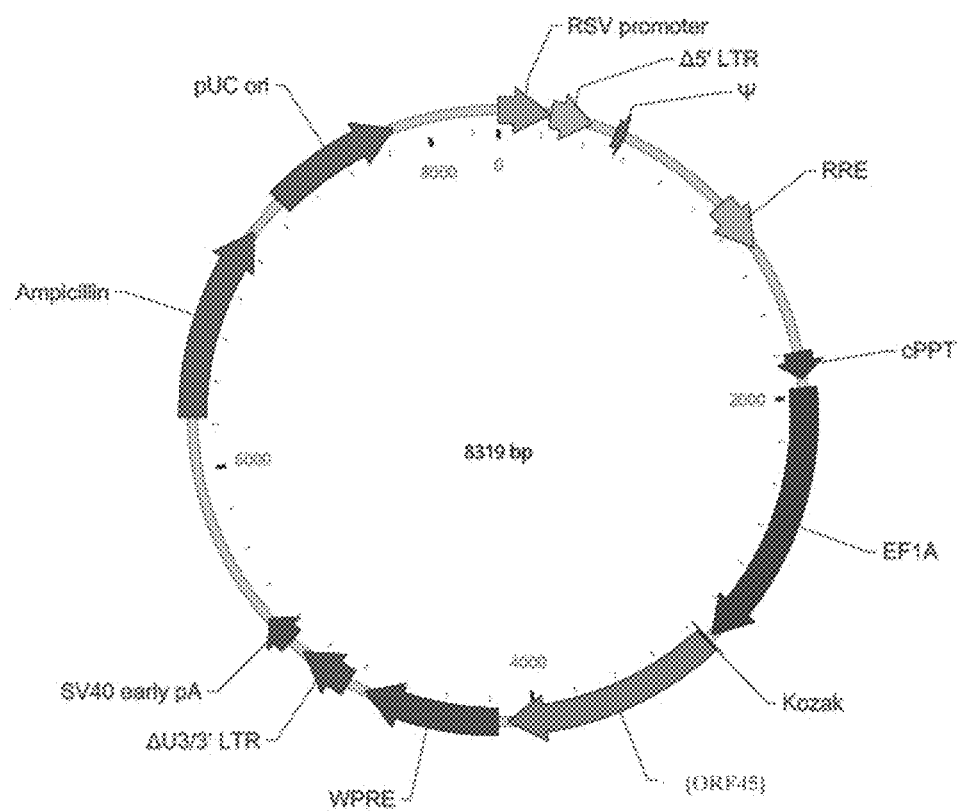
FIG. 47 shows a schematic of vector 45.

FIG. 47 shows a schematic of vector 45.

Table 52 below, shows the vector component name, the corresponding nucleotide position, the full name of the component and a description.

TABLE 52

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1959-3137 | 1179 | Human eukaryotic translation elongation factor 1 α1 promoter |
| Kozak | 3162-3167 | 6 | Kozak translation initiation sequence |
| {ORF45} | 3168-4121 | 954 | None |
| WPRE | 4160-4757 | 598 | Woodchuck hepatitis virus posttranscriptional regulatory element |
| ΔU3/3' LTR | 4839-5073 | 235 | Truncated HIV-1 3' long terminal repeat |
| SV40 early pA | 5146-5280 | 135 | Simian virus 40 early polyadenylation signal |
| Ampicillin | 6234-7094 | 861 | Ampicillin resistance gene |
| pUC ori | 7265-7853 | 589 | pUC origin of replication |

Vector 60

Figure 48:
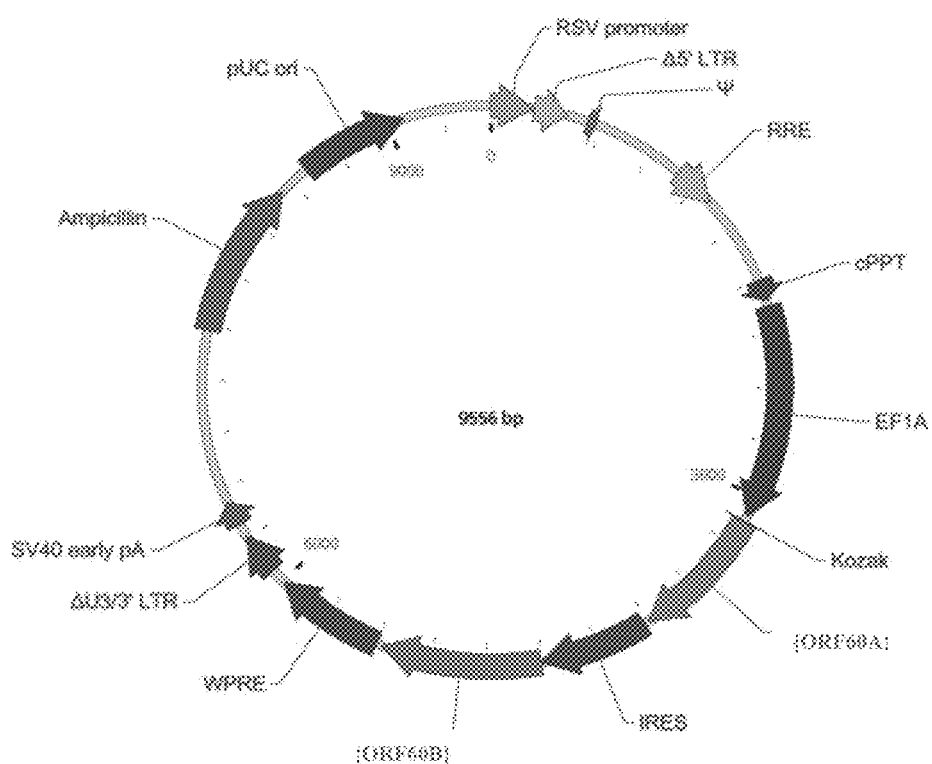
FIG. 48 shows a schematic of vector 60.

FIG. 48 shows a schematic of vector 60.

Table 53 below, shows the vector component name, the corresponding nucleotide position, the full name of the component and a description.

TABLE 53

| Component Name | Nucleotide Position | Size (bp) | Description |
| --- | --- | --- | --- |
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF60A} + Spacer | 3159-3900 | 742 | None |
| IRES | 3925-4512 | 588 | Linker |
| {ORF60B} | 4513-5367 | 855 | None |
| WPRE | 5397-5994 | 598 | Woodchuck hepatitis virus posttranscriptional regulatory element |
| ΔU3/3' LTR | 6076-6310 | 235 | Truncated HIV-1 3' long terminal repeat |
| SV40 early pA | 6383-6517 | 135 | Simian virus 40 early polyadenylation signal |
| Ampicillin | 7471-8331 | 861 | Ampicillin resistance gene |
| pUC ori | 8502-9090 | 589 | pUC origin of replication |

Figure 49:
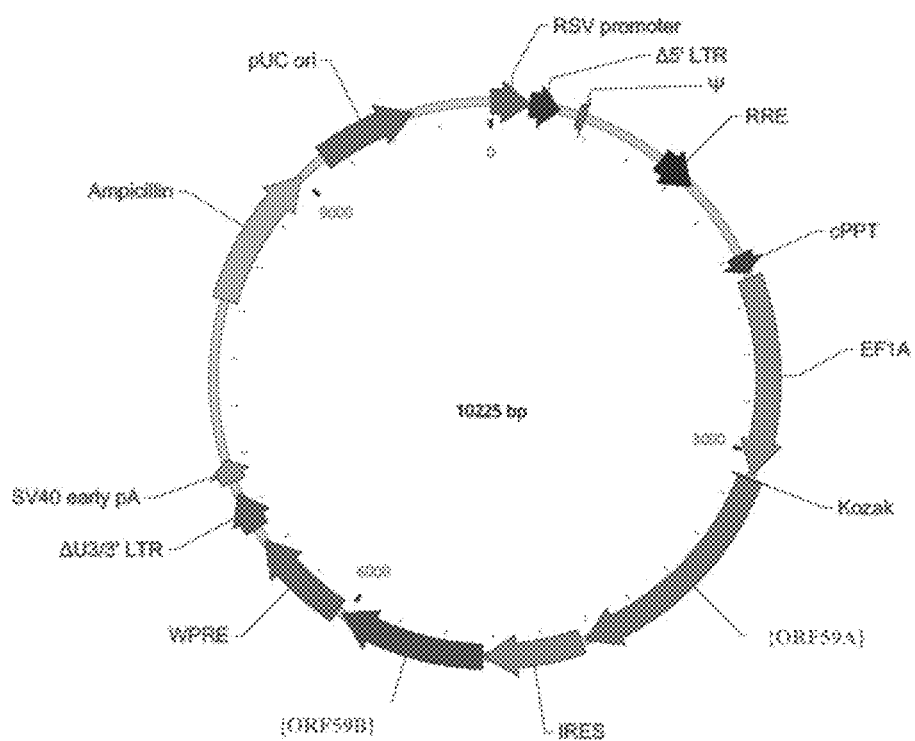
FIG. 49 shows a schematic of vector 59.

Vector 59
FIG. 49 shows a schematic of vector 59.
Table 54 below, shows the vector component name, the corresponding nucleotide position, the full name of the component and a description.

TABLE 54

| Component Name | Nucleotide Position | Size (bp) | Description |
| --- | --- | --- | --- |
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF60A} + Spacer | 3159-4548 | 1390 | None |
| IRES | 4573-5160 | 588 | Linker |
| {ORF59B} | 5161-6036 | 876 | None |
| WPRE | 6066-6663 | 598 | Woodchuck hepatitis virus posttranscriptional regulatory element |
| ΔU3/3' LTR | 6745-6979 | 235 | Truncated HIV-1 3' long terminal repeat |
| SV40 early pA | 7052-7186 | 135 | Simian virus 40 early polyadenylation signal |
| Ampicillin | 8140-9000 | 861 | Ampicillin resistance gene |
| pUC ori | 9171-9759 | 589 | pUC origin of replication |

Figure 50:
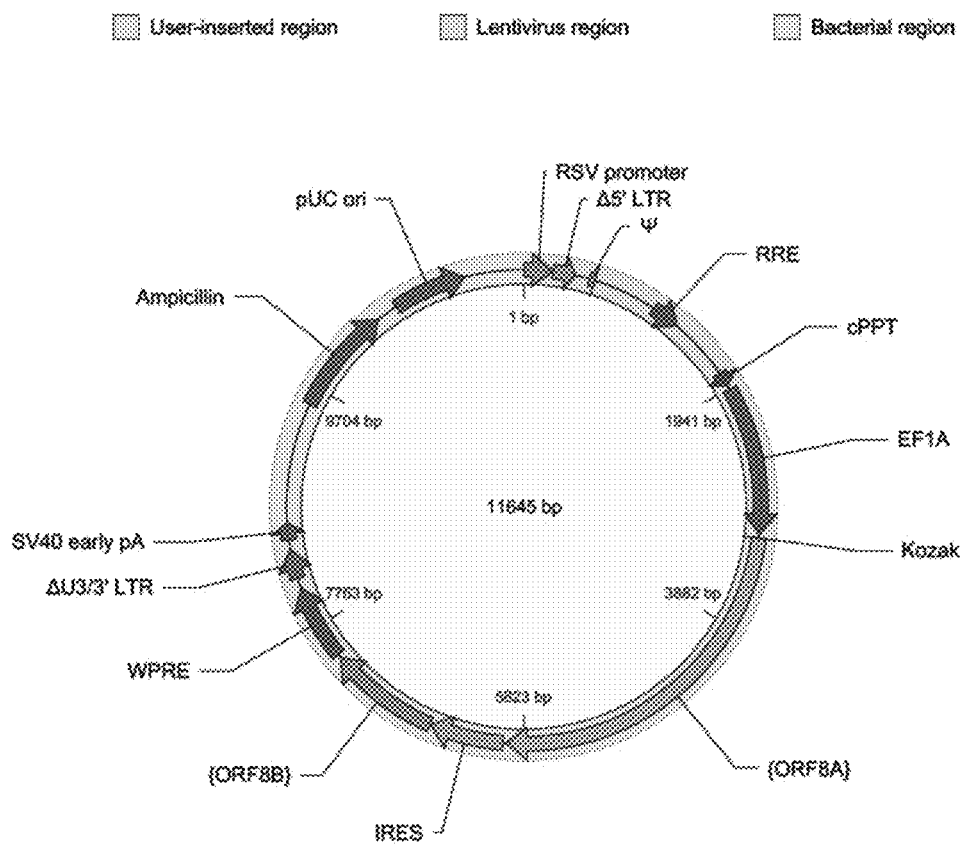
FIG. 50 shows a schematic of vector 8.

Vector 8
FIG. 50 shows a schematic of vector 8.
Table 55 below, shows the vector component name, the corresponding nucleotide position, the full name of the component and a description.

TABLE 55

| Component Name | Nucleotide Position | Size (bp) | Description |
| --- | --- | --- | --- |
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF8A} | 3159-5960 | | None |
| IRES | 5985-6572 | 588 | Linker |

TABLE 55-continued

| Component Name | Nucleotide Position | Size (bp) | Description |
|---|---|---|---|
| {ORF8B} | 6573-7456 | | None |
| WPRE | 7486-8083 | 598 | Woodchuck hepatitis virus posttranscriptional regulatory element |
| ΔU3/3' LTR | 8165-8399 | 235 | Truncated HIV-1 3' long terminal repeat |
| SV40 early pA | 8472-8606 | 135 | Simian virus 40 early polyadenylation signal |
| Ampicillin | 9560-10420 | 861 | Ampicillin resistance gene |
| pUC ori | 10591-11179 | 589 | pUC origin of replication |

Figure 51:
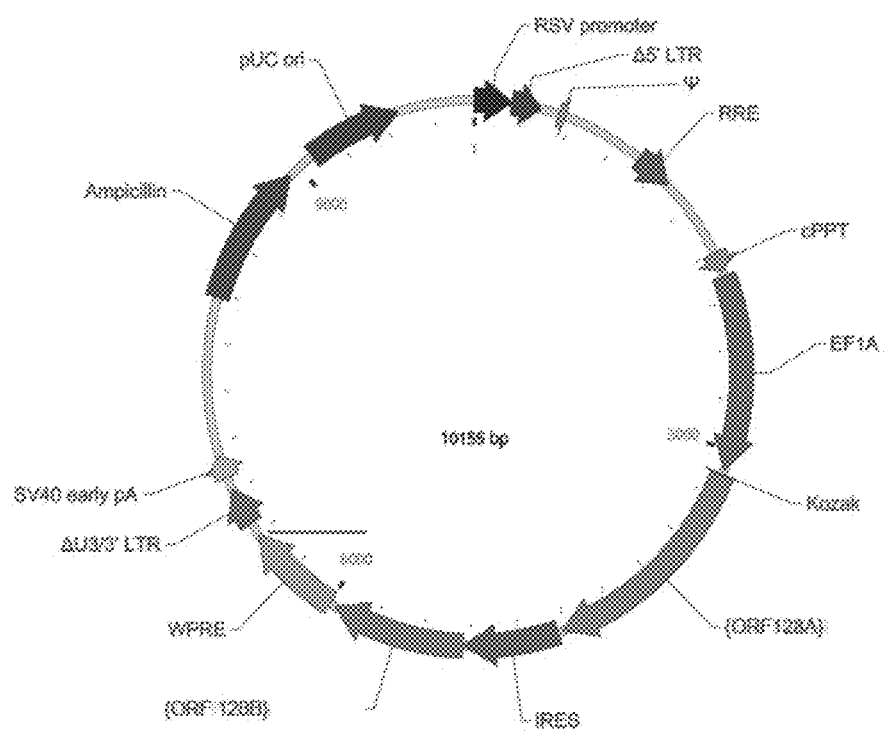
FIG. 51 shows a schematic of vector 128.

Vector 128
FIG. 51 shows a schematic of vector 128.
Table 56 below, shows the vector component name, the corresponding nucleotide position, the full name of the component and a description.

TABLE 56

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF128A} | 3159-4535 | 1377 | None |
| IRES | 4560-5147 | 588 | Linker |
| {ORF128B} | 5148-5966 | 819 | None |
| WPRE | 5996-6593 | 598 | Woodchuck hepatitis virus posttranscriptional regulatory element |
| ΔU3/3' LTR | 6675-6909 | 235 | Truncated HIV-1 3' long terminal repeat |
| SV40 early pA | 6982-7116 | 135 | Simian virus 40 early polyadenylation signal |
| Ampicillin | 8070-8930 | 861 | Ampicillin resistance gene |
| pUC ori | 9101-9689 | 589 | pUC origin of replication |

Figure 52:
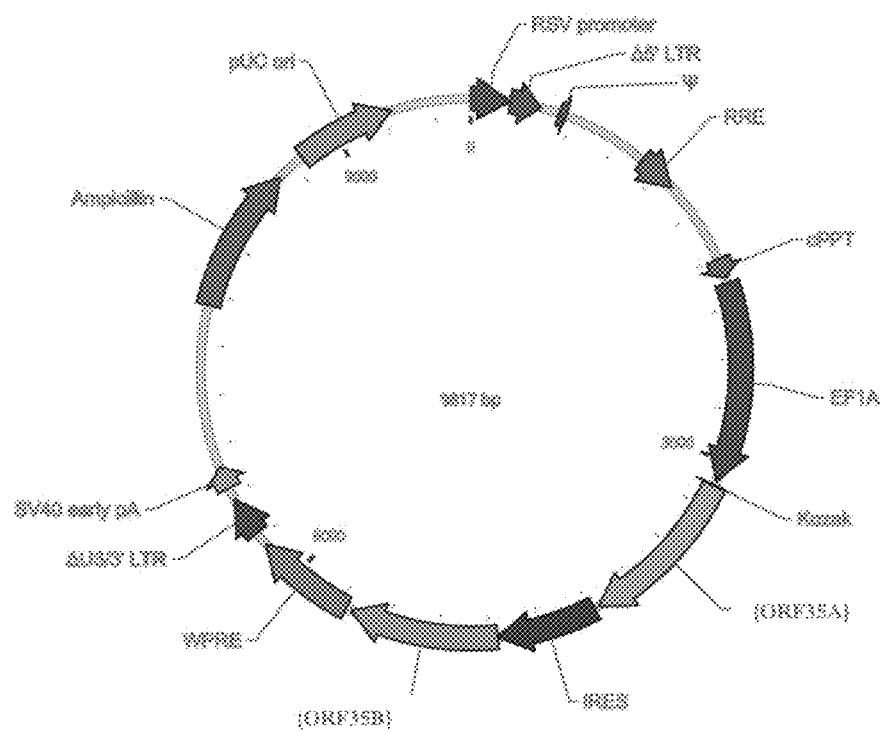
FIG. 52 shows a schematic of vector 35.

Vector 35
FIG. 52 shows a schematic of vector 35
Table 57 below, shows the vector component name, the corresponding nucleotide position, the full name of the component and a description.

TABLE 57

| Component Name | Nucleotide Position | Size (bp) | Description |
|---|---|---|---|
| RSV promoter | 1-229 | 229 | Rous sarcoma virus enhancer/promoter |
| Δ5' LTR | 230-410 | 181 | Truncated HIV-1 5' long terminal repeat |
| Ψ | 521-565 | 45 | HIV-1 packaging signal |
| RRE | 1075-1308 | 234 | HIV-1 Rev response element |
| cPPT | 1803-1920 | 118 | Central polypurine tract |
| EF1A | 1950-3128 | 1179 | Human eukaryotic translation elongation factor 1 α1 promoter |
| Kozak | 3153-3158 | 6 | Kozak translation initiation sequence |
| {ORF35A} + SPACER | 3159-4140 | 982 | None |
| IRES | 4165-4752 | 588 | Linker |
| {ORF35B} | 4753-5628 | 876 | None |
| WPRE | 5658-6255 | 598 | Woodchuck hepatitis virus posttranscriptional regulatory element |
| ΔU3/3' LTR | 6337-6571 | 235 | Truncated HIV-1 3' long terminal repeat |
| SV40 early pA | 6644-6778 | 135 | Simian virus 40 early polyadenylation signal |
| Ampicillin | 7732-8592 | 861 | Ampicillin resistance gene |
| pUC ori | 8763-9351 | 589 | pUC origin of replication |

According to one embodiment, a tumor cell line is selected for modification, and vector 2 is used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 3 is used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 4 is used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 5 is used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 6 is used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 14 is used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 18 is used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 30 is used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 15 is used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 19 is used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 22 is used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 23 is used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 29 is used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 2 and vector 3 are used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 2 and vector 4 are used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 2 and vector 5 are used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 2 and vector 6 are used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 3 and vector 4 are used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 3 and vector 5 are used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 3 and vector 6 are used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 2, vector 3 and vector 4 are used to stably integrate between 3-14 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 2, vector 3 and vector 5 are used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 2, vector 3 and vector 6 are used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 2, vector 3 and vector 6 are used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 3, vector 4 and vector 5 are used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 3, vector 4 and vector 6 are used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 2, vector 3, vector 4 and vector 5 are used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 2, vector 3, vector 4 and vector 6 are used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 2, vector 3, vector 5 and vector 6 are used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 3, vector 4, vector 5 and vector 6 are used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 2, vector 3, vector 4, vector 5 and vector 6 are used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 14 and vector 18 are used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 14 and vector 30 are used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 18 and vector 30 are used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 14, vector 18 and vector 30 are used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and one or more of vector 15, vector 19, vector 22, vector 23 and vector 29 are used to stably integrate between 3-30 immunomodulators into the cell genome, wherein at least three immunomodulators are OX40L, CD27L and CD28L, optionally wherein additional immunomodulators are selected from $R^1$-$R^{44}$ in Table 3.

According to one embodiment, a tumor cell line is selected for modification, and vector 44 is used to stably integrate between 3-25 immunomodulators into the cell genome. According to one embodiment, a tumor cell line is selected for modification, and vector 97 is used to stably integrate between 3-25 immunomodulators into the cell genome. According to one embodiment, a tumor cell line is selected for modification, and vector 84 is used to stably integrate between 3-25 immunomodulators into the cell genome. According to one embodiment, a tumor cell line is selected for modification, and vector 29 is used to stably integrate between 3-25 immunomodulators into the cell genome. According to one embodiment, a tumor cell line is selected for modification, and vector 107 is used to stably integrate between 3-25 immunomodulators into the cell genome. According to one embodiment, a tumor cell line is selected for modification, and vector 116 is used to stably integrate between 3-25 immunomodulators into the cell genome. According to one embodiment, a tumor cell line is selected for modification, and vector 86 is used to stably integrate between 3-25 immunomodulators into the cell genome. According to one embodiment, a tumor cell line is selected for modification, and vector 18 is used to stably integrate between 3-25 immunomodulators into the cell genome. According to one embodiment, a tumor cell line is selected for modification, and vector 17 is used to stably integrate between 3-25 immunomodulators into the cell genome. According to one embodiment, a tumor cell line is selected for modification, and vector 98 is used to stably integrate between 3-25 immunomodulators into the cell genome. According to one embodiment, a tumor cell line is selected for modification, and vector 5 is used to stably integrate between 3-25 immunomodulators into the cell genome. According to one embodiment, a tumor cell line is selected for modification, and vector 30 is used to stably integrate between 3-25 immunomodulators into the cell genome. According to one embodiment, a tumor cell line is selected for modification, and vector 109 is used to stably integrate between 3-25 immunomodulators into the cell genome. According to one embodiment, a tumor cell line is selected for modification, and vector 3 is used to stably integrate between 3-25 immunomodulators into the cell genome. According to one embodiment, a tumor cell line is selected for modification, and vector 4 is used to stably integrate between 3-25 immunomodulators into the cell genome. According to one embodiment, a tumor cell line is selected for modification, and vector 106 is used to stably integrate between 3-25 immunomodulators into the cell genome. According to one embodiment, a tumor cell line is selected for modification, and vector 16 is used to stably integrate between 3-25 immunomodulators into the cell genome. According to one embodiment, a tumor cell line is selected for modification, and vector 83 is used to stably integrate between 3-25 immunomodulators into the cell genome. According to one embodiment, a tumor cell line is selected for modification, and vector 31 is used to stably integrate between 3-25 immunomodulators into the cell genome. According to one embodiment, a tumor cell line is selected for modification, and vector 12 is used to stably integrate between 3-25 immunomodulators into the cell genome. According to one embodiment, a tumor cell line is selected for modification, and vector 99 is used to stably integrate between 3-25 immunomodulators into the cell genome. According to one embodiment, a tumor cell line is selected for modification, and vector 121 is used to stably integrate between 3-25 immunomodulators into the cell genome. According to one embodiment, a tumor cell line is selected for modification, and vector 105 is used to stably integrate between 3-25 immunomodulators into the cell genome. According to one embodiment, a tumor cell line is selected for modification, and vector 32 is used to stably integrate between 3-25 immunomodulators into the cell genome. According to one embodiment, a tumor cell line is selected for modification, and vector 37 is used to stably integrate between 3-25 immunomodulators into the cell genome. According to one embodiment, a tumor cell line is selected for modification, and vector 22 is used to stably integrate between 3-25 immunomodulators into the cell genome. According to one embodiment, a tumor cell line is selected for modification, and vector 19 is used to stably integrate between 3-25 immunomodulators into the cell genome. According to one embodiment, a tumor cell line is selected for modification, and vector 20 is used to stably integrate between 3-25 immunomodulators into the cell genome. According to one embodiment, a tumor cell line is selected for modification, and vector 89 is used to stably integrate between 3-25 immunomodulators into the cell genome. According to one embodiment, a tumor cell line is selected for modification, and vector 21 is used to stably integrate between 3-25 immunomodulators into the cell genome. According to one embodiment, a tumor cell line is selected for modification, and vector 23 is used to stably integrate between 3-25 immunomodulators into the cell genome. According to one embodiment, a tumor cell line is selected for modification, and vector 108 is used to stably integrate between 3-25 immunomodulators into the cell genome. According to one embodiment, a tumor cell line is selected for modification, and vector 15 is used to stably integrate between 3-25 immunomodulators into the cell genome. According to one embodiment, a tumor cell line is selected for modification, and vector 124 is used to stably integrate between 3-25 immunomodulators into the cell genome. According to one embodiment, a tumor cell line is selected for modification, and vector 65 is used to stably integrate between 3-25 immunomodulators into the cell genome. According to one embodiment, a tumor cell line is selected for modification, and vector 64 is used to stably integrate between 3-25 immunomodulators into the cell genome. According to one embodiment, a tumor cell line is selected for modification, and vector 88 is used to stably integrate between 3-25 immunomodulators into the cell genome. According to one embodiment, a tumor cell line is selected for modification, and vector 96 is used to stably integrate between 3-25 immunomodulators into the cell genome. According to one embodiment, a tumor cell line is selected for modification, and vector 14 is used to stably integrate between 3-25 immunomodulators into the cell genome. According to one embodiment, a tumor cell line is selected for modification, and vector 119 is used to stably integrate between 3-25 immunomodulators into the cell genome. According to one embodiment, a tumor cell line is selected for modification, and vector 120 is used to stably integrate between 3-25 immunomodulators into the cell genome. According to one embodiment, a tumor cell line is selected for modification, and vector 45 is used to stably integrate between 3-25 immunomodulators into the cell genome. According to one embodiment, a tumor cell line is selected for modification, and vector 60 is used to stably integrate between 3-25 immunomodulators into the cell genome. According to one embodiment, a tumor cell line is selected for modification, and vector 59 is used to stably integrate between 3-25 immunomodulators into the cell genome. According to one embodiment, a tumor cell line is selected for modification, and vector 8 is used to stably integrate between 3-25 immunomodulators into the cell genome. According to one embodiment, a tumor cell line is selected for modification, and vector 128 is used to stably integrate between 3-25 immunomodulators into the cell genome. According to one embodiment, a tumor cell line is selected for modification, and vector 35 is used to stably integrate between 3-25 immunomodulators into the cell genome. According to one embodiment, a tumor cell line is selected for modification, and vector 6 is used to stably integrate between 3-25 immunomodulators into the cell genome.

According to one embodiment, a tumor cell line is selected for modification, and one or more of vector 44, vector 29, vector 18, vector 17, vector 5, vector 16, vector 99, vector 15, vector 14, vector 45, and vector 6 are used to stably integrate between 3-14 TNF family immunomodulators into the cell genome. According to one embodiment, the 3-14 TNF family member immunomodulators are selected from those listed in Table 2.

According to one embodiment, a tumor cell line is selected for modification, and one or more of vector 97, vector 84, vector 107, vector 98, vector 30, vector 83, vector 121, and vector 119 are used to stably integrate between 3-25 Ig family immunomodulators into the cell genome. According to one embodiment, the 3-25 Ig family member immunomodulators are selected from those listed in Table 2.

According to one embodiment, a tumor cell line is selected for modification, and vector 109 is used to stably integrate between 3-25 growth factor immunomodulators into the cell genome.

According to one embodiment, a tumor cell line is selected for modification, and one or more of vector 3, vector 4, vector 32, vector 22, vector 19, vector 20, vector 89, vector 21, vector 23, vector 121, vector 65, vector 64, vector 88, vector 96, vector 60, vector 59, and vector 128 are used to stably integrate between 3-25 cytokine immunomodulators into the cell genome. According to one embodiment, the 3-25 cytokine immunomodulators are selected from those listed in Table 2.

According to one embodiment, a tumor cell line is selected for modification, and one or more of vector 37, vector 124, vector 88, and vector 8 are used to stably integrate between 3-25 receptor immunomodulators into the cell genome. According to one embodiment, the 3-25 receptor immunomodulators are selected from those listed in Table 2.

According to one embodiment, a tumor cell line is selected for modification, and one or more of vector 86, vector 106, vector 107, vector 31, vector 12, vector 105, vector 108, vector 120, and vector 35 are used to stably integrate between 3-25 other immunomodulators into the cell genome. According to one embodiment, the 3-25 other immunomodulators are selected from those listed in Table 2.

Example 4

Figure 53:
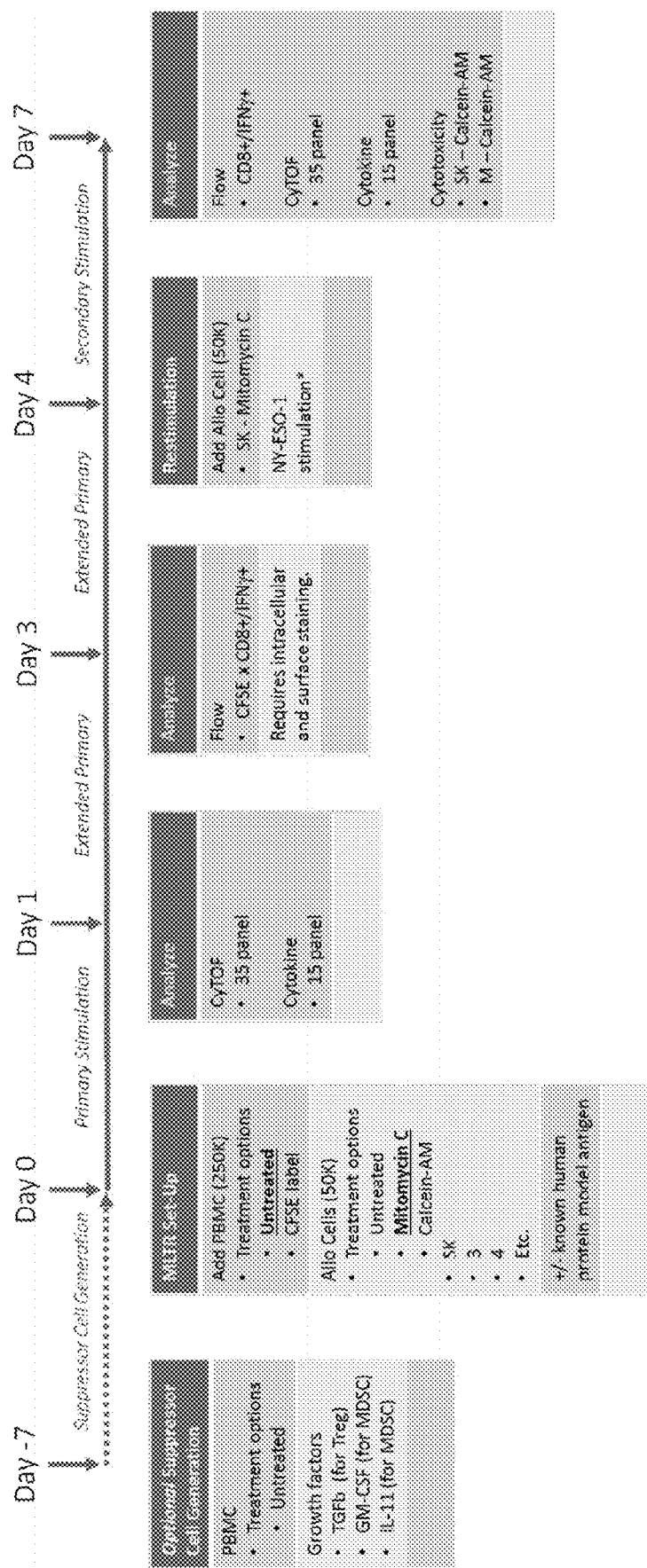
FIG. 53 is a schematic that shows the general experimental format.

Experiments were carried out to demonstrate that the immunomodulators described herein, expressed on the melanoma tumor cell line SK-MEL2 differentially impact the proliferation and differentiation of human PBMCs. FIG. 53 is a schematic that shows the general experimental design. The following allogenic cell lines were tested:

SK-MEL (Parental line) ("SK")
SK modified with Vector 2 only ("2"))
SK modified with Vector 3 only ("3")
SK modified with Vector 4 only (4")
SK modified with Vector 5 only (5")
SK modified with Vector 6 only (6"
SK modified with Vector 2 and Vector 3 ("2-3")
SK modified with Vector 3, Vector 4 and Vector 5 ("3-4-5")
SK modified with Vector 3, Vector 5 and Vector 6 ("3-5-6")
SK modified with Vector 3, Vector 4, Vector 5 and Vector 6 ("3-4-5-6")
SK modified with Vector 2, Vector 3, Vector 4, Vector 5 and Vector 6

Functional characterization of the allogeneic cell lines was performed using a primary MLTR assay, as described herein. The MLTR assay was set up with 250,000 freshly thawed PBMC and 50,000 of select engineered allogeneic cell lines. The following outputs were measured: 1) Proliferation is measured by flow on CFSE labeled PMBC; 2) Differentiation is measured by CyTOF on unlabeled PMBC; 3) Cytokine profiling is performed by Luminex.

Flow Cytometry Data

"Allorecognition" is a term used to define immunological recognition of histoincompatible antigens between genetically disparate individuals within the same species. "Direct allorecognition" is a mechanism by which recipient T cells recognize determinants on MHC-molecule-peptide complexes displayed on the surface of transplanted cells without the requirement for antigen processing by recipient APCs. The direct response can most readily be demonstrated in vitro by the mixed lymphocyte reaction in which only direct allopresentation can occur "Indirect allorecognition" refers to recognition of processed peptides of allogeneic histocompatibility antigens presented by self-MHC in a self-restricted manner. Indirect alloantigen presentation invariably results in alloresponses that are dominated by CD4+ T cells.

Approximately 10% of peripheral blood T cells bear a TCR capable of allorecognition of the allogeneic tumor type specific cells used for vaccination. This is called "direct allorecognition" and occurs early in the course of events post vaccination. Direct allorecognition targets a T cell mediated immune response against the allogeneic cells resulting in their death and release of tumor type specific neoantigens and shared normal antigens. These tumor neoantigens (and normal antigens) are taken up by host antigen presenting cells, processed and presented in the context of host HLA. This "indirect allorecognition" occurs late in the course of events post vaccination. The TCRs activated during indirect allorecognition are different from those involved earlier during direct allorecognition, but both processes occur in a local environment repeatedly exposed to allogeneic cells bearing high density immunomodulators (e.g. monthly vaccinations).

Epitope spreading is a process of expanding an immune response to include distinct but closely related T cell epitopes. This is generally described as a maturation of the immune response. The differential maturation of the immune response against tumor neoantigens versus self-antigens is driven by the fact that tolerance mechanisms are in place to differentially protect against immune responses against self-antigens. While self-tolerance can be broken, it is more difficult than the response against a tumor neoantigen.

Without being limited by theory, since all tumors of a given type share many antigens, the T-cell mediated response initially driven by indirect allorecognition of the immune response will cross react against the host tumor of the same type. According to some embodiments, since the tumor microenvironment may provide an insurmountable negative immunomodulatory hurdle, this approach may be used in combination with checkpoint inhibitors in the setting of minimal residual disease after a debulking therapy (e.g. surgery, radiation or oncolytic viruses).

The experiments described herein use hPBMC Activation via Direct Allorecognition versus Pan-Stimulation. Primary human pan-T cells include CD4 and CD8 T cells as well as some gamma/delta T cell subsets. In Pan-Stimulation, non-target cells, i.e., monocytes, neutrophils, eosinophils, B cells, stem cells, dendritic cells, NK cells, granulocytes, or erythroid cells are labeled by using a cocktail of biotin-conjugated antibodies. T cells are isolated from peripheral blood (PB) mononuclear cells (MNCs) using the negative immunomagnetic separation technique without the use of columns. Cells are untouched by the separation process and ready for downstream usage. It was found that hPBMC activation via direct allorecognition display a fundamentally different response to tumor cells. Three key observations were made with regard to hPBMC activation by this method: 1) that ~10% of hPBMC proliferate compared to ~50% with anti-CD3/CD28 treatment; 2) it induces more cell divisions than anti-CD3/CD28 treatment; 3) it induces a more varied morphology.

Figure 54:
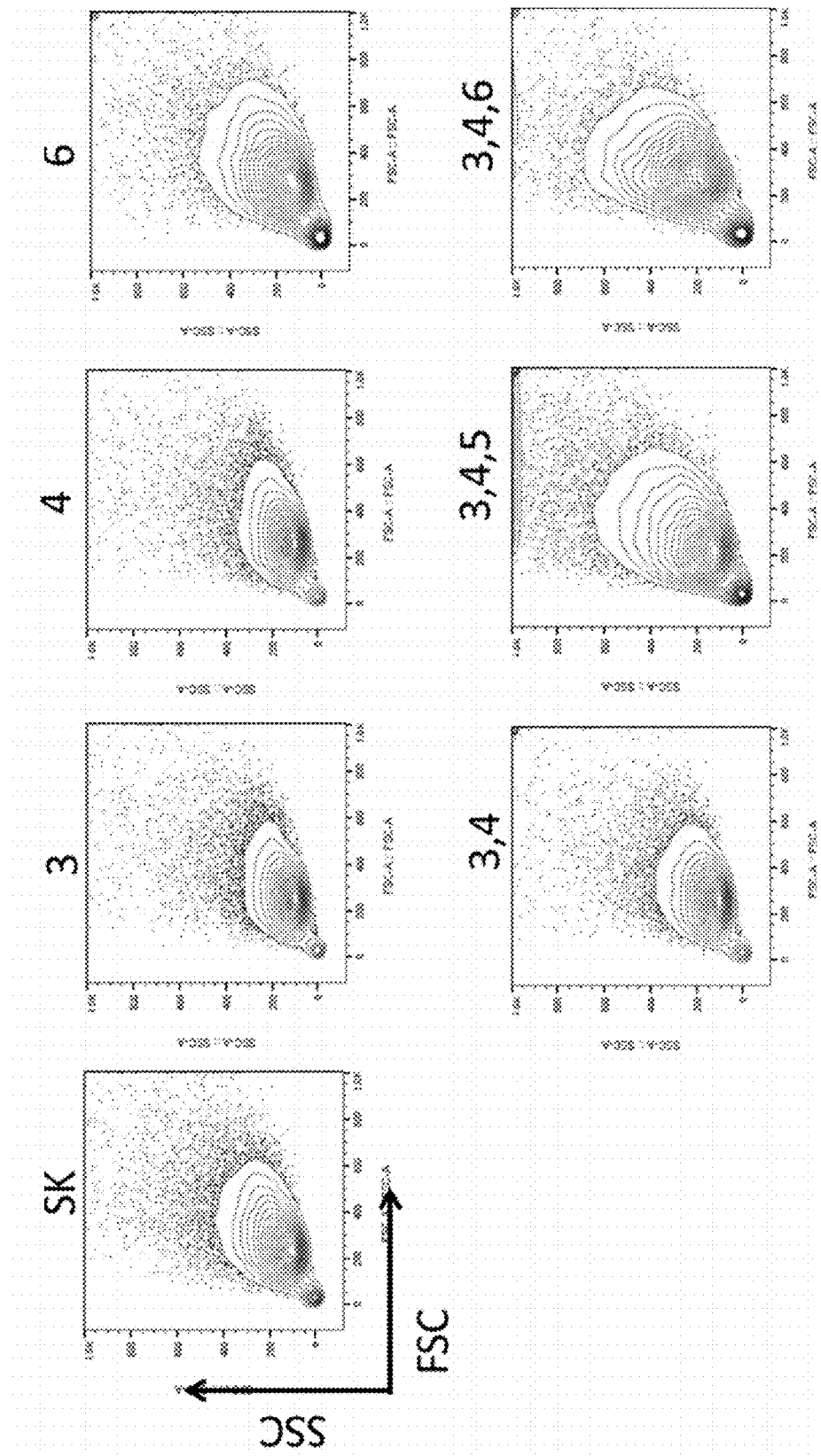
FIG. 54 is a panel of graphs that show the results of flow cytometry experiments. Forward (FSC) and side scatter (SSC) plots for size and granularity. SK lines are represented by a number code; SK, unmodified parent line; 3, secreted GM-CSF and membrane expressed FLT-3L; 4, secreted FLT3L and membrane expressed GM-CSF; 5, a non-cleavable form of CD40L; 6, a non-cleavable form of TNF-a; 3-4 is a combination of 3 and 4; 3-4-5 is a combination of 3,4 and 5; and 3-4-6 is a combination of 3,4 and 6. Cell lines 6, 3-4-5 and 3-4-6 display a larger and more granular phenotype likely owing to the presence of receptors for TNF-a and CD40L on cells of epithelial origin

FIG. 54 is a panel of graphs that show the results of flow cytometry experiments. Forward (FSC) and side scatter (SSC) plots for size and granularity are shown. SK tumor cell lines are represented by a number code; SK, unmodified parent line; vector 3, secreted GM-CSF and membrane expressed FLT-3L; vector 4, secreted FLT3L and membrane expressed GM-CSF; vector 5, a non-cleavable form of CD40L; vector 6, a non-cleavable form of TNF-a; 3-4 is a combination of vectors 3 and 4; 3-4-5 is a combination of vectors 3,4 and 5; and 3-4-6 is a combination of vectors 3,4 and 6. Cell lines 6, 3-4-5 and 3-4-6 display a larger and more granular phenotype likely owing to the presence of receptors for TNF-a and CD40L on cells of epithelial origin.

Figure 55:
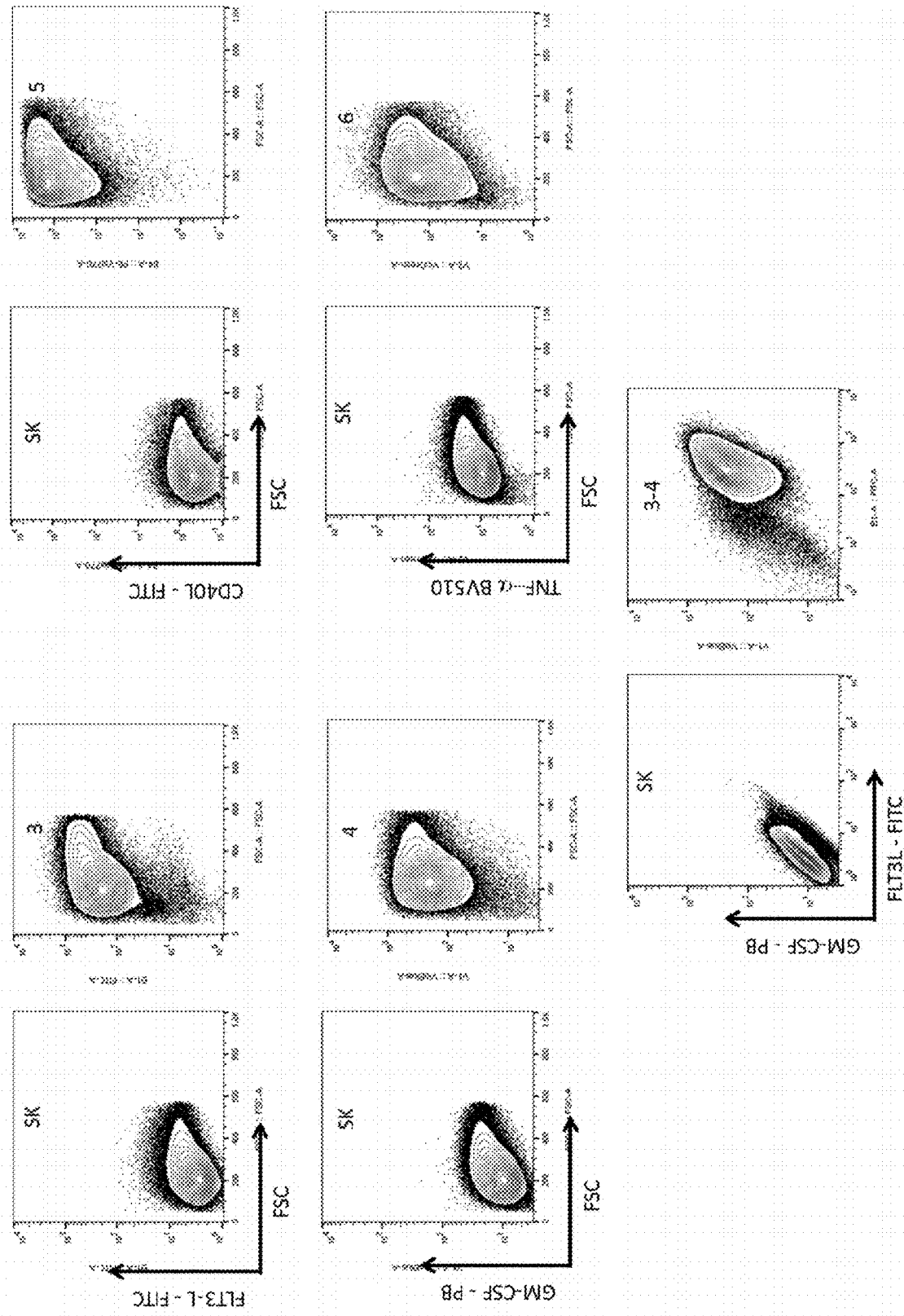
FIG. 55 is a panel of graphs that show representative flow cytometry stains for CD4 cells in hPBMC in response to the indicated engineered cell lines with the indicated immunomodulators. SK cell lines are represented by the following code; SK, unmodified parent line; 2, membrane expressed IgG1, 3, secreted GM-CSF and membrane expressed FLT-3L; 4, secreted FLT3L and membrane expressed GM-CSF; 5, a non-cleavable form of CD40L; and 6, a non-cleavable form of TNF.

FIG. 55 is a panel of graphs that show representative flow cytometry stains for the indicated engineered surface markers; GM-CSF, FLT3L, TNF-a and CD40L. SK tumor cell lines are represented by a number code; SK, unmodified parent line; vector 3, secreted GM-CSF and membrane expressed FLT-3L; vector 4, secreted FLT3L and membrane expressed GM-CSF; 5, a non-cleavable form of CD40L; vector 6, a non-cleavable form of TNF-a; 3-4 is a combination of vectors 3 and 4; 3-4-5 is a combination of vectors 3,4 and 5; and 3-4-6 is a combination of vectors 3, 4 and 6.

Figure 56:
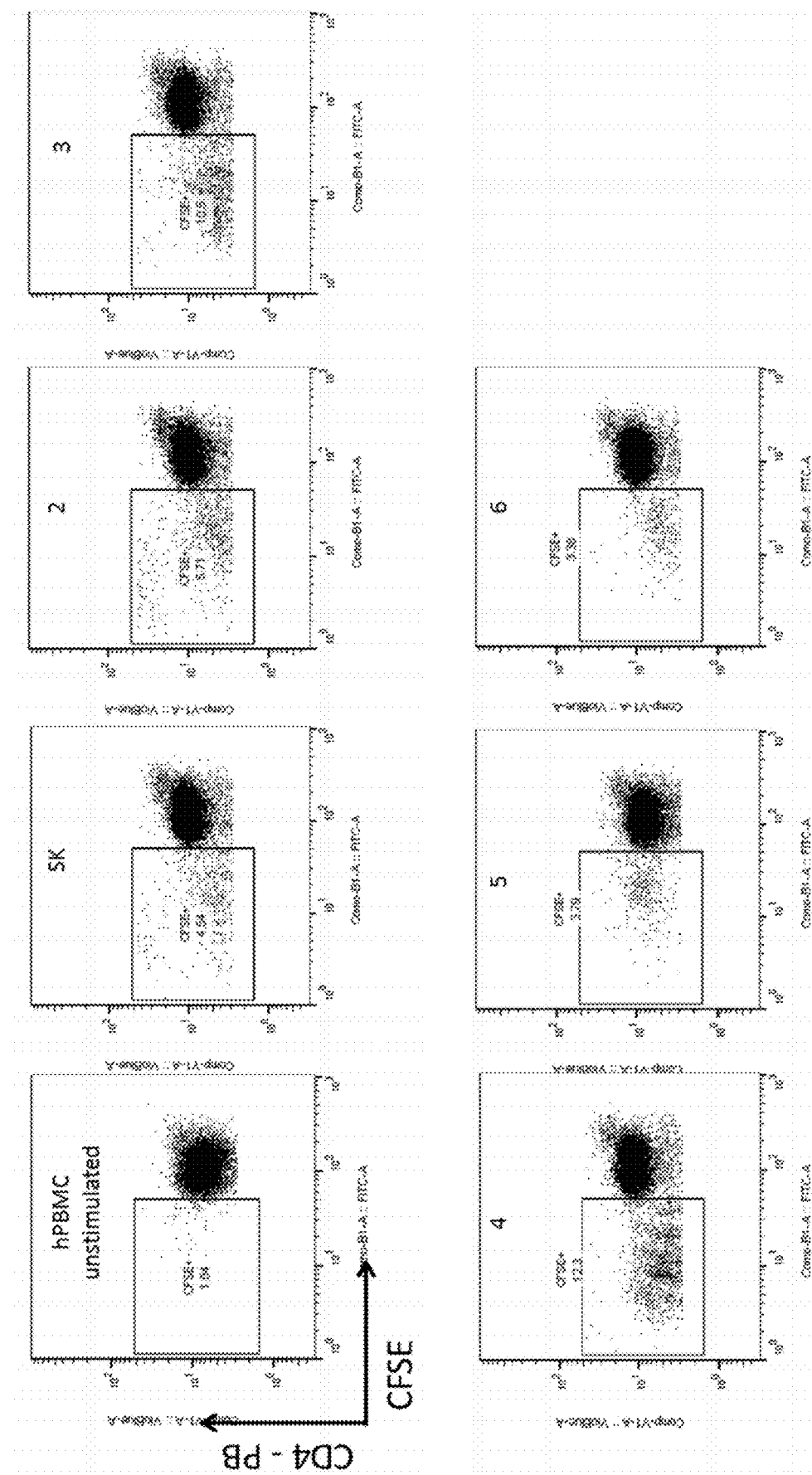
FIG. 56 is a panel of graphs that show representative flow cytometry stains for the indicated engineered surface markers; GM-CSF, FLT3L, TNF-a and CD40L. SK lines are represented by a number code; SK, unmodified parent line; 3, secreted GM-CSF and membrane expressed FLT-3L; 4, secreted FLT3L and membrane expressed GM-CSF; 5, a non-cleavable form of CD40L; 6, a non-cleavable form of TNF-a; 3-4 is a combination of 3 and 4; 3-4-5 is a combination of 3,4 and 5; and 3-4-6 is a combination of 3,4 and 6.

FIG. 56 is a panel of graphs that show representative flow cytometry stains for the indicated engineered surface markers; GM-CSF, FLT3L, TNF-a and CD40L. SK tumor cell lines are represented by a number code; SK, unmodified parent line; vector 3, secreted GM-CSF and membrane expressed FLT-3L; vector 4, secreted FLT3L and membrane expressed GM-CSF; vector 5, a non-cleavable form of CD40L; vector 6, a non-cleavable form of TNF-a; 3-4 is a combination of vectors 3 and 4; 3-4-5 is a combination of vectors 3,4 and 5; and 3-4-6 is a combination of vectors 3,4 and 6.

CyTOF Data

CyTOF mass cytometry single-cell phenotype analysis of hPBMC response to SK melanoma cells with modification by expression of immunomodulatory factors is shown in FIG. 14A and FIG. 14B. The SK melanoma cell line and hPBMCs were cultured for 24 hours. Cells were harvested from cultures and stained with a 32-marker CyTOF antibody panel to detect multiple immune cell subsets as well as cell-surface and intracellular phenotyping markers. CyTOF mass cytometry data was generated on a Helios instrument. The data were normalized for signal using equilibration beads. Cell staining data were analyzed using Cytobank—a cloud computing suite for CyTOF data analysis that includes cell gating functions and an array of data visualization methods.

Figure 57A:
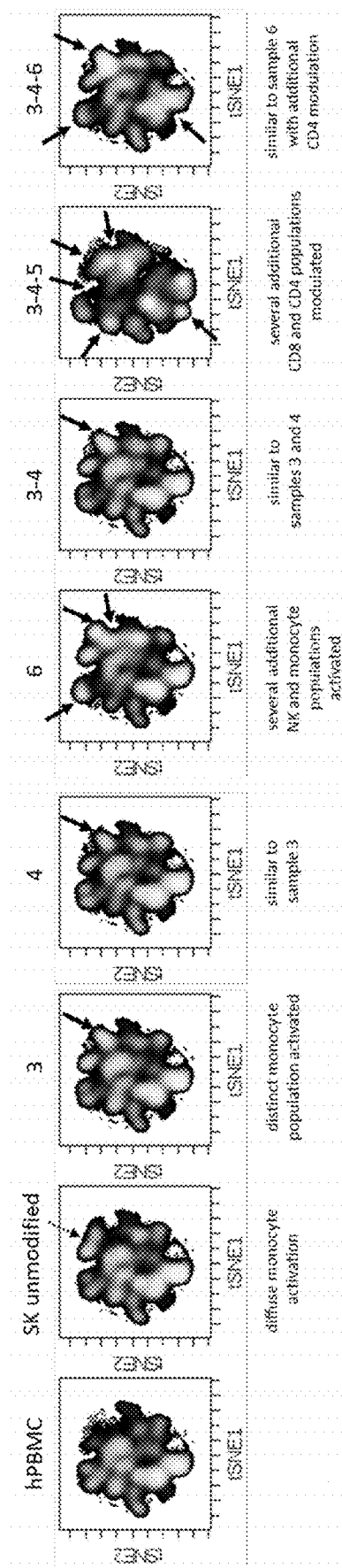
FIG. 57A and FIG. 57B show the results of CyTOF mass cytometry single-cell phenotype analysis of hPBMC response to SK melanoma cells with modification by expression of immunomodulatory factors.
Figure 57B:
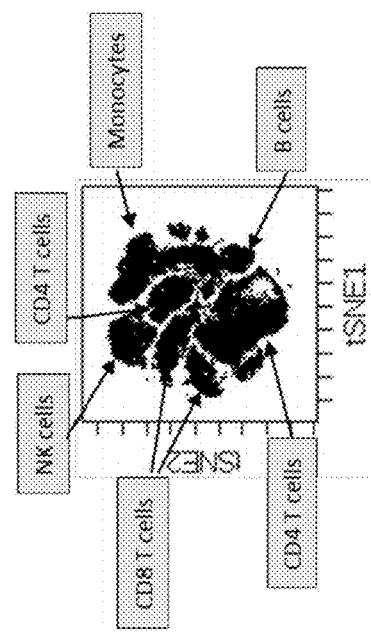

The data shown in FIG. 57A and FIG. 57B were plotted using viSNE, which is a dimensional reduction method that converts multidimensional staining signals from single cells into plots for visualization. FIG. 57A shows viSNE density contour plots of CyTOF staining data showing relative changes in immune cell subset abundance and phenotype. FIG. 57B shows single-cell phenotype analysis. viSNE density contour plots were generated by viSNE from ungated total PBMCs that were cultured with SK melanoma cells or modified SK melanoma cells. The plots illustrate relative changes in cell density for hPBMC immune cell subsets. The inserted viSNE plot identifies the immune cell subsets that are found within the clusters of the viSNE density plots. The arrows in the density contour plots point to the visible changes in immune cell subsets between hPBMCs, SK cells, and the modified SK cells. SK tumor cell lines are represented by a number code; SK, unmodified parent line; vector 3, secreted GM-CSF and membrane expressed FLT-3L; vector 4, secreted FLT3L and membrane expressed GM-CSF; vector 5, a non-cleavable form of CD40L; vector 6, a non-cleavable form of TNF-a; 3-4 is a combination of vectors 3 and 4; 3-4-5 is a combination of vectors 3,4 and 5; and 3-4-6 is a combination of vectors 3,4 and 6.

Figure 58A:
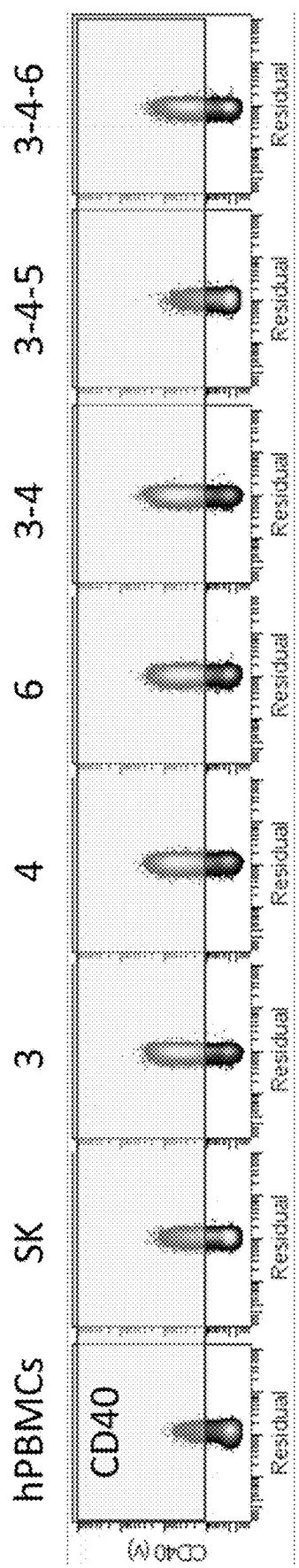
FIG. 58A-FIG. 58D shows CyTOF monocyte cluster analysis of hPBMCs indicating changes in the activation markers CD40 (FIG. 58A), CD86 (FIG. 58B), CD69 (FIG. 58C) and CD25 (FIG. 58D) expression following 1 day stimulation with the indicated genetically modified SK lines at a 1:5 cell ratio. SK lines are represented by a number code; SK, unmodified parent line; 3, secreted GM-CSF and membrane expressed FLT-3L; 4, secreted FLT3L and membrane expressed GM-CSF; 5, a non-cleavable form of CD40L; 6, a non-cleavable form of TNF-a; 3-4 is a combination of 3 and 4; 3-4-5 is a combination of 3,4 and 5; and 3-4-6 is a combination of 3,4 and 6.
Figure 58B:
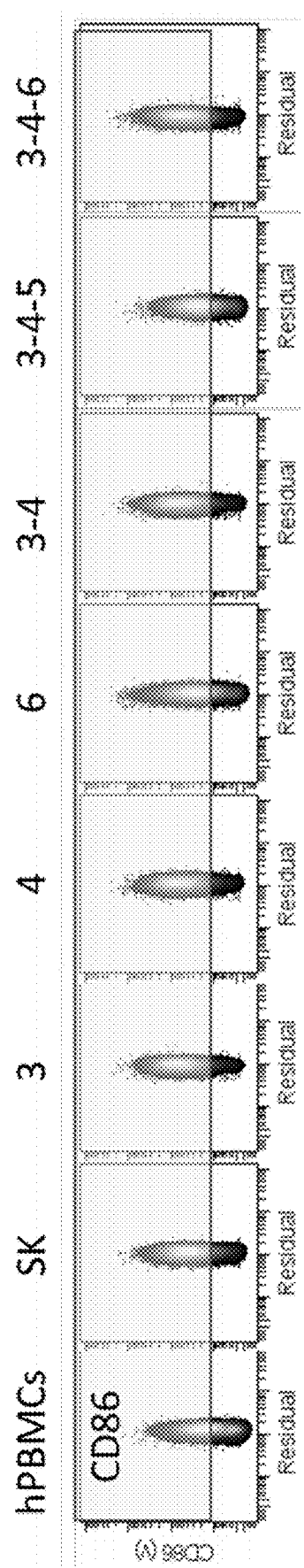
Figure 58C:
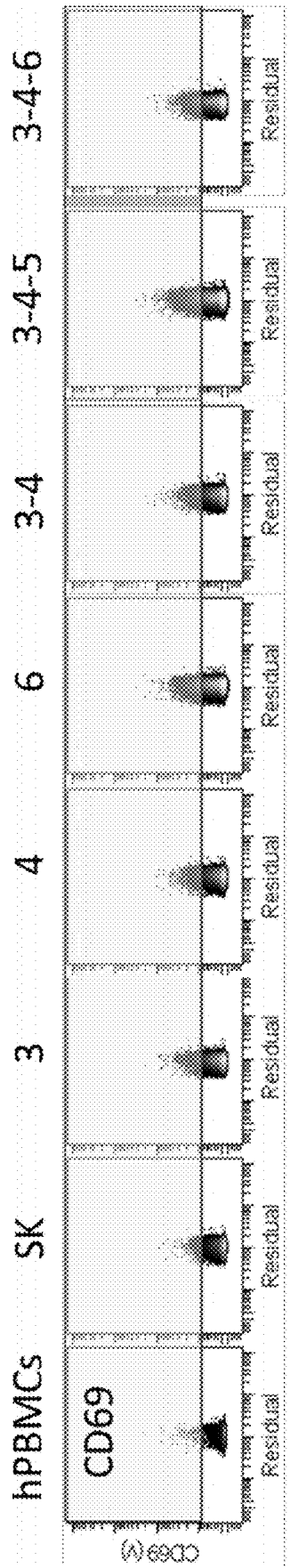
Figure 58D:
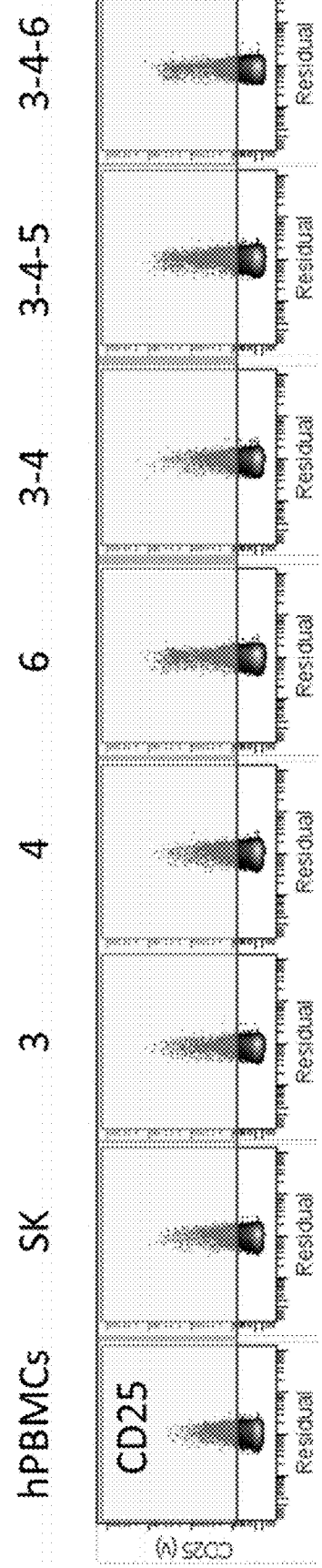
Figure 58E:
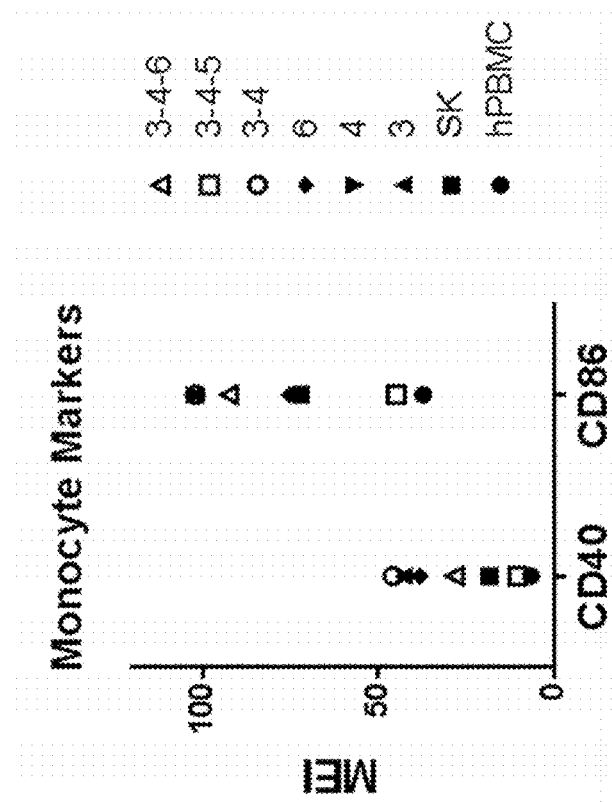
FIG. 58E shows CyTOF monocyte cluster analysis of hPBMCs indicating relative median expression levels (MEI) of monocyte markers CD40 and CD86.
Figure 58F:
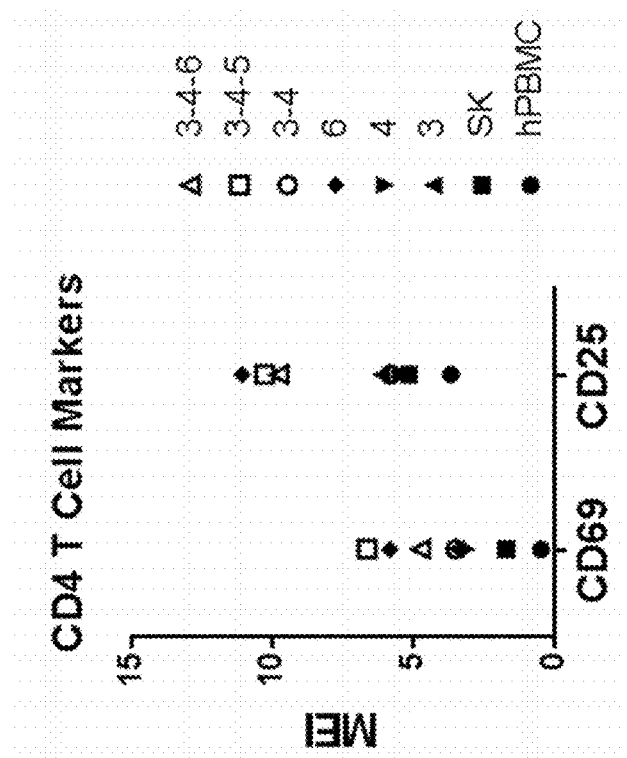
FIG. 58F shows CyTOF monocyte cluster analysis of hPBMCs indicating relative median expression index (MEI) of CD4 T cell markers CD69 and CD25.

FIG. 58A-FIG. 58D show CyTOF monocyte cluster analysis of hPBMC indicating changes in the activation markers CD40 (FIG. 58A), CD86 (FIG. 58B), CD69 (FIG. 58C) and CD25 (FIG. 58D) expression following 1 day stimulation with the indicated genetically modified SK lines at a 1:5 cell ratio. FIG. 58E shows CyTOF monocyte cluster analysis of hPBMC indicating relative median expression levels of monocyte markers CD40 and CD86. FIG. 58F shows CyTOF monocyte cluster analysis of hPBMC indicating relative median expression index (MEI) of CD4 T cell markers CD69 and CD25. SK tumor cell lines are represented by a number code; SK, unmodified parent line; vector 3, secreted GM-CSF and membrane expressed FLT-3L; vector 4, secreted FLT3L and membrane expressed GM-CSF; vector 5, a non-cleavable form of CD40L; vector 6, a non-cleavable form of TNF-a; 3-4 is a combination of vectors 3 and 4; 3-4-5 is a combination of vectors 3,4 and 5; and 3-4-6 is a combination of vectors 3,4 and 6.

Cytokine Data

Figure 59:
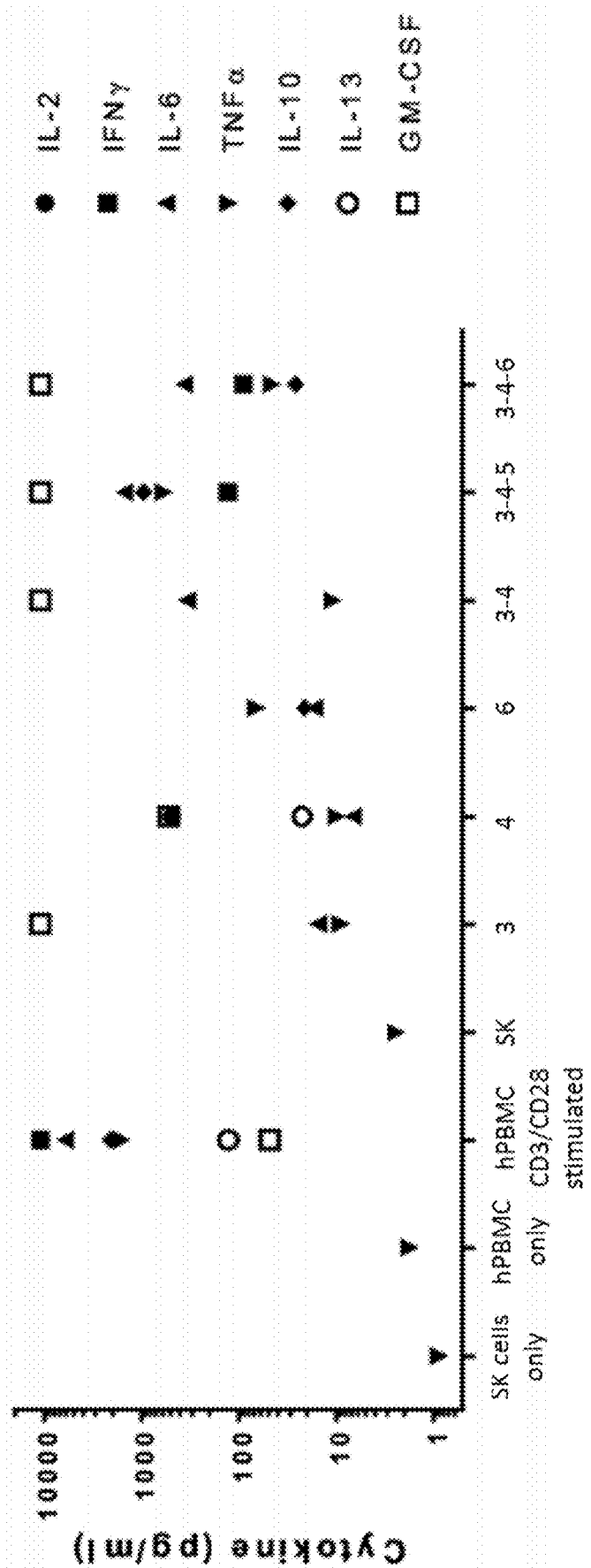
FIG. 59 is a graph that shows the results of luminex multiplex cytokine profiling of human PBMC responses to SK parent line and genetically modified SK lines. Control cultures included SK cells alone, hPBMCs alone, and hPBMCs stimulated with a mixture of anti-CD3 and anti-CD28 antibodies (1 µg/ml final concentration). Symbols indicate cytokine levels in pg/ml as estimated from a standard curve using recombinant cytokines. Absence of symbols indicates the cytokine was not detected. SK lines are represented by a number code; SK, unmodified parent line; 3, secreted GM-CSF and membrane expressed FLT-3L; 4, secreted FLT3L and membrane expressed GM-CSF; 5, a non-cleavable form of CD40L; 6, a non-cleavable form of TNF-a; 3-4 is a combination of 3 and 4; 3-4-5 is a combination of 3,4 and 5; and 3-4-6 is a combination of 3,4 and 6.

Luminex multiplex cytokine profiling of human PBMC responses to SK parent line and genetically modified SK lines is shown in FIG. 59. SK cells or the indicated modified cell lines were cultured for 24 hours with human PBMCs at a 1:5 cell ratio. Control cultures included SK cells alone, hPBMCs alone, and hPBMCs stimulated with a mixture of anti-CD3 and anti-CD28 antibodies (1 µg/ml final concentration). Supernatants were screened for cytokine levels using a multiplexed Luminex bead array assay to detect IL-1a, IL-1b, IL-1ra, IL-2, IL-4, IL-6, IL-8, IL-10, IL-12p40, IL-12p70, IL-13, IL-17A, IL-23, TNFa, IFNg, G-CSF, GM-CSF, MIP1b, MCP-1, Rantes, Tweak, and TREM-1. Those cytokines found to be specifically induced by the SK parent line and modified SK lines are shown in the plots. Symbols indicate cytokine levels in pg/ml as estimated from a standard curve using recombinant cytokines. Absence of symbols indicates the cytokine was not detected. SK lines are represented by a number code; SK, unmodified parent line; 3, secreted GM-CSF and membrane expressed FLT-3L; 3, secreted FLT3L and membrane expressed GM-CSF; 5, a non-cleavable form of CD40L; 6, a non-cleavable form of TNF-a; 3-4 is a combination of 3 and 4; 3-4-5 is a combination of 3,4 and 5; and 3-4-6 is a combination of 3,4 and 6.

The described study provides a proof of concept that the complex combinatorial space of immunomodulators can be rapidly and efficiently assessed using an all human in vitro MLTR assay.

Example 5

Experiments were carried out to determine the effect of the immunomodulators described herein, expressed on the tumor cell line SK-MEL2, on CD8+ T cell and NK cell activation and expansion.

The following allogenic cell lines are tested:
SK-MEL (Parental line, used as control)
SK modified with Vector 14, Vector 18 and Vector 30 ("14-18-30")
SK modified with Vector 15 only ("15")
SK modified with Vector 19 only ("19")
SK modified with Vector 22 only ("22")
SK modified with Vector 23 only ("23")
SK modified with Vector 29 ("29")

Figures 61A, 61B:
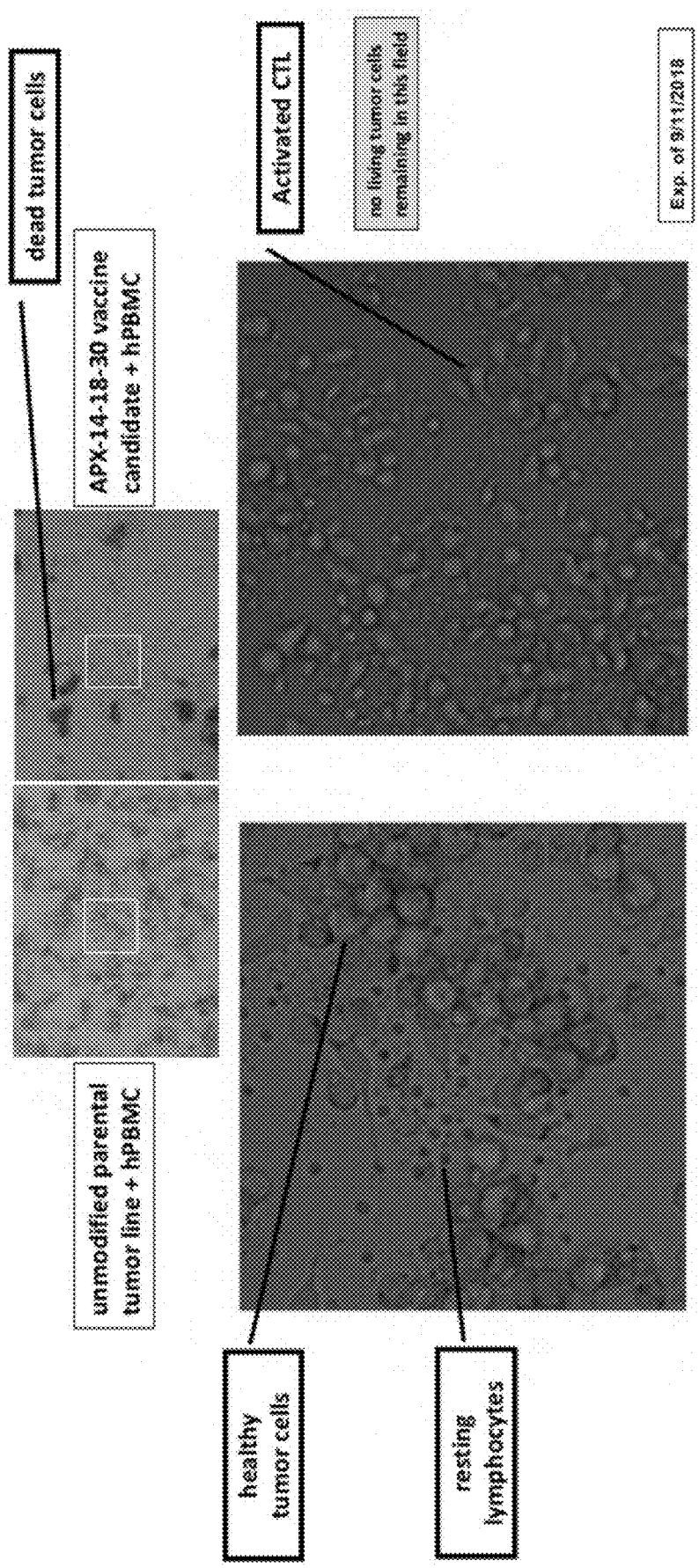
Figure 62:
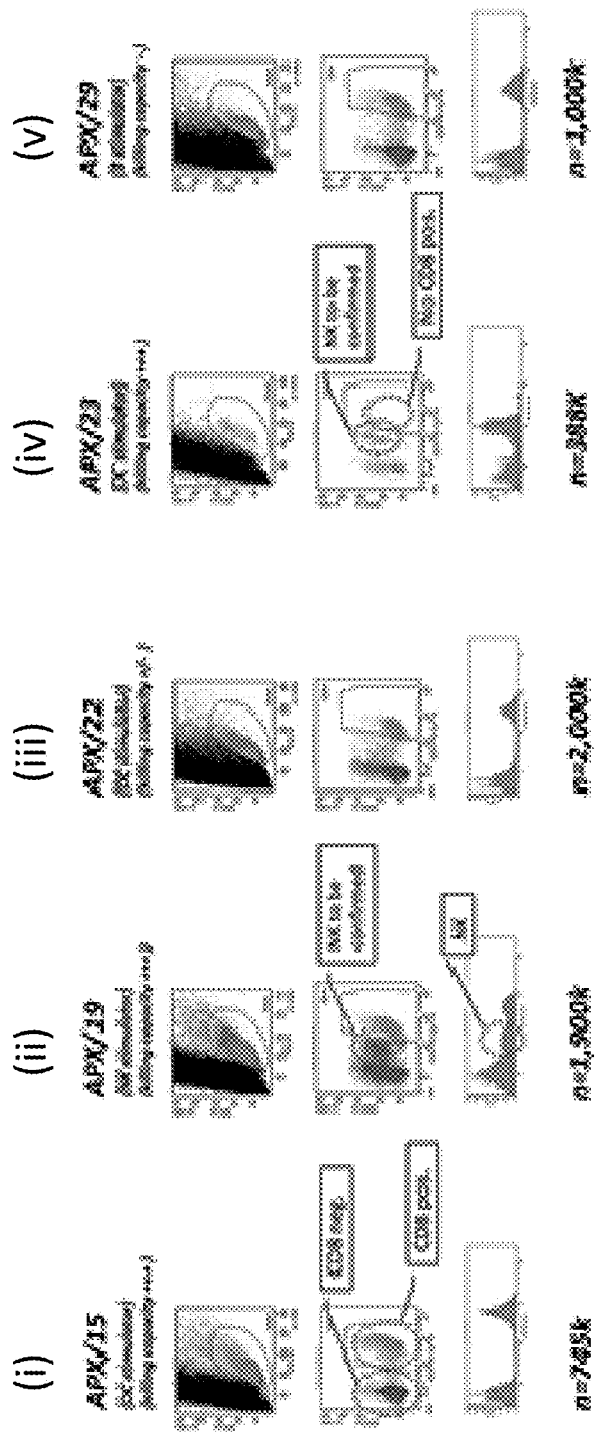
FIG. 62 shows the results of flow cytometry demonstrating stimulation of dendritic cell (DC), natural killer (NK) cell and B cell subpopulations in genetically modified SK lines (i) APX/15; (ii) APX/19; (iii) APX/22; (iv) APX/23; (v) APX/29.

Functional characterization of the allogeneic cell lines was performed using a primary MLTR assay, as described in Example 1. The following outputs were measured: 1) CD8+ T-cell proliferation was measured by flow cytometry (FIG. 60); 2) tumor cell killing using live/dead staining on day 9 (FIG. 61); 3) Natural Killer (NK) cell, dendritic cell (DC) and B cell expansion is measured by flow cytometry (FIG. 62).

Figure 60:
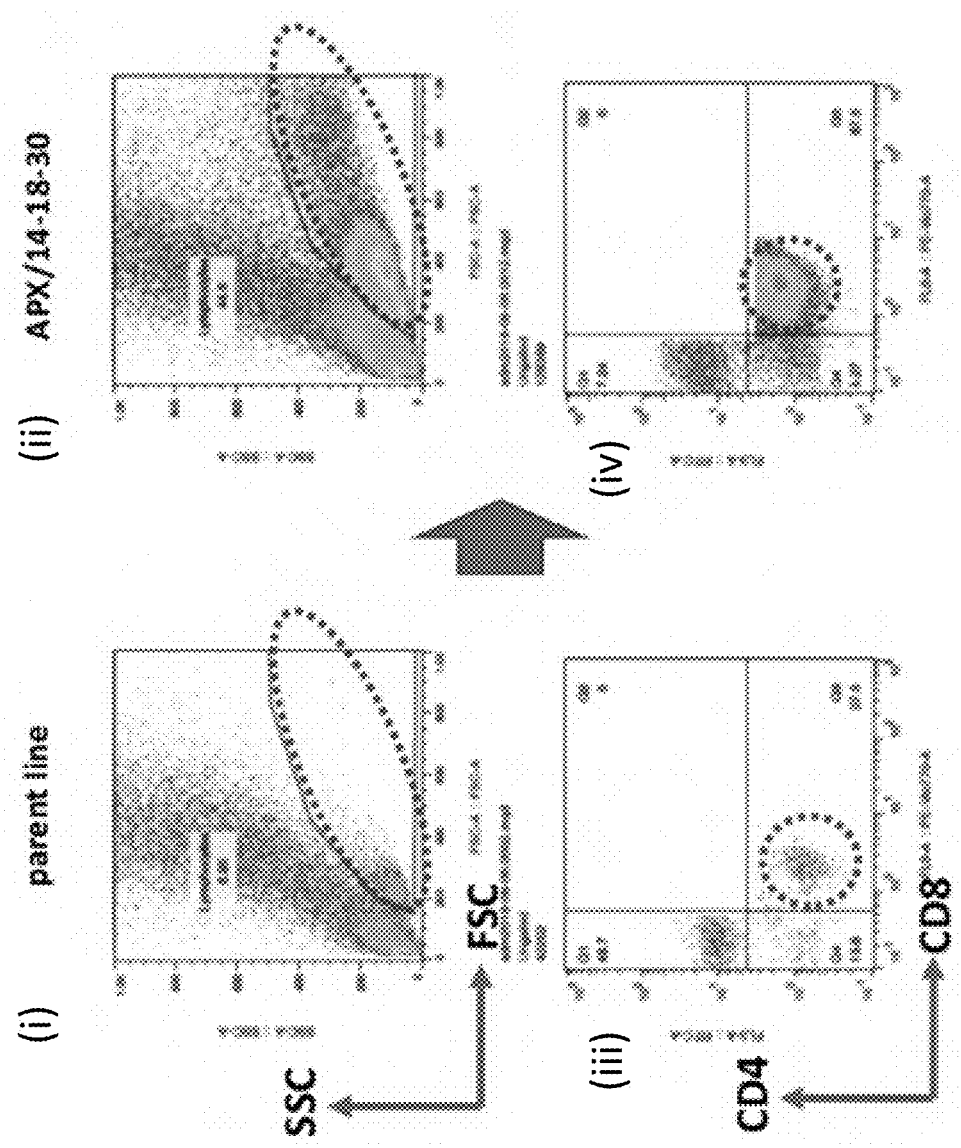
FIG. 60 shows the results of flow cytometry experiments demonstrating that CD8+ T cells can be activated by genetically modified SK lines expressing immunomodulatory molecules. Flow cytometry forward (FSC) and side scatter (SSC) plot for size and granularity after incubating parental cell line SKMEL2 (FIG. 60(*i*)) and genetically modified 14-18-30 expressing SK-MEL-2 tumor cells (FIG. 60(*ii*)) with PBMCs in a mixed lymphocyte tumor response assay are shown. The dotted oval in FIGS. 60(*i*) and 60(*ii*) indicates the lymphocyte gate.

In a first set of experiments, it was found that CD8+ T cell stimulation can be specifically enhanced by "14-18-30." FIG. 60 compares the effect of the parental line with tumor cells modified with Vector 14, Vector 18 and Vector 30 ("14-18-30"). The dotted oval in the top panel of graphs indicates the lymphocyte gate. In the parent line (i), the lymphocytes are quiescent, whereas in the "14-18-30" line (ii) there is a considerable expansion of lymphocytes. The dotted circle in the bottom panel of graphs shows the CD8 gate. In the parent line (iii), there is a small number of CD8+ T cells, whereas in the "14-18-30" line (iv) there is a large increase in the number of CD8+ T cells. It was found that the CD8+ T cell count enhancement was ~300-fold over baseline, and that the CD8/CD4 ratio, indicative of immune activation, was found to increase ~15-fold over baseline. Further, the CCR7+/CCR7− ratio (a surrogate for CTL memory phenotype) increased ~15-fold over baseline.

Further, when comparing the parental line and tumor cells modified with Vector 14, Vector 18 and Vector 30 ("14-18-30") at culture day 9, in the parental line ("unmodified parental tumor line+hPBMC") healthy tumor cells and resting lymphocytes could be visualized, whereas in the tumor cells modified with Vector 14, Vector 18 and Vector 30 ("APX-14-18-30 vaccine candidate+hPBMC"), no living tumor cells were visualized, while activated CTL were seen.

In a further set of experiments, the effect of tumor cells modified with Vector 15, Vector 19, Vector 22, Vector 23 and Vector 29 on immune cell stimulation was determined. In particular, as shown in FIG. 62, it was possible to determine, using flow cytometry, which subset of immune cell each particular immunomodulator was stimulating. Killing capacity was determined visually. As shown in FIG. 62, Vector 15 ("APX/15") stimulated DCs, Vector 19 ("APX/19") stimulated NK cells, Vector 22 ("APX/22") stimulated DCs, Vector 23 ("APX/23") stimulated DCs cells and Vector 29 ("APX/29") stimulated B cells.

Figure 65:
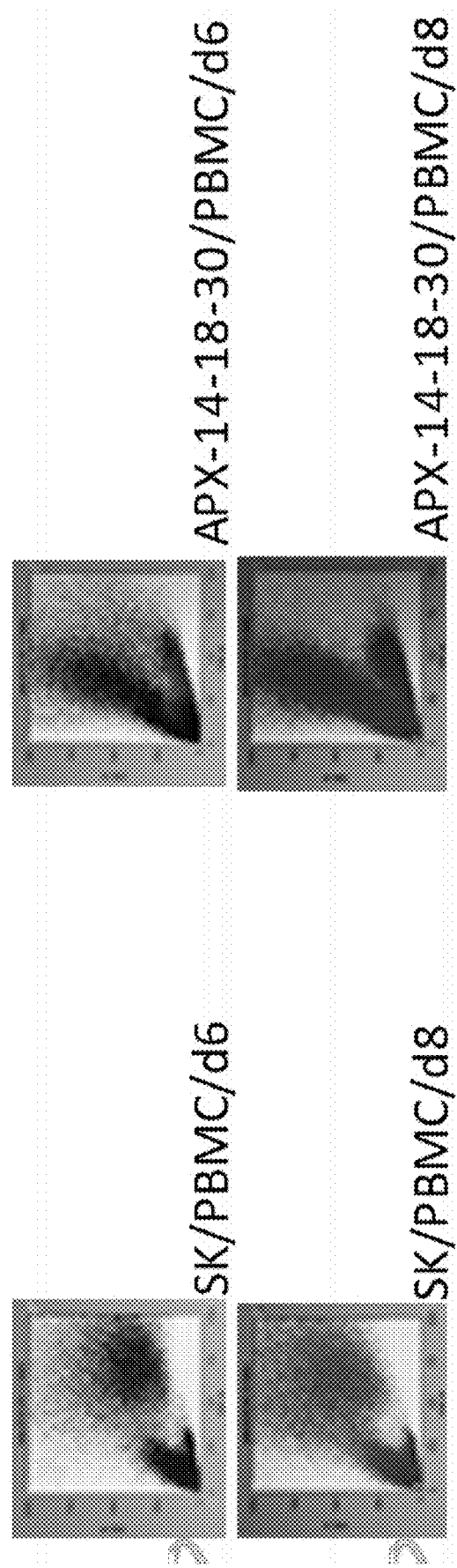
FIG. 65 shows the results of flow cytometry comparing day 6 and day 8 time points in a CD8 expansion assay using SK-parent line (left panels) versus a genetically modified 14-18-30 expressing SK-MEL-2 tumor cell lines expressing a combination of the immunomodulators shown in Table 2 (right panels).

FIG. 65 shows the results from another set of experiments, where flow cytometry was used to assess CD8+ T cell expansion and cell killing. Day 6 and day 8 time points were compared in a CD8 expansion assay using SK-parent line versus modified SK lines expressing immunomodulatory molecules 14, 18 and 30 ("14-18-30"). The lower left panel (iii) represents CD8+ T cells. Comparing panel (iii) to panel (iv), it can be seen that the CD8+ T cells increased in number, with the flow cytometry readout extended to the right, indicating an activation morphology. The upper right-hand panel (ii) shows allogeneic cells. Comparing the allogeneic cells (panels (i) and (ii)), it was observed that the flow cytometry results shifted to the left in panel (ii), with the modified SK lines expressing immunomodulatory molecules 14, 18 and 30. These results represent a transition to dead and dying cells. Thus, not only did the CD8+ T cells expand, but they also killed the allogeneic cells in their midst. These results demonstrated that the allogeneic tumor cells interacted with blood cells to kill the injected cells. Thus, in a clinical scenario, the allogenic tumor cell vaccine can be used to activate and expand the patient's lymphocytes, and in particular, subsets of immune killer cells (CD8+ T cells and NK cells), which in turn kill the patient's tumor cells. While the tumor cell vaccine is allogeneic to the subject, the blood cells and tumor cells have the same HLA.

Dendritic Cell (DC) Expansion

CyTOF was carried out as described in Example 1. CyTOF mass cytometry single-cell phenotype analysis of hPBMC response to SK melanoma cells with modification by expression of immunomodulatory molecules (Vector 3 ("APX/3"), Vector 3 and Vector 4 ("APX/3-4"); Vector 3, Vector 4, Vector 5 ("APX/3-4-5") and Vector 3, Vector 4, Vector 6 ("APX/3-4-6") is shown in FIG. 20 and FIG. 21. CyTOF provides extreme multiplexing with atomic mass spec resolution, as compared to flow cytometry, and therefore was used here to define the various PBMC subpopulations following stimulation with the various immunomodulatory molecules. The SK melanoma cell line and hPBMCs were cultured for 24 hours. Cells were harvested from cultures and stained with a 32-marker CyTOF antibody panel to detect multiple immune cell subsets as well as cell-surface and intracellular phenotyping markers. CyTOF mass cytometry data was generated on a Helios instrument. The data were normalized for signal using equilibration beads. Cell staining data were analyzed using Cytobank—a cloud computing suite for CyTOF data analysis that includes cell gating functions and an array of data visualization methods.

Figure 63:
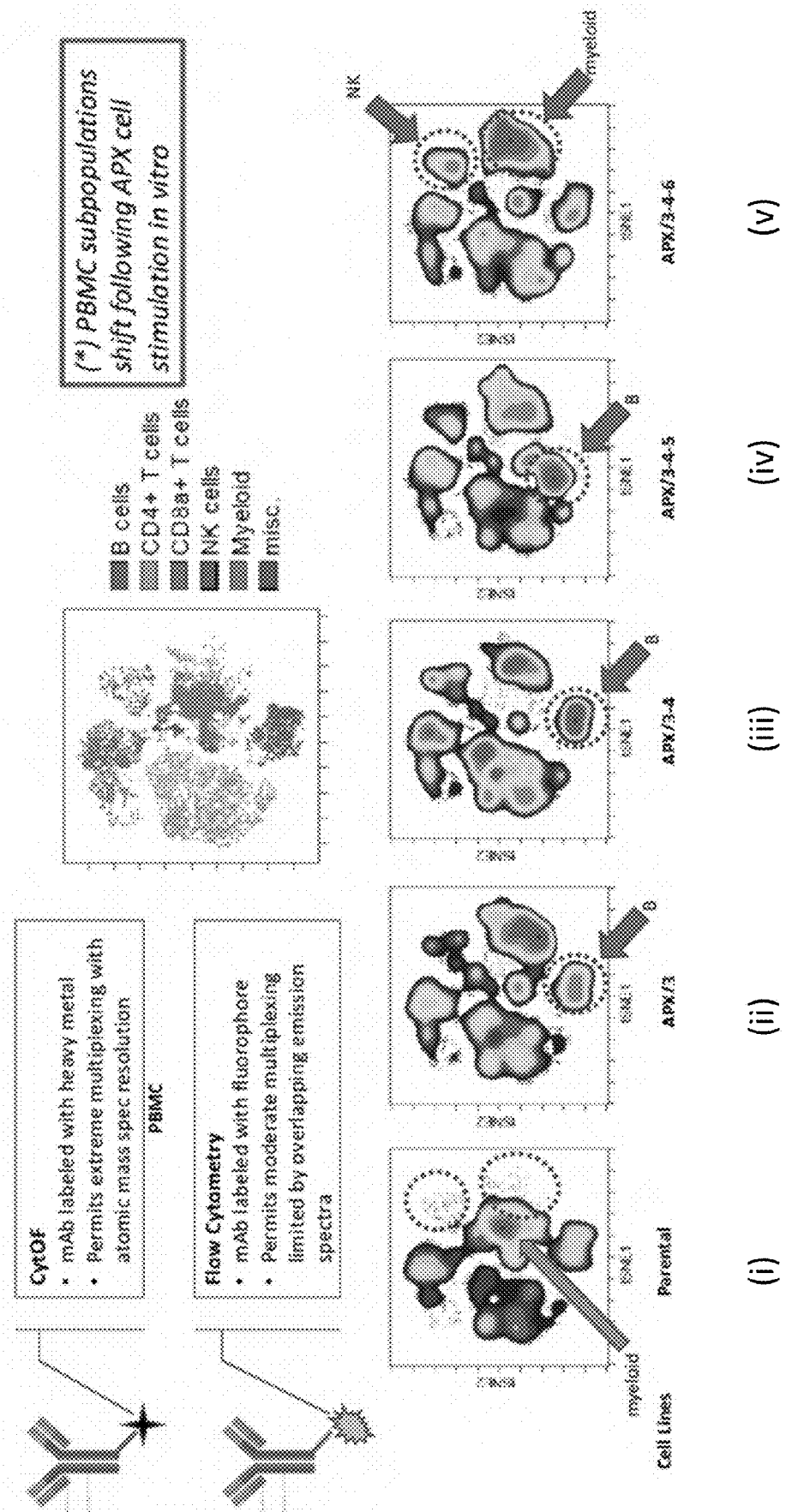
FIG. 63 shows CyTOF data demonstrating differentiation of various subsets of PBMCs following stimulation with genetically modified SK lines expressing immunomodulatory molecules ((i) parental; (ii) APX/3; (iii) APX/3-4; (iv) APX/3-4-5; (v) APX/3-4-6)). SK lines are represented by a number code; 3, secreted GM-CSF and membrane expressed FLT-3L; 4, secreted FLT3L and membrane expressed GM-CSF; 5, a non-cleavable form of CD40L; 6, a non-cleavable form of TNF-a.
Figure 64:
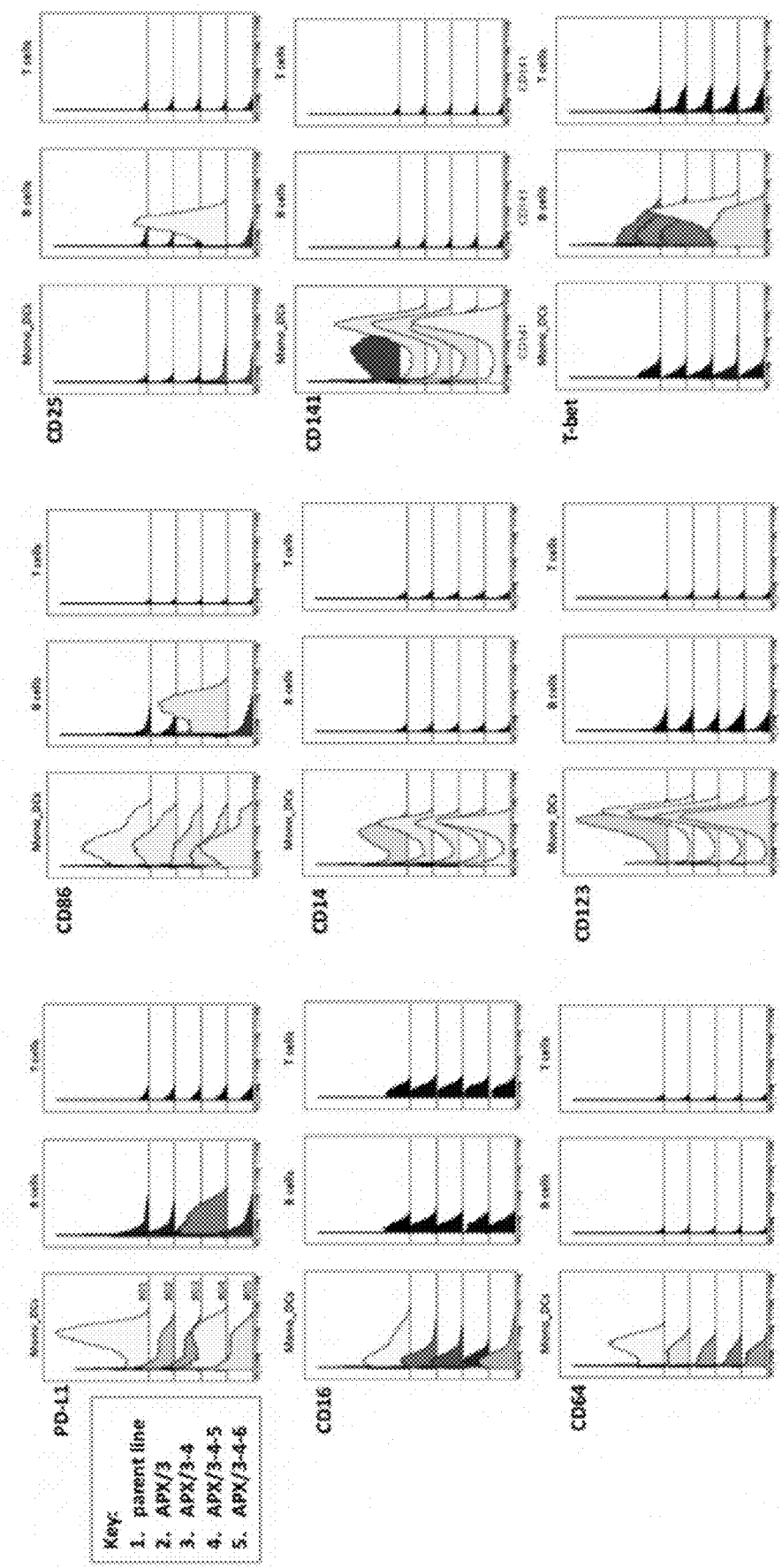
FIG. 64 shows detailed CyTOF data showing DC activation following stimulation with genetically modified SK lines expressing immunomodulatory molecules ((i) parental; (ii) APX/3; (iii) APX/3-4; (iv) APX/3-4-5; (v) APX/3-4-6)). SK lines are represented by a number code; 3, secreted GM-CSF and membrane expressed FLT-3L; 4, secreted FLT3L and membrane expressed GM-CSF; 5, a non-cleavable form of CD40L; 6, a non-cleavable form of TNF-a.

The data shown in FIG. 63 and FIG. 64 were plotted using viSNE, which is a dimensional reduction method that converts multidimensional staining signals from single cells into plots for visualization. FIG. 63 shows viSNE density contour plots of CyTOF staining data showing relative changes in immune cell subset abundance and phenotype. In FIG. 63, the dotted circles follow sub-population(s) of cells that were not present in the parent line ("parental"). As can be seen from FIG. 63, populations of NK cells and myeloid cells that were not present in the parental cell line are present in FIG. 64, which shows CyTOF monocyte cluster analysis of hPBMC indicating changes in the markers PD-L1, CD86, CD25, CD16, CD14, CD141, CD64, CD123, and T-bet expression following nine-stimulation with the indicated SK lines modified with the immunomodulatory molecules. As shown in FIG. 64, expression of CD123 and CD141, known DC markers, was increased in the cell lines modified with the immunomodulatory molecules. Further, expression of CD14, a myeloid marker, was increased in the cell lines modified with the immunomodulatory molecules.

Example 6. In Vivo Xenograft Mouse Experiments

Six week old female in-bred SCID mice are obtained from Charles River Laboratories (Hartford, Conn., USA). Animals are handled according to a protocol approved by the Institutional Animal Care and Use Committee of the facility. Mice are allowed to acclimate to animal housing.

Figure 66:
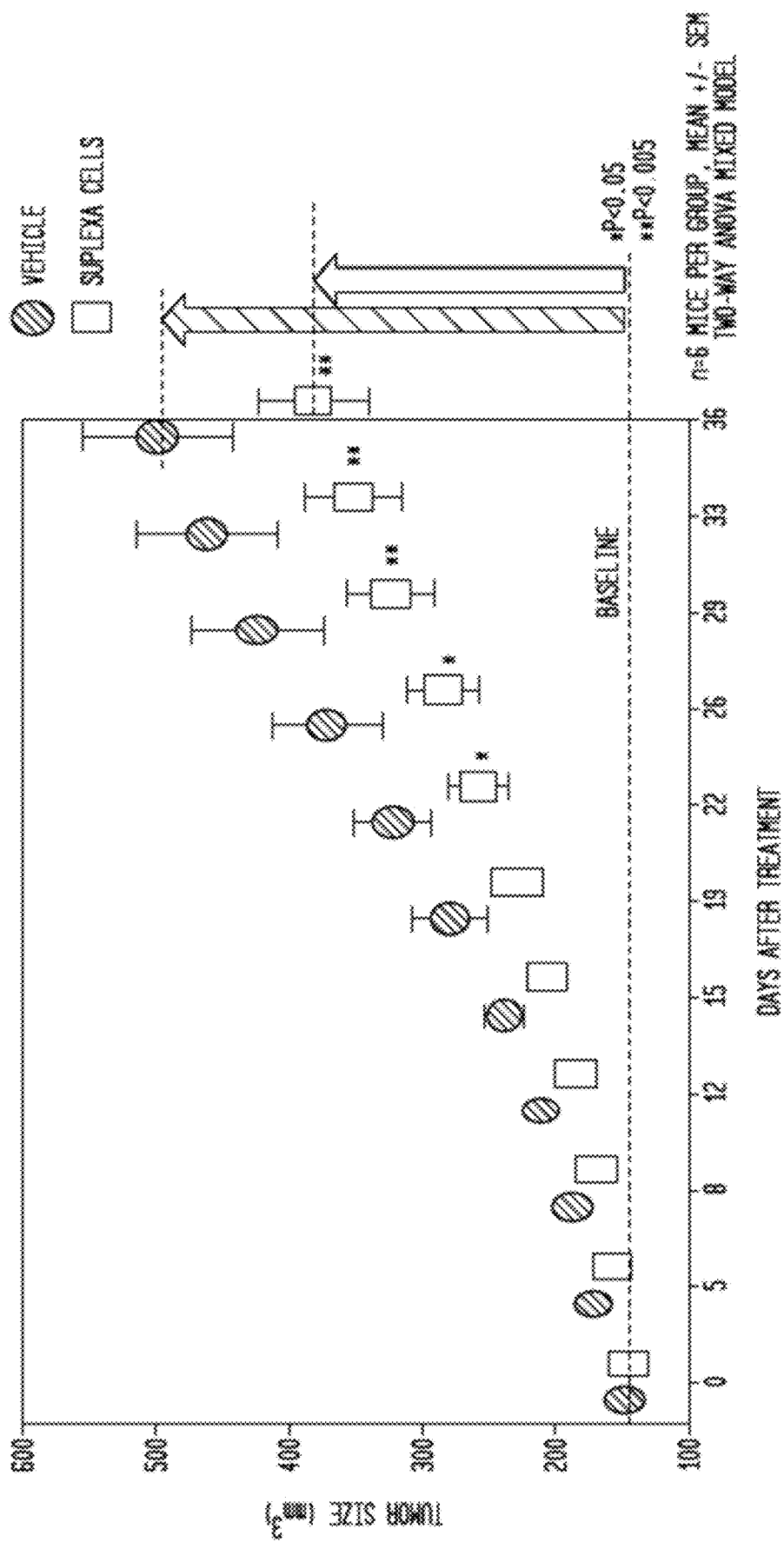
FIG. 66 is a plot showing mean and standard deviation results of a xenograft treatment study using NGS mice. The ends of each box are the upper and lower quartiles; the median is marked by a vertical line inside the box, and the whiskers are the two lines outside the box that extend to the highest and lowest observations. Human tumor cells were implanted on the flank of NGS (NOD scid gamma) mice. The tumors were allowed to grow to 150 mm$^3$. Mice were divided into two groups, a control and a treated group, with 6 mice per group. On day 30 (t=0) mice in the control group were inoculated with vehicle only, and mice in the treated group were inoculated with 3×10$^6$ PBMCs activated by 14-18-30 expressing ENLIST™ cells ("SUPLEXA™ cells"). Tumor size was measured at intervals through 36 days after inoculation. Divergence between the two groups appeared within 5 days. After day 22, the divergence became statistically significant (*P<0.05; ** P<005).

A human tumor xenograft was established in NSG (NOD scid gamma mice (Jackson Laboratory). Human tumors were implanted on the flank of the NSG mice Human tumor cells were implanted on the flank of NGS (NOD scid gamma) mice and allowed to grow to 150 mm$^3$. Mice were randomly divided into two groups, a control and a treated group, with 6 mice per group. The treated group was treated with expanded activated PBMCs comprising expanded activated serial killer cells activated by 14-18-30 expressing ENLIST™ cells. On day 30 (t=0) mice in the control group were inoculated with vehicle only, and mice in the treated group were inoculated with $3 \times 10^6$ expanded activated PBMCs comprising expanded activated serial killer cells. Tumor size was measured by caliper over time after inoculation in both groups. FIG. 66 is a plot showing mean and standard deviation results of a xenograft treatment study using NGS mice. The ends of each box are the upper and lower quartiles; the median is marked by a vertical line inside the box, and the whiskers are the two lines outside the box that extend to the highest and lowest observations. Human tumor cells were implanted on the flank of NGS (NOD scid gamma) mice. The tumors were allowed to grow to 150 mm$^3$. Mice were randomly divided into two groups, a control and a treated group, with 6 mice per group. On day 30 (t=0) mice in the control group were inoculated with vehicle only, and mice in the treated group were inoculated with $3 \times 10^6$ PBMCs activated by 14-18-30 expressing ENLIST™ cells ("SUPLEXA™ cells"). Tumor size was measured at intervals through 36 days after inoculation. Divergence between the two groups appeared within 5 days. After day 22, the divergence became statistically significant (*$P<0.05$; ** $P<005$).

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A method of treating a cancer in a subject, wherein the cancer is melanoma or colorectal cancer, comprising
preparing an allogeneic tumor cell vaccine comprising:
(1) a population of live, proliferation-incompetent melanoma or colorectal cancer tumor cells expressing one or more tumor specific antigens, wherein the melanoma tumor cell comprises one or more melanoma tumor specific antigens, and the colorectal cancer tumor cell comprises one or more colorectal cancer tumor specific antigens, wherein the population of live, proliferation-incompetent melanoma or colorectal cancer tumor cells are genetically engineered to stably express at least three exogenous immune modulators at the cell surface by transfecting or transducing recombinant DNA sequences coding for at least three immune modulators, wherein the at least three immune modulators are OX40 Ligand (OX40L), CD27 Ligand (CD70) and CD28 Ligand (CD28L), wherein OX40L comprises an amino acid sequence at least 90% identical to SEQ ID NO:108; wherein CD70 comprises an amino acid sequence at least 90% identical to SEQ ID NO:109; wherein CD28L comprises an amino acid sequence at least 90% identical to SEQ ID NO: 110 or an amino acid sequence at least 90% identical to SEQ ID NO: 111; and (2) a pharmaceutically acceptable carrier,
selecting for melanoma or colorectal cancer tumor cell clones that stably express an immunogenic amount of the exogenous immune modulator;
co-culturing the melanoma or colorectal cancer tumor cell clones selected in (1) with peripheral blood mononuclear cells (PBMCs) to activate one or more subpopulations of PBMCs in response to the melanoma or colorectal cancer tumor cell clones;

measuring in vitro one or more of cellular proliferation of the lymphocytes, cellular subset differentiation of the lymphocytes, cytokine release profile of the lymphocytes, and tumor cell death to select activated subpopulations, wherein the subpopulations of PBMC cells comprise one or more of T-lymphocytes, natural killer (NK) cells, dendritic cells (DCs) or B lymphocytes; and administering the allogeneic tumor cell vaccine to the subject, in an amount effective to reduce tumor burden, in the subject, improve progression free survival, overall survival, or both, of the subject relative to a placebo control.

2. The method of claim 1, wherein the population of live, proliferation-incompetent genetically engineered melanoma or colorectal cancer tumor cells expressing one or more tumor specific antigens further comprises one or more additional stably expressed immune modulator selected from the group consisting of: APRIL, BAFF, 4-IBB Ligand, CD30 Ligand, CD40 Ligand, CD80, CD86, FLT-3 Ligand, HSP-70, HSP-90, ICOS Ligand, IL-10R, IL-12, IL-15, IL-18, IL-2, IL-21, IL-23, IL-7, LIGHT, RANK ligand, TGF-b Receptor, TNF, CD86 variant engineered with an IRES compatible signal sequence, FLT3L variant engineered to remove the transmembrane region, GMCSF variant with a CD8 membrane anchor and IRES compatible Signal Sequence, HSP70 variant with a CD8 membrane anchor, HSP-90B1 (GRP94/96) variant engineered with a CD8 membrane anchor, HSP90 variant engineered with a CD8 membrane anchor, ICOSL variant engineered with an IRES compatible signal sequence, IL10R variant engineered to remove the transmembrane region, IL-Rα variant engineered to remove transmembrane region (VSV-GM-CSF tag), IL12 variant engineered to be a single chain with a CD8 membrane anchor, IL15 variant engineered with CD8 membrane anchor, IL18 variant engineered with a CD8 membrane anchor, IL2 variant engineered with a CD8 membrane anchor and IRES compatible sequence, IL21 variant engineered with a CD8 membrane anchor, IL23 variant engineered to be a single chain with a CD8 membrane anchor, IL7 variant engineered with a CD8 membrane anchor, TGFb-R variant engineered to remove transmembrane region, TGFb Receptor III variant engineered to remove transmembrane region, mIFNα variant modified to be membrane bound, mIFNαγ variant which is modified to be membrane bound, and CD40L variant which is cleavage resistant.

3. The method of claim 1, wherein the population of live, proliferation-incompetent genetically engineered melanoma or colorectal cancer tumor cells is rendered proliferation-incompetent by irradiation.

4. The method of claim 1, wherein
   (a) the population of live, proliferation incompetent melanoma or colorectal cancer tumor cells is derived from a biological sample derived from a melanoma or colorectal cancer patient; or
   (b) the population of live proliferation-incompetent melanoma or colorectal cancer tumor cells is derived from a melanoma or colorectal cancer tumor cell line; or
   (c) inducing of the T-lymphocytes comprises activation of the subpopulation of T lymphocytes, expansion of the T lymphocytes, or both; or
   (d) inducing of the NK cells comprises activation of the subpopulation of NK cells, expansion of the subpopulation of NK cells or both; or
   (e) inducing of the subpopulation of DCs comprises activation of the subpopulation of DCs, expansion of the subpopulation of DCs or both; or
   (f) inducing of the subpopulation of B lymphocytes comprises activation of the subpopulation of B lymphocytes, expansion of the subpopulation of B lymphocytes or both.

5. The method of claim 1, wherein CD28 Ligand (CD28L) comprises CD80, CD86, or both.

6. The method of claim 1, wherein the one or more melanoma tumor specific antigens is selected from the group consisting of: gp100, tyrosinase, Melan-A, tyrosinase-related protein (TRP-2-INT2), melanoma antigen-1 (MAGE-A1), NY-ESO-1, preferentially expressed antigen of melanoma (PRAME) CDK4 and multiple myeloma oncogene 1 (MUM-1).

7. The method of claim 1, wherein the one of more colorectal cancer tumor specific antigens selected from the group consisting of: carcinoembryonic antigen (CEA), MAGE, HPV, human telomerase reverse transcriptase (hTERT), EPCAM, PD-1, PD-L1, p53, and cell surface-associated mucin 1 (MUC1).

* * * * *

```
                            SEQUENCE LISTING

<160> NUMBER OF SEQ ID NOS: 111

<210> SEQ ID NO 1
<211> LENGTH: 399
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: membrane IgG-1 heavy chain

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Glu Leu Gln Leu Glu Glu Ser Cys
                325                 330                 335

Ala Glu Ala Gln Asp Gly Glu Leu Asp Gly Leu Trp Thr Thr Ile Thr
            340                 345                 350

Ile Phe Ile Thr Leu Phe Leu Leu Ser Val Cys Tyr Ser Ala Thr Val
        355                 360                 365

Thr Phe Phe Lys Val Lys Trp Ile Phe Ser Ser Val Val Asp Leu Lys
    370                 375                 380

Gln Thr Ile Ile Pro Asp Tyr Arg Asn Met Ile Gly Gln Gly Ala
385                 390                 395

<210> SEQ ID NO 2
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: secreted IgG-1 heavy chain

<400> SEQUENCE: 2

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 3
<211> LENGTH: 295
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: fragment secreted IgG-1 heavy chain

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Tyr Lys Cys Lys Val Ser Asn Lys Ala Leu
                165                 170                 175

Pro Ala Pro Ile Glu Lys Thr Ile Ser Lys Ala Lys Gly Gln Pro Arg
            180                 185                 190

Glu Pro Gln Val Tyr Thr Leu Pro Pro Ser Arg Asp Glu Leu Thr Lys
        195                 200                 205

Asn Gln Val Ser Leu Thr Cys Leu Val Lys Gly Phe Tyr Pro Ser Asp
    210                 215                 220

Ile Ala Val Glu Trp Glu Ser Asn Gly Gln Pro Glu Asn Asn Tyr Lys
225                 230                 235                 240

Thr Thr Pro Pro Val Leu Asp Ser Asp Gly Ser Phe Phe Leu Tyr Ser
                245                 250                 255

Lys Leu Thr Val Asp Lys Ser Arg Trp Gln Gln Gly Asn Val Phe Ser
            260                 265                 270
```

Cys Ser Val Met His Glu Ala Leu His Asn His Tyr Thr Gln Lys Ser
              275                 280                 285

Leu Ser Leu Ser Pro Gly Lys
              290                 295

<210> SEQ ID NO 4
<211> LENGTH: 377
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG-3 heavy chain constant region

<400> SEQUENCE: 4

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

```
Tyr Asn Thr Thr Pro Pro Met Leu Asp Ser Asp Gly Ser Phe Phe Leu
            325                 330                 335

Tyr Ser Lys Leu Thr Val Asp Lys Ser Arg Trp Gln Gln Gly Asn Ile
        340                 345                 350

Phe Ser Cys Ser Val Met His Glu Ala Leu His Asn Arg Phe Thr Gln
    355                 360                 365

Lys Ser Leu Ser Leu Ser Pro Gly Lys
370                 375

<210> SEQ ID NO 5
<211> LENGTH: 184
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: mGM-CSF HLA derived TM and SHORTENED
      cytoplasmic domain

<400> SEQUENCE: 5

Met Trp Leu Gln Ser Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
            85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

Glu Leu Ser Ser Gln Pro Thr Ile Pro Ile Val Gly Ile Ile Ala Gly
145                 150                 155                 160

Leu Val Leu Leu Gly Ala Val Ile Thr Gly Ala Val Val Ala Ala Val
            165                 170                 175

Met Trp Arg Arg Lys Ser Ser Asp
            180

<210> SEQ ID NO 6
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CD40L

<400> SEQUENCE: 6

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
```

```
            20                  25                  30
Ile Thr Gln Met Ile Gly Ser Ala Leu Phe Ala Val Tyr Leu His Arg
            35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
            115                 120                 125

Glu Ala Ser Ser Lys Thr Thr Ser Val Leu Gln Trp Ala Glu Lys Gly
            130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
            195                 200                 205

Ala Asn Thr His Ser Ser Ala Lys Pro Cys Gly Gln Gln Ser Ile His
            210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 7
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: non-cleavable CD40L

<400> SEQUENCE: 7

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
```

```
                    100                 105                 110
Met Pro Arg Gly Glu Glu Asp Ser Gln Ile Ala Ala His Val Ile Ser
            115                 120                 125

Glu Ala Ser Ser Lys Thr Thr Ser Val Leu Gln Trp Ala Glu Lys Gly
        130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 8
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TNF

<400> SEQUENCE: 8

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
```

```
                180              185               190
Pro Ile Tyr Leu Gly Gly Val Phe Gln Leu Glu Lys Gly Asp Arg Leu
            195                 200             205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230

<210> SEQ ID NO 9
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CD40L piece

<400> SEQUENCE: 9

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu
            100                 105

<210> SEQ ID NO 10
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TNF piece

<400> SEQUENCE: 10

Val Ala Asn Pro Gln Ala Glu Gly Gln Leu Gln Trp Leu Asn Arg Arg
1               5                   10                  15

Ala Asn Ala Leu Leu Ala Asn Gly Val Glu Leu Arg Asp Asn Gln Leu
            20                  25                  30

Val Val Pro Ser Glu Gly Leu Tyr Leu Ile Tyr Ser Gln Val Leu Phe
        35                  40                  45

Lys Gly Gln Gly Cys Pro Ser Thr His Val Leu Leu Thr His Thr Ile
    50                  55                  60

Ser Arg Ile Ala Val Ser Tyr Gln Thr Lys Val Asn Leu Leu Ser Ala
65                  70                  75                  80

Ile Lys Ser Pro Cys Gln Arg Glu Thr Pro Glu Gly Ala Glu Ala Lys
                85                  90                  95

Pro Trp Tyr Glu Pro Ile Tyr Leu Gly Gly Val Phe Gln Leu Glu Lys
            100                 105                 110
```

Gly Asp Arg Leu Ser Ala Glu Ile Asn Arg Pro Asp Tyr Leu Asp Phe
            115                 120                 125

Ala Glu Ser Gly Gln Val Tyr Phe Gly Ile Ile Ala Leu
    130                 135                 140

<210> SEQ ID NO 11
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: mTNF-a

<400> SEQUENCE: 11

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
50                  55                  60

Arg Asp Leu Ser Leu Ile Ser Pro Leu Ala Gln Ala Ser Gly Ser Gly
65                  70                  75                  80

Ser Gly Ser Gly Ser Gly Glu Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230

<210> SEQ ID NO 12
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC Constant Region 3 from IgG1

<400> SEQUENCE: 12

Gly Gln Pro Arg Glu Pro Gln Val Tyr Thr Leu Pro Pro Ser Arg Asp
1               5                   10                  15

```
Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Glu Leu Gln Leu Glu Glu Ser
            100                 105                 110

Cys

<210> SEQ ID NO 13
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: native GM-CSF

<400> SEQUENCE: 13

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
        50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

<210> SEQ ID NO 14
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Flt3L

<400> SEQUENCE: 14

Met Thr Val Leu Ala Pro Ala Trp Ser Pro Thr Thr Tyr Leu Leu Leu
1               5                   10                  15

Leu Leu Leu Leu Ser Ser Gly Leu Ser Gly Thr Gln Asp Cys Ser Phe
            20                  25                  30
```

```
Gln His Ser Pro Ile Ser Ser Asp Phe Ala Val Lys Ile Arg Glu Leu
        35                  40                  45

Ser Asp Tyr Leu Leu Gln Asp Tyr Pro Val Thr Val Ala Ser Asn Leu
 50                  55                  60

Gln Asp Glu Glu Leu Cys Gly Gly Leu Trp Arg Leu Val Leu Ala Gln
 65                  70                  75                  80

Arg Trp Met Glu Arg Leu Lys Thr Val Ala Gly Ser Lys Met Gln Gly
                 85                  90                  95

Leu Leu Glu Arg Val Asn Thr Glu Ile His Phe Val Thr Lys Cys Ala
                100                 105                 110

Phe Gln Pro Pro Ser Cys Leu Arg Phe Val Gln Thr Asn Ile Ser
            115                 120                 125

Arg Leu Leu Gln Glu Thr Ser Glu Gln Leu Val Ala Leu Lys Pro Trp
130                 135                 140

Ile Thr Arg Gln Asn Phe Ser Arg Cys Leu Glu Leu Gln Cys Gln Pro
145                 150                 155                 160

Asp Ser Ser Thr Leu Pro Pro Pro Trp Ser Pro Arg Pro Leu Glu Ala
                165                 170                 175

Thr Ala Pro Thr Ala Pro Gln Pro Pro Leu Leu Leu Leu Leu Leu Leu
                180                 185                 190

Pro Val Gly Leu Leu Leu Leu Ala Ala Ala Trp Cys Leu His Trp Gln
                195                 200                 205

Arg Thr Arg Arg Arg Thr Pro Arg Pro Gly Glu Gln Val Pro Pro Val
210                 215                 220

Pro Ser Pro Gln Asp Leu Leu Leu Val Glu His
225                 230                 235

<210> SEQ ID NO 15
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Kozak sequence

<400> SEQUENCE: 15
gccgccrcca ugg                                                          13

<210> SEQ ID NO 16
<211> LENGTH: 377
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG-3 heavy chain constant region E213Q

<400> SEQUENCE: 16

Ala Ser Thr Lys Gly Pro Ser Val Phe Pro Leu Ala Pro Cys Ser Arg
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Leu Gly Thr Gln Thr
 65                  70                  75                  80

Tyr Thr Cys Asn Val Asn His Lys Pro Ser Asn Thr Lys Val Asp Lys
                 85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Gln Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 17
<211> LENGTH: 377
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG-3 heavy chain constant region P221L

<400> SEQUENCE: 17

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30
```

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Leu Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 18
<211> LENGTH: 377
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG-3 heavy chain constant region E224Q

<400> SEQUENCE: 18

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
                100                 105                 110

Arg Cys Pro Glu Pro Lys Ser Cys Asp Thr Pro Pro Pro Cys Pro Arg
            115                 120                 125

Cys Pro Glu Pro Lys Ser Cys Asp Thr Pro Pro Pro Cys Pro Arg Cys
        130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
                180                 185                 190

Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Gln
        210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
                260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
        290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
                340                 345                 350

Phe Ser Cys Ser Val Met His Glu Ala Leu His Asn Arg Phe Thr Gln
            355                 360                 365

Lys Ser Leu Ser Leu Ser Pro Gly Lys
    370                 375

<210> SEQ ID NO 19
<211> LENGTH: 377
<212> TYPE: PRT
<213> ORGANISM: Artificial Sequence
<220> FEATURE:

<223> OTHER INFORMATION: Description of Artificial Sequence: Synthetic
      polypeptide
<220> FEATURE:
<223> OTHER INFORMATION: IgG-3 heavy chain constant region Y226F

<400> SEQUENCE: 19

```
Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
            115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Phe Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375
```

<210> SEQ ID NO 20
<211> LENGTH: 377
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: IgG-3 heavy chain constant region D242N

<400> SEQUENCE: 20

```
Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asn Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350
```

Phe Ser Cys Ser Val Met His Glu Ala Leu His Asn Arg Phe Thr Gln
            355                 360                 365
Lys Ser Leu Ser Leu Ser Pro Gly Lys
    370                 375

<210> SEQ ID NO 21
<211> LENGTH: 377
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG-3 heavy chain constant region N245D

<400> SEQUENCE: 21

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asp Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

```
Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
                340                 345                 350

Phe Ser Cys Ser Val Met His Glu Ala Leu His Asn Arg Phe Thr Gln
                355                 360                 365

Lys Ser Leu Ser Leu Ser Pro Gly Lys
                370                 375

<210> SEQ ID NO 22
<211> LENGTH: 377
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG-3 heavy chain constant region T269A

<400> SEQUENCE: 22

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
                100                 105                 110

Arg Cys Pro Glu Pro Lys Ser Cys Asp Thr Pro Pro Cys Pro Arg
                115                 120                 125

Cys Pro Glu Pro Lys Ser Cys Asp Thr Pro Pro Cys Pro Arg Cys
                130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
                180                 185                 190

Val Val Asp Val Ser His Glu Asp Pro Glu Val Gln Phe Lys Trp Tyr
                195                 200                 205

Val Asp Gly Val Glu Val His Asn Ala Lys Thr Lys Pro Arg Glu Glu
                210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Ala Lys Gly Gln
                260                 265                 270

Pro Arg Glu Pro Gln Val Tyr Thr Leu Pro Pro Ser Arg Glu Glu Met
                275                 280                 285
```

Thr Lys Asn Gln Val Ser Leu Thr Cys Leu Val Lys Gly Phe Tyr Pro
            290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
            355                 360                 365

Lys Ser Leu Ser Leu Ser Pro Gly Lys
            370                 375

<210> SEQ ID NO 23
<211> LENGTH: 377
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG-3 heavy chain constant region S314N

<400> SEQUENCE: 23

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

```
Ala Leu Pro Ala Pro Ile Glu Lys Thr Ile Ser Lys Thr Lys Gly Gln
                260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
        290                 295                 300

Ser Asp Ile Ala Val Glu Trp Glu Ser Asn Gly Gln Pro Glu Asn Asn
305                 310                 315                 320

Tyr Asn Thr Thr Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
                340                 345                 350

Phe Ser Cys Ser Val Met His Glu Ala Leu His Asn Arg Phe Thr Gln
                355                 360                 365

Lys Ser Leu Ser Leu Ser Pro Gly Lys
                370                 375

<210> SEQ ID NO 24
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG-3 heavy chain constant region S314 del

<400> SEQUENCE: 24

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220
```

```
Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
            245                 250                 255

Ala Leu Pro Ala Pro Ile Glu Lys Thr Ile Ser Lys Thr Lys Gly Gln
        260                 265                 270

Pro Arg Glu Pro Gln Val Tyr Thr Leu Pro Pro Ser Arg Glu Glu Met
    275                 280                 285

Thr Lys Asn Gln Val Ser Leu Thr Cys Leu Val Lys Gly Phe Tyr Pro
290                 295                 300

Ser Asp Ile Ala Val Glu Trp Glu Ser Gly Gln Pro Glu Asn Asn Tyr
305                 310                 315                 320

Asn Thr Thr Pro Pro Met Leu Asp Ser Asp Gly Ser Phe Phe Leu Tyr
            325                 330                 335

Ser Lys Leu Thr Val Asp Lys Ser Arg Trp Gln Gln Gly Asn Ile Phe
        340                 345                 350

Ser Cys Ser Val Met His Glu Ala Leu His Asn Arg Phe Thr Gln Lys
    355                 360                 365

Ser Leu Ser Leu Ser Pro Gly Lys
    370                 375

<210> SEQ ID NO 25
<211> LENGTH: 377
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG-3 heavy chain constant region F366Y

<400> SEQUENCE: 25

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190
```

```
Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Tyr Thr Gln
        355                 360                 365

Lys Ser Leu Ser Leu Ser Pro Gly Lys
    370                 375

<210> SEQ ID NO 26
<211> LENGTH: 221
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TNF - VRSSSRTPSDKP del

<400> SEQUENCE: 26

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Ala His Val
65                  70                  75                  80

Val Ala Asn Pro Gln Ala Glu Gly Gln Leu Gln Trp Leu Asn Arg Arg
                85                  90                  95

Ala Asn Ala Leu Leu Ala Asn Gly Val Glu Leu Arg Asp Asn Gln Leu
            100                 105                 110

Val Val Pro Ser Glu Gly Leu Tyr Leu Ile Tyr Ser Gln Val Leu Phe
        115                 120                 125

Lys Gly Gln Gly Cys Pro Ser Thr His Val Leu Leu Thr His Thr Ile
    130                 135                 140

Ser Arg Ile Ala Val Ser Tyr Gln Thr Lys Val Asn Leu Leu Ser Ala
145                 150                 155                 160
```

```
Ile Lys Ser Pro Cys Gln Arg Glu Thr Pro Glu Gly Ala Glu Ala Lys
            165                 170                 175

Pro Trp Tyr Glu Pro Ile Tyr Leu Gly Gly Val Phe Gln Leu Glu Lys
        180                 185                 190

Gly Asp Arg Leu Ser Ala Glu Ile Asn Arg Pro Asp Tyr Leu Asp Phe
    195                 200                 205

Ala Glu Ser Gly Gln Val Tyr Phe Gly Ile Ile Ala Leu
210                 215                 220

<210> SEQ ID NO 27
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TNF - FSFLIVAGATTLFCLLHFGVI del

<400> SEQUENCE: 27

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Gly Pro Gln Arg Glu Glu Phe Pro Arg Asp Leu Ser Leu
        35                  40                  45

Ile Ser Pro Leu Ala Gln Ala Val Arg Ser Ser Arg Thr Pro Ser
    50                  55                  60

Asp Lys Pro Val Ala His Val Val Ala Asn Pro Gln Ala Glu Gly Gln
65                  70                  75                  80

Leu Gln Trp Leu Asn Arg Arg Ala Asn Ala Leu Leu Ala Asn Gly Val
                85                  90                  95

Glu Leu Arg Asp Asn Gln Leu Val Val Pro Ser Glu Gly Leu Tyr Leu
            100                 105                 110

Ile Tyr Ser Gln Val Leu Phe Lys Gly Gln Gly Cys Pro Ser Thr His
        115                 120                 125

Val Leu Leu Thr His Thr Ile Ser Arg Ile Ala Val Ser Tyr Gln Thr
    130                 135                 140

Lys Val Asn Leu Leu Ser Ala Ile Lys Ser Pro Cys Gln Arg Glu Thr
145                 150                 155                 160

Pro Glu Gly Ala Glu Ala Lys Pro Trp Tyr Glu Pro Ile Tyr Leu Gly
                165                 170                 175

Gly Val Phe Gln Leu Glu Lys Gly Asp Arg Leu Ser Ala Glu Ile Asn
            180                 185                 190

Arg Pro Asp Tyr Leu Asp Phe Ala Glu Ser Gly Gln Val Tyr Phe Gly
        195                 200                 205

Ile Ile Ala Leu
    210

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: HA tag seq

<400> SEQUENCE: 28
```

```
Tyr Pro Tyr Asp Val Pro Asp Tyr Ala
1               5
```

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: FLAG TAG

<400> SEQUENCE: 29

```
Asp Tyr Lys Asp Asp Asp Asp Lys
1               5
```

<210> SEQ ID NO 30
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: mIgG Heavy Chain IgG 1/3 hybrid anti-biotin
      heavy chain - E325A mutant

<400> SEQUENCE: 30

```
Met Glu Phe Gly Leu Ser Trp Val Phe Leu Val Ala Leu Phe Arg Gly
1               5                   10                  15

Val Gln Cys Gln Val Lys Leu Gln Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Thr Ala Tyr Gly Val Asp Trp Val Arg Gln Pro Pro Gly Lys Gly Leu
    50                  55                  60

Glu Trp Leu Gly Val Ile Trp Gly Gly Gly Arg Thr Asn Tyr Asn Ser
65                  70                  75                  80

Gly Leu Met Ser Arg Leu Ser Ile Arg Lys Asp Asn Ser Lys Ser Gln
                85                  90                  95

Val Phe Leu Thr Met Asn Ser Leu Gln Thr Asp Asp Thr Ala Lys Tyr
            100                 105                 110

Tyr Cys Val Lys His Thr Asn Trp Asp Gly Phe Ala Tyr Trp Gly
        115                 120                 125

Gln Gly Thr Thr Val Thr Val Ser Ser Ala Ser Thr Lys Gly Pro Ser
    130                 135                 140

Val Phe Pro Leu Ala Pro Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Leu Lys Thr Pro
225                 230                 235                 240
```

```
Leu Gly Asp Thr Thr His Thr Cys Pro Arg Cys Pro Glu Pro Lys Ser
            245                 250                 255

Cys Asp Thr Pro Pro Cys Pro Arg Cys Pro Glu Pro Lys Ser Cys
        260                 265                 270

Asp Thr Pro Pro Cys Pro Arg Cys Pro Glu Pro Lys Ser Cys Asp
        275                 280                 285

Thr Pro Pro Cys Pro Arg Cys Pro Ala Pro Glu Leu Leu Gly Gly
        290                 295                 300

Pro Ser Val Phe Leu Phe Pro Pro Lys Pro Lys Asp Thr Leu Met Ile
305                 310                 315                 320

Ser Arg Thr Pro Ala Val Thr Cys Val Val Asp Val Ser His Glu
                325                 330                 335

Asp Pro Glu Val Lys Phe Asn Trp Tyr Val Asp Gly Val Glu Val His
            340                 345                 350

Asn Ala Lys Thr Lys Pro Arg Glu Glu Gln Tyr Asn Ser Thr Tyr Arg
            355                 360                 365

Val Val Ser Val Leu Thr Val Leu His Gln Asp Trp Leu Asn Gly Lys
370                 375                 380

Glu Tyr Lys Cys Lys Val Ser Asn Lys Ala Leu Pro Ala Pro Ile Glu
385                 390                 395                 400

Lys Thr Ile Ser Lys Ala Lys Gly Gln Pro Arg Glu Pro Gln Val Tyr
                405                 410                 415

Thr Leu Pro Pro Ser Arg Asp Glu Leu Thr Lys Asn Gln Val Ser Leu
                420                 425                 430

Thr Cys Leu Val Lys Gly Phe Tyr Pro Ser Asp Ile Ala Val Glu Trp
            435                 440                 445

Glu Ser Asn Gly Gln Pro Glu Asn Asn Tyr Lys Thr Thr Pro Pro Val
450                 455                 460

Leu Asp Ser Asp Gly Ser Phe Phe Leu Tyr Ser Lys Leu Thr Val Asp
465                 470                 475                 480

Lys Ser Arg Trp Gln Gln Gly Asn Val Phe Ser Cys Ser Val Met His
                485                 490                 495

Glu Ala Leu His Asn His Tyr Thr Gln Lys Ser Leu Ser Leu Ser Pro
            500                 505                 510

Glu Leu Gln Leu Glu Glu Ser Cys Ala Glu Ala Gln Asp Gly Glu Leu
            515                 520                 525

Asp Gly Leu Trp Thr Thr Ile Thr Ile Phe Ile Thr Leu Phe Leu Leu
        530                 535                 540

Ser Val Cys Tyr Ser Ala Thr Val Thr Phe Phe Lys Val Lys Trp Ile
545                 550                 555                 560

Phe Ser Ser Val Val Asp Leu Lys Gln Thr Ile Ile Pro Asp Tyr Arg
                565                 570                 575

Asn Met Ile Gly Gln Gly Ala
            580
```

<210> SEQ ID NO 31
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CD40L-TNFa fusion protein

<400> SEQUENCE: 31

```
Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Pro Val Ala
65                  70                  75                  80

His Val Val Ala Asn Pro Gln Ala Glu Gly Gln Leu Gln Trp Leu Asn
                85                  90                  95

Arg Arg Ala Asn Ala Leu Leu Ala Asn Gly Val Glu Leu Arg Asp Asn
            100                 105                 110

Gln Leu Val Val Pro Ser Glu Gly Leu Tyr Leu Ile Tyr Ser Gln Val
        115                 120                 125

Leu Phe Lys Gly Gln Gly Cys Pro Ser Thr His Val Leu Leu Thr His
    130                 135                 140

Thr Ile Ser Arg Ile Ala Val Ser Tyr Gln Thr Lys Val Asn Leu Leu
145                 150                 155                 160

Ser Ala Ile Lys Ser Pro Cys Gln Arg Glu Thr Pro Glu Gly Ala Glu
                165                 170                 175

Ala Lys Pro Trp Tyr Glu Pro Ile Tyr Leu Gly Gly Val Phe Gln Leu
            180                 185                 190

Glu Lys Gly Asp Arg Leu Ser Ala Glu Ile Asn Arg Pro Asp Tyr Leu
        195                 200                 205

Asp Phe Ala Glu Ser Gly Gln Val Tyr Phe Gly Ile Ile Ala Leu
    210                 215                 220

<210> SEQ ID NO 32
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: HC Signal

<400> SEQUENCE: 32

Met Glu Phe Gly Leu Ser Trp Val Phe Leu Val Ala Leu Phe Arg Gly
1               5                   10                  15

Val Gln Cys

<210> SEQ ID NO 33
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC Variable anti-biotin

<400> SEQUENCE: 33

Gln Val Lys Leu Gln Glu Ser Gly Pro Gly Leu Val Ala Pro Ser Gln
1               5                   10                  15

Ser Leu Ser Ile Thr Cys Thr Val Ser Gly Phe Ser Leu Thr Ala Tyr
            20                  25                  30
```

```
Gly Val Asp Trp Val Arg Gln Pro Gly Lys Gly Leu Glu Trp Leu
            35                  40                  45

Gly Val Ile Trp Gly Gly Arg Thr Asn Tyr Asn Ser Gly Leu Met
 50                      55                  60

Ser Arg Leu Ser Ile Arg Lys Asp Asn Ser Lys Ser Gln Val Phe Leu
 65                  70                  75                  80

Thr Met Asn Ser Leu Gln Thr Asp Asp Thr Ala Lys Tyr Tyr Cys Val
                 85                  90                  95

Lys His Thr Asn Trp Asp Gly Phe Ala Tyr Trp Gly Gln Gly Thr
                100                 105                 110

Thr Val Thr Val Ser Ser
             115
```

<210> SEQ ID NO 34
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC Constant Region 1 from IgG1

<400> SEQUENCE: 34

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu
```

<210> SEQ ID NO 35
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC Hinge Region from IgG3

<400> SEQUENCE: 35

```
Leu Lys Thr Pro Leu Gly Asp Thr Thr His Thr Cys Pro Arg Cys Pro
 1               5                  10                  15

Glu Pro Lys Ser Cys Asp Thr Pro Pro Cys Pro Arg Cys Pro Glu
             20                  25                  30

Pro Lys Ser Cys Asp Thr Pro Pro Cys Pro Arg Cys Pro Glu Pro
         35                  40                  45

Lys Ser Cys Asp Thr Pro Pro Cys Pro Arg Cys Pro
     50                  55                  60
```

<210> SEQ ID NO 36
<211> LENGTH: 110

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC Constant Region 2  from IgG1

<400> SEQUENCE: 36

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 37
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC Transmembrane and Cytoplasmic region from
      IgG1

<400> SEQUENCE: 37

Ala Glu Ala Gln Asp Gly Glu Leu Asp Gly Leu Trp Thr Thr Ile Thr
1               5                   10                  15

Ile Phe Ile Thr Leu Phe Leu Leu Ser Val Cys Tyr Ser Ala Thr Val
            20                  25                  30

Thr Phe Phe Lys Val Lys Trp Ile Phe Ser Ser Val Val Asp Leu Lys
        35                  40                  45

Gln Thr Ile Ile Pro Asp Tyr Arg Asn Met Ile Gly Gln Gly Ala
    50                  55                  60

<210> SEQ ID NO 38
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: LC Signal

<400> SEQUENCE: 38

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 39
<211> LENGTH: 99
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: LC Variable

<400> SEQUENCE: 39

Gly Ser Pro Gly Gln Ser Val Ser Ile Ser Cys Ser Gly Ser Ser Ser
1               5                   10                  15

Asn Ile Gly Asn Asn Tyr Val Tyr Trp Tyr Gln His Leu Pro Gly Thr
            20                  25                  30

Ala Pro Lys Leu Leu Ile Tyr Ser Asp Thr Lys Arg Pro Ser Gly Val
        35                  40                  45

Pro Asp Arg Ile Ser Gly Ser Lys Ser Gly Thr Ser Ala Ser Leu Ala
    50                  55                  60

Ile Ser Gly Leu Gln Ser Glu Asp Glu Ala Asp Tyr Tyr Cys Ala Ser
65                  70                  75                  80

Trp Asp Asp Ser Leu Asp Gly Pro Val Phe Gly Gly Gly Thr Lys Leu
                85                  90                  95

Thr Val Leu

<210> SEQ ID NO 40
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: LC Constant Region 1

<400> SEQUENCE: 40

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 41
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: mIgG Heavy Chain IgG 1/3 hybrid anti-biotin
      heavy chain - T323A mutant

<400> SEQUENCE: 41

Met Glu Phe Gly Leu Ser Trp Val Phe Leu Val Ala Leu Phe Arg Gly
```

-continued

```
1               5                   10                  15
Val Gln Cys Gln Val Lys Leu Gln Glu Ser Gly Pro Gly Leu Val Ala
                20                  25                  30
Pro Ser Gln Ser Leu Ser Ile Thr Cys Thr Val Ser Gly Phe Ser Leu
                35                  40                  45
Thr Ala Tyr Gly Val Asp Trp Val Arg Gln Pro Pro Gly Lys Gly Leu
 50                  55                  60
Glu Trp Leu Gly Val Ile Trp Gly Gly Arg Thr Asn Tyr Asn Ser
 65                  70                  75                  80
Gly Leu Met Ser Arg Leu Ser Ile Arg Lys Asp Asn Ser Lys Ser Gln
                85                  90                  95
Val Phe Leu Thr Met Asn Ser Leu Gln Thr Asp Asp Thr Ala Lys Tyr
                100                 105                 110
Tyr Cys Val Lys His Thr Asn Trp Asp Gly Phe Ala Tyr Trp Gly
                115                 120                 125
Gln Gly Thr Thr Val Thr Val Ser Ser Ala Ser Thr Lys Gly Pro Ser
                130                 135                 140
Val Phe Pro Leu Ala Pro Ser Ser Lys Ser Thr Ser Gly Gly Thr Ala
145                 150                 155                 160
Ala Leu Gly Cys Leu Val Lys Asp Tyr Phe Pro Glu Pro Val Thr Val
                165                 170                 175
Ser Trp Asn Ser Gly Ala Leu Thr Ser Gly Val His Thr Phe Pro Ala
                180                 185                 190
Val Leu Gln Ser Ser Gly Leu Tyr Ser Leu Ser Ser Val Val Thr Val
                195                 200                 205
Pro Ser Ser Ser Leu Gly Thr Gln Thr Tyr Ile Cys Asn Val Asn His
 210                 215                 220
Lys Pro Ser Asn Thr Lys Val Asp Lys Lys Val Glu Leu Lys Thr Pro
225                 230                 235                 240
Leu Gly Asp Thr Thr His Thr Cys Pro Arg Cys Pro Glu Pro Lys Ser
                245                 250                 255
Cys Asp Thr Pro Pro Pro Cys Pro Arg Cys Pro Glu Pro Lys Ser Cys
                260                 265                 270
Asp Thr Pro Pro Pro Cys Pro Arg Cys Pro Glu Pro Lys Ser Cys Asp
                275                 280                 285
Thr Pro Pro Pro Cys Pro Arg Cys Pro Ala Pro Glu Leu Leu Gly Gly
                290                 295                 300
Pro Ser Val Phe Leu Phe Pro Pro Lys Pro Lys Asp Thr Leu Met Ile
305                 310                 315                 320
Ser Arg Ala Pro Glu Val Thr Cys Val Val Val Asp Val Ser His Glu
                325                 330                 335
Asp Pro Glu Val Lys Phe Asn Trp Tyr Val Asp Gly Val Glu Val His
                340                 345                 350
Asn Ala Lys Thr Lys Pro Arg Glu Glu Gln Tyr Asn Ser Thr Tyr Arg
                355                 360                 365
Val Val Ser Val Leu Thr Val Leu His Gln Asp Trp Leu Asn Gly Lys
                370                 375                 380
Glu Tyr Lys Cys Lys Val Ser Asn Lys Ala Leu Pro Ala Pro Ile Glu
385                 390                 395                 400
Lys Thr Ile Ser Lys Ala Lys Gly Gln Pro Arg Glu Pro Gln Val Tyr
                405                 410                 415
Thr Leu Pro Pro Ser Arg Asp Glu Leu Thr Lys Asn Gln Val Ser Leu
                420                 425                 430
```

```
Thr Cys Leu Val Lys Gly Phe Tyr Pro Ser Asp Ile Ala Val Glu Trp
            435                 440                 445

Glu Ser Asn Gly Gln Pro Glu Asn Asn Tyr Lys Thr Thr Pro Pro Val
        450                 455                 460

Leu Asp Ser Asp Gly Ser Phe Phe Leu Tyr Ser Lys Leu Thr Val Asp
465                 470                 475                 480

Lys Ser Arg Trp Gln Gln Gly Asn Val Phe Ser Cys Ser Val Met His
                485                 490                 495

Glu Ala Leu His Asn His Tyr Thr Gln Lys Ser Leu Ser Leu Ser Pro
            500                 505                 510

Glu Leu Gln Leu Glu Glu Ser Cys Ala Glu Ala Gln Asp Gly Glu Leu
        515                 520                 525

Asp Gly Leu Trp Thr Thr Ile Thr Ile Phe Ile Thr Leu Phe Leu Leu
530                 535                 540

Ser Val Cys Tyr Ser Ala Thr Val Thr Phe Phe Lys Val Lys Trp Ile
545                 550                 555                 560

Phe Ser Ser Val Val Asp Leu Lys Gln Thr Ile Ile Pro Asp Tyr Arg
                565                 570                 575

Asn Met Ile Gly Gln Gly Ala
            580

<210> SEQ ID NO 42
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GM-CSF - HLA-I fusion peptide

<400> SEQUENCE: 42

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
                20                  25                  30

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
        50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
130                 135                 140

Glu Leu Ser Ser Gln Pro Thr Ile Pro Ile Val Gly Ile Ile Ala Gly
145                 150                 155                 160

Leu Val Leu Leu Gly Ala Val Ile Thr Gly Ala Val Val Ala Ala Val
                165                 170                 175

Met Trp Arg Arg Lys Ser Ser Asp Arg Lys Gly Gly Ser Tyr Thr Gln
            180                 185                 190
```

```
Ala Ala Ser Ser Asp Ser Ala Gln Gly Ser Asp Val Ser Leu Thr Ala
        195                 200                 205

Cys Lys Val
    210

<210> SEQ ID NO 43
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: mIgG Heavy Chain IgG 1/3 hybrid anti-biotin
      heavy chain - E325A, T323A mutant

<400> SEQUENCE: 43

Met Glu Phe Gly Leu Ser Trp Val Phe Leu Val Ala Leu Phe Arg Gly
1               5                   10                  15

Val Gln Cys Gln Val Lys Leu Gln Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Thr Ala Tyr Gly Val Asp Trp Val Arg Gln Pro Pro Gly Lys Gly Leu
    50                  55                  60

Glu Trp Leu Gly Val Ile Trp Gly Gly Gly Arg Thr Asn Tyr Asn Ser
65                  70                  75                  80

Gly Leu Met Ser Arg Leu Ser Ile Arg Lys Asp Asn Ser Lys Ser Gln
                85                  90                  95

Val Phe Leu Thr Met Asn Ser Leu Gln Thr Asp Asp Thr Ala Lys Tyr
            100                 105                 110

Tyr Cys Val Lys His Thr Asn Trp Asp Gly Phe Ala Tyr Trp Gly
        115                 120                 125

Gln Gly Thr Thr Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Leu Lys Thr Pro
225                 230                 235                 240

Leu Gly Asp Thr Thr His Thr Cys Pro Arg Cys Pro Glu Pro Lys Ser
                245                 250                 255

Cys Asp Thr Pro Pro Pro Cys Pro Arg Cys Pro Glu Pro Lys Ser Cys
            260                 265                 270

Asp Thr Pro Pro Pro Cys Pro Arg Cys Pro Glu Pro Lys Ser Cys Asp
        275                 280                 285

Thr Pro Pro Pro Cys Pro Arg Cys Pro Ala Pro Glu Leu Leu Gly Gly
    290                 295                 300

Pro Ser Val Phe Leu Phe Pro Pro Lys Pro Lys Asp Thr Leu Met Ile
```

```
            305                 310                 315                 320
        Ser Arg Ala Pro Ala Val Thr Cys Val Val Asp Val Ser His Glu
                        325                 330                 335

Asp Pro Glu Val Lys Phe Asn Trp Tyr Val Asp Gly Val Glu Val His
                        340                 345                 350

Asn Ala Lys Thr Lys Pro Arg Glu Glu Gln Tyr Asn Ser Thr Tyr Arg
                        355                 360                 365

Val Val Ser Val Leu Thr Val Leu His Gln Asp Trp Leu Asn Gly Lys
                        370                 375                 380

Glu Tyr Lys Cys Lys Val Ser Asn Lys Ala Leu Pro Ala Pro Ile Glu
        385                 390                 395                 400

Lys Thr Ile Ser Lys Ala Lys Gly Gln Pro Arg Glu Pro Gln Val Tyr
                        405                 410                 415

Thr Leu Pro Pro Ser Arg Asp Glu Leu Thr Lys Asn Gln Val Ser Leu
                        420                 425                 430

Thr Cys Leu Val Lys Gly Phe Tyr Pro Ser Asp Ile Ala Val Glu Trp
                        435                 440                 445

Glu Ser Asn Gly Gln Pro Glu Asn Asn Tyr Lys Thr Thr Pro Pro Val
                        450                 455                 460

Leu Asp Ser Asp Gly Ser Phe Phe Leu Tyr Ser Lys Leu Thr Val Asp
        465                 470                 475                 480

Lys Ser Arg Trp Gln Gln Gly Asn Val Phe Ser Cys Ser Val Met His
                        485                 490                 495

Glu Ala Leu His Asn His Tyr Thr Gln Lys Ser Leu Ser Leu Ser Pro
                        500                 505                 510

Glu Leu Gln Leu Glu Glu Ser Cys Ala Glu Ala Gln Asp Gly Glu Leu
                        515                 520                 525

Asp Gly Leu Trp Thr Thr Ile Thr Ile Phe Ile Thr Leu Phe Leu Leu
                        530                 535                 540

Ser Val Cys Tyr Ser Ala Thr Val Thr Phe Phe Lys Val Lys Trp Ile
        545                 550                 555                 560

Phe Ser Ser Val Val Asp Leu Lys Gln Thr Ile Ile Pro Asp Tyr Arg
                        565                 570                 575

Asn Met Ile Gly Gln Gly Ala
                        580

<210> SEQ ID NO 44
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Soluble Flt3-L

<400> SEQUENCE: 44

Met Thr Val Leu Ala Pro Ala Trp Ser Pro Thr Thr Tyr Leu Leu Leu
        1               5                   10                  15

Leu Leu Leu Leu Ser Ser Gly Leu Ser Gly Thr Gln Asp Cys Ser Phe
                        20                  25                  30

Gln His Ser Pro Ile Ser Ser Asp Phe Ala Val Lys Ile Arg Glu Leu
                        35                  40                  45

Ser Asp Tyr Leu Leu Gln Asp Tyr Pro Val Thr Val Ala Ser Asn Leu
                        50                  55                  60

Gln Asp Glu Glu Leu Cys Gly Gly Leu Trp Arg Leu Val Leu Ala Gln
```

```
                65                  70                  75                  80
Arg Trp Met Glu Arg Leu Lys Thr Val Ala Gly Ser Lys Met Gln Gly
                    85                  90                  95

Leu Leu Glu Arg Val Asn Thr Glu Ile His Phe Val Thr Lys Cys Ala
                100                 105                 110

Phe Gln Pro Pro Ser Cys Leu Arg Phe Val Gln Thr Asn Ile Ser
                115                 120                 125

Arg Leu Leu Gln Glu Thr Ser Glu Gln Leu Val Ala Leu Lys Pro Trp
            130                 135                 140

Ile Thr Arg Gln Asn Phe Ser Arg Cys Leu Glu Leu Gln Cys Gln Pro
145                 150                 155                 160

Asp Ser Ser Thr Leu Pro Pro Trp Ser Pro Arg Pro Leu Glu Ala
                165                 170                 175

Thr Ala Pro Thr Ala Pro Gln
                180

<210> SEQ ID NO 45
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: mIgG Heavy Chain IgG 1/3 hybrid anti-biotin
      heavy chain

<400> SEQUENCE: 45

Met Glu Phe Gly Leu Ser Trp Val Phe Leu Val Ala Leu Phe Arg Gly
1               5                   10                  15

Val Gln Cys Gln Val Lys Leu Gln Glu Ser Gly Pro Gly Leu Val Ala
                20                  25                  30

Pro Ser Gln Ser Leu Ser Ile Thr Cys Thr Val Ser Gly Phe Ser Leu
            35                  40                  45

Thr Ala Tyr Gly Val Asp Trp Val Arg Gln Pro Pro Gly Lys Gly Leu
    50                  55                  60

Glu Trp Leu Gly Val Ile Trp Gly Gly Gly Arg Thr Asn Tyr Asn Ser
65                  70                  75                  80

Gly Leu Met Ser Arg Leu Ser Ile Arg Lys Asp Asn Ser Lys Ser Gln
                85                  90                  95

Val Phe Leu Thr Met Asn Ser Leu Gln Thr Asp Asp Thr Ala Lys Tyr
                100                 105                 110

Tyr Cys Val Lys His Thr Asn Trp Asp Gly Phe Ala Tyr Trp Gly
            115                 120                 125

Gln Gly Thr Thr Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
                180                 185                 190

Val Leu Gln Ser Ser Gly Leu Tyr Ser Leu Ser Ser Val Val Thr Val
            195                 200                 205

Pro Ser Ser Ser Leu Gly Thr Gln Thr Tyr Ile Cys Asn Val Asn His
    210                 215                 220
```

```
Lys Pro Ser Asn Thr Lys Val Asp Lys Lys Val Glu Leu Lys Thr Pro
225                 230                 235                 240

Leu Gly Asp Thr Thr His Thr Cys Pro Arg Cys Pro Glu Pro Lys Ser
            245                 250                 255

Cys Asp Thr Pro Pro Cys Pro Arg Cys Pro Glu Pro Lys Ser Cys
        260                 265                 270

Asp Thr Pro Pro Pro Cys Pro Arg Cys Pro Glu Pro Lys Ser Cys Asp
        275                 280                 285

Thr Pro Pro Pro Cys Pro Arg Cys Pro Ala Pro Glu Leu Leu Gly Gly
    290                 295                 300

Pro Ser Val Phe Leu Phe Pro Pro Lys Pro Lys Asp Thr Leu Met Ile
305                 310                 315                 320

Ser Arg Thr Pro Glu Val Thr Cys Val Val Val Asp Val Ser His Glu
                325                 330                 335

Asp Pro Glu Val Lys Phe Asn Trp Tyr Val Asp Gly Val Glu Val His
                340                 345                 350

Asn Ala Lys Thr Lys Pro Arg Glu Glu Gln Tyr Asn Ser Thr Tyr Arg
            355                 360                 365

Val Val Ser Val Leu Thr Val Leu His Gln Asp Trp Leu Asn Gly Lys
370                 375                 380

Glu Tyr Lys Cys Lys Val Ser Asn Lys Ala Leu Pro Ala Pro Ile Glu
385                 390                 395                 400

Lys Thr Ile Ser Lys Ala Lys Gly Gln Pro Arg Glu Pro Gln Val Tyr
                405                 410                 415

Thr Leu Pro Pro Ser Arg Asp Glu Leu Thr Lys Asn Gln Val Ser Leu
            420                 425                 430

Thr Cys Leu Val Lys Gly Phe Tyr Pro Ser Asp Ile Ala Val Glu Trp
        435                 440                 445

Glu Ser Asn Gly Gln Pro Glu Asn Asn Tyr Lys Thr Thr Pro Pro Val
450                 455                 460

Leu Asp Ser Asp Gly Ser Phe Phe Leu Tyr Ser Lys Leu Thr Val Asp
465                 470                 475                 480

Lys Ser Arg Trp Gln Gln Gly Asn Val Phe Ser Cys Ser Val Met His
                485                 490                 495

Glu Ala Leu His Asn His Tyr Thr Gln Lys Ser Leu Ser Leu Ser Pro
            500                 505                 510

Glu Leu Gln Leu Glu Glu Ser Cys Ala Glu Ala Gln Asp Gly Glu Leu
        515                 520                 525

Asp Gly Leu Trp Thr Thr Ile Thr Ile Phe Ile Thr Leu Phe Leu Leu
    530                 535                 540

Ser Val Cys Tyr Ser Ala Thr Val Thr Phe Phe Lys Val Lys Trp Ile
545                 550                 555                 560

Phe Ser Ser Val Val Asp Leu Lys Gln Thr Ile Ile Pro Asp Tyr Arg
                565                 570                 575

Asn Met Ile Gly Gln Gly Ala
            580

<210> SEQ ID NO 46
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG Light Chain
```

<400> SEQUENCE: 46

```
Met Lys Tyr Leu Leu Pro Thr Ala Ala Ala Gly Leu Leu Leu Ala
1               5                  10                  15

Ala Gln Pro Ala Met Ala Gly Ser Pro Gly Gln Ser Val Ser Ile Ser
            20                  25                  30

Cys Ser Gly Ser Ser Ser Asn Ile Gly Asn Asn Tyr Val Tyr Trp Tyr
        35                  40                  45

Gln His Leu Pro Gly Thr Ala Pro Lys Leu Leu Ile Tyr Ser Asp Thr
    50                  55                  60

Lys Arg Pro Ser Gly Val Pro Asp Arg Ile Ser Gly Ser Lys Ser Gly
65                  70                  75                  80

Thr Ser Ala Ser Leu Ala Ile Ser Gly Leu Gln Ser Glu Asp Glu Ala
                85                  90                  95

Asp Tyr Tyr Cys Ala Ser Trp Asp Asp Ser Leu Asp Gly Pro Val Phe
            100                 105                 110

Gly Gly Gly Thr Lys Leu Thr Val Leu Gly Gln Pro Lys Ala Asn Pro
        115                 120                 125

Thr Val Thr Leu Phe Pro Pro Ser Ser Glu Glu Leu Gln Ala Asn Lys
    130                 135                 140

Ala Thr Leu Val Cys Leu Ile Ser Asp Phe Tyr Pro Gly Ala Val Thr
145                 150                 155                 160

Val Ala Trp Lys Ala Asp Gly Ser Pro Val Lys Ala Gly Val Glu Thr
                165                 170                 175

Thr Lys Pro Ser Lys Gln Ser Asn Asn Lys Tyr Ala Ala Ser Ser Tyr
            180                 185                 190

Leu Ser Leu Thr Pro Glu Gln Trp Lys Ser His Arg Ser Tyr Ser Cys
        195                 200                 205

Gln Val Thr His Glu Gly Ser Thr Val Glu Lys Thr Val Ala Pro Thr
    210                 215                 220

Glu Cys Ser
225
```

<210> SEQ ID NO 47
<211> LENGTH: 9203
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Vector 1

<400> SEQUENCE: 47

```
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt     180
gccgcattgc agagatattg tatttaagtg cctagctcga tacataaacg ggtctctctg     240
gttagaccag atctgagcct gggagctctc tggctaacta gggaacccac tgcttaagcc     300
tcaataaagc ttgccttgag tgcttcaagt agtgtgtgcc cgtctgttgt gtgactctgg     360
taactagaga tccctcagac ccttttagtc agtgtggaaa atctctagca gtggcgcccg     420
aacagggact tgaaagcgaa agggaaacca ggagagctct ctcgacgcag gactcggctt     480
gctgaagcgc gcacggcaag aggcgagggg cggcgactgg tgagtacgcc aaaaattttg     540
```

```
actagcggag gctagaagga gagagatggg tgcgagagcg tcagtattaa gcggggggaga    600
attagatcgc gatgggaaaa aattcggtta aggccagggg gaaagaaaaa atataaatta    660
aaacatatag tatgggcaag cagggagcta gaacgattcg cagttaatcc tggcctgtta    720
gaaacatcag aaggctgtag acaaatactg ggacagctac aaccatccct tcagacagga    780
tcagaagaac ttagatcatt atataataca gtagcaaccc tctattgtgt gcatcaaagg    840
atagagataa aagacaccaa ggaagcttta gacaagatag aggaagagca aaacaaaagt    900
aagaccaccg cacagcaagc ggccgctgat cttcagacct ggaggaggag atatgaggga    960
caattggaga agtgaattat ataaatataa agtagtaaaa attgaaccat taggagtagc   1020
acccaccaag gcaaagagaa gagtggtgca gagagaaaaa agagcagtgg gaataggagc   1080
tttgttcctt gggttcttgg gagcagcagg aagcactatg ggcgcagcgt caatgacgct   1140
gacggtacag gccagacaat tattgtctgg tatagtgcag cagcagaaca atttgctgag   1200
ggctattgag gcgcaacagc atctgttgca actcacagtc tggggcatca agcagctcca   1260
ggcaagaatc ctggctgtgg aaagatacct aaaggatcaa cagctcctgg ggatttgggg   1320
ttgctctgga aaactcattt gcaccactgc tgtgccttgg aatgctagtt ggagtaataa   1380
atctctggaa cagatttgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620
agttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcgcta   1800
gcttttaaaa gaaaaggggg gattgggggg tacagtgcag gggaaagaat agtagacata   1860
atagcaacag acatacaaac taagaagaatta caaaaacaaa ttacaaaaat tcaaaatttt   1920
actagtgatt atcggatcaa cttttgtatag aaaagttggg ctccggtgcc cgtcagtggg   1980
cagagcgcac atcgcccaca gtccccgaga agttgggggg aggggtcggc aattgaaccg   2040
gtgcctagag aaggtggcgc ggggtaaact gggaaagtga tgtcgtgtac tggctccgcc   2100
ttttttcccga gggtgggggga gaaccgtata taagtgcagt agtcgccgtg aacgttcttt   2160
ttcgcaacgg gtttgccgcc agaacacagg taagtgccgt gtgtggttcc cgcgggcctg   2220
gcctctttac gggttatggc ccttgcgtgc cttgaattac ttccacctgg ctgcagtacg   2280
tgattcttga tcccgagctt cgggttggaa gtgggtggga gagttcgagg ccttgcgctt   2340
aaggagcccc ttcgcctcgt gcttgagttg aggcctggcc tgggcgctgg ggccgccgcg   2400
tgcgaatctg gtggcacctt cgcgcctgtc tcgctgcttt cgataagtct ctagccattt   2460
aaaattttg atgacctgct gcgacgcttt ttttctggca agatagtctt gtaaatgcgg   2520
gccaagatct gcacactggt atttcggttt ttggggccgc gggcggcgac ggggcccgtg   2580
cgtcccagcg cacatgttcg gcgaggcggg gcctgcgagc gcggccaccg agaatcggac   2640
gggggtagtc tcaagctggc cggcctgctc tggtgcctgg tctcgcgccg ccgtgtatcg   2700
ccccgccctg ggcggcaagg ctggcccggt cggcaccagt tgcgtgagcg gaaagatggc   2760
cgcttcccgg ccctgctgca gggagctcaa aatggaggac gcggcgctcg ggagagcggg   2820
cgggtgagtc acccacacaa aggaaaaggg ccttttccgtc ctcagccgtc gcttcatgtg   2880
actccacgga gtaccgggcg ccgtccaggc acctcgatta gttctcgagc ttttggagta   2940
```

```
cgtcgtctttt aggttggggg gagggggtttt atgcgatgga gtttccccac actgagtggg    3000
tggagactga agttaggcca gcttggcact tgatgtaatt ctccttggaa tttgcccttt     3060
ttgagtttgg atcttggttc attctcaagc ctcagacagt ggttcaaagt ttttttcttc    3120
catttcaggt gtcgtgacaa gtttgtacaa aaaagcaggc tgccaccatg gagttcggcc    3180
tgagctgggt gttcctggtg gccctgttca gaggcgtgca gtgccaggtg aagctgcagg    3240
agagcggccc cggcctggtg gccccagcc agagcctgag catcacctgc accgtgagcg     3300
gcttcagcct gaccgcctac ggcgtggact gggtgagaca gccccccggc aagtgcctgg    3360
agtggctggg cgtgatctgg ggcggcggca gaaccaacta caacagcggc ctgatgagca    3420
gactgagcat cagaaaggac aacagcaaga gccaggtgtt cctgaccatg aacagcctgc    3480
agaccgacga caccgccaag tactactgcg tgaagcacac caactgggac ggcggcttcg    3540
cctactgggg ccagggcacc accgtgaccg tgagcagcgg cggcggcggc agcggcggcg    3600
gcggcagcgg cggcggcggc agcggcagcc cggccagag cgtgagcatc agctgcagcg     3660
gcagcagcag caacatcggc aacaactacg tgtactggta ccagcacctg cccggcaccg    3720
cccccaagct gctgatctac agcgacacca gagacccag cggcgtgccc gacagaatca     3780
gcggcagcaa gagcggcacc agcgccagcc tggccatcag cggcctgcag agcgaggacg    3840
aggccgacta ctactgcgcc agctgggacg acagcctgga cggccccgtg ttcggctgcg    3900
gcaccaagct gaccgtgctg ctgaagaccc ccctgggcga caccacccac acctgcccca    3960
gatgccccga gccaagagc tgcgacaccc cccccccctg cccagatgc cccgagccca      4020 agagctgcga cacccccccc cctgccccca gatgcccccga gccaagagc tgcgacaccc     4080 cccccccctg cccagatgc cccgccccg agctgctggg cggccccagc gtgttcctgt       4140
tcccccccaa gcccaaggac accctgatga tcagcagagc ccccgaggtg acctgcgtgg    4200
tggtggacgt gagccacgag gaccccgagg tgaagttcaa ctggtacgtg gacggcgtgg    4260
aggtgcacaa cgccaagacc aagcccagag aggagcagta caacagcacc tacagagtgg    4320
tgagcgtgct gaccgtgctg caccaggact ggctgaacgg caaggagtac aagtgcaagg    4380
tgagcaacaa ggcctgccc gccccatcg agaaagccat cagcaaggcc aagggccagc       4440
ccagagagcc ccaggtgtac accctgcccc cagcagaga cgagctgacc aagaaccagg     4500
tgagcctgac ctgcctggtg aagggcttct accccagcga catcgccgtg gagtgggaga    4560
gcaacggcca gcccgagaac aactacaaga ccacccccc cgtgctggac agcgacggca     4620
gcttcttcct gtacagcaag ctgaccgtgg acaagagcag atggcagcag ggcaacgtgt    4680
tcagctgcag cgtgatgcac gaggccctgc acaaccacta cacccagaag agcctgagcc    4740
tgagccccga gctgcagctg gaggagagct gcgccgaggc ccaggacggc gagctggacg    4800
gcctgtggac caccatcacc atcttcatca ccctgttcct gctgagcgtg tgctacagcg    4860
ccaccgtgac cttcttcaag gtgaagtgga tcttcagcag cgtggtggac ctgaagcaga    4920
ccatcatccc cgactacaga aacatgatcg gccagggcgc ctaaacccag ctttcttgta    4980
caaagtggtg ataatcgaat tctaaaccca gctttcttgt acaaagtggt gataatcgaa    5040
ttccgataat caacctctgg attacaaaat ttgtgaaaga ttgactggta ttcttaacta    5100
tgttgctcct tttacgctat gtggatacgc tgctttaatg cctttgtatc atgctattgc    5160
ttcccgtatg gctttcattt tctcctcctt gtataaatcc tggttgctgt ctctttatga    5220
ggagttgtgg cccgttgtca ggcaacgtgg cgtggtgtgc actgtgtttg ctgacgcaac    5280
```

```
ccccactggt tggggcattg ccaccacctg tcagctcctt tccgggactt tcgctttccc    5340
cctccctatt gccacggcgg aactcatcgc cgcctgcctt gcccgctgct ggacaggggc    5400
tcggctgttg ggcactgaca attccgtggt gttgtcgggg aagctgacgt cctttccatg    5460
gctgctcgcc tgtgttgcca cctggattct gcgcgggacg tccttctgct acgtcccttc    5520
ggccctcaat ccagcggacc ttccttcccg cggcctgctg ccggctctgc ggcctcttcc    5580
gcgtcttcgc cttcgccctc agacgagtcg gatctccctt gggccgcct ccccgcatcg     5640
ggaattcccg cggttcgctt taagaccaat gacttacaag gcagctgtag atcttagcca    5700
cttttttaaaa gaaaggggg gactggaagg gctaattcac tcccaacgaa gacaagatct    5760
gcttttgct tgtactgggt ctctctggtt agaccagatc tgagcctggg agctctctgg     5820
ctaactaggg aacccactgc ttaagcctca ataaagcttg ccttgagtgc ttcaagtagt    5880
gtgtgcccgt ctgttgtgtg actctggtaa ctagagatcc ctcagaccct tttagtcagt    5940
gtggaaaatc tctagcagta gtagttcatg tcatcttatt attcagtatt tataacttgc    6000
aaagaaatga atatcagaga gtgagaggaa cttgtttatt gcagcttata atggttacaa    6060
ataaagcaat agcatcacaa atttcacaaa taaagcattt ttttcactgc attctagttg    6120
tggtttgtcc aaactcatca atgtatctta tcatgtctgg ctctagctat cccgccccta    6180
actccgccca tcccgcccct aactccgccc agttccgccc attctccgcc ccatggctga    6240
ctaatttttt ttatttatgc agaggccgag gccgcctcgg cctctgagct attccagaag    6300
tagtgaggag gcttttttgg aggcctaggg acgtacccaa ttcgccctat agtgagtcgt    6360
attacgcgcg ctcactggcc gtcgttttac aacgtcgtga ctgggaaaac cctggcgtta    6420
cccaacttaa tcgccttgca gcacatcccc ctttcgccag ctggcgtaat agcgaagagg    6480
cccgcaccga tcgcccttcc caacagttgc gcagcctgaa tggcgaatgg gacgcgccct    6540
gtagcggcgc attaagcgcg gcgggtgtgg tggttacgcg cagcgtgacc gctacacttg    6600
ccagcgccct agcgcccgct cctttcgctt tcttcccttc ctttctcgcc acgttcgccg    6660
gctttccccg tcaagctcta aatcgggggc tccctttagg gttccgattt agtgctttac    6720
ggcacctcga ccccaaaaaa cttgattagg gtgatggttc acgtagtggg ccatcgccct    6780
gatagacggt ttttcgccct ttgacgttgg agtccacgtt ctttaatagt ggactcttgt    6840
tccaaactgg aacaacactc aaccctatct cggtctattc ttttgattta agggatttt    6900
tgccgatttc ggcctattgg ttaaaaaatg agctgattta caaaaattt aacgcgaatt    6960
ttaacaaaat attaacgctt acaatttagg tggcactttt cggggaaatg tgcgcggaac    7020
ccctatttgt ttatttttct aaatacattc aaatatgtat ccgctcatga caataaacc     7080
ctgataaatg cttcaataat attgaaaaag gaagagtatg agtattcaac atttccgtgt    7140
cgcccttatt ccctttttg cggcatttg ccttcctgtt tttgctcacc cagaaacgct     7200
ggtgaaagta aaagatgctg aagatcagtt gggtgcacga gtgggttaca tcgaactgga    7260
tctcaacagc ggtaagatcc ttgagagttt tcgccccgaa gaacgttttc caatgatgag    7320
cactttttaaa gttctgctat gtggcgcggt attatcccgt attgacgccg ggcaagagca    7380
actcggtcgc cgcatacact attctcagaa tgacttggtt gagtactcac cagtcacaga    7440
aaagcatctt acggatggca tgacagtaag agaattatgc agtgctgcca taaccatgag    7500
tgataacact gcggccaact tacttctgac aacgatcgga ggaccgaagg agctaaccgc    7560
ttttttgcac aacatggggg atcatgtaac tcgccttgat cgttgggaac cggagctgaa    7620
tgaagccata ccaaacgacg agcgtgacac cacgatgcct gtagcaatgg caacaacgtt    7680
```

```
gcgcaaacta ttaactggcg aactacttac tctagcttcc cggcaacaat taatagactg    7740
gatggaggcg gataaagttg caggaccact tctgcgctcg gcccttccgg ctggctggtt    7800
tattgctgat aaatctggag ccggtgagcg tgggtctcgc ggtatcattg cagcactggg    7860
gccagatggt aagccctccc gtatcgtagt tatctacacg acggggagtc aggcaactat    7920
ggatgaacga aatagacaga tcgctgagat aggtgcctca ctgattaagc attggtaact    7980
gtcagaccaa gtttactcat atactttta gattgattta aaacttcatt tttaatttaa    8040
aaggatctag gtgaagatcc ttttgataa tctcatgacc aaaatccctt aacgtgagtt    8100
ttcgttccac tgagcgtcag accccgtaga aaagatcaaa ggatcttctt gagatccttt    8160
ttttctgcgc gtaatctgct gcttgcaaac aaaaaaacca ccgctaccag cggtggtttg    8220
tttgccggat caagagctac caactctttt tccgaaggta actggcttca gcagagcgca    8280
gataccaaat actgttcttc tagtgtagcc gtagttaggc caccacttca agaactctgt    8340
agcaccgcct acatacctcg ctctgctaat cctgttacca gtggctgctg ccagtggcga    8400
taagtcgtgt cttaccgggt tggactcaag acgatagtta ccggataagg cgcagcggtc    8460
gggctgaacg gggggttcgt gcacacagcc cagcttggag cgaacgacct acaccgaact    8520
gagataccta cagcgtgagc tatgagaaag cgccacgctt cccgaagaga aaaggcgga    8580 caggtatccg gtaagcggca gggtcggaac aggagagcgc acgagggagc ttccaggggg    8640
aaacgcctgg tatctttata gtcctgtcgg gtttcgccac ctctgacttg agcgtcgatt    8700
tttgtgatgc tcgtcagggg ggcggagcct atggaaaaac gccagcaacg cggccttttt    8760
acggttcctg gccttttgct ggccttttgc tcacatgttc tttcctgcgt tatccctga    8820 ttctgtggat aaccgtatta ccgcctttga gtgagctgat accgctcgcc gcagccgaac    8880
gaccgagcgc agcgagtcag tgagcgagga agcggaagag cgcccaatac gcaaaccgcc    8940
tctccccgcg cgttggccga ttcattaatg cagctggcac gacaggtttc ccgactggaa    9000
agcgggcagt gagcgcaacg caattaatgt gagttagctc actcattagg caccccaggc    9060
tttacacttt atgcttccgg ctcgtatgtt gtgtggaatt gtgagcggat aacaatttca    9120
cacaggaaac agctatgacc atgattacgc caagcgcgca attaaccctc actaaaggga    9180
acaaaagctg gagctgcaag ctt                                            9203
```

<210> SEQ ID NO 48
<211> LENGTH: 10862
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Vector 2

<400> SEQUENCE: 48

```
aatgtagtct tatgcaatac tcttgtagtc ttgcaacatg gtaacgatga gttagcaaca     60
tgccttacaa ggagagaaaa agcaccgtgc atgccgattg gtggaagtaa ggtggtacga    120
tcgtgcctta ttaggaaggc aacagacggg tctgacatgg attggacgaa ccactgaatt    180
gccgcattgc agagatattg tatttaagtg cctagctcga tacataaacg ggtctctctg    240
gttagaccag atctgagcct gggagctctc tggctaacta gggaacccac tgcttaagcc    300
tcaataaagc ttgccttgag tgcttcaagt agtgtgtgcc cgtctgttgt gtgactctgg    360
taactagaga tccctcagac cctttagtc agtgtggaaa atctctagca gtggcgcccg    420
```

-continued

```
aacagggact tgaaagcgaa agggaaacca gaggagctct ctcgacgcag gactcggctt    480
gctgaagcgc gcacggcaag aggcgagggg cggcgactgg tgagtacgcc aaaaattttg    540
actagcggag gctagaagga gagagatggg tgcgagagcg tcagtattaa gcggggggaga   600
attagatcgc gatgggaaaa aattcggtta aggccagggg gaaagaaaaa atataaatta   660
aaacatatag tatgggcaag cagggagcta gaacgattcg cagttaatcc tggcctgtta   720
gaaacatcag aaggctgtag acaaatactg ggacagctac aaccatccct tcagacagga   780
tcagaagaac ttagatcatt ataataca gtagcaaccc tctattgtgt gcatcaaagg    840
atagagataa aagacaccaa ggaagcttta gacaagatag aggaagagca aaacaaaagt   900
aagaccaccg cacagcaagc ggccgctgat cttcagacct ggaggaggag atatgaggga    960
caattggaga agtgaattat ataaatataa agtagtaaaa attgaaccat taggagtagc   1020
acccaccaag gcaaagagaa gagtggtgca gagagaaaaa agagcagtgg gaataggagc   1080
tttgttcctt gggttcttgg gagcagcagg aagcactatg ggcgcagcgt caatgacgct   1140
gacggtacag gccagacaat tattgtctgg tatagtgcag cagcagaaca atttgctgag   1200
ggctattgag gcgcaacagc atctgttgca actcacagtc tggggcatca agcagctcca   1260
ggcaagaatc ctggctgtgg aaagatacct aaaggatcaa cagctcctgg ggatttgggg   1320
ttgctctgga aaactcattt gcaccactgc tgtgccttgg aatgctagtt ggagtaataa   1380
atctctggaa cagatttgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620
agttttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcgcta   1800
gcttttaaaa gaaaagggggg gattgggggg tacagtgcag gggaagaat agtagacata   1860
atagcaacag acatacaaac taagaatta caaaacaaa ttacaaaaat tcaaaatttt    1920
actagtatca actttgtata gaaaagttgg gctccggtgc ccgtcagtgg gcagagcgca   1980
catcgcccac agtccccgag aagttggggg gaggggtcgg caattgaacc ggtgcctaga   2040
gaaggtggcg cggggtaaac tgggaaagtg atgtcgtgta ctggctccgc ctttttcccg   2100
agggtggggg agaaccgtat ataagtgcag tagtcgccgt gaacgttctt tttcgcaacg   2160
ggtttgccgc cagaacacag gtaagtgccg tgtgtggttc ccgcgggcct ggcctcttta   2220
cgggttatgg ccccttgcgtg ccttgaatta cttccacctg gctgcagtac gtgattcttg   2280
atcccgagct tcgggttgga agtgggtggg agagttcgag gccttgcgct taaggagccc   2340
cttcgcctcg tgcttgagtt gaggcctggc ctgggcgctg gggccgccgc gtgcgaatct   2400
ggtggcacct tcgcgcctgt ctcgctgctt tcgataagtc tctagccatt taaaattttt   2460
gatgacctgc tgcgacgctt tttttctggc aagatagtct tgtaaatgcg ggccaagatc   2520
tgcacactgg tatttcggtt tttggggccg cggcggcga cggggcccgt gcgtcccagc   2580
gcacatgttc ggcgaggcgg ggcctgcgag cgcggccacc gagaatcgga cggggggtagt   2640
ctcaagctgg ccggcctgct ctggtgcctg gtctcgcgcc gccgtgtatc gccccgccct   2700
gggcggcaag gctggcccgg tcggcaccag ttgcgtgagc ggaaagatgg ccgcttcccg   2760
```

```
gccctgctgc agggagctca aaatggagga cgcggcgctc gggagagcgg gcgggtgagt    2820
cacccacaca aaggaaaagg gcctttccgt cctcagccgt cgcttcatgt gactccacgg    2880
agtaccgggc gccgtccagg cacctcgatt agttctcgag cttttggagt acgtcgtctt    2940
taggttgggg ggaggggttt tatgcgatgg agtttcccca cactgagtgg gtggagactg    3000
aagttaggcc agcttggcac ttgatgtaat tctccttgga atttgcccttt tttgagtttg    3060 gatcttggtt cattctcaag cctcagacag tggttcaaag ttttttttctt ccatttcagg    3120 tgtcgtgaca agtttgtaca aaaagcagg ctgccaccat ggagttcggc ctgagctggg    3180
tgttcctggt ggccctgttc agaggcgtgc agtgccaggt gaagctgcag gagagcggcc    3240
ccggcctggt ggcccccagc cagagcctga gcatcacctg caccgtgagc ggcttcagcc    3300
tgaccgccta cggcgtggac tgggtgagac agcccccgg caagggcctg gagtggctgg    3360
gcgtgatctg gggcggcggc agaaccaact acaacagcgg cctgatgagc agactgagca    3420
tcagaaagga caacagcaag agccaggtgt tcctgaccat gaacagcctg cagaccgacg    3480
acaccgccaa gtactactgc gtgaagcaca ccaactggga cggcggcttc gcctactggg    3540
gccagggcac caccgtgacc gtgagcagcc cagcgtgtt ccccctggcc ccagcagca    3600 agagcaccag cggcggcacc gccgccctgg gctgcctggt gaaggactac ttccccgagc    3660
ccgtgaccgt gagctggaac agcggcgccc tgaccagcgg cgtgcacacc ttccccgccg    3720
tgctgcagag cagcggcctg tacagcctga gcagcgtggt gaccgtgccc agcagcagcc    3780
tgggcaccca gacctacatc tgcaacgtga accacaagcc cagcaacacc aaggtggaca    3840
agaaggtgga gctgaagacc cccctgggcg acaccaccca cacctgcccc agatgccccg    3900
agcccaagag ctgcgacacc ccccccccct gccccagatg cccgagccc aagagctgcg    3960 acacccccc cccctgcccc agatgccccg agcccaagag ctgcgacacc cccccccct    4020 gccccagatg cccgccccc gagctgctgg gcggccccag cgtgttcctg ttccccccca    4080
agcccaagga caccctgatg atcagcagag cccccgaggt gacctgcgtg gtggtggacg    4140
tgagccacga ggaccccgag gtgaagttca actggtacgt ggacggcgtg gaggtgcaca    4200
acgccaagac caagcccaga gaggagcagt acaacagcac ctacagagtg gtgagcgtgc    4260
tgaccgtgct gcaccaggac tggctgaacg gcaaggagta caagtgcaag gtgagcaaca    4320
aggccctgcc cgcccccatc gagaagacca tcagcaaggc caagggccag cccagagagc    4380
cccaggtgta caccctgccc cccagcagag acgagctgac caagaaccag gtgagcctga    4440
cctgcctggt gaagggcttc taccccagcg acatcgccgt ggagtgggag agcaacggcc    4500
agcccgagaa caactacaag accaccccccc ccgtgctgga cagcgacggc agcttcttcc    4560
tgtacagcaa gctgaccgtg acaagagca gatggcagca gggcaacgtg ttcagctgca    4620
gcgtgatgca cgaggccctg cacaaccact acacccagaa gagcctgagc ctgagccccg    4680
agctgcagct ggaggagagc tgcgccgagg cccaggacgg cgagctggac ggcctgtgga    4740
ccaccatcac catcttcatc accctgttcc tgctgagcgt gtgctacagc gccaccgtga    4800
ccttcttcaa ggtgaagtgg atcttcagca gcgtggtgga cctgaagcag accatcatcc    4860
ccgactacaa aaacatgatc ggccaggcg cctaaaacaa caacaattgc attcatttta    4920
tgtttcaggt tcaggggag gtgtgggagg ttttttaaag caagtaaaac ctctacaaat    4980
gtggtacgcg ttaacaacaa caattgcatt catttttatgt ttcaggttca gggggaggtg    5040
tgggaggttt tttaaagcaa gtaaaacctc tacaaatgtg gtacgcgtta cccagctttc    5100
ttgtacaaag tggtaaatag atagaacaac aacaattgca ttcattttg atttcaggtt    5160
```

```
caggggagg tgtgggaggt ttttaaagc aagtaaaacc tctacactga cggtacgcgt    5220
taacaacaac aattgcattc atttgtagtt tcaggttcag ggggaggtgt gggaggtttt    5280
ttaaagcaag ttaaacctct aaaatagtgg tacgcgttac ccagctttct tgtacaaagt    5340
ggacccagct ttcttgtaca aagtgggccc ctctccctcc ccccccccta acgttactgg    5400
ccgaagccgc ttggaataag gccggtgtgc gtttgtctat atgttatttt ccaccatatt    5460
gccgtctttt ggcaatgtga gggcccggaa acctggccct gtcttcttga cgagcattcc    5520
taggggtctt tcccctctcg ccaaaggaat gcaaggtctg ttgaatgtcg tgaaggaagc    5580
agttcctctg gaagcttctt gaagacaaac aacgtctgta cgaccctt gcaggcagcg    5640 gaaccccca cctggcgaca ggtgcctctg cggccaaaag ccacgtgtat aagatacacc    5700
tgcaaaggcg gcacaacccc agtgccacgt tgtgagttgg atagttgtgg aaagagtcaa    5760
atggctctcc tcaagcgtat tcaacaaggg gctgaaggat gcccagaagg taccccattg    5820
tatgggatct gatctggggc ctcggtgcac atgctttaca tgtgtttagt cgaggttaaa    5880
aaaacgtcta ggccccccga accacgggga cgtggttttc ctttgaaaaa cacgatgata    5940
atatggccac aaccatggcc accgacatga gagtgcccgc ccagctgctg ggcctgctgc    6000
tgctgtggct gagcggcgcc agatgcggca gccccggcca gagcgtgagc atcagctgca    6060
gcggcagcag cagcaacatc ggcaacaact acgtgtactg gtaccagcac ctgcccggca    6120
ccgcccccaa gctgctgatc tacagcgaca ccaagagacc cagcggcgtg cccgacagaa    6180
tcagcggcag caagagcggc accagcgcca gcctggccat cagcggcctg cagagcgagg    6240
acgaggccga ctactactgc gccagctggg acgacagcct ggacggcccc gtgttcggcg    6300
gcggcaccaa gctgaccgtg ctgggccagc ccaaggccaa ccccaccgtg accctgttcc    6360
cccccagcag cgaggagctg caggccaaca aggccaccct ggtgtgcctg atcagcgact    6420
tctaccccgg cgccgtgacc gtggcctgga aggccgacgg cagccccgtg aaggccggcg    6480
tggagaccac caagcccagc aagcagagca acaacaagta cgccgccagc agctacctga    6540
gcctgacccc cgagcagtgg aagagccaca gaagctacag ctgccaggtg acccacgagg    6600
gcagcaccgt ggagaagacc gtggccccca ccgagtgcag ctaacaactt tattatacat    6660
agttgatcaa ttccaacttt attatacata gttgatcaat tccgataatc aacctctgga    6720
ttacaaaatt tgtgaaagat tgactggtat tcttaactat gttgctcctt ttacgctatg    6780
tggatacgct gctttaatgc ctttgtatca tgctattgct tcccgtatgg ctttcatttt    6840
ctcctccttg tataaatcct ggttgctgtc tctttatgag gagttgtggc ccgttgtcag    6900
gcaacgtggc gtggtgtgca ctgtgtttgc tgacgcaacc cccactggtt ggggcattgc    6960
caccacctgt cagctccttt ccgggacttt cgctttcccc ctccctattg ccacggcgga    7020
actcatcgcc gcctgccttg cccgctgctg acaggggct cggctgttgg cactgacaa    7080 ttccgtggtt ttgtcgggga agctgacgtc ctttccatgg ctgctcgcct gtgttgccac    7140
ctggattctg cgcgggacgt ccttctgcta cgtcccttcg ccctcaatc cagcggacct    7200 tccttcccgc ggcctgctgc cggctctgcg gcctcttccg cgtcttcgcc ttcgccctca    7260
gacgagtcga atctcccttt gggccgcctc cccgcatcgg gaattcccgc ggttcgcttt    7320
aagaccaatg acttacaagg cagctgtaga tcttagccac ttttaaaag aaaggggggg    7380 actgaagggg ctaattcact cccaacgaag acaagatctg cttttgctt gtactgggtc    7440 tctctggtta gaccagatct gagcctggga gctctctggc taactaggga acccactgct    7500
```

```
taagcctcaa taaagcttgc cttgagtgct tcaagtagtg tgtgcccgtc tgttgtgtga    7560
ctctggtaac tagagatccc tcagacccct ttagtcagtg tggaaaatct ctagcagtag    7620
tagttcatgt catcttatta ttcagtattt ataacttgca aagaaatgaa tatcagagag    7680
tgagaggaac ttgtttattg cagcttataa tggttacaaa taaagcaata gcatcacaaa    7740
tttcacaaat aaagcatttt tttcactgca ttctagttgt ggtttgtcca aactcatcaa    7800
tgtatcttat catgtctggc tctagctatc ccgcccctaa ctccgcccat cccgcccta    7860 actccgccca gttccgccca ttctccgccc catggctgac taatttttttt tatttatgca    7920 gaggccgagg ccgcctcggc ctctgagcta ttccagaagt agtgaggagg cttttttgga    7980
ggcctaggga cgtacccaat tcgccctata gtgagtcgta ttacgcgcgc tcactggccg    8040
tcgttttaca acgtcgtgac tgggaaaacc ctggcgttac ccaacttaat cgccttgcag    8100
cacatccccc tttcgccagc tggcgtaata gcgaagaggc ccgcaccgat cgcccttccc    8160
aacagttgcg cagcctgaat ggcgaatggg acgcgccctg tagcggcgca ttaagcgcgg    8220
cgggtgtggt ggttacgcgc agcgtgaccg ctacacttgc cagcgcccta gcgcccgctc    8280
ctttcgcttt cttcccttcc tttctcgcca cgttcgccgg ctttccccgt caagctctaa    8340 atcggggct ccctttaggg ttccgattta gtgctttacg gcacctcgac cccaaaaaac    8400
ttgattaggg tgatggttca cgtagtgggc catcgccctg atagacggtt tttcgccctt    8460
tgacgttgga gtccacgttc tttaatagtg gactcttgtt ccaaactgga acaacactca    8520
accctatctc ggtctattct tttgatttat aagggatttt gccgatttcg gcctattggt    8580 taaaaatga gctgatttaa caaaaattta acgcgaattt taacaaaata ttaacgctta    8640
caatttaggt ggcacttttc ggggaaatgt gcgcggaacc cctatttgtt tatttttcta    8700
aatacattca aatatgtatc cgctcatgag acaataaccc tgataaatgc ttcaataata    8760
ttgaaaaagg aagagtatga gtattcaaca tttccgtgtc gcccttattc ccttttttgc    8820
ggcattttgc cttcctgttt ttgctcaccc agaaacgctg gtgaaagtaa aagatgctga    8880
agatcagttg ggtgcacgag tgggttacat cgaactggat ctcaacagcg gtaagatcct    8940
tgagagtttt cgccccgaag aacgttttcc aatgatgagc acttttaaag ttctgctatg    9000
tggcgcggta ttatcccgta ttgacgccgg gcaagagcaa ctcggtcgcc gcatacacta    9060
ttctcagaat gacttggttg agtactcacc agtcacagaa aagcatctta cggatggcat    9120
gacagtaaga gaattatgca gtgctgccat aaccatgagt gataacactg cggccaactt    9180
acttctgaca acgatcggag gaccgaagga gctaaccgct tttttgcaca acatggggga    9240
tcatgtaact cgccttgatc gttgggaacc ggagctgaat gaagccatac caaacgacga    9300
gcgtgacacc acgatgcctg tagcaatggc aacaacgttg cgcaaactat taactggcga    9360
actacttact ctagcttccc ggcaacaatt aatagactgg atggaggcgg ataaagttgc    9420
aggaccactt ctgcgctcgg cccttccggc tggctggttt attgctgata aatctggagc    9480
cggtgagcgt gggtctcgcg gtatcattgc agcactgggg ccagatggta agccctcccg    9540
tatcgtagtt atctacacga cggggagtca ggcaactatg gatgaacgaa atagacagat    9600
cgctgagata ggtgcctcac tgattaagca ttggtaactg tcagaccaag tttactcata    9660
tatactttag attgatttaa aacttcattt ttaatttaaa aggatctagg tgaagatcct    9720
ttttgataat ctcatgacca aaatccctta acgtgagttt tcgttccact gagcgtcaga    9780
ccccgtagaa aagatcaaag gatcttcttg agatcctttt tttctgcgcg taatctgctg    9840
cttgcaaaca aaaaaaccac cgctaccagc ggtggtttgt ttgccggatc aagagctacc    9900
```

```
aactctttttt ccgaaggtaa ctggcttcag cagagcgcag ataccaaata ctgttcttct      9960
agtgtagccg tagttaggcc accacttcaa gaactctgta gcaccgccta catacctcgc     10020
tctgctaatc ctgttaccag tggctgctgc cagtggcgat aagtcgtgtc ttaccgggtt     10080
ggactcaaga cgatagttac cggataaggc gcagcggtcg ggctgaacgg ggggttcgtg     10140
cacacagccc agcttggagc gaacgaccta caccgaactg agatacctac agcgtgagct     10200
atgagaaagc gccacgcttc ccgaagagag aaaggcggac aggtatccgg taagcggcag     10260
ggtcggaaca ggagagcgca cgagggagct tccaggggga aacgcctggt atctttatag     10320
tcctgtcggg tttcgccacc tctgacttga gcgtcgattt ttgtgatgct cgtcaggggg     10380
gcggagccta tggaaaaacg ccagcaacgc ggccttttta cggttcctgg ccttttgctg     10440
gccttttgct cacatgttct ttcctgcgtt atcccctgat tctgtggata accgtattac     10500
cgcctttgag tgagctgata ccgctcgccg cagccgaacg accgagcgca gcgagtcagt     10560
gagcgaggaa gcggaagagc gcccaatacg caaaccgcct ctccccgcgc gttggccgat     10620
tcattaatgc agctggcacg acaggtttcc cgactggaaa gcgggcagtg agcgcaacgc     10680
aattaatgtg agttagctca ctcattaggc accccaggct ttacacttta tgcttccggc     10740
tcgtatgttg tgtggaattg tgagcggata acaatttcac acaggaaaca gctatgacca     10800
tgattacgcc aagcgcgcaa ttaaccctca ctaaagggaa caaaagctgg agctgcaagc     10860
tt                                                                   10862

<210> SEQ ID NO 49
<211> LENGTH: 9581
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Vector 3

<400> SEQUENCE: 49
aatgtagtct tatgcaatac tcttgtagtc ttgcaacatg gtaacgatga gttagcaaca       60
tgccttacaa ggagagaaaa agcaccgtgc atgccgattg gtggaagtaa ggtggtacga      120
tcgtgcctta ttaggaaggc aacagacggg tctgacatgg attggacgaa ccactgaatt      180
gccgcattgc agagatattg tatttaagtg cctagctcga tacataaacg ggtctctctg      240
gttagaccag atctgagcct gggagctctc tggctaacta gggaacccac tgcttaagcc      300
tcaataaagc ttgccttgag tgcttcaagt agtgtgtgcc cgtctgttgt gtgactctgg      360
taactagaga tccctcagac ccttttagtc agtgtggaaa atctctagca gtggcgcccg      420
aacagggact tgaaagcgaa agggaaacca gaggagctct ctcgacgcag gactcggctt      480
gctgaagcgc gcacggcaag aggcgagggg cggcgactgg tgagtacgcc aaaaattttg      540
actagcggag gctagaagga gagagatggg tgcgagagcg tcagtattaa gcgggggaga      600
attagatcgc gatgggaaaa aattcggtta aggccagggg gaaagaaaaa atataaatta      660
aaacatatag tatgggcaag cagggagcta gaacgattcg cagttaatcc tggcctgtta      720
gaaacatcag aaggctgtag acaaatactg ggacagctac aaccatccct tcagacagga      780
tcagaagaac ttagatcatt atataataca gtagcaaccc tctattgtgt gcatcaaagg      840
atagagataa aagacaccaa ggaagcttta gacaagatag aggaagagca aaacaaaagt      900
aagaccaccg cacagcaagc ggccgctgat cttcagacct ggaggaggag atatgaggga      960
```

```
caattggaga agtgaattat ataaatataa agtagtaaaa attgaaccat taggagtagc    1020
acccaccaag gcaaagagaa gagtggtgca gagagaaaaa agagcagtgg gaataggagc    1080
tttgttcctt gggttcttgg gagcagcagg aagcactatg ggcgcagcgt caatgacgct    1140
gacggtacag gccagacaat tattgtctgg tatagtgcag cagcagaaca atttgctgag    1200
ggctattgag gcgcaacagc atctgttgca actcacagtc tggggcatca agcagctcca    1260
ggcaagaatc ctggctgtgg aaagatacct aaaggatcaa cagctcctgg ggatttgggg    1320
ttgctctgga aaactcattt gcaccactgc tgtgccttgg aatgctagtt ggagtaataa    1380
atctctggaa cagatttgga atcacacgac ctggatggag tgggacagag aaattaacaa    1440
ttacacaagc ttaatacact ccttaattga agaatcgcaa aaccagcaag aaaagaatga    1500
acaagaatta ttggaattag ataaatgggc aagtttgtgg aattggttta acataacaaa    1560
ttggctgtgg tatataaaat tattcataat gatagtagga ggcttggtag gtttaagaat    1620
agtttttgct gtactttcta tagtgaatag agttaggcag ggatattcac cattatcgtt    1680
tcagacccac ctcccaaccc cgaggggacc cgacaggccc gaaggaatag aagaagaagg    1740
tggagagaga gacagagaca gatccattcg attagtgaac ggatctcgac ggtatcgcta    1800
gcttttaaaa gaaaaggggg gattgggggg tacagtgcag gggaagaat agtagacata    1860 atagcaacag acatcaaaac taagaattac aaaaacaaa ttacaaaaat tcaaaatttt    1920
actagtatca actttgtata gaaaagttgg gctccggtgc ccgtcagtgg gcagagcgca    1980
catcgcccac agtccccgag aagttggggg gaggggtcgg caattgaacc ggtgcctaga    2040
gaaggtggcg cggggtaaac tgggaaagtg atgtcgtgta ctggctccgc cttttttccg    2100
agggtggggg agaaccgtat ataagtgcag tagtcgccgt gaacgttctt tttcgcaacg    2160
ggtttgccgc cagaacacag gtaagtgccg tgtgtggttc ccgcgggcct ggcctcttta    2220
cgggttatgg cccttgcgtg ccttgaatta cttccacctg gctgcagtac gtgattcttg    2280
atcccgagct tcgggttgga agtgggtggg agagttcgag gccttgcgct taaggagccc    2340
cttcgcctcg tgcttgagtt gaggcctggc ctgggcgctg gggccgccgc gtgcgaatct    2400
ggtggcacct tcgcgcctgt ctcgctgctt tcgataagtc tctagccatt taaaattttt    2460
gatgacctgc tgcgacgctt tttttctggc aagatagtct tgtaaatgcg ggccaagatc    2520
tgcacactgg tatttcggtt tttggggccg cgggcggcga cggggcccgt gcgtcccagc    2580
gcacatgttc ggcgaggcgg ggcctgcgag cgcggccacc gagaatcgga cgggggtagt    2640
ctcaagctgc ccggcctgct ctggtgcctg gtctcgcgcc gccgtgtatc gccccgcccT    2700
gggcggcaag gctggcccgg tcggcaccag ttgcgtgagc ggaaagatgg ccgcttcccg    2760
gccctgctgc agggagctca aaatggagga cgcggcgctc gggagagcgg gcgggtgagt    2820
cacccacaca aaggaaaagg cctttccgt cctcagccgt cgcttcatgt gactccacgg    2880
agtaccgggc gccgtccagg cacctcgatt agttctcgag cttttggagt acgtcgtctt    2940
taggttgggg ggaggggttt tatgcgatgg agtttcccca cactgagtgg gtggagactg    3000
aagttaggcc agcttggcac ttgatgtaat tctccttgga atttgccctt tttgagtttg    3060
gatcttggtt cattctcaag cctcagacag tggttcaaag tttttttctt ccatttcagg    3120
tgtcgtgaca agtttgtaca aaaaagcagg ctgccaccat gtggctgcag agcctgctgc    3180
tgctgggcac cgtggcctgc agcatcagcg ccccgccag aagccccagc ccagcaccc    3240 agccctggga gcacgtgaac gccatccagg aggccagaag actgctgaac ctgagcagag    3300
```

```
acaccgccgc cgagatgaac gagaccgtgg aggtgatcag cgagatgttc gacctgcagg    3360
agcccacctg cctgcagacc agactggagc tgtacaagca gggcctgaga ggcagcctga    3420
ccaagctgaa gggccccctg accatgatgg ccagccacta caagcagcac tgccccccca    3480
cccccgagac cagctgcgcc acccagatca tcaccttcga gagcttcaag agaaacctga    3540
aggacttcct gctggtgatc cccttcgact gctgggagcc cgtgcaggag taaaacaaca    3600
acaattgcat tcattttatg tttcaggttc aggggggaggt gtgggaggtt ttttaaagca    3660
agtaaaacct ctacaaatgt ggtacgcgtt aacaacaaca attgcattca ttttatgttt    3720
caggttcagg gggaggtgtg ggaggttttt taaagcaagt aaaacctcta caaatgtggt    3780
acgcgttacc cagcttctt gtacaaagtg gtaaatagat agaacaacaa caattgcatt    3840
cattttgat ttcaggttca gggggaggtg tgggaggttt tttaaagcaa gtaaaacctc    3900
tacactgacg gtacgcgtta acaacaacaa ttgcattcat ttgtagtttc aggttcaggg    3960
ggaggtgtgg gaggtttttt aaagcaagtt aaacctctaa aatagtggta cgcgttaccc    4020
agctttcttg tacaaagtgg acccagcttt cttgtacaaa gtgggcccct ctccctcccc    4080
cccccctaac gttactggcc gaagccgctt ggaataaggc cggtgtgcgt ttgtctatat    4140
gttattttcc accatattgc cgtcttttgg caatgtgagg gcccggaaac ctggccctgt    4200
cttcttgacg agcattccta ggggtctttc ccctctcgcc aaaggaatgc aaggtctgtt    4260
gaatgtcgtg aaggaagcag ttcctctgga gcttcttga agacaaacaa cgtctgtagc    4320
gacccttgc aggcagcgga accccccacc tggcgacagg tgcctctgcg gccaaaagcc    4380
acgtgtataa gatacccctg caaaggcggc acaaccccag tgccacgttg tgagttggat    4440
agttgtggaa agagtcaaat ggctctcctc aagcgtattc aacaaggggc tgaaggatgc    4500
ccagaaggta cccccattgta tgggatctga tctggggcct cggtgcacat gctttacatg    4560
tgtttagtcg aggttaaaaa aacgtctagg ccccccgaac cacggggacg tggttttcct    4620
ttgaaaaaca cgatgataat atggccacaa ccatggccac cgtgctggcc cccgcctgga    4680
gccccaccac ctacctgctg ctgctgctgc tgctgagcag cggcctgagc ggcacccagg    4740
actgcagctt ccagcacagc cccatcagca gcgacttcgc cgtgaagatc agagagctga    4800
gcgactacct gctgcaggac taccccgtga ccgtggccag caacctgcag gacgaggagc    4860
tgtgcggcgg cctgtggaga ctggtgctgg cccagagatg gatggagaga ctgaagaccg    4920
tggccggcag caagatgcag ggcctgctgg agagagtgaa caccgagatc cacttcgtga    4980
ccaagtgcgc cttccagccc cccccagct gcctgagatt cgtgcagacc aacatcagca    5040
gactgctgca ggagaccagc gagcagctgg tggccctgaa gcctggatc accagacaga    5100
acttcagcag atgcctggag ctgcagtgcc agcccgacag cagcaccctg ccccccccct    5160
ggagccccag accctggag gccaccgccc ccaccgcccc ccagccccc ctgctgctgc    5220
tgctgctgct gcccgtgggc ctgctgctgc tggccgccgc ctggtgcctg cactggcaga    5280
gaaccagaag aagaacccc agaccccggcg agcaggtgcc cccgtgccc agcccccagg    5340
acctgctgct ggtggagcac taacaacttt attatacata gttgatcaat ccaactttta    5400
ttatacatag ttgatcaatt ccgataatca acctctggat tacaaaattt gtgaaagatt    5460
gactggtatt cttaactatg ttgctccttt tacgctatgt ggatacgctg ctttaatgcc    5520
tttgtatcat gctattgctt cccgtatggc tttcattttc tcctccttgt ataaatcctg    5580
gttgctgtct ctttatgagg agttgtggcc cgttgtcagg caacgtggcg tggtgtgcac    5640
tgtgtttgct gacgcaaccc ccactggttg gggcattgcc accacctgtc agctccttc    5700
```

```
cgggactttc gctttccccc tccctattgc cacggcggaa ctcatcgccg cctgccttgc    5760
ccgctgctgg acaggggctc ggctgttggg cactgacaat tccgtggtgt tgtcggggaa    5820
gctgacgtcc tttccatggc tgctcgcctg tgttgccacc tggattctgc gcgggacgtc    5880
cttctgctac gtcccttcgg ccctcaatcc agcggacctt ccttcccgcg cctgctgcc     5940 ggctctgcgg cctcttccgc gtcttcgcct tcgccctcag acgagtcgga tctcccttg     6000 ggccgcctcc ccgcatcggg aattcccgcg gttcgcttta agaccaatga cttacaaggc    6060
agctgtagat cttagccact ttttaaaaga aagggggga ctggaagggc taattcactc      6120
ccaacgaaga caagatctgc tttttgcttg tactgggtct ctctggttag accagatctg    6180
agcctgggag ctctctggct aactagggaa cccactgctt aagcctcaat aaagcttgcc    6240
ttgagtgctt caagtagtgt gtgcccgtct gttgtgtgac tctggtaact agagatccct    6300
cagacccttt tagtcagtgt ggaaaatctc tagcagtagt agttcatgtc atcttattat    6360
tcagtattta aacttgcaa agaaatgaat atcagagagt gagaggaact tgtttattgc      6420
agcttataat ggttacaaat aaagcaatag catcacaaat ttcacaaata aagcattttt    6480
ttcactgcat tctagttgtg gtttgtccaa actcatcaat gtatcttatc atgtctggct    6540
ctagctatcc cgcccctaac tccgcccatc ccgccctaa ctccgcccag ttccgcccat      6600
tctccgcccc atggctgact aattttttt atttatgcag aggccgaggc cgcctcggcc      6660
tctgagctat tccagaagta gtgaggaggc ttttttggag gcctagggac gtacccaatt   6720
cgccctatag tgagtcgtat tacgcgcgct cactggccgt cgttttacaa cgtcgtgact   6780
gggaaaaccc tggcgttacc caacttaatc gccttgcagc acatccccct ttcgccagct    6840
ggcgtaatag cgaagaggcc cgcaccgatc gcccttccca acagttgcgc agcctgaatg    6900
gcgaatggga cgcgccctgt agcggcgcat taagcgcggc gggtgtggtg gttacgcgca   6960
gcgtgaccgc tacacttgcc agcgccctag cgcccgctcc tttcgctttc ttcccttcct   7020
ttctcgccac gttcgccggc tttccccgtc aagctctaaa tcggggggctc cctttagggt   7080 tccgatttag tgctttacgg cacctcgacc ccaaaaaact tgattagggt gatggttcac   7140
gtagtgggcc atcgccctga tagacggttt ttcgcccttt gacgttggag tccacgttct   7200
ttaatagtgg actcttgttc caaactggaa caacactcaa ccctatctcg gtctattctt    7260
ttgatttata agggattttg ccgatttcgg cctattggtt aaaaaatgag ctgatttaac   7320
aaaaatttaa cgcgaatttt aacaaaatat taacgcttac aatttaggtg cacttttcg     7380 gggaaatgtg cgcggaaccc ctatttgttt attttctaa atacattcaa atatgtatcc     7440
gctcatgaga caataaccct gataaatgct tcaataatat tgaaaaagga agagtatgag   7500
tattcaacat ttccgtgtcg cccttattcc cttttttgcg gcattttgcc ttcctgtttt    7560
tgctcaccca gaaacgctgg tgaaagtaaa agatgctgaa gatcagttgg gtgcacgagt   7620
gggttacatc gaactggatc tcaacagcgg taagatcctt gagagttttc gccccgaaga    7680
acgttttcca atgatgagca cttttaaagt tctgctatgt ggcgcggtat tatcccgtat   7740
tgacgccggg caagagcaac tcggtcgccg catacactat tctcagaatg acttggttga   7800
gtactcacca gtcacagaaa agcatcttac ggatggcatg acagtaagag aattatgcag   7860
tgctgccata accatgagtg ataacactgc ggccaactta cttctgacaa cgatcggagg   7920
accgaaggag ctaaccgctt ttttgcacaa catgggggat catgtaactc gccttgatcg   7980
ttgggaaccg gagctgaatg aagccatacc aaacgacgag cgtgacacca cgatgcctgt   8040
```

| | | | | | |
|---|---|---|---|---|---|
| agcaatggca | acaacgttgc | gcaaactatt | aactggcgaa | ctacttactc | tagcttcccg | 8100 |
| gcaacaatta | atagactgga | tggaggcgga | taaagttgca | ggaccacttc | tgcgctcggc | 8160 |
| ccttccggct | ggctggttta | ttgctgataa | atctggagcc | ggtgagcgtg | gtctcgcgg | 8220 |
| tatcattgca | gcactggggc | cagatggtaa | gccctcccgt | atcgtagtta | tctacacgac | 8280 |
| ggggagtcag | gcaactatgg | atgaacgaaa | tagacagatc | gctgagatag | gtgcctcact | 8340 |
| gattaagcat | tggtaactgt | cagaccaagt | ttactcatat | atactttaga | ttgatttaaa | 8400 |
| acttcatttt | taatttaaaa | ggatctaggt | gaagatcctt | tttgataatc | tcatgaccaa | 8460 |
| aatcccttaa | cgtgagtttt | cgttccactg | agcgtcagac | cccgtagaaa | agatcaaagg | 8520 |
| atcttcttga | gatccttttt | ttctgcgcgt | aatctgctgc | ttgcaaacaa | aaaaaccacc | 8580 |
| gctaccagcg | gtggtttgtt | tgccggatca | agagctacca | actctttttc | cgaaggtaac | 8640 |
| tggcttcagc | agagcgcaga | taccaaatac | tgttcttcta | gtgtagccgt | agttaggcca | 8700 |
| ccacttcaag | aactctgtag | caccgcctac | atacctcgct | ctgctaatcc | tgttaccagt | 8760 |
| ggctgctgcc | agtggcgata | agtcgtgtct | taccgggttg | gactcaagac | gatagttacc | 8820 |
| ggataaggcg | cagcggtcgg | gctgaacggg | gggttcgtgc | acacagccca | gcttggagcg | 8880 |
| aacgacctac | accgaactga | gatacctaca | gcgtgagcta | tgagaaagcg | ccacgcttcc | 8940 |
| cgaagagaga | aaggcggaca | ggtatccggt | aagcggcagg | gtcggaacag | gagagcgcac | 9000 |
| gagggagctt | ccaggggggaa | acgcctggta | tctttatagt | cctgtcgggt | ttcgccacct | 9060 |
| ctgacttgag | cgtcgatttt | tgtgatgctc | gtcagggggg | cggagcctat | ggaaaaacgc | 9120 |
| cagcaacgcg | gccttttac | ggttcctggc | cttttgctgg | cctttgctc | acatgttctt | 9180 |
| tcctgcgtta | tcccctgatt | ctgtggataa | ccgtattacc | gcctttgagt | gagctgatac | 9240 |
| cgctcgccgc | agccgaacga | ccgagcgcag | cgagtcagtg | agcgaggaag | cggaagagcg | 9300 |
| cccaatacgc | aaaccgcctc | tccccgcgcg | ttggccgatt | cattaatgca | gctggcacga | 9360 |
| caggtttccc | gactggaaag | cgggcagtga | gcgcaacgca | attaatgtga | gttagctcac | 9420 |
| tcattaggca | ccccaggctt | tacactttat | gcttccggct | cgtatgttgt | gtggaattgt | 9480 |
| gagcggataa | caatttcaca | caggaaacag | ctatgaccat | gattacgcca | agcgcgcaat | 9540 |
| taaccctcac | taaagggaac | aaaagctgga | gctgcaagct | t | | 9581 |

<210> SEQ ID NO 50
<211> LENGTH: 9746
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Vector 4

<400> SEQUENCE: 50

| | | | | | |
|---|---|---|---|---|---|
| aatgtagtct | tatgcaatac | tcttgtagtc | ttgcaacatg | gtaacgatga | gttagcaaca | 60 |
| tgccttacaa | ggagagaaaa | agcaccgtgc | atgccgattg | gtggaagtaa | ggtggtacga | 120 |
| tcgtgcctta | ttaggaaggc | aacagacggg | tctgacatgg | attggacgaa | ccactgaatt | 180 |
| gccgcattgc | agagatattg | tatttaagtg | cctagctcga | tacataaacg | ggtctctctg | 240 |
| gttagaccag | atctgagcct | gggagctctc | tggctaacta | gggaacccac | tgcttaagcc | 300 |
| tcaataaagc | ttgccttgag | tgcttcaagt | agtgtgtgcc | cgtctgttgt | gtgactctgg | 360 |
| taactagaga | tccctcagac | ccttttagtc | agtgtggaaa | atctctagca | gtggcgcccg | 420 |

```
aacagggact tgaaagcgaa agggaaacca gaggagctct ctcgacgcag gactcggctt    480
gctgaagcgc gcacggcaag aggcgagggg cggcgactgg tgagtacgcc aaaaattttg    540
actagcggag gctagaagga gagagatggg tgcgagagcg tcagtattaa gcggggagag    600
attagatcgc gatgggaaaa aattcggtta aggccagggg gaagaaaaaa atataaatta    660
aaacatatag tatgggcaag cagggagcta gaacgattcg cagttaatcc tggcctgtta    720
gaaacatcag aaggctgtag acaaatactg ggacagctac aaccatccct tcagacagga    780
tcagaagaac ttagatcatt atataataca gtagcaaccc tctattgtgt gcatcaaagg    840
atagagataa aagacaccaa ggaagcttta gacaagatag aggaagagca aaacaaaagt    900
aagaccaccg cacagcaagc ggccgctgat cttcagacct ggaggaggag atatgaggga    960
caattggaga agtgaattat ataaatataa agtagtaaaa attgaaccat taggagtagc   1020
acccaccaag gcaaagagaa gagtggtgca gagagaaaaa agagcagtgg gaataggagc   1080
tttgttcctt gggttcttgg gagcagcagg aagcactatg ggcgcagcgt caatgacgct   1140
gacggtacag gccagacaat tattgtctgg tatagtgcag cagcagaaca atttgctgag   1200
ggctattgag gcgcaacagc atctgttgca actcacagtc tggggcatca agcagctcca   1260
ggcaagaatc ctggctgtgg aaagatacct aaaggatcaa cagctcctgg ggatttgggg   1320
ttgctctgga aaactcattt gcaccactgc tgtgccttgg aatgctagtt ggagtaataa   1380
atctctggaa cagatttgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620
agttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcgcta   1800
gcttttaaaa gaaaaggggg gattgggggg tacagtgcag gggaaagaat agtagacata   1860
atagcaacag acatacaaac taagaaatta caaaaacaaa ttacaaaaat tcaaaatttt   1920
actagtatca actttgtata gaaaagttgg gctccggtgc ccgtcagtgg gcagagcgca   1980
catcgcccac agtccccgag aagttggggg gaggggtcgg caattgaacc ggtgcctaga   2040
gaaggtggcg cggggtaaac tgggaaagtg atgtcgtgta ctggctccgc ctttttcccg   2100
agggtggggg agaaccgtat ataagtgcag tagtcgccgt gaacgttctt tttcgcaacg   2160
ggtttgccgc cagaacacag gtaagtgccg tgtgtggttc ccgcgggcct ggcctcttta   2220
cgggttatgg cccttgcgtg ccttgaatta cttccacctg gctgcagtac gtgattcttg   2280
atcccgagct tcgggttgga agtgggtggg agagttcgag gccttgcgct taaggagccc   2340
cttcgcctcg tgcttgagtt gaggcctggc ctgggcgctg gggccgccgc gtgcgaatct   2400
ggtggcacct tcgcgcctgt ctcgctgctt tcgataagtc tctagccatt taaaattttt   2460
gatgacctgc tgcgacgctt ttttctggc aagatagtct tgtaaatgcg ggccaagatc   2520
tgcacactgg tatttcggtt tttggggccg cggcggcga cggggcccgt gcgtcccagc   2580
gcacatgttc ggcgaggcgg ggcctgcgag cgcggccacc gagaatcgga cggggtagt   2640
ctcaagctgg ccggcctgct ctggtgcctg gtctcgcgcc gccgtgtatc gccccgccct   2700
gggcggcaag gctggcccgg tcggcaccag ttgcgtgagc ggaaagatgg ccgcttcccg   2760
gccctgctgc agggagctca aaatggagga cgcggcgctc gggagagcgg gcgggtgagt   2820
```

```
cacccacaca aaggaaaagg gcctttccgt cctcagccgt cgcttcatgt gactccacgg    2880
agtaccgggc gccgtccagg cacctcgatt agttctcgag cttttggagt acgtcgtctt    2940
taggttgggg ggagggtttt tatgcgatgg agtttcccca cactgagtgg gtggagactg    3000
aagttaggcc agcttggcac ttgatgtaat tctccttgga atttgccctt tttgagtttg    3060
gatcttggtt cattctcaag cctcagacag tggttcaaag ttttttttctt ccatttcagg    3120 tgtcgtgaca agtttgtaca aaaagcagg ctgccaccat gaccgtgctg gcccccgcct    3180
ggagccccac cacctacctg ctgctgctgc tgctgctgag cagcggcctg agcggcaccc    3240
aggactgcag cttccagcac agccccatca gcagcgactt cgccgtgaag atcagagagc    3300
tgagcgacta cctgctgcag gactaccccg tgaccgtggc cagcaacctg caggacgagg    3360
agctgtgcgg cggcctgtgg agactggtgc tgccccagag atggatggag agactgaaga    3420
ccgtggccgg cagcaagatg cagggcctgc tggagagagt gaacaccgag atccacttcg    3480
tgaccaagtg cgccttccag ccccccccca gctgcctgag attcgtgcag accaacatca    3540
gcagactgct gcaggagacc agcgagcagc tggtggcccct gaagccctgg atcaccagac    3600
agaacttcag cagatgcctg gagctgcagt gccagcccga cagcagcacc ctgccccccc    3660
cctggagccc cagaccctg gaggccaccg ccccaccgc cccagtaa aacaacaaca    3720 attgcattca ttttatgttt caggttcagg ggaggtgtg ggaggttttt taaagcaagt    3780
aaaacctcta caaatgtggt acgcgttaac aacaacaatt gcattcattt tatgtttcag    3840
gttcaggggg aggtgtggga ggttttttaa gcaagtaaa acctctacaa atgtggtacg    3900
cgttacccag ctttcttgta caaagtggta aatagataga caacaacaa ttgcattcat    3960 ttttgatttc aggttcaggg ggaggtgtgg gagttttttt aaagcaagta aaacctctac    4020
actgacggta cgcgttaaca acaacaattg cattcatttg tagtttcagg ttcaggggga    4080
ggtgtgggag gtttttaaa gcaagttaaa cctctaaat agtggtacgc gttacccagc    4140
tttcttgtac aaagtggacc cagctttctt gtacaaagtg ggcccctctc cctcccccc    4200 ccctaacgtt actggccgaa gccgcttgga ataaggccgg tgtgcgtttg tctatatgtt    4260 atttttccacc atattgccgt cttttggcaa tgtgagggcc cggaaacctg gccctgtctt    4320
cttgacgagc attcctaggg gtcttttccc tctcgccaaa ggaatgcaag gtctgttgaa    4380
tgtcgtgaag gaacgcagttc ctctggaagc ttcttgaaga caaacaacgt ctgtagcgac    4440
cctttgcagg cagcggaacc ccccaccctgg cgacaggtgc tcctgcggcc aaaagccacg    4500
tgtataagat acacctgcaa aggcggcaca accccagtgc cacgttgtga gttggatagt    4560
tgtggaaaga gtcaaatggc tctcctcaag cgtattcaac aaggggctga aggatgccca    4620
gaaggtaccc cattgtatgg gatctgatct ggggcctcgg tgcacatgct ttacatgtgt    4680
ttagtcgagg ttaaaaaac gtctaggccc cccgaaccac ggggacgtgg ttttcctttg    4740
aaaaacacga tgataatatg gccacaacca tggccaccgt gctggccccc gcctggagcc    4800
ccaccaccta cctgctgctg ctgctgctgc tgagcagcgg cctgagcgcc cccgccagaa    4860
gccccagccc cagcacccag ccctgggagc acgtgaacgc catccaggag gccagaagac    4920
tgctgaacct gagcagagac accgccgccg agatgaacga gaccgtggag gtgatcagcg    4980
agatgttcga cctgcaggag cccacctgcc tgcagaccag actggagctg tacaagcagg    5040
gcctgagagg cagcctgacc aagctgaagg gccccctgac catgatggcc agccactaca    5100
agcagcactg ccccccccacc cccgagacca gctgcgccac ccagatcatc accttcgaga    5160
```

```
gcttcaagga gaacctgaag gacttcctgc tggtgatccc cttcgactgc tgggagcccg   5220
tgcaggagcc caccaccacc cccgccccca gacccccac cccgccccc accatcgcca     5280
gccagcccct gagcctgaga cccgaggcct gcagacccgc cgccggcggc gccgtgcaca   5340
ccagaggcct ggacttcgcc tgcgacatct acatctgggc cccctggcc ggcacctgcg    5400
gcgtgctgct gctgagcctg gtgatcaccc tgtactgcaa ccacagaaac agaagaagag   5460
tgtgcaagtg ccccagaccc gtggtgaaga gcggcgacaa gcccagcctg agcgccagat   5520
acgtgtaaca actttattat acatagttga tcaattccaa ctttattata catagttgat   5580
caattccgat aatcaacctc tggattacaa aatttgtgaa agattgactg gtattcttaa   5640
ctatgttgct ccttttacgc tatgtggata cgctgcttta atgcctttgt atcatgctat   5700
tgcttcccgt atggctttca ttttctcctc cttgtataaa tcctggttgc tgtctcttta   5760
tgaggagttg tggcccgttg tcaggcaacg tggcgtggtg tgcactgtgt ttgctgacgc   5820
aacccccact ggttggggca ttgccaccac ctgtcagctc cttccgggac ttccgcttt    5880
cccctccct attgccacgg cggaactcat cgccgcctgc cttgcccgct gctggacagg   5940
ggctcggctg ttgggcactg acaattccgt ggtgttgtcg gggaagctga cgtccttcc    6000
atggctgctc gcctgtgttg ccacctggat tctgcgcggg acgtccttct gctacgtccc   6060
ttcggccctc aatccagcgg accttccttc ccgcggcctg ctgccggctc tgcggcctct   6120
tccgcgtctt cgccttcgcc ctcagacgag tcggatctcc cttgggccg cctcccgca    6180
tcggaattc ccgcggttcg ctttaagacc aatgacttac aaggcagctg tagatcttag    6240
ccacttttta aaagaaaagg ggggactgga agggctaatt cactcccaac gaagacaaga   6300
tctgcttttt gcttgtactg ggtctctctg gttagaccag atctgagcct gggagctctc   6360
tggctaacta gggaacccac tgcttaagcc tcaataaagc ttgccttgag tgcttcaagt   6420
agtgtgtgcc cgtctgttgt gtgactctgg taactagaga tccctcagac ccttttagtc   6480
agtgtggaaa atctctagca gtagtagttc atgtcatctt attattcagt atttataact   6540
tgcaaagaaa tgaatatcag agagtgagag gaacttgttt attgcagctt ataatggtta   6600
caaataaagc aatagcatca caaatttcac aaataaagca ttttttttcac tgcattctag   6660
ttgtggtttg tccaaactca tcaatgtatc ttatcatgtc tggctctagc tatcccgccc   6720
ctaactccgc ccatcccgcc cctaactccg ccagttccg cccattctcc gccccatggc    6780
tgactaattt ttttatttta tgcagaggcc gaggccgcct cggcctctga gctattccag   6840
aagtagtgag gaggcttttt tggaggccta gggacgtacc caattcgccc tatagtgagt   6900
cgtattacgc gcgctcactg gccgtcgttt tacaacgtcg tgactgggaa aaccctggcg   6960
ttacccaact taatcgcctt gcagcacatc cccctttcgc cagctggcgt aatagcgaag   7020
aggcccgcac cgatcgccct tcccaacagt tgcgcagcct gaatggcgaa tgggacgcgc   7080
cctgtagcgg cgcattaagc gcggcgggtg tgtggttac gcgcagcgtg accgctacac    7140
ttgccagcgc cctagcgccc gctcctttcg ctttcttccc ttcctttctc gccacgttcg   7200
ccggctttcc ccgtcaagct ctaaatcggg ggctcccttt agggttccga tttagtgctt   7260
tacggcacct cgaccccaaa aaacttgatt agggtgatgg ttcacgtagt gggccatcgc   7320
cctgatagac ggtttttcgc cctttgacgt tggagtccac gttctttaat agtggactct   7380
tgttccaaac tggaacaaca ctcaacccta tctcggtcta ttcttttgat ttataaggga   7440
ttttgccgat ttcggcctat tggttaaaaa atgagctgat ttaacaaaaa tttaacgcga   7500
attttaacaa aatattaacg cttacaattt aggtggcact tttcggggaa atgtgcgcgg   7560
```

```
aacccctatt tgtttatttt tctaaataca ttcaaatatg tatccgctca tgagacaata    7620
accctgataa atgcttcaat aatattgaaa aggaagagt  atgagtattc aacatttccg    7680
tgtcgccctt attccttttt tgcggcatt  ttgccttcct gttttgctc  acccagaaac    7740
gctggtgaaa gtaaaagatg ctgaagatca gttgggtgca cgagtgggtt acatcgaact    7800
ggatctcaac agcggtaaga tccttgagag ttttcgcccc gaagaacgtt ttccaatgat    7860
gagcactttt aaagttctgc tatgtggcgc ggtattatcc cgtattgacg ccgggcaaga    7920
gcaactcggt cgccgcatac actattctca gaatgacttg gttgagtact caccagtcac    7980
agaaaagcat cttacggatg gcatgacagt aagagaatta tgcagtgctg ccataaccat    8040
gagtgataac actgcggcca acttacttct gacaacgatc ggaggaccga aggagctaac    8100
cgcttttttg cacaacatgg ggatcatgt  aactcgcctt gatcgttggg aaccggagct    8160
gaatgaagcc ataccaaacg acgagcgtga caccacgatg cctgtagcaa tggcaacaac    8220
gttgcgcaaa ctattaactg gcgaactact tactctagct tcccggcaac aattaataga    8280
ctggatggag gcggataaag ttgcaggacc acttctgcgc tcggcccttc cggctggctg    8340
gtttattgct gataaatctg gagccggtga gcgtgggtct cgcggtatca ttgcagcact    8400
ggggccagat ggtaagccct cccgtatcgt agttatctac acgacgggga gtcaggcaac    8460
tatgatgaa  cgaaatagac agatcgctga gataggtgcc tcactgatta agcattggta    8520
actgtcagac caagtttact catatatact ttagattgat ttaaaacttc atttttaatt    8580
taaaaggatc taggtgaaga tcctttttga taatctcatg accaaaatcc cttaacgtga    8640
gttttcgttc cactgagcgt cagacccgt  agaaaagatc aaaggatctt cttgagatcc    8700
ttttttctg  cgcgtaatct gctgcttgca acaaaaaaa  ccaccgctac cagcggtggt    8760
ttgtttgccg gatcaagagc taccaactct ttttccgaag gtaactggct tcagcagagc    8820
gcagatacca aatactgttc ttctagtgta gccgtagtta ggccaccact tcaagaactc    8880
tgtagcaccg cctacatacc tcgctctgct aatcctgtta ccagtggctg ctgccagtgg    8940
cgataagtcg tgtcttaccg ggttggactc aagacgatag ttaccggata aggcgcagcg    9000
gtcgggctga acggggggtt cgtgcacaca gcccagcttg gagcgaacga cctacaccga    9060
actgagatac ctacagcgtg agctatgaga aagcgccacg cttcccgaag agagaaaggc    9120
ggacaggtat ccggtaagcg gcagggtcgg aacaggagag cgcacgaggg agcttccagg    9180
gggaaacgcc tggtatcttt atagtcctgt cgggtttcgc cacctctgac ttgagcgtcg    9240
atttttgtga tgctcgtcag ggggcggag  cctatgaaa  aacgccagca acgcggcctt    9300
tttacggttc ctggcctttt gctggccttt tgctcacatg ttctttcctg cgttatcccc    9360
tgattctgtg gataaccgta ttaccgcctt tgagtgagct gataccgctc gccgcagccg    9420
aacgaccgag cgcagcgagt cagtgagcga ggaagcggaa gagcgcccaa tacgcaaacc    9480
gcctctcccc gcgcgttggc cgattcatta atgcagctgg cacgacaggt ttcccgactg    9540
gaaagcgggc agtgagcgca acgcaattaa tgtgagttag ctcactcatt aggcacccca    9600
ggctttacac tttatgcttc cggctcgtat gttgtgtgga attgtgagcg gataacaatt    9660
tcacacagga aacagctatg accatgatta cgccaagcgc gcaattaacc ctcactaaag    9720
ggaacaaaag ctggagctgc aagctt                                         9746
```

<210> SEQ ID NO 51
<211> LENGTH: 8189
<212> TYPE: DNA

<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Vector 5

<400> SEQUENCE: 51

```
aatgtagtct tatgcaatac tcttgtagtc ttgcaacatg gtaacgatga gttagcaaca    60
tgccttacaa ggagagaaaa agcaccgtgc atgccgattg gtggaagtaa ggtggtacga   120
tcgtgcctta ttaggaaggc aacagacggg tctgacatgg attggacgaa ccactgaatt   180
gccgcattgc agagatattg tatttaagtg cctagctcga tacataaacg ggtctctctg   240
gttagaccag atctgagcct gggagctctc tggctaacta gggaacccac tgcttaagcc   300
tcaataaagc ttgccttgag tgcttcaagt agtgtgtgcc cgtctgttgt gtgactctgg   360
taactagaga tccctcagac cctttagtc agtgtggaaa atctctagca gtggcgcccg   420
aacaggact tgaaagcgaa agggaaacca gaggagctct ctcgacgcag gactcggctt   480
gctgaagcgc gcacggcaag aggcgagggg cggcgactgg tgagtacgcc aaaaattttg   540
actagcggag gctagaagga gagagatggg tgcgagagcg tcagtattaa gcggggagga   600
attagatcgc gatgggaaaa aattcggtta aggccagggg gaaagaaaaa atataaatta   660
aaacatatag tatgggcaag cagggagcta gaacgattcg cagttaatcc tggcctgtta   720
gaaacatcag aaggctgtag acaaatactg ggacagctac aaccatccct tcagacagga   780
tcagaagaac ttagatcatt atataataca gtagcaaccc tctattgtgt gcatcaaagg   840
atagagataa aagacaccaa ggaagcttta gacaagatag aggaagagca aaacaaaagt   900
aagaccaccg cacagcaagc ggccgctgat cttcagacct ggaggaggag atatgaggga   960
caattggaga agtgaattat ataaatataa agtagtaaaa attgaaccat taggagtagc  1020
acccaccaag gcaaagagaa gagtggtgca gagagaaaaa agagcagtgg gaataggagc  1080
tttgttcctt gggttcttgg gagcagcagg aagcactatg ggcgcagcgt caatgacgct  1140
gacggtacag gccagacaat tattgtctgg tatagtgcag cagcagaaca atttgctgag  1200
ggctattgag gcgcaacagc atctgttgca actcacagtc tggggcatca agcagctcca  1260
ggcaagaatc ctggctgtgg aaagatacct aaaggatcaa cagctcctgg ggatttgggg  1320
ttgctctgga aaactcattt gcaccactgc tgtgccttgg aatgctagtt ggagtaataa  1380
atctctggaa cagatttgga atcacacgac ctggatggag tgggacagag aaattaacaa  1440
ttacacaagc ttaatacact ccttaattga agaatcgcaa aaccagcaag aaaagaatga  1500
acaagaatta ttggaattag ataaatgggc aagtttgtgg aattggttta cataacaaa  1560
ttggctgtgg tatataaaat tattcataat gatagtagga ggcttggtag gtttaagaat  1620
agtttttgct gtactttcta tagtgaatag agttaggcag ggatattcac cattatcgtt  1680
tcagacccac ctcccaaccc cgaggggacc cgacaggccc gaaggaatag aagaagaagg  1740
tggagagaga gacagagaca gatccattcg attagtgaac ggatctcgac ggtatcgcta  1800
gcttttaaaa gaaaaggggg gattggggg tacagtgcag gggaaagaat agtagacata  1860
atagcaacag acatacaaac taagaatta caaaacaaa ttacaaaaat tcaaaatttt  1920
actagtgatt atcggatcaa ctttgtatag aaaagttggg ctccggtgcc cgtcagtggg  1980
cagagcgcac atcgcccaca gtccccgaga agttggggg aggggtcggc aattgaaccg  2040
gtgcctagag aaggtggcgc ggggtaaact gggaaagtga tgtcgtgtac tggctccgcc  2100
```

-continued

```
tttttcccga gggtggggga gaaccgtata taagtgcagt agtcgccgtg aacgttcttt    2160
ttcgcaacgg gtttgccgcc agaacacagg taagtgccgt gtgtggttcc cgcgggcctg    2220
gcctctttac gggttatggc ccttgcgtgc cttgaattac ttccacctgg ctgcagtacg    2280
tgattcttga tcccgagctt cgggttggaa gtgggtggga gagttcgagg ccttgcgctt    2340
aaggagcccc ttcgcctcgt gcttgagttg aggcctggcc tgggcgctgg ggccgccgcg    2400
tgcgaatctg gtggcacctt cgcgcctgtc tcgctgcttt cgataagtct ctagccattt    2460 aaaattttg atgacctgct gcgacgcttt ttttctggca agatagtctt gtaaatgcgg     2520
gccaagatct gcacactggt atttcggttt tggggccgc gggcggcgac ggggcccgtg     2580
cgtcccagcg cacatgttcg gcgaggcggg gcctgcgagc gcggccaccg agaatcggac    2640
gggggtagtc tcaagctggc cggcctgctc tggtgcctgg tctcgcgccg ccgtgtatcg    2700
ccccgccctg ggcggcaagg ctggcccggt cggcaccagt tgcgtgagcg gaaagatggc    2760
cgcttcccgg ccctgctgca gggagctcaa aatggaggac gcggcgctcg ggagagcggg    2820
cgggtgagtc acccacacaa aggaaaaggg cctttccgtc ctcagccgtc gcttcatgtg    2880
actccacgga gtaccgggcg ccgtccaggc acctcgatta gttctcgagc ttttggagta    2940
cgtcgtcttt aggttggggg gaggggtttt atgcgatgga gtttccccac actgagtggg    3000
tggagactga agttaggcca gcttggcact tgatgtaatt ctccttggaa tttgcccttt    3060
ttgagtttgg atcttggttc attctcaagc ctcagacagt ggttcaaagt tttttcttc    3120 catttcaggt gtcgtgacaa gtttgtacaa aaaagcaggc tgccaccatg atcgagacct    3180
acaaccagac cagccccaga agcgccgcca ccggcctgcc catcagcatg aagatcttca    3240
tgtacctgct gaccgtgttc ctgatcaccc agatgatcgg cagcgccctg ttcgccgtgt    3300
acctgcacag aagactggac aagatcgagg acgagagaaa cctgcacgag gacttcgtgt    3360
tcatgaagac catccagaga tgcaacaccg gcgagagaag cctgagcctg ctgaactgcg    3420
aggagatcaa gagccagttc gagggcttcg tgaaggacat catgctgaac aaggaggaga    3480
ccaagaagga gaacagcttc gagatgccca gaggcgagga ggacagccag atcgccgccc    3540
acgtgatcag cgaggccagc agcaagacca ccagcgtgct gcagtgggcc gagaagggct    3600
actacaccat gagcaacaac ctggtgaccc tggagaacgg caagcagctg accgtgaaga    3660
gacagggcct gtactacatc tacgcccagg tgacctttctg cagcaacaga gaggccagca    3720
gccaggcccc cttcatcgcc agcctgtgcc tgaagagccc cggcagattc gagagaatcc    3780
tgctgagagc cgccaacacc cacagcagcg ccaagccctg cggccagcag agcatccacc    3840
tgggcggcgt gttcgagctg cagcccggcg ccagcgtgtt cgtgaacgtg accgaccca    3900 gccaggtgag ccacggcacc ggcttcacca gcttcggcct gctgaagctg taaacccagc    3960
tttcttgtac aaagtggtga taatcgaatt cacccagctt tcttgtacaa agtggtgata    4020
atcgaattcc gataatcaac ctctggatta caaaatttgt gaaagattga ctggtattct    4080
taactatgtt gctcctttta cgctatgtgg atacgctgct ttaatgcctt tgtatcatgc    4140
tattgcttcc cgtatggctt tcattttctc ctccttgtat aaatcctggt tgctgtctct    4200
ttatgaggag ttgtggcccg ttgtcaggca acgtggcgtg gtgtgcactg tgtttgctga    4260 cgcaacccc actggttggg gcattgccac cacctgtcag ctccttccg ggactttcgc     4320 tttccccctc cctattgcca cggcggaact catcgccgcc tgccttgccc gctgctggac    4380
aggggctcgc tgttgggca ctgacaattc cgtggtgttg tcggggaagc tgacgtcctt    4440
tccatggctg ctcgcctgtg ttgccacctg gattctgcgc gggacgtcct tctgctacgt    4500
```

```
cccttcggcc ctcaatccag cggaccttcc ttcccgcggc ctgctgccgg ctctgcggcc    4560
tcttccgcgt cttcgccttc gccctcagac gagtcggatc tcccttt ggg ccgcctcccc    4620 gcatcgggaa ttcccgcggt tcgctttaag accaatgact tacaaggcag ctgtagatct    4680
tagccacttt ttaaaagaaa aggggggact ggaagggcta attcactccc aacgaagaca    4740
agatctgctt tttgcttgta ctgggtctct ctggttagac cagatctgag cctgggagct    4800
ctctggctaa ctagggaacc cactgcttaa gcctcaataa agcttgcctt gagtgcttca    4860
agtagtgtgt gcccgtctgt tgtgtgactc tggtaactag agatccctca gacccttta    4920 gtcagtgtgg aaaatctcta gcagtagtag ttcatgtcat cttattattc agtatttata    4980
acttgcaaag aaatgaatat cagagagtga gaggaacttg tttattgcag cttataatgg    5040
ttacaaataa agcaatagca tcacaaattt cacaataaa gcattttttt cactgcattc    5100
tagttgtggt ttgtccaaac tcatcaatgt atcttatcat gtctggctct agctatcccg    5160
cccctaactc cgcccatccc gcccctaact ccgcccagtt ccgcccattc tccgccccat    5220
ggctgactaa ttttttttat ttatgcagag gccgaggccg cctcggcctc tgagctattc    5280
cagaagtagt gaggaggctt ttttggaggc ctagggacgt acccaattcg ccctatagtg    5340
agtcgtatta cgcgcgctca ctggccgtcg ttttacaacg tcgtgactgg gaaaaccctg    5400
gcgttaccca acttaatcgc cttgcagcac atccccctt cgccagctgg cgtaatagcg    5460
aagaggcccg caccgatcgc ccttcccaac agttgcgcag cctgaatggc gaatgggacg    5520
cgccctgtag cggcgcatta agcgcggcgg gtgtggtggt tacgcgcagc gtgaccgcta    5580
cacttgccag cgccctagcg cccgctcctt tcgctttctt cccttccttt ctcgccacgt    5640
tcgccggctt tccccgtcaa gctctaaatc ggggg ctccc tttagggttc cgatttagtg    5700
ctttacggca cctcgacccc aaaaaacttg attagggtga tggttcacgt agtgggccat    5760
cgccctgata cacggttttt cgccctttga cgttggagtc cacgttcttt aatagtggac    5820
tcttgttcca aactggaaca cactcaacc ctatctcggt ctattctttt gatttataag    5880
ggattttgcc gatttcggcc tattggttaa aaaatgagct gatttaacaa aaatttaacg    5940
cgaattttaa caaaatatta acgcttacaa tttaggtggc acttttcggg gaaatgtgcg    6000
cggaacccct atttgtttat ttttctaaat acattcaaat atgtatccgc tcatgagaca    6060
ataaccctga taaatgcttc aataatattg aaaaaggaag agtatgagta ttcaacattt    6120
ccgtgtcgcc cttattccct ttttgcggc attttgcctt cctgtttttg ctcacccaga    6180
aacgctggtg aaagtaaaag atgctgaaga tcagttgggt gcacgagtgg gttacatcga    6240
actggatctc aacagcggta agatccttga gagttttcgc cccgaagaac gttttccaat    6300
gatgagcact tttaaagttc tgctatgtgg cgcggtatta tcccgtattg acgccgggca    6360
agagcaactc ggtcgccgca tacactattc tcagaatgac ttggttgagt actcaccagt    6420
cacagaaaag catcttacgg atggcatgac agtaagagaa ttatgcagtg ctgccataac    6480
catgagtgat aacactgcgg ccaacttact tctgacaacg atcggaggac cgaaggagct    6540
aaccgctttt ttgcacaaca tgggggatca tgtaactcgc cttgatcgtt gggaaccgga    6600
gctgaatgaa gccataccaa acgacgagcg tgacaccacg atgcctgtag caatggcaac    6660
aacgttgcgc aaactattaa ctggcgaact acttactcta gcttcccggc aacaattaat    6720
agactggatg gaggcggata aagttgcagg accacttctg cgctcggccc ttccggctgg    6780
ctggtttatt gctgataaat ctggagccgg tgagcgtggg tctcgcggta tcattgcagc    6840
```

| | |
|---|---|
| actgggccaa gatggtaagc cctcccgtat cgtagttatc tacacgacgg ggagtcaggc | 6900 |
| aactatggat gaacgaaata gacagatcgc tgagataggt gcctcactga ttaagcattg | 6960 |
| gtaactgtca gaccaagttt actcatatat actttagatt gatttaaaac ttcattttta | 7020 |
| atttaaaagg atctaggtga agatcctttt tgataatctc atgaccaaaa tcccttaacg | 7080 |
| tgagttttcg ttccactgag cgtcagaccc cgtagaaaag atcaaaggat cttcttgaga | 7140 |
| tcctttttttt ctgcgcgtaa tctgctgctt gcaaacaaaa aaaccaccgc taccagcggt | 7200 |
| ggtttgtttg ccggatcaag agctaccaac tcttttccg aaggtaactg gcttcagcag | 7260 |
| agcgcagata ccaaatactg ttcttctagt gtagccgtag ttaggccacc acttcaagaa | 7320 |
| ctctgtagca ccgcctacat acctcgctct gctaatcctg ttaccagtgg ctgctgccag | 7380 |
| tggcgataag tcgtgtctta ccgggttgga ctcaagacga tagttaccgg ataaggcgca | 7440 |
| gcggtcgggc tgaacggggg gttcgtgcac acagcccagc ttggagcgaa cgacctacac | 7500 |
| cgaactgaga tacctacagc gtgagctatg agaaagcgcc acgcttcccg aagagagaaa | 7560 |
| ggcggacagg tatccggtaa gcggcagggt cggaacagga gagcgcacga gggagcttcc | 7620 |
| agggggaaac gcctggtatc tttatagtcc tgtcgggttt cgccacctct gacttgagcg | 7680 |
| tcgatttttg tgatgctcgt caggggggcg gagcctatgg aaaaacgcca gcaacgcggc | 7740 |
| cttttttacgg ttcctggcct tttgctggcc ttttgctcac atgttctttc ctgcgttatc | 7800 |
| ccctgattct gtggataacc gtattaccgc ctttgagtga gctgataccg ctcgccgcag | 7860 |
| ccgaacgacc gagcgcagcg agtcagtgag cgaggaagcg gaagagcgcc caatacgcaa | 7920 |
| accgcctctc cccgcgcgtt ggccgattca ttaatgcagc tggcacgaca ggtttcccga | 7980 |
| ctggaaagcg ggcagtgagc gcaacgcaat taatgtgagt tagctcactc attaggcacc | 8040 |
| ccaggcttta cactttatgc ttccggctcg tatgttgtgt ggaattgtga gcggataaca | 8100 |
| atttcacaca ggaaacagct atgaccatga ttacgccaag cgcgcaatta accctcacta | 8160 |
| aagggaacaa aagctggagc tgcaagctt | 8189 |

<210> SEQ ID NO 52
<211> LENGTH: 8069
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Vector 6

<400> SEQUENCE: 52

| | |
|---|---|
| aatgtagtct tatgcaatac tcttgtagtc ttgcaacatg gtaacgatga gttagcaaca | 60 |
| tgccttacaa ggagagaaaa agcaccgtgc atgccgattg gtggaagtaa ggtggtacga | 120 |
| tcgtgcctta ttaggaaggc aacagacggg tctgacatgg attggacgaa ccactgaatt | 180 |
| gccgcattgc agagatattg tatttaagtg cctagctcga tacataaacg ggtctctctg | 240 |
| gttagaccag atctgagcct gggagctctc tggctaacta gggaacccac tgcttaagcc | 300 |
| tcaataaagc ttgccttgag tgcttcaagt agtgtgtgcc cgtctgttgt gtgactctgg | 360 |
| taactagaga tccctcagac ccttttagtc agtgtggaaa atctctagca gtggcgcccg | 420 |
| aacagggact tgaaagcgaa agggaaacca gaggagctct ctcgacgcag gactcggctt | 480 |
| gctgaagcgc gcacggcaag aggcgagggg cggcgactgg tgagtacgcc aaaaattttg | 540 |
| actagcggag gctagaagga gagagatggg tgcgagagcg tcagtattaa gcggggga | 600 |

```
attagatcgc gatgggaaaa aattcggtta aggccagggg gaaagaaaaa atataaatta    660
aaacatatag tatgggcaag cagggagcta gaacgattcg cagttaatcc tggcctgtta    720
gaaacatcag aaggctgtag acaaatactg ggacagctac aaccatccct tcagacagga    780
tcagaagaac ttagatcatt atataataca gtagcaaccc tctattgtgt gcatcaaagg    840
atagagataa aagacaccaa ggaagcttta gacaagatag aggaagagca aaacaaaagt    900
aagaccaccg cacagcaagc ggccgctgat cttcagacct ggaggaggag atatgaggga    960
caattgggaga agtgaattat ataaatataa agtagtaaaa attgaaccat taggagtagc   1020
acccaccaag gcaaagagaa gagtggtgca gagagaaaaa agagcagtgg gaataggagc   1080
tttgttcctt gggttcttgg gagcagcagg aagcactatg ggcgcagcgt caatgacgct   1140
gacggtacag gccagacaat tattgtctgg tatagtgcag cagcagaaca atttgctgag   1200
ggctattgag gcgcaacagc atctgttgca actcacagtc tggggcatca agcagctcca   1260
ggcaagaatc ctggctgtgg aaagatacct aaaggatcaa cagctcctgg ggatttgggg   1320
ttgctctgga aaactcattt gcaccactgc tgtgccttgg aatgctagtt ggagtaataa   1380
atctctggaa cagatttgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620
agtttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcgcta   1800
gcttttaaaa gaaaaggggg gattgggggg tacagtgcag gggaaagaat agtagacata   1860
atagcaacag acatacaaac taaagaatta caaaaacaaa ttacaaaaat tcaaaatttt   1920
actagtgatt atcggatcaa cttttgtatag aaaagttggg ctccggtgcc cgtcagtggg   1980
cagagcgcac atcgcccaca gtccccgaga agttgggggg aggggtcggc aattgaaccg   2040
gtgcctagag aaggtggcgc ggggtaaact gggaaagtga tgtcgtgtac tggctccgcc   2100
tttttcccga gggtggggga gaaccgtata taagtgcagt agtcgccgtg aacgttcttt   2160
ttcgcaacgg gtttgccgcc agaacacagg taagtgccgt gtgtggttcc cgcgggcctg   2220
gcctctttac gggttatggc ccttgcgtgc cttgaattac ttccacctgg ctgcagtacg   2280
tgattcttga tcccgagctt cgggttggaa gtgggtggga gagttcgagg ccttgcgctt   2340
aaggagcccc ttcgcctcgt gcttgagttg aggcctggcc tgggcgctgg ggccgccgcg   2400
tgcgaatctg gtggcacctt cgcgcctgtc tcgctgcttt cgataagtct ctagccattt   2460
aaaatttttg atgacctgct gcgacgcttt ttttctggca agatagtctt gtaaatgcgg   2520
gccaagatct gcacactggt atttcggttt ttggggccgc gggcggcgac ggggcccgtg   2580
cgtcccagcg cacatgttcg gcgaggcggg gcctgcgagc gcggccaccg agaatcggac   2640
gggggtagtc tcaagctggc cggcctgctc tggtgcctgg tctcgcgccg ccgtgtatcg   2700
ccccgccctg ggcggcaagg ctggcccggt cggcaccagt tgcgtgagcg aaagatggc   2760
cgcttcccgg ccctgctgca gggagctcaa aatggaggac gcggcgctcg ggagagcggg   2820
cgggtgagtc acccacacaa aggaaaaggg cctttccgtc ctcagccgtc gcttcatgtg   2880
actccacgga gtaccgggcg ccgtccaggc acctcgatta gttctcgagc ttttggagta   2940
cgtcgtcttt aggttggggg gaggggtttt atgcgatgga gtttccccac actgagtggg   3000
```

```
tggagactga agttaggcca gcttggcact tgatgtaatt ctccttggaa tttgcccttt    3060
ttgagtttgg atcttggttc attctcaagc ctcagacagt ggttcaaagt ttttttcttc    3120
catttcaggt gtcgtgacaa gtttgtacaa aaaagcaggc tgccaccatg agcaccgaga    3180
gcatgatcag agacgtggag ctggccgagg aggccctgcc caagaagacc ggcggccccc    3240
agggcagcag aagatgcctg ttcctgagcc tgttcagctt cctgatcgtg gccggcgcca    3300
ccaccctgtt ctgcctgctg cacttcggcg tgatcggccc ccagagagag gagttcccca    3360
gagacctgag cctgatcagc cccctggccc aggccgtggc ccacgtggtg gccaaccccc    3420
aggccgaggg ccagctgcag tggctgaaca aagagccaa cgccctgctg ccaacggcg      3480 tggagctgag agacaaccag ctggtggtgc ccagcgaggg cctgtacctg atctacagcc    3540
aggtgctgtt caagggccag ggctgcccca gcacccacgt gctgctgacc cacaccatca    3600
gcagaatcgc cgtgagctac cagaccaagg tgaacctgct gagcgccatc aagagcccct    3660
gccagagaga ccccccgag ggcgccgagg ccaagccctg gtacgagccc atctacctgg     3720
gcggcgtgtt ccagctggag aagggcgaca gactgagcgc cgagatcaac agacccgact    3780
acctggactt cgccgagagc ggccaggtgt acttcggcat catcgccctg taaacccagc    3840
tttcttgtac aaagtggtga taatcgaatt cacccagctt tcttgtacaa agtggtgata    3900
atcgaattcc gataatcaac ctctggatta caaaatttgt gaaagattga ctggtattct    3960
taactatgtt gctcctttta cgctatgtgg atacgctgct ttaatgcctt tgtatcatgc    4020
tattgcttcc cgtatggctt tcattttctc ctccttgtat aaatcctggt tgctgtctct    4080
ttatgaggag ttgtggcccg ttgtcaggca acgtggcgtg gtgtgcactg tgtttgctga    4140 cgcaacccc actggttggg gcattgccac cacctgtcag ctccttccg ggactttcgc      4200 tttccccctc cctattgcca cggcggaact catcgccgcc tgccttgccc gctgctggac    4260 agggctcgg ctgttgggca ctgacaattc cgtggtgttg tcggggaagc tgacgtcctt    4320
tccatggctg ctcgcctgtg ttgccacctg gattctgcgc gggacgtcct tctgctacgt    4380
cccttcggcc ctcaatccag cggaccttcc ttcccgcggc ctgctgccgg ctctgcggcc    4440
tcttccgcgt cttcgccttc gccctcagac gagtcggatc tccctttggg ccgcctcccc    4500
gcatcgggaa ttcccgcggt tcgctttaag accaatgact tacaaggcag ctgtagatct    4560
tagccacttt ttaaaagaaa aggggggact ggaagggcta attcactccc aacgaagaca    4620
agatctgctt tttgcttgta ctgggtctct ctggttagac cagatctgag cctgggagct    4680
ctctggctaa ctagggaacc cactgcttaa gcctcaataa agcttgcctt gagtgcttca    4740
agtagtgtgt gcccgtctgt tgtgtgactc tggtaactag agatccctca gaccctttta    4800
gtcagtgtgg aaaatctcta gcagtagtag ttcatgtcat cttattattc agtatttata    4860
acttgcaaag aaatgaatat cagagagtga gaggaacttg tttattgcag cttataatgg    4920
ttacaaataa agcaatagca tcacaaattt cacaaataaa gcattttttt cactgcattc    4980
tagttgtggt ttgtccaaac tcatcaatgt atcttatcat gtctggctct agctatcccg    5040
cccctaactc cgcccatccc gcccctaact ccgcccagtt ccgcccattc tccgccccat    5100
ggctgactaa ttttttttat ttatgcagag gccgaggccg cctcggcctc tgagctattc    5160
cagaagtagt gaggaggctt ttttggaggc ctagggacgt acccaattcg ccctatagtg    5220
agtcgtatta cgcgcgctca ctggccgtcg ttttacaacg tcgtgactgg gaaaaccctg    5280
gcgttaccca acttaatcgc cttgcagcac atccccctt cgccagctgg cgtaatagcg      5340
```

-continued

```
aagaggcccg caccgatcgc ccttcccaac agttgcgcag cctgaatggc gaatgggacg   5400
cgccctgtag cggcgcatta agcgcggcgg gtgtggtggt tacgcgcagc gtgaccgcta   5460
cacttgccag cgccctagcg cccgctcctt tcgctttctt cccttccttt ctcgccacgt   5520
tcgccggctt tccccgtcaa gctctaaatc ggggctccc tttagggttc cgatttagtg    5580
ctttacggca cctcgacccc aaaaaacttg attagggtga tggttcacgt agtgggccat   5640
cgccctgata gacggttttt cgcccttttga cgttggagtc cacgttcttt aatagtggac   5700
tcttgttcca aactggaaca acactcaacc ctatctcggt ctattctttt gatttataag   5760
ggattttgcc gatttcggcc tattggttaa aaaatgagct gatttaacaa aaatttaacg   5820
cgaattttaa caaaatatta acgcttacaa tttaggtggc acttttcggg gaaatgtgcg   5880
cggaacccct atttgtttat ttttctaaat acattcaaat atgtatccgc tcatgagaca   5940
ataaccctga taaatgcttc aataatattg aaaaggaag agtatgagta ttcaacattt    6000
ccgtgtcgcc cttattccct ttttgcggc attttgcctt cctgttttg ctcacccaga     6060 aacgctggtg aaagtaaaag atgctgaaga tcagttgggt gcacgagtgg gttacatcga   6120
actggatctc aacagcggta agatccttga gagttttcgc cccgaagaac gttttccaat   6180
gatgagcact tttaaagttc tgctatgtgg cgcggtatta tcccgtattg acgccgggca   6240
agagcaactc ggtcgccgca tacactattc tcagaatgac ttggttgagt actcaccagt   6300
cacagaaaag catcttacgg atggcatgac agtaagagaa ttatgcagtg ctgccataac   6360
catgagtgat aacactgcgg ccaacttact tctgacaacg atcggaggac cgaaggagct   6420
aaccgctttt ttgcacaaca tgggggatca tgtaactcgc cttgatcgtt gggaaccgga   6480
gctgaatgaa gccataccaa acgacgagcg tgacaccacg atgcctgtag caatggcaac   6540
aacgttgcgc aaactattaa ctggcgaact acttactcta gcttcccggc aacaattaat   6600
agactggatg gaggcggata agttgcagg accacttctg cgctcggccc ttccggctgg   6660
ctggtttatt gctgataaat ctggagccgg tgagcgtggg tctcgcggta tcattgcagc   6720
actggggcca gatggtaagc cctcccgtat cgtagttatc tacacgacgg ggagtcaggc   6780
aactatggat gaacgaaata gacagatcgc tgagataggt gcctcactga ttaagcattg   6840
gtaactgtca gaccaagttt actcatatat actttagatt gatttaaaac ttcattttta   6900
atttaaaagg atctaggtga agatccttt tgataatctc atgaccaaaa tcccttaacg    6960
tgagttttcg ttccactgag cgtcagaccc cgtagaaaag atcaaaggat cttcttgaga   7020 tcctttttt ctgcgcgtaa tctgctgctt gcaaacaaaa aaaccaccgc taccagcggt    7080
ggtttgtttg ccggatcaag agctaccaac tcttttttcg aaggtaactg gcttcagcag   7140
agcgcagata ccaaatactg ttcttctagt gtagccgtag ttaggccacc acttcaagaa   7200
ctctgtagca ccgcctacat acctcgctct gctaatcctg ttaccagtgg ctgctgccag   7260
tggcgataag tcgtgtctta ccgggttgga ctcaagacga tagttaccgg ataaggcgca   7320
gcggtcgggc tgaacggggg gttcgtgcac acagcccagc ttggagcgaa cgacctacac   7380
cgaactgaga tacctacagc gtgagctatg agaaagcgcc acgcttcccg aagagagaaa   7440
ggcggacagg tatccggtaa gcggcagggt cggaacagga gagcgcacga gggagcttcc   7500
agggggaaac gcctggtatc tttatagtcc tgtcgggttt cgccacctct gacttgagcg   7560
tcgatttttg tgatgctcgt caggggggcg gagcctatgg aaaaacgcca gcaacgcggc   7620 cttttacgg ttcctggcct tttgctggcc ttttgctcac atgttctttc ctgcgttatc     7680
ccctgattct gtggataacc gtattaccgc ctttgagtga gctgataccg ctcgccgcag   7740
```

-continued

```
ccgaacgacc gagcgcagcg agtcagtgag cgaggaagcg gaagagcgcc caatacgcaa      7800
accgcctctc cccgcgcgtt ggccgattca ttaatgcagc tggcacgaca ggtttcccga      7860
ctggaaagcg ggcagtgagc gcaacgcaat taatgtgagt tagctcactc attaggcacc      7920
ccaggcttta ctttatgc ttccggctcg tatgttgtgt ggaattgtga gcggataaca        7980
atttcacaca ggaaacagct atgaccatga ttacgccaag cgcgcaatta accctcacta      8040
aagggaacaa aagctggagc tgcaagctt                                         8069

<210> SEQ ID NO 53
<211> LENGTH: 10067
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Vector 7

<400> SEQUENCE: 53
aatgtagtct tatgcaatac tcttgtagtc ttgcaacatg gtaacgatga gttagcaaca       60
tgccttacaa ggagagaaaa agcaccgtgc atgccgattg gtggaagtaa ggtggtacga      120
tcgtgcctta ttaggaaggc aacagacggg tctgacatgg attggacgaa ccactgaatt      180
gccgcattgc agagatattg tatttaagtg cctagctcga tacataaacg ggtctctctg      240
gttagaccag atctgagcct gggagctctc tggctaacta gggaacccac tgcttaagcc      300
tcaataaagc ttgccttgag tgcttcaagt agtgtgtgcc cgtctgttgt gtgactctgg      360
taactagaga tccctcagac ccttttagtc agtgtggaaa atctctagca gtggcgcccg      420
aacagggact tgaaagcgaa agggaaacca gaggagctct ctcgacgcag gactcggctt      480
gctgaagcgc gcacggcaag aggcgagggg cggcgactgg tgagtacgcc aaaaattttg      540
actagcggag gctagaagga gagagatggg tgcgagagcg tcagtattaa gcggggagaa      600
attagatcgc gatgggaaaa aattcggtta aggccagggg gaagaaaaaa atataaatta      660
aaacatatag tatgggcaag cagggagcta gaacgattcg cagttaatcc tggcctgtta      720
gaaacatcag aaggctgtag acaaatactg ggacagctac aaccatccct tcagacagga      780
tcagaagaac ttagatcatt atataataca gtagcaaccc tctattgtgt gcatcaaagg      840
atagagataa aagacaccaa ggaagcttta gacaagatag aggaagagca aaacaaaagt      900
aagaccaccg cacagcaagc ggccgctgat cttcagacct ggaggaggag atatgaggga      960
caattggaga agtgaattat ataaatataa agtagtaaaa attgaaccat taggagtagc     1020
acccaccaag gcaaagagaa gagtggtgca gagagaaaaa agagcagtgg gaataggagc     1080
tttgttcctt gggttcttgg gagcagcagg aagcactatg ggcgcagcgt caatgacgct     1140
gacggtacag gccagacaat tattgtctgg tatagtgcag cagcagaaca atttgctgag     1200
ggctattgag gcgcaacagc atctgttgca actcacagtc tggggcatca agcagctcca     1260
ggcaagaatc ctggctgtgg aaagatacct aaaggatcaa cagctcctgg ggatttgggg     1320
ttgctctgga aaactcattt gcaccactgc tgtgccttgg aatgctagtt ggagtaataa     1380
atctctggaa cagatttgga atcacacgac ctggatggag tgggacagag aaattaacaa     1440
ttacacaagc ttaatacact ccttaattga agaatcgcaa aaccagcaag aaaagaatga     1500
acaagaatta ttggaattag ataaatgggc aagtttgtgg aattggttta acataacaaa     1560
ttggctgtgg tatataaaat tattcataat gatagtagga ggcttggtag gtttaagaat     1620
```

```
agtttttgct gtactttcta tagtgaatag agttaggcag ggatattcac cattatcgtt    1680
tcagacccac ctcccaaccc cgagggacc cgacaggccc gaaggaatag aagaagaagg    1740
tggagagaga gacagagaca gatccattcg attagtgaac ggatctcgac ggtatcgcta    1800
gcttttaaaa gaaaaggggg gattgggggg tacagtgcag gggaagaat agtagacata    1860
atagcaacag acatacaaac taagaatta caaaaacaaa ttacaaaaat tcaaaatttt    1920
actagtatca acttttgtata gaaaagttgg gctccggtgc ccgtcagtgg gcagagcgca    1980
catcgcccac agtccccgag aagttggggg gaggggtcgg caattgaacc ggtgcctaga    2040
gaaggtggcg cggggtaaac tgggaaagtg atgtcgtgta ctggctccgc cttttcccg     2100
agggtggggg agaaccgtat ataagtgcag tagtcgccgt gaacgttctt tttcgcaacg    2160
ggtttgccgc cagaacacag gtaagtgccg tgtgtggttc ccgcgggcct ggcctcttta    2220
cgggttatgg cccttgcgtg ccttgaatta cttccacctg gctgcagtac gtgattcttg    2280
atcccgagct tcgggttgga agtgggtggg agagttcgag gccttgcgct taaggagccc    2340
cttcgcctcg tgcttgagtt gaggcctggc ctgggcgctg gggccgccgc gtgcgaatct    2400
ggtggcacct tcgcgcctgt ctcgctgctt tcgataagtc tctagccatt taaaatttt     2460
gatgacctgc tgcgacgctt tttttctggc aagatagtct tgtaaatgcg ggccaagatc    2520
tgcacactgg tatttcggtt tttggggccg cgggcggcga cggggcccgt gcgtcccagc    2580
gcacatgttc ggcgaggcgg ggcctgcgag cgcggccacc gagaatcgga cggggggtagt   2640
ctcaagctgg ccggcctgct ctggtgcctg gtctcgcgcc gccgtgtatc gccccgccct    2700
gggcggcaag gctggcccgg tcggcaccag ttgcgtgagc ggaaagatgg ccgcttcccg    2760
gccctgctgc agggagctca aaatggagga cgcggcgctc gggagagcgg gcgggtgagt    2820
cacccacaca aaggaaaagg gccttccgt cctcagccgt cgcttcatgt gactccacgg     2880
agtaccgggc gccgtccagg cacctcgatt agttctcgag cttttggagt acgtcgtctt    2940
taggttgggg ggagggggttt tatgcgatgg agtttccca cactgagtgg gtggagactg    3000
aagttaggcc agcttggcac ttgatgtaat tctccttgga atttgccctt tttgagtttg    3060
gatcttggtt cattctcaag cctcagacag tggttcaaag ttttttttctt ccatttcagg   3120
tgtcgtgaca agttttgtaca aaaaagcagg ctgccaccat gagcaccgag agcatgatca    3180
gagacgtgga gctggccgag gaggccctgc ccaagaagac cggcggcccc cagggcagca    3240
gaagatgcct gttcctgagc ctgttcagct tcctgatcgt ggccggcgcc accaccctgt    3300
tctgcctgct gcacttcggc gtgatcggcc cccagagaga ggagttcccc agagacctga    3360
gcctgatcag ccccctggcc caggccgtgg cccacgtggt ggccaacccc caggccgagg    3420
gccagctgca gtggctgaac agaagagcca acgccctgct ggccaacggc gtggagctga    3480
gagacaacca gctggtggtg cccagcgagg gcctgtacct gatctacagc caggtgctgt    3540
tcaagggcca gggctgcccc agcacccacg tgctgctgac ccacaccatc agcagaatcg    3600
ccgtgagcta ccagaccaag gtgaacctgc tgagcgccat caagagcccc tgccagagag    3660
agacccccga gggcgccgag gccaagccct ggtacgagcc catctacctg ggcggcgtgt    3720
tccagctgga aagggcgac agactgagcg ccgagatcaa cagacccgac tacctggact    3780
tcgccgagag cggccaggtg tacttcggca tcatcgccct gtaaacccag ctttcttgta    3840
caaagtggtg ataatcgaat tctaaataga tagaacaaca acaattgcat tcatttttga   3900
tttcaggttc agggggaggt gtgggaggtt ttttaaagca agtaaaacct ctacactgac    3960
```

-continued

```
ggtacgcgtt aacaacaaca attgcattca tttgtagttt caggttcagg gggaggtgtg   4020
ggaggttttt taaagcaagt taaacctcta aatagtggt acgcgttacc cagctttctt   4080
gtacaaagtg gacccagctt tcttgtacaa agtgggcccc tctccctccc ccccccctaa   4140
cgttactggc cgaagccgct tggaataagg ccggtgtgcg tttgtctata tgttattttc   4200
caccatattg ccgtcttttg gcaatgtgag ggcccggaaa cctggccctg tcttcttgac   4260
gagcattcct aggggtcttt cccctctcgc caaaggaatg caaggtctgt tgaatgtcgt   4320
gaaggaagca gttcctctgg aagcttcttg aagacaaaca acgtctgtag cgaccctttg   4380
caggcagcgg aaccccccac ctggcgacag gtgcctctgc ggccaaaagc cacgtgtata   4440
agatacacct gcaaaggcgg cacaacccca gtgccacgtt gtgagttgga tagttgtgga   4500
aagagtcaaa tggctctcct caagcgtatt caacaagggg ctgaaggatg cccagaaggt   4560
accccattgt atgggatctg atctggggcc tcggtgcaca tgctttacat gtgtttagtc   4620
gaggttaaaa aaacgtctag gccccccgaa ccacggggac gtggttttcc tttgaaaaac   4680
acgatgataa tatggccaca accatggcca ccgtgctggc cccgcctgg agccccacca   4740
cctacctgct gctgctgctg ctgctgagca gcggcctgag cggcggcggc ggcagcggca   4800
agcccatccc caacccctg ctgggcctgg acagcaccgg cggcggcggc agccaggtga   4860
agctgcagga gagcggcccc ggcctggtgg cccccagcca gagcctgagc atcacctgca   4920
ccgtgagcgg cttcagcctg accgcctacg gcgtggactg ggtgagacag ccccccggca   4980
agtgcctgga gtggctgggc gtgatctggg gcggcggcag aaccaactac aacagcggcc   5040
tgatgagcag actgagcatc agaaaggaca acagcaagag ccaggtgttc ctgaccatga   5100
acagcctgca gaccgacgac accgccaagt actactgcgt gaagcacacc aactgggacg   5160
gcggcttcgc ctactggggc cagggcacca ccgtgaccgt gagcagcggc ggcggcggca   5220
gcggcggcgg cggcagcggc ggcggcggca gcggcagccc cggccagagc gtgagcatca   5280
gctgcagcgg cagcagcagc aacatcggca caaactacgt gtactggtac cagcacctgc   5340
ccggcaccgc ccccaagctg ctgatctaca gcgacaccaa gagacccagc ggcgtgcccg   5400
acagaatcag cggcagcaag agcggcacca cgccagcct ggccatcagc ggcctgcaga   5460
gcgaggacga ggccgactac tactgcgcca gctgggacga cagcctggac ggccccgtgt   5520
tcggctgcgg caccaagctg accgtgctgc ccaccaccac ccccgccccc agaccccccat   5580
cccccgcccc caccatcgcc agccagcccc tgagcctgag accgaggcc tgcagacccg   5640
ccgcggcgg cgccgtgcac accagaggcc tggacttcgc ctgcgacatc tacatctggg   5700
cccccctggc cggcacctgc ggcgtgctgc tgctgagcct ggtgatcacc ctgtactgca   5760
accacagaaa cagaagaaga gtgtgcaagt gccccagacc cgtggtgaag agcggcgaca   5820
agcccagcct gagcgccaga tacgtgtaac aactttatta tacatagttg atcaattcca   5880
actttattat acatagttga tcaattccga taatcaacct ctggattaca aaatttgtga   5940
aagattgact ggtattctta actatgttgc tccttttacg ctatgtggat acgctgcttt   6000
aatgcctttg tatcatgcta ttgcttcccg tatggctttc attttctcct ccttgtataa   6060
atcctggttg ctgtctcttt atgaggagtt gtggcccgtt gtcaggcaac gtggcgtggt   6120
gtgcactgtg tttgctgacg caaccccac tggttgggc attgccacca cctgtcagct   6180
cctttccggg actttcgctt tccccctccc tattgccacg cggaactca tcgccgcctg   6240
ccttgcccgc tgctgacag gggctcggct gttgggcact gacaattccg tggtgttgtc   6300
ggggaagctg acgtcctttc catggctgct cgcctgtgtt gccacctgga ttctgcgcgg   6360
```

```
gacgtccttc tgctacgtcc cttcggccct aatccagcg gaccttcctt cccgcggcct    6420
gctgccggct ctgcggcctc ttccgcgtct tcgccttcgc cctcagacga gtcggatctc    6480
cctttgggcc gcctcccgc atcgggaatt cccgcggttc gctttaagac caatgactta    6540
caaggcagct gtagatctta gccacttttt aaaagaaaag gggggactgg aagggctaat    6600
tcactcccaa cgaagacaag atctgctttt tgcttgtact gggtctctct ggttagacca    6660
gatctgagcc tgggagctct ctggctaact agggaaccca ctgcttaagc ctcaataaag    6720
cttgccttga gtgcttcaag tagtgtgtgc ccgtctgttg tgtgactctg gtaactagag    6780
atccctcaga cccttttagt cagtgtggaa aatctctagc agtagtagtt catgtcatct    6840
tattattcag tatttataac ttgcaaagaa atgaatatca gagagtgaga ggaacttgtt    6900
tattgcagct tataatggtt acaaataaag caatagcatc acaaatttca caaataaagc    6960
atttttttca ctgcattcta gttgtggttt gtccaaactc atcaatgtat cttatcatgt    7020
ctggctctag ctatcccgcc cctaactccg cccatcccgc cctaactccg cccagttcc     7080 gcccattctc cgccccatgg ctgactaatt ttttttattt atgcagaggc cgaggccgcc    7140
tcggcctctg agctattcca gaagtagtga ggaggctttt ttggaggcct agggacgtac    7200
ccaattcgcc ctatagtgag tcgtattacg cgcgctcact ggccgtcgtt ttacaacgtc    7260
gtgactggga aaaccctggc gttacccaac ttaatcgcct tgcagcacat ccccctttcg    7320
ccagctggcg taatagcgaa gaggcccgca ccgatcgccc ttcccaacag ttgcgcagcc    7380
tgaatggcga atgggacgcg ccctgtagcg gcgcattaag cgcggcgggt gtggtggtta    7440
cgcgcagcgt gaccgctaca cttgccagcg ccctagcgcc cgctcctttc gctttcttcc    7500
cttcctttct cgccacgttc gccggctttc ccgtcaagc tctaaatcgg gggctccctt     7560
tagggttccg atttagtgct ttacggcacc tcgaccccaa aaaacttgat tagggtgatg    7620
gttcacgtag tgggccatcg ccctgataga cggtttttcg ccctttgacg ttggagtcca    7680
cgttctttaa tagtggactc ttgttccaaa ctggaacaac actcaaccct atctcggtct    7740 attctttga tttataaggg attttgccga tttcggccta ttggttaaaa aatgagctga    7800
tttaacaaaa atttaacgcg aattttaaca aatattaac gcttacaatt taggtggcac     7860
ttttcgggga aatgtgcgcg gaaccctat ttgtttattt ttctaaatac attcaaatat    7920
gtatccgctc atgagacaat aaccctgata aatgcttcaa taatattgaa aaaggaagag    7980
tatgagtatt caacatttcc gtgtcgccct tattcccttt tttgcggcat tttgccttcc    8040 tgttttgct cacccagaaa cgctggtgaa agtaaaagat gctgaagatc agttgggtgc     8100
acgagtgggt tacatcgaac tggatctcaa cagcggtaag atccttgaga gttttcgccc    8160
cgaagaacgt tttccaatga tgagcacttt taaagttctg ctatgtggcg cggtattatc    8220
ccgtattgac gccgggcaag agcaactcgg tcgccgcata cactattctc agaatgactt    8280
ggttgagtac tcaccagtca cagaaaagca tcttacggat ggcatgacag taagagaatt    8340
atgcagtgct gccataacca tgagtgataa cactgcggcc aacttacttc tgacaacgat    8400
cggaggaccg aaggagctaa ccgcttttt gcacaacatg gggatcatg taactcgcct     8460 tgatcgttgg gaaccggagc tgaatgaagc cataccaaac gacgagcgtg acaccacgat    8520
gcctgtagca atggcaacaa cgttgcgcaa actattaact ggcgaactac ttactctagc    8580
ttcccggcaa caattaatag actggatgga ggcggataaa gttgcaggac cacttctgcg    8640
ctcggccctt ccggctggct ggtttattgc tgataaatct ggagccggtg agcgtgggtc    8700
```

```
tcgcggtatc attgcagcac tgggccaga tggtaagccc tcccgtatcg tagttatcta    8760
cacgacgggg agtcaggcaa ctatggatga acgaaataga cagatcgctg agataggtgc    8820
ctcactgatt aagcattggt aactgtcaga ccaagtttac tcatatatac tttagattga    8880
tttaaaactt catttttaat ttaaaaggat ctaggtgaag atccttttg ataatctcat    8940 gaccaaaatc ccttaacgtg agttttcgtt ccactgagcg tcagaccccg tagaaaagat    9000
caaaggatct tcttgagatc cttttttct gcgcgtaatc tgctgcttgc aaacaaaaaa    9060
accaccgcta ccagcggtgg tttgtttgcc ggatcaagag ctaccaactc tttttccgaa    9120
ggtaactggc ttcagcagag cgcagatacc aaatactgtt cttctagtgt agccgtagtt    9180
aggccaccac ttcaagaact ctgtagcacc gcctacatac ctcgctctgc taatcctgtt    9240
accagtggct gctgccagtg gcgataagtc gtgtcttacc gggttggact caagacgata    9300
gttaccggat aaggcgcagc ggtcgggctg aacggggggt tcgtgcacac agcccagctt    9360
ggagcgaacg acctacaccg aactgagata cctacagcgt gagctatgag aaagcgccac    9420
gcttcccgaa gagagaaagg cggacaggta tccggtaagc ggcagggtcg aacaggaga     9480 gcgcacgagg gagcttccag ggggaaacgc ctggtatctt tatagtcctg tcgggtttcg    9540
ccacctctga cttgagcgtc gatttttgtg atgctcgtca gggggcgga gcctatggaa     9600 aaacgccagc aacgcggcct ttttacggtt cctggccttt tgctggcctt ttgctcacat    9660
gttctttcct gcgttatccc ctgattctgt ggataaccgt attaccgcct ttgagtgagc    9720
tgataccgct cgccgcagcc gaacgaccga gcgcagcgag tcagtgagcg aggaagcgga    9780
agagcgccca atacgcaaac cgcctctccc gcgcgttgg ccgattcatt aatgcagctg     9840
gcacgacagg tttcccgact ggaaagcggg cagtgagcgc aacgcaatta atgtgagtta    9900
gctcactcat taggcacccc aggctttaca ctttatgctt ccggctcgta tgttgtgtgg    9960
aattgtgagc ggataacaat ttcacacagg aaacagctat gaccatgatt acgccaagcg    10020
cgcaattaac cctcactaaa gggaacaaaa gctggagctg caagctt               10067
```

<210> SEQ ID NO 54
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: H7 heavy chain leader

<400> SEQUENCE: 54

Met Glu Phe Gly Leu Ser Trp Val Phe Leu Val Ala Leu Phe Arg Gly
1               5                   10                  15

Val Gln Cys

<210> SEQ ID NO 55
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: anti-biotin murine vH with inserted Cys for
      inter-domain linkage

<400> SEQUENCE: 55

Gln Val Lys Leu Gln Glu Ser Gly Pro Gly Leu Val Ala Pro Ser Gln

```
                1               5                   10                  15
Ser Leu Ser Ile Thr Cys Thr Val Ser Gly Phe Ser Leu Thr Ala Tyr
            20                  25                  30

Gly Val Asp Trp Val Arg Gln Pro Gly Lys Cys Leu Glu Trp Leu
            35                  40                  45

Gly Val Ile Trp Gly Gly Arg Thr Asn Tyr Asn Ser Gly Leu Met
            50                  55                  60

Ser Arg Leu Ser Ile Arg Lys Asp Asn Ser Lys Ser Gln Val Phe Leu
65                  70                  75                  80

Thr Met Asn Ser Leu Gln Thr Asp Asp Thr Ala Lys Tyr Tyr Cys Val
                85                  90                  95

Lys His Thr Asn Trp Asp Gly Gly Phe Ala Tyr Trp Gly Gln Gly Thr
                100                 105                 110

Thr Val Thr Val Ser Ser
            115

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker

<400> SEQUENCE: 56

Gly Gly Gly Gly Ser Gly Gly Gly Gly Ser Gly Gly Gly Gly Ser
1               5                   10                  15

<210> SEQ ID NO 57
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light Chain Variable (human lambda variable)

<400> SEQUENCE: 57

Gly Ser Pro Gly Gln Ser Val Ser Ile Ser Cys Ser Gly Ser Ser Ser
1               5                   10                  15

Asn Ile Gly Asn Asn Tyr Val Tyr Trp Tyr Gln His Leu Pro Gly Thr
            20                  25                  30

Ala Pro Lys Leu Leu Ile Tyr Ser Asp Thr Lys Arg Pro Ser Gly Val
            35                  40                  45

Pro Asp Arg Ile Ser Gly Ser Lys Ser Gly Thr Ser Ala Ser Leu Ala
            50                  55                  60

Ile Ser Gly Leu Gln Ser Glu Asp Glu Ala Asp Tyr Tyr Cys Ala Ser
65                  70                  75                  80

Trp Asp Asp Ser Leu Asp Gly Pro Val Phe Gly Cys Gly Thr Lys Leu
                85                  90                  95

Thr Val Leu

<210> SEQ ID NO 58
<211> LENGTH: 61
<212> TYPE: PRT
<213> ORGANISM: Artificial Sequence
<220> FEATURE:
<223> OTHER INFORMATION: Description of Artificial Sequence: Synthetic
```

```
                    polypeptide
<220> FEATURE:
<223> OTHER INFORMATION: IgG3 hinge for greater accessibility to FcyR

<400> SEQUENCE: 58

Leu Lys Thr Pro Leu Gly Asp Thr Thr His Thr Cys Pro Arg Cys Pro
1               5                   10                  15

Glu Pro Lys Ser Cys Asp Thr Pro Pro Cys Pro Arg Cys Pro Glu
            20                  25                  30

Pro Lys Ser Cys Asp Thr Pro Pro Cys Pro Arg Cys Pro Glu Pro
            35                  40                  45

Lys Ser Cys Asp Thr Pro Pro Cys Pro Arg Cys Pro
        50                  55                  60

<210> SEQ ID NO 59
<211> LENGTH: 283
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG1 CH2, CH3 Tm and cytoplasmic tail (T256A)

<400> SEQUENCE: 59

Leu Leu Gly Gly Pro Ser Val Phe Leu Phe Pro Pro Lys Pro Lys Asp
1               5                   10                  15

Thr Leu Met Ile Ser Arg Ala Pro Glu Val Thr Cys Val Val Val Asp
            20                  25                  30

Val Ser His Glu Asp Pro Glu Val Lys Phe Asn Trp Tyr Val Asp Gly
        35                  40                  45

Val Glu Val His Asn Ala Lys Thr Lys Pro Arg Glu Glu Gln Tyr Asn
    50                  55                  60

Ser Thr Tyr Arg Val Val Ser Val Leu Thr Val Leu His Gln Asp Trp
65                  70                  75                  80

Leu Asn Gly Lys Glu Tyr Lys Cys Lys Val Ser Asn Lys Ala Leu Pro
                85                  90                  95

Ala Pro Ile Glu Lys Thr Ile Ser Lys Ala Lys Gly Gln Pro Arg Glu
            100                 105                 110

Pro Gln Val Tyr Thr Leu Pro Pro Ser Arg Asp Glu Leu Thr Lys Asn
        115                 120                 125

Gln Val Ser Leu Thr Cys Leu Val Lys Gly Phe Tyr Pro Ser Asp Ile
    130                 135                 140

Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Tyr Ser Lys
                165                 170                 175

Leu Thr Val Asp Lys Ser Arg Trp Gln Gln Gly Asn Val Phe Ser Cys
            180                 185                 190

Ser Val Met His Glu Ala Leu His Asn His Tyr Thr Gln Lys Ser Leu
        195                 200                 205

Ser Leu Ser Pro Glu Leu Gln Leu Glu Glu Ser Cys Ala Glu Ala Gln
    210                 215                 220

Asp Gly Glu Leu Asp Gly Leu Trp Thr Thr Ile Thr Ile Phe Ile Thr
225                 230                 235                 240

Leu Phe Leu Leu Ser Val Cys Tyr Ser Ala Thr Val Thr Phe Phe Lys
                245                 250                 255
```

```
Val Lys Trp Ile Phe Ser Ser Val Val Asp Leu Lys Gln Thr Ile Ile
            260                 265                 270

Pro Asp Tyr Arg Asn Met Ile Gly Gln Gly Ala
        275                 280

<210> SEQ ID NO 60
<211> LENGTH: 598
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: scFv-anti-biotin-G3hinge-IgG1-Tm (598 ORF1)

<400> SEQUENCE: 60

Met Glu Phe Gly Leu Ser Trp Val Phe Leu Val Ala Leu Phe Arg Gly
1               5                   10                  15

Val Gln Cys Gln Val Lys Leu Gln Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Thr Ala Tyr Gly Val Asp Trp Val Arg Gln Pro Pro Gly Lys Cys Leu
    50                  55                  60

Glu Trp Leu Gly Val Ile Trp Gly Gly Arg Thr Asn Tyr Asn Ser
65                  70                  75                  80

Gly Leu Met Ser Arg Leu Ser Ile Arg Lys Asp Asn Ser Lys Ser Gln
                85                  90                  95

Val Phe Leu Thr Met Asn Ser Leu Gln Thr Asp Asp Thr Ala Lys Tyr
            100                 105                 110

Tyr Cys Val Lys His Thr Asn Trp Asp Gly Gly Phe Ala Tyr Trp Gly
        115                 120                 125

Gln Gly Thr Thr Val Thr Val Ser Ser Gly Gly Gly Ser Gly Gly
    130                 135                 140

Gly Gly Ser Gly Gly Gly Ser Gly Ser Pro Gly Gln Ser Val Ser
145                 150                 155                 160

Ile Ser Cys Ser Gly Ser Ser Ser Asn Ile Gly Asn Asn Tyr Val Tyr
                165                 170                 175

Trp Tyr Gln His Leu Pro Gly Thr Ala Pro Lys Leu Leu Ile Tyr Ser
            180                 185                 190

Asp Thr Lys Arg Pro Ser Gly Val Pro Asp Arg Ile Ser Gly Ser Lys
        195                 200                 205

Ser Gly Thr Ser Ala Ser Leu Ala Ile Ser Gly Leu Gln Ser Glu Asp
    210                 215                 220

Glu Ala Asp Tyr Tyr Cys Ala Ser Trp Asp Asp Ser Leu Asp Gly Pro
225                 230                 235                 240

Val Phe Gly Cys Gly Thr Lys Leu Thr Val Leu Leu Lys Thr Pro Leu
                245                 250                 255

Gly Asp Thr Thr His Thr Cys Pro Arg Cys Pro Glu Pro Lys Ser Cys
            260                 265                 270

Asp Thr Pro Pro Pro Cys Pro Arg Cys Pro Glu Pro Lys Ser Cys Asp
        275                 280                 285

Thr Pro Pro Pro Cys Pro Arg Cys Pro Glu Pro Lys Ser Cys Asp Thr
    290                 295                 300

Pro Pro Pro Cys Pro Arg Cys Pro Ala Pro Glu Leu Leu Gly Gly Pro
305                 310                 315                 320
```

-continued

Ser Val Phe Leu Phe Pro Pro Lys Pro Lys Asp Thr Leu Met Ile Ser
            325                 330                 335

Arg Ala Pro Glu Val Thr Cys Val Val Val Asp Val Ser His Glu Asp
        340                 345                 350

Pro Glu Val Lys Phe Asn Trp Tyr Val Asp Gly Val Glu Val His Asn
    355                 360                 365

Ala Lys Thr Lys Pro Arg Glu Glu Gln Tyr Asn Ser Thr Tyr Arg Val
370                 375                 380

Val Ser Val Leu Thr Val Leu His Gln Asp Trp Leu Asn Gly Lys Glu
385                 390                 395                 400

Tyr Lys Cys Lys Val Ser Asn Lys Ala Leu Pro Ala Pro Ile Glu Lys
                405                 410                 415

Thr Ile Ser Lys Ala Lys Gly Gln Pro Arg Glu Pro Gln Val Tyr Thr
            420                 425                 430

Leu Pro Pro Ser Arg Asp Glu Leu Thr Lys Asn Gln Val Ser Leu Thr
                435                 440                 445

Cys Leu Val Lys Gly Phe Tyr Pro Ser Asp Ile Ala Val Glu Trp Glu
    450                 455                 460

Ser Asn Gly Gln Pro Glu Asn Asn Tyr Lys Thr Thr Pro Pro Val Leu
465                 470                 475                 480

Asp Ser Asp Gly Ser Phe Phe Leu Tyr Ser Lys Leu Thr Val Asp Lys
                485                 490                 495

Ser Arg Trp Gln Gln Gly Asn Val Phe Ser Cys Ser Val Met His Glu
            500                 505                 510

Ala Leu His Asn His Tyr Thr Gln Lys Ser Leu Ser Leu Ser Pro Glu
        515                 520                 525

Leu Gln Leu Glu Glu Ser Cys Ala Glu Ala Gln Asp Gly Glu Leu Asp
    530                 535                 540

Gly Leu Trp Thr Thr Ile Thr Ile Phe Ile Thr Leu Phe Leu Leu Ser
545                 550                 555                 560

Val Cys Tyr Ser Ala Thr Val Thr Phe Phe Lys Val Lys Trp Ile Phe
                565                 570                 575

Ser Ser Val Val Asp Leu Lys Gln Thr Ile Ile Pro Asp Tyr Arg Asn
            580                 585                 590

Met Ile Gly Gln Gly Ala
        595

<210> SEQ ID NO 61
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: L1 light chain leader/signal

<400> SEQUENCE: 61

Met Ala Thr Asp Met Arg Val Pro Ala Gln Leu Leu Gly Leu Leu Leu
1               5                   10                  15

Leu Trp Leu Ser Gly Ala Arg Cys
            20

<210> SEQ ID NO 62
<211> LENGTH: 118
<212> TYPE: PRT
<213> ORGANISM: Artificial Sequence
<220> FEATURE:

```
<223> OTHER INFORMATION: Description of Artificial Sequence: Synthetic
      polypeptide
<220> FEATURE:
<223> OTHER INFORMATION: anti-biotin vH

<400> SEQUENCE: 62

Gln Val Lys Leu Gln Glu Ser Gly Pro Gly Leu Val Ala Pro Ser Gln
1               5                   10                  15

Ser Leu Ser Ile Thr Cys Thr Val Ser Gly Phe Ser Leu Thr Ala Tyr
            20                  25                  30

Gly Val Asp Trp Val Arg Gln Pro Pro Gly Lys Gly Leu Glu Trp Leu
        35                  40                  45

Gly Val Ile Trp Gly Gly Gly Arg Thr Asn Tyr Asn Ser Gly Leu Met
    50                  55                  60

Ser Arg Leu Ser Ile Arg Lys Asp Asn Ser Lys Ser Gln Val Phe Leu
65                  70                  75                  80

Thr Met Asn Ser Leu Gln Thr Asp Asp Thr Ala Lys Tyr Tyr Cys Val
                85                  90                  95

Lys His Thr Asn Trp Asp Gly Gly Phe Ala Tyr Trp Gly Gln Gly Thr
            100                 105                 110

Thr Val Thr Val Ser Ser
            115

<210> SEQ ID NO 63
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CH1

<400> SEQUENCE: 63

Pro Ser Val Phe Pro Leu Ala Pro Ser Ser Lys Ser Thr Ser Gly Gly
1               5                   10                  15

Thr Ala Ala Leu Gly Cys Leu Val Lys Asp Tyr Phe Pro Glu Pro Val
            20                  25                  30

Thr Val Ser Trp Asn Ser Gly Ala Leu Thr Ser Gly Val His Thr Phe
        35                  40                  45

Pro Ala Val Leu Gln Ser Ser Gly Leu Tyr Ser Leu Ser Ser Val Val
    50                  55                  60

Thr Val Pro Ser Ser Ser Leu Gly Thr Gln Thr Tyr Ile Cys Asn Val
65                  70                  75                  80

Asn His Lys Pro Ser Asn Thr Lys Val Asp Lys Lys Val Glu
                85                  90

<210> SEQ ID NO 64
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG3 hinge

<400> SEQUENCE: 64

Leu Lys Thr Pro Leu Gly Asp Thr Thr His Thr Cys Pro Arg Cys Pro
1               5                   10                  15

Glu Pro Lys Ser Cys Asp Thr Pro Pro Pro Cys Pro Arg Cys Pro Glu
```

-continued

```
                20                  25                  30
Pro Lys Ser Cys Asp Thr Pro Pro Cys Pro Arg Cys Pro Glu Pro
            35                  40                  45

Lys Ser Cys Asp Thr Pro Pro Cys Pro Arg Cys Pro
        50                  55                  60

<210> SEQ ID NO 65
<211> LENGTH: 286
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG1 CH2, CH3 Tm and cytoplasmic tail

<400> SEQUENCE: 65

Ala Pro Glu Leu Leu Gly Gly Pro Ser Val Phe Leu Phe Pro Pro Lys
1               5                   10                  15

Pro Lys Asp Thr Leu Met Ile Ser Arg Ala Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Glu Leu Gln Leu Glu Glu Ser Cys Ala
    210                 215                 220

Glu Ala Gln Asp Gly Glu Leu Asp Gly Leu Trp Thr Thr Ile Thr Ile
225                 230                 235                 240

Phe Ile Thr Leu Phe Leu Leu Ser Val Cys Tyr Ser Ala Thr Val Thr
                245                 250                 255

Phe Phe Lys Val Lys Trp Ile Phe Ser Ser Val Val Asp Leu Lys Gln
            260                 265                 270

Thr Ile Ile Pro Asp Tyr Arg Asn Met Ile Gly Gln Gly Ala
        275                 280                 285

<210> SEQ ID NO 66
<211> LENGTH: 578
<212> TYPE: PRT
```

<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Summary (578 ORF2a)

<400> SEQUENCE: 66

Met Glu Phe Gly Leu Ser Trp Val Phe Leu Val Ala Leu Phe Arg Gly
1               5                   10                  15

Val Gln Cys Gln Val Lys Leu Gln Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Thr Ala Tyr Gly Val Asp Trp Val Arg Gln Pro Pro Gly Lys Gly Leu
    50                  55                  60

Glu Trp Leu Gly Val Ile Trp Gly Gly Gly Arg Thr Asn Tyr Asn Ser
65                  70                  75                  80

Gly Leu Met Ser Arg Leu Ser Ile Arg Lys Asp Asn Ser Lys Ser Gln
                85                  90                  95

Val Phe Leu Thr Met Asn Ser Leu Gln Thr Asp Asp Thr Ala Lys Tyr
            100                 105                 110

Tyr Cys Val Lys His Thr Asn Trp Asp Gly Phe Ala Tyr Trp Gly
        115                 120                 125

Gln Gly Thr Thr Val Thr Val Ser Ser Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Leu Lys Thr Pro Leu Gly Asp Thr Thr
225                 230                 235                 240

His Thr Cys Pro Arg Cys Pro Glu Pro Lys Ser Cys Asp Thr Pro Pro
                245                 250                 255

Pro Cys Pro Arg Cys Pro Glu Pro Lys Ser Cys Asp Thr Pro Pro
            260                 265                 270

Cys Pro Arg Cys Pro Glu Pro Lys Ser Cys Asp Thr Pro Pro Cys
        275                 280                 285

Pro Arg Cys Pro Ala Pro Glu Leu Leu Gly Gly Pro Ser Val Phe Leu
    290                 295                 300

Phe Pro Pro Lys Pro Lys Asp Thr Leu Met Ile Ser Arg Ala Pro Glu
305                 310                 315                 320

Val Thr Cys Val Val Val Asp Val Ser His Glu Asp Pro Glu Val Lys
                325                 330                 335

Phe Asn Trp Tyr Val Asp Gly Val Glu Val His Asn Ala Lys Thr Lys
            340                 345                 350

Pro Arg Glu Glu Gln Tyr Asn Ser Thr Tyr Arg Val Val Ser Val Leu
        355                 360                 365

Thr Val Leu His Gln Asp Trp Leu Asn Gly Lys Glu Tyr Lys Cys Lys

```
            370                 375                 380
Val Ser Asn Lys Ala Leu Pro Ala Pro Ile Glu Lys Thr Ile Ser Lys
385                 390                 395                 400

Ala Lys Gly Gln Pro Arg Glu Pro Gln Val Tyr Thr Leu Pro Pro Ser
                405                 410                 415

Arg Asp Glu Leu Thr Lys Asn Gln Val Ser Leu Thr Cys Leu Val Lys
            420                 425                 430

Gly Phe Tyr Pro Ser Asp Ile Ala Val Glu Trp Glu Ser Asn Gly Gln
        435                 440                 445

Pro Glu Asn Asn Tyr Lys Thr Thr Pro Pro Val Leu Asp Ser Asp Gly
    450                 455                 460

Ser Phe Phe Leu Tyr Ser Lys Leu Thr Val Asp Lys Ser Arg Trp Gln
465                 470                 475                 480

Gln Gly Asn Val Phe Ser Cys Ser Val Met His Glu Ala Leu His Asn
                485                 490                 495

His Tyr Thr Gln Lys Ser Leu Ser Leu Ser Pro Glu Leu Gln Leu Glu
            500                 505                 510

Glu Ser Cys Ala Glu Ala Gln Asp Gly Glu Leu Asp Gly Leu Trp Thr
        515                 520                 525

Thr Ile Thr Ile Phe Ile Thr Leu Phe Leu Leu Ser Val Cys Tyr Ser
    530                 535                 540

Ala Thr Val Thr Phe Phe Lys Val Lys Trp Ile Phe Ser Ser Val Val
545                 550                 555                 560

Asp Leu Lys Gln Thr Ile Ile Pro Asp Tyr Arg Asn Met Ile Gly Gln
                565                 570                 575

Gly Ala
```

<210> SEQ ID NO 67

<400> SEQUENCE: 67

000

<210> SEQ ID NO 68

<400> SEQUENCE: 68

000

<210> SEQ ID NO 69
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: LC Variable

<400> SEQUENCE: 69

```
Gly Ser Pro Gly Gln Ser Val Ser Ile Ser Cys Ser Gly Ser Ser Ser
1               5                   10                  15

Asn Ile Gly Asn Asn Tyr Val Tyr Trp Tyr Gln His Leu Pro Gly Thr
            20                  25                  30

Ala Pro Lys Leu Leu Ile Tyr Ser Asp Thr Lys Arg Pro Ser Gly Val
        35                  40                  45

Pro Asp Arg Ile Ser Gly Ser Lys Ser Gly Thr Ser Ala Ser Leu Ala
    50                  55                  60
```

```
Ile Ser Gly Leu Gln Ser Glu Asp Glu Ala Asp Tyr Tyr Cys Ala Ser
 65                  70                  75                  80

Trp Asp Asp Ser Leu Asp Gly Pro Val Phe Gly Gly Gly Thr Lys Leu
                 85                  90                  95

Thr Val Leu
```

<210> SEQ ID NO 70
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: LC Constant Region 1

<400> SEQUENCE: 70

```
Gly Gln Pro Lys Ala Asn Pro Thr Val Thr Leu Phe Pro Pro Ser Ser
  1               5                  10                  15

Glu Glu Leu Gln Ala Asn Lys Ala Thr Leu Val Cys Leu Ile Ser Asp
                 20                  25                  30

Phe Tyr Pro Gly Ala Val Thr Val Ala Trp Lys Ala Asp Gly Ser Pro
             35                  40                  45

Val Lys Ala Gly Val Glu Thr Thr Lys Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105
```

<210> SEQ ID NO 71
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Summary (229 ORF2b)

<400> SEQUENCE: 71

```
Met Ala Thr Asp Met Arg Val Pro Ala Gln Leu Leu Gly Leu Leu Leu
  1               5                  10                  15

Leu Trp Leu Ser Gly Ala Arg Cys Gly Ser Pro Gly Gln Ser Val Ser
                 20                  25                  30

Ile Ser Cys Ser Gly Ser Ser Ser Asn Ile Gly Asn Asn Tyr Val Tyr
             35                  40                  45

Trp Tyr Gln His Leu Pro Gly Thr Ala Pro Lys Leu Leu Ile Tyr Ser
 50                  55                  60

Asp Thr Lys Arg Pro Ser Gly Val Pro Asp Arg Ile Ser Gly Ser Lys
 65                  70                  75                  80

Ser Gly Thr Ser Ala Ser Leu Ala Ile Ser Gly Leu Gln Ser Glu Asp
                 85                  90                  95

Glu Ala Asp Tyr Tyr Cys Ala Ser Trp Asp Asp Ser Leu Asp Gly Pro
            100                 105                 110

Val Phe Gly Gly Gly Thr Lys Leu Thr Val Leu Gly Gln Pro Lys Ala
        115                 120                 125
```

```
Asn Pro Thr Val Thr Leu Phe Pro Pro Ser Ser Glu Glu Leu Gln Ala
    130                 135                 140

Asn Lys Ala Thr Leu Val Cys Leu Ile Ser Asp Phe Tyr Pro Gly Ala
145                 150                 155                 160

Val Thr Val Ala Trp Lys Ala Asp Gly Ser Pro Val Lys Ala Gly Val
                165                 170                 175

Glu Thr Thr Lys Pro Ser Lys Gln Ser Asn Asn Lys Tyr Ala Ala Ser
                180                 185                 190

Ser Tyr Leu Ser Leu Thr Pro Glu Gln Trp Lys Ser His Arg Ser Tyr
        195                 200                 205

Ser Cys Gln Val Thr His Glu Gly Ser Thr Val Glu Lys Thr Val Ala
    210                 215                 220

Pro Thr Glu Cys Ser
225

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: GM-CSF signal sequence

<400> SEQUENCE: 72

Met Trp Leu Gln Ser Leu Leu Leu Leu Gly Thr Val Ala Cys Ser Ile
1               5                   10                  15

Ser

<210> SEQ ID NO 73
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: wild type GM-CSF sequence

<400> SEQUENCE: 73

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
                20                  25                  30

Ala Ala Glu Met Asn Glu Thr Val Glu Val Ile Ser Glu Met Phe Asp
            35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
    115                 120                 125

<210> SEQ ID NO 74
```

```
<400> SEQUENCE: 74

000

<210> SEQ ID NO 75
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: FLT3L signal

<400> SEQUENCE: 75

Met Ala Thr Val Leu Ala Pro Ala Trp Ser Pro Thr Thr Tyr Leu Leu
1               5                   10                  15

Leu Leu Leu Leu Leu Ser Ser Gly Leu Ser
            20                  25

<210> SEQ ID NO 76
<211> LENGTH: 210
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: FLT3L

<400> SEQUENCE: 76

Gly Thr Gln Asp Cys Ser Phe Gln His Ser Pro Ile Ser Ser Asp Phe
1               5                   10                  15

Ala Val Lys Ile Arg Glu Leu Ser Asp Tyr Leu Leu Gln Asp Tyr Pro
            20                  25                  30

Val Thr Val Ala Ser Asn Leu Gln Asp Glu Glu Leu Cys Gly Gly Leu
        35                  40                  45

Trp Arg Leu Val Leu Ala Gln Arg Trp Met Glu Arg Leu Lys Thr Val
    50                  55                  60

Ala Gly Ser Lys Met Gln Gly Leu Leu Glu Arg Val Asn Thr Glu Ile
65                  70                  75                  80

His Phe Val Thr Lys Cys Ala Phe Gln Pro Pro Pro Ser Cys Leu Arg
                85                  90                  95

Phe Val Gln Thr Asn Ile Ser Arg Leu Leu Gln Glu Thr Ser Glu Gln
            100                 105                 110

Leu Val Ala Leu Lys Pro Trp Ile Thr Arg Gln Asn Phe Ser Arg Cys
        115                 120                 125

Leu Glu Leu Gln Cys Gln Pro Asp Ser Ser Thr Leu Pro Pro Pro Trp
    130                 135                 140

Ser Pro Arg Pro Leu Glu Ala Thr Ala Pro Thr Ala Pro Gln Pro Pro
145                 150                 155                 160

Leu Leu Leu Leu Leu Leu Leu Pro Val Gly Leu Leu Leu Leu Ala Ala
                165                 170                 175

Ala Trp Cys Leu His Trp Gln Arg Thr Arg Arg Arg Thr Pro Arg Pro
            180                 185                 190

Gly Glu Gln Val Pro Pro Val Pro Ser Pro Gln Asp Leu Leu Leu Val
        195                 200                 205

Glu His
    210
```

```
<210> SEQ ID NO 77
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Summary (144 ORF3a)

<400> SEQUENCE: 77

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

<210> SEQ ID NO 78
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Summary (236 ORF3b)

<400> SEQUENCE: 78

Met Ala Thr Val Leu Ala Pro Ala Trp Ser Pro Thr Thr Tyr Leu Leu
1               5                   10                  15

Leu Leu Leu Leu Leu Ser Ser Gly Leu Ser Gly Thr Gln Asp Cys Ser
            20                  25                  30

Phe Gln His Ser Pro Ile Ser Ser Asp Phe Ala Val Lys Ile Arg Glu
        35                  40                  45

Leu Ser Asp Tyr Leu Leu Gln Asp Tyr Pro Val Thr Val Ala Ser Asn
    50                  55                  60

Leu Gln Asp Glu Glu Leu Cys Gly Gly Leu Trp Arg Leu Val Leu Ala
65                  70                  75                  80

Gln Arg Trp Met Glu Arg Leu Lys Thr Val Ala Gly Ser Lys Met Gln
                85                  90                  95

Gly Leu Leu Glu Arg Val Asn Thr Glu Ile His Phe Val Thr Lys Cys
            100                 105                 110

Ala Phe Gln Pro Pro Pro Ser Cys Leu Arg Phe Val Gln Thr Asn Ile
        115                 120                 125

Ser Arg Leu Leu Gln Glu Thr Ser Glu Gln Leu Val Ala Leu Lys Pro
    130                 135                 140
```

```
Trp Ile Thr Arg Gln Asn Phe Ser Arg Cys Leu Glu Leu Gln Cys Gln
145                 150                 155                 160

Pro Asp Ser Ser Thr Leu Pro Pro Pro Trp Ser Pro Arg Pro Leu Glu
                165                 170                 175

Ala Thr Ala Pro Thr Ala Pro Gln Pro Pro Leu Leu Leu Leu Leu Leu
            180                 185                 190

Leu Pro Val Gly Leu Leu Leu Ala Ala Ala Trp Cys Leu His Trp
        195                 200                 205

Gln Arg Thr Arg Arg Thr Pro Arg Pro Gly Glu Gln Val Pro Pro
    210                 215                 220

Val Pro Ser Pro Gln Asp Leu Leu Leu Val Glu His
225                 230                 235
```

<210> SEQ ID NO 79
<211> LENGTH: 183
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: wild type FLT3L sequence with transmembrane deleted

<400> SEQUENCE: 79

```
Met Thr Val Leu Ala Pro Ala Trp Ser Pro Thr Thr Tyr Leu Leu Leu
1               5                   10                  15

Leu Leu Leu Leu Ser Ser Gly Leu Ser Gly Thr Gln Asp Cys Ser Phe
                20                  25                  30

Gln His Ser Pro Ile Ser Ser Asp Phe Ala Val Lys Ile Arg Glu Leu
            35                  40                  45

Ser Asp Tyr Leu Leu Gln Asp Tyr Pro Val Thr Val Ala Ser Asn Leu
    50                  55                  60

Gln Asp Glu Glu Leu Cys Gly Gly Leu Trp Arg Leu Val Leu Ala Gln
65                  70                  75                  80

Arg Trp Met Glu Arg Leu Lys Thr Val Ala Gly Ser Lys Met Gln Gly
                85                  90                  95

Leu Leu Glu Arg Val Asn Thr Glu Ile His Phe Val Thr Lys Cys Ala
            100                 105                 110

Phe Gln Pro Pro Pro Ser Cys Leu Arg Phe Val Gln Thr Asn Ile Ser
        115                 120                 125

Arg Leu Leu Gln Glu Thr Ser Glu Gln Leu Val Ala Leu Lys Pro Trp
    130                 135                 140

Ile Thr Arg Gln Asn Phe Ser Arg Cys Leu Glu Leu Gln Cys Gln Pro
145                 150                 155                 160

Asp Ser Ser Thr Leu Pro Pro Pro Trp Ser Pro Arg Pro Leu Glu Ala
                165                 170                 175

Thr Ala Pro Thr Ala Pro Gln
            180
```

<210> SEQ ID NO 80

<400> SEQUENCE: 80

000

<210> SEQ ID NO 81
<211> LENGTH: 26
<212> TYPE: PRT

<213> ORGANISM: Artificial Sequence
<220> FEATURE:
<223> OTHER INFORMATION: Description of Artificial Sequence: Synthetic peptide
<220> FEATURE:
<223> OTHER INFORMATION: FLT3L signal

<400> SEQUENCE: 81

Met Ala Thr Val Leu Ala Pro Ala Trp Ser Pro Thr Thr Tyr Leu Leu
1               5                   10                  15
Leu Leu Leu Leu Leu Ser Ser Gly Leu Ser
            20                  25

<210> SEQ ID NO 82
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: wild type GM-CSF sequence

<400> SEQUENCE: 82

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125

<210> SEQ ID NO 83
<211> LENGTH: 99
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CD8alpha transmembrane and cytoplasmic domain

<400> SEQUENCE: 83

Pro Thr Thr Thr Pro Ala Pro Arg Pro Pro Thr Pro Ala Pro Thr Ile
1               5                   10                  15

Ala Ser Gln Pro Leu Ser Leu Arg Pro Glu Ala Cys Arg Pro Ala Ala
            20                  25                  30

Gly Gly Ala Val His Thr Arg Gly Leu Asp Phe Ala Cys Asp Ile Tyr
        35                  40                  45

Ile Trp Ala Pro Leu Ala Gly Thr Cys Gly Val Leu Leu Leu Ser Leu
    50                  55                  60

Val Ile Thr Leu Tyr Cys Asn His Arg Asn Arg Arg Arg Val Cys Lys
65                  70                  75                  80

Cys Pro Arg Pro Val Val Lys Ser Gly Asp Lys Pro Ser Leu Ser Ala
                85                  90                  95

Arg Tyr Val

<210> SEQ ID NO 84
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Summary (183 ORF4a)

<400> SEQUENCE: 84

Met Thr Val Leu Ala Pro Ala Trp Ser Pro Thr Thr Tyr Leu Leu Leu
1               5                   10                  15

Leu Leu Leu Ser Ser Gly Leu Ser Gly Thr Gln Asp Cys Ser Phe
            20                  25                  30

Gln His Ser Pro Ile Ser Ser Asp Phe Ala Val Lys Ile Arg Glu Leu
            35                  40                  45

Ser Asp Tyr Leu Leu Gln Asp Tyr Pro Val Thr Val Ala Ser Asn Leu
    50                  55                  60

Gln Asp Glu Glu Leu Cys Gly Gly Leu Trp Arg Leu Val Leu Ala Gln
65                  70                  75                  80

Arg Trp Met Glu Arg Leu Lys Thr Val Ala Gly Ser Lys Met Gln Gly
                85                  90                  95

Leu Leu Glu Arg Val Asn Thr Glu Ile His Phe Val Thr Lys Cys Ala
            100                 105                 110

Phe Gln Pro Pro Pro Ser Cys Leu Arg Phe Val Gln Thr Asn Ile Ser
            115                 120                 125

Arg Leu Leu Gln Glu Thr Ser Glu Gln Leu Val Ala Leu Lys Pro Trp
    130                 135                 140

Ile Thr Arg Gln Asn Phe Ser Arg Cys Leu Glu Leu Gln Cys Gln Pro
145                 150                 155                 160

Asp Ser Ser Thr Leu Pro Pro Pro Trp Ser Pro Arg Pro Leu Glu Ala
                165                 170                 175

Thr Ala Pro Thr Ala Pro Gln
            180

<210> SEQ ID NO 85
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Summary for CYAGEN (253 ORF4b)

<400> SEQUENCE: 85

Met Ala Thr Val Leu Ala Pro Ala Trp Ser Pro Thr Thr Tyr Leu Leu
1               5                   10                  15

Leu Leu Leu Leu Ser Ser Gly Leu Ser Ala Pro Arg Ser Pro
            20                  25                  30

Ser Pro Ser Thr Gln Pro Trp Glu His Val Asn Ala Ile Gln Glu Ala
            35                  40                  45

Arg Arg Leu Leu Asn Leu Ser Arg Asp Thr Ala Ala Glu Met Asn Glu
    50                  55                  60

```
Thr Val Glu Val Ile Ser Glu Met Phe Asp Leu Gln Glu Pro Thr Cys
65                  70                  75                  80

Leu Gln Thr Arg Leu Glu Leu Tyr Lys Gln Gly Leu Arg Gly Ser Leu
                85                  90                  95

Thr Lys Leu Lys Gly Pro Leu Thr Met Met Ala Ser His Tyr Lys Gln
            100                 105                 110

His Cys Pro Pro Thr Pro Glu Thr Ser Cys Ala Thr Gln Ile Ile Thr
            115                 120                 125

Phe Glu Ser Phe Lys Glu Asn Leu Lys Asp Phe Leu Leu Val Ile Pro
130                 135                 140

Phe Asp Cys Trp Glu Pro Val Gln Glu Pro Thr Thr Thr Pro Ala Pro
145                 150                 155                 160

Arg Pro Pro Thr Pro Ala Pro Thr Ile Ala Ser Gln Pro Leu Ser Leu
                165                 170                 175

Arg Pro Glu Ala Cys Arg Pro Ala Ala Gly Gly Ala Val His Thr Arg
            180                 185                 190

Gly Leu Asp Phe Ala Cys Asp Ile Tyr Ile Trp Ala Pro Leu Ala Gly
            195                 200                 205

Thr Cys Gly Val Leu Leu Leu Ser Leu Val Ile Thr Leu Tyr Cys Asn
        210                 215                 220

His Arg Asn Arg Arg Val Cys Lys Cys Pro Arg Pro Val Val Lys
225                 230                 235                 240

Ser Gly Asp Lys Pro Ser Leu Ser Ala Arg Tyr Val
                245                 250

<210> SEQ ID NO 86
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: mCD40L modified to stop cleavage

<400> SEQUENCE: 86

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
                20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu His Glu Asp Phe Val
50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Pro Arg Gly Glu Glu Asp Ser Gln Ile Ala Ala His Val Ile Ser
            115                 120                 125

Glu Ala Ser Ser Lys Thr Thr Ser Val Leu Gln Trp Ala Glu Lys Gly
130                 135                 140

Tyr Tyr Thr Met Ser Asn Asn Leu Val Thr Leu Glu Asn Gly Lys Gln
145                 150                 155                 160
```

```
Leu Thr Val Lys Arg Gln Gly Leu Tyr Tyr Ile Tyr Ala Gln Val Thr
            165                 170                 175

Phe Cys Ser Asn Arg Glu Ala Ser Ser Gln Ala Pro Phe Ile Ala Ser
        180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 87
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Summary (261 ORF5)

<400> SEQUENCE: 87

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Pro Arg Gly Glu Glu Asp Ser Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240
```

```
Val Thr Asp Pro Ser Gln Val Ser His Gly Thr Gly Phe Thr Ser Phe
                245                 250                 255

Gly Leu Leu Lys Leu
            260

<210> SEQ ID NO 88
<211> LENGTH: 221
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: mTNFalpha modified to stop cleavage

<400> SEQUENCE: 88

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60
Arg Asp Leu Ser Leu Ile Ser Pro Leu Ala Gln Ala Val Ala His Val
65                  70                  75                  80

Val Ala Asn Pro Gln Ala Glu Gly Gln Leu Gln Trp Leu Asn Arg Arg
                85                  90                  95

Ala Asn Ala Leu Leu Ala Asn Gly Val Glu Leu Arg Asp Asn Gln Leu
            100                 105                 110

Val Val Pro Ser Glu Gly Leu Tyr Leu Ile Tyr Ser Gln Val Leu Phe
        115                 120                 125

Lys Gly Gln Gly Cys Pro Ser Thr His Val Leu Leu Thr His Thr Ile
    130                 135                 140

Ser Arg Ile Ala Val Ser Tyr Gln Thr Lys Val Asn Leu Leu Ser Ala
145                 150                 155                 160

Ile Lys Ser Pro Cys Gln Arg Glu Thr Pro Glu Gly Ala Glu Ala Lys
                165                 170                 175

Pro Trp Tyr Glu Pro Ile Tyr Leu Gly Gly Val Phe Gln Leu Glu Lys
            180                 185                 190

Gly Asp Arg Leu Ser Ala Glu Ile Asn Arg Pro Asp Tyr Leu Asp Phe
        195                 200                 205

Ala Glu Ser Gly Gln Val Tyr Phe Gly Ile Ile Ala Leu
    210                 215                 220

<210> SEQ ID NO 89
<211> LENGTH: 221
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Summary (221 ORF6)

<400> SEQUENCE: 89

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
```

```
                     20                  25                  30
Leu Ser Leu Phe Ser Phe Leu Ile Val Ala Gly Ala Thr Thr Leu Phe
             35                  40                  45

Cys Leu Leu His Phe Gly Val Ile Gly Pro Gln Arg Glu Glu Phe Pro
         50                  55                  60

Arg Asp Leu Ser Leu Ile Ser Pro Leu Ala Gln Ala Val Ala His Val
 65                  70                  75                  80

Val Ala Asn Pro Gln Ala Glu Gly Gln Leu Gln Trp Leu Asn Arg Arg
                 85                  90                  95

Ala Asn Ala Leu Leu Ala Asn Gly Val Glu Leu Arg Asp Asn Gln Leu
            100                 105                 110

Val Val Pro Ser Glu Gly Leu Tyr Leu Ile Tyr Ser Gln Val Leu Phe
        115                 120                 125

Lys Gly Gln Gly Cys Pro Ser Thr His Val Leu Thr His Thr Ile
130                 135                 140

Ser Arg Ile Ala Val Ser Tyr Gln Thr Lys Val Asn Leu Leu Ser Ala
145                 150                 155                 160

Ile Lys Ser Pro Cys Gln Arg Glu Thr Pro Glu Gly Ala Glu Ala Lys
                165                 170                 175

Pro Trp Tyr Glu Pro Ile Tyr Leu Gly Gly Val Phe Gln Leu Glu Lys
            180                 185                 190

Gly Asp Arg Leu Ser Ala Glu Ile Asn Arg Pro Asp Tyr Leu Asp Phe
        195                 200                 205

Ala Glu Ser Gly Gln Val Tyr Phe Gly Ile Ile Ala Leu
    210                 215                 220

<210> SEQ ID NO 90
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: wild-type

<400> SEQUENCE: 90

Met Asp Pro Asn Arg Ile Ser Glu Asp Gly Thr His Cys Ile Tyr Arg
1               5                  10                  15

Ile Leu Arg Leu His Glu Asn Ala Asp Phe Gln Asp Thr Thr Leu Glu
            20                  25                  30

Ser Gln Asp Thr Lys Leu Ile Pro Asp Ser Cys Arg Arg Ile Lys Gln
        35                  40                  45

Ala Phe Gln Gly Ala Val Gln Lys Glu Leu Gln His Ile Val Gly Ser
    50                  55                  60

Gln His Ile Arg Ala Glu Lys Ala Met Val Asp Gly Ser Trp Leu Asp
65                  70                  75                  80

Leu Ala Lys Arg Ser Lys Leu Glu Ala Gln Pro Phe Ala His Leu Thr
                85                  90                  95

Ile Asn Ala Thr Asp Ile Pro Ser Gly Ser His Lys Val Ser Leu Ser
            100                 105                 110

Ser Trp Tyr His Asp Arg Gly Trp Ala Lys Ile Ser Asn Met Thr Phe
        115                 120                 125

Ser Asn Gly Lys Leu Ile Val Asn Gln Asp Gly Phe Tyr Tyr Leu Tyr
    130                 135                 140

Ala Asn Ile Cys Phe Arg His His Glu Thr Ser Gly Asp Leu Ala Thr
```

```
                145                 150                 155                 160
Glu Tyr Leu Gln Leu Met Val Tyr Val Thr Lys Thr Ser Ile Lys Ile
                165                 170                 175

Pro Ser Ser His Thr Leu Met Lys Gly Gly Ser Thr Lys Tyr Trp Ser
                180                 185                 190

Gly Asn Ser Glu Phe His Phe Tyr Ser Ile Asn Val Gly Gly Phe Phe
                195                 200                 205

Lys Leu Arg Ser Gly Glu Glu Ile Ser Ile Glu Val Ser Asn Pro Ser
        210                 215                 220

Leu Leu Asp Pro Asp Gln Asp Ala Thr Tyr Phe Gly Ala Phe Lys Val
225                 230                 235                 240

Arg Asp Ile Asp

<210> SEQ ID NO 91

<400> SEQUENCE: 91

000

<210> SEQ ID NO 92
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: FLT3L signal

<400> SEQUENCE: 92

Met Ala Thr Val Leu Ala Pro Ala Trp Ser Pro Thr Thr Tyr Leu Leu
1               5                   10                  15

Leu Leu Leu Leu Leu Ser Ser Gly Leu Ser
            20                  25

<210> SEQ ID NO 93
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker

<400> SEQUENCE: 93

Gly Gly Gly Gly Ser
1               5

<210> SEQ ID NO 94
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: V5 epitope tag for flow detection

<400> SEQUENCE: 94

Gly Lys Pro Ile Pro Asn Pro Leu Leu Gly Leu Asp Ser Thr
1               5                   10

<210> SEQ ID NO 95
```

```
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: anti-biotin murine vH with inserted Cys for
      intralinkage

<400> SEQUENCE: 95
```

Gln Val Lys Leu Gln Glu Ser Gly Pro Gly Leu Val Ala Pro Ser Gln
1               5                   10                  15

Ser Leu Ser Ile Thr Cys Thr Val Ser Gly Phe Ser Leu Thr Ala Tyr
            20                  25                  30

Gly Val Asp Trp Val Arg Gln Pro Pro Gly Lys Cys Leu Glu Trp Leu
        35                  40                  45

Gly Val Ile Trp Gly Gly Gly Arg Thr Asn Tyr Asn Ser Gly Leu Met
    50                  55                  60

Ser Arg Leu Ser Ile Arg Lys Asp Asn Ser Lys Ser Gln Val Phe Leu
65                  70                  75                  80

Thr Met Asn Ser Leu Gln Thr Asp Asp Thr Ala Lys Tyr Tyr Cys Val
                85                  90                  95

Lys His Thr Asn Trp Asp Gly Gly Phe Ala Tyr Trp Gly Gln Gly Thr
            100                 105                 110

Thr Val Thr Val Ser Ser
            115

```
<210> SEQ ID NO 96
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker

<400> SEQUENCE: 96
```

Gly Gly Gly Gly Ser Gly Gly Gly Gly Ser Gly Gly Gly Gly Ser
1               5                   10                  15

```
<210> SEQ ID NO 97
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: LC Variable

<400> SEQUENCE: 97
```

Gly Ser Pro Gly Gln Ser Val Ser Ile Ser Cys Ser Gly Ser Ser
1               5                   10                  15

Asn Ile Gly Asn Asn Tyr Val Tyr Trp Tyr Gln His Leu Pro Gly Thr
            20                  25                  30

Ala Pro Lys Leu Leu Ile Tyr Ser Asp Thr Lys Arg Pro Ser Gly Val
        35                  40                  45

Pro Asp Arg Ile Ser Gly Ser Lys Ser Gly Thr Ser Ala Ser Leu Ala
    50                  55                  60

Ile Ser Gly Leu Gln Ser Glu Asp Glu Ala Asp Tyr Tyr Cys Ala Ser
65                  70                  75                  80

-continued

```
Trp Asp Asp Ser Leu Asp Gly Pro Val Phe Gly Cys Gly Thr Lys Leu
            85                  90                  95

Thr Val Leu

<210> SEQ ID NO 98
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CD8alpha transmembrane and cytoplasmic domain

<400> SEQUENCE: 98

Pro Thr Thr Thr Pro Ala Pro Arg Pro Pro Thr Pro Ala Pro Thr Ile
1               5                   10                  15

Ala Ser Gln Pro Leu Ser Leu Arg Pro Glu Ala Cys Arg Pro Ala Ala
                20                  25                  30

Gly Gly Ala Val His Thr Arg Gly Leu Asp Phe Ala Cys Asp Ile Tyr
            35                  40                  45

Ile Trp Ala Pro Leu Ala Gly Thr Cys Gly Val Leu Leu Leu Ser Leu
    50                  55                  60

Val Ile Thr Leu Tyr Cys Asn His Arg Asn Arg Arg Arg Val Cys Lys
65                  70                  75                  80

Cys Pro Arg Pro Val Val Lys Ser Gly Asp Lys Pro Ser Leu Ser Ala
                85                  90                  95

Arg Tyr Val

<210> SEQ ID NO 99
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Summary (244 ORF7a)

<400> SEQUENCE: 99

Met Asp Pro Asn Arg Ile Ser Glu Asp Gly Thr His Cys Ile Tyr Arg
1               5                   10                  15

Ile Leu Arg Leu His Glu Asn Ala Asp Phe Gln Asp Thr Thr Leu Glu
                20                  25                  30

Ser Gln Asp Thr Lys Leu Ile Pro Asp Ser Cys Arg Arg Ile Lys Gln
            35                  40                  45

Ala Phe Gln Gly Ala Val Gln Lys Glu Leu Gln His Ile Val Gly Ser
    50                  55                  60

Gln His Ile Arg Ala Glu Lys Ala Met Val Asp Gly Ser Trp Leu Asp
65                  70                  75                  80

Leu Ala Lys Arg Ser Lys Leu Glu Ala Gln Pro Phe Ala His Leu Thr
                85                  90                  95

Ile Asn Ala Thr Asp Ile Pro Ser Gly Ser His Lys Val Ser Leu Ser
            100                 105                 110

Ser Trp Tyr His Asp Arg Gly Trp Ala Lys Ile Ser Asn Met Thr Phe
        115                 120                 125

Ser Asn Gly Lys Leu Ile Val Asn Gln Asp Gly Phe Tyr Tyr Leu Tyr
    130                 135                 140
```

-continued

```
Ala Asn Ile Cys Phe Arg His His Glu Thr Ser Gly Asp Leu Ala Thr
145                 150                 155                 160

Glu Tyr Leu Gln Leu Met Val Tyr Val Thr Lys Thr Ser Ile Lys Ile
                165                 170                 175

Pro Ser Ser His Thr Leu Met Lys Gly Gly Ser Thr Lys Tyr Trp Ser
            180                 185                 190

Gly Asn Ser Glu Phe His Phe Tyr Ser Ile Asn Val Gly Gly Phe Phe
        195                 200                 205

Lys Leu Arg Ser Gly Glu Glu Ile Ser Ile Glu Val Ser Asn Pro Ser
    210                 215                 220

Leu Leu Asp Pro Asp Gln Asp Ala Thr Tyr Phe Gly Ala Phe Lys Val
225                 230                 235                 240

Arg Asp Ile Asp

<210> SEQ ID NO 100
<211> LENGTH: 381
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Summary  (381aa ORF7b)

<400> SEQUENCE: 100

Met Ala Thr Val Leu Ala Pro Ala Trp Ser Pro Thr Thr Tyr Leu Leu
1               5                   10                  15

Leu Leu Leu Leu Leu Ser Ser Gly Leu Ser Gly Gly Gly Gly Ser Gly
                20                  25                  30

Lys Pro Ile Pro Asn Pro Leu Leu Gly Leu Asp Ser Thr Gly Gly Gly
            35                  40                  45

Gly Ser Gln Val Lys Leu Gln Glu Ser Gly Pro Gly Leu Val Ala Pro
        50                  55                  60

Ser Gln Ser Leu Ser Ile Thr Cys Thr Val Ser Gly Phe Ser Leu Thr
65                  70                  75                  80

Ala Tyr Gly Val Asp Trp Val Arg Gln Pro Pro Gly Lys Cys Leu Glu
                85                  90                  95

Trp Leu Gly Val Ile Trp Gly Gly Arg Thr Asn Tyr Asn Ser Gly
                100                 105                 110

Leu Met Ser Arg Leu Ser Ile Arg Lys Asp Asn Ser Lys Ser Gln Val
            115                 120                 125

Phe Leu Thr Met Asn Ser Leu Gln Thr Asp Asp Thr Ala Lys Tyr Tyr
        130                 135                 140

Cys Val Lys His Thr Asn Trp Asp Gly Gly Phe Ala Tyr Trp Gly Gln
145                 150                 155                 160

Gly Thr Thr Val Thr Val Ser Ser Gly Gly Gly Ser Gly Gly Gly
                165                 170                 175

Gly Ser Gly Gly Gly Gly Ser Ser Pro Gln Ser Val Ser Ile
            180                 185                 190

Ser Cys Ser Gly Ser Ser Ser Asn Ile Gly Asn Asn Tyr Val Tyr Trp
        195                 200                 205

Tyr Gln His Leu Pro Gly Thr Ala Pro Lys Leu Leu Ile Tyr Ser Asp
    210                 215                 220

Thr Lys Arg Pro Ser Gly Val Pro Asp Arg Ile Ser Gly Ser Lys Ser
225                 230                 235                 240

Gly Thr Ser Ala Ser Leu Ala Ile Ser Gly Leu Gln Ser Glu Asp Glu
```

```
            245                 250                 255
Ala Asp Tyr Tyr Cys Ala Ser Trp Asp Asp Ser Leu Asp Gly Pro Val
            260                 265                 270

Phe Gly Cys Gly Thr Lys Leu Thr Val Leu Pro Thr Thr Pro Ala
            275                 280             285

Pro Arg Pro Pro Thr Pro Ala Pro Thr Ile Ala Ser Gln Pro Leu Ser
        290                 295                 300

Leu Arg Pro Glu Ala Cys Arg Pro Ala Ala Gly Gly Ala Val His Thr
305                 310                 315                 320

Arg Gly Leu Asp Phe Ala Cys Asp Ile Tyr Ile Trp Ala Pro Leu Ala
                325                 330                 335

Gly Thr Cys Gly Val Leu Leu Leu Ser Leu Val Ile Thr Leu Tyr Cys
                340                 345                 350

Asn His Arg Asn Arg Arg Val Cys Lys Cys Pro Arg Pro Val Val
                355                 360                 365

Lys Ser Gly Asp Lys Pro Ser Leu Ser Ala Arg Tyr Val
    370                 375                 380
```

```
<210> SEQ ID NO 101
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic peptide

<400> SEQUENCE: 101

Gln Met Gln Gly Val Asn Cys Thr Val Ser Ser
1               5                   10

<210> SEQ ID NO 102
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CpG
<220> FEATURE:
<221> NAME/KEY: modified_base
<222> LOCATION: (1)..(2)
<223> OTHER INFORMATION: g-phosphorothioate
<220> FEATURE:
<221> NAME/KEY: modified_base
<222> LOCATION: (25)..(29)
<223> OTHER INFORMATION: g-phosphorothioate

<400> SEQUENCE: 102
ggaaccgtat cggcgatatc ggttgggggg                                  30

<210> SEQ ID NO 103
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CpG
<220> FEATURE:
<221> NAME/KEY: modified_base
<222> LOCATION: (1)..(2)
<223> OTHER INFORMATION: g-phosphorothioate
```

-continued

```
<220> FEATURE:
<221> NAME/KEY: modified_base
<222> LOCATION: (25)..(29)
<223> OTHER INFORMATION: g-phosphorothioate

<400> SEQUENCE: 103
ggaaccgtat gcggcatatc ggttgggggg                                        30

<210> SEQ ID NO 104
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Synthetic peptide

<400> SEQUENCE: 104

Val Arg Ser Ser Ser Arg Thr Pro Ser Asp Lys Pro
1               5                   10

<210> SEQ ID NO 105
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Met Tyr Pro Pro Pro Tyr
1               5

<210> SEQ ID NO 106
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Tyr Met Asn Met
1

<210> SEQ ID NO 107
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Pro Tyr Ala Pro
1

<210> SEQ ID NO 108
<211> LENGTH: 183
<212> TYPE: PRT
<213> ORGANISM: Unknown
<220> FEATURE:
<223> OTHER INFORMATION: Description of Unknown:
      OX40L sequence

<400> SEQUENCE: 108

Met Glu Arg Val Gln Pro Leu Glu Glu Asn Val Gly Asn Ala Ala Arg
```

```
            1               5                   10                  15
        Pro Arg Phe Glu Arg Asn Lys Leu Leu Leu Val Ala Ser Val Ile Gln
                        20                  25                  30

Gly Leu Gly Leu Leu Leu Cys Phe Thr Tyr Ile Cys Leu His Phe Ser
                        35                  40                  45

Ala Leu Gln Val Ser His Arg Tyr Pro Arg Ile Gln Ser Ile Lys Val
                        50                  55                  60

Gln Phe Thr Glu Tyr Lys Lys Glu Lys Gly Phe Ile Leu Thr Ser Gln
        65                      70                  75                  80

Lys Glu Asp Glu Ile Met Lys Val Gln Asn Asn Ser Val Ile Ile Asn
                                85                  90                  95

Cys Asp Gly Phe Tyr Leu Ile Ser Leu Lys Gly Tyr Phe Ser Gln Glu
                        100                 105                 110

Val Asn Ile Ser Leu His Tyr Gln Lys Asp Glu Glu Pro Leu Phe Gln
                        115                 120                 125

Leu Lys Lys Val Arg Ser Val Asn Ser Leu Met Val Ala Ser Leu Thr
                        130                 135                 140

Tyr Lys Asp Lys Val Tyr Leu Asn Val Thr Thr Asp Asn Thr Ser Leu
        145                     150                 155                 160

Asp Asp Phe His Val Asn Gly Gly Glu Leu Ile Leu Ile His Gln Asn
                        165                 170                 175

Pro Gly Glu Phe Cys Val Leu
                        180

<210> SEQ ID NO 109
<211> LENGTH: 193
<212> TYPE: PRT
<213> ORGANISM: Unknown
<220> FEATURE:
<223> OTHER INFORMATION: Description of Unknown:
      CD27L sequence

<400> SEQUENCE: 109

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
                20                  25                  30

Cys Leu Val Val Cys Ile Gln Arg Phe Ala Gln Ala Gln Gln Gln Leu
            35                  40                  45

Pro Leu Glu Ser Leu Gly Trp Asp Val Ala Glu Leu Gln Leu Asn His
        50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
        115                 120                 125

Ala Val Gly Ile Cys Ser Pro Ala Ser Arg Ser Ile Ser Leu Leu Arg
    130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175
```

```
Pro Ser Arg Asn Thr Asp Glu Thr Phe Phe Gly Val Gln Trp Val Arg
            180                 185                 190

Pro

<210> SEQ ID NO 110
<211> LENGTH: 288
<212> TYPE: PRT
<213> ORGANISM: Homo sapiens

<400> SEQUENCE: 110

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val
        275                 280                 285

<210> SEQ ID NO 111
<211> LENGTH: 329
<212> TYPE: PRT
<213> ORGANISM: Homo sapiens

<400> SEQUENCE: 111

Met Asp Pro Gln Cys Thr Met Gly Leu Ser Asn Ile Leu Phe Val Met
1               5                   10                  15

Ala Phe Leu Leu Ser Gly Ala Ala Pro Leu Lys Ile Gln Ala Tyr Phe
```

```
                    20                  25                  30
Asn Glu Thr Ala Asp Leu Pro Cys Gln Phe Ala Asn Ser Gln Asn Gln
            35                  40                  45
Ser Leu Ser Glu Leu Val Val Phe Trp Gln Asp Gln Glu Asn Leu Val
 50                  55                  60
Leu Asn Glu Val Tyr Leu Gly Lys Glu Lys Phe Asp Ser Val His Ser
 65                  70                  75                  80
Lys Tyr Met Gly Arg Thr Ser Phe Asp Ser Asp Ser Trp Thr Leu Arg
                85                  90                  95
Leu His Asn Leu Gln Ile Lys Asp Lys Gly Leu Tyr Gln Cys Ile Ile
                100                 105                 110
His His Lys Lys Pro Thr Gly Met Ile Arg Ile His Gln Met Asn Ser
            115                 120                 125
Glu Leu Ser Val Leu Ala Asn Phe Ser Gln Pro Glu Ile Val Pro Ile
        130                 135                 140
Ser Asn Ile Thr Glu Asn Val Tyr Ile Asn Leu Thr Cys Ser Ser Ile
145                 150                 155                 160
His Gly Tyr Pro Glu Pro Lys Lys Met Ser Val Leu Leu Arg Thr Lys
                165                 170                 175
Asn Ser Thr Ile Glu Tyr Asp Gly Val Met Gln Lys Ser Gln Asp Asn
                180                 185                 190
Val Thr Glu Leu Tyr Asp Val Ser Ile Ser Leu Ser Val Ser Phe Pro
            195                 200                 205
Asp Val Thr Ser Asn Met Thr Ile Phe Cys Ile Leu Glu Thr Asp Lys
        210                 215                 220
Thr Arg Leu Leu Ser Ser Pro Phe Ser Ile Glu Leu Glu Asp Pro Gln
225                 230                 235                 240
Pro Pro Pro Asp His Ile Pro Trp Ile Thr Ala Val Leu Pro Thr Val
            245                 250                 255
Ile Ile Cys Val Met Val Phe Cys Leu Ile Leu Trp Lys Trp Lys Lys
            260                 265                 270
Lys Lys Arg Pro Arg Asn Ser Tyr Lys Cys Gly Thr Asn Thr Met Glu
        275                 280                 285
Arg Glu Glu Ser Glu Gln Thr Lys Lys Arg Glu Lys Ile His Ile Pro
    290                 295                 300
Glu Arg Ser Asp Glu Ala Gln Arg Val Phe Lys Ser Ser Lys Thr Ser
305                 310                 315                 320
Ser Cys Asp Lys Ser Asp Thr Cys Phe
                325
```